(12) United States Patent
Yang et al.

(10) Patent No.: US 12,054,756 B2
(45) Date of Patent: Aug. 6, 2024

(54) ENGINEERED NUCLEASES, COMPOSITIONS, AND METHODS OF USE THEREOF

(71) Applicant: Epicrispr Biotechnologies, Inc., South San Francisco, CA (US)

(72) Inventors: Xiao Yang, Albany, CA (US); Lei S. Qi, Palo Alto, CA (US); Vincent Cutillas, San Francisco, CA (US); Gabriella Alvarez, South San Francisco, CA (US); Tabitha Tcheau, Atherton, CA (US); Daniel O. Hart, Oakland, CA (US)

(73) Assignee: Epicrispr Biotechnologies, Inc., South San Francisco, CA (US)

( * ) Notice: Subject to any disclaimer, the term of this patent is extended or adjusted under 35 U.S.C. 154(b) by 0 days.

(21) Appl. No.: 18/348,948

(22) Filed: Jul. 7, 2023

(65) Prior Publication Data
US 2024/0035009 A1 Feb. 1, 2024

Related U.S. Application Data

(63) Continuation of application No. PCT/US2023/063446, filed on Mar. 1, 2023.

(60) Provisional application No. 63/385,171, filed on Nov. 28, 2022, provisional application No. 63/380,178, filed on Oct. 19, 2022, provisional application No. 63/315,159, filed on Mar. 1, 2022.

(51) Int. Cl.
*C12N 9/22* (2006.01)
*C12N 15/11* (2006.01)
*C12N 15/90* (2006.01)

(52) U.S. Cl.
CPC ............ *C12N 9/22* (2013.01); *C12N 15/111* (2013.01); *C12N 15/907* (2013.01); *C12N 2310/20* (2017.05)

(58) Field of Classification Search
CPC ...... C12N 9/22; C12N 15/111; C12N 15/907; C12N 2310/20
See application file for complete search history.

(56) References Cited

U.S. PATENT DOCUMENTS

| | | | |
|---|---|---|---|
| 9,790,490 B2 | 10/2017 | Zhang et al. | |
| 10,648,020 B2 | 5/2020 | Zhang et al. | |
| 10,669,540 B2 | 6/2020 | Zhang et al. | |
| 10,934,536 B2 | 3/2021 | Hou et al. | |
| 11,091,798 B2 | 8/2021 | Zhang et al. | |
| 11,180,743 B2 | 11/2021 | Doudna et al. | |
| 11,180,751 B2 | 11/2021 | Koonin et al. | |
| 11,371,031 B2 | 6/2022 | Doudna et al. | |
| 11,441,137 B2 | 9/2022 | Doudna et al. | |
| 11,453,866 B2 | 9/2022 | Doudna et al. | |
| 2016/0355795 A1 | 12/2016 | Ran et al. | |
| 2019/0256900 A1 | 8/2019 | Zhang et al. | |
| 2020/0087640 A1 | 3/2020 | Doudna et al. | |
| 2020/0199555 A1 | 6/2020 | Zhang | |
| 2020/0308583 A1 | 10/2020 | Kim et al. | |
| 2020/0318172 A1 | 10/2020 | Zhang et al. | |
| 2020/0318173 A1 | 10/2020 | Zhang et al. | |
| 2021/0040546 A1 | 2/2021 | Zhang et al. | |
| 2021/0139874 A1 | 5/2021 | Hou et al. | |
| 2021/0163908 A1 | 6/2021 | Hou et al. | |
| 2021/0348156 A1 | 11/2021 | Koonin et al. | |
| 2021/0348157 A1 | 11/2021 | Koonin et al. | |
| 2022/0049241 A1 | 2/2022 | Harrington et al. | |
| 2022/0073890 A1 | 3/2022 | Hou et al. | |
| 2022/0195503 A1 | 6/2022 | Zhang et al. | |
| 2022/0307018 A1 | 9/2022 | Kim et al. | |
| 2023/0074840 A1 | 3/2023 | Zhang et al. | |
| 2023/0108784 A1 | 4/2023 | Zhang et al. | |
| 2023/0340439 A1 | 10/2023 | Qi et al. | |

FOREIGN PATENT DOCUMENTS

| | | |
|---|---|---|
| EP | 2931898 | 3/2016 |
| EP | 3436575 A1 | 2/2019 |
| EP | 3604532 A1 | 2/2020 |
| EP | 3704239 A1 | 9/2020 |
| KR | 20230007218 A | 1/2023 |
| WO | WO-2019089808 A1 | 5/2019 |
| WO | WO-2019089820 A1 | 5/2019 |
| WO | WO-2020088450 A1 | 5/2020 |
| WO | WO-2020123887 A2 | 6/2020 |
| WO | WO-2021023887 A1 | 2/2021 |
| WO | WO-2021084533 A1 | 5/2021 |
| WO | WO-2021086083 A2 | 5/2021 |
| WO | WO-2022051250 A1 | 3/2022 |
| WO | WO-2022075813 A1 | 4/2022 |
| WO | WO-2022075816 A1 | 4/2022 |
| WO | WO-2022140572 A1 | 6/2022 |

(Continued)

OTHER PUBLICATIONS

Altschul et al. Basic local alignment search tool. J Mol Biol 215(3):403-410 (1990).

(Continued)

*Primary Examiner* — Nelson B Moseley, II
*Assistant Examiner* — Alyssa Rae Stonebraker
(74) *Attorney, Agent, or Firm* — KNOBBE, MARTENS, OLSON & BEAR, LLP

(57) ABSTRACT

The present disclosure provides one or more engineered nucleases and systems, compositions, and methods thereof, wherein the one or more engineered nucleases can be used to effect binding, cleaving, and/or editing a target polynucleotide sequence. The one or more engineered nucleases can be engineered variants of a small CRISPR/Cas protein.

13 Claims, 13 Drawing Sheets

Specification includes a Sequence Listing.

(56) References Cited

FOREIGN PATENT DOCUMENTS

| WO | WO-2022150372 A1 | 7/2022 |
| WO | WO-2022220503 A1 | 10/2022 |
| WO | WO-2022266324 A1 | 12/2022 |
| WO | WO 2023/004338 | 1/2023 |
| WO | WO-2023010135 A1 | 2/2023 |
| WO | WO 2023/172995 | 9/2023 |
| WO | WO 2023/173072 | 9/2023 |
| WO | WO 2023/173110 | 9/2023 |
| WO | WO 2023/173120 | 9/2023 |
| WO | WO 2023/183893 | 9/2023 |
| WO | WO-2023168242 A1 | 9/2023 |

OTHER PUBLICATIONS

Altschul, et al. Gapped BLAST and PSI-BLAST: a new generation of protein database search programs. Nucleic Acids Res 25:3389-3402 (1997).

Chavez, Alejandro et al. Comparison of Cas9 activators in multiple species. Nature methods vol. 13,7 (2016): 563-567. doi:10.1038/nmeth.3871.

Chen, Baohui et al. Dynamic imaging of genomic loci in living human cells by an optimized CRISPR/Cas system. Cell vol. 155,7 (2013): 1479-91. doi:10.1016/j.cell.2013.12.001.

Cong, Le et al. Multiplex genome engineering using CRISPR/Cas systems. Science (New York, N.Y.) vol. 339,6121 (2013): 819-23. doi:10.1126/science.1231143.

Co-pending U.S. Appl. No. 18/174,552, inventors Qi; Lei S. et al., filed Feb. 24, 2023.

Dang et al. Optimizing sgRNA Structure to Improve CRISPR-Cas9 Knockout Efficiency. Genome Biology, vol. 16, No. 280, Dec. 15, 2015, pp. 1-10.

Fellmann, Christof et al. Cornerstones of CRISPR-Cas in drug discovery and therapy. Nature reviews. Drug discovery vol. 16,2 (2017): 89-100. doi:10.1038/nrd.2016.238.

Harrington, Lucas B et al. Programmed DNA destruction by miniature CRISPR-Cas14 enzymes. Science (New York, N.Y.) vol. 362,6416 (2018): 839-842. doi:10.1126/science.aav4294.

Harrow, Jennifer et al. Gencode: the reference human genome annotation for the Encode Project. Genome research vol. 22,9 (2012): 1760-74. doi:10.1101/gr.135350.111.

Hilton, Isaac B et al. Epigenome editing by a CRISPR-Cas9-based acetyltransferase activates genes from promoters and enhancers. Nature biotechnology vol. 33,5 (2015): 510-7. doi:10.1038/nbt.3199.

Huang, Tony P et al. Precision genome editing using cytosine and adenine base editors in mammalian cells. Nature protocols vol. 16,2 (2021): 1089-1128. doi:10.1038/s41596-020-00450-9.

Jinek, Martin et al. A programmable dual-RNA-guided DNA endonuclease in adaptive bacterial immunity. Science (New York, N.Y.) vol. 337,6096 (2012): 816-21. doi:10.1126/science.1225829.

Karlin, et al. Applications and statistics for multiple high-scoring segments in molecular sequences. PNAS USA 90:5873-5877 (1993).

Karlin et al. Methods for assessing the statistical significance of molecular sequence features by using general scoring schemes. PNAS USA 87:2264-2268 (1990).

Karvelis, Tautvydas et al. PAM recognition by miniature CRISPR-Cas12f nucleases triggers programmable double-stranded DNA target cleavage. Nucleic acids research vol. 48,9 (2020): 5016-5023. doi:10.1093/nar/gkaa208.

Kempton, et al. Multiple Input Sensing and Signal Integration Using a Split Cas12a System. Mol. Cell 78,1 (2020): 184-191.

Kim et al. Genome-wide analysis reveals specificities of Cpf1 endonucleases in human cells. Nature Biotechnology Advance Online Publication. Published online Jun. 6, 2016. 7 pages. DOI: 10.1038/nbt.3609.

Klann, Tyler S et al. CRISPR-Cas9 epigenome editing enables high-throughput screening for functional regulatory elements in the human genome. Nature biotechnology vol. 35,6 (2017): 561-568. doi:10.1038/nbt.3853.

Kleinstiver, Benjamin P et al. Engineered CRISPR-Cas12a variants with increased activities and improved targeting ranges for gene, epigenetic and base editing. Nature biotechnology vol. 37,3 (2019): 276-282. doi:10.1038/s41587-018-0011-0.

Konermann, Silvana et al. Genome-scale transcriptional activation by an engineered CRISPR-Cas9 complex. Nature vol. 517,7536 (2015): 583-8. doi:10.1038/nature14136.

Li et al. Base editing with a Cpf1-cytidine deaminase fusion. Nature Biotechnology Advance Online Publication. Published online Mar. 19, 2018. 8 pages. DOI: 10.1038/nbt.4102.

Pausch, Patrick et al. CRISPR-CasΦ from huge phages is a hypercompact genome editor. Science (New York, N.Y.) vol. 369,6501 (2020): 333-337. doi:10.1126/science.abb1400.

PCT/US2021/048362 International Preliminary Report on Patentability dated Mar. 7, 2023.

PCT/US2021/048362 International Search Report and Written Opinion dated Jan. 10, 2022.

Qi, Lei S et al. Repurposing CRISPR as an RNA-guided platform for sequence-specific control of gene expression. Cell vol. 152,5 (2013): 1173-83. doi:10.1016/j.cell.2013.02.022.

Qu et al. The Crucial Role of Methodology Development in Directed Evolution of Selective Enzymes. Accepted Article. Angew. Chem. Int. Ed. 10.1002/anie.201901491. First published Jul. 2, 2019.

Reetz, Manfred T, and José Daniel Carballeira. Iterative saturation mutagenesis (ISM) for rapid directed evolution of functional enzymes. Nature protocols vol. 2,4 (2007): 891-903. doi:10.1038/nprot.2007.72.

Richter, Michelle F et al. Phage-assisted evolution of an adenine base editor with improved Cas domain compatibility and activity. Nature biotechnology vol. 38,7 (2020): 883-891. doi:10.1038/s41587-020-0453-z.

Swarts, Daan C et al. Structural Basis for Guide RNA Processing and Seed-Dependent DNA Targeting by CRISPR-Cas12a. Molecular cell vol. 66,2 (2017): 221-233.e4. doi:10.1016/j.molcel.2017.03.016.

Tak, Y Esther et al. Inducible and multiplex gene regulation using CRISPR-Cpf1-based transcription factors. Nature methods vol. 14,12 (2017): 1163-1166. doi:10.1038/nmeth.4483.

Takeda, Satoru N et al. Structure of the miniature type V-F CRISPR-Cas effector enzyme. Molecular cell vol. 81,3 (2021): 558-570.e3. doi:10.1016/j.molcel.2020.11.035.

Wootton et al. Statistics of local complexity in amino acid sequences and sequence databases. Computers & Chemistry 17(2):149-163 (Jun. 1993).

Xu et al. Engineered Miniature CRISPR-Cas System for Mammalian Genome Regulation and Editing. Molecular Cell, vol. 81, No. 20, Oct. 21, 2021, pp. 4333-4345.

Xu, Xiaoshu, and Lei S Qi. A CRISPR-dCas Toolbox for Genetic Engineering and Synthetic Biology. Journal of molecular biology vol. 431,1 (2019): 34-47. doi:10.1016/j.jmb.2018.06.037.

Xu, Xiaoshu et al. Mutagenesis of Key Residues in the Binding Center of l-Aspartate-b-Semialdehyde Dehydrogenase from *Escherichia coli* Enhances Utilization of the Cofactor NAD(H). Chembiochem : a European journal of chemical biology vol. 17,1 (2016): 56-64. doi:10.1002/cbic.201500534.

Zetsche, Bernd et al. Cpf1 is a single RNA-guided endonuclease of a class 2 CRISPR-Cas system. Cell vol. 163,3 (2015): 759-71. doi:10.1016/j.cell.2015.09.038.

PCT/US2023/063446 International Search Report and Written Opinion dated Jun. 19, 2023.

Restriction Requirement in U.S. Appl. No. 18/174,552, dated Sep. 15, 2023, in 9 pages.

Non-Final Office Action in U.S. Appl. No. 18/174,552, dated Mar. 8, 2024, in 41 pages.

ENGINEERED NUCLEASES, COMPOSITIONS, AND METHODS OF USE THEREOF

CROSS REFERENCE

This application is a continuation application of International Patent Application No. PCT/US2023/063446, filed on Mar. 1, 2023, which claims the benefit of U.S. Provisional Application No. 63/315,159, filed Mar. 1, 2022, U.S. Provisional Application No. 63/380,178, filed Oct. 19, 2022, and U.S. Provisional Application No. 63/385,171, filed Nov. 28, 2022, which applications are incorporated herein by reference in their entirety.

INCORPORATION BY REFERENCE OF SEQUENCE LISTING

The present application is being filed along with a Sequence Listing in electronic format. The Sequence Listing is provided as a file entitled 55176-726_601_SL.XML, created Feb. 15, 2023, which is 426 kilobytes in size. The information in the electronic format of the Sequence Listing is incorporated by reference in its entirety.

BACKGROUND

Various nucleases (e.g., endonucleases) can be utilized to edit a target sequence in a cell, or regulate expression or activity of the target gene in the cell. For example, a heterologous nuclease can be introduced (e.g., delivered, expressed, etc.) to the cell, and the heterologous nuclease, either alone or along with an additional agent, can effect such editing or regulation of the target gene. For example, clustered regularly interspaced short palindromic repeats (CRISPR)/CRISPR-associated protein (Cas) is a family of nucleases that are involved in specifically binding, cleaving, and/or editing a target deoxyribonucleic acid (DNA) sequence or ribonucleic acid (RNA) sequence (e.g., foreign DNA sequence or RNA sequence). The programmable nature of these nucleases has facilitated their use as a versatile technology that is revolutionizing the field of target gene manipulation, e.g., as gene therapy to treat or ameliorate a condition (e.g., a disease) of a subject.

SUMMARY

Various endonucleases, such as CRISPR/Cas proteins (e.g., Cas12f proteins utilized thus far), can have smaller sizes as compared to Cas9 or Cas12a. However, the sizes of the endonuclease may not be small enough to package them along with at least one additional agent (e.g., a guide RNA, a transgene encoding a therapeutic polynucleotide or protein, etc.) in a delivery mode (e.g., viral vectors, such as adeno-associated virus (AAV) vectors). Thus, various aspects of the present disclosure, for example, provide engineered nucleases that are smaller, yet effective, in binding, cleaving, and/or editing a target polynucleotide sequence, compositions thereof, and methods of use thereof.

An aspect of the present disclosure provides an engineered polypeptide comprising an engineered nuclease, wherein the engineered nuclease comprises an amino acid sequence that is at least 80% identical to the polypeptide sequence of SEQ ID NO: 1, wherein the amino acid sequence comprises at least one deletion from the amino acid resides 2-100, as compared to the polypeptide sequence of SEQ ID NO: 1.

Another aspect of the present disclosure provides an engineered polypeptide comprising an engineered nuclease, wherein the engineered nuclease comprises an amino acid sequence that is greater than 92% identical to the polypeptide sequence of SEQ ID NO: 12.

Another aspect of the present disclosure provides an engineered polypeptide comprising an engineered nuclease variant, wherein the engineered nuclease variant comprises an amino acid sequence that is at least 70% identical to the polypeptide sequence of SEQ ID NO: 12, wherein the amino acid sequence comprises a modification as compared to the polypeptide sequence of SEQ ID NO: 1, wherein the modification comprises one or more members selected from the group consisting of A21Q, V23I, N32E, D29E, N33R, E35K, K36Q, I37A, A38G, E40D, K73G, A74T, R75G, K76E, Q83K, G87K, E151A, A340S, H353K, A374K, I387E, N423D, K473Q, T474L, T474R, H497K, L515R, N519T, K521D, K521N, L522I, and at least one deletion from the amino acid residues 400-529 of SEQ ID NO: 1.

Another aspect of the present disclosure provides an engineered polypeptide comprising an engineered nuclease variant, wherein the engineered nuclease variant is a chimeric polypeptide comprising: a first polypeptide sequence comprising at least 3 contiguous amino acid residues in common with a first Cas protein; and a second polypeptide sequence comprising at least 3 contiguous amino acid residues in common with a second Cas protein, wherein the second Cas protein is different from the first Cas protein, wherein the first Cas protein comprises an amino acid sequence that is at least 80% identical to the polypeptide sequence of SEQ ID NO: 1.

Another aspect of the present disclosure provides an engineered polypeptide comprising an engineered nuclease variant, wherein the engineered nuclease is a chimeric polypeptide comprising: a first polypeptide sequence (CP1) comprising at least 3 contiguous amino acid residues in common with a portion of a first Cas protein; a second polypeptide sequence (CP2) comprising at least 3 contiguous amino acid residues in common with a portion of a second Cas protein that is different from the first Cas protein; and a third polypeptide sequence (CPx) comprising at least 3 contiguous amino acid residues in common with: (i) an additional portion of the first Cas protein, wherein the portion and the additional portion of the first Cas protein are not directly adjacent to each other in the first Cas protein; (ii) an additional portion of the second Cas protein, wherein the portion and the additional portion of the second Cas protein are not directly adjacent to each other in the second Cas protein; or (iii) a portion of a third Cas protein that is different from the first Cas protein and the second Cas protein, wherein the chimeric polypeptide has a length of less than or equal to about 1,000 amino acids.

Another aspect of the present disclosure provides an engineered polypeptide comprising an engineered nuclease variant, wherein the engineered nuclease variant is a chimeric polypeptide comprising: a first polypeptide comprising at least 3 contiguous amino acid residues in common with a first Cas protein; and a second polypeptide comprising at least 3 contiguous amino acid residues in common with a second Cas protein, wherein the second Cas protein is different from the first Cas protein, wherein a length of the second polypeptide sequence is less than about 20% than that of the first polypeptide sequence.

Another aspect of the present disclosure provides an engineered polypeptide comprising an engineered nuclease variant, wherein the engineered nuclease variant: (i) comprises an amino acid sequence that is at least 80% identical to the polypeptide sequence of a member selected from TABLE 3B, TABLE 4B, or TABLE 5C; (ii) is not any one of SEQ ID NOs: 1-3, 10, and 13-19; and (iii) has a length of less than or equal to about 800 amino acids.

Another aspect of the present disclosure provides an engineered polypeptide comprising an engineered nuclease variant operatively coupled to a gene modulator, wherein the engineered nuclease variant: (i) comprises an amino acid sequence that is at least 70% identical to the polypeptide sequence of SEQ ID NO: 1; and (ii) when operatively coupled to the gene modulator, induces an enhanced modulation of a target gene in a cell, as compared to that by a control engineered polypeptide comprising SEQ ID NO: 10 operatively coupled to the gene modulator.

Another aspect of the present disclosure provides a method of controlling a target gene in a cell, the method comprising contacting the cell with any one of the engineered polypeptide disclosed herein.

Another aspect of the present disclosure provides a method of modulating a target gene in a cell, the method comprising: contacting the cell with an engineered polypeptide comprising an engineered nuclease variant operatively coupled to a gene modulator, wherein the engineered nuclease variant comprises an amino acid sequence that is at least 70% identical to the polypeptide sequence of SEQ ID NO: 1, wherein the contacting effects enhanced modulation of the target gene in the cell, as compared to that by a control engineered polypeptide comprising SEQ ID NO: 10 operatively coupled to the gene modulator.

Another aspect of the present disclosure provides a composition comprising a guide nucleic acid molecule configured to form a complex with a Cas protein, wherein the guide nucleic acid molecule comprises:

Another aspect of the present disclosure provides a composition comprising a guide nucleic acid molecule configured to form a complex with a Cas protein, wherein the guide nucleic acid molecule comprises: a spacer sequence exhibiting specific binding to a target polynucleotide sequence; and a scaffold sequence for forming the complex with the Cas protein, wherein the scaffold sequence is characterized by:
  (i) having a consecutive polynucleotide sequence having at least 96% sequence identity to the polynucleotide sequence of SEQ ID NO: 555; or having a consecutive polynucleotide sequence having at least 84% sequence identity to the polynucleotide sequence of SEQ ID NO: 597;
  (ii) having a consecutive polynucleotide sequence having at least 97% sequence identity to the polynucleotide sequence of SEQ ID NO: 557; or having a consecutive polynucleotide sequence having at least 88% sequence identity to the polynucleotide sequence of SEQ ID NO: 598;
  (iii) having a consecutive polynucleotide sequence having at least 90% sequence identity to the polynucleotide sequence of SEQ ID NO: 578; having a consecutive polynucleotide sequence having at least 84% sequence identity to the polynucleotide sequence of SEQ ID NO: 597; or having a consecutive polynucleotide sequence having at least 81% sequence identity to the polynucleotide sequence of SEQ ID NO: 599;
  (iv) having a consecutive polynucleotide sequence having at least 93% sequence identity to the polynucleotide sequence of SEQ ID NO: 568; having a consecutive polynucleotide sequence having at least 84% sequence identity to the polynucleotide sequence of SEQ ID NO: 597; or having a consecutive polynucleotide sequence having at least 67% sequence identity to the polynucleotide sequence of SEQ ID NO: 600; or
  (v) having a consecutive polynucleotide sequence having at least 95% sequence identity to the polynucleotide sequence of SEQ ID NO: 569; having a consecutive polynucleotide sequence having at least 84% sequence identity to the polynucleotide sequence of SEQ ID NO: 597; or having a consecutive polynucleotide sequence having at least 71% sequence identity to the polynucleotide sequence of SEQ ID NO: 601.

Another aspect of the present disclosure provides a composition comprising a guide nucleic acid molecule configured to form a complex with a Cas protein, wherein the guide nucleic acid molecule comprises: a spacer sequence exhibiting specific binding to a target polynucleotide sequence operatively coupled to a target gene; and a scaffold sequence for forming the complex with the Cas protein, wherein the scaffold sequence exhibits at least 80% sequence identity to the polynucleotide sequence of a member selected from TABLE 6B, TABLE 7B, and TABLE 8B, wherein the scaffold sequence is not identical to SEQ ID NO: 500, wherein binding of the complex to the target polynucleotide sequence in a cell effects modulated expression level of the target gene in the cell, wherein (A1) the modulated expression level of the target gene by the complex is comparable to or superior than (A2) that by a control complex comprising the Cas protein and a control guide nucleic acid molecule comprising the polynucleotide sequence of SEQ ID NO: 500.

Another aspect of the present disclosure provides a composition comprising a guide nucleic acid molecule configured to form a complex with a Cas protein, wherein the guide nucleic acid molecule comprises: a spacer sequence exhibiting specific binding to a target polynucleotide sequence operatively coupled to a target gene; and a scaffold sequence for forming the complex with the Cas protein, wherein the scaffold sequence has a length of at most about 158 nucleotides, wherein binding of the complex to the target polynucleotide sequence in a cell effects modulated expression level of the target gene in the cell, wherein (A1) the modulated expression level of the target gene by the complex is comparable to or superior than (A2) that by a control complex comprising the Cas protein and a control guide nucleic acid molecule comprising the polynucleotide sequence of SEQ ID NO: 500.

Another aspect of the present disclosure provides a composition comprising a vector encoding a Cas protein and a guide nucleic acid molecule configured to form a complex with the Cas protein, wherein the vector comprises: a first polynucleotide sequence encoding the Cas protein; and a second polynucleotide sequence encoding a scaffold sequence of the guide nucleic acid molecule, for forming the complex with the Cas protein, wherein a sum of a length of the first polynucleotide sequence and a length of the second polynucleotide sequence combined is at most about 1700 nucleotides.

Another aspect of the present disclosure provides a method of controlling a target gene in a cell, the method comprising contacting the cell with any one of the compositions disclosed herein.

Another aspect of the present disclosure provides a method of modulating a target gene in a cell, the method comprising: contacting the cell with a complex comprising a guide nucleic acid molecule and a Cas protein, wherein the complex exhibits specific binding to a target polynucleotide sequence operatively coupled to the target gene, wherein binding of the complex to the target polynucleotide sequence effects modulated expression level of the target gene in the cell, wherein (A1) the modulated expression level of the target gene by the complex is comparable to or superior than (A2) that by a control complex comprising the Cas protein and a control guide nucleic acid molecule comprising the polynucleotide sequence of SEQ ID NO: 500.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
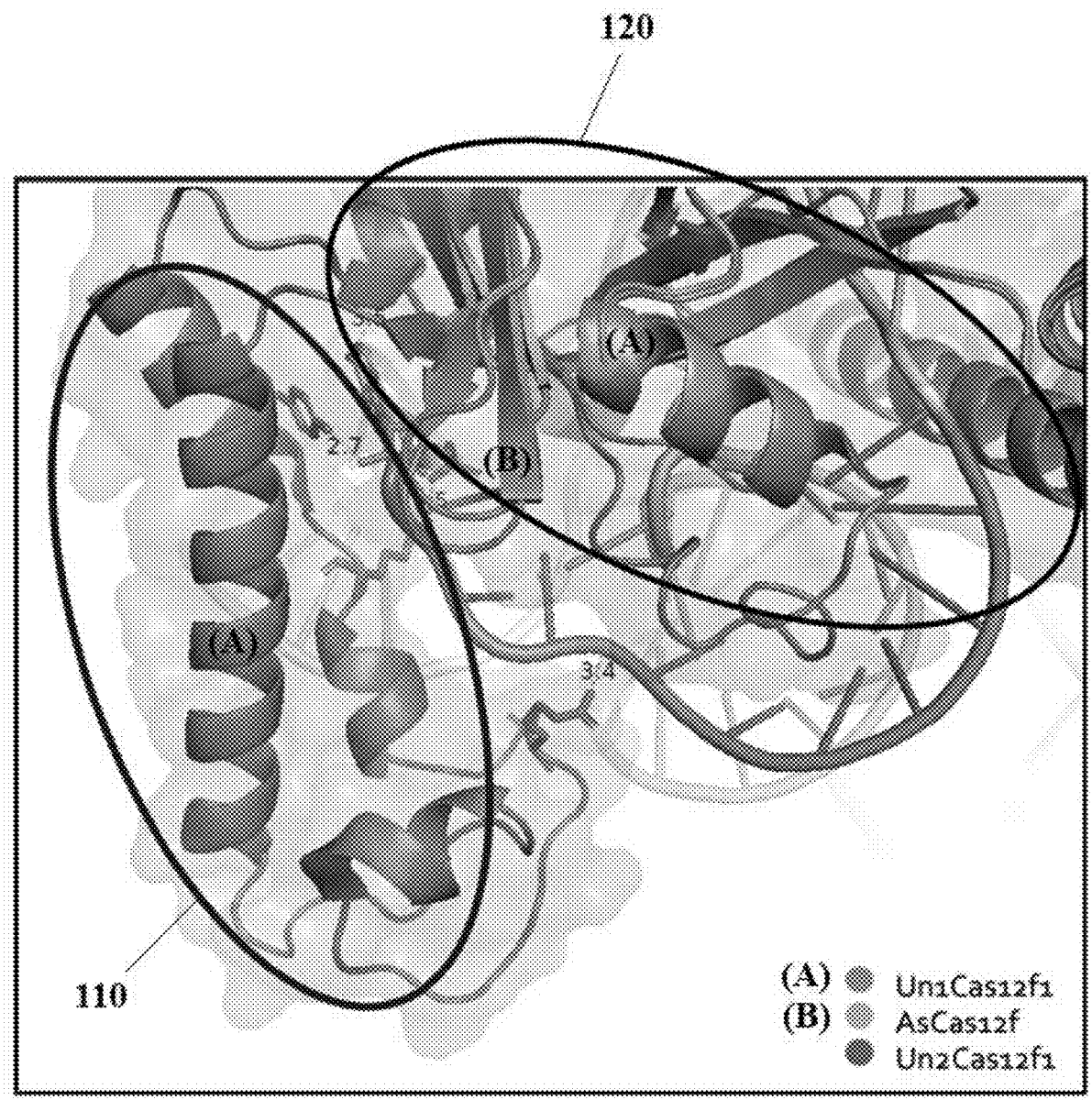
FIG. 1 schematically illustrates structural alignment between Un1Cas12f1 and AsCas12f, to identify one or more domains in Un1Cas12f1 that may not be conserved in one or more additional Cas12f homologous structures.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "about" or "approximately" generally means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The use of the alternative (e.g., "or") should be understood to mean either one, both, or any combination thereof of the alternatives. The term "and/or" should be understood to mean either one, or both of the alternatives.

The term "cell" generally refers to a biological cell. A cell can be the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens* C. Agardh, and the like), seaweeds (e.g., kelp), a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not originating from a natural organism (e.g., a cell can be a synthetically made, sometimes termed an artificial cell).

The term "nucleotide," as used herein, generally refers to a base-sugar-phosphate combination. A nucleotide can comprise a synthetic nucleotide. A nucleotide can comprise a synthetic nucleotide analog. Nucleotides can be monomeric units of a nucleic acid sequence (e.g., deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide may be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'S-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides can include [R6G]dUTP, [TAMRA]dUTP, [R110]dCTP, [R6G] dCTP, [TAMRA] dCTP, [JOE] ddATP, [R6G] ddATP, [FAM] ddCTP, [R110]ddCTP, [TAMRA] ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g., biotin-11-dUTP, biotin-16-dUTP, biotin-20-dUTP).

The term "polynucleotide," "oligonucleotide," or "nucleic acid," as used interchangeably herein, generally refers to a polymeric form of nucleotides of any length, either deoxyribonucleotides or ribonucleotides, or analogs thereof, either in single-, double-, or multi-stranded form. A polynucleotide can be exogenous or endogenous to a cell. A polynucleotide can exist in a cell-free environment. A polynucleotide can be a gene or fragment thereof. A polynucleotide can be DNA. A polynucleotide can be RNA. A polynucleotide can have any three dimensional structure, and can perform any function, known or unknown. A polynucleotide can comprise one or more analogs (e.g., altered backbone, sugar, or nucleobase). If present, modifications to the nucleotide structure can be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides can be interrupted by non-nucleotide components.

The term "gene" generally refers to a nucleic acid (e.g., DNA such as genomic DNA and cDNA) and its corresponding nucleotide sequence that is involved in encoding an RNA transcript. The term as used herein with reference to genomic DNA includes intervening, non-coding regions as well as regulatory regions and can include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes non-transcribed regions including upstream and downstream regulatory regions, enhancers and promoters. A gene can refer to an "endogenous gene" or a native gene in its natural location in the genome of an organism. A gene can refer to an "exogenous gene" or a non-native gene. A non-native gene can refer to a gene not normally found in the host organism but which is introduced into the host organism by gene transfer. A non-native gene can also refer to a gene not in its natural location in the genome of an organism. A non-native gene can also refer to a naturally occurring nucleic acid or polypeptide sequence that comprises mutations, insertions and/or deletions (e.g., non-native sequence).

The term "deletion" generally refers to the removal (or loss) of one or more (or a specified number of) amino acids (e.g., contiguous or non-contiguous amino acids) from a polypeptide sequence, or the removal (or loss) one or more (or a specified number of) nucleic acid bases (e.g., contiguous or non-contiguous nucleic acid bases) from a polynucleotide sequence (e.g., that encodes the polypeptide sequence. The term "internal deletion" generally refers to a deletion that does not include the N- or C-terminus of a polypeptide or the 5' or 3' end of a polynucleotide. A deletion (e.g., an internal deletion) can be identified by comparing to a reference sequence, e.g., by specifying the start and end positions of the deletion relative to the reference sequence. A deletion (e.g., an internal deletion) is different and distinct from a substitution. For example, deletion of at least one amino acid is not followed by an insertion of at least one different amino acid at the same position as the at least one amino acid as compared to a reference polypeptide sequence, such that the size (e.g., a number of the amino acid residue(s)) of a modified (or engineered) polypeptide sequence comprising the deletion of the at least one amino acid is smaller than the reference polypeptide sequence by the size of the at least one amino acid that has been deleted.

The term "sequence identity" generally refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the longer sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA, 87:2264-2268 (1990) and as discussed in Altschul, et al., J. Mol. Biol., 215:403-410 (1990); Karlin And Altschul, Proc. Natl. Acad. Sci. USA, 90:5873-5877 (1993); and Altschul et al., Nucleic Acids Res., 25:3389-3402 (1997). The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 50% to 100% and integer values therebetween. In general, this disclosure encompasses sequences with at least 50%, at least 55%, at least 60%, at least 65%, at least 70%, at least 75%, at least 80%, at least 85%, at least 90%, at least 95%, or at least 98% sequence identity with any sequence provided herein.

The term "expression" generally refers to one or more processes by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides can be collectively referred to as "gene product." If the polynucleotide is derived from genomic DNA, expression can include splicing of the mRNA in a eukaryotic cell. "Up-regulated," with reference to expression, generally refers to an increased expression level of a polynucleotide (e.g., RNA such as mRNA) and/or polypeptide sequence relative to its expression level in a wild-type state while "down-regulated" generally refers to a decreased expression level of a polynucleotide (e.g., RNA such as mRNA) and/or polypeptide sequence relative to its expression in a wild-type state. Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "expression profile" generally refers to quantitative (e.g., abundance) and qualitative expression of one or more genes in a sample (e.g., a cell). The one or more genes can be expressed and ascertained in the form of a nucleic acid molecule (e.g., an mRNA or other RNA transcript). Alternatively or in addition to, the one or more genes can be expressed and ascertained in the form of a polypeptide (e.g., a protein measured via Western blot). An expression profile of a gene may be defined as a shape of an expression level of the gene over a time period (e.g., at least or up to about 1 hour, at least or up to about 2 hours, at least or up to about 3 hours, at least or up to about 4 hours, at least or up to about 5 hours, at least or up to about 6 hours, at least or up to about 7 hours, at least or up to about 8 hours, at least or up to about 9 hours, at least or up to about 10 hours, at least or up to about 11 hours, at least or up to about 12 hours, at least or up to about 16 hours, at least or up to about 18 hours, at least or up to about 24 hours, at least or up to about 36 hours, at least or up to about 48 hours, at least up to about 3 days, at least up to about 4 days, at least up to about 5 days, at least up to about 6 days, at least up to about 7 days, at least up to about 8 days, at least up to about 9 days, at least up to about 10 days, at least up to about 11 days, at least up to about 12 days, at least up to about 13 days, at least up to about 14 days, etc.). Alternatively, an expression profile of a gene may be defined as an expression level of the gene at a time point of interest (e.g., the expression level of the gene measured at least or up to about 1 hour, at least or up to about 2 hours, at least or up to about 3 hours, at least or up to about 4 hours, at least or up to about 5 hours, at least or up to about 6 hours, at least or up to about 7 hours, at least or up to about 8 hours, at least or up to about 9 hours, at least or up to about 10 hours, at least or up to about 11 hours, at least or up to about 12 hours, at least or up to about 16 hours, at least or up to about 18 hours, at least or up to about 24 hours, at least or up to about 36 hours, at least or up to about 48 hours, at least up to about 3 days, at least up to about 4 days, at least up to about 5 days, at least up to about 6 days, at least up to about 7 days, at least up to about 8 days, at least up to about 9 days, at least up to about 10 days, at least up to about 11 days, at least up to about 12 days, at least up to about 13 days, or at least up to about 14 days after treating a cell to induce such expression level.)

The term "peptide," "polypeptide," or "protein," as used interchangeably herein, generally refers to a polymer of at least two amino acid residues joined by peptide bond(s). This term does not connote a specific length of polymer, nor is it intended to imply or distinguish whether the peptide is produced using recombinant techniques, chemical or enzymatic synthesis, or is naturally occurring. The terms apply to naturally occurring amino acid polymers as well as amino acid polymers comprising at least one modified amino acid. In some cases, the polymer can be interrupted by non-amino acids. The terms include amino acid chains of any length, including full length proteins, and proteins with or without secondary and/or tertiary structure (e.g., domains). The terms also encompass an amino acid polymer that has been modified, for example, by disulfide bond formation, glycosylation, lipidation, acetylation, phosphorylation, oxidation, and any other manipulation such as conjugation with a labeling component. The terms "amino acid" and "amino acids," as used herein, generally refer to natural and non-natural amino acids, including, but not limited to, modified amino acids and amino acid analogues. Modified amino acids can include natural amino acids and non-natural amino acids, which have been chemically modified to include a group or a chemical moiety not naturally present on the amino acid. Amino acid analogues can refer to amino acid derivatives. The term "amino acid" includes both D-amino acids and L-amino acids.

The term "derivative," "variant," or "fragment," as used herein with reference to a polypeptide, generally refers to a polypeptide related to a wild type polypeptide, for example either by amino acid sequence, structure (e.g., secondary and/or tertiary), activity (e.g., enzymatic activity) and/or function. Derivatives, variants and fragments of a polypeptide can comprise one or more amino acid variations (e.g., mutations, insertions, and deletions), truncations, modifications, or combinations thereof compared to a wild type polypeptide.

The term "engineered," "chimeric," or "recombinant," as used herein with respect to a polypeptide molecule (e.g., a protein), generally refers to a polypeptide molecule having a heterologous amino acid sequence or an altered amino acid sequence as a result of the application of genetic engineering techniques to nucleic acids which encode the polypeptide molecule, as well as cells or organisms which express the polypeptide molecule. The term "engineered" or "recombinant," as used herein with respect to a polynucleotide molecule (e.g., a DNA or RNA molecule), generally refers to a polynucleotide molecule having a heterologous nucleic acid sequence or an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In some cases, an engineered or recombinant polynucleotide (e.g., a genomic DNA sequence) can be modified or altered by a gene editing moiety.

For example, an engineered nuclease (e.g., an engineered Cas protein) as disclosed herein is not a naturally occurring nuclease (e.g., not a naturally occurring Cas protein). The terms "engineered nuclease" and "engineered nuclease variant" may be used interchangeable herein.

The terms "engineered" and "modified" are used interchangeably herein. The terms "engineering" and "modifying" are used interchangeably herein. The terms "engineered cell" or "modified cell" are used interchangeably herein. The terms "engineered characteristic" and "modified characteristic" are used interchangeably herein.

The term "enhanced expression," "increased expression," or "upregulated expression" generally refers to production of a moiety of interest (e.g., a polynucleotide or a polypeptide) to a level that is above a normal level of expression of the moiety of interest in a host strain (e.g., a host cell). The normal level of expression can be substantially zero (or null) or higher than zero. The moiety of interest can comprise an endogenous gene or polypeptide construct of the host strain. The moiety of interest can comprise a heterologous gene or polypeptide construct that is introduced to or into the host strain. For example, a heterologous gene encoding a polypeptide of interest can be knocked-in (KI) to a genome of the host strain for enhanced expression of the polypeptide of interest in the host strain.

The term "enhanced activity," "increased activity," or "upregulated activity" generally refers to activity of a moiety of interest (e.g., a polynucleotide or a polypeptide) that is modified to a level that is above a normal level of activity of the moiety of interest in a host strain (e.g., a host cell). The normal level of activity can be substantially zero (or null) or higher than zero. The moiety of interest can comprise a polypeptide construct of the host strain. The moiety of interest can comprise a heterologous polypeptide construct that is introduced to or into the host strain. For example, a heterologous gene encoding a polypeptide of interest can be knocked-in (KI) to a genome of the host strain for enhanced activity of the polypeptide of interest in the host strain.

The term "reduced expression," "decreased expression," or "downregulated expression" generally refers to a production of a moiety of interest (e.g., a polynucleotide or a polypeptide) to a level that is below a normal level of expression of the moiety of interest in a host strain (e.g., a host cell). The normal level of expression is higher than zero. The moiety of interest can comprise an endogenous gene or polypeptide construct of the host strain. In some cases, the moiety of interest can be knocked-out or knocked-down in the host strain. In some examples, reduced expression of the moiety of interest can include a complete inhibition of such expression in the host strain.

The term "reduced activity," "decreased activity," or "downregulated activity" generally refers to activity of a moiety of interest (e.g., a polynucleotide or a polypeptide) that is modified to a level that is below a normal level of activity of the moiety of interest in a host strain (e.g., a host cell). The normal level of activity is higher than zero. The moiety of interest can comprise an endogenous gene or polypeptide construct of the host strain. In some cases, the moiety of interest can be knocked-out or knocked-down in the host strain. In some examples, reduced activity of the moiety of interest can include a complete inhibition of such activity in the host strain.

The term "subject," "individual," or "patient," as used interchangeably herein, generally refers to a vertebrate, preferably a mammal such as a human. Mammals include, but are not limited to, murines, simians, humans, farm animals, sport animals, and pets. Tissues, cells and their progeny of a biological entity obtained in vivo or cultured in vitro are also encompassed.

The term "treatment" or "treating" generally refers to an approach for obtaining beneficial or desired results including but not limited to a therapeutic benefit and/or a prophylactic benefit. For example, a treatment can comprise administering a system or cell population disclosed herein. By therapeutic benefit is meant any therapeutically relevant improvement in or effect on one or more diseases, conditions, or symptoms under treatment. For prophylactic benefit, a composition can be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" generally refers to the quantity of a composition, for example a composition comprising heterologous polypeptides, heterologous polynucleotides, and/or modified cells (e.g., modified stem cells), that is sufficient to result in a desired activity upon administration to a subject in need thereof. Within the context of the present disclosure, the term "therapeutically effective" generally refers to that quantity of a composition that is sufficient to delay the manifestation, arrest the progression, relieve or alleviate at least one symptom of a disorder treated by the methods of the present disclosure.

Overview

Various aspects of the present disclosure can provide engineered nucleases that are smaller, yet effective, in binding, cleaving, and/or editing a target polynucleotide sequence, compositions thereof, and methods of use thereof. Such engineered nucleases (e.g., engineered CRISPR/Cas nuclease) can, for example, effect manipulation of expression or activity of a target gene (e.g., a target endogenous gene) in a cell, e.g., to treat or ameliorate a condition (e.g., a disease) of a subject. Gene expression can underpin various physiological and pathological effects in cells and tissues, contributing to many diseases and conditions, and thus compositions and methods utilizing the engineered nucleases of the present disclosure can modulate expression of specific genes in a desirable way to have therapeutic benefit.

Engineered Nucleases, Compositions, and Methods Thereof

In some aspects, the present disclosure provides an engineered nuclease comprising an amino acid sequence that is at least 50% identical to the polypeptide sequence of SEQ ID NO: 1. The amino acid sequence of the engineered nuclease can comprise at least one deletion, as compared to (e.g., when aligned to) the polypeptide sequence of SEQ ID NO: 1 (or SEQ ID NO: 10). The at least one deletion can be selectively removed in accordance with the present disclosure. As disclosed herein, SEQ ID NO: 1 encodes the polypeptide sequence of Un1Cas12f1 (or Cas14a1). As disclosed herein, SEQ ID NO: 10 encodes an engineered variant of Un1Cas12f1 with reduced nuclease activity. Thus, the amino acid sequence of the engineered nuclease as disclosed herein can be a mutant sequence (or a mutant variant) of Un1Cas12f1 (or a deactivated variant thereof).

Without wishing to be bound by theory, the at least one deletion of the amino acid sequence of the engineered nuclease, as disclosed herein, can be found in one or more regions of the native Un1Cas12f1 nuclease that do not structurally align to a control CRISPR/Cas protein. The control CRISPR/Cas protein can be from Class 1 CRISPR system or Class 2 CRISPR system (e.g., as a wild type CRISPR/Cas protein). Class 1 CRISPR system can be divided into types I, III, and IV, and Class 2 CRISPR system can be divided into types II, V, and VI. In some cases, the control CRISPR/Cas protein can be a type V Cas protein, e.g., a type V-A Cas protein, a type V-B Cas protein, a type V-C Cas protein, a type V-D Cas protein, a type V-E Cas protein, a type V-F Cas protein, a type V-G Cas protein, a type V-H Cas protein, a type V-I Cas protein, a type V-J Cas protein, a type V-K Cas protein, or a type V-U Cas protein. In some cases, the control CRISPR/Cas protein can be a type V-J protein, such as a wild-type CasΦ (Cas 12J) protein. In some cases, the control CRISPR/Cas protein can be Un2Cas12f1 (SEQ ID NO: 2) or AsCas12f (SEQ ID NO: 3).

Without wishing to be bound by theory, the at least one deletion of the amino acid sequence of the engineered nuclease, as disclosed herein, can be determined by performing a deletion landscape study (e.g., iterative and/or comprehensive deletion) of the Cas nuclease encoded by the polypeptide sequence of SEQ ID NO: 1 (or SEQ ID NO: 10).

Without wishing to be bound by theory, a plurality of different variants of the engineered nuclease, as disclosed herein, can exhibit different activities (e.g., different binding affinities to a control sgRNA, different binding affinities to a control target gene, different target gene cleaving level, different target gene activation level, different target gene repression level, etc.). In some embodiments, a first variant of the plurality of different variants can comprise the at least one deletion at the amino acid resides 1-100 (e.g., when aligned to the polypeptide sequence of SEQ ID NO: 1), and a second variant of the plurality of different variants can comprise the at least one deletion at the amino acid resides 101-529 (e.g., when aligned to the polypeptide sequence of SEQ ID NO: 1), and the first variant and the second variant can exhibit different activities (e.g., the first variant can effect enhanced target gene activation and/or expression as compared to that of the second variant, or vice versa). Alternatively, the first variant and the second variant can exhibit comparable activities. In some embodiments, a first variant of the plurality of different variants can comprise a single deletion at the amino acid resides 1-100 (e.g., when aligned to the polypeptide sequence of SEQ ID NO: 1), and a second variant of the plurality of different variants can comprise a plurality of deletions at the amino acid resides 1-100 (e.g., when aligned to the polypeptide sequence of SEQ ID NO: 1), and the first variant and the second variant can exhibit different activities (e.g., the second variant can effect enhanced target gene activation and/or expression as compared to that of the first variant, or vice versa). Alternatively, the first variant and the second variant can exhibit comparable activities.

```
(Un1Cas12f1)
                                                   SEQ ID NO: 1
    1  MAKNTITKTL KLRIVRPYNS AEVEKIVADE KNNREKIALE

KNKDKVKEAC

51  SKHLKVAAYC TTQVERNACL FCKARKLDDK FYQKLRGQFP

DAVEWQEISE

101  IFRQLQKQAA EIYNQSLIEL YYEIFIKGKG IANASSVEHY

LSDVCYTRAA

151  ELFKNAAIAS GLRSKIKSNF RLKELKNMKS GLPTTKSDNF

PIPLVKQKGG

201  QYTGFEISNH NSDFIIKIPF GRWQVKKEID KYRPWEKFDF

EQVQKSPKPI

251  SLLLSTQRRK RNKGWSKDEG TEAEIKKVMN GDYQTSYIEV

KRGSKIGEKS

301  AWMLNLSIDV PKIDKGVDPS IIGGIDVGVK SPLVCAINNA

FSRYSISDND

351  LFHENKKMFA RRRILLKKNR HKRAGHGAKN KLKPITILTE

KSERFRKKLI

401  ERWACEIADE FIKNKVGTVQ MENLESMKRK EDSYFNIRLR

GEWPYAEMQN

451  KIEFKLKQYG IEIRKVAPNN TSKTCSKCGH LNNYENFEYR

KKNKFPHFKC

501  EKCNFKENAD YNAALNISNP KLKSTKEEP (deactivated nuclease variant
of Un1Cas12f1, i.e., dCasMINI)
                                                   SEQ ID NO: 10
    1  MAKNTITKTL KLRIVRPYNS AEVEKIVADE KNNREKIALE

KNKDKVKEAC

51  SKHLKVAAYC TTQVERNACL FCKARKLDDK FYQKLRGQFP

DAVEWQEISE

-continued
  101  IFRQLQKQAA EIYNQSLIEL YYEIFIKGKG IANASSVEHY

LSRVCYRRAA

151  ELFKNAAIAS GLRSKIKSNF RLKELKNMKS GLPTTKSDNF

PIPLVKQKGG

201  QYTGFEISNH NSDFIIKIPF GRWQVKKEID KYRPWEKFDF

EQVQKSPKPI

251  SLLLSTQRRK RNKGWSKDEG TEAEIKKVMN GDYQTSYIEV

KRGSKICEKS

301  AWMLNLSIDV PKIDKGVDPS IIGGIAVGVR SPLVCAINNA

FSRYSISDND

351  LFHENKKMFA RRRILLKKNR HKRAGHGAKN KLKPITILTE

KSERFRKKLI

401  ERWACEIADF FIKNKVGTVQ MENLESMKRK EDSYENIRLR

GEWPYAEMON

451  KIEFKLKQYG IEIRKVAPNN TSKTCSKCGH LNNYENFEYR

KKNKFPHFKC

501  EKCNFKENAA YNAALNISNP KLKSTKERP (Un2Cas12f1)
                                                   SEQ ID NO: 2
    1  MEVQKTVMKT LSLRILRPLY SQEIEKEIKE EKERRKQAGG

TGELDGGFYK

51  KLEKKHSEMF SFDRLNLLLN QLQREIAKVY NHAISELYIA

TIAQGNKSNK

101  HYISSIVYNR AYGYFYNAYI ALGICSKVEA NERSNELLTQ

QSALPTAKSD

151  NFPIVLHKQK GAEGEDGGER ISTEGSDLIF EIPIPFYEYN

GENRKEPYKW

201  VKKGGQKPVL KLILSTERRQ RNKGWAKDEG TDAEIRKVTE

GKYQVSQIEI

251  NRGKKLGEHQ KWFANFSIEQ PIYERKPNRS IVGGLDVGIR

SPLVCAINNS

301  FSRYSVDSND VFKESKQVFA FRRRLLSKNS LKRKGHGAAH

KLEPITEMTE

351  KNDKERKKII ERWAKEVINF FVKNQVGIVQ IEDLSTMKDR

EDHFFNQYLR

401  GFWPYYQMQT LIENKLKEYG IEVKRVQAKY TSQLCSNPNC

RYWNNYENFE

451  YRKVNKFPKF KCEKCNLEIS ADYNAARNLS TPDIEKFVAK

ATKGINLPEK
```

```
(AsCas12f)
                                             SEQ ID NO: 3
   1 MIKVYRYEIV KPLDLDWKEF GTILRQLQQE TRFALNKATQ

LAWEWMGESS

51 DYKDNHGEYP KSKDILGYTN VHGYAYHTIK TKAYRLNSGN

LSQTIKRATD

101 RFKAYQKEIL RGDMSIPSYK RDIPLDLIKE NISVNRMNHG

DYIASLSLLS

151 NPAKQEMNVK RKISVIIIVR GAGKTIMDRI LSGEYQVSAS

QIIHDDRKNK

201 WYLNISYDFE PQTRVLDLNK IMGIDLGVAV AVYMAFQHTP

ARYKLEGGEI

251 ENFRRQVESR RISMLRQGKY AGGARGGHGR DKRIKPIEQL

RDKIANERDT

301 TNHRYSRYIV DMAIKEGCGT IQMEDLTNIR DIGSRFLONW

TYYDLQQKII

351 YKAEEAGIKV IKIDPQYTSQ RCSECGNIDS GNRIGQAIFK

CRACGYEANA

401 DYNAARNIAI PNIDKIIAES IK
```

Throughout the present disclosure, (i) a sequence comparison between the amino acid sequence of the engineered nuclease disclosed herein and the polypeptide sequence of SEQ ID NO: 1 may be comparable (e.g., substantially identical) to (ii) a sequence comparison between the amino acid sequence of the engineered nuclease disclosed herein and the polypeptide sequence of SEQ ID NO: 10.

In some embodiments, the amino acid sequence of the engineered nuclease disclosed herein can be at least or up to about 50%, at least or up to about 55%, at least or up to about 60%, at least or up to about 62%, at least or up to about 64%, at least or up to about 65%, at least or up to about 66%, at least or up to about 68%, at least or up to about 70%, at least or up to about 72%, at least or up to about 74%, at least or up to about 75%, at least or up to about 76%, at least or up to about 78%, at least or up to about 80%, at least or up to about 82%, at least or up to about 84%, at least or up to about 85%, at least or up to about 86%, at least or up to about 88%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99% identical to (i) the polypeptide sequence of SEQ ID NO: 1 or (ii) the polypeptide sequence of any one of the Cas proteins selected from TABLE 2. For example, the amino acid sequence of the engineered nuclease can be between about 80% and about 100% identical to (i) the polypeptide sequence of SEQ ID NO: 1 or (ii) the polypeptide sequence of any one of the Cas proteins selected from TABLE 2.

In some embodiments, the amino acid sequence of the engineered nuclease disclosed herein is not identical to (i) the polypeptide sequence of SEQ ID NO: 1 or (ii) the polypeptide sequence of any one of the Cas proteins selected from TABLE 2.

In some embodiments, the at least one deletion of the amino acid sequence of the engineered nuclease disclosed herein can comprise an N-terminus deletion, a C-terminus deletion, and/or an internal deletion. For example, the at least one deletion may not comprise an N-terminus deletion, but rather an internal deletion and/or a C-terminus deletion.

In some embodiments, the at least one deletion of the amino acid sequence of the engineered nuclease disclosed herein can be from the amino acid residues 1-100 (e.g., the amino acid residues 2-100), the amino acid resides 101-429, the amino acid residues 101-200, the amino acid residues 201-300, the amino acid residues 301-400, the amino acid residues 401-500, or the amino acid residues 500-529, and/or amino acid residues 430-529, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease disclosed herein can be from at least one deletion from the amino acid resides 2-100, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease can be from the amino acid residues 2-98, the amino acid residues 2-96, the amino acid residues 2-95 the amino acid residues 2-94, the amino acid residues 2-92, the amino acid residues 2-90, the amino acid residues 2-88, the amino acid residues 2-86, the amino acid residues 2-85, the amino acid residues 2-84, the amino acid residues 2-82, the amino acid residues 2-80, the amino acid residues 2-78, the amino acid residues 2-76, the amino acid residues 2-75, the amino acid residues 2-74, the amino acid residues 2-72, the amino acid residues 2-70, the amino acid residues 2-68, the amino acid residues 2-66, the amino acid residues 2-65, the amino acid residues 2-64, the amino acid residues 2-62, the amino acid residues 2-60, the amino acid residues 2-58, the amino acid residues 2-56, the amino acid residues 2-55, the amino acid residues 2-54, the amino acid residues 2-52, the amino acid residues 2-50, the amino acid residues 2-48, the amino acid residues 2-46, the amino acid residues 2-45, the amino acid residues 2-44, the amino acid residues 2-42, the amino acid residues 2-40, the amino acid residues 2-38, the amino acid residues 2-36, the amino acid residues 2-35, the amino acid residues 2-34, the amino acid residues 2-32, the amino acid residues 2-30, the amino acid residues 2-28, the amino acid residues 2-26, the amino acid residues 2-25, the amino acid residues 2-24, the amino acid residues 2-22, the amino acid residues 2-20, the amino acid residues 2-18, the amino acid residues 2-16, the amino acid residues 2-15, the amino acid residues 2-14, the amino acid residues 2-12, the amino acid residues 2-10, the amino acid residues 2-8, the amino acid residues 2-6, the amino acid residues 2-5, or the amino acid residues 2-4, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease can be from the amino acid residues 2-100, the amino acid residues 4-100, the amino acid residues 5-100, the amino acid residues 6-100, the amino acid residues 8-100, the amino acid residues 10-100, the amino acid residues 12-100, the amino acid residues 14-100, the amino acid residues 15-100, the amino acid residues 16-100, the amino acid residues 18-100, the amino acid residues 20-100, the amino acid residues 22-100, the amino acid residues 24-100, the amino acid residues 25-100, the amino acid residues 26-100, the amino acid residues 28-100, the amino acid residues 30-100, the amino acid residues 32-100, the amino acid residues 34-100, the amino acid residues 35-100, the amino acid residues 36-100, the amino acid residues 38-100, the amino acid residues 40-100, the amino acid residues 42-100, the amino acid residues 44-100, the amino acid residues 45-100, the amino acid residues 46-100, the amino acid residues 48-100, the amino acid residues 50-100, the amino acid residues 52-100, the amino acid residues 54-100, the amino acid residues 55-100, the amino acid residues 56-100, the amino acid residues 58-100, the amino acid residues 60-100, the amino acid residues 62-100, the amino acid residues 64-100, the amino acid residues 65-100, the amino acid residues 66-100, the amino acid residues 68-100, the amino acid residues 70-100, the amino acid residues 72-100, the amino acid residues 75-100, the amino acid residues 76-100, the amino acid residues 78-100, the amino acid residues 80-100, the amino acid residues 82-100, the amino acid residues 84-100, the amino acid residues 85-100, the amino acid residues 86-100, the amino acid residues 88-100, the amino acid residues 90-100, the amino acid residues 92-100, the amino acid residues 94-100, the amino acid residues 95-100, the amino acid residues 96-100, or the amino acid residues 98-100, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease can be from the amino acid residues 30-100, the amino acid residues 30-98, the amino acid residues 30-96, the amino acid residues 30-95, the amino acid residues 30-94, the amino acid residues 30-92, the amino acid residues 30-90, the amino acid residues 30-88, the amino acid residues 30-86, the amino acid residues 30-85, the amino acid residues 30-84, the amino acid residues 30-82, the amino acid residues 30-80, the amino acid residues 30-78, the amino acid residues 30-76, the amino acid residues 30-75, the amino acid residues 30-74, the amino acid residues 30-72, the amino acid residues 30-70, the amino acid residues 30-68, the amino acid residues 30-66, the amino acid residues 30-65, the amino acid residues 30-64, the amino acid residues 30-62, the amino acid residues 30-60, the amino acid residues 30-58, the amino acid residues 30-56, the amino acid residues 30-55, the amino acid residues 30-54, the amino acid residues 30-52, the amino acid residues 30-50, the amino acid residues 30-48, the amino acid residues 30-46, the amino acid residues 30-45, the amino acid residues 30-44, the amino acid residues 30-42, the amino acid residues 30-40, the amino acid residues 30-38, the amino acid residues 30-36, the amino acid residues 30-34, or the amino acid residues 30-32, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease can comprise one or more deletions from (e.g., deletions of substantially all of the amino acid residues from) the amino acid residues 55-56, the amino acid residues 54-57, the amino acid residues 54-58, the amino acid residues 53-59, the amino acid residues 52-60, the amino acid residues 51-61, the amino acid residues 50-62, the amino acid residues 49-63, the amino acid residues 48-64, the amino acid residues 47-65, the amino acid residues 46-66, the amino acid residues 45-67, the amino acid residues 44-68, the amino acid residues 43-69, the amino acid residues 42-70, the amino acid residues 41-71, the amino acid residues 40-72, the amino acid residues 39-73, the amino acid residues 38-74, the amino acid residues 37-73, the amino acid residues 36-74, or the amino acid residues 35-75, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease can be from one or more members (e.g., a single member, at least 2 members, at least 3 members, at least 4 members, at least 5 members, or more) selected from the group consisting of the amino acid resides 2-10, the amino acid resides 11-20, the amino acid resides 21-30, the amino acid resides 31-40, the amino acid resides 41-50, the amino acid resides 51-60, the amino acid resides 61-70, and the amino acid resides 71-80, as compared to the polypeptide sequence of SEQ ID NO: 1.

In some embodiments, the at least one deletion of the amino acid sequence of the engineered nuclease can be from one or more members (e.g., a single member, at least 2 members, at least 3 members, at least 4 members, at least 5 members, or more) selected from the group consisting of the amino acid resides 2-5, the amino acid resides 6-10, the amino acid resides 11-15, the amino acid resides 16-20, the amino acid resides 21-25, the amino acid resides 26-30, the amino acid resides 31-35, the amino acid resides 36-40, the amino acid resides 41-45, the amino acid resides 46-50, the amino acid resides 51-55, the amino acid resides 56-60, the amino acid resides 61-65, the amino acid resides 66-70, the amino acid resides 71-75, and the amino acid resides 76-80, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease disclosed herein can be from one or more members (e.g., two or more members, three or more members, four or more members, five or more members, etc.) selected from the group consisting of the amino acid resides 10-90, the amino acid residues 15-85, the amino acid residues 20-80, the amino acid residues 25-75, the amino acid residues 30-70, the amino acid residues 35-75, the amino acid residues 40-70, the amino acid residues 45-65, or the amino acid residues 50-60, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease disclosed herein can be from one or more members (e.g., two or more members, three or more members, four or more members, five or more members, etc.) selected from the group consisting of the amino acid residues 20-30, the amino acid resides 25-35, the amino acid residues 30-40, the amino acid residues 35-45, the amino acid residues 40-50, the amino acid residues 45-55, the amino acid residues 50-60, the amino acid residues 55-65, the amino acid residues 60-70, the amino acid residues 65-75, the amino acid residues 70-80, the amino acid residues 75-85, and the amino acid residues 80-90, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease disclosed herein can be from one or more members (e.g., two or more members, three or more members, four or more members, five or more members, etc.) selected from the group consisting of the amino acid residues 20-25, the amino acid residues 25-30, the amino acid residues 30-35, the amino acid residues 35-40, the amino acid residues 40-45, the amino acid residues 45-50, the amino acid residues 50-55, the amino acid residues 55-60, the amino acid residues 60-65, the amino acid residues 65-70, the amino acid residues 70-75, the amino acid residues 75-80, and the amino acid residues 85-90, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease disclosed herein can be from the amino acid resides 430-529, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease can be from the amino acid residues 430-528, the amino acid residues 430-526, the amino acid residues 430-525, the amino acid residues 430-524, the amino acid residues 430-522, the amino acid residues 430-520, the amino acid residues 430-518, the amino acid residues 430-516, the amino acid residues 430-515, the amino acid residues 430-514, the amino acid residues 430-512, the amino acid residues 430-510, the amino acid residues 430-508, the amino acid residues 430-506, the amino acid residues 430-505, the amino acid residues 430-504, the amino acid residues 430-502, the amino acid residues 430-500, the amino acid residues 430-498, the amino acid residues 430-496, the amino acid residues 430-495, the amino acid residues 430-494, the amino acid residues 430-492, the amino acid residues 430-490, the amino acid residues 430-488, the amino acid residues 430-486, the amino acid residues 430-485, the amino acid residues 430-484, the amino acid residues 430-482, the amino acid residues 430-480, the amino acid residues 430-478, the amino acid residues 430-476, the amino acid residues 430-475, the amino acid residues 430-474, the amino acid residues 430-472, the amino acid residues 430-470, the amino acid residues 430-468, the amino acid residues 430-466, the amino acid residues 430-465, the amino acid residues 430-464, the amino acid residues 430-462, the amino acid residues 430-460, the amino acid residues 430-458, the amino acid residues 430-456, the amino acid residues 430-455, the amino acid residues 430-454, the amino acid residues 430-452, the amino acid residues 430-450, the amino acid residues 430-448, the amino acid residues 430-446, the amino acid residues 430-445, the amino acid residues 430-444, the amino acid residues 430-442, the amino acid residues 430-440, the amino acid residues 430-438, the amino acid residues 430-436, the amino acid residues 430-435, the amino acid residues 430-434, or the amino acid residues 430-432, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease can be from the amino acid residues 430-529, the amino acid residues 432-529, the amino acid residues 434-529, the amino acid residues 435-529, the amino acid residues 436-529, the amino acid residues 438-529, the amino acid residues 440-529, the amino acid residues 442-529, the amino acid residues 444-529, the amino acid residues 445-529, the amino acid residues 446-529, the amino acid residues 448-529, the amino acid residues 450-529, the amino acid residues 452-529, the amino acid residues 454-529, the amino acid residues 455-529, the amino acid residues 456-529, the amino acid residues 458-529, the amino acid residues 460-529, the amino acid residues 462-529, the amino acid residues 464-529, the amino acid residues 465-529, the amino acid residues 466-529, the amino acid residues 468-529, the amino acid residues 470-529, the amino acid residues 472-529, the amino acid residues 474-529, the amino acid residues 475-529, the amino acid residues 476-529, the amino acid residues 478-529, the amino acid residues 480-529, the amino acid residues 482-529, the amino acid residues 484-529, the amino acid residues 485-529, the amino acid residues 486-529, the amino acid residues 488-529, the amino acid residues 490-529, the amino acid residues 492-529, the amino acid residues 494-529, the amino acid residues 495-529, the amino acid residues 496-529, the amino acid residues 498-529, the amino acid residues 500-529, the amino acid residues 502-529, the amino acid residues 504-529, the amino acid residues 505-529, the amino acid residues 506-529, the amino acid residues 508-529, the amino acid residues 510-529, the amino acid residues 512-529, the amino acid residues 514-529, the amino acid residues 515-529, the amino acid residues 516-529, the amino acid residues 518-529, the amino acid residues 520-529, the amino acid residues 522-529, the amino acid residues 524-529, the amino acid residues 525-529, the amino acid residues 526-529, or the amino acid residues 528-529, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease can be from one or more members (e.g., a single member, at least 2 members, at least 3 members, at least 4 members, at least 5 members, or more) selected from the group consisting of the amino acid resides 450-459, the amino acid resides 460-469, the amino acid resides 470-479, the amino acid resides 480-489, the amino acid resides 490-499, the amino acid resides 500-509, the amino acid resides 510-519, and the amino acid resides 520-529, as compared to (i) the polypeptide sequence of SEQ ID NO: 1 or (ii) the polypeptide sequence of any one of the Cas proteins selected from TABLE 2 (when applicable). In some embodiments, the at least one deletion of the amino acid sequence of the engineered nuclease can be from one or more members (e.g., a single member, at least 2 members, at least 3 members, at least 4 members, at least 5 members, or more) selected from the group consisting of the amino acid resides 450-459, the amino acid resides 460-465, the amino acid resides 466-469, the amino acid resides 470-475, the amino acid resides 476-479, the amino acid resides 480-485, the amino acid resides 486-489, the amino acid resides 490-495, the amino acid resides 496-499, the amino acid resides 500-505, the amino acid resides 506-509, the amino acid resides 510-515, the amino acid resides 516-519, the amino acid resides 520-525, and the amino acid resides 526-529, as compared to (i) the polypeptide sequence of SEQ ID NO: 1 or (ii) the polypeptide sequence of any one of the Cas proteins selected from TABLE 2 (when applicable).

In some embodiments, the at least one deletion of the amino acid sequence of the engineered nuclease can comprise deletion of a single amino acid residue, as compared to (i) the polypeptide sequence of SEQ ID NO: 1 or (ii) the polypeptide sequence of any one of the Cas proteins selected from TABLE 2 (when applicable). In some embodiments, the at least one deletion of the amino acid sequence of the engineered nuclease can comprise deletion of a plurality of amino acid residues, as compared to (i) the polypeptide sequence of SEQ ID NO: 1 or (ii) the polypeptide sequence of any one of the Cas proteins selected from TABLE 2 (when applicable). The plurality of amino acid residues that are deleted can be adjacent to each other (e.g., consecutive) when aligned to (i) the polypeptide sequence of SEQ ID NO: 1 or (ii) the polypeptide sequence of any one of the Cas proteins selected from TABLE 2 (when applicable). Alternatively or in addition to, the plurality of amino acid residues that are deleted may not be adjacent to each other, when aligned to (i) the polypeptide sequence of SEQ ID NO: 1 or (ii) the polypeptide sequence of any one of the Cas proteins selected from TABLE 2 (when applicable). The plurality of amino acid residues can comprise at least or up to about 2 amino acid residues, at least or up to about 3 amino acid residues, at least or up to about 4 amino acid residues, at least or up to about 5 amino acid residues, at least or up to about 6 amino acid residues, at least or up to about 7 amino acid residues, at least or up to about 8 amino acid residues, at least or up to about 9 amino acid residues, at least or up to about 10 amino acid residues, at least or up to about 11 amino acid residues, at least or up to about 12 amino acid residues, at least or up to about 13 amino acid residues, at least or up to about 14 amino acid residues, at least or up to about 15 amino acid residues, at least or up to about 16 amino acid residues, at least or up to about 17 amino acid residues, at least or up to about 18 amino acid residues, at least or up to about 19 amino acid residues, at least or up to about 20 amino acid residues, at least or up to about 22 amino acid residues, at least or up to about 24 amino acid residues, at least or up to about 25 amino acid residues, at least or up to about 26 amino acid residues, at least or up to about 28 amino acid residues, at least or up to about 30 amino acid residues, at least or up to about 32 amino acid residues, at least or up to about 34 amino acid residues, at least or up to about 35 amino acid residues, at least or up to about 36 amino acid residues, at least or up to about 38 amino acid residues, at least or up to about 40 amino acid residues, at least or up to about 42 amino acid residues, at least or up to about 44 amino acid residues, at least or up to about 45 amino acid residues, at least or up to about 46 amino acid residues, at least or up to about 48 amino acid residues, at least or up to about 50 amino acid residues, at least or up to about 52 amino acid residues, at least or up to about 54 amino acid residues, at least or up to about 55 amino acid residues, at least or up to about 56 amino acid residues, at least or up to about 58 amino acid residues, at least or up to about 60 amino acid residues, at least or up to about 62 amino acid residues, at least or up to about 64 amino acid residues, at least or up to about 65 amino acid residues, at least or up to about 66 amino acid residues, at least or up to about 68 amino acid residues, at least or up to about 70 amino acid residues, at least or up to about 72 amino acid residues, at least or up to about 74 amino acid residues, at least or up to about 75 amino acid residues, at least or up to about 76 amino acid residues, at least or up to about 78 amino acid residues, at least or up to about 80 amino acid residues, at least or up to about 82 amino acid residues, at least or up to about 84 amino acid residues, at least or up to about 85 amino acid residues, at least or up to about 86 amino acid residues, at least or up to about 88 amino acid residues, at least or up to about 90 amino acid residues, at least or up to about 92 amino acid residues, at least or up to about 94 amino acid residues, at least or up to about 95 amino acid residues, at least or up to about 96 amino acid residues, at least or up to about 98 amino acid residues, or at least or up to about 100 amino acid residues.

In some embodiments, the deletion of the plurality of amino acid residues to generate the amino acid sequence of the engineered nuclease can comprise deletion of a plurality of non-consecutive amino acid residues, e.g., as compared to (i) the polypeptide sequence of SEQ ID NO: 1 or (ii) the polypeptide sequence of any one of the Cas proteins selected from TABLE 2 (when applicable). In some cases, the deletion of the plurality of non-consecutive amino acid residues in the amino acid sequence of the engineered nuclease can comprise deletion of a first amino acid residue (e.g., a first single amino acid residue or a first set of multiple amino acid residues, such as a first set of consecutive amino acid residues) and a second amino acid residue (e.g., a second single amino acid residue or a second set of multiple amino acid residues, such as a second set of consecutive amino acid residues) that are not consecutive to each other, when aligned to (i) the polypeptide sequence of SEQ ID NO: 1 or (ii) the polypeptide sequence of any one of the Cas proteins selected from TABLE 2 (when applicable). For example, the position of the first amino acid residue and the second amino acid residue (e.g., when aligned to the polypeptide sequence of SEQ ID NO: 1) can be separated by at least or up to about 1, at least or up to about 2, at least or up to about 3, at least or up to about 4, at least or up to about 5, at least or up to about 10, at least or up to about 15, at least or up to about 20, at least or up to about 30, at least or up to about 40, at least or up to about 50, at least or up to about 60, at least or up to about 70, at least or up to about 80, at least or up to about 90, at least or up to about 100, at least or up to about 120, at least or up to about 150, at least or up to about 200, at least or up to about 250, at least or up to about 300, at least or up to about 350, at least or up to about 400, at least or up to about 450, at least or up to about 500, at least or up to about 510, at least or up to about 520, or at least or up to about 525 amino acid residues.

In some embodiments, the deletion of the plurality of amino acid residues to generate the amino acid sequence of the engineered nuclease can comprise deletion of a plurality of consecutive amino acid residues, e.g., as compared to (i) the polypeptide sequence of SEQ ID NO: 1 or (ii) the polypeptide sequence of any one of the Cas proteins selected from TABLE 2 (when applicable). In some cases, the deletion of the plurality of consecutive amino acid residues can comprise deletion of at least or up to about 2 consecutive amino acid residues, at least or up to about 3 consecutive amino acid residues, at least or up to about 4 consecutive amino acid residues, at least or up to about 5 consecutive amino acid residues, at least or up to about 6 consecutive amino acid residues, at least or up to about 7 consecutive amino acid residues, at least or up to about 8 consecutive amino acid residues, at least or up to about 9 consecutive amino acid residues, at least or up to about 10 consecutive amino acid residues, at least or up to about 11 consecutive amino acid residues, at least or up to about 12 consecutive amino acid residues, at least or up to about 13 consecutive amino acid residues, at least or up to about 14 consecutive amino acid residues, at least or up to about 15 consecutive amino acid residues, at least or up to about 16 consecutive amino acid residues, at least or up to about 17 consecutive amino acid residues, at least or up to about 18 consecutive amino acid residues, at least or up to about 19 consecutive amino acid residues, at least or up to about 20 consecutive amino acid residues, at least or up to about 21 consecutive amino acid residues, at least or up to about 22 consecutive amino acid residues, at least or up to about 23 consecutive amino acid residues, at least or up to about 24 consecutive amino acid residues, at least or up to about 25 consecutive amino acid residues, at least or up to about 26 consecutive amino acid residues, at least or up to about 27 consecutive amino acid residues, at least or up to about 28 consecutive amino acid residues, at least or up to about 29 consecutive amino acid residues, at least or up to about 30 consecutive amino acid residues, at least or up to about 31 consecutive amino acid residues, at least or up to about 32 consecutive amino acid residues, at least or up to about 34 consecutive amino acid residues, at least or up to about 35 consecutive amino acid residues, at least or up to about 36 consecutive amino acid residues, at least or up to about 37 consecutive amino acid residues, at least or up to about 38 consecutive amino acid residues, at least or up to about 39 consecutive amino acid residues, at least or up to about 40 consecutive amino acid residues, at least or up to about 45 consecutive amino acid residues, at least or up to about 50 consecutive amino acid residues, at least or up to about 55 consecutive amino acid residues, at least or up to about 60 consecutive amino acid residues, at least or up to about 65 consecutive amino acid residues, at least or up to about 70 consecutive amino acid residues, at least or up to about 75 consecutive amino acid residues, at least or up to about 80 consecutive amino acid residues, at least or up to about 85 consecutive amino acid residues, at least or up to about 80 consecutive amino acid residues 90, at least or up to about 95 consecutive amino acid residues, or at least or up to about 100 consecutive amino acid residues, e.g., as compared to (i) the polypeptide sequence of SEQ ID NO: 1 or (ii) the polypeptide sequence of any one of the Cas proteins selected from TABLE 2 (when applicable).

For example, the deletion can comprise a single deletion of a plurality of consecutive amino acid residues. In another example, the deletion can comprise a first deletion of a first plurality of consecutive amino acid resides and a second deletion of a second plurality of consecutive amino acid resides, and the first plurality of consecutive amino acid resides and the second plurality of consecutive amino acid resides may not be consecutive (e.g., may not be adjacent to each other), when aligned to (i) the polypeptide sequence of SEQ ID NO: 1 or (ii) the polypeptide sequence of any one of the Cas proteins selected from TABLE 2 (when applicable).

In some embodiments, the amino acid sequence of the engineered nuclease as disclosed herein can comprise addition of one or more heterologous amino acid residues (e.g., one or more polypeptide sequences), as compared to (i) the polypeptide sequence of SEQ ID NO: 1 or (ii) the polypeptide sequence of any one of the Cas proteins selected from TABLE 2 (when applicable). The one or more heterologous amino acid residues may be at the position of the at least one deletion of the engineered nuclease. Alternatively or in addition to, the one or more heterologous amino acid residues may not be at the position of the at least one deletion of the engineered nuclease. For example, the one or more heterologous amino acid residues may be upstream and/or downstream of the position of the at least one deletion of the engineered nuclease.

In some embodiments, the one or more heterologous amino acid residues of the engineered nuclease may comprise a single amino acid residue. In some embodiments, the one or more heterologous amino acid residues of the engineered nuclease may comprise a plurality of amino acid residues, such as, at least or up to about 2 amino acid residues, at least or up to about 3 amino acid residues, at least or up to about 4 amino acid residues, at least or up to about 5 amino acid residues, at least or up to about 6 amino acid residues, at least or up to about 7 amino acid residues, at least or up to about 8 amino acid residues, at least or up to about 9 amino acid residues, at least or up to about 10 amino acid residues, at least or up to about 11 amino acid residues, at least or up to about 12 amino acid residues, at least or up to about 13 amino acid residues, at least or up to about 14 amino acid residues, at least or up to about 15 amino acid residues, at least or up to about 16 amino acid residues, at least or up to about 17 amino acid residues, at least or up to about 18 amino acid residues, at least or up to about 19 amino acid residues, at least or up to about 20 amino acid residues, at least or up to about 22 amino acid residues, at least or up to about 24 amino acid residues, at least or up to about 25 amino acid residues, at least or up to about 26 amino acid residues, at least or up to about 28 amino acid residues, at least or up to about 30 amino acid residues, at least or up to about 32 amino acid residues, at least or up to about 34 amino acid residues, at least or up to about 35 amino acid residues, at least or up to about 36 amino acid residues, at least or up to about 38 amino acid residues, at least or up to about 40 amino acid residues, at least or up to about 42 amino acid residues, at least or up to about 44 amino acid residues, at least or up to about 45 amino acid residues, at least or up to about 46 amino acid residues, at least or up to about 48 amino acid residues, at least or up to about 50 amino acid residues, at least or up to about 52 amino acid residues, at least or up to about 54 amino acid residues, at least or up to about 55 amino acid residues, at least or up to about 56 amino acid residues, at least or up to about 58 amino acid residues, at least or up to about 60 amino acid residues, at least or up to about 62 amino acid residues, at least or up to about 64 amino acid residues, at least or up to about 65 amino acid residues, at least or up to about 66 amino acid residues, at least or up to about 68 amino acid residues, at least or up to about 70 amino acid residues, at least or up to about 72 amino acid residues, at least or up to about 74 amino acid residues, at least or up to about 75 amino acid residues, at least or up to about 76 amino acid residues, at least or up to about 78 amino acid residues, at least or up to about 80 amino acid residues, at least or up to about 82 amino acid residues, at least or up to about 84 amino acid residues, at least or up to about 85 amino acid residues, at least or up to about 86 amino acid residues, at least or up to about 88 amino acid residues, at least or up to about 90 amino acid residues, at least or up to about 92 amino acid residues, at least or up to about 94 amino acid residues, at least or up to about 95 amino acid residues, at least or up to about 96 amino acid residues, at least or up to about 98 amino acid residues, or at least or up to about 100 amino acid residues.

In some embodiments, the plurality of amino acid residues of the one or more heterologous amino acid residues may be consecutive amino acid residues. In some embodiments, the plurality of amino acid residues of the one or more heterologous amino acid residues may comprise a plurality of non-consecutive amino acid residues.

In some embodiments, the one or more heterologous amino acid residues of the engineered nuclease may comprise a heterologous polypeptide sequence (e.g., heterologous to (i) the polypeptide sequence of SEQ ID NO: 1 or (ii) the polypeptide sequence of any one of the Cas proteins selected from TABLE 2 (when applicable)). The heterologous polypeptide sequence can exhibit a net positive charge (e.g., net +1 charge, net +2 charge, net +3 charge, net +4 charge, net +5 charge, etc., e.g., as measured in a buffer at about pH 7.4). The heterologous polypeptide sequence can exhibit a net negative charge (e.g., net −1 charge, net −2 charge, net −3 charge, net −4 charge, net −5 charge, etc., e.g., as measured in a buffer at about pH 7.4). The heterologous polypeptide sequence can exhibit a neutral charge, e.g., as measured in a buffer at about pH 7.4. In some cases, the heterologous polypeptide sequence can comprise an amino acid sequence that is at least about 50%, at least about 60%, at least about 65%, at least about 70%, at least about 75%, at least about 80%, at least about 85%, at least about 90%, at least about 95%, at least about 99%, or about 100% identical to the polypeptide sequence of SEQ ID NO: 11.

```
                  (heterologous polypeptide)
                                         SEQ ID NO: 11
        1 ERRKQAGGTG E
```

In some embodiments, the amino acid sequence of the engineered nuclease as disclosed herein can comprise deletion of one or more amino acid residues from (i) the amino acid resides 2-100 as compared to the polypeptide sequence of SEQ ID NO: 1 and/or (ii) the amino acid resides 430-529 as compared to the polypeptide sequence of SEQ ID NO: 1, and the amino acid sequence can further comprise deletion of one or more additional amino acid residues (e.g., at least 1, at least 2, at least 3, at least 4, at least 5, at least 6, at least 7, at least 8, at least 9, at least 10, at least 15, at least 20, or more additional amino acid residues) from the amino acid residues 101-429 as disclosed herein, as compared to the polypeptide sequence of SEQ ID NO: 1.

In some embodiments, the amino acid sequence of the engineered nuclease as disclosed herein can comprise deletion of one or more amino acid residues from (i) the amino acid resides 2-100 as compared to the polypeptide sequence of any one of the Cas proteins selected from TABLE 2 and/or (ii) the last 100 C-terminal amino acid resides as compared to the polypeptide sequence of any one of the Cas proteins selected from TABLE 2, and the amino acid sequence can further comprise deletion of one or more additional amino acid residues (e.g., at least 1, at least 2, at least 3, at least 4, at least 5, at least 6, at least 7, at least 8, at least 9, at least 10, at least 15, at least 20, or more additional amino acid residues) from the amino acid residues there between, as compared to the polypeptide sequence of any one of the Cas proteins selected from TABLE 2.

In some embodiments, the engineered polypeptide as disclosed herein can comprise one or more heterologous amino acid residues (e.g., other than mutations) as compared to the native Un1Cas12f1 nuclease as provided in SEQ ID NO: 1. The presence of the one or more heterologous amino acid residues can enhance, for example, activity, stability, expression, binding to the respective guide nucleic acid molecule, etc. of the engineered polypeptide.

In some embodiments, of the engineered polypeptide as disclosed herein (e.g., a deactivated Cas nuclease variant) can comprises an amino acid sequence that is at least or up to about 50%, at least or up to about 55%, at least or up to about 60%, at least or up to about 65%, at least or up to about 70%, at least or up to about 75%, at least or up to about 80%, at least or up to about 85%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99%, or about 100% identical to the polypeptide sequence of SEQ ID NO: 12.

```
   (example engineered nuclease polypeptide)
                                         SEQ ID NO: 12
     1 MAKNTITKTL KLRIVRPYNS AEVEKIVADE KERRKQAGGT

GELDDKFYQK

51 LRGQFPDAVF WQEISEIFRQ LOKQAAEIYN QSLIELYYEI

FIKGKGIANA

101 SSVEHYLSRV CYRRAAELFK NAAIASGLRS KIKSNERLKE

LKNMKSGLPT

151 TKSDNFPIPL VKQKGGQYTG FEISNHNSDF IIKIPFGRWQ

VKKEIDKYRP

201 WEKFDFEQVQ KSPKPISLLL STQRRKRNKG WSKDEGTEAE

IKKVMNGDYQ

251 TSYIEVKRGS KICEKSAWML NLSIDVPKID KGVDPSIIGG

IAVGVRSPLV

301 CAINNAFSRY SISDNDLFHF NKKMFARRRI LLKKNRHKRA

GHGAKNKLKP

351 ITILTEKSER FRKKLIERWA CEIADFFIKN KVGTVQMENL

ESMKRKEDSY

401 FNIRLRGFWP YAEMQNKIEF KLKQYGIEIR KVAPNNTSKT

CSKCGHLNNY

451 FNFEYRKKNK FPHEKCEKCN FKENAAYNAA LNISNPKLKS

TKERP
```

In some embodiments, the engineered polypeptide as disclosed herein can comprise an amino acid sequence that is at least or up to about 50%, at least or up to about 55%, at least or up to about 60%, at least or up to about 65%, at least or up to about 70%, at least or up to about 75%, at least or up to about 80%, at least or up to about 85%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99%, or about 100% identical to the polypeptide sequence of an engineered nuclease variant from TABLE 3B (e.g., one or more of SEQ ID NOs: 20-27), TABLE 4B (e.g., one or more of SEQ ID NOs: 28-111), and/or TABLE 5C (e.g., one or more of SEQ ID NOs: 112-201).

In some embodiments, the engineered polypeptide as disclosed herein may not be identical to any one of: SEQ ID NO: 1 and any Cas protein from TABLE 2 (SEQ ID NOs: 2, 3, and 13-19).

In some embodiments, the engineered polypeptide as disclosed herein can comprise at least one amino acid modification as compared to the polypeptide sequence of SEQ ID NO: 1 or SEQ ID NO: 10. The at least one amino acid modification can comprise one or more members selected from the group consisting of A21Q, V23I, N32E, D29E, N33R, E35K, K36Q, I37A, A38G, E40D, K73G, A74T, R75G, K76E, Q83K, G87K, E151A, A340S, H353K, A374K, I387E, N423D, K473Q, T474L, T474R, H497K, L515R, N519T, K521D, K521N, L522I, and any deletion of one or more amino acid residues relative to the polypeptide sequence of SEQ ID NO: 1 or SEQ ID NO: 10 as disclosed herein (e.g., at least one deletion from the amino acid residues 400-529 of SEQ ID NO: 1 or SEQ ID NO: 10). The one or more members can comprise at least or up to about 1, at least or up to about 2, at least or up to about 3, at least or up to about 4, at least or up to about 5, at least or up to about 6, at least or up to about 7, at least or up to about 8, at least or up to about 9, at least or up to about 10, at least or up to about 11, at least or up to about 12, at least or up to about 13, at least or up to about 14, at least or up to about 15, at least or up to about 20 amino acid, at least or up to about 25 amino acid, or at least or up to about 30 amino acid modifications selected from the group consisting of A21Q, V23I, N32E, D29E, N33R, E35K, K36Q, I37A, A38G, E40D, K73G, A74T, R75G, K76E, Q83K, G87K, E151A, A340S, H353K, A374K, I387E, N423D, K473Q, T474L, T474R, H497K, L515R, N519T, K521D, K521N, L522I, as compared to the polypeptide sequence of SEQ ID NO: 1 or SEQ ID NO: 10. In some cases, the at least one amino acid modification can comprise at least one set of modifications selected from TABLE 5A. In some cases, the at least one amino acid modification can comprise at least one combination of modifications selected from TABLE 5B. For example, the at least one combination of modifications selected from TABLE 5B may not be cA2.55 or cA2.84.

In some embodiments, the engineered polypeptide as disclosed herein can comprise at least one amino acid modification as compared to the polypeptide sequence of SEQ ID NO: 1 or SEQ ID NO: 10. The at least one amino acid modification can comprise one or more members (e.g., at least 1, 2, 3, 4, 5, 6, 7, 8, 9, 10, 11, 12, 13, 14, 15, or more members) selected from the group consisting of A21Q, V23I, D29E, N33R, E40D, Q83K, G87K, E151A, A340S, H353K, A374K, I387E, N423D, K473Q, T474L, T474R, H497K, L515R, N519T, K521D, K521N, and L522I.

In some embodiments, the engineered polypeptide as disclosed herein can comprise at least one amino acid modification as compared to the polypeptide sequence of SEQ ID NO: 1 or SEQ ID NO: 10. The at least one amino acid modification can comprise one or more members (e.g., at least 1, 2, 3, 4, 5, 6, 7, 8, 9, or 10 members) selected from the group consisting of N32E, N33R, E35K, K36Q, I37A, A38G, K73G, A74T, R75G, and K76E.

In some embodiments, the engineered nuclease variant of the engineered polypeptide as disclosed herein can be a chimeric polypeptide comprising different polynucleotide sequence domains derived from different Cas proteins. The chimeric polypeptide can comprise a first polypeptide sequence comprising at least 3 contiguous amino acid residues in common with a first Cas protein and a second polypeptide sequence comprising at least 3 contiguous amino acid residues in common with a second Cas protein, which second Cas protein is different from the first Cas protein. The first Cas protein and the second Cas protein can be different naturally occurring Cas proteins. The first Cas protein and the second Cas protein can have a size (or amino acid sequence length) that is different from each other by no more than 500, no more than 400, no more than 350, no more than 300, no more than 250, no more than 200, no more than 150, no more than 140, no more than 130, no more than 120, no more than 110, no more than 100, no more than 90, no more than 80, no more than 70, no more than 60, no more than 50, no more than 40, no more than 30, or no more than 20 amino acid residues.

In some cases, a length of the first polypeptide sequence can be substantially the same as a length of the second polypeptide sequence. Alternatively, the length of the first polypeptide sequence can be different from the length of the second polypeptide sequence. The length of the second polypeptide sequence can be less than or equal to about 90%, less than or equal to about 85%, less than or equal to about 80%, less than or equal to about 75%, less than or equal to about 70%, less than or equal to about 65%, less than or equal to about 60%, less than or equal to about 55%, less than or equal to about 50%, less than or equal to about 45%, less than or equal to about 40%, less than or equal to about 35%, less than or equal to about 30%, less than or equal to about 25%, less than or equal to about 20%, less than or equal to about 18%, less than or equal to about 16%, less than or equal to about 15%, less than or equal to about 14%, less than or equal to about 12%, less than or equal to about 10%, less than or equal to about 9%, less than or equal to about 8%, less than or equal to about 7%, less than or equal to about 6%, less than or equal to about 5%, less than or equal to about 4%, less than about 3%, less than or equal to about 2%, or less than or equal to about 1% of the length of the first polypeptide sequence. The length of the second polypeptide sequence can be at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 12%, at least or up to about 14%, at least or up to about 15%, at least or up to about 16%, at least or up to about 18%, at least or up to about 20%, at least or up to about 25%, at least or up to about 30%, at least or up to about 35%, at least or up to about 40%, at least or up to about 45%, at least or up to about 50%, at least or up to about 55%, at least or up to about 60%, at least or up to about 70%, at least or up to about 80%, at least or up to about 90%, or at least or up to about 95% of the length of the first polypeptide sequence.

In some cases, the first Cas protein and the second Cas protein can be two different members selected from: SEQ ID NO: 1 and any Cas protein from TABLE 2 (SEQ ID NOs: 2, 3, and 13-19). The first Cas protein or the second Cas protein can comprise an amino acid sequence that is at least or up to about 5%, at least or up to about 10%, at least or up to about 15%, at least or up to about 20%, at least or up to about 30%, at least or up to about 40%, at least or up to about 50%, at least or up to about 60%, at least or up to about 70%, at least or up to about 75%, at least or up to about 80%, at least or up to about 85%, at least or up to about 90%, at least or up to about 92%, at least or up to about 95%, at least or up to about 96%, at least or up to about 97%, at least or up to about 98%, at least or up to about 99%, or substantially about 100% identical to the polypeptide sequence of a member selected from: SEQ ID NO: 1 and any Cas protein from TABLE 2 (SEQ ID NOs: 2, 3, and 13-19). For example, such member can be SEQ ID NO: 1 or SEQ ID NO: 2.

In some cases, the first polypeptide of the chimeric polypeptide of the engineered nuclease variant can comprise at least or up to about 4 continuous amino acid residues, at least or up to about 5 contiguous amino acid residues, at least or up to about 6 continuous amino acid residues, at least or up to about 7 continuous amino acid residues, at least or up to about 8 continuous amino acid residues, at least or up to about 9 continuous amino acid residues, at least or up to about 10 contiguous amino acid residues, at least or up to about 11 continuous amino acid residues, at least or up to about 12 continuous amino acid residues, at least or up to about 13 continuous amino acid residues, at least or up to about 14 continuous amino acid residues, at least or up to about 15 continuous amino acid residues, at least or up to about 18 continuous amino acid residues, at least or up to about 20 contiguous amino acid residues, at least or up to about 30 contiguous amino acid residues, at least or up to about 40 contiguous amino acid residues, or at least or up to about 50 contiguous amino acid residues in common with the first Cas protein.

In some cases, the second polypeptide of the chimeric polypeptide of the engineered nuclease variant can comprise at least or up to about 4 continuous amino acid residues, at least or up to about 5 contiguous amino acid residues, at least or up to about 6 continuous amino acid residues, at least or up to about 7 continuous amino acid residues, at least or up to about 8 continuous amino acid residues, at least or up to about 9 continuous amino acid residues, at least or up to about 10 contiguous amino acid residues, at least or up to about 11 continuous amino acid residues, at least or up to about 12 continuous amino acid residues, at least or up to about 13 continuous amino acid residues, at least or up to about 14 continuous amino acid residues, at least or up to about 15 continuous amino acid residues, at least or up to about 18 continuous amino acid residues, at least or up to about 20 contiguous amino acid residues, at least or up to about 30 contiguous amino acid residues, at least or up to about 40 contiguous amino acid residues, or at least or up to about 50 contiguous amino acid residues in common with the second Cas protein.

In some cases, in the second polypeptide of the chimeric polypeptide of the engineered nuclease variant, a length of the first polypeptide can be greater than a length of the second polypeptide by at least or up to about 1 amino acid, at least or up to about 2 amino acids, at least or up to about 5 amino acids, at least or up to about 10 amino acids, at least or up to about 15 amino acids, at least or up to about 20 amino acids, at least or up to about 25 amino acids, at least or up to about 30 amino acids, at least or up to about 35 amino acids, at least or up to about 40 amino acids, at least or up to about 45 amino acids, at least or up to about 50 amino acids, at least or up to about 55 amino acids, at least or up to about 60 amino acids, at least or up to about 70 amino acids, at least or up to about 80 amino acids, at least or up to about 90 amino acids, at least or up to about 100 amino acids, at least or up to about 110 amino acids, at least or up to about 120 amino acids, at least or up to about 130 amino acids, at least or up to about 140 amino acids, at least or up to about 150 amino acids, at least or up to about 200 amino acids, at least or up to about 250 amino acids, at least or up to about 300 amino acids, at least or up to about 350 amino acids, at least or up to about 400 amino acids, at least or up to about 450 amino acids, or at least or up to about 500 amino acids.

In some cases, the first polypeptide can be derived from the N-terminal 50%, the N-terminal 45%, the N-terminal 40%, the N-terminal 35%, the N-terminal 30%, the N-terminal 25%, the N-terminal 20%, the N-terminal 15%, the N-terminal 10%, or the N-terminal 5% of the first Cas protein. Alternatively or in addition to, the first polypeptide can be derived from the C-terminal 50%, the C-terminal 45%, the C-terminal 40%, the C-terminal 35%, the C-terminal 30%, the C-terminal 25%, the C-terminal 20%, the C-terminal 15%, the C-terminal 10%, or the C-terminal 5% of the first Cas protein. In some cases, the second polypeptide can be derived from the N-terminal 50%, the N-terminal 45%, the N-terminal 40%, the N-terminal 35%, the N-terminal 30%, the N-terminal 25%, the N-terminal 20%, the N-terminal 15%, the N-terminal 10%, or the N-terminal 5% of the second Cas protein. Alternatively or in addition to, the second polypeptide can be derived from the C-terminal 50%, the C-terminal 45%, the C-terminal 40%, the C-terminal 35%, the C-terminal 30%, the C-terminal 25%, the C-terminal 20%, the C-terminal 15%, the C-terminal 10%, or the C-terminal 5% of the second Cas protein.

In some cases, the first polypeptide can be derived from the first 5 amino acid residues, the first amino acid residues, the first 15 amino acid residues, the first 20 amino acid residues, the first 30 amino acid residues, the first 40 amino acid residues, the first 50 amino acid residues, the first 60 amino acid residues, the first 70 amino acid residues, the first 80 amino acid residues, the first 90 amino acid residues, the first 100 amino acid residues, the first 150 amino acid residues, the first 200 amino acid residues, the first 250 amino acid residues, or the first 300 amino acid residues from the N-terminus of the first Cas protein. Alternatively or in addition to, the first polypeptide can be derived from the first 5 amino acid residues, the first 10 amino acid residues, the first 15 amino acid residues, the first 20 amino acid residues, the first 30 amino acid residues, the first 40 amino acid residues, the first 50 amino acid residues, the first 60 amino acid residues, the first 70 amino acid residues, the first 80 amino acid residues, the first 90 amino acid residues, the first 100 amino acid residues, the first 150 amino acid residues, the first 200 amino acid residues, the first 250 amino acid residues, or the first 300 amino acid residues from the C-terminus of the first Cas protein.

In some cases, the second polypeptide can be derived from the first 5 amino acid residues, the first 10 amino acid residues, the first 15 amino acid residues, the first 20 amino acid residues, the first 30 amino acid residues, the first 40 amino acid residues, the first 50 amino acid residues, the first 60 amino acid residues, the first 70 amino acid residues, the first 80 amino acid residues, the first 90 amino acid residues, the first 100 amino acid residues, the first 150 amino acid residues, the first 200 amino acid residues, the first 250 amino acid residues, or the first 300 amino acid residues from the N-terminus of the second Cas protein. Alternatively or in addition to, the second polypeptide can be derived from the first 5 amino acid residues, the first 10 amino acid residues, the first 15 amino acid residues, the first 20 amino acid residues, the first 30 amino acid residues, the first 40 amino acid residues, the first 50 amino acid residues, the first 60 amino acid residues, the first 70 amino acid residues, the first 80 amino acid residues, the first 90 amino acid residues, the first 100 amino acid residues, the first 150 amino acid residues, the first 200 amino acid residues, the first 250 amino acid residues, or the first 300 amino acid residues from the C-terminus of the second Cas protein.

In some cases, the engineered nuclease variant of the engineered polypeptide as disclosed herein can comprise a third polypeptide sequence comprising at least 3 contiguous amino acid residues (or more as disclosed herein) in common with the first Cas protein. In such cases, the first polypeptide sequence and the third polypeptide sequence may or may not be contiguous to each other within the chimeric polypeptide. Alternatively or in addition to, the third polypeptide sequence can comprise at least 3 contiguous amino acid residues (or more as disclosed herein) in common with the second Cas protein. The first polypeptide sequence and the third polypeptide sequence may not be contiguous to each other in the chimeric polypeptide. Alternatively, the first polypeptide sequence and the third polypeptide sequence may be contiguous to each other in the chimeric polypeptide. The second polypeptide sequence and the third polypeptide sequence may not be contiguous to each other in the chimeric polypeptide. Alternatively, the second polypeptide sequence and the third polypeptide sequence may be contiguous to each other in the chimeric polypeptide. Yet in another alternative or additionally, the third polypeptide sequence can comprise at least 3 contiguous amino acid residues in common with a third Cas protein that is different from the first Cas protein and the second Cas protein. For example, the first Cas protein, the second Cas protein, and the third Cas protein can be three different members selected from SEQ ID NO: 1 and any Cas protein selected from TABLE 2.

In some cases, the third polypeptide of the chimeric polypeptide of the engineered nuclease variant can comprise at least or up to about 4 continuous amino acid residues, at least or up to about 5 contiguous amino acid residues, at least or up to about 6 continuous amino acid residues, at least or up to about 7 continuous amino acid residues, at least or up to about 8 continuous amino acid residues, at least or up to about 9 continuous amino acid residues, at least or up to about 10 contiguous amino acid residues, at least or up to about 11 continuous amino acid residues, at least or up to about 12 continuous amino acid residues, at least or up to about 13 continuous amino acid residues, at least or up to about 14 continuous amino acid residues, at least or up to about 15 continuous amino acid residues, at least or up to about 18 continuous amino acid residues, at least or up to about 20 contiguous amino acid residues, at least or up to about 30 contiguous amino acid residues, at least or up to about 40 contiguous amino acid residues, or at least or up to about 50 contiguous amino acid residues in common with the third Cas protein.

In some cases, the third polypeptide can be derived from the first 5 amino acid residues, the first 10 amino acid residues, the first 15 amino acid residues, the first 20 amino acid residues, the first 30 amino acid residues, the first 40 amino acid residues, the first 50 amino acid residues, the first 60 amino acid residues, the first 70 amino acid residues, the first 80 amino acid residues, the first 90 amino acid residues, the first 100 amino acid residues, the first 150 amino acid residues, the first 200 amino acid residues, the first 250 amino acid residues, or the first 300 amino acid residues from the N-terminus of the third Cas protein. Alternatively or in addition to, the third polypeptide can be derived from the first 5 amino acid residues, the first 10 amino acid residues, the first 15 amino acid residues, the first 20 amino acid residues, the first 30 amino acid residues, the first 40 amino acid residues, the first 50 amino acid residues, the first 60 amino acid residues, the first 70 amino acid residues, the first 80 amino acid residues, the first 90 amino acid residues, the first 100 amino acid residues, the first 150 amino acid residues, the first 200 amino acid residues, the first 250 amino acid residues, or the first 300 amino acid residues from the C-terminus of the third Cas protein.

In some cases, within the chimeric polypeptide of the engineered nuclease variant as disclosed herein, the first polypeptide sequence, the second polypeptide sequence, and the third polypeptide sequence can be arranged in any of the following structures, from N-terminus to C-terminus of the chimeric polypeptide: CP1-CP2-CPx (I), CP1-CPx-CP2 (II), CP2-CP1-CPx (III), CP2-CPx-CP1 (IV), CPx-CP1-CP2 (V), or CPx-CP2-CP1 (VI), in which "-" can be either an amino acid linker (e.g., comprising one or more amino acid sequences) or a direct covalent bond. The amino acid linker as disclosed herein can comprise a single amino acid, at least or up to about 2 amino acids, at least or up to about 3 amino acids, at least or up to about 4 amino acids, at least or up to about 5 amino acids, at least or up to about 8 amino acids, at least or up to about 10 amino acids, at least or up to about 12 amino acids, at least or up to about 15 amino acids, at least or up to about 16 amino acids, or at least or up to about 20 amino acids. The amino acid linker can comprise at least one Glycine, at least one Serine, or at least one Glycine-Serine dipeptide.

In some embodiments, the amino acid sequence of the engineered nuclease as disclosed herein (e.g., the chimeric polypeptide as disclosed herein) can have a length of at most 528 amino acids, at most 527 amino acids, at most 526 amino acids, at most 525 amino acids, at most 524 amino acids, at most 523 amino acids, at most 522 amino acids, at most 521 amino acids, at most 520 amino acids, at most 519 amino acids, at most 518 amino acids, at most 517 amino acids, at most 516 amino acids, at most 515 amino acids, at most 514 amino acids, at most 513 amino acids, at most 512 amino acids, at most 511 amino acids, at most 510 amino acids, at most 509 amino acids, at most 508 amino acids, at most 507 amino acids, at most 506 amino acids, at most 505 amino acids, at most 504 amino acids, at most 503 amino acids, at most 502 amino acids, at most 501 amino acids, at most about 500 amino acids, at most about 495 amino acids, at most about 490 amino acids, at most about 485 amino acids, at most about 480 amino acids, at most about 475 amino acids, at most about 470 amino acids, at most about 465 amino acids, at most about 460 amino acids, at most about 455 amino acids, at most about 450 amino acids, at most about 445 amino acids, at most about 440 amino acids, at most about 435 amino acids, at most about 430 amino acids, at most about 425 amino acids, at most about 420 amino acids, at most about 415 amino acids, at most about 410 amino acids, at most about 405 amino acids, at most about 400 amino acids, at most about 395 amino acids, at most about 390 amino acids, at most about 385 amino acids, at most about 380 amino acids, at most about 375 amino acids, at most about 370 amino acids, at most about 365 amino acids, at most about 360 amino acids, at most about 355 amino acids, at most about 350 amino acids, at most about 345 amino acids, at most about 340 amino acids, at most about 335 amino acids, at most about 330 amino acids, at most about 325 amino acids, at most about 320 amino acids, at most about 315 amino acids, at most about 310 amino acids, at most about 305 amino acids, or at most about 300 amino acids.

In some embodiments, the engineered nuclease comprising the amino acid sequence as disclosed herein can have a length of at most about 1000 amino acids, at most about 950 amino acids, at most about 900 amino acids, at most about 850 amino acids, at most about 800 amino acids, at most about 750 amino acids, at most about 700 amino acids, at most about 650 amino acids, at most about 640 amino acids, at most about 630 amino acids, at most about 620 amino acids, at most about 610 amino acids, at most about 600 amino acids, at most about 590 amino acids, at most about 580 amino acids, at most about 570 amino acids, at most about 560 amino acids, at most about 550 amino acids, at most about 540 amino acids, at most about 530 amino acids, at most about 520 amino acids, at most about 510 amino acids, at most about 500 amino acids, at most about 490 amino acids, at most about 480 amino acids, at most about 470 amino acids, at most about 460 amino acids, at most about 450 amino acids, at most about 440 amino acids, at most about 430 amino acids, at most about 420 amino acids, at most about 410 amino acids, at most about 400 amino acids, at most about 350 amino acids, or at most about 300 amino acids.

In some embodiments, at least a portion of the engineered nuclease variant as disclosed herein may be derived from (e.g., via engineering of) a naturally occurring Cas protein (e.g., the first Cas protein, the second Cas protein, or the third Cas protein as described herein). In some cases, the naturally occurring Cas protein can have a length of at most about 800 amino acids, at most about 750 amino acids, at most about 700 amino acids, at most about 650 amino acids, at most about 600 amino acids, at most about 550 amino acids, at most about 540 amino acids, at most about 530 amino acids, at most about 510 amino acids, at most about 500 amino acids, at most about 490 amino acids, at most about 480 amino acids, at most about 470 amino acids, at most about 460 amino acids, at most about 450 amino acids, or at most about 400 amino acids. The naturally occurring Cas protein, for example, can be a member from SEQ ID NO: 1 and any Cas protein selected from TABLE 2.

In some embodiments, the first polypeptide sequence, the second polypeptide sequence, and/or the third polypeptide sequence of the chimeric polypeptide of the engineered nuclease variant as disclosed herein may not be derived from Cas12a. In some embodiments, the chimeric polypeptide of the engineered nuclease variant may not be derived from Cas12a. In some embodiments, the chimeric polypeptide of the engineered nuclease variant may be entirely derived from one or more Cas12f type orthologous (e.g., SEQ ID NO:1 or a Cas protein selected from TABLE 2).

In some embodiments, the engineered nuclease comprising the amino acid sequence as disclosed herein can be is mutated and/or modified to yield a nuclease deficient protein or a protein with decreased nuclease activity relative to a wild-type Cas protein. A nuclease deficient protein can retain the ability to bind a target gene (e.g., DNA), but may lack or have reduced nucleic acid cleavage activity. In some embodiments, the engineered nuclease comprising the amino acid sequence as disclosed herein can exhibit reduced nuclease activity (e.g., nuclease deficient or nuclease null) as compared to the Cas nuclease encoded by SEQ ID NO: 1 or a Cas protein selected from TABLE 2. The reduced nuclease activity can be at most about 95%, at most about 90%, at most about 80%, at most about 70%, at most about 60%, at most about 50%, at most about 40%, at most about 30%, at most about 20%, at most about 10%, at most about 5%, at most about 1%, at most about 0.5%, at most about 0.1%, or less than that of the Cas nuclease encoded by SEQ ID NO: 1 or that of the Cas protein selected from TABLE 2. In some cases, the engineered nuclease can comprise a substitution at D326 and/or D510, as compared to the polypeptide sequence of SEQ ID NO: 1. For example, the D326 and/or the D510 substitution(s) can be alanine substitutions (e.g., D326A and/or D510A).

In some embodiments, the amino acid sequence of the engineered nuclease as disclosed herein can comprise one or more substitutions in the native amino acid sequence, where the positions of at least some of these substitutions follow one or more particular rules determined to have surprising advantages for the engineered nuclease. In some cases, the particular substitution rules have been selected for their ability to produce variants of the engineered nuclease, e.g., that can be capable of functioning within eukaryotic cells. According to these particular rules, all or some of the one or more substitutions in the native amino acid sequence are either (1) within or no more than 30 amino acids downstream of a (D/E/K/N)X(R/F)(E/K)N motif of the native amino acid sequence, (2) at or no more than 30 amino acids upstream or downstream of position 241 of the native amino acid sequence, (3) at or no more than 30 amino acids upstream or downstream of position 516 of the native amino acid sequence, and/or (4) having an electrically charged amino acid in the native amino acid sequence.

In some embodiments, the amino acid sequence of the engineered nuclease as disclosed herein can comprise one or more substitutions at amino acid positions within or no more than a threshold length (e.g., 30 amino acid residues) upstream and/or downstream of a (D/E/K/N)X(R/F)(E/K)N motif, as compared to (i) the polypeptide sequence of SEQ ID NO: 1 or (ii) the amino acid sequence of the engineered nuclease as disclosed herein without the one or more substitutions. In some cases, at least one of the one or more substitutions can be, for example, within or no more than 28 amino acids, 26 amino acids, 24 amino acids, 22 amino acids, 20 amino acids, 18 amino acids, 16 amino acids, 14 amino acids, 12 amino acids, or 10 amino acids of the motif. In some cases, at least one of the one or more substitutions can be to an R, A, S, or G amino acid residue. In some cases, the one or more substitutions can include substitutions are at one or more positions selected from the group consisting of D143, T147, E151, and K154 (e.g., D143R, T147R, E151R, and/or K154R). In some cases, the one or more substitutions can include substitutions are at one or more positions selected from the group consisting of N504, E507, N516, N519, E527, and E528 (e.g., N504R, E507R, N516R, N519R, E527R, and/or E528R). In some cases, the one or more substitutions can include substitutions are at one or more positions selected from the group consisting of K11, K73, D143, T147, E151, K154, E241, D318, K330, K457, E425, E462, N504, E507, N516, N519, E527, and E528 (e.g., K11R, K73R, D143R, T147R, E151R, K154R, E241R, D318R, K330R, E425N, K457R, E462R, N504R, E507R, N516R, N519R, E527R, and/or E528R).

In some embodiments, the amino acid sequence of the engineered nuclease comprising the one or more substitutions upstream and/or downstream of the (D/E/K/N)X(R/F)(E/K)N motif, as disclosed herein, can exhibit a cationic charge (e.g., a positive) that is greater than that of a control amino acid sequence of the engineered nuclease lacking the one or more substitutions, by at least or up to about 1 cationic charge, at least or up to about 2 cationic charges, at least or up to about 3 cationic charges, at least or up to about 4 cationic charges, at least or up to about 5 cationic charges, at least or up to about 6 cationic charges, at least or up to about 7 cationic charges, at least or up to about 8 cationic charges, at least or up to about 9 cationic charges, at least or up to about 10 cationic charges, at least or up to about 11 cationic charges, at least or up to about 12 cationic charges, at least or up to about 13 cationic charges, at least or up to about 14 cationic charges, at least or up to about 15 cationic charges, at least or up to about 16 cationic charges, at least or up to about 17 cationic charges, or at least or up to about 18 cationic charges.

Without wishing to be bound by theory, the amino acid sequence of the engineered nuclease comprising the one or more substitutions upstream and/or downstream of the (D/E/K/N)X(R/F)(E/K)N motif, as disclosed herein, can exhibit enhanced (e.g., higher) binding affinity to (i) a guide nucleic acid sequence (e.g., a guide RNA sequence) and/or (ii) a target polynucleotide sequence (e.g., a target gene in a cell, such as a target endogenous gene) of the Cas/guide nucleic complex, as compared to (A) a control amino acid sequence of the engineered nuclease lacking the one or more substitutions and/or (B) the CRISPR/Cas protein encoded by SEQ ID NO: 1, by at least or up to about 1%, at least or up to about 5%, at least or up to about 10%, at least or up to about 15%, at least or up to about 20%, at least or up to about 25%, at least or up to about 30%, at least or up to about 40%, at least or up to about 50%, at least or up to about 60%, at least or up to about 70%, at least or up to about 80%, at least or up to about 90%, at least or up to about 100%, at least or up to about 110%, at least or up to about 120%, at least or up to about 125%, at least or up to about 150%, at least or up to about 200%, at least or up to about 250%, at least or up to about 300%, at least or up to about 350%, at least or up to about 400%, at least or up to about 450%, or at least or up to about 500%, as ascertained by surface plasmon resonance (SPR) or isothermal titration calorimetry (IRC) assays.

Without wishing to be bound by theory, the amino acid sequence of the engineered nuclease comprising the one or more substitutions upstream and/or downstream of the (D/E/K/N)X(R/F)(E/K)N motif, as disclosed herein, can exhibit enhanced (e.g., higher) binding affinity to (i) a guide nucleic acid sequence (e.g., a guide RNA sequence) and/or (ii) a target polynucleotide sequence (e.g., a target gene in a cell, such as a target endogenous gene) of the Cas/guide nucleic complex, as compared to (A) a control amino acid sequence of the engineered nuclease lacking the one or more substitutions and/or (B) the CRISPR/Cas protein encoded by SEQ ID NO: 1, by at least or up to about 0.1-fold, at least or up to about 0.2-fold, at least or up to about 0.5-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 25-fold, at least or up to about 30-fold, at least or up to about 35-fold, or at least or up to about 40-fold, as ascertained by surface plasmon resonance (SPR) or isothermal titration calorimetry (IRC) assays.

In some embodiments, the present disclosure provides a system comprising the engineered nuclease as disclosed herein. In some embodiments, the system can comprise recombinantly expressed (or generated) form of the engineered nuclease. In some embodiments, the system can comprise one or more polynucleotides encoding at least the engineered nuclease. In some embodiments, the system can comprise a cell (or a population of cells) comprising (e.g., engineered to comprise, such as transfected or transduced to express) at least the engineered nuclease.

Methods of Use of the Engineered Nuclease

In some embodiments, the engineered nuclease as disclosed herein can be used to effect binding, cleaving, and/or editing a target polynucleotide sequence, e.g., to regulate expression and/or activity level of the target polynucleotide sequence of a polypeptide (e.g., a protein) encoded by the target polynucleotide sequence or operatively coupled to the target polynucleotide sequence. In some cases, a heterologous polypeptide comprising the engineered nuclease can be introduced to a cell (e.g., a mammalian cell) to effect binding, cleaving, and/or editing a target polynucleotide sequence of the cell (e.g., endogenous gene or heterologous gene of the cell). In some embodiments, the engineered nuclease as disclosed herein, or a protein comprising the engineered nuclease can be referred to as an actuator moiety.

In some embodiments, the engineered nuclease as disclosed herein can retain at least a portion (e.g., substantially all of) of the nuclease activity of the nuclease encoded by the polypeptide sequence of SEQ ID NO: 1 or that of the nuclease activity of a Cas protein selected from TABLE 2.

In some embodiments, is the engineered nuclease as disclosed herein can be nuclease-deficient. In some embodiments, the engineered nuclease can be a nuclease-null DNA binding protein that does not induce transcriptional activation or repression of a target DNA sequence unless it is present in a complex with one or more heterologous gene effectors of the disclosure. In some embodiments, the engineered nuclease can be a nuclease-null DNA binding protein that can induce transcriptional activation or repression of a target DNA sequence (e.g., which can be altered or augmented by the presence of a heterologous gene effector as provided herein). The terms "gene effector" and "gene modulator" may be used interchangeably herein. The terms "gene effector polypeptide" and "gene modulator polypeptides" may be used interchangeably herein.

In some embodiments, the engineered nuclease as disclosed herein can be an RNA nuclease such as an engineered (e.g., programmable or targetable) RNA nuclease. In some embodiments, the engineered nuclease as disclosed herein can be a nuclease-null RNA binding protein that does not induce transcriptional activation or repression of a target RNA sequence unless it is present in a complex with one or more heterologous gene effectors of the disclosure. In some embodiments, the engineered nuclease as disclosed herein can be a nuclease-null RNA binding protein that can induce transcriptional activation or repression of a target RNA sequence (e.g., which can be altered or augmented by the presence of a heterologous gene effector as provided herein).

In some embodiments, the engineered nuclease can be a nucleic acid-guided targeting system. In some embodiments, the engineered nuclease can be a DNA-guided targeting system. In some embodiments, the engineered nuclease can be an RNA-guided targeting system. The nucleic acid-guided targeting system can comprise and utilize, for example, a guide nucleic acid sequence that facilitates specific binding of a CRISPR-Cas system (e.g., a nuclease deficient form thereof, such as dCas9 or dCas14) to a target gene (e.g., target endogenous gene) or target gene regulatory sequence. For example, the target gene may be any one of the genes listed in TABLE 1, and the target gene regulatory sequence may be operatively coupled to any one of the genes listed in TABLE 1. Binding specificity can be determined by use of a guide nucleic acid, such as a single guide RNA (sgRNA) or a part thereof. In some embodiments, the use of different sgRNAs allows the compositions and methods of the disclosure to be used with (e.g., targeted to) different target genes (e.g., target endogenous genes) or target gene regulatory sequences.

In some embodiments, the engineered nuclease can form a complex with a guide nucleic acid, such as a guide RNA or a part thereof. In some embodiments, the engineered nuclease can form a complex with a single guide nucleic acid, such as a single guide RNA (sgRNA). In some embodiments, the engineered nuclease can be a RNA-binding protein (RBP) optionally complexed with a guide nucleic acid, such as a guide RNA (e.g., sgRNA), which is able to form a complex with a Cas protein. In some embodiments, the engineered nuclease can be a nuclease-null DNA binding protein that can induce transcriptional activation or repression of a target DNA sequence. In some embodiments, the engineered nuclease can be a nuclease-null RNA binding protein derived from a RNA.

A guide nucleic acid used in compositions and methods of the disclosure can be, for example, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 nucleotides.

In some embodiments, a guide nucleic acid used in compositions and methods of the disclosure is at most at most 10, at most 11, at most 12, at most 13, at most 14, at most 15, at most 16, at most 17, at most 18, at most 19, at most 20, at most 21, at most 22, at most 23, at most 24, at most 25, at most 26, at most 27, at most 28, at most 29, at most 30, at most 31, at most 32, at most 33, at most 34, at most 35, at most 36, at most 37, at most 38, at most 39, or at most 40 nucleotides.

In some embodiments, a guide nucleic acid used in compositions and methods of the disclosure is between about 8 and about 40 nucleotides, between about 10 and about 40 nucleotides, between about 11 and about 40 nucleotides, between about 12 and about 40 nucleotides, between about 13 and about 40 nucleotides, between about 14 and about 40 nucleotides, between about 15 and about 40 nucleotides, between about 16 and about 40 nucleotides, between about 17 and about 40 nucleotides, between about 18 and about 40 nucleotides, between about 19 and about 40 nucleotides, between about 20 and about 40 nucleotides, between about 22 and about 40 nucleotides, between about 24 and about 40 nucleotides, between about 26 and about 40 nucleotides, between about 28 and about 40 nucleotides, between about 30 and about 40 nucleotides, between about 8 and about 30 nucleotides, between about 10 and about 30 nucleotides, between about 11 and about 30 nucleotides, between about 12 and about 30 nucleotides, between about 13 and about 30 nucleotides, between about 14 and about 30 nucleotides, between about 15 and about 30 nucleotides, between about 16 and about 30 nucleotides, between about 17 and about 30 nucleotides, between about 18 and about 30 nucleotides, between about 19 and about 30 nucleotides, between about 20 and about 30 nucleotides, between about 22 and about 30 nucleotides, between about 24 and about 30 nucleotides, between about 26 and about 30 nucleotides, between about 28 and about 30 nucleotides, between about 8 and about 25 nucleotides, between about 10 and about 25 nucleotides, between about 11 and about 25 nucleotides, between about 12 and about 25 nucleotides, between about 13 and about 25 nucleotides, between about 14 and about 25 nucleotides, between about 15 and about 25 nucleotides, between about 16 and about 25 nucleotides, between about 17 and about 25 nucleotides, between about 18 and about 25 nucleotides, between about 19 and about 25 nucleotides, between about 20 and about 25 nucleotides, between about 22 and about 25 nucleotides, between about 24 and about 25 nucleotides, between about 8 and about 20 nucleotides, between about 10 and about 20 nucleotides, between about 11 and about 20 nucleotides, between about 12 and about 20 nucleotides, between about 13 and about 20 nucleotides, between about 14 and about 20 nucleotides, between about 15 and about 20 nucleotides, between about 16 and about 20 nucleotides, between about 17 and about 20 nucleotides, between about 18 and about 20 nucleotides, between about 19 and about 20 nucleotides, between about 8 and about 18 nucleotides, between about 10 and about 18 nucleotides, between about 11 and about 18 nucleotides, between about 12 and about 18 nucleotides, between about 13 and about 18 nucleotides, between about 14 and about 18 nucleotides, between about 15 and about 18 nucleotides, between about 16 and about 18 nucleotides, between about 8 and about 16 nucleotides, between about 10 and about 16 nucleotides, between about 11 and about 16 nucleotides, between about 12 and about 16 nucleotides, between about 13 and about 16 nucleotides, between about 14 and about 16 nucleotides, or between about 15 and about 16 nucleotides. In some embodiments, a guide nucleic acid can be a guide RNA or a part thereof.

The engineered nuclease as disclosed herein can be modified to enhance regulation of gene expression by compositions and methods of the disclosure, e.g., as part of a complex disclosed herein. The engineered nuclease can be modified to increase or decrease nucleic acid binding affinity, nucleic acid binding specificity, enzymatic activity, and/or binding to other factors, such as heterodimerization or oligomerization domains and induce ligands. The engineered nuclease can also be modified to change any other activity or property of the protein, such as stability. For example, one or more nuclease domains of the engineered nuclease can be modified, deleted, or inactivated, or at least a portion of the engineered nuclease can be truncated to remove domains that are not essential for the desired function of the protein or complex. The engineered nuclease can be modified to modulate (e g, enhance or reduce) the activity of the engineered nuclease for regulating gene expression by a complex of the disclosure that comprises a heterologous gene effector.

For example, the engineered nuclease can be coupled (e.g., fused, covalently coupled, or non-covalently coupled) to a heterologous gene effector (e.g., an epigenetic modification domain, a transcriptional activation domain, and/or a transcriptional repressor domain). The engineered nuclease can be coupled (e.g., fused, covalently coupled, or non-covalently coupled) to an oligomerization or dimerization domain as disclosed herein (e.g., a heterodimerization domain). The engineered nuclease can be coupled (e.g., fused, covalently coupled, or non-covalently coupled) to a heterologous polypeptide that provides increased or decreased stability. The engineered nuclease can be coupled (e.g., fused, covalently coupled, or non-covalently coupled) to a sequence that can facilitate degradation of the engineered nuclease or a complex containing the engineered nuclease. The engineered nuclease can be coupled (e.g., fused, covalently coupled, or non-covalently coupled) to a gene editing moiety (e.g., heterologous protein, or domain or functional fragment thereof), that edits, mutates, or modifies (either directly or indirectly) a target polynucleotide sequence.

The engineered nuclease can be coupled (e.g., fused, covalently coupled, or non-covalently coupled) to any suitable number of partners, for example, at least one, at least two, at least three, at least four, or at least five, at least six, at least seven, or at least 8 partners. In some embodiments, the engineered nuclease of the disclosure is coupled (e.g., fused, covalently coupled, or non-covalently coupled) to at most two, at most three, at most four, at most five, at most six, at most seven, at most eight, or at most ten partners. In some embodiments, the engineered nuclease of the disclosure is coupled (e.g., fused, covalently coupled, or non-covalently coupled) to 1-5, 1-4, 1-3, 1-2, 2-5, 2-4, 2-3, 3-5, 3-4, or 4-5 partners. In some embodiments, the engineered nuclease of the disclosure is coupled (e.g., fused, covalently coupled, or non-covalently coupled) to one partner. In some embodiments, the engineered nuclease of the disclosure is coupled (e.g., fused, covalently coupled, or non-covalently coupled) to two partners. In some embodiments, the engineered nuclease of the disclosure is coupled (e.g., fused, covalently coupled, or non-covalently coupled) to three partners. In some embodiments, the engineered nuclease of the disclosure is coupled (e.g., fused, covalently coupled, or non-covalently coupled) to four partners. In some embodiments, the engineered nuclease of the disclosure is coupled (e.g., fused, covalently coupled, or non-covalently coupled) to five partners. In some embodiments, the engineered nuclease of the disclosure is coupled (e.g., fused, covalently coupled, or non-covalently coupled) to six partners.

The engineered nuclease as disclosed herein can be a fusion protein, e.g., a fusion comprising the engineered nuclease and one or more of the partners as disclosed herein. The fused domain or heterologous polypeptide can be located at the N-terminus, the C-terminus, or internally within the engineered nuclease.

A partner of the engineered nuclease (e.g., covalently or non-covalently coupled to a nuclease deficient or null variant of the engineered nuclease as disclosed herein) can be a transcriptional effector (e.g., a transcriptional activator or a transcriptional repressor). The transcriptional effector can be heterologous to the cell as provided herein.

In some embodiments, the transcriptional effector can be a histone epigenetic modifier (or a histone modifier). In some cases, the histone epigenetic modifier can modulate histones through methylation (e.g., a histone methylation modifier, such as an amino acid methyltransferase, e.g., KRAB). In some cases, the histone epigenetic modifier can modulate histones through acetylation. In some cases, the histone epigenetic modifier can modulate histones through phosphorylation. In some cases, the histone epigenetic modifier can modulate histones through ADP-ribosylation. In some cases, the histone epigenetic modifier can modulate histones through glycosylation. In some cases, the histone epigenetic modifier can modulate histones through SUMOylation. In some cases, the histone epigenetic modifier can modulate histones through ubiquitination. In some cases, the histone epigenetic modifier can modulate histones by remodeling histone structure, e.g., via an ATP hydrolysis-dependent process.

In some embodiments, the transcriptional effector can be a gene epigenetic modifier (or a gene modifier). In some cases, a gene modifier can modulate genes through methylation (e.g., a gene methylation modifier, such as a DNA methyltransferase or DNMT). In some cases, a gene modifier can modulate genes through acetylation.

In some embodiments, the transcriptional effector is from a family of related histone acetyltransferases. Non-limiting examples of histone acetyltransferases include GNAT subfamily, MYST subfamily, p300/CBP subfamily, HAT1 subfamily, GCN5, PCAF, Tip60, MOZ, MORF, MOF, HBO1, p300, CBP, HAT1, ATF-2, SRC1, and TAFII250.

In some embodiments, the transcriptional effector can comprise an epigenetic modifier. In some embodiments, the transcriptional effector comprises a histone epigenetic modifier (e.g., a histone lysine methyltransferase, a histone lysine demethylase, or a DNA methylase). Non-limiting examples of an epigenetic modifier can include EZH subfamily, Non-SET subfamily, Other SET subfamily, PRDM subfamily, SET1 subfamily, SET2 subfamily, SUV39 subfamily, SYMD subfamily, ASH1L, EHMT1, EHMT2, EZH1, EZH2, MLL, MLL2, MLL3, MLL4, MLL5, NSD1, NSD2, NSD3, PRDM1, PRDM10, PRDM11, PRDM12, PRDM13, PRDM14, PRDM15, PRDM16, PRDM2, PRDM4, PRDM5, PRDM6, PRDM7, PRDM8, PRDM9, SET1, SET1L, SET2L, SETD2, SETD3, SETD4, SETD5, SETD6, SETD7, SETD8, SETDB1, SETDB2, SETMAR, SUV39H1, SUV39H2, SUV420H1, SUV420H2, SYMD1, SYMD2, SYMD3, SYMD4, and SYMD5.

Examples of proteins (or fragments thereof) that can be used as a fusion partner to increase transcription include but are not limited to: transcriptional activators such as VP16, VP64, VP48, VP160, p65 subdomain (e.g., from NFkB), and activation domain of EDLL and/or TAL activation domain (e.g., for activity in plants), SET1A, SET1B, MLL1 to 5, ASH1, SYMD2, NSD1, JHDM2a/b, UTX, JMJD3, GCN5, PCAF, CBP, p300, TAF1, TIP60/PLIP, MOZMYST3, MORFMYST4, SRC1, ACTR, PI 60, CLOCK, Ten-Eleven Translocation (TET) dioxygenase 1 (TET1CD), TET1, DME, DML1, DML2, ROS1, etc. An additional example of such gene activating modulator is VP64-p65-Rta fusion polypeptide (VPR). Examples of proteins (or fragments thereof) that can be used as a fusion partner to decrease transcription include but are not limited to: transcriptional repressors such as the Kruppel associated box (KRAB or SKD); KOX1 repression domain; the Mad mSIN3 interaction domain (SID); the ERF repressor domain (ERD), the SRDX repression domain (e.g, for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARJD 1 A/RBP2, JARID1B/PLU-1, JARID 1C/SMCX, JARIDID/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as Hhal DNA m5c-methyltransferase (M.Hhal), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In various aspects, an engineered nuclease provided herein may effect editing or mutating of a target polynucleotide, as described herein. In some embodiments, editing or mutating a target polynucleotide sequence involves changing one or more nucleotides in a target polynucleotide to one or more different nucleotides. In some embodiments, editing or mutating a target polynucleotide involves changing a guanine (G) to a different nucleotide. In some cases, a guanine (G) may be changed to an adenine (A). In some cases, a guanine (G) may be changed to a thymine (T). In some cases, a guanine (G) may be changed to a cytosine (C). In some cases, a guanine (G) may be changed to a uracil (U). In some cases, a guanine (G) may be changed to an inosine (I). In some embodiments, editing or mutating a target polynucleotide involves changing a cytosine (C) to a different nucleotide. In some cases, a cytosine (C) may be changed to a guanine (G). In some cases, a cytosine (C) may be changed to an adenine (A). In some cases, a cytosine (C) may be changed to a thymine (T). In some cases, a cytosine (C) may be changed to a uracil (U). In some cases, a cytosine (C) may be changed to an inosine (I). In some embodiments, editing or mutating a target polynucleotide involves changing a thymine (T) to a different nucleotide. In some cases, a thymine (T) may be changed to a cytosine (C). In some cases, a thymine (T) may be changed to a guanine (G). In some cases, a thymine (T) may be changed to an adenine (A). In some cases, a thymine (T) may be changed to a uracil (U). In some cases, a thymine (T) may be changed to an inosine (I). In some embodiments, editing or mutating a target polynucleotide involves changing an adenine (A) to a different nucleotide. In some cases, an adenine (A) may be changed to a guanine (G). In some cases, an adenine (A) may be changed to a cytosine (C). In some cases, an adenine (A) may be changed to a thymine (T). In some cases, an adenine (A) may be changed to a uracil (U). In some cases, an adenine (A) may be changed to an inosine (I). In some embodiments, editing or mutating a target polynucleotide involves changing a uracil (U) to a different nucleotide. In some cases, a uracil (U) may be changed to a guanine (G). In some cases, a uracil (U) may be changed to a cytosine (C).

In some cases, a uracil (U) may be changed to a thymine (T). In some cases, a uracil (U) may be changed to an adenine (A). In some cases, a uracil (U) may be changed to an inosine (I). In some embodiments, editing or mutating a target polynucleotide involves changing an inosine (I) to a different nucleotide. In some cases, an inosine (I) may be changed to a guanine (G). In some cases, an inosine (I) may be changed to a cytosine (C). In some cases, an inosine (I) may be changed to a thymine (T). In some cases, an inosine (I) may be changed to an adenine (A). In some cases, an inosine (I) may be changed to a uracil (U).

In some embodiments, editing or mutating a target polynucleotide involves introducing one or more point mutations into a target polynucleotide. In some embodiments, editing or mutating a target polynucleotide involves introducing one or more deletions (e.g., of one or more nucleotides) into a target polynucleotide. In some embodiments, editing or mutating a target polynucleotide involves introducing one or more insertions (e.g., of one or more nucleotides) into a target polynucleotide. In some embodiments, editing or mutating a target polynucleotide involves introducing one or more inversions (e.g., of two or more nucleotides) in a target polynucleotide. In some embodiments, editing or mutating a target polynucleotide involves introducing one or more translocations (e.g., of one or more nucleotides) in a target polynucleotide. In some embodiments, editing or mutating a target polynucleotide involves introducing one or more transpositions in a target polynucleotide.

In some cases, an engineered nuclease as described herein may be coupled to a partner (e.g., a gene editing moiety) that effects editing or mutating of a target polynucleotide, as described herein. In some cases, a nuclease-deficient or nuclease-null engineered nuclease as provided herein is covalently or non-covalently coupled to a gene editing moiety (e.g., a protein, or functional domain or functional fragment thereof) that effects editing or mutating of a target polynucleotide. In some embodiments, the gene editing moiety (e.g., a protein, or functional domain or functional fragment thereof) that effects editing or mutating of a target polynucleotide is a gene editing moiety that changes one or more nucleotides to a different nucleotide. In some embodiments, the gene editing moiety (e.g., a protein, or functional domain or functional fragment thereof) that effects editing or mutating of a target polynucleotide is a gene editing moiety that changes a guanine (G) to a different nucleotide. In some cases, the gene editing moiety that effects editing or mutating of a target polynucleotide changes a guanine (G) to a cytosine (C). In some cases, the gene editing moiety that effects editing or mutating of a target polynucleotide changes a guanine (G) to a thymine (T). In some cases, the gene editing moiety that effects editing or mutating of a target polynucleotide changes a guanine (G) to an adenine (A). In some cases, the gene editing moiety that effects editing or mutating of a target polynucleotide changes a guanine (G) to a uracil (U). In some cases, the gene editing moiety that effects editing or mutating of a target polynucleotide changes a guanine (G) to an inosine (I). In some embodiments, the gene editing moiety (e.g., a protein, or functional domain or functional fragment thereof) that effects editing or mutating of a target polynucleotide sequence is a gene editing moiety that changes a cytosine (C) to a different nucleotide. In some cases, the gene editing moiety that effects editing or mutating of a target polynucleotide changes a cytosine (C) to a guanine (G). In some cases, the gene editing moiety that effects editing or mutating of a target polynucleotide changes a cytosine (C) to a thymine (T). In some cases, the gene editing moiety that effects editing or mutating of a target polynucleotide changes a cytosine (C) to an adenine (A). In some cases, the gene editing moiety that effects editing or mutating of a target polynucleotide changes a cytosine (C) to a uracil (U). In some cases, the gene editing moiety that effects editing or mutating of a target polynucleotide changes a cytosine (C) to an inosine (I). In some embodiments, the gene editing moiety (e.g., a protein, or functional domain or functional fragment thereof) that effects editing or mutating of a target polynucleotide sequence is a gene editing moiety that changes a thymine (T) to a different nucleotide. In some cases, the gene editing moiety that effects editing or mutating of a target polynucleotide changes a thymine (T) to a cytosine (C). In some cases, the gene editing moiety that effects editing or mutating of a target polynucleotide changes a thymine (T) to a guanine (G). In some cases, the gene editing moiety that effects editing or mutating of a target polynucleotide changes a thymine (T) to an adenine (A). In some cases, the gene editing moiety that effects editing or mutating of a target polynucleotide changes a thymine (T) to a uracil (U). In some cases, the gene editing moiety that effects editing or mutating of a target polynucleotide changes a thymine (T) to an inosine (I). In some embodiments, the gene editing moiety (e.g., a protein, or functional domain or functional fragment thereof) that effects editing or mutating of a target polynucleotide sequence is a gene editing moiety that changes an adenine (A) to a different nucleotide. In some cases, the gene editing moiety that effects editing or mutating of a target polynucleotide changes an adenine (A) to a cytosine (C). In some cases, the gene editing moiety that effects editing or mutating of a target polynucleotide changes an adenine (A) to a thymine (T). In some cases, the gene editing moiety that effects editing or mutating of a target polynucleotide changes an adenine (A) to a guanine (G). In some cases, the gene editing moiety that effects editing or mutating of a target polynucleotide changes an adenine (A) to a uracil (U). In some cases, the gene editing moiety that effects editing or mutating of a target polynucleotide changes an adenine (A) to an inosine (I). In some embodiments, the gene editing moiety (e.g., a protein, or functional domain or functional fragment thereof) that effects editing or mutating of a target polynucleotide sequence is a gene editing moiety that changes a uracil (U) to a different nucleotide. In some cases, the gene editing moiety that effects editing or mutating of a target polynucleotide changes a uracil (U) to a cytosine (C). In some cases, the gene editing moiety that effects editing or mutating of a target polynucleotide changes a uracil (U) to a thymine (T). In some cases, the gene editing moiety that effects editing or mutating of a target polynucleotide changes a uracil (U) to an adenine (A). In some cases, the gene editing moiety that effects editing or mutating of a target polynucleotide changes a uracil (U) to a guanine (G). In some cases, the gene editing moiety that effects editing or mutating of a target polynucleotide changes a uracil (U) to an inosine (I). In some embodiments, the gene editing moiety (e.g., a protein, or functional domain or functional fragment thereof) that effects editing or mutating of a target polynucleotide sequence is a gene editing moiety that changes an inosine (I) to a different nucleotide. In some cases, the gene editing moiety that effects editing or mutating of a target polynucleotide changes an inosine (I) to a cytosine (C). In some cases, the gene editing moiety that effects editing or mutating of a target polynucleotide changes an inosine (I) to a thymine (T). In some cases, the gene editing moiety that effects editing or mutating of a target polynucleotide changes an inosine (I) to an adenine (A). In some cases, the gene editing moiety that effects editing or mutating of a target polynucleotide changes an inosine (I) to a uracil (U). In some cases, the gene editing moiety that effects editing or mutating of a target polynucleotide changes an inosine (I) to a guanine (G).

In some embodiments, the engineered nuclease as described herein (e.g., a nuclease-deficient or nuclease-null engineered nuclease, as described herein) may be coupled (e.g., covalently or non-covalently) to a partner (e.g., a gene editing moiety) that introduces one or more point mutations into a target polynucleotide. In some embodiments, the engineered nuclease as described herein (e.g., a nuclease-deficient or nuclease-null engineered nuclease, as described herein) may be coupled (e.g., covalently or non-covalently) to a partner (e.g., a gene editing moiety) that introduces one or more deletions (e.g., of one or more nucleotides) into a target polynucleotide. In some embodiments, the engineered nuclease as described herein (e.g., a nuclease-deficient or nuclease-null engineered nuclease, as described herein) may be coupled (e.g., covalently or non-covalently) to a partner (e.g., a gene editing moiety) that introduces one or more insertions (e.g., of one or more nucleotides) into a target polynucleotide. In some embodiments, the engineered nuclease as described herein (e.g., a nuclease-deficient or nuclease-null engineered nuclease, as described herein) may be coupled (e.g., covalently or non-covalently) to a partner (e.g., a gene editing moiety) that introduces one or more inversions (e.g., of two or more nucleotides) in a target polynucleotide. In some embodiments, the engineered nuclease as described herein (e.g., a nuclease-deficient or nuclease-null engineered nuclease, as described herein) may be coupled (e.g., covalently or non-covalently) to a partner (e.g., a gene editing moiety) that introduces one or more translocations (e.g., of one or more nucleotides) in a target polynucleotide. In some embodiments, the engineered nuclease as described herein (e.g., a nuclease-deficient or nuclease-null engineered nuclease, as described herein) may be coupled (e.g., covalently or non-covalently) to a partner (e.g., a gene editing moiety) that introduces one or more transpositions in a target polynucleotide.

In some embodiments, the gene editing moiety may be a base-editing protein or a base-editing enzyme. In some embodiments, the base-editing protein or base-editing enzyme is a deaminase. In some cases, the deaminase is a cytidine deaminase. In some cases, the cytidine deaminase catalyzes the reaction of a cytosine (C) to a uracil (U), which has the base-pairing properties of thymine. In some embodiments, for example where the polynucleotide is double-stranded (e.g., double-stranded DNA), the uridine base can then be substituted with a thymidine base (e.g., by cellular repair machinery) to give rise to a CG to a TA transition. In some embodiments, the deaminase is an adenine deaminase. In some cases, the adenine deaminase catalyzes the reaction of an adenosine (A) to an inosine (I). Non-limiting examples of deaminases suitable for use herein include, without limitation, APOBEC 1 deaminase, APOBEC2 deaminase, APOBEC3 deaminase, APOBEC3A deaminase, APOBEC3B deaminase, APOBEC3C deaminase, APOBEC3D deaminase, APOBEC3E deaminase, APOBEC3F deaminase, APOBEC3G deaminase, APOBEC3H deaminase, APOBEC4 deaminase, activation-induced cytidine deaminase (AID), adenosine deaminase 1 (ADAR1), adenosine deaminase 2 (ADAR2), adenosine deaminase 3 (ADAR3), or TadA.

In some embodiments, the engineered nucleases described herein may be used for prime editing. For example, an engineered nuclease as described herein may be coupled to a reverse transcriptase enzyme (e.g., an engineered M-MLV reverse transcriptase) and a prime editing RNA (pegRNA). In such cases, the engineered nuclease may comprise nickase activity. In some embodiments, prime editing may be used to mediate targeted insertions, deletions, or base-to-base conversions.

In some embodiments, the engineered nucleases described herein may be used for gene writing.

In some embodiments, the engineered nucleases described herein may be coupled to a partner (e.g., a protein, or functional domain or functional fragment thereof) that methylates a target substrate. In some cases, the partner (e.g., a protein, or functional domain or functional fragment thereof) that methylates a target substrate is a methyltransferase. In some cases, the methyltransferase is a DNA methyltransferase, a histone methyltransferase, or an RNA methyltransferase. In some cases, the DNA methyltransferase is DNMT1 or DNMT3.

In some embodiments, the engineered nucleases described herein may be coupled to a partner (e.g., a protein, or functional domain or functional fragment thereof) that has demethylase activity (e.g., can remove methyl groups from nucleic acids, proteins, or other molecules). In some cases, the partner (e.g., a protein, or functional domain or functional fragment thereof) that has demethylase activity is a histone lysine demethylase, such as, but not limited to KDM1, KDM2, KDM3, KDM4, KDM5, and KDM6.

In some embodiments, the engineered nucleases described herein may be coupled to a partner (e.g., a protein, or functional domain or functional fragment thereof) that has dismutase activity. In some cases, the partner (e.g., a protein, or functional domain or functional fragment thereof) that has dismutase activity is superoxide dismutase, formaldehyde dismutase, or chlorite dismutase.

In some embodiments, the engineered nucleases described herein may be coupled to a partner (e.g., a protein, or functional domain or functional fragment thereof) that has alkylation activity. In some cases, the partner (e.g., a protein, or functional domain or functional fragment thereof) that has alkylation activity is a prenyltransferase, a terpene cyclase, or a terpene synthase.

In some embodiments, the engineered nucleases described herein may be coupled to a partner (e.g., a protein, or functional domain or functional fragment thereof) that has depurination activity. In some cases, the partner (e.g., a protein, or functional domain or functional fragment thereof) that has depurination activity is DNA glycosylase.

In some embodiments, the engineered nucleases described herein may be coupled to a partner (e.g., a protein, or functional domain or functional fragment thereof) that has oxidation activity. In some cases, the partner (e.g., a protein, or functional domain or functional fragment thereof) that has oxidation activity is a peroxidase or an oxidase.

In some embodiments, the engineered nucleases described herein may be coupled to a partner (e.g., a protein, or functional domain or functional fragment thereof) that has pyrimidine dimer forming activity.

In some embodiments, the engineered nucleases described herein may be coupled to a partner (e.g., a protein, or functional domain or functional fragment thereof) that has integrase activity. In some cases, the partner (e.g., a protein, or functional domain or functional fragment thereof) that has integrase activity is retroviral integrase or HIV integrase.

In some embodiments, the engineered nucleases described herein may be coupled to a partner (e.g., a protein, or functional domain or functional fragment thereof) that has transposase activity. In some cases, the partner (e.g., a protein, or functional domain or functional fragment thereof) that has transposase activity is ty1, Mariner transposase, Tn3, transposase (Tnp) Tn5, or Tn7 transposon.

In some embodiments, the engineered nucleases described herein may be coupled to a partner e.g., a protein, or functional domain or functional fragment thereof) that has recombinase activity. In some cases, the partner (e.g., a protein, or functional domain or functional fragment thereof) that has recombinase activity is tyrosine recombinase, Rad51 recombinase, RecA recombinase, or Dmc1 recombinase.

In some embodiments, the engineered nucleases described herein may be coupled to a partner (e.g., a protein, or functional domain or functional fragment thereof) that has polymerase activity. In some cases, the partner (e.g., a protein, or functional domain or functional fragment thereof) that has polymerase activity is DNA polymerase, RNA polymerase, reverse transcriptase, or RdRp replicase.

In some embodiments, the engineered nucleases described herein may be coupled to a partner (e.g., a protein, or functional domain or functional fragment thereof) that has ligase activity. In some cases, the partner (e.g., a protein, or functional domain or functional fragment thereof) that has ligase activity is ubiquitin ligases, glutamate-cysteine ligase, aminoacyl tRNA synthetase, succinyl coenzyme A synthetase, acetyl-CoA synthetase, pyruvate carboxylase, acetyl-CoA carboxylase, propionyl-CoA carboxylase, methylcrotonyl-CoA carboxylase, DNA ligase, magnesium chelatase, cobalt chelatase, or DNA synthetase.

In some embodiments, the engineered nucleases described herein may be coupled to a partner (e.g., a protein, or functional domain or functional fragment thereof) that has helicase activity. In some cases, the partner (e.g., a protein, or functional domain or functional fragment thereof) that has helicase activity is a DNA helicase, an RNA helicase, chromodomain helicase, or DEAD box/DEAD/DEAH box helicase.

In some embodiments, the engineered nucleases described herein may be coupled to a partner (e.g., a protein, or functional domain or functional fragment thereof) that has photolyase activity. In some cases, the partner (e.g., a protein, or functional domain or functional fragment thereof) that has photolyase activity is photoreactivating enzyme, DNA photolyase, DNA-photoreactivating enzyme, DNA cyclobutane dipyrimidine photolyase, DNA photolyase, deoxyribonucleic photolyase, deoxyribodipyrimidine photolyase, photolyase, PRE, PhrB photolyase, deoxyribonucleic cyclobutane dipyrimidine photolyase, phr A photolyase, dipyrimidine photolyase (photosensitive), or deoxyribonucleate pyrimidine dimer lyase (photosensitive).

In some embodiments, the engineered nucleases described herein may be coupled to a partner (e.g., a protein, or functional domain or functional fragment thereof) that has glycosylase activity. In some cases, the partner (e.g., a protein, or functional domain or functional fragment thereof) that has glycosylase activity is N-methylpurine DNA glycosylase, UNG, hOGG1, hNTH1, hNEIL1, hMYH, hSMUG1, TDG, MBD4, Mag1, Ung1, Ogg1, Ntg1, AlkE, Ntg2, hNEIL2, hNEIL3, AlkC, AlkD, MutY, Nei, Nth, Fpg, or UDG.

In some embodiments, the engineered nucleases described herein may be coupled to a partner (e.g., a protein, or functional domain or functional fragment thereof) that has acetyltransferase activity. In some cases, the partner (e.g., a protein, or functional domain or functional fragment thereof) that has acetyltransferase activity is CBP histone acetyltransferase, choline acetyltransferase, chloramphenicol acetyltransferase, serotonin N-acetyltransferase, NatA Acetyltransferase, or NatB acetyltransferase.

In some embodiments, the engineered nucleases described herein may be coupled to a partner (e.g., a protein, or functional domain or functional fragment thereof) that has deacetylase activity. In some cases, the partner (e.g., a protein, or functional domain or functional fragment thereof) that has deacetylase activity is HDAC-1, HDAC-2, HDAC-3, HDAC-4, HDAC-5, HDAC-6, HDAC-7, or HDAC-8.

In some embodiments, the engineered nucleases described herein may be coupled to a partner (e.g., a protein, or functional domain or functional fragment thereof) that has kinase activity. In some cases, the partner (e.g., a protein, or functional domain or functional fragment thereof) that has kinase activity is Ca2+/calmodulin-dependent protein kinase, cyclin-dependent kinase, nucleoside-diphosphate kinase, a phosphatidylinositol phosphate kinase, thymidine kinase, thymidylate kinase, or wall-associated kinase.

In some embodiments, the engineered nucleases described herein may be coupled to a partner (e.g., a protein, or functional domain or functional fragment thereof) that has phosphatase activity. In some cases, the partner (e.g., a protein, or functional domain or functional fragment thereof) that has phosphatase activity is acid phosphatase, alkaline phosphatase, endonuclease/exonuclease/phosphatase family, kinase, phosphatome, phosphotransferase, protein phosphatase, or protein phosphatase 2.

In some embodiments, the engineered nucleases described herein may be coupled to a partner (e.g., a protein, or functional domain or functional fragment thereof) that has ubiquitin ligase activity. In some cases, the partner (e.g., a protein, or functional domain or functional fragment thereof) that has ubiquitin ligase activity is E3A, mdm2, Anaphase-promoting complex (APC), UBR5 (EDD1), SOCS/BC-box/eloBC/CUL5I RING, LNXp80, CBX4, CBLL1, HACE1, HECTD1, HECTD2, HECTD3, HECTD4, HECW1, HECW2, HERC1, HERC2, HERC3, HERC4, HERC5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL, WWP1, WWP2, Parkin, or MKRN1.

In some embodiments, the engineered nucleases described herein may be coupled to a partner (e.g., a protein, or functional domain or functional fragment thereof) that has deubiquitinating activity. In some cases, the partner (e.g., a protein, or functional domain or functional fragment thereof) that has deubiquitinating activity is a deubiquitinating peptidase, a deubiquitinating isopeptidase, a deubiquitinase, a ubiquitin protease, a ubiquitin hydrolase, or a ubiquitin isopeptidase.

In some embodiments, the engineered nucleases described herein may be coupled to a partner (e.g., a protein, or functional domain or functional fragment thereof) that has adenylation activity. In some cases, the partner (e.g., a protein, or functional domain or functional fragment thereof) that has adenylation activity is carboxylic acid reductase.

In some embodiments, the engineered nucleases described herein may be coupled to a partner (e.g., a protein, or functional domain or functional fragment thereof) that has deadenylation activity. In some cases, the partner (e.g., a protein, or functional domain or functional fragment thereof) that has deadenylation activity is 5'-deadenylase, CNOT6 deadenylase, CNOT6L deadenylase, or CCR4-NOT deadenylase, In some embodiments, the engineered nucleases described herein may be coupled to a partner (e.g., a protein, or functional domain or functional fragment thereof) that has SUMOylating activity. In some cases, the partner (e.g., a protein, or functional domain or functional fragment thereof) that has SUMOylating activity is small ubiquitin-related modifier (SUMO-1), SUMO-2, or SUMO-3.

In some embodiments, the engineered nucleases described herein may be coupled to a partner (e.g., a protein, or functional domain or functional fragment thereof) that has deSUMOylating activity. In some cases, the partner (e.g., a protein, or functional domain or functional fragment thereof) that has deSUMOylating activity is SENP1, SENP2, SENP3, or SENP5.

In some embodiments, the engineered nucleases described herein may be coupled to a partner (e.g., a protein, or functional domain or functional fragment thereof) that has ribosylation activity. In some cases, the partner (e.g., a protein, or functional domain or functional fragment thereof) that has ribosylation activity is a mono(ADP-ribosyl)transferase, a poly(ADP-ribose)polymerase, or histone ribosylase.

In some embodiments, the engineered nucleases described herein may be coupled to a partner (e.g., a protein, or functional domain or functional fragment thereof) that has deribosylation activity. In some cases, the partner (e.g., a protein, or functional domain or functional fragment thereof) that has deribosylation activity is histone lysine deribosylase or ADP-ribose deribosylase.

In some embodiments, the engineered nucleases described herein may be coupled to a partner (e.g., a protein, or functional domain or functional fragment thereof) that has myristoylation activity. In some cases, the partner (e.g., a protein, or functional domain or functional fragment thereof) that has myristoylation activity is N-myristoltransferase (NMT) 1, N-myristoltransferase (NMT) 2, or glycylpeptide N-tetradecanoyltransferase.

In some embodiments, the engineered nucleases described herein may be coupled to a partner (e.g., a protein, or functional domain or functional fragment thereof) that has remodeling activity. In some cases, the partner (e.g., a protein, or functional domain or functional fragment thereof) that has remodeling activity is a histone acetyltransferase (HAT), a deacetylase, or a methyltransferase.

In some embodiments, the engineered nucleases described herein may be coupled to a partner (e.g., a protein, or functional domain or functional fragment thereof) that has protease activity. In some cases, the partner (e.g., a protein, or functional domain or functional fragment thereof) that has protease activity is trypsin, chymotrypsin, elastase, papain, bromelain, a serine protease, a cysteine protease, a threonine protease, an aspartic protease, a glutamic protease, a metalloprotease, or an asparagine peptide lyase.

In some embodiments, the engineered nucleases described herein may be coupled to a partner (e.g., a protein, or functional domain or functional fragment thereof) that has oxidoreductase activity. In some cases, the partner (e.g., a protein, or functional domain or functional fragment thereof) that has oxidoreductase activity is donor dehydrogenase, peroxidase, reductase, dehydrogenase, oxidase, oxygenase, hydroxylase, luciferase, DMSO reductase, glucose oxidase, L-gulonolactone oxidase, thiamine oxidase, xanthine oxidase, acetaldehyde dehydrogenase, pyruvate dehydrogenase, oxoglutarate dehydrogenase, monoamine oxidase, biliverdin reductase, dihydrofolate reductase, methylenetetrahydrofolate reductase, sarcosine oxidase, or dihydrobenzophenanthridine oxidase.

In some embodiments, the engineered nucleases described herein may be coupled to a partner (e.g., a protein, or functional domain or functional fragment thereof) that has transferase activity. In some cases, the partner (e.g., a protein, or functional domain or functional fragment thereof) that has transferase activity is coenzyme A transferase, acyl transferase, peptidyl transferase, N-acetyltransferase, or pyruvate dehydrogenase.

In some embodiments, the engineered nucleases described herein may be coupled to a partner (e.g., a protein, or functional domain or functional fragment thereof) that has hydrolase activity. In some cases, the partner (e.g., a protein, or functional domain or functional fragment thereof) that has hydrolase activity is an esterase, a protease, a glycosidase, or a lipase.

In some embodiments, the engineered nucleases described herein may be coupled to a partner (e.g., a protein, or functional domain or functional fragment thereof) that has lyase activity. In some cases, the partner (e.g., a protein, or functional domain or functional fragment thereof) that has lyase activity is phenylalanine ammonia-lyase, citrate lyase, isocitrate lyase, hydroxynitrile, pectate lyase, argininosuccinate lyase, pyruvate formate lyase, alginate lyase, or pectin lyase.

In some embodiments, the engineered nucleases described herein may be coupled to a partner (e.g., a protein, or functional domain or functional fragment thereof) that has isomerase activity. In some cases, the partner (e.g., a protein, or functional domain or functional fragment thereof) that has isomerase activity is ribose phosphate isomerase, bisphosphoglycerate mutase, or photoisomerase.

In some embodiments, the engineered nucleases described herein may be coupled to a partner (e.g., a protein, or functional domain or functional fragment thereof) that has synthase activity. In some cases, the partner (e.g., a protein, or functional domain or functional fragment thereof) that has synthase activity is ATP synthase, citrate synthase, tryptophan synthase, pseudouridine synthase, or fatty acid synthase.

In some embodiments, the engineered nucleases described herein may be coupled to a partner (e.g., a protein, or functional domain or functional fragment thereof) that has demyristoylation activity. In some cases, the partner (e.g., a protein, or functional domain or functional fragment thereof) that has demyristoylation activity is T3SS effector protein.

In some embodiments, the engineered nucleases described herein may be coupled to a partner (e.g., a protein, or functional domain or functional fragment thereof) that has transposition activity. In some cases, the partner (e.g., a protein, or functional domain or functional fragment thereof) that has transposition activity is transposase Tn5 or Sleeping Beauty transposase.

The engineered nuclease as disclosed herein can be provided in any form. For example, the engineered nuclease can be provided in the form of a protein, such as the engineered nuclease alone or complexed with a guide nucleic acid as a ribonucleoprotein. The engineered nuclease can be provided in a complex, for example, complexed with a guide nucleic acid and/or one or more heterologous gene effectors of the disclosure. The engineered nuclease can be provided in the form of a nucleic acid encoding at least the engineered nuclease, such as an RNA (e.g., messenger RNA (mRNA)), or DNA. The nucleic acid encoding at least the engineered nuclease can be codon optimized for efficient translation into protein in a particular cell or organism (e.g., human codon optimized).

Nucleic acids encoding at least the engineered nuclease as disclosed herein, fragments, or derivatives thereof can be stably integrated in the genome of a cell. Nucleic acids encoding at least the engineered nuclease can be operably linked to a promoter, for example, a promoter that is constitutively or inducibly active in the cell. Nucleic acids encoding at least the engineered nuclease can be operably linked to a promoter in an expression construct. Expression constructs can include any nucleic acid constructs capable of directing expression of a gene or other nucleic acid sequence of interest (e.g., at least the engineered nuclease) and which can transfer such a nucleic acid sequence of interest to a target cell.

In some embodiments, the engineered nuclease as disclosed herein can associate with a single guide RNA (sgRNA) to activate or repress transcription of a target gene (e.g., target endogenous gene), for example, in combination with heterologous gene effector(s) disclosed herein. sgRNAs can be introduced into cells expressing the engineered nuclease or variant thereof, as provided herein. In some cases, such cells can contain one or more different sgRNAs that target the same target gene (e.g., target endogenous gene) or target gene regulatory sequence. In other cases, the sgRNAs target different nucleic acids in the cell (e.g., different target genes, different target gene regulatory sequences, or different sequences within the same target gene or target gene regulatory sequence).

Enzymatically inactive (e.g., nuclease deficient) can refer to a nuclease that can bind to a nucleic acid sequence in a polynucleotide in a sequence-specific manner, but may not cleave a target polynucleotide or will cleave it at a substantially reduced frequency. An enzymatically inactive guide moiety can comprise an enzymatically inactive domain (e.g., nuclease domain). Enzymatically inactive can refer to no activity. Enzymatically inactive can refer to substantially no activity. Enzymatically inactive can refer to essentially no activity. Enzymatically inactive can refer to an activity no more than 1%, no more than 2%, no more than 3%, no more than 4%, no more than 5%, no more than 6%, no more than 7%, no more than 8%, no more than 9%, or no more than 10% activity compared to a comparable wild-type activity (e.g., nucleic acid cleaving activity, wild-type Cas activity).

In some embodiments, the target nucleic acid of the engineered nuclease as disclosed herein can be dsDNA. In such embodiments, dsDNA-targeting specificity is determined, at least in part, by two parameters: the gRNA spacer targeting a protospacer in the target dsDNA (the sequence in the target dsDNA corresponding to the gRNA spacer on the non-complementary DNA strand) and a short sequence, the protospacer-adjacent motif (PAM), located immediately 5' (upstream) of the protospacer on the non-complementary DNA strand. In some embodiments, the PAM is 5'-TTTG-3', 5'-TTTA-3', or 5'-TTTR-3'. In some embodiments, the PAM is 5'-TTTG-3'. In some embodiments, the PAM is 5'-TTTA-3'. In some embodiments, the PAM is 5'-TTTR-3'.

In some embodiments, the target nucleic acid of the engineered nuclease as disclosed herein can be RNA. In such embodiments, RNA-targeting specificity is determined, at least in part, by the gRNA spacer targeting a protospacer-like sequence in the target RNA (the sequence in the target RNA complementary to the gRNA spacer), and is independent of the sequence located immediately 5' (upstream) of the protospacer-like sequence. In some embodiments, the engineered nuclease can be further capable of targeting a dsDNA molecule, wherein the gRNA spacer is selected such that it targets a protospacer in the target dsDNA molecule having a PAM selected from 5'-TTTG-3', 5'-TTTA-3', and 5'-TTTR-3'. In other embodiments, the engineered nuclease is incapable of targeting a dsDNA molecule, wherein the gRNA spacer is selected such that any protospacers in the dsDNA molecule targeted by the gRNA spacer do not have a PAM selected from 5'-TTTA-3', and 5'-TTTR-3'.

In some embodiments, the heterologous polypeptide comprising the engineered nuclease (e.g., and/or a complex comprising the heterologous polypeptide) can regulate expression and/or activity of a target gene (e.g., target endogenous gene). In some embodiments, the heterologous polypeptide and/or a complex thereof can edit the sequence of a nucleic acid (e.g., a gene and/or gene product). A nuclease-active variant of the engineered nuclease can edit a nucleic acid sequence by generating a double-stranded break or single-stranded break in a target polynucleotide.

In some embodiments, the heterologous polypeptide comprising the engineered nuclease (e.g., and/or a complex comprising the heterologous polypeptide) can generate a double-strand break in a target polynucleotide, such as DNA. A double-strand break in DNA can result in DNA break repair which allows for the introduction of gene modification(s) (e.g., nucleic acid editing). In some embodiments, a nuclease induces site-specific single-strand DNA breaks or nicks, thus resulting in HDR.

A double-strand break in DNA can result in DNA break repair which allows for the introduction of gene modification(s) (e.g., nucleic acid editing). DNA break repair can occur via non-homologous end joining (NHEJ) or homology-directed repair (HDR). In HDR, a donor DNA repair template or template polynucleotide that contains homology arms flanking sites of the target DNA can be provided.

In some embodiments, the heterologous polypeptide comprising the engineered nuclease (e.g., and/or a complex comprising the heterologous polypeptide) does not generate a double-strand break in a target polynucleotide, such as DNA. Binding of the heterologous polypeptide or the complex comprising the heterologous polypeptide (e.g., a complex comprising a nuclease deficient variant of the engineered nuclease and a guide RNA) without a nucleic acid break can be sufficient to regulate expression (e g, enhance or suppress) of a target gene (e.g., endogenous target gene).

Target Gene

The disclosure provides compositions, methods, and systems for modulating expression of one or more target genes. The target gene(s) can be one or more endogenous target genes, such as (i) a disease causing allele, e.g., a mutant allele, and/or (ii) a non-disease causing allele, e.g., a wild type allele. For example, disclosed herein are one or more complexes that comprise a guide moiety and one or more heterologous polypeptides comprising the engineered polypeptide (e.g., comprising the engineered nuclease) as disclosed herein that can modulate (e.g., increase or decrease) an activity or expression level of a target gene (e.g., in a cell). Such complex comprising a guide moiety (e.g., small guide RNA) and an engineered nuclease can effect the modulation of expression of target gene(s) via cleavage of the target gene(s). Alternatively or in addition to, such complex comprise a gene modulator operatively coupled to (e.g., fused to) the engineered nuclease, such that the complex can effect the modulation of expression of target gene(s) without cleaving the target gene(s). In some cases, the gene modulator may effect an increase in expression of the target gene. In some cases, the gene modulator may effect a decrease in expression of the target gene. In some cases, the gene modulator (e.g., a gene editing moiety, as described herein) may effect editing of a target gene, for example, to correct an undesirable mutation in a target gene such that expression of the mutated gene is decreased, and expression of the corrected gene is increased.

In some embodiments, a target gene or regulatory sequence thereof is endogenous to a cell, for example, present in the cell's genome, or endogenous to a subject, for example, present in the subject's genome. In some embodiments, a target gene or regulatory sequence thereof is not part of an engineered reporter system.

In some embodiments, a target gene is exogenous to a host subject, for example, a pathogen target gene or an exogenous gene expressed as a result of a therapeutic intervention, such as a gene therapy and/or cell therapy. In some embodiments, a target gene is an exogenous reporter gene. In some embodiments, a target gene is an exogenous synthetic gene.

In some embodiments, the systems and methods as disclosed herein can modulate (e.g., increase or decrease) expression of a target gene (e.g., upon introducing a complex comprising the heterologous polypeptide into a cell or population of cells) or a duration thereof. In some embodiments, an expression level is an RNA expression level can be measured by, for example, RNAseq, qPCR, microarray, gene array, FISH, etc. In some embodiments, an expression level is a protein expression level can be measured by, for example, Western Blot, ELISA, multiplex immunoassay, mass spectrometry, NMR, proteomics, flow cytometry, mass cytometry, etc.

In some embodiments, the systems and methods as disclosed herein can modulate (e.g., increase or decrease) expression of a target gene (e.g., upon introducing a complex comprising the heterologous polypeptide into a cell or population of cells) or a duration thereof by at least about 10%, at least about 20%, at least about 30%, at least about 40%, at least about 50%, at least about 60%, at least about 70%, at least about 80%, at least about 90%, at least about 2-fold, at least about 3 fold, at least about 4 fold, at least about 5 fold, at least about 6 fold, at least about 7 fold, at least about 8 fold, at least about 9 fold, at least about 10 fold, at least about 11 fold, at least about 12 fold, at least about 13 fold, at least about 14, at least fold about 15 fold, at least about 20 fold, at least about 30 fold, at least about 40 fold, at least about 50 fold, at least about 60 fold, at least about 70 fold, at least about 80 fold, at least about 90 fold, at least about 100 fold, at least about 150 fold, at least about 200 fold, at least about 250 fold, at least about 300 fold, at least about 350 fold, at least about 400 fold, at least about 500 fold, at least about 600 fold, at least about 700 fold, at least about 800 fold, at least about 900 fold, at least about 1000 fold, at least about 1500 fold, at least about 2000 fold, or at least about 3000 fold.

In some embodiments, the systems and methods as disclosed herein can modulate (e.g., increase or decrease) expression of a target gene (e.g., upon introducing a complex comprising the heterologous polypeptide into a cell or population of cells) or a duration thereof by at most about 50%, at most about 60%, at most about 70%, at most about 80%, at most about 90%, at most about 2-fold, at most about 3 fold, at most about 4 fold, at most about 5 fold, at most about 6 fold, at most about 7 fold, at most about 8 fold, at most about 9 fold, at most about 10 fold, at most about 11 fold, at most about 12 fold, at most about 13 fold, at most about 14, at most fold about 15 fold, at most about 20 fold, at most about 30 fold, at most about 40 fold, at most about 50 fold, at most about 60 fold, at most about 70 fold, at most about 80 fold, at most about 90 fold, at most about 100 fold, at most about 150 fold, at most about 200 fold, at most about 250 fold, at most about 300 fold, at most about 350 fold, at most about 400 fold, at most about 500 fold, at most about 600 fold, at most about 700 fold, at most about 800 fold, at most about 900 fold, at most about 1000 fold, at most about 1500 fold, at most about 2000 fold, at most about 3000 fold, at most about 5000 fold, or at most about 10000 fold.

In some embodiments, the systems and methods as disclosed herein can modulate (e.g., increase or decrease) expression of a target gene (e.g., upon introducing a complex comprising the heterologous polypeptide into a cell or population of cells) or a duration thereof by about 10%, about 20%, about 30%, about 40%, about 50%, about 60%, about 70%, about 80%, about 90%, about 2-fold, about 3 fold, about 4 fold, about 5 fold, about 6 fold, about 7 fold, about 8 fold, about 9 fold, about 10 fold, about 11 fold, about 12 fold, about 13 fold, about 14, about 15 fold, about 20 fold, about 30 fold, about 40 fold, about 50 fold, about 60 fold, about 70 fold, about 80 fold, about 90 fold, about 100 fold, about 150 fold, about 200 fold, about 250 fold, about 300 fold, about 350 fold, about 400 fold, about 500 fold, about 600 fold, about 700 fold, about 800 fold, about 900 fold, about 1000 fold, about 1500 fold, about 2000 fold, about 3000 fold, about 5000 fold, or about 10000 fold.

In some embodiments, the systems and methods as disclosed herein can modulate (e.g., increase or decrease) expression of a target gene (e.g., upon introducing a complex comprising the heterologous polypeptide into a cell or population of cells) or a duration thereof from below a limit of detection to a detectable level.

In some embodiments, the degree in change of expression or duration thereof is relative to before introducing the system of the present disclosure (e.g., a complex comprising the heterologous polypeptide) into the cell or population of cells. In some embodiments, the degree in change of expression or duration thereof is relative to a corresponding control cell or population of cells that are not treated with the system of the present disclosure. In some embodiments, the degree in change of expression or duration thereof is relative to a corresponding control cell or population of cells that are treated with an alternative to the system of the present disclosure.

In some embodiments, the degree in change of expression or duration thereof is relative to a control nuclease. The control nuclease can comprise a naturally occurring nuclease (e.g., (i) the polypeptide sequence of SEQ ID NO: 1 or (ii) the polypeptide sequence of any one of the Cas proteins selected from TABLE 2) or any modification thereof (e.g., a variant thereof with reduced nuclease activity and operatively coupled to a gene modulator). For example, the control nuclease can be dCasMINI that is coupled to (e.g., fused to) the same gene modulator, which same gene modulator is coupled to the engineered nuclease as disclosed herein.

In some embodiments, the systems and methods as disclosed herein can modulate (e.g., increase or decrease) an activity level of a target gene (e.g., upon introducing a complex comprising the heterologous polypeptide comprising the engineered nuclease as disclosed herein into a cell or population of cells) or a duration thereof. An activity level can be determined by a suitable functional assay for the target gene in question depending on the functional characteristics of the target gene. For example, an activity level of a target gene that is a mitogen could be determined by measuring cell proliferation; an activity level of a target gene that induces apoptosis could be measured by an annexin V assay or other suitable cell death assay; an activity level of an anti-inflammatory cytokine could be measured by an LPS-induced cytokine release assay.

The systems and methods of the present disclosure can, in some cases, elicit changes in expression and/or activity level of a target gene (e.g., target endogenous gene) that persists for longer than can be achieved with alternative compositions and methods (e.g., suppression via RNAi, e.g., using siRNA). In some embodiments, persistent modulation of gene expression is advantageous as compared to transient modulation.

In some embodiments, the systems and methods as disclosed herein can modulate (e.g., increase or decrease) expression and/or activity level of a target gene for at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 12 hours, at least about 14 hours, at least about 18 hours, at least about 20 hours, at least about 1 day, at least about 2 days, at least about 3 days, at least about 4 days, at least about 5 days, at least about 6 days, at least about 7 days, at least about 8 days, at least about 9 days, at least about 10 days, at least about 14 days, at least about 21 days, at least about 28 days, at least about 5 weeks, at least about 6 weeks, at least about 7 weeks, at least about 8 weeks, at least about 9 weeks, at least about 10 weeks, at least about 12 weeks, at least about 14 weeks, at least about 18 weeks, at least about 20 weeks, at least about 26 weeks, or at least about 5 months, at least about 6 months, at least about 9 months, at least about 12 months, or more.

In some embodiments the systems and methods as disclosed herein can modulate (e.g., increase or decrease) expression and/or activity level of a target gene (e.g., target endogenous gene) to above a certain threshold for at least or up to about 1 hour, at least or up to about 2 hours, at least or up to about 3 hours, at least or up to about 4 hours, at least or up to about 5 hours, at least or up to about 6 hours, at least or up to about 7 hours, at least or up to about 8 hours, at least or up to about 9 hours, at least or up to about 10 hours, at least or up to about 12 hours, at least or up to about 14 hours, at least or up to about 18 hours, at least or up to about 20 hours, at least or up to about 1 day, at least or up to about 2 days, at least or up to about 3 days, at least or up to about 4 days, at least or up to about 5 days, at least or up to about 6 days, at least or up to about 7 days, at least or up to about 8 days, at least or up to about 9 days, at least or up to about 10 days, at least or up to about 14 days, at least or up to about 21 days, at least or up to about 28 days, at least or up to about 5 weeks, at least or up to about 6 weeks, at least or up to about 7 weeks, at least or up to about 8 weeks, at least or up to about 9 weeks, at least or up to about 10 weeks, at least or up to about 12 weeks, at least or up to about 14 weeks, at least or up to about 18 weeks, at least or up to about 20 weeks, at least or up to about 26 weeks, or at least or up to about 5 months, at least or up to about 6 months, at least or up to about 9 months, or at least or up to about 12 months.

In some embodiments, the systems and methods as disclosed herein can modulate (e.g., increase or decrease) expression and/or activity level of a target gene (e.g., target endogenous gene) to above a certain threshold for about 1 hour, about 2 hours, about 3 hours, about 4 hours, about 5 hours, about 6 hours, about 7 hours, about 8 hours, about 9 hours, about 10 hours, about 12 hours, about 14 hours, about 18 hours, about 20 hours, about 1 day, about 2 days, about 3 days, about 4 days, about 5 days, about 6 days, about 7 days, about 8 days, about 9 days, about 10 days, about 14 days, about 21 days, about 28 days, about 5 weeks, about 6 weeks, about 7 weeks, about 8 weeks, about 9 weeks, about 10 weeks, about 12 weeks, about 14 weeks, about 18 weeks, about 20 weeks, about 26 weeks, about 5 months, about 6 months, about 9 months, or about 12 months.

In some embodiments, the engineered polypeptide as disclosed herein (e.g., an engineered nuclease operatively coupled to a gene modulator) can be capable of or can effect enhanced modulation of a target gene, as compared to modulation of the target gene by a control polypeptide (e.g., a control nuclease operatively coupled to the same gene modulator). The control nuclease can be a naturally occurring nuclease (e.g., (i) the polypeptide sequence of SEQ ID NO: 1 or (ii) the polypeptide sequence of any one of the Cas proteins selected from TABLE 2) or any modification thereof (e.g., dCasMINI as disclosed herein).

In some cases, the enhanced modulation of the target gene can be characterized by a change in expression level of the target gene that is greater than that by the control polypeptide. In some examples, such change can be increased expression level of the target gene. The increased expression level of the target gene by the engineered polypeptide as disclosed herein can be greater than that by the control polypeptide, by at least or up to about 1%, at least or up to about 2%, at least or up to about 3%, at least or up to about 4%, at least or up to about 5%, at least or up to about 10%, at least or up to about 15%, at least or up to about 20%, at least or up to about 30%, at least or up to about 40%, at least or up to about 50%, at least or up to about 60%, at least or up to about 70%, at least or up to about 80%, at least or up to about 90%, at least or up to about 100%, at least or up to about 110%, at least or up to about 120%, at least or up to about 150%, at least or up to about 200%, at least or up to about 300%, at least or up to about 400%, or at least or up to about 500%. The increased expression level of the target gene by the engineered polypeptide as disclosed herein can be greater than that by the control polypeptide, by at least or up to about 0.1-fold, at least or up to about 0.2-fold, at least or up to about 0.5-fold, at least or up to about 1-fold, at least or up to about 1.5-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, or at least or up to about 100-fold. In some examples, such change can be decreased (or reduced) expression level of the target gene. The decreased expression level of the target gene by the engineered polypeptide as disclosed herein can be less than that by the control polypeptide, by at least or up to about 1%, at least or up to about 2%, at least or up to about 3%, at least or up to about 4%, at least or up to about 5%, at least or up to about 10%, at least or up to about 15%, at least or up to about 20%, at least or up to about 30%, at least or up to about 40%, at least or up to about 50%, at least or up to about 60%, at least or up to about 70%, at least or up to about 80%, at least or up to about 90%, at least or up to about 100%, at least or up to about 110%, at least or up to about 120%, at least or up to about 150%, at least or up to about 200%, at least or up to about 300%, at least or up to about 400%, or at least or up to about 500%. The decreased (or reduced) expression level of the target gene by the engineered polypeptide as disclosed herein can be less than that by the control polypeptide, by at least or up to about 0.1-fold, at least or up to about 0.2-fold, at least or up to about 0.5-fold, at least or up to about 1-fold, at least or up to about 1.5-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, or at least or up to about 100-fold.

In some cases, the enhanced modulation of the target gene can be characterized by a prolonged change in expression level of the target gene (e.g., increased expression or decreased expression above certain threshold as disclosed herein) that is longer than that by the control polypeptide. The prolonged change in the expression level of the target gene by the engineered polypeptide as disclosed herein can be longer than that by the control polypeptide, by at least or up to about 1%, at least or up to about 2%, at least or up to about 3%, at least or up to about 4%, at least or up to about 5%, at least or up to about 10%, at least or up to about 15%, at least or up to about 20%, at least or up to about 30%, at least or up to about 40%, at least or up to about 50%, at least or up to about 60%, at least or up to about 70%, at least or up to about 80%, at least or up to about 90%, at least or up to about 100%, at least or up to about 110%, at least or up to about 120%, at least or up to about 150%, at least or up to about 200%, at least or up to about 300%, at least or up to about 400%, or at least or up to about 500%. The prolonged change in the expression level of the target gene by the engineered polypeptide as disclosed herein can be longer than that by the control polypeptide, by at least or up to about 0.1-fold, at least or up to about 0.2-fold, at least or up to about 0.5-fold, at least or up to about 1-fold, at least or up to about 1.5-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, or at least or up to about 100-fold. For example, the threshold level can be relative to (i) expression level of the target gene prior to the enhanced modulation, (ii) the greatest increase in the expression level of the target gene for activating the target gene or a portion thereof (e.g., at least 50%, at least 60%, at least 70%, at least 80%, or at least 90% thereof), or (iii) the greatest decrease in the expression level of the target gene for repressing the target gene or a portion thereof (e.g., at least 50%, at least 60%, at least 70%, at least 80%, or at least 90% thereof) In some embodiments, the target gene (e.g., endogenous target gene) can be a disease-causing allele, such as a mutant variant of a wild type allele. The disease can be a genetic disease, such as a hereditary disorder. Non-limiting examples of the genetic disorder can include Duchenne muscular dystrophy (DMD), hemophilia, cystic fibrosis, Huntington's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and Tay-Sachs disease. In some cases, the target gene can be a gene encoding a protein. In some cases, the target gene can be a gene regulatory sequence (e.g., promoters, enhancers, repressors, silencers, insulators, cis-regulatory elements, trans-regulatory elements, epigenetic modification (e.g., DNA methylation) sites, etc.) that can influence expression of a gene encoding a protein of interest as provided herein. For example, target gene regulatory sequences can be physically located outside of the transcriptional unit or open reading frame that encodes a product of the target gene.

In some embodiments, a target gene regulatory sequence does not contain a nucleotide sequence that is exogenous to the subject or host cell. In some embodiments, a target gene regulatory sequence does not contain an engineered or artificially generated or introduced nucleotide sequence.

In some embodiments, a target gene (e.g., target endogenous gene) is a gene that is over-expressed or under-expressed in a disease or condition. In some embodiments, a target gene is a gene that is over-expressed or under-expressed in a heritable genetic disease.

In some embodiments, a target gene (e.g., target endogenous gene) is a gene that is over-expressed or under-expressed in a cancer, for example, acute leukemia, astrocytomas, biliary cancer (cholangiocarcinoma), bone cancer, breast cancer, brain stem glioma, bronchioloalveolar cell lung cancer, cancer of the adrenal gland, cancer of the anal region, cancer of the bladder, cancer of the endocrine system, cancer of the esophagus, cancer of the head or neck, cancer of the kidney, cancer of the parathyroid gland, cancer of the penis, cancer of the pleural/peritoneal membranes, cancer of the salivary gland, cancer of the small intestine, cancer of the thyroid gland, cancer of the ureter, cancer of the urethra, carcinoma of the cervix, carcinoma of the endometrium, carcinoma of the fallopian tubes, carcinoma of the renal pelvis, carcinoma of the vagina, carcinoma of the vulva, cervical cancer, chronic leukemia, colon cancer, colorectal cancer, cutaneous melanoma, ependymoma, epidermoid tumors, Ewings sarcoma, gastric cancer, glioblastoma, glioblastoma multiforme, glioma, hematologic malignancies, hepatocellular (liver) carcinoma, hepatoma, Hodgkin's Disease, intraocular melanoma, Kaposi sarcoma, lung cancer, lymphomas, medulloblastoma, melanoma, meningioma, mesothelioma, multiple myeloma, muscle cancer, neoplasms of the central nervous system (CNS), neuronal cancer, small cell lung cancer, non-small cell lung cancer, osteosarcoma, ovarian cancer, pancreatic cancer, pediatric malignancies, pituitary adenoma, prostate cancer, rectal cancer, renal cell carcinoma, sarcoma of soft tissue, schwanoma, skin cancer, spinal axis tumors, squamous cell carcinomas, stomach cancer, synovial sarcoma, testicular cancer, uterine cancer, or tumors and their metastases, including refractory versions of any of the above cancers, or a combination thereof.

Non-limiting examples of a target gene or a gene encoding a protein of interest, as disclosed herein, are included in TABLE 1.

Guide Nucleic Acid Molecule

In some aspects, the present disclosure provides a guide nucleic acid molecule (e.g., an engineered guide nucleic acid molecule) configured to form a complex with a Cas protein. The Cas protein can be a naturally occurring protein. The Cas protein can be an engineered nuclease variant as provided herein. The guide nucleic acid molecule can comprise a spacer sequence exhibiting specific binding to a target polynucleotide sequence operatively coupled to a target gene (e.g., in a cell). The target polynucleotide sequence can be part of the target gene. Alternatively, the target polynucleotide sequence can be upstream (e.g., part of or adjacent to a promoter sequence of the target gene) or downstream of the target gene (e.g., part of or adjacent to a termination sequence of the target gene). The guide nucleic acid molecule can comprise a scaffold sequence for forming the complex with the Cas protein. The spacer sequence and the scaffold sequence can be part of a single polynucleotide sequence (e.g., a single guide nucleic acid molecule, such as sgRNA). Alternatively, the spacer sequence and the scaffold sequence can be separate molecules that are hybridize for forming the complex with the Cas protein.

Without wishing to be bound by theory, the guide nucleic acid molecule as disclosed herein can be operatively coupled to (e.g., can form a functional complex with) one or more Cas proteins, including, but not limited to, Un1Cas12f1, a selected from TABLE 2, or any of the engineered nuclease variant provided throughout the present disclosure (e.g., the polypeptide of SEQ ID NO: 12).

In some embodiments, the scaffold sequence as disclosed herein is not identical to the polynucleotide sequence of SEQ ID NO: 500. The scaffold sequence can comprise at least one deletion, as compared to (e.g., when aligned to) the polynucleotide sequence of SEQ ID NO: 500. Without wishing to be bound by theory, the at least one deletion of the scaffold sequence can be determined by performing a deletion landscape study (e.g., iterative and/or comprehensive deletion) of the control scaffold sequence of SEQ ID NO: 500. The scaffold sequence can comprise at least one mutation, as compared to (e.g., when aligned to) the polynucleotide sequence of SEQ ID NO: 500. Without wishing to be bound by theory, the at least one mutation of the scaffold sequence can be determined by performing a mutation landscape study (e.g., iterative and/or comprehensive mutation) of the control scaffold sequence of SEQ ID NO: 500. The at least one deletion as disclosed herein can be removal of a nucleotide. Alternatively, the at least one deletion can be replacement of a nucleotide with a different nucleotide (e.g., mutation).

In some embodiments, the scaffold sequence can comprise one or more nucleotide deletions when aligned to (or compared to) the control polynucleotide sequence of SEQ ID NO: 500. The one or more nucleotide deletions can comprise a single deletion. The one or more nucleotide deletions can comprise a plurality of nucleotide deletions, such as at least or up to about 2 deletions, at least or up to about 3 deletions, at least or up to about 4 deletions, at least or up to about 5 deletions, at least or up to about 6 deletions, at least or up to about 7 deletions, at least or up to about 8 deletions, at least or up to about 9 deletions, at least or up to about 10 deletions, at least or up to about 11 deletions, at least or up to about 12 deletions, at least or up to about 13 deletions, at least or up to about 14 deletions, at least or up to about 15 deletions, at least or up to about 16 deletions, at least or up to about 17 deletions, at least or up to about 18 deletions, at least or up to about 19 deletions, at least or up to about 20 deletions, at least or up to about 22 deletions, at least or up to about 24 deletions, at least or up to about 25 deletions, at least or up to about 26 deletions, at least or up to about 28 deletions, at least or up to about 30 deletions, at least or up to about 32 deletions, at least or up to about 34 deletions, at least or up to about 35 deletions, at least or up to about 36 deletions, at least or up to about 38 deletions, at least or up to about 40 deletions, at least or up to about 42 deletions, at least or up to about 44 deletions, at least or up to about 45 deletions, at least or up to about 46 deletions, at least or up to about 48 deletions, at least or up to about 50 deletions, at least or up to about 52 deletions, at least or up to about 54 deletions, at least or up to about 55 deletions, at least or up to about 56 deletions, at least or up to about 58 deletions, at least or up to about 60 deletions, at least or up to about 70 deletions, or at least or up to about 80 deletions. The plurality of nucleotide deletions can be adjacent to each other (e.g., consecutive), when aligned to the polynucleotide sequence of SEQ ID NO: 500. The scaffold sequence can comprise a single consecutive deletion. The scaffold sequence can comprise a plurality of consecutive deletions, in which one consecutive deletion is not directly adjacent to another consecutive deletion when aligned to the polynucleotide sequence of SEQ ID NO: 500.

In some embodiments, when aligned to the control polynucleotide sequence of SEQ ID NO: 500, the scaffold sequence as disclosed herein can comprise one or more nucleotide deletions in one or more members from the nucleotides 1-10, the nucleotides 11-20, the nucleotides 21-30, the nucleotides 31-40, the nucleotides 41-50, the nucleotides 51-60, the nucleotides 61-70, the nucleotides 71-80, the nucleotides 81-90, the nucleotides 91-100, the nucleotides 101-110, the nucleotides 111-120, the nucleotides 121-130, the nucleotides 131-140, the nucleotides 141-150, and/or the nucleotides 151-159 of SEQ ID NO: 500.

In some embodiments, when aligned to the control polynucleotide sequence of SEQ ID NO: 500, the scaffold sequence as disclosed herein can comprise one or more nucleotide deletions in the nucleotides 1-25 of the polynucleotide sequence of SEQ ID NO: 500, such as the nucleotides 1-23, the nucleotides 3-23, the nucleotides 5-23, the nucleotides 7-23, the nucleotides 9-23, the nucleotides 11-23, the nucleotides 13-23, the nucleotides 15-23, the nucleotides 17-23, the nucleotides 19-23, and/or the nucleotides 21-23 of the polynucleotide sequence of SEQ ID NO: 500. When aligned to the control polynucleotide sequence of SEQ ID NO: 500, the scaffold sequence as disclosed herein can comprise one or more nucleotide deletions in the nucleotides 1-23, the nucleotides 1-21, the nucleotides 1-19, the nucleotides 1-17, the nucleotides 1-15, the nucleotides 1-13, the nucleotides 1-11, the nucleotides 1-9, the nucleotides 1-7, the nucleotides 1-5, and/or the nucleotides 1-3 of the polynucleotide sequence of SEQ ID NO: 500. When aligned to the control polynucleotide sequence of SEQ ID NO: 500, the scaffold sequence as disclosed herein can comprise one or more nucleotide deletions in the nucleotides 1-5, the nucleotides 6-10, the nucleotides 11-15, the nucleotides 16-20, and/or the nucleotides 21-23 of the polynucleotide sequence of SEQ ID NO: 500. When aligned to the control polynucleotide sequence of SEQ ID NO: 500, the scaffold sequence as disclosed herein can comprise one or more nucleotide deletions in the nucleotide 1, nucleotide 2, nucleotide 3, nucleotide 4, nucleotide 5, nucleotide 6, nucleotide 7, nucleotide 8, nucleotide 9, nucleotide 10, nucleotide 11, nucleotide 12, nucleotide 13, nucleotide 14, nucleotide 15, nucleotide 16, nucleotide 17, nucleotide 18, nucleotide 19, nucleotide 20, nucleotide 21, nucleotide 22, nucleotide 23, nucleotide 24, and/or nucleotide 25 of the polynucleotide sequence of SEQ ID NO: 500.

In some embodiments, when aligned to the control polynucleotide sequence of SEQ ID NO: 500, the scaffold sequence as disclosed herein can comprise one or more nucleotide deletions in the nucleotides 35-65 of the polynucleotide sequence of SEQ ID NO: 500, such as the nucleotides 35-61, the nucleotides 37-61, the nucleotides 39-61, the nucleotides 41-61, the nucleotides 43-61, the nucleotides 45-61, the nucleotides 47-61, the nucleotides 49-61, the nucleotides 51-61, the nucleotides 53-61, the nucleotides 55-61, the nucleotides 57-61, and/or the nucleotides 59-61 of the polynucleotide sequence of SEQ ID NO: 500. When aligned to the control polynucleotide sequence of SEQ ID NO: 500, the scaffold sequence as disclosed herein can comprise one or more nucleotide deletions in the nucleotides 35-61, the nucleotides 35-59, the nucleotides 35-57, the nucleotides 35-55, the nucleotides 35-53, the nucleotides 35-51, the nucleotides 35-49, the nucleotides 35-47, the nucleotides 35-45, the nucleotides 35-43, the nucleotides 35-41, the nucleotides 35-39, and/or the nucleotides 35-37 of the polynucleotide sequence of SEQ ID NO: 500. When aligned to the control polynucleotide sequence of SEQ ID NO: 500, the scaffold sequence as disclosed herein can comprise one or more nucleotide deletions in the nucleotide 35, nucleotide 36, nucleotide 37, nucleotide 38, nucleotide 39, nucleotide 40, nucleotide 41, nucleotide 42, nucleotide 43, nucleotide 44, nucleotide 45, nucleotide 46, nucleotide 47, nucleotide 48, nucleotide 49, nucleotide 50, nucleotide 51, nucleotide 52, nucleotide 53, nucleotide 54, nucleotide 55, nucleotide 56, nucleotide 57, nucleotide 58, nucleotide 59, nucleotide 60, nucleotide 61, nucleotide 62, nucleotide 63, nucleotide 64, and/or nucleotide 65 of the polynucleotide sequence of SEQ ID NO: 500.

In some embodiments, when aligned to the control polynucleotide sequence of SEQ ID NO: 500, the scaffold sequence as disclosed herein can comprise one or more nucleotide deletions in the nucleotides 135-150 of the polynucleotide sequence of SEQ ID NO: 500, such as the nucleotides 136-149, the nucleotides 137-149, the nucleotides 139-149, the nucleotides 141-149, the nucleotides 143-149, the nucleotides 145-149, and/or the nucleotides 147-149 nucleotides of the polynucleotide sequence of SEQ ID NO: 500. When aligned to the control polynucleotide sequence of SEQ ID NO: 500, the scaffold sequence as disclosed herein can comprise one or more nucleotide deletions in the nucleotides 136-149, the nucleotides 136-147, the nucleotides 136-145, the nucleotides 136-143, the nucleotides 136-141, the nucleotides 136-139, and/or the nucleotides 136-137 of the polynucleotide sequence of SEQ ID NO: 500. When aligned to the control polynucleotide sequence of SEQ ID NO: 500, the scaffold sequence as disclosed herein can comprise one or more nucleotide deletions in the nucleotide 135, nucleotide 136, nucleotide 137, nucleotide 138, nucleotide 139, nucleotide 140, nucleotide 141, nucleotide 142, nucleotide 143, nucleotide 144, nucleotide 145, nucleotide 146, nucleotide 147, nucleotide 148, nucleotide 149, and/or nucleotide 150 of the polynucleotide sequence of SEQ ID NO: 500.

In some embodiments, when aligned to the control polynucleotide sequence of SEQ ID NO: 500, the scaffold sequence as disclosed herein can comprise one or more nucleotide deletions in the nucleotides 136-151 of the polynucleotide sequence of SEQ ID NO: 500. In some cases, the scaffold sequence as disclosed herein can comprise one or more nucleotide deletions in the nucleotide T136, T137, C138, A139, T140, T141, T142, G143, A144, A145, T146, G147, A148, A149, G150, and/or G151 of the polynucleotide sequence of SEQ ID NO: 500. In some cases, the scaffold sequence as disclosed herein can comprise one or more nucleotide deletions (e.g., at least 1, at least 2, at least 3, at least 4, at least 5, at least 6, at least 7, at least 8, at least 9, at least 10, at least 11, or all 12 of) in the nucleotide T136, T137, C138, A139, T140, T141, T142, A144, A145, T146, A148, and/or A149 of the polynucleotide sequence of SEQ ID NO: 500. In some cases, the scaffold sequence as disclosed herein can comprise at least or up to about 1 nucleotide, at least or up to about 2 nucleotides, at least or up to about 3 nucleotides, or all 4 nucleotides selected from the group consisting of G143, G147, G150, and G151, when aligned to the polynucleotide sequence of SEQ ID NO: 500.

In some embodiments, the scaffold sequence as disclosed herein is not identical to the polynucleotide sequence of a combination of SEQ ID NO: 549 and SEQ ID NO: 550. For example, the polynucleotides of SEQ ID NO: 549 and SEQ ID NO: 550 may be coupled to the 5' end the 3' end of a spacer sequence, respectively, to be used as a control sgRNA molecule to compare the activity of any of the scaffold sequence provided herein. In some embodiments, the scaffold sequence as disclosed herein is not identical to the polynucleotide sequence of a combination of SEQ ID NO: 551 and SEQ ID NO: 552. For example, the polynucleotides of SEQ ID NO: 551 and SEQ ID NO: 552 may be coupled to the 5' end the 3' end of a spacer sequence, respectively, to be used as a control sgRNA molecule to compare the activity of any of the scaffold sequence provided herein.

In some embodiments, the scaffold sequence (e.g., a consecutive polynucleotide sequence of the scaffold sequence) can be characterized by exhibiting at least or up to about 60%, at least or up to about 65%, at least or up to about 70%, at least or up to about 71%, at least or up to about 72%, at least or up to about 73%, at least or up to about 74%, at least or up to about 75%, at least or up to about 76%, at least or up to about 77%, at least or up to about 78%, at least or up to about 79%, at least or up to about 80%, at least or up to about 81%, at least or up to about 82%, at least or up to about 83%, at least or up to about 84%, at least or up to about 85%, at least or up to about 86%, at least or up to about 87%, at least or up to about 88%, at least or up to about 89%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99, or substantially 100% sequence identity (or complementarity) to the polynucleotide sequence of a member selected from TABLE 6B, TABLE 7B, and TABLE 8B.

In some cases the member can be selected from the group consisting of SEQ ID NOs: 503-152, 519, 524, 528, and 553. In some cases, the member can be selected from the group consisting of SEQ ID NOs: 555, 557, 558, 568, 569, 578, and 580. In some cases, the member can be selected from the group consisting of SEQ ID NOs: 555, 557, 568, 569, 576, 577, 578, 580, 593, 519, and 528.

In some cases, the length of the scaffold sequence can be at least or up to about 80 nucleotides, at least or up to about 85 nucleotides, at least or up to about 90 nucleotides, at least or up to about 91 nucleotides, at least or up to about 92 nucleotides, at least or up to about 93 nucleotides, at least or up to about 94 nucleotides, at least or up to about 95 nucleotides, at least or up to about 96 nucleotides, at least or up to about 97 nucleotides, at least or up to about 98 nucleotides, at least or up to about 99 nucleotides, at least or up to about 100 nucleotides, at least or up to about 101 nucleotides, at least or up to about 102 nucleotides, at least or up to about 103 nucleotides, at least or up to about 104 nucleotides, at least or up to about 105 nucleotides, at least or up to about 106 nucleotides, at least or up to about 107 nucleotides, at least or up to about 108 nucleotides, at least or up to about 109 nucleotides, at least or up to about 110 nucleotides, at least or up to about 112 nucleotides, at least or up to about 114 nucleotides, at least or up to about 115 nucleotides, at least or up to about 116 nucleotides, at least or up to about 118 nucleotides, at least or up to about 120 nucleotides, at least or up to about 122 nucleotides, at least or up to about 124 nucleotides, at least or up to about 125 nucleotides, at least or up to about 126 nucleotides, at least or up to about 128 nucleotides, at least or up to about 130 nucleotides, at least or up to about 135 nucleotides, at least or up to about 140 nucleotides, at least or up to about 145 nucleotides, at least or up to about 150 nucleotides, at least or up to about 155 nucleotides, or at least or up to about 160 nucleotides.

In some embodiments, the scaffold sequence can comprise a consecutive polynucleotide sequence exhibiting at least or up to about 60%, at least or up to about 65%, at least or up to about 70%, at least or up to about 71%, at least or up to about 72%, at least or up to about 73%, at least or up to about 74%, at least or up to about 75%, at least or up to about 76%, at least or up to about 77%, at least or up to about 78%, at least or up to about 79%, at least or up to about 80%, at least or up to about 81%, at least or up to about 82%, at least or up to about 83%, at least or up to about 84%, at least or up to about 85%, at least or up to about 86%, at least or up to about 87%, at least or up to about 88%, at least or up to about 89%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99, or substantially 100% sequence identity (or complementarity) to the polynucleotide sequence of SEQ ID NO: 597 or SEQ ID NO: 598. The consecutive polynucleotide sequence of the scaffold sequence can have a length of at least or up to about 15 nucleotides, at least or up to about 16 nucleotides, at least or up to about 17 nucleotides, at least or up to about 18 nucleotides, at least or up to about 19 nucleotides, at least or up to about 20 nucleotides, at least or up to about 21 nucleotides, at least or up to about 22 nucleotides, at least or up to about 23 nucleotides, at least or up to about 24 nucleotides, at least or up to about 25 nucleotides, at least or up to about 26 nucleotides, at least or up to about 27 nucleotides, at least or up to about 28 nucleotides, at least or up to about 29 nucleotides, at least or up to about 30 nucleotides, at least or up to about 31 nucleotides, at least or up to about 32 nucleotides, at least or up to about 33 nucleotides, at least or up to about 34 nucleotides, at least or up to about 35 nucleotides, at least or up to about 36 nucleotides, at least or up to about 37 nucleotides, at least or up to about 38 nucleotides, at least or up to about 39 nucleotides, or at least or up to about 40 nucleotides. The consecutive polynucleotide sequence can be disposed at the N-terminus or at the C-terminus of the scaffold sequence. The consecutive polynucleotide sequence can be disposed at the N-terminal 50%, at the N-terminal 45%, at the N-terminal 40%, at the N-terminal 35%, at the N-terminal 30%, at the N-terminal 25%, at the N-terminal 20%, at the N-terminal 15%, or at the N-terminal 10% of the scaffold sequence. Alternatively, the consecutive polynucleotide sequence can be disposed at the C-terminal 50%, at the C-terminal 45%, at the C-terminal 40%, at the C-terminal 35%, at the C-terminal 30%, at the C-terminal 25%, at the C-terminal 20%, at the C-terminal 15%, or at the C-terminal 10% of the scaffold sequence. The consecutive polynucleotide sequence can be disposed between the scaffold sequence.

In some embodiments, the spacer sequence of the guide nucleic acid molecule can have a length of at least or up to about 12 nucleotides, at least or up to about 13 nucleotides, at least or up to about 14 nucleotides, at least or up to about 15 nucleotides, at least or up to about 16 nucleotides, at least or up to about 17 nucleotides, at least or up to about 18 nucleotides, at least or up to about 19 nucleotides, at least or up to about 20 nucleotides, at least or up to about 21 nucleotides, or at least or up to about 22 nucleotides.

In some embodiments, the guide nucleic acid molecule can have a length of at least or up to about nucleotides, at least or up to about 85 nucleotides, at least or up to about 90 nucleotides, at least or up to about 95 nucleotides, at least or up to about 96 nucleotides, at least or up to about 97 nucleotides, at least or up to about 98 nucleotides, at least or up to about 99 nucleotides, at least or up to about 100 nucleotides, at least or up to about 101 nucleotides, at least or up to about 102 nucleotides, at least or up to about 103 nucleotides, at least or up to about 104 nucleotides, at least or up to about 105 nucleotides, at least or up to about 106 nucleotides, at least or up to about 107 nucleotides, at least or up to about 108 nucleotides, at least or up to about 109 nucleotides, at least or up to about 110 nucleotides, at least or up to about 111 nucleotides, at least or up to about 112 nucleotides, at least or up to about 113 nucleotides, at least or up to about 114 nucleotides, at least or up to about 115 nucleotides, at least or up to about 116 nucleotides, at least or up to about 117 nucleotides, at least or up to about 118 nucleotides, at least or up to about 119 nucleotides, at least or up to about 120 nucleotides, at least or up to about 121 nucleotides, at least or up to about 122 nucleotides, at least or up to about 123 nucleotides, at least or up to about 124 nucleotides, at least or up to about 125 nucleotides, at least or up to about 130 nucleotides, at least or up to about 135 nucleotides, at least or up to about 140 nucleotides, at least or up to about 145 nucleotides, at least or up to about 150 nucleotides, at least or up to about 155 nucleotides, or at least or up to about 160 nucleotides.

In some examples, the consecutive polynucleotide sequence of the scaffold sequence can be at least about 20, at least about 25, or at least about 30 nucleotides long, and such consecutive polynucleotide sequence can exhibit at least or up to about 60%, at least or up to about 65%, at least or up to about 70%, at least or up to about 71%, at least or up to about 72%, at least or up to about 73%, at least or up to about 74%, at least or up to about 75%, at least or up to about 76%, at least or up to about 77%, at least or up to about 78%, at least or up to about 79%, at least or up to about 80%, at least or up to about 81%, at least or up to about 82%, at least or up to about 83%, at least or up to about 84%, at least or up to about 85%, at least or up to about 86%, at least or up to about 87%, at least or up to about 88%, at least or up to about 89%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99, or substantially 100% sequence identity (or complementarity) to the polynucleotide sequence of (i) the N-terminal 30 nucleotide sequence or (ii) the C-terminal 30 nucleotide sequence of a member selected from TABLE 6B, TABLE 7B, and TABLE 8B (e.g., one or more members from SEQ ID NOs: 555, 557, 568, 569, 576, 577, 578, 580, 593, 519, and 528)

Heterologous Polynucleotide

In some embodiments, a target gene can be targeted by the systems of the present disclosure (e.g., comprising a variant of the engineered nuclease that retains at least a portion of its nuclease activity) to edit the target gene. In some cases, a complex comprising (i) the heterologous polypeptide that comprises the engineered nuclease as disclosed herein and (ii) a guide nucleic acid (e.g., sgRNA) can recognize, bind to, and create a nick (one strand) or a break (two strands) in the target gene, e.g., at or near a target sequence of complex within the target gene. In some cases, the nick or break can be repaired via Non-Homologous End Joining (NHEJ). In some cases, the nick or break can be repaired via Homology-Directed Repair (HDR) or via Homologous Recombination (HR), with a polynucleotide modification template (e.g., a donor template, such as a donor DNA template). In some examples, a heterologous polynucleotide modification template encoding a gene of interest can be provided to the cell, such that the gene of interest can be inserted into the target gene, e.g., for a gene replacement therapy.

In some embodiments, the systems and compositions of the present disclosure a heterologous polynucleotide (e.g., encoding a gene of interest, such as one or more genes selected from TABLE 1) that is introduced to the cell without being interested into a genome of the cell via action of the engineered nuclease of the present disclosure. In some cases, such heterologous polynucleotide encoding the gene of interest can be interested into the genome of the cell via other means, e.g., via adeno-associated virus vectors (e.g., AAV2 or AAV8). Alternatively, such heterologous polynucleotide encoding the gene of interest may be introduced to the intracellular portion of the cell and remain achromosomal (e.g., as an achromosomal plasmid).

Thus, the systems and compositions can comprise the non-disease causing wild type or variant of the target gene, as abovementioned. Alternatively or in addition to, the systems and compositions can comprise a heterologous polynucleotide sequence encoding (or comprising) at least the non-disease causing wild type or variant of the target gene (e.g., that of the endogenous target gene) as disclosed herein.

Composition

In some aspects, the present disclosure provides a composition comprising at least a portion of the system as described, e.g., (i) the heterologous polypeptide comprising the engineered nuclease or a heterologous polynucleotide encoding the heterologous polypeptide and/or (ii) the guide nucleic acid or a heterologous polynucleotide encoding the guide nucleic acid, as disclosed herein, for use in any of the methods as disclosed herein. The subject composition can be usable for modifying a cell in vitro, ex vivo, or in vivo. The subject composition can be usable for treating or enhancing a condition of a subject, as disclosed herein.

The composition as disclosed herein can comprise an active ingredient (e.g., the heterologous polypeptide comprising the engineered nuclease, the guide nucleic acid, etc.) and optionally an additional ingredient (e.g., excipient). If necessary and/or desirable, the composition can be divided, shaped and/or packaged into a desired single- or multi-dose unit or single- or multi-implantation unit.

In some embodiments, the composition can comprise one or more heterologous polynucleotides encoding the active ingredients as disclosed herein. When there are different members within the active ingredients, each member can be encoded by a different heterologous polynucleotide. Alternatively, two or more (e.g., all of) the ingredients can be encoded by a single heterologous polynucleotide. In some cases, a single heterologous polynucleotide an encode (i) the heterologous polypeptide comprising the engineered nuclease (e.g., dCas-transcriptional effector fusion protein, such as dCas-KRAB, dCas-DNMT, dCas-ADA) and (ii) one or more guide nucleic acids (e.g., at least 1, at least 2, at least 3, at least 4, at least 5, or more guide nucleic acids) for targeting specific region(s) or sequence(s) of the target gene.

The one or more heterologous polynucleotides can further comprise one or more promoters (or one or more transcriptional control elements, as used interchangeably herein). Different active ingredients encoded by the one or more heterologous polynucleotides can be under the control of the same promoter or different promoters. A promoter as disclosed herein can be active in a eukaryotic, mammalian, non-human mammalian or human cell. The promoter can be an inducible or constitutively active promoter. Alternatively or additionally, the promoter can be tissue or cell specific. Non-limiting examples of suitable eukaryotic promoters (i.e. promoters functional in a eukaryotic cell) can include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-active promoter (CAG), murine stem cell virus promoter (MSCV), phosphoglycerate kinase-1 locus promoter (PGK) and mouse metallothionein-I. The promoter can be a fungi promoter. The promoter can be a plant promoter. A database of plant promoters can be found (e.g., PlantProm). The expression vector may also contain a ribosome binding site for translation initiation and a transcription terminator. The expression vector may also include appropriate sequences for amplifying expression. In some cases, a promoter as disclosed herein can be a promoter specific for any of the tissues provided herein, or a promoter specific for any of the cell types provided herein.

A heterologous polynucleotide of the one or more heterologous polynucleotides (e.g., the single heterologous polynucleotide) can have a size of at least or up to about 2.5 kilobases, at least or up to about 2.6 kilobases, at least or up to about 2.7 kilobases, at least or up to about 2.8 kilobases, at least or up to about 2.9 kilobases, at least or up to about 3.0 kilobases, at least or up to about 3.1 kilobases, at least or up to about 3.2 kilobases, at least or up to about 3.3 kilobases, at least or up to about 3.4 kilobases, at least or up to about 3.5 kilobases, at least or up to about 3.6 kilobases, at least or up to about 3.7 kilobases, at least or up to about 3.8 kilobases, at least or up to about 3.9 kilobases, at least or up to about 4.0 kilobases, at least or up to about 4.1 kilobases, at least or up to about 4.2 kilobases, at least or up to about 4.3 kilobases, at least or up to about 4.4 kilobases, at least or up to about 4.5 kilobases, at least or up to about 4.6 kilobases, at least or up to about 4.7 kilobases, at least or up to about 4.8 kilobases, at least or up to about 4.9 kilobases, at least or up to about 5.0 kilobases, at least or up to about 5.5 kilobases, at least or up to about 6.0 kilobases, at least or up to about 6.5 kilobases, at least or up to about 7.0 kilobases, at least or up to about 7.5 kilobases, at least or up to about 8.0 kilobases, at least or up to about 9.0 kilobases, or at least or up to about 10 kilobases. In some cases, the heterologous polynucleotide of the one or more heterologous polynucleotides (e.g., the single heterologous polynucleotide) can have a size of between about 3 kilobases and about 5 kilobases, between about 3 kilobases and about 4.8 kilobases, between about 3 kilobases and about 4.6 kilobases, between about 3 kilobases and about 4.4 kilobases, between about 3 kilobases and about 4.2 kilobases, between about 3 kilobases and about 4.0 kilobases, between about 3 kilobases and about 3.5 kilobases, between about 3.5 kilobases and about 5 kilobases, between about 3.5 kilobases and about 4.8 kilobases, between about 3.5 kilobases and about 4.6 kilobases, between about 3.5 kilobases and about 4.4 kilobases, between about 3.5 kilobases and about 4.2 kilobases, between about 3.5 kilobases and about 4 kilobases, between about 4 kilobases and about 5 kilobases, between about 4 kilobases and about 4.9 kilobases, between about 4 kilobases and about 4.8 kilobases, between about 4 kilobases and about 4.7 kilobases, between about 4 kilobases and about 4.6 kilobases, between about 4 kilobases and about 4.5 kilobases, between about 4 kilobases and about 4.4 kilobases, between about 4 kilobases and about 4.3 kilobases, between about 4 kilobases and about 4.2 kilobases, or between about 4 kilobases and about 4.1 kilobases.

A vector (or an expression cassette) can encode at least (i) a Cas protein and (ii) a guide nucleic acid molecule comprising a spacer sequence and a scaffold sequence, as provided herein. The vector can comprise a first polynucleotide sequence encoding the Cas protein, a second polynucleotide sequencing encoding the scaffold sequence, and/ or a third polynucleotide sequence encoding the scaffold sequence. A sum of a length of the first polynucleotide sequence and a length of the second polynucleotide sequence combined can be at least or up to about 1400 nucleotide, at least or up to about 1420 nucleotide, at least or up to about 1440 nucleotide, at least or up to about 1450 nucleotide, at least or up to about 1460 nucleotide, at least or up to about 1480 nucleotide, at least or up to about 1500 nucleotide, at least or up to about 1520 nucleotide, at least or up to about 1540 nucleotide, at least or up to about 1550 nucleotide, at least or up to about 1560 nucleotide, at least or up to about 1580 nucleotide, at least or up to about 1600 nucleotide, at least or up to about 1620 nucleotide, at least or up to about 1640 nucleotide, at least or up to about 1650 nucleotide, at least or up to about 1660 nucleotide, at least or up to about 1680 nucleotide, at least or up to about 1700 nucleotide, at least or up to about 1720 nucleotide, at least or up to about 1740 nucleotide, or at least or up to about 1750 nucleotides. In some embodiments, the sum of the length of the first polynucleotide sequence and the length of the second polynucleotide sequence combined can be less than 1746 nucleotides, less than 1737 nucleotides, or less than 1720 nucleotides.

In some embodiments, the length of the first polynucleotide sequence can be at least or up to about 1400 nucleotides, at least or up to about 1420 nucleotides, at least or up to about 1440 nucleotides, at least or up to about 1450 nucleotides, at least or up to about 1460 nucleotides, at least or up to about 1480 nucleotides, at least or up to about 1500 nucleotides, at least or up to about 1520 nucleotides, at least or up to about 1540 nucleotides, at least or up to about 1550 nucleotides, at least or up to about 1560 nucleotides, at least or up to about 1580 nucleotides, at least or up to about 1600 nucleotides, at least or up to about 1620 nucleotides, at least or up to about 1640 nucleotides, at least or up to about 1650 nucleotides, at least or up to about 1660 nucleotides, at least or up to about 1680 nucleotides, or at least or up to about 1700 nucleotides.

In some embodiments, the length of the second polynucleotide sequence can be at least or up to about 80 nucleotides, at least or up to about 85 nucleotides, at least or up to about 90 nucleotides, at least or up to about 91 nucleotides, at least or up to about 92 nucleotides, at least or up to about 93 nucleotides, at least or up to about 94 nucleotides, at least or up to about 95 nucleotides, at least or up to about 96 nucleotides, at least or up to about 97 nucleotides, at least or up to about 98 nucleotides, at least or up to about 99 nucleotides, at least or up to about 100 nucleotides, at least or up to about 101 nucleotides, at least or up to about 102 nucleotides, at least or up to about 103 nucleotides, at least or up to about 104 nucleotides, at least or up to about 105 nucleotides, at least or up to about 106 nucleotides, at least or up to about 107 nucleotides, at least or up to about 108 nucleotides, at least or up to about 109 nucleotides, at least or up to about 110 nucleotides, at least or up to about 112 nucleotides, at least or up to about 114 nucleotides, at least or up to about 115 nucleotides, at least or up to about 116 nucleotides, at least or up to about 118 nucleotides, at least or up to about 120 nucleotides, at least or up to about 122 nucleotides, at least or up to about 124 nucleotides, at least or up to about 125 nucleotides, at least or up to about 126 nucleotides, at least or up to about 128 nucleotides, at least or up to about 130 nucleotides, at least or up to about 135 nucleotides, at least or up to about 140 nucleotides, at least or up to about 145 nucleotides, at least or up to about 150 nucleotides, at least or up to about 155 nucleotides, or at least or up to about 160 nucleotides.

In some embodiments, sum of the length of the first polynucleotide sequence and the length of the second polynucleotide sequence combined may be sufficiently small, such that the vector encoding at least the Cas protein and the guide nucleic acid molecule can be (i) small/compact and/or (ii) have enough room for additional cargo (e.g., gene modulator(s) operatively coupled to the Cas protein, or the heterologous polynucleotide as provided herein). Even with the small/compact size of the vector, a complex comprising the Cas protein and the guide nucleic acid molecule encoded by the vector may be functional. In some cases, the complex encoded by the vector can be functionally active to bind a target polynucleotide sequence and edit (e.g., cleave, delete nucleotide(s), add nucleotide(s), edit base(s), etc.) at least a portion of the target polynucleotide sequence. In some cases, the complex encoded by the vector can be functionally active to effect modulated expression level of the target gene in the cell. Accordingly, (A1) the modulated expression level of the target gene (alternatively or in addition to, the activity level thereof) by the complex can be comparable to or superior than (A2) that by a control complex comprising the Cas protein and a control guide nucleic acid molecule.

In some cases, (A1) the modulated expression level of the target gene by the complex can be comparable to (A2), such that (A1) does not differ from (A2) by no more than 50%, no more than 45%, no more than 40%, no more than 35%, no more than 30%, no more than 25%, no more than 20%, no more than 15%, no more than 10%, no more than 8%, no more than 6%, no more than 5%, no more than 4%, no more than 3%, no more than 2%, or no more than 1% of (A2).

In some cases, the expression level of the target gene can be activated by the engineered nuclease variant and/or guide nucleic acid molecule disclosed herein, and (A1) the modulated expression level of the target gene by the complex can be superior than (A2), such that (A1) is greater than (A2) by at least or up to about 1%, at least or up to about 2%, at least or up to about 5%, at least or up to about 10%, at least or up to about 15%, at least or up to about 20%, at least or up to about 30%, at least or up to about 40%, at least or up to about 50%, at least or up to about 60%, at least or up to about 70%, at least or up to about 80%, at least or up to about 90%, at least or up to about 100%, at least or up to about 150%, at least or up to about 200%, at least or up to about 250%, at least or up to about 300%, at least or up to about 350%, at least or up to about 400%, at least or up to about 450%, or at least or up to about 500% of (A2), or such that (A1) is greater than (A2) by at least or up to about 0.1-fold, at least or up to about 0.2-fold, at least or up to about 0.3-fold, at least or up to about 0.4-fold, at least or up to about 0.5-fold, at least or up to about 1-fold, at least or up to about 1.5-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, or at least or up to about 10-fold as compared to (A2).

In some cases, the expression level of the target gene can be reduced (e.g., repressed) by the engineered nuclease variant and/or guide nucleic acid molecule disclosed herein, and (A1) the modulated expression level of the target gene by the complex can be superior than (A2), such that (A1) is less than (A2) by at least or up to about 1%, at least or up to about 2%, at least or up to about 5%, at least or up to about 10%, at least or up to about 15%, at least or up to about 20%, at least or up to about 30%, at least or up to about 40%, at least or up to about 50%, at least or up to about 60%, at least or up to about 70%, at least or up to about 80%, at least or up to about 90%, at least or up to about 100%, at least or up to about 150%, at least or up to about 200%, at least or up to about 250%, at least or up to about 300%, at least or up to about 350%, at least or up to about 400%, at least or up to about 450%, or at least or up to about 500% of (A2), or such that (A1) is less than (A2) by at least or up to about 0.1-fold, at least or up to about 0.2-fold, at least or up to about 0.3-fold, at least or up to about 0.4-fold, at least or up to about 0.5-fold, at least or up to about 1-fold, at least or up to about 1.5-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, or at least or up to about 10-fold as compared to (A2).

In some cases, the control guide nucleic acid molecule can be longer than the guide nucleic acid molecule encoded by the vector disclosed herein. A control scaffold sequence of the control guide nucleic acid molecule can be longer than the scaffold sequence of the guide nucleic acid molecule encoded by the vector, by at least or up to about 1 nucleotide, at least or up to about 2 nucleotides, at least or up to about 5 nucleotides, at least or up to about 10 nucleotides, at least or up to about 15 nucleotides, at least or up to about 20 nucleotides, at least or up to about 25 nucleotides, at least or up to about 30 nucleotides, at least or up to about 35 nucleotides, at least or up to about 40 nucleotides, at least or up to about 45 nucleotides, at least or up to about 50 nucleotides, at least or up to about 55 nucleotides, at least or up to about 60 nucleotides, at least or up to about 65 nucleotides, at least or up to about 70 nucleotides, at least or up to about 75 nucleotides, or at least or up to about 80 nucleotides. For example, the control guide nucleic acid molecule can comprise the polypeptide sequence of SEQ ID NO: 10.

A method of delivery of the one or more heterologous polynucleotides provided herein to the cell can involve viral delivery methods or non-viral delivery methods. Thus, the one or more heterologous polynucleotides can be one or more viral vectors (e.g., one or more AAV vectors). Alternatively, the one or more heterologous polynucleotides can be non-viral vectors that are complexed with or encapsulated by non-viral delivery moieties, such as cationic lipids and/or lipid particles (e.g., lipid nanoparticles (LNP)).

Methods of non-viral delivery of nucleic acids can include lipofection, nucleofection, microinjection, biolistics, virosomes, liposomes, immunoliposomes, polycation or lipid:nucleic acid conjugates, naked DNA, artificial virions, and agent-enhanced uptake of DNA. Cationic and neutral lipids that are suitable for efficient receptor-recognition lipofection of polynucleotides can be used. Delivery can be to cells (e.g., in vitro or ex vivo administration) or target tissues (e.g., in vivo administration).

RNA or DNA viral based systems can be used to target specific cells in the body and trafficking the viral payload to the nucleus of the cell. Viral vectors can be administered directly (in vivo), or they can be used to treat cells in vitro, and the modified cells can optionally be administered (ex vivo). Viral based systems can include retroviral, lentivirus, adenoviral, adeno-associated and herpes simplex virus vectors for gene transfer. Integration in the host genome can occur with the retrovirus, lentivirus, and adeno-associated virus gene transfer methods, which can result in long term expression of the inserted transgene. High transduction efficiencies can be observed in many different cell types and target tissues.

The tropism of a retrovirus can be altered by incorporating foreign envelope proteins, expanding the potential target population of target cells. Lentiviral vectors are retroviral vectors that can transduce or infect non-dividing cells and produce high viral titers. Selection of a retroviral gene transfer system can depend on the target tissue. Retroviral vectors can comprise cis-acting long terminal repeats with packaging capacity for up to 6-10 kb of foreign sequence. The minimum cis-acting LTRs can be sufficient for replication and packaging of the vectors, which can be used to integrate the therapeutic gene into the target cell to provide permanent transgene expression. Retroviral vectors can include those based upon murine leukemia virus (MuLV), gibbon ape leukemia virus (GaLV), Simian Immuno deficiency virus (SIV), human immuno deficiency virus (HIV), and combinations thereof.

An adenoviral-based systems can be used. Adenoviral-based systems can lead to transient expression of the transgene. Adenoviral based vectors can have high transduction efficiency in cells and may not require cell division. High titer and levels of expression can be obtained with adenoviral based vectors. Adeno-associated virus ("AAV") vectors can be used to transduce cells with target nucleic acids, e.g., in the in vitro production of nucleic acids and peptides, and for in vivo and ex vivo gene therapy procedures.

Packaging cells can be used to form virus particles capable of infecting a host cell. Such cells can include 293 cells, (e.g., for packaging adenovirus), and Psi2 cells or PA317 cells (e.g., for packaging retrovirus). Viral vectors can be generated by producing a cell line that packages a nucleic acid vector into a viral particle. The vectors can contain the minimal viral sequences required for packaging and subsequent integration into a host. The vectors can contain other viral sequences being replaced by an expression cassette for the polynucleotide(s) to be expressed. The missing viral functions can be supplied in trans by the packaging cell line. For example, AAV vectors can comprise ITR sequences from the AAV genome which are required for packaging and integration into the host genome. Viral DNA can be packaged in a cell line, which can contain a helper plasmid encoding the other AAV genes, namely rep and cap, while lacking ITR sequences. The cell line can also be infected with adenovirus as a helper. The helper virus can promote replication of the AAV vector and expression of AAV genes from the helper plasmid. Contamination with adenovirus can be reduced by, e.g., heat treatment to which adenovirus is more sensitive than AAV.

A host cell can be transiently or non-transiently transfected with one or more vectors described herein. A cell can be transfected as it naturally occurs in a subject. A cell can be taken or derived from a subject and transfected. A cell can be derived from cells taken from a subject, such as a cell line. In some embodiments, a cell transfected with one or more vectors described herein is used to establish a new cell line comprising one or more vector-derived sequences. In some embodiments, a cell transiently transfected with the compositions of the disclosure (such as by transient transfection of one or more vectors, or transfection with RNA), and modified through the activity of the heterologous polypeptide comprising the engineered nuclease as disclosed herein, is used to establish a new cell line comprising cells containing the modification but lacking any other exogenous sequence.

Any suitable vector compatible with the host cell can be used with the methods of the disclosure. Non-limiting examples of vectors for eukaryotic host cells include pXT1, pSG5 (Stratagene™), pSVK3, pBPV, pMSG, and pSVLSV40 (Pharmacia™).

In some embodiments, the additional ingredient of the composition as disclosed herein can comprise an excipient. Non-limiting examples of the excipient can include solvents, dispersion media, diluents, or other liquid vehicles, dispersion or suspension aids, surface active agents, isotonic agents, thickening or emulsifying agents, preservatives, lipidoids, liposomes, lipid nanoparticles, polymers, lipoplexes, core-shell nanoparticles, peptides, proteins, hyaluronidase, nanoparticle mimics, inert diluents, buffering agents, lubricating agents, oils, and combinations thereof. In some examples, the composition as disclosed herein can include one or more excipients, each in an amount that together increases the stability of (i) the heterologous polypeptide or the heterologous gene encoding thereof and/or (ii) cells or modified cells.

In some aspects, the present disclosure provides a kit comprising such composition and instructions directing (i) contacting the cell with the composition (e.g., in vitro, ex vivo, or in vivo), or (ii) administration of cells comprising any one of the compositions disclosed herein to a subject. The subject may have or may be suspected of having a condition, such as a hereditary disease.

In some embodiments, any of the compositions as disclosed herein, can be administered to the subject via orally, intraperitoneally, intravenously, intraarterially, transdermally, intramuscularly, liposomally, via local delivery by catheter or stent, subcutaneously, intraadiposally, or intrathecally.

The compositions (e.g., pharmaceutical compositions) as disclosed herein can be suitable for administration to humans. In addition, such compositions can be suitable for administration to any other animal, e.g., to non-human animals, e.g., non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Cells

In some embodiments, a cell as provided herein may be referred to as a target cell. In some embodiments, the systems, compositions, and methods as provided herein can be applied to modify a target cell (e.g., modify expression profile of a target gene of the target cell, such as one or genes in TABLE 1). A target cell can include a wide variety of cell types. A target cell can be in vitro. A target cell can be in vivo. A target cell can be ex vivo. A target cell can be an isolated cell. A target cell can be a cell inside of an organism. A target cell can be an organism. A target cell can be a cell in a cell culture. A target cell can be one of a collection of cells. A target cell can be a mammalian cell or derived from a mammalian cell. A target cell can be a rodent cell or derived from a rodent cell. A target cell can be a human cell or derived from a human cell. A target cell can be a prokaryotic cell or derived from a prokaryotic cell. A target cell can be a bacterial cell or can be derived from a bacterial cell. A target cell can be an archaeal cell or derived from an archaeal cell. A target cell can be a eukaryotic cell or derived from a eukaryotic cell. A target cell can be a pluripotent stem cell. A target cell can be a plant cell or derived from a plant cell. A target cell can be an animal cell or derived from an animal cell. A target cell can be an invertebrate cell or derived from an invertebrate cell. A target cell can be a vertebrate cell or derived from a vertebrate cell. A target cell can be a microbe cell or derived from a microbe cell. A target cell can be a fungi cell or derived from a fungi cell. A target cell can be from a specific organ or tissue.

A target cell can be a stem cell or progenitor cell. Target cells can include stem cells (e.g., adult stem cells, embryonic stem cells, induced pluripotent stem (iPS) cells) and progenitor cells (e.g., cardiac progenitor cells, neural progenitor cells, etc.). Target cells can include mammalian stem cells and progenitor cells, including rodent stem cells, rodent progenitor cells, human stem cells, human progenitor cells, etc. Clonal cells can comprise the progeny of a cell. A target cell can comprise a target nucleic acid. A target cell can be in a living organism. A target cell can be a genetically modified cell. A target cell can be a host cell.

A target cell can be a primary cell. For example, cultures of primary cells can be passaged 0 times, 1 time, 2 times, 4 times, 5 times, 10 times, 15 times or more. Cells can be unicellular organisms. Cells can be grown in culture.

A target cell can be a diseased cell. A diseased cell can have altered metabolic, gene expression, and/or morphologic features. A diseased cell can be a cancer cell, a diabetic cell, and a apoptotic cell. A diseased cell can be a cell from a diseased subject. Exemplary diseases can include blood disorders, cancers, metabolic disorders, eye disorders, organ disorders, musculoskeletal disorders, cardiac disease, and the like.

If the target cells are primary cells, they may be harvested from an individual by any method. For example, leukocytes may be harvested by apheresis, leukocytapheresis, density gradient separation, etc. Cells from tissues such as skin, muscle, bone marrow, spleen, liver, pancreas, lung, intestine, stomach, etc. can be harvested by biopsy.

Non-limiting examples of cells which can be target cells include, but are not limited to, lymphoid cells, such as B cell, T cell (Cytotoxic T cell, Natural Killer T cell, Regulatory T cell, T helper cell), Natural killer cell, cytokine induced killer (CIK) cells; myeloid cells, such as granulocytes (Basophil granulocyte, Eosinophil granulocyte, Neutrophil granulocyte/Hypersegmented neutrophil), Monocyte/Macrophage, Red blood cell (Reticulocyte), Mast cell, Thrombocyte/Megakaryocyte, Dendritic cell; cells from the endocrine system, including thyroid (Thyroid epithelial cell, Parafollicular cell), parathyroid (Parathyroid chief cell, Oxyphil cell), adrenal (Chromaffin cell), pineal (Pinealocyte) cells; cells of the nervous system, including glial cells (Astrocyte, Microglia), Magnocellular neurosecretory cell, Stellate cell, Boettcher cell, and pituitary (Gonadotrope, Corticotrope, Thyrotrope, Somatotrope, Lactotroph); cells of the Respiratory system, including Pneumocyte (Type I pneumocyte, Type II pneumocyte), Clara cell, Goblet cell, Dust cell; cells of the circulatory system, including Myocardiocyte, Pericyte; cells of the digestive system, including stomach (Gastric chief cell, Parietal cell), Goblet cell, Paneth cell, G cells, D cells, ECL cells, I cells, K cells, S cells; enteroendocrine cells, including enterochromaffin cell, APUD cell, liver (Hepatocyte, Kupffer cell), Cartilage/bone/muscle; bone cells, including Osteoblast, Osteocyte, Osteoclast, teeth (Cementoblast, Ameloblast); cartilage cells, including Chondroblast, Chondrocyte; skin cells, including Trichocyte, Keratinocyte, Melanocyte (Nevus cell); muscle cells, including Myocyte; urinary system cells, including Podocyte, Juxtaglomerular cell, Intraglomerular mesangial cell/Extraglomerular mesangial cell, Kidney proximal tubule brush border cell, Macula densa cell; reproductive system cells, including Spermatozoon, Sertoli cell, Leydig cell, Ovum; and other cells, including Adipocyte, Fibroblast, Tendon cell, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet stratified barrier epithelial cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts), Exocrine secretory epithelial cells, Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion). Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), Paneth cell of small intestine (lysozyme secretion), Type II pneumocyte of lung (surfactant secretion), Clara cell of lung, Hormone secreting cells, Anterior pituitary cells, Somatotropes, Lactotropes, Thyrotropes, Gonadotropes, Corticotropes, Intermediate pituitary cell, Magnocellular neurosecretory cells, Gut and respiratory tract cells, Thyroid gland cells, thyroid epithelial cell, parafollicular cell, Parathyroid gland cells, Parathyroid chief cell, Oxyphil cell, Adrenal gland cells, chromaffin cells, Leydig cell of testes, Theca interna cell of ovarian follicle, Corpus luteum cell of ruptured ovarian follicle, Granulosa lutein cells, Theca lutein cells, Juxtaglomerular cell (renin secretion), Macula densa cell of kidney, Metabolism and storage cells, Barrier function cells (Lung, Gut, Exocrine Glands and Urogenital Tract), Kidney, Type I pneumocyte (lining air space of lung), Pancreatic duct cell (centroacinar cell), Nonstriated duct cell (of sweat gland, salivary gland, mammary gland, etc.), Duct cell (of seminal vesicle, prostate gland, etc.), Epithelial cells lining closed internal body cavities, Ciliated cells with propulsive function, Extracellular matrix secretion cells, Contractile cells; Skeletal muscle cells, stem cell, Heart muscle cells, Blood and immune system cells, Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types), Pluripotent stem cells, Totipotent stem cells, Induced pluripotent stem cells, adult stem cells, Sensory transducer cells, Autonomic neuron cells, Sense organ and peripheral neuron supporting cells, Central nervous system neurons and glial cells, Lens cells, Pigment cells, Melanocyte, Retinal pigmented epithelial cell, Germ cells, Oogonium/Oocyte, Spermatid, Spermatocyte, Spermatogonium cell (stem cell for spermatocyte), Spermatozoon, Nurse cells, Ovarian follicle cell, Sertoli cell (in testis), Thymus epithelial cell, Interstitial cells, and Interstitial kidney cells.

The cell (or target cell) can be engineered to comprise (or exhibit) any one of the systems or compositions as disclosed herein or can be treated by any one of the methods disclosed herein in vitro or ex vivo, then administered to the subject, e.g., to treat a condition of the subject. For example, any subject modified cell product can be administered to the subject to treat a condition of a bodily tissue of the subject. In some cases, the cell can be resident inside the subject's body, and any of the systems or compositions thereof can be administered to the subject, to contact the cell by the systems/compositions (e.g., to engineer the cell with the systems/compositions).

EXAMPLES

Example 1: Engineered Nuclease

The Cas protein encoded by the polypeptide sequence of SEQ ID NO: 1 has a size of 529 amino acid residues. When delivering a gene encoding the Cas protein in a vector, e.g., in a viral vector such as AAV vector, reducing the size of such Cas protein can provide more cargo space within the vector (e.g., the viral vector that has a cargo size or length limitation). The increased cargo space within the vector can be used to deliver (e.g., encode) at least one additional component (e.g., one or more heterologous gene effector(s), one or more guide nucleic acid molecules, one or more cDNAs for therapeutic gene delivery, etc.), to effect a desired outcome (e.g., therapeutic effect). Alternatively or in addition to, when delivering a recombinant version of the Cas protein as disclosed herein in a delivery vehicle (e.g., lipid nanoparticles, viral capsids, etc.), reducing the size of the Cas protein can provide more cargo space to fit in, e.g., the at least one additional component, to effect the desired outcome. Without wishing to be bound by theory, use of the engineered nuclease as disclose herein, along with the at least one additional component, can enhance its activity (e.g., targeted gene binding, cleaving, editing, and/or regulation thereof), as compared to a control nuclease that is different.

In some embodiments, throughout the Examples of the present disclosure, one or more engineered nucleases of the present disclosure can be assessed (e.g., in vitro) to assess each of the one or more engineered nucleases activity in binding, cleaving, and/or editing a target polynucleotide sequence, e.g., to regulate expression and/or activity level of the target polynucleotide sequence of a polypeptide (e.g., a protein) encoded by the target polynucleotide sequence or operatively coupled to the target polynucleotide sequence. In some examples, a heterologous polypeptide comprising the engineered nuclease and a heterologous polynucleotide comprising a guide nucleic acid (e.g., sgRNA) against a target polynucleotide can be tested in a cell (e.g., in vitro) to assess the gene knockout efficiency at the target polynucleotide. In some examples, a heterologous polypeptide comprising a nuclease deficient variant of the engineered nuclease that is coupled to (e.g., fused to) a gene effector that is heterologous to the engineered nuclease (e.g., gene activator, gene repressor) and a heterologous polynucleotide comprising a guide nucleic acid (e.g., sgRNA) against a target polynucleotide can be tested in a cell (e.g., in vitro) to assess the ability to regulate expression and/or activity level of a gene coupled to (or comprising) the target polynucleotide.

In some embodiments, throughout the Examples of the present disclosure, a library of a plurality of engineered nuclease candidates can be generated by using full-plasmid amplification via opposite-facing primers spanning the deletion region.

Example 2: Engineered Nuclease Based on Structural Comparison

A. Approach

In some embodiments, the size (e.g., the number of amino acid residues) of CasMini or deactivated CasMini (dCasMini) (e.g., mutated variant of the polypeptide sequence of SEQ ID NO: 1) can be further reduced while maintaining or enhancing its activity (e.g., overall epigenetic gene regulatory activity). For example, additional Cas proteins (e.g., naturally occurring Cas12f proteins, such as Un2Cas12f1 (SEQ ID NO: 2) or AsCas12f (SEQ ID NO: 3)) that are smaller than that of SEQ ID NO: 1 can serve as a reference point to determine at least one amino acid residue and/or at least one tertiary structure of the Cas protein of SEQ ID NO: 1 that can be modified (e.g., deleted), e.g., with minimal or no comprise of its activity.

In some embodiments, the native Un nuclease encoded by SEQ ID NO: 1 can be engineered by creating at least one deletion, to generate the engineered nuclease as disclosed herein, e.g., for one or more reasons described in Example 1.

In some cases, the at least one deletion of the amino acid sequence of the engineered nuclease can be found in one or more regions of the native Un nuclease that do not structurally align to a AsCas12f (SEQ ID NO: 3). When compared to AsCas12f, Un1Cas12f1 comprises the additional amino acid residues 1-71 domain, and at least a portion of the domain and/or one or more amino acid residues near the domain may be removed, e.g., with minimal or substantially no reduction of the engineered nuclease's activity (e.g., the engineered nuclease's interaction with the guide nucleic acid molecule (e.g., crRNA). As shown in FIG. 1, Un1Cas12f1 comprises domain 110 (e.g., comprising at least a portion of the additional amino acid residues 1-71 domain) that may not be conserved in AsCas12f. On the other hand, Un1Cas12f1 comprises domain 120 that may be conserved in AsCas12f.

Figure 2:
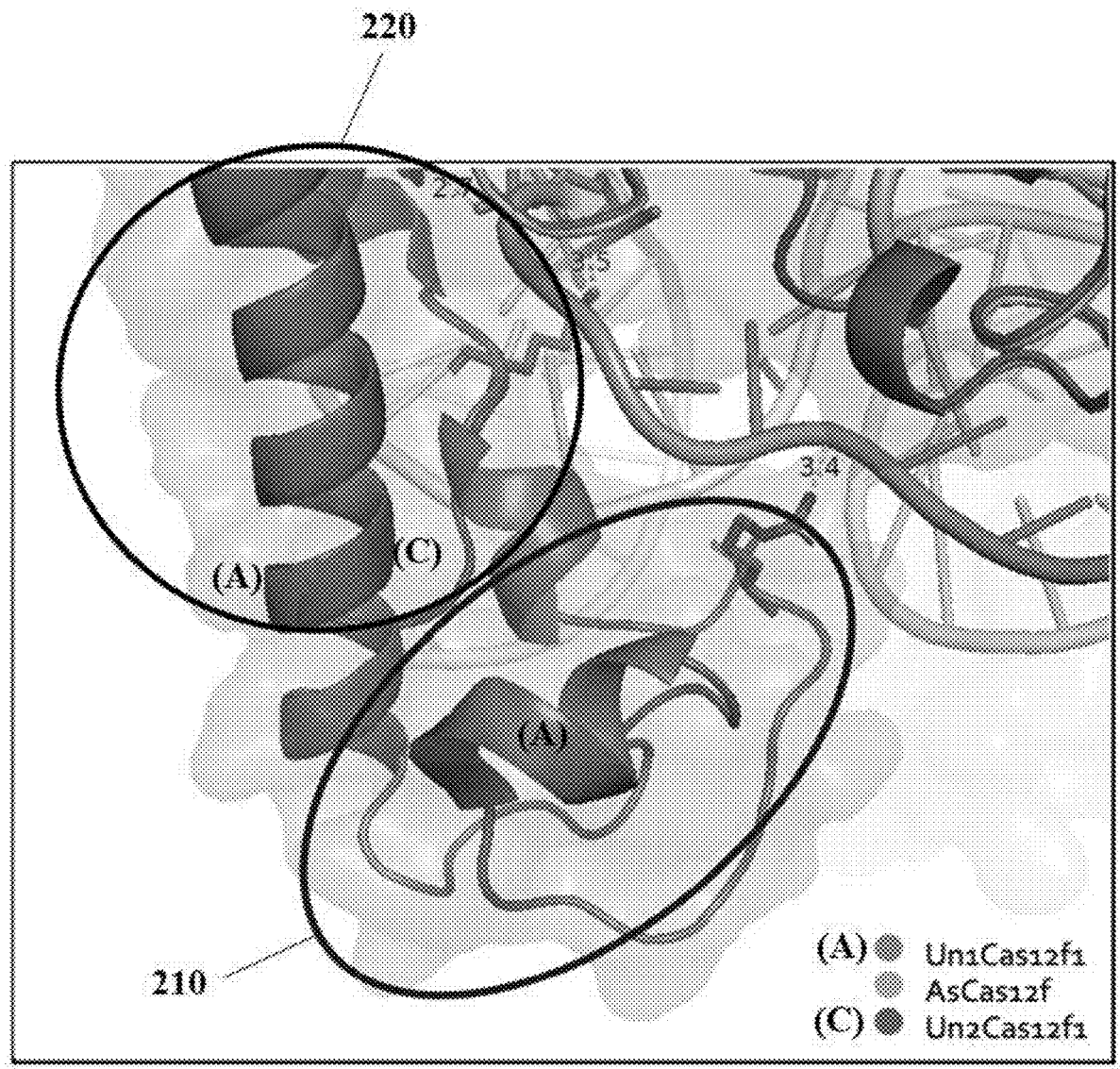
FIG. 2 schematically illustrates structural alignment between Un1Cas12f1 and Un2Cas12f1, to identify one or more domains in Un1Cas12f1 that may not be conserved in one or more additional Cas12f homologous structures.

In some cases, the at least one deletion of the amino acid sequence of the engineered nuclease can be found in one or more regions of the native Un nuclease that do not structurally align to a Un2Cas12f1 (SEQ ID NO: 2). When compared to Un2Cas12f1, Un1Cas12f1 comprises the additional amino acid residues 41-71 domain, and at least a portion of the domain and/or one or more amino acid residues near the domain may be removed, e.g., with minimal or substantially no reduction of the engineered nuclease's activity (e.g., the engineered nuclease's interaction with the guide nucleic acid molecule (e.g., crRNA). As shown in FIG. 2, Un1Cas12f1 comprises domain 210 (e.g., comprising at least a portion of the additional amino acid residues 41-71 domain) that may not be conserved in Un2Cas12f1. On the other hand, Un1Cas12f1 comprises domain 220 that may be conserved in Un2Cas12f1.

B. Example Library Designs

Figure 3A:
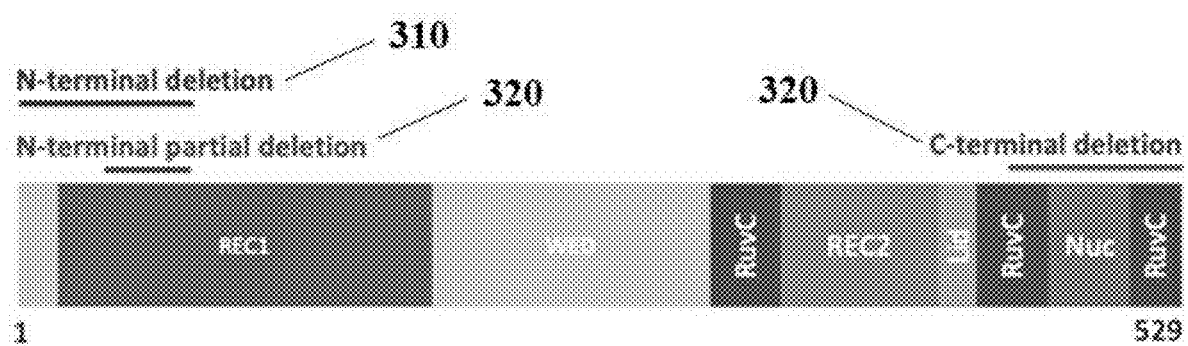
FIG. 3A schematically illustrates selection of various domains of Un1Cas12f1 that are to be at least partially deleted to generate one or more engineered nucleases.

FIG. 3A schematically illustrates different regions of Un1Cas12f1, as encoded by SEQ ID NO: 1, and example domains (310, 320, and 330) that can be at least partially deleted to generate one or engineered nucleases as disclosed herein. For example, the domain 310 can refer to N-terminal deletion (e.g., the amino acid residues 2-76 when aligned to SEQ ID NO: 1) can be evaluated by generating 25 variants via incremental removal of 3 amino acids at a time from the N-terminus of the protein. In another example, the domain 320 can refer to a N-terminal partial deletion (e.g., the amino acid residues 41-71 when aligned to SEQ ID NO: 1) can be evaluated by generating 16 variants via incremental removal of additional 2 amino acids at a time from the middle of this region (e.g., del55-56, del54-57, del54-58, del53-59, del52-60, del51-61, del50-62, del49-63, del48-64, del47-65, del46-66, del45-67, del44-68, del43-69, del42-70, del41-71, etc.). In a different example, the domain 330 can refer to C-terminal deletion (e.g., the last 75 amino acid residues when aligned to SEQ ID NO: 1) can be evaluated by generating 25 variants by incremental removal of 3 amino acids at a time from the C-terminus.

Examples of engineered nucleases with reduced nuclease activity, as generated in accordance with the present disclosure, can include SEQ ID NOs: 4-9, as provided herein.

```
(comprising N-terminal deletion, e.g., the
amino acid residues 2-21 (AKNTITKTLKLRIVRP
YNSA), when aligned to SEQ ID NO: 1)
                                    SEQ ID NO: 4
  1 MEVEKIVADE KNNREKIALE KNKDKVKEAC SKHLKVAAYC

TTQVERNACL

51 FCKARKLDDK FYQKLRGQFP DAVEWQEISE IFRQLQKQAA

EIYNQSLIEL

101 YYEIFIKGKG IANASSVEHY LSRVCYRRAA ELFKNAAIAS

GLRSKIKSNE

151 RLKELKNMKS GLPTTKSDNF PIPLVKQKGG QYTGFEISNH

NSDFIIKIPE

201 GRWQVKKEID KYRPWEKFDF EQVQKSPKPI SLLLSTQRRK

RNKGWSKDEG

251 TEAEIKKVMN GDYQTSYIEV KRGSKICEKS AWMLNLSIDV

PKIDKGVDPS

301 IIGGIAVGVR SPLVCAINNA FSRYSISDND LFHENKKMFA

RRRILLKKNR
```

```
351 HKRAGHGAKN KLKPITILTE KSERFRKKLI ERWACEIADE
    FIKNKVGTVQ

401 MENLESMKRK EDSYFNIRLR GFWPYAEMQN KIEFKLKQYG
    IEIRKVAPNN

451 TSKTCSKCGH LNNYFNFEYR KKNKFPHFKC EKCNEKENAA
    YNAALNISNP

501 KLKSTKERP
```

(comprising N-terminal deletion, e.g., the amino acid residues 2-31 (AKNTITKTLKLRIVRP YNSAEVEKIVADEK), when aligned to SEQ ID NO: 1)

```
                                              SEQ ID NO: 5
  1 MNNREKIALE KNKDKVKEAC SKHLKVAAYC TTQVERNACL
    FCKARKLDDK

51 FYQKLRGQFP DAVFWQEISE IFRQLQKQAA EIYNQSLIEL
    YYEIFIKGKG

101 IANASSVEHY LSRVCYRRAA ELFKNAAIAS GLRSKIKSNF
    RLKELKNMKS

151 GLPTTKSDNF PIPLVKQKGG QYTGFEISNH NSDFIIKIPF
    GRWQVKKEID

201 KYRPWEKFDF EQVQKSPKPI SLLLSTQRRK RNKGWSKDEG
    TEAEIKKVMN

251 GDYQTSYIEV KRGSKICEKS AWMLNLSIDV PKIDKGVDPS
    IIGGIAVGVR

301 SPLVCAINNA FSRYSISDND LFHENKKMFA RRRILLKKNR
    HKRAGHGAKN

351 KLKPITILTE KSERFRKKLI ERWACEIADE FIKNKVGTVQ
    MENLESMKRK

401 EDSYFNIRLR GFWPYAEMQN KIEFKLKQYG IEIRKVAPNN
    TSKTCSKCGH

451 LNNYFNFEYR KKNKFPHFKC EKCNFKENAA YNAALNISNP
    KLKSTKERP
```

(comprising C-terminal deletion, e.g., the amino acid residues 510-529 (DYNAALNISNPKL KSTKEEP), when aligned to SEQ ID NO: 1)

```
                                              SEQ ID NO: 6
  1 MAKNTITKTL KLRIVRPYNS AEVEKIVADE KNNREKIALE
    KNKDKVKEAC

51 SKHLKVAAYC TTQVERNACL FCKARKLDDK FYQKLRGQFP
    DAVEWQEISE

101 IFRQLQKQAA EIYNQSLIEL YYEIFIKGKG IANASSVEHY
    LSRVCYRRAA

151 ELFKNAAIAS GLRSKIKSNF RLKELKNMKS GLPTTKSDNF
    PIPLVKQKGG

201 QYTGFEISNH NSDFIIKIPF GRWQVKKEID KYRPWEKFDF
    EQVQKSPKPI

251 SLLLSTQRRK RNKGWSKDEG TEAEIKKVMN GDYQTSYIEV
    KRGSKICEKS

301 AWMLNLSIDV PKIDKGVDPS IIGGIAVGVR SPLVCAINNA
    FSRYSISDND

351 LFHENKKMFA RRRILLKKNR HKRAGHGAKN KLKPITILTE
    KSERFRKKLI

401 ERWACEIADF FIKNKVGTVQ MENLESMKRK EDSYFNIRLR
    GFWPYAEMQN

451 KIEFKLKQYG IEIRKVAPNN TSKTCSKCGH LNNYENFEYR
    KKNKFPHFKC

501 EKCNFKENA
```

(comprising C-terminal deletion, e.g., the amino acid residues 500-529 (CEKCNFKENADYN AALNISNPKLKSTKEEP), when aligned to SEQ ID NO: 1)

```
                                              SEQ ID NO: 7
  1 MAKNTITKTL KLRIVRPYNS AEVEKIVADE KNNREKIALE
    KNKDKVKEAC

51 SKHLKVAAYC TTQVERNACL FCKARKLDDK FYQKLRGQFP
    DAVEWQEISE

101 IFRQLQKQAA EIYNQSLIEL YYEIFIKGKG IANASSVEHY
    LSRVCYRRAA

151 ELFKNAAIAS GLRSKIKSNF RLKELKNMKS GLPTTKSDNF
    PIPLVKQKGG

201 QYTGFEISNH NSDFIIKIPF GRWQVKKEID KYRPWEKFDF
    EQVQKSPKPI

251 SLLLSTQRRK RNKGWSKDEG TEAEIKKVMN GDYQTSYIEV
    KRGSKICEKS

301 AWMLNLSIDV PKIDKGVDPS IIGGIAVGVR SPLVCAINNA
    FSRYSISDND

351 LFHENKKMFA RRRILLKKNR HKRAGHGAKN KLKPITILTE
    KSERERKKLI

401 ERWACEIADF FIKNKVGTVQ MENLESMKRK EDSYFNIRLR
    GFWPYAEMQN

451 KIEFKLKQYG IEIRKVAPNN TSKTCSKCGH LNNYENFEYR
    KKNKFPHFK
```

(comprising partial N-terminal deletion, e.g., the amino acid residues 47-66 (KEACSKHLKVAAYCTTQVER), when aligned to SEQ ID NO: 1)

```
                                              SEQ ID NO: 8
  1 MAKNTITKTL KLRIVRPYNS AEVEKIVADE KNNREKIALE
    KNKDKVNACL
```

```
 51 FCKARKLDDK FYQKLRGQFP DAVEWQEISE IFRQLQKQAA

EIYNQSLIEL

101 YYEIFIKGKG IANASSVEHY LSRVCYRRAA ELFKNAAIAS

GLRSKIKSNF

151 RLKELKNMKS GLPTTKSDNF PIPLVKOKGG QYTGFEISNH

NSDFIIKIPF

201 GRWQVKKEID KYRPWEKFDF EQVQKSPKPI SLLLSTQRRK

RNKGWSKDEG

251 TEAEIKKVMN GDYQTSYIEV KRGSKICEKS AWMLNLSIDV

PKIDKGVDPS

301 IIGGIAVGVR SPLVCAINNA FSRYSISDND LFHENKKMFA

RRRILLKKNR

351 HKRAGHGAKN KLKPITILTE KSERFRKKLI ERWACEIADE

FIKNKVGTVQ

401 MENLESMKRK EDSYENIRLR GFWPYAEMQN KIEFKLKQYG

IEIRKVAPNN

451 TSKTCSKCGH LNNYENFEYR KKNKFPHFKC EKCNFKENAA

YNAALNISNP

501 KLKSTKERP
(comprising partial N-terminal deletion,
e.g., the amino acid residues 41-71
(KNKDKVKEACSKHLKVAAYCTTQVERNACLF),
when aligned to SEQ ID NO: 1)
                                  SEQ ID NO: 9
  1 MAKNTITKTL KLRIVRPYNS AEVEKIVADE KNNREKIALE

CKARKLDDKE

51 YQKLRGQFPD AVFWQEISEI FRQLQKQAAE IYNQSLIELY

YEIFIKGKGI

101 ANASSVEHYL SRVCYRRAAE LFKNAAIASG LRSKIKSNER

LKELKNMKSG

151 LPTTKSDNFP IPLVKOKGGQ YTGFEISNHN SDFIIKIPFG

RWQVKKEIDK

201 YRPWEKEDFE QVQKSPKPIS LLLSTQRRKR NKGWSKDEGT

EAEIKKVMNG

251 DYQTSYIEVK RGSKICEKSA WMLNLSIDVP KIDKGVDPSI

IGGIAVGVRS

301 PLVCAINNAF SRYSISDNDL FHENKKMFAR RRILLKKNRH

KRAGHGAKNK

351 LKPITILTEK SERFRKKLIE RWACEIADFF IKNKVGTVQM

ENLESMKRKE

401 DSYFNIRLRG FWPYAEMQNK IEFKLKQYGI EIRKVAPNNT

SKTCSKCGHL

451 NNYFNFEYRK KNKFPHEKCE KCNFKENAAY NAALNISNPK
```

```
    LKSTKERP
```

Example 3: Engineered Nuclease Based on Deletion Landscape

The native Un1Cas12f1 nuclease encoded by SEQ ID NO: 1 can be engineered by creating at least one deletion, to generate the engineered nuclease of the present disclosure, e.g., for one or more reasons described in Example 1. The at least one deletion of the amino acid sequence of the engineered nuclease, as disclosed herein, can be determined based on deletion (or truncation) landscape of the Cas protein (or the nuclease-deficient variant thereof).

Figure 4:
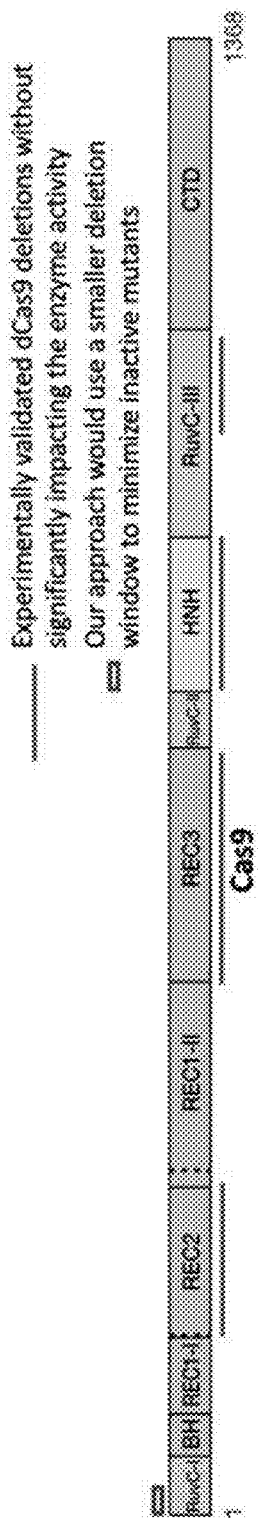
FIG. 4 schematically illustrates example deletion landscape of a Cas protein (e.g., dCas9), to identify one or more domains in the Cas protein that may be deleted with minimal or substantially no effect on the Cas protein's activity (e.g., the ability to induce transcription expression when the modified variant of dCas9 is operatively coupled to a gene repressor).

For example, as illustrated in FIG. 4, mapping of the truncation landscape of dCas9 suggests tolerance for significant deletions, e.g., deletions of the amino acid residues 167-316 of the dCas9. Thus, a similar deletion landscape can be utilized to determine one or more amino acid residues (e.g., a plurality of consecutive amino acid residues) of the native Un (or the nuclease-deficient variant thereof), to generate deletion mutants of the Un1 Cas12f1 protein without significantly impacting activity (e.g., without impacting activity). In some cases, a deletion of about 20 amino acid residues (e.g., from one consecutive region, or from two non-consecutive regions) can be determined to generate a mutant variant of Un that still exhibits comparable (or enhanced) activity as compared to the wild type Un1Cas12f1. In some cases, a small deletion window (e.g., a window of between about 3 and about 5 amino acids) can be assessed throughout the native Un protein for the deletion landscape.

Figure 3B:
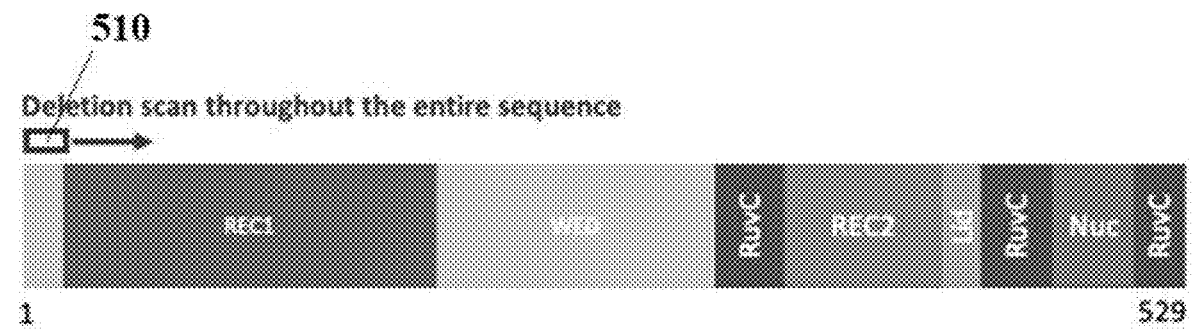
FIG. 3B schematically illustrates deletion landscape approach to generate engineered nuclease variants of Un1Cas12f1.

FIG. 3B schematically illustrates deletion landscape approach to generate engineered nuclease variants of Un1Cas12f1. A deletion tile 510 of a plurality of amino acid residues (e.g., a plurality of consecutive amino acid residues, such as 5 consecutive amino acid residues) can be scanned throughout at least a portion of Un1Cas12f1 (e.g., the entire Un1Cas12f1, except for the dimerization domain and/or the PAM domain) to generate, e.g., up to 95 variants for individual transfection screening.

Example 4: Engineered Nuclease Based on Deletion Landscape

In addition to deletion of one or more amino acid residues from the native Un1Cas12f1 nuclease encoded by SEQ ID NO: 1 to generate the engineered nuclease, one or more amino acid residues can be mutated as compared to the native Un1Cas12f1 nuclease, to further modify the engineered nuclease of the present disclosure, e.g., for one or more reasons described in Example 1. The at least one deletion of the amino acid sequence of the engineered nuclease, as disclosed herein, can be determined based on Site Saturation Mutagenesis (SSM). For example, a single codon or set of codons of a polynucleotide encoding the native Un1Cas12f1 protein (or the nuclease-deficient variant thereof) can be substituted with one or more possible amino acids at the position for enhanced activity (e.g., for epigenetic regulation improvement, such as enhanced activation/repression, different PAM recognition, etc.), stability, expression, binding to the respective guide nucleic acid molecule, etc.

Example 5: Assessment of Engineered Nuclease(s)

Nuclease-deficient variants of the engineered nucleases as disclosed herein (e.g., generated in accordance with Examples 1-4) can be coupled to (e.g., fused to) heterologous gene effectors (e.g., VP16, VP64, p65, Rta, VPR, etc.), and one or more heterologous polypeptides encoding such fusion protein and/or a guide RNA can be transfected into a cell to assess activation of expression/activity level of a target gene. For example, engineered HEK93T cells bearing a synthetic reporter can be used, in which fluorescence activation may be measured as a readout. When a plurality of engineered nucleases are identified, the screening method (e.g., via using the engineered HEK93T cells) can be repeated to (i) confirm the prior screening results and/or (ii) identify top hits.

Depending on the result from the first round of engineering, a plurality of deletions of amino acid residues (e.g., when aligned to the polypeptide sequence of SEQ ID NO: 1) can be combined to generate one or more additional engineered nucleases. Alternatively or in addition to, one or more additional engineered nucleases can be generated by assessing one or more granular deletions around one or more leads from the first round of engineering.

A. First Round of Engineering

Multiple sequence alignments of dCasMINI (SEQ ID NO: 10) with one or more naturally occurring Cas12f protein orthologs with reported nuclease activity in bacteria (e.g., Un1Cas12f1, Un2Cas12f1, AsCas12f, and other orthologs as provided in TABLE 2), to, for example, identify one or more potentially beneficial mutations in generating engineered nuclease variants as disclosed herein. Homology modeling of the Cas12f orthologs was also performed to identify structural conservation (e.g., not entirely based on amino acid based conservation), to generate the engineered nuclease variants. Combining these two approaches (e.g., sequence alignment and structural conservation analysis), stretches of amino acid sequences as well as combinations of individual residue mutations were identified as promising candidates to generate the engineered nuclease variants. Based on the identified information, chimeric protein variants were designed via sequence swapping, and mutation variants were designed via one or more residue mutations. In some cases, the sequence swapping variants also resulted in overall reduced protein size.

In the first round of engineering, engineered nuclease variants (e.g., truncation variants, chimeric protein variants, and/or mutation variants) were generated, tested, and screened to identify lead hits. For example, various chimeric engineered nuclease variants with reduced nuclease activity were designed (as provided in TABLE 3B) and tested in combination with (e.g., fused to) a gene modulator such as a gene activator or a gene repressor, to test their efficacy in gene modulation as compared to a control dCasMINI (SEQ ID NO: 10).

Gene activation was assessed by fusing each engineered nuclease variant with a gene activator. Each engineered nuclease variant with reduced nuclease activity was individually cloned into a dCas plasmid in frame with a gene activator (e.g., VPR) for transcriptional activation. HEK293T cells were transfected with identical sgRNA plasmid and individual dCas variant plasmid as triplicate or quadruplicate repeats in 96-well plate format. After several days post-transfection (e.g., after 2 days, after 3 days, or after 4 days), CD2 protein levels were quantified by cell surface antibody staining of live cells followed by flow cytometry, while secreted IFN gamma (IFNγ) protein levels were measured using ELISA on cell culture supernatants. The level of gene activation of each engineered nuclease variant was compared to the activity of a dCasMINI fused to the same gene activator as a control.

Gene repression was assessed by fusing each engineered nuclease variant with a gene repressor. Each engineered nuclease variant with reduced nuclease activity was individually cloned into the dCas plasmid in frame with a gene repressor for transcriptional inhibition. In 96-well plate format, HEK293T GFP reporter cells (e.g., ESR221) were transfected with identical sgRNA plasmid and individual dCas variant plasmid as triplicate or quadruplicate repeats. After several days post-transfection (e.g., 5 to 7 days), suppression of GFP expression was measured by flow cytometry. The level of gene repression of each engineered nuclease variant was compared to the activity of a dCas-MINI fused to the same gene activator as a control.

Figure 5:
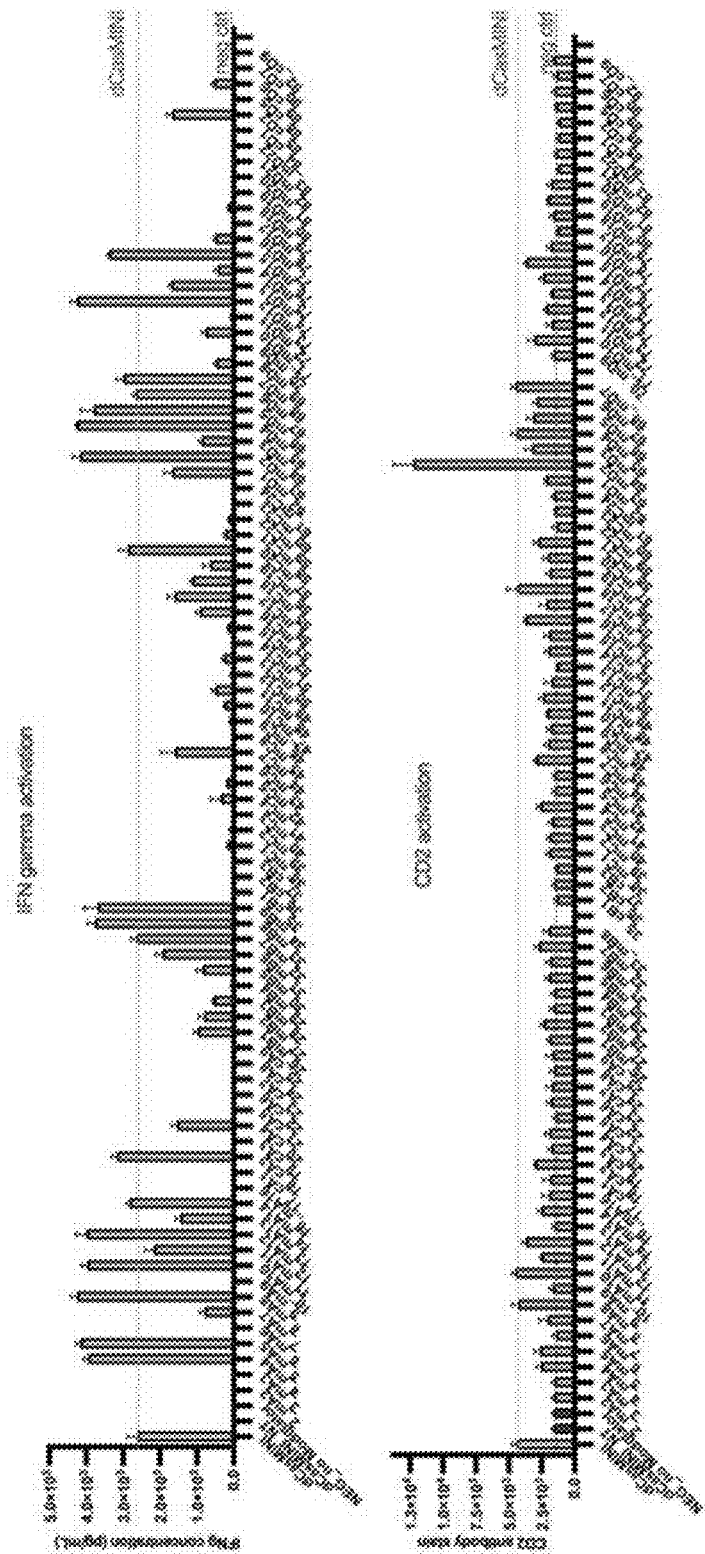
FIG. 5 shows enhanced expression of endogenous IFN gamma (top plot) and endogenous CD2 (bottom plot) in cells by various engineered nuclease variants disclosed herein. The engineered nuclease variants were engineered to exhibit reduced nuclease activity (e.g., dCas variants), and were fused with a gene activating modulator.
Figure 6:
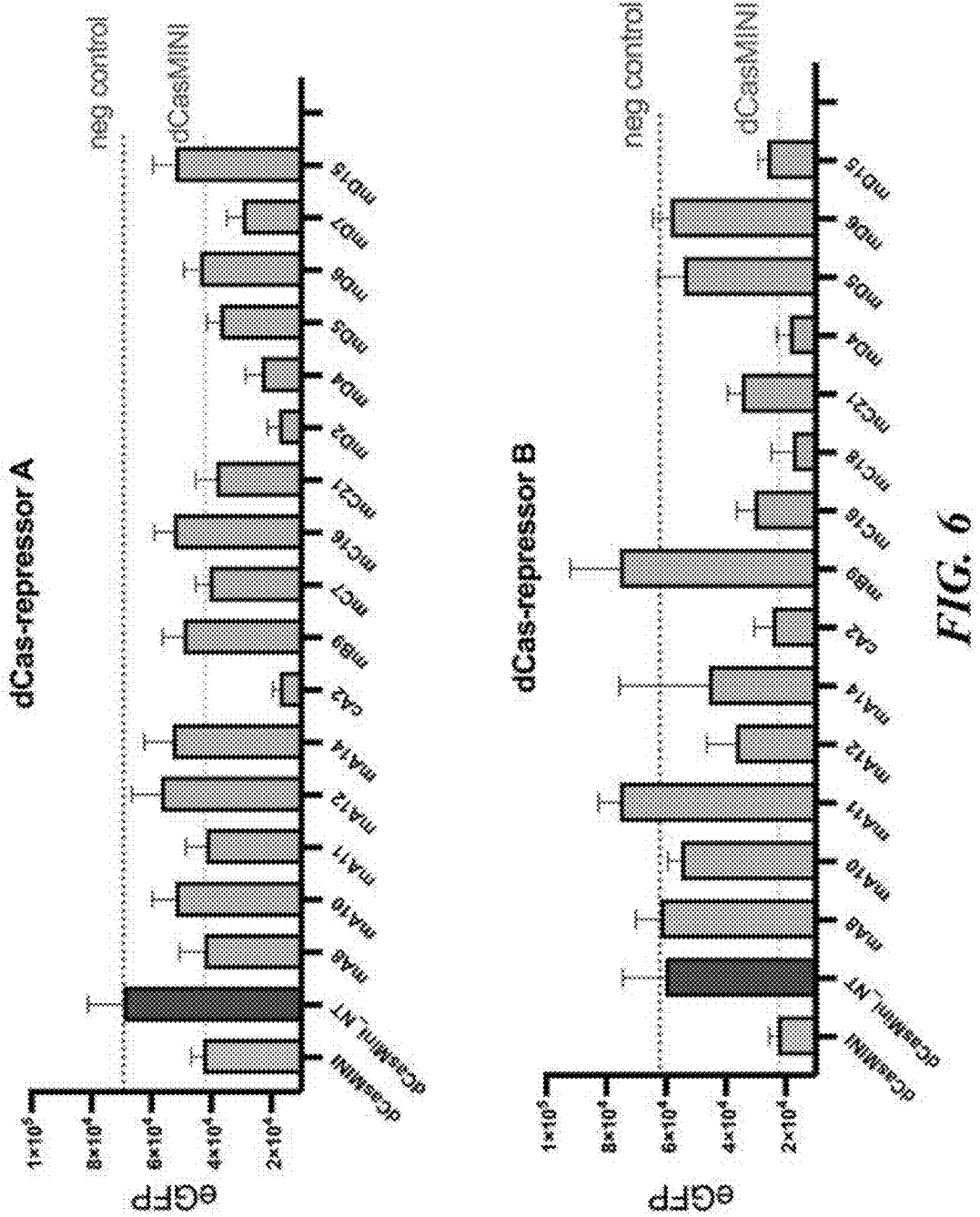
FIG. 6 shows reduced expression of a target gene (e.g., GFP) in cells by various engineered nuclease variants disclosed herein. The engineered nuclease variants were engineered to exhibit reduced nuclease activity (e.g., dCas variants), and were fused with a gene repressing modulator. Two different gene repressing modulators were used: gene repressor A (top plot) and gene repressor B (bottom plot).
Figure 15:
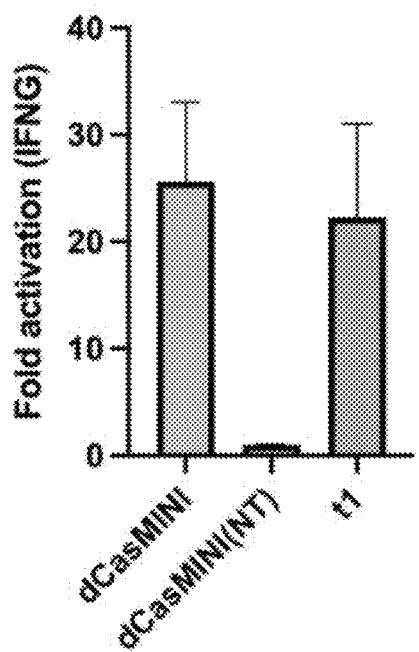
FIG. 15 shows increased expression of endogenous IFN gamma (IFNγ) in cells by the truncation nuclease variant t1 disclosed herein. The engineered nuclease variant t1 was fused with a gene activating modulator, VPR.

As shown in FIG. 5, out of the chimeric engineered nuclease variants cA1 through cA9, the chimeric engineered nuclease variant cA2 resulted in the greatest activation of IFN gamma expression (e.g., greater than that by the dCasMINI control) and also of CD2 activation (as summarized in TABLE 3A). Additional engineered nuclease variants were designed with one or more mutations relative to Un1Cas12f1, without significantly changing the overall size of the engineered nuclease variant as compared to dCasMINI. See TABLE 4B for the amino acid sequences of such engineered nuclease variants. As shown in FIG. 5, when fused to a gene activator, various engineered nuclease (e.g., mD2, mD4) exhibited comparable or greater efficacy in activating target genes (e.g., IFN gamma or CD2) as compared to the control dCasMINI (as summarized in TABLE 4A). As shown in FIG. 6, some of the various engineered nuclease (e.g., mD2, mD4) exhibited comparable or greater efficacy in repressing target genes (e.g., eGFP) as compared to the control dCasMINI (as summarized in TABLE 4A). Another engineered nuclease variant (a) comprising deletion on the C-terminal region as compared to SEQ ID NO: 1 was also identified without sacrificing the gene modulation activity. As shown in FIG. 15, when fused to a gene activator, the engineered nuclease variant t1 exhibited comparable efficacy in activating a target gene (e.g., IFN gamma) as compared to the control dCasMINI.

The chimeric engineered nuclease variant cA2 was designed with sequence deletions at the zinc-binding motif. Without wishing to be bound by theory, such deletions at the particular zinc-binding motif resulted in a smaller nuclease variant that maintained or even improved the gene modulation activity (e.g., epigenetic modification activity) when operatively linked to (e.g., fused with) one or more gene modulators.

TABLE 5A summarizes each set of modifications relative to the amino acid sequence of Un1Cas12f1 (SEQ ID NO: 1) that is embedded in each engineered nuclease variant, to yield enhanced gene modulation activity as compared to dCasMINI (SEQ ID NO: 10).

Without wishing to be bound by theory, one or more additional modification can be made to any of the engineered nuclease variants from TABLE 3A, TABLE 4A, TABLE 5A, and TABLE 5B to enhance desired activity (e.g., forming a complex with guide nucleic acid molecule, target sequence nuclease activity, increasing expression of a target gene, decreasing expression of a target gene, etc.)

B. Second Round of Engineering

Figure 7:
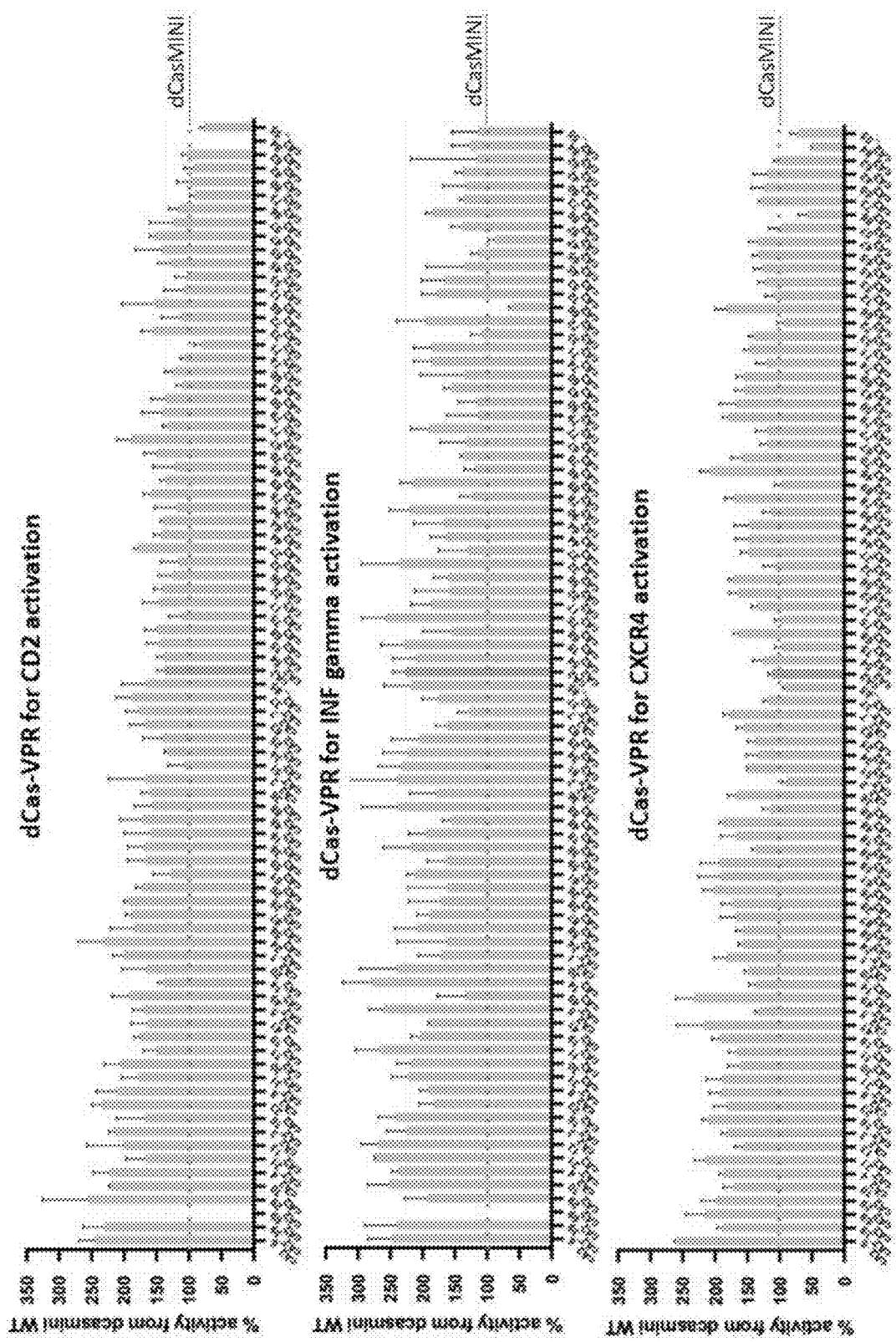
FIG. 7 shows enhanced expression of endogenous CD2 (top plot), endogenous IFN gamma (middle plot), and endogenous CXCR4 (bottom plot) in cells by various engineered nuclease variants disclosed herein. The engineered nuclease variants were engineered to exhibit reduced nuclease activity (e.g., dCas variants), and were fused with a gene activating modulator.
Figure 16:
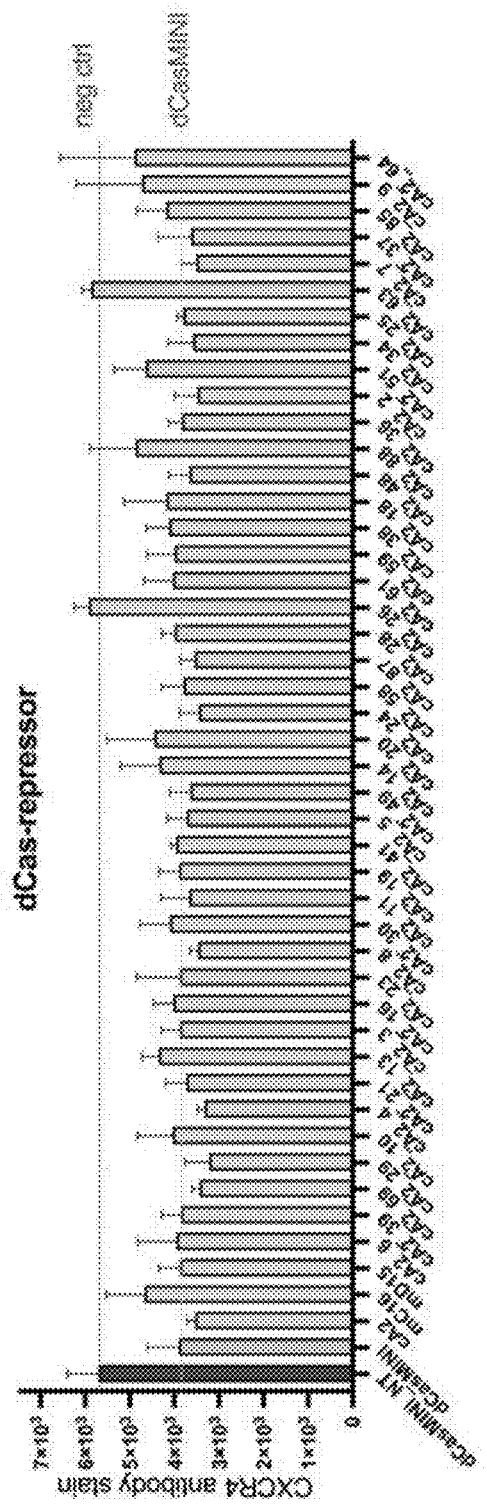
FIG. 16 shows reduced expression of endogenous CXCR4 in cells by the chimeric nuclease variants disclosed herein. The engineered nuclease variant t1 was fused with a gene repressing modulator (ZNF10-KRAB-hDNMT3L).

In the second round of engineering, the engineered nuclease variant "cA2" (SEQ ID NO: 12) was selected as scaffold, to generate a new library of engineered nuclease variants by grafting, onto the cA2 scaffold, one or more combinations of the mutation and/or truncations identified and listed in TABLE 5A. TABLE 5B shows a list of the engineered nuclease variants in the new library, indicating the combination of modification that has been grafted onto each of the engineered nuclease variant. TABLE 5C shows the respective amino acid sequence of each of the engineered nuclease variants listed in TABLE 5B. As shown in FIG. 7, upon testing for their ability to activate target genes (e.g., CD2, IFN gamma, and CXCR4) when in combination with a gene activator (e.g., VPR), various engineered nuclease variants exhibited comparable or enhanced gene activation than the control dCasMINI, some outperforming the starting scaffold cA2 (e.g., cA2.6, cA2.39, cA2.69, cA2.29, cA2.10, cA2.4, cA2.21, cA2.13, cA2.3, cA2.16, cA2.23, cA2.8, cA2.31, cA2.30, cA2.11, cA2.5, cA2.41, cA2.49, cA2.26, cA2.14, cA2.20, cA2.1, cA2.24, cA2.58, cA2.61, cA2.38, cA2.88, cA2.2, cA2.51, cA2.34, cA2.25, cA2.85, cA2.54, cA2.15, cA2.75, cA2.32, cA2.90, cA2.89, or cA2.46). In contrast, some newly engineered nuclease variants did not exhibit enhanced activity as compared to the control dCasMINI (e.g., cA2.55, cA2.84). As shown in FIG. 16, upon testing for their ability to suppress a target gene (e.g., CXCR4) when in combination with a gene repressing modulator (e.g., ZNF10-KRAB-hDNMT3L), various engineered nuclease variants exhibited comparable or enhanced gene suppression than the control dCasMINI, with some engineered nuclease variants performing comparable to the starting scaffold cA2 (e.g., cA2.69, cA.2.29, cA2.4, cA2.2, cA2.34, or cA2.7). In contrast, some newly engineered nuclease did not exhibit enhanced gene suppression activity as compared to the control dCasMINI (e.g., cA2.26, cA2.63).

In sum, two regions of sequence deletions were identified herein as a compact Cas variant. Additional point mutations were also identified that contributed to the improved gene modulation activity when used in conjunction with a gene modulator and a guide nucleic acid molecule. Combining these sequence modifications, the cA2 protein (SEQ ID NO: 12) and variants thereof (with additional point mutations and sequence deletions, see TABLE 5C) outperformed the control dCasMINI, in terms of both transcriptional activation and suppression activity over multiple endogenous loci.

Without wishing to be bound by theory, any amino acid deletion, structural deletion, or amino acid modification (e.g., mutation/substitution) identified herein to enhance gene modulating efficacy of the engineered nuclease variants can be "grafted" back into any other naturally or non-naturally occurring Cas proteins (e.g., a naturally occurring Cas protein selected from TABLE 2 or a deactivated nuclease variant thereof) to generate one or more additional engineered nuclease variants that my yield greater gene modulation efficacy than a control Cas protein (e.g., dCas-MINI as disclosed herein).

Example 6: Assessment of Engineered Nuclease(s)

An engineered nuclease variant of the engineered nucleases as disclosed herein (e.g., generated in accordance with Examples 1-4) that maintains at least a portion of the nuclease activity (e.g., as compared to SEQ ID NO: 1) can be tested in a cell for its nuclease activity. A polypeptide comprising the engineered nuclease variant and/or a guide RNA can be transfected into a cell to assess the ability of a complex comprising the engineered nuclease and the guide RNA to create a break in a target polynucleotide sequence (e.g., create a double-strand break in, or adjacent to, the target polynucleotide sequence that comprises an appropriate PAM). Such nuclease activity can be observed by in vitro enzymatic assay (e.g., with purified enzyme or cell lysate), or in vivo (e.g., in *E. coli* or in eukaryotic cell).

Example 7: Guide Nucleic Acid Scaffold Engineering

A Cas protein can comprise a naturally occurring Cas protein (e.g., (i) the polypeptide sequence of SEQ ID NO: 1 or (ii) the polypeptide sequence of any one of the Cas proteins selected from TABLE 2) or any modification thereof (e.g., an engineered polypeptide comprising an engineered nuclease variant as disclosed herein). The Cas protein can form a complex (e.g., a ribonucleoprotein (RNP) complex) with a guide nucleic acid molecule (e.g., sgRNA), which complex can bind a target polynucleotide sequence to modulate a target gene. The guide nucleic acid molecule can comprise (i) a scaffold sequence to at least form a complex with the Cas protein and (ii) a spacer sequence that exhibits at least partial sequence complementarity to the target polynucleotide sequence. Without wishing to be bound by theory, generating a smaller and more compact guide nucleic acid scaffold sequence (e.g., as compared to that for dCas-MINI) can enhance the bioactivity of the complex overall (e.g., enhanced modulation of target gene, reduced off-target effects, etc.).

Figure 8:
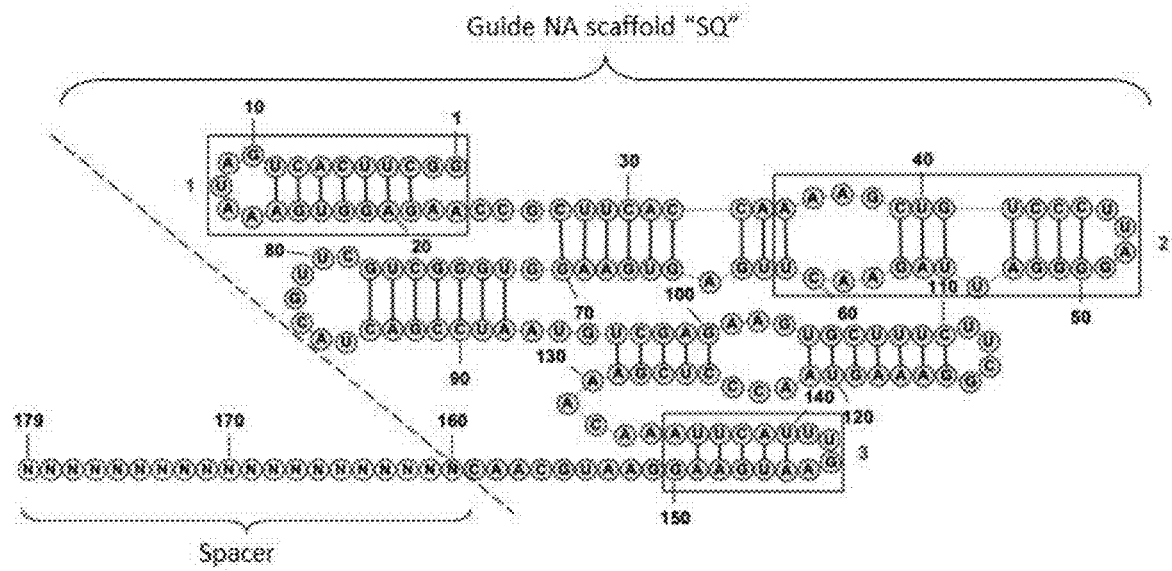
FIG. 8 schematically illustrates a guide nucleic acid molecule configured to form a complex with a Cas protein.

A control guide nucleic acid used throughout this Example is denoted as "SQ" (see schematic in FIG. 8 and its scaffold polynucleotide sequence in TABLE 6B). The control guide nucleic acid SQ is 179 nucleotide (nt) long, including a 20 nt spacer sequence.

Figure 9:
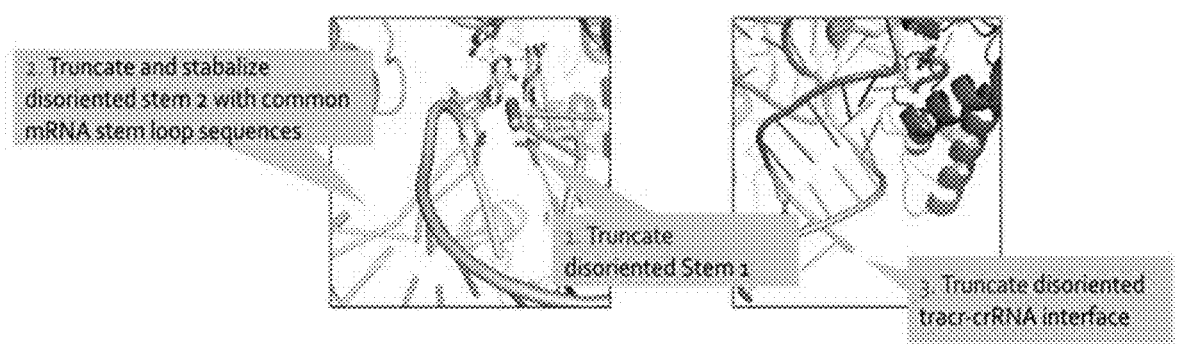
FIG. 9 schematically illustrates regions of a scaffold region of a guide nucleic acid molecule that can be modified (e.g., mutated or deleted) to engineer the guide nucleic acid molecule.

Without wishing to be bound by theory, one or more of the following regions from a guide nucleic acid sequence (e.g., SQ) can be modified (e.g., mutated or deleted) while either maintaining the bioactivity of the resulting RNP complex or improving such bioactivity. As shown in FIG. 9, such regions can include structurally disoriented and/or solvent exposed loops (e.g., stem loops) within the scaffold sequence. For the SQ guide nucleic acid sequence, non-limiting examples of such region can include region 1 (e.g., 1-23 nt), region 2 (e.g., 35-61 nt), and region 3 (e.g., 138-143 nt), each nt position relative to the polynucleotide sequence of SQ.

A. Truncated Guide Nucleic Acid Molecules

Guide RNA scaffold variant were generated to comprise combinations of stepwise deletions in the three regions discussed above. For region 1, stepwise base pair trimming was performed. For region 2, in addition to removing the disoriented stem loop, we installed stable hairpin structures commonly found in RNA (e.g., cUUCGg). For region 3 and its adjacent sequences, one or more deletions was performed (e.g., deletion of 136-149 nt), and additional stepwise truncations of other sequence(s) was performed to further reduce the scaffold size near region 3.

Gene repression was assessed by testing the gRNA scaffold variants with an engineered nuclease variant that is fused with a gene repressor. Each gRNA scaffold variant was individually cloned into the sgRNA plasmid with identical spacer sequence targeting the gene of interest. In 96-well plate format, HEK293T GFP reporter cells ESR221 (in each well) were transfected with identical dCas plasmid (e.g., encoding a gene suppression modulator, e.g., a dCas (such as dCasMINI as disclosed herein) that is fused with a gene repressor, such as KRAB), and individual sgRNA variant plasmid as triplicate or quadruplicate repeats. After five to seven days post-transfection, suppression of GFP expression was measured by flow cytometry. The level of GFP suppression of each gRNA scaffold variant was compared to the activity of the SQ control gRNA.

Gene activation was assessed by testing the gRNA scaffold variants with an engineered nuclease variant that is fused with a gene activator. Each gRNA scaffold variant was individually cloned into the sgRNA plasmid with identical spacer sequence targeting the gene of interest. HEK293T cells were transfected with identical dCas plasmid (e.g., encoding a gene activation modulator, e.g., a dCas (such as dCasMINI as disclosed herein) that is fused with a gene activator, such as VPR), and individual sgRNA variant plasmid as triplicate or quadruplicate repeats in 96-well plate format. Two to four days post-transfection, target gene activation was measured (e.g., CD2 protein levels were quantified by cell surface antibody staining of live cells followed by flow cytometry, while secreted IFNγ protein levels were measured using ELISA on cell culture supernatants). The level of gene activation of each gRNA scaffold variant was compared to the activity of the SQ control gRNA.

B. First Round

Figure 10:
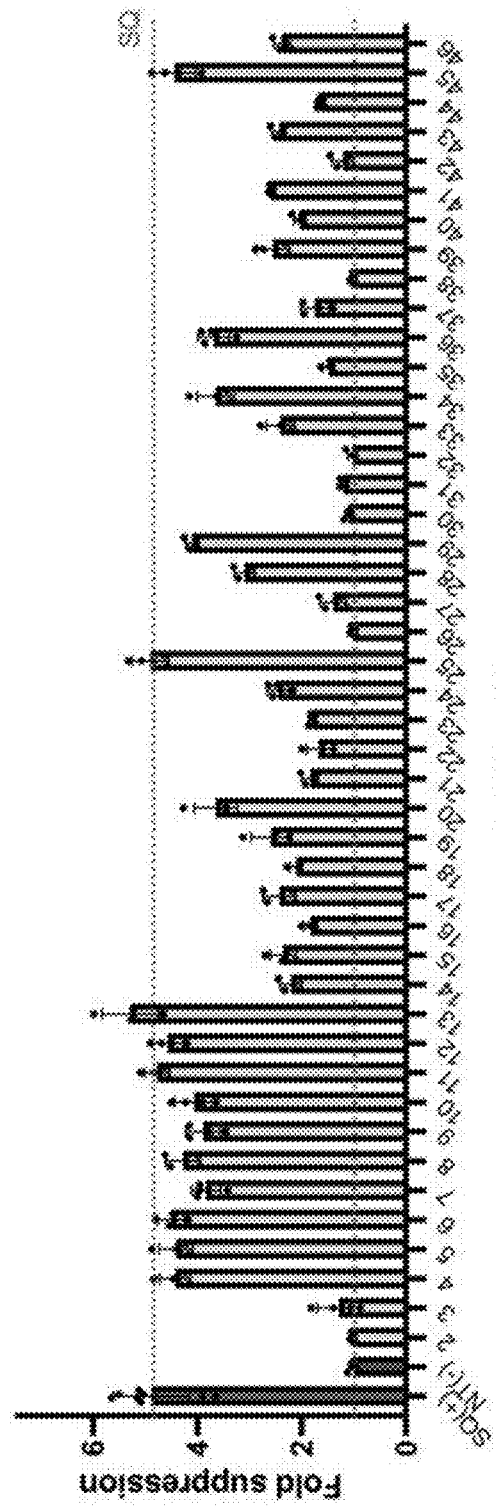
FIG. 10 shows reduced expression of a target gene (e.g., GFP) in cells by a plurality of engineered guide RNA variants disclosed herein. The plurality of engineered guide RNA variants was modified at least in the scaffold region, as compared to a control guide RNA sequence ("SQ"). The reduced gene expression was performed with the same dCas protein coupled to a gene repressing modulator.

In the first round, gRNA scaffold variants provided in TABLE 6B (e.g., SEQ ID NOs: 501-554 and 600) and the control gRNA scaffold sequence SQ (SEQ ID NO: 500) were tested with identical spacer sequence targeting synthetic GFP promoter region and with an identical gene suppression modulator. On day 5 post-transfection, GFP expression levels were quantified by flow cytometry and normalized to the negative control (SQ scaffold with non-targeting spacer sequence). As shown in FIG. 10 and summarized in TABLE 6A, various gRNA scaffold variants that were smaller than the SQ positive control exhibited either (i) comparable gene repression to the SQ positive control or (ii) greater gene repression than the SQ positive control (e.g., SEQ ID NOs: 503-152, 519, 524, 528, 553, etc.).

C. Second Round

Figure 11:
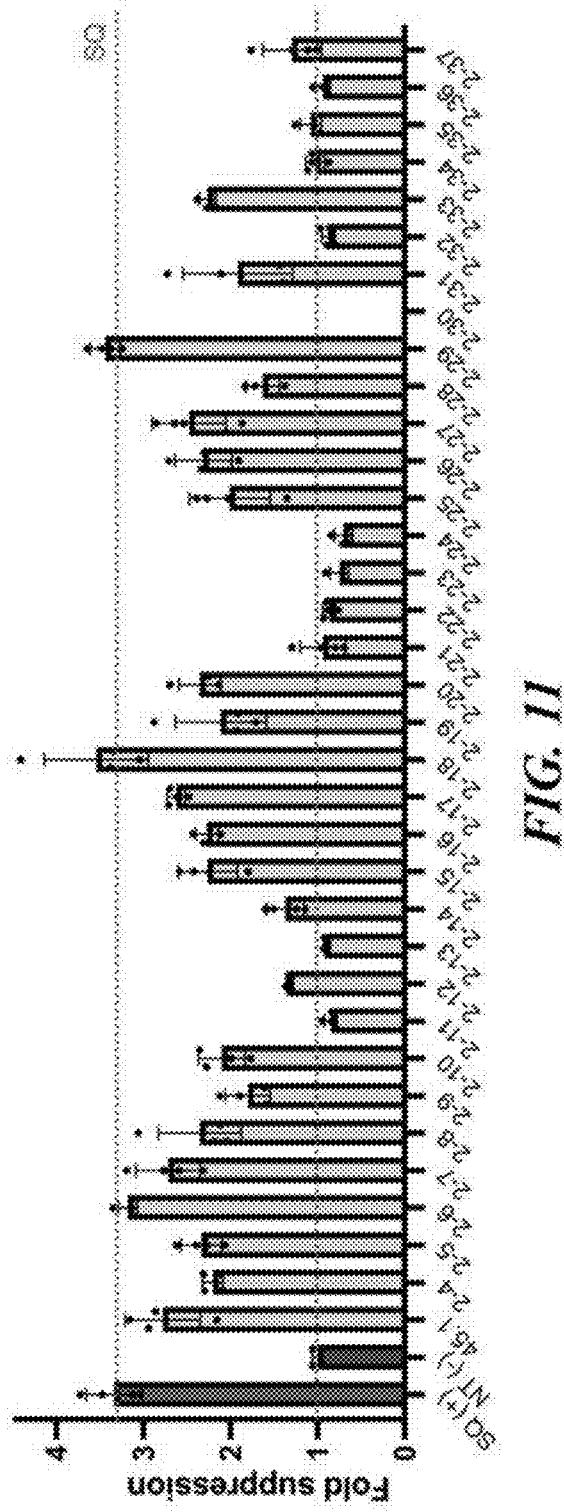
FIG. 11 shows reduced expression of a target gene (e.g., GFP) in cells by an additional plurality of engineered guide RNA variants disclosed herein. The additional plurality of engineered guide RNA variants was modified at least in the scaffold region, as compared to a control guide RNA sequence ("SQ"). The reduced gene expression was performed with the same dCas protein coupled to a gene repressing modulator.

In the second round, gRNA scaffold variants provided in TABLE 7B (e.g., SEQ ID NOs: 555-588) and the control gRNA scaffold sequence SQ (SEQ ID NO: 500) were tested with identical spacer sequence targeting synthetic GFP promoter region and with an identical gene suppression modulator. On day 5 post-transfection, eGFP expression levels were quantified by flow cytometry and normalized to the negative control (SQ scaffold with non-targeting spacer sequence). As shown in FIG. 11 and summarized in TABLE 7A, various gRNA scaffold variants that were smaller than the SQ positive control exhibited either (i) comparable gene repression to the SQ positive control or (ii) greater gene repression than the SQ positive control (e.g., SEQ ID NOs: 555, 557, 558, 568, 569, 578, 580, etc.).

D. Third Round

Figure 12:
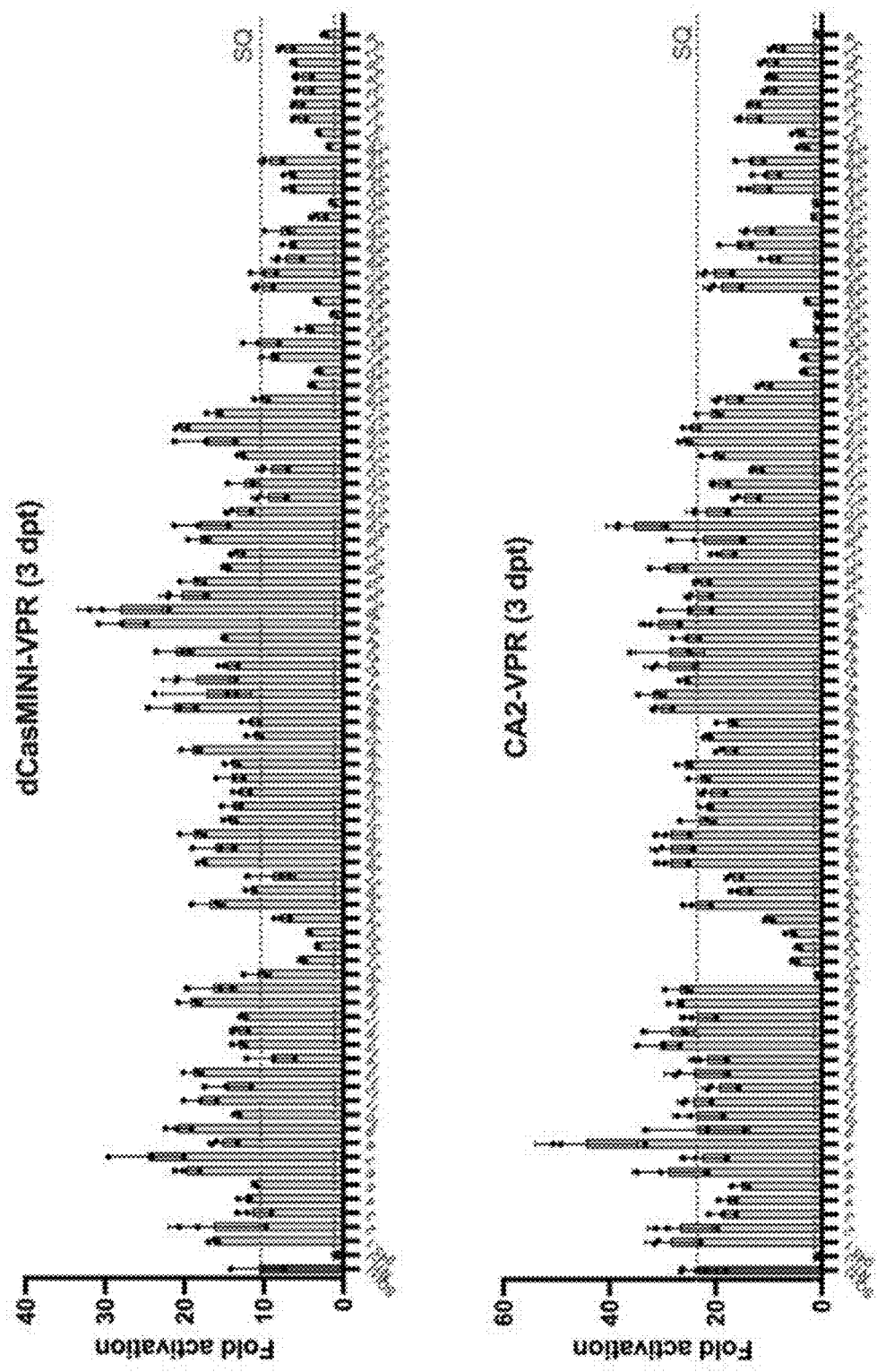
FIG. 12 shows enhanced expression of endogenous CD2 in cells by a different plurality of engineered guide RNA variants disclosed herein. The different plurality of engineered guide RNA variants was modified at least in the scaffold region, as compared to a control guide RNA sequence ("SQ"). The enhanced gene expression was performed with the same dCas protein coupled to a gene activating modulator.
Figure 13:
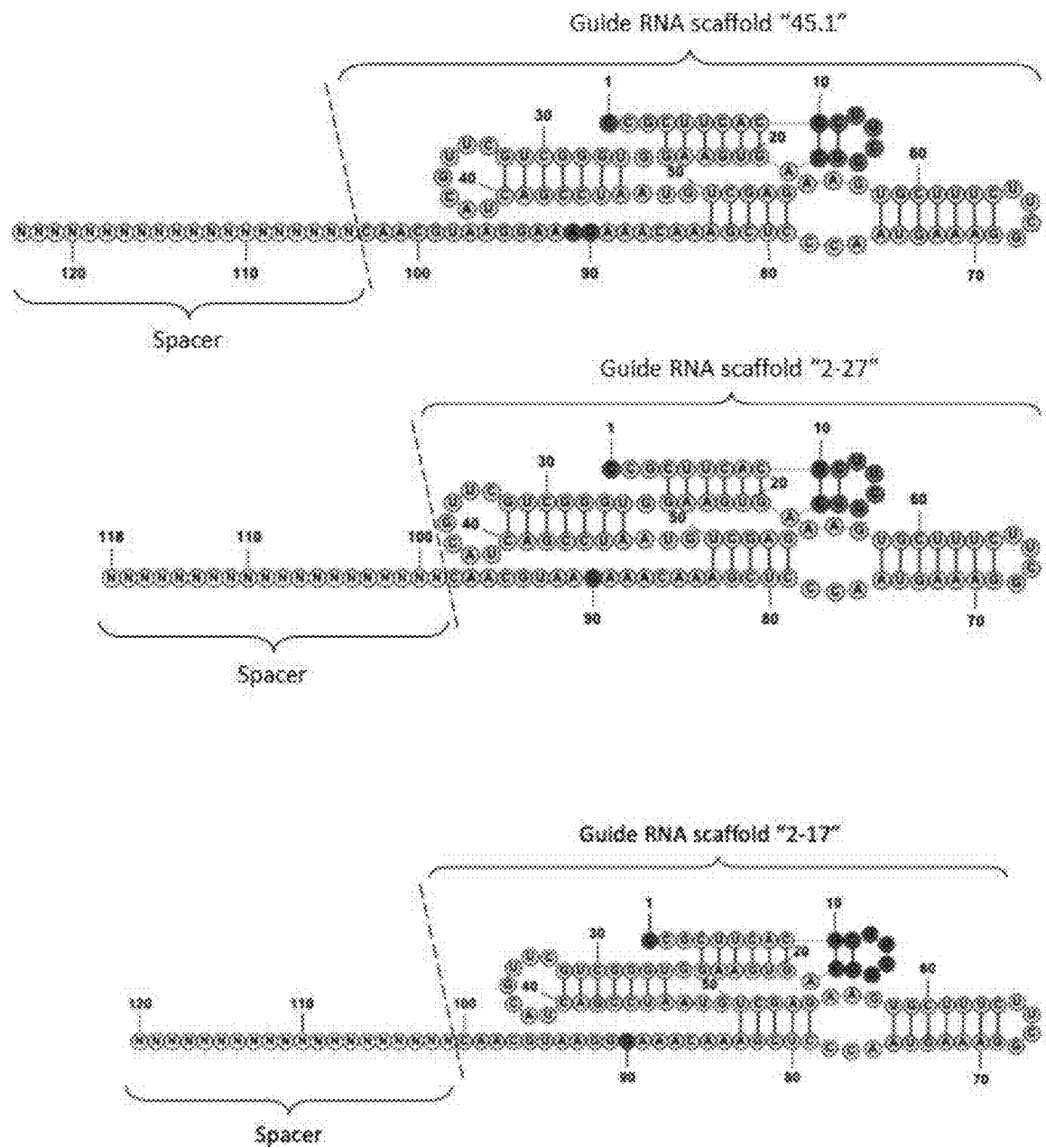
FIG. 13 schematically illustrates examples of the engineered guide nucleic acid molecules disclosed herein.

In the third round, lead gRNA scaffold variants (e.g., provided throughout TABLE 6B, TABLE 7B, and TABLE 8B) from the first and second rounds and the control gRNA scaffold sequence SQ (SEQ ID NO: 500) were tested with identical spacer sequence targeting upstream of CD2 locus (e.g., targeting endogenous DNA sequence) and with an identical gene activation modulator. On day 2 post-transfection, CD2 expression levels were quantified by antibody staining and flow cytometry and normalized to the negative control (SQ scaffold with non-targeting spacer sequence). As shown in FIG. 12 and summarized in TABLE 8A, various gRNA scaffold variants that were smaller than the SQ positive control exhibited either (i) comparable gene activation to the SQ positive control or (ii) greater gene activation than the SQ positive control (e.g., SEQ ID NOs: 555, 557, 568, 569, 576, 577, 578, 580, 593, 519, 528, etc.). For example, the gRNA scaffold variants such as SEQ ID NO: 555 (gRNA scaffold variant "45.1"), SEQ ID NO: 557 (gRNA scaffold variant "2-6"), SEQ ID NO: 556 (gRNA scaffold variant "2-17"), and SEQ ID NO: 578 (gRNA scaffold variant "2-27") resulted in greater CD2 activation than that by the SQ positive control (e.g., greater than 0.5-fold, greater than 1-fold, or greater than 1.5-fold increase in the degree of gene activation as compared to the SQ positive control). Single guide RNA molecules comprising the gRNA scaffold variants 45.1 and 2-27, and 2-17 are schematically illustrated in FIG. 13.

The gRNA scaffold variant disclosed herein (e.g., 45.1, 2-17 or 2-27) can be characterized to comprise at least a portion of its N-terminal sequence, e.g., the polynucleotide sequence of SEQ ID NO: 597 from TABLE 9.

The gRNA scaffold variant disclosed herein (e.g., 2-6) can be characterized to comprise at least a portion of its N-terminal sequence, e.g., the polynucleotide sequence of SEQ ID NO: 598 from TABLE 9.

Figure 14:
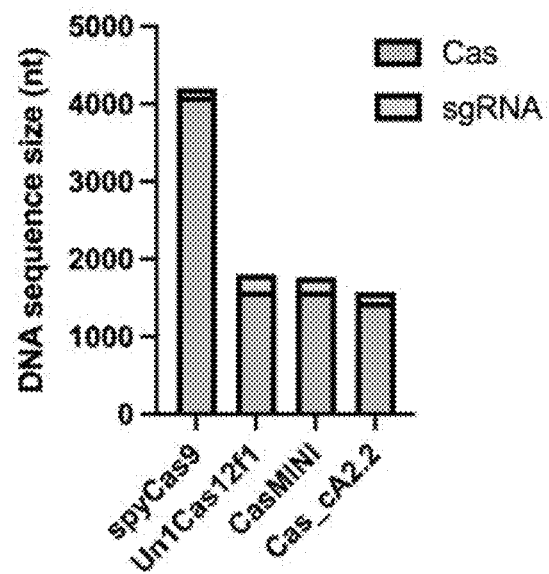
FIG. 14 shows comparison of sizes of various DNA vectors, each encoding a Cas protein and a respective single guide nucleic acid molecule.

E. RNP Complex Comprising a gRNA Scaffold Variant and an Engineered Nuclease Variant A gRNA scaffold variant disclosed herein (e.g., 45.1 or SEQ ID NO: 555) can be used to generate a sgRNA, which can be used in conjunction with any of the engineered nuclease variants disclosed herein (e.g., SEQ ID NO: 12) to (i) reduce the size of a vector encoding the sgRNA and the engineered nuclease variant, as illustrated in FIG. 14, and/or (ii) further improve target gene modulation (e.g., greater degree or modulation, longer duration of modulation, etc.).

Tables

TABLE 1

List of examples of target genes (e.g., encoding a protein of interest)
List of target genes/proteins of interest A1BG, CCND3, FAM163A, KCNK10, NRG4, REM1, TECTB, A1CF, CCNDBP1, FAM163B, KCNK12, NRGN, REM2, TEDDM1, A2M, CCNE1, FAM166A, KCNK13, NRIP1, REN, TEF, A2ML1, CCNE2, FAM166B, KCNK15, NRIP2, RENBP, TEFM, A3GALT2, CCNF, FAM167A, KCNK16, NRIP3, REP15, TEK, A4GALT, CCNG1, FAM167B, KCNK17, NRK, REPIN1, TEKT1, A4GNT, CCNG2, FAM168A, KCNK18, NRL, REPS1, TEKT2, AAAS, CCNH, FAM168B, KCNK2, NRM, REPS2, TEKT3, AACS, CCNI, FAM169A, KCNK3, NRN1, RER1, TEKT4, AADAC, CCNI2, FAM169B, KCNK4, NRN1L, RERE, TEKT5, AADACL2, CCNJ, FAM170A, KCNK5, NRP1, RERG, TELO2, AADACL3, CCNJL, FAM170B, KCNK6, NRP2, RERGL, TEN1, AADACL4, CCNK, FAM171A1, KCNK7, NRROS, RESP18, TENC1, AADAT, CCNL1, FAM171A2, KCNK9, NRSN1, REST, TENM1, AAED1, CCNL2, FAM171B, KCNMA1, NRSN2, RET, TENM2, AAGAB, CCNO, FAM172A, KCNMB1, NRTN, RETN, TENM3, AAK1, CCNT1, FAM173A, KCNMB2, NRXN1, RETNLB, TENM4, AAMDC, CCNT2, FAM173B, KCNMB3, NRXN2, RETSAT, TEP1, AAMP, CCNY, FAM174A, KCNMB4, NRXN3, REV1, TEPP, AANAT, CCNYL1, FAM174B, KCNN1, NSA2, REV3L, TERF1, AAR2, CCP110, FAM175A, KCNN2, NSD1, REXO1, TERF2, AARD, CCPG1, TABLE 1-continued List of examples of target genes (e.g., encoding a protein of interest)
List of target genes/proteins of interest FAM175B, KCNN3, NSDHL, REXO2, TERF2IP, AARS, CCR1, FAM177A1, KCNN4, NSF, REXO4, TERT, AARS2, CCR10, FAM177B, KCNQ1, NSFL1C, RFC1, TES, AARSD1, CCR2, FAM178A, KCNQ2, NSG1, RFC2, TESC, AASDH, CCR3, FAM178B, KCNQ3, NSL1, RFC3, TESK1, AASDHPPT, CCR4, FAM179A, KCNQ4, NSMAF, RFC4, TESK2, AASS, CCR5, FAM179B, KCNQ5, NSMCE1, RFC5, TESPA1, AATF, CCR6, FAM180A, KCNRG, NSMCE2, RFESD, TET1, AATK, CCR7, FAM180B, KCNS1, NSMCE4A, RFFL, TET2, ABAT, CCR8, FAM181A, KCNS2, NSMF, RFK, TET3, ABCA1, CCR9, FAM181B, KCNS3, NSRP1, RFNG, TEX10, ABCA10, CCRL2, FAM183A, KCNT1, NSUN2, RFPL1, TEX101, ABCA12, CCRN4L, FAM184A, KCNT2, NSUN3, RFPL2, TEX11, ABCA13, CCS, FAM184B, KCNU1, NSUN4, RFPL3, TEX12, ABCA2, CCSAP, FAM185A, KCNV1, NSUN5, RFPL4A, TEX13A, ABCA3, CCSER1, FAM186A, KCNV2, NSUN6, RFPL4AL1, TEX13B, ABCA4, CCSER2, FAM186B, KCP, NSUN7, RFPL4B, TEX14, ABCA5, CCT2, FAM187B, KCTD1, NT5C, RFT1, TEX15, ABCA6, CCT3, FAM188A, KCTD10, NT5C1A, RFTN1, TEX19, ABCA7, CCT4, FAM188B, KCTD11, NT5C1B, RFTN2, TEX2, ABCA8, CCT5, FAM189A1, KCTD12, NT5C1B-RDH14, RFWD2, TEX22, ABCA9, CCT6A, FAM189A2, KCTD13, NT5C2, RFWD3, TEX26, ABCB1, CCT6B, FAM189B, KCTD14, NT5C3A, RFX1, TEX261, ABCB10, CCT7, FAM192A, KCTD15, NT5C3B, RFX2, TEX264, ABCB11, CCT8, FAM193A, KCTD16, NT5DC1, RFX3, TEX28, ABCB4, CCT8L2, FAM193B, KCTD17, NT5DC2, RFX4, TEX29, ABCB5, CCZ1, FAM194A, KCTD18, NT5DC3, RFX5, TEX30, ABCB6, CCZ1B, FAM194B, KCTD19, NT5E, RFX6, TEX33, ABCB7, CD101, FAM195A, KCTD2, NT5M, RFX7, TEX35, ABCB8, CD109, FAM195B, KCTD20, NTAN1, RFX8, TEX36, ABCB9, CD14, FAM196A, KCTD21, NTF3, RFXANK, TEX37, ABCC1, CD151, FAM196B, KCTD3, NTF4, RFXAP, TEX38, ABCC10, CD160, FAM198A, KCTD4, NTHL1, RGAG1, TEX40, ABCC11, CD163, FAM198B, KCTD5, NTM, RGAG4, TEX9, ABCC12, CD163L1, FAM199X, KCTD6, NTMT1, RGCC, TF, ABCC2, CD164, FAM19A1, KCTD7, NTN1, RGL1, TFAM, ABCC3, CD164L2, FAM19A2, KCTD8, NTN3, RGL2, TFAP2A, ABCC4, CD177, FAM19A3, KCTD9, NTN4, RGL3, TFAP2B, ABCC5, CD180, FAM19A4, KDELC1, NTN5, RGL4, TFAP2C, ABCC6, CD19, FAM19A5, KDELC2, NTNG1, RGMA, TFAP2D, ABCC8, CD1A, FAM200A, KDELR1, NTNG2, RGMB, TFAP2E, ABCC9, CD1B, FAM203A, KDELR2, NTPCR, RGN, TFAP4, ABCD1, CD1C, FAM203B, KDELR3, NTRK1, RGP1, TFB1M, ABCD2, CD1D, FAM204A, KDM1A, NTRK2, RGPD1, TFB2M, ABCD3, CD1E, FAM205A, KDM1B, NTRK3, RGPD2, TFCP2, ABCD4, CD2, FAM206A, KDM2A, NTS, RGPD3, TFCP2L1, ABCE1, CD200, FAM207A, KDM2B, NTSR1, RGPD4, TFDP1, ABCF1, CD200R1, FAM208A, KDM3A, NTSR2, RGPD5, TFDP2, ABCF2, CD200R1L, FAM208B, KDM3B, NUAK1, RGPD6, TFDP3, ABCF3, CD207, FAM209A, KDM4A, NUAK2, RGPD8, TFE3, ABCG1, CD209, FAM209B, KDM4B, NUB1, RGR, TFEB, ABCG2, CD22, FAM20A, KDM4C, NUBP1, RGS1, TFEC, ABCG4, CD226, FAM20B, KDM4D, NUBP2, RGS10, TFF1, ABCG5, CD24, FAM20C, KDM4E, NUBPL, RGS11, TFF2, ABCG8, CD244, FAM210A, KDM5A, NUCB1, RGS12, TFF3, ABHD1, CD247, FAM210B, KDM5B, NUCB2, RGS13, TFG, ABHD10, CD248, FAM211A, KDM5C, NUCKS1, RGS14, TFIP11, ABHD11, CD27, FAM211B, KDM5D, NUDC, RGS16, TFPI, ABHD12, CD274, FAM212A, KDM6A, NUDCD1, RGS17, TFPI2, ABHD12B, CD276, FAM212B, KDM6B, NUDCD2, RGS18, TFPT, ABHD13, CD28, FAM213A, KDM8, NUDCD3, RGS19, TFR2, ABHD14A, CD2AP, FAM213B, KDR, NUDT1, RGS2, TFRC, ABHD14B, CD2BP2, FAM214A, KDSR, NUDT10, RGS20, TG, ABHD15, CD300A, FAM214B, KEAP1, NUDT11, RGS21, TGDS, ABHD16A, CD300C, FAM216A, KEL, NUDT12, RGS22, TGFA, ABHD16B, CD300E, FAM216B, KERA, NUDT13, RGS3, TGFB1, ABHD17A, CD300LB, FAM217A, KHDC1, NUDT14, RGS4, TGFB1I1, ABHD17B, CD300LD, FAM217B, KHDC1L, NUDT15, RGS5, TGFB2, ABHD17C, CD300LF, FAM218A, KHDC3L, NUDT16, RGS6, TGFB3, ABHD2, CD300LG, FAM219A, KHDRBS1, NUDT16L1, RGS7, TGFBI, ABHD3, CD302, FAM219B, KHDRBS2, NUDT17, RGS7BP, TGFBR1, ABHD4, CD320, FAM21A, KHDRBS3, NUDT18, RGS8, TGFBR2, ABHD5, CD33, FAM21B, KHK, NUDT19, RGS9, TGFBR3, ABHD6, CD34, FAM21C, KHNYN, NUDT2, RGS9BP, TGFBR3L, ABHD8, CD36, FAM220A, KHSRP, NUDT21, RGSL1, TGFBRAP1, ABI1, CD37, FAM221A, KIAA0020, NUDT22, RHAG, TGIF1, ABI2, CD38, FAM221B, KIAA0040, NUDT3, RHBDD1, TGIF2, ABI3, CD3D, FAM222A, KIAA0100, NUDT4, RHBDD2, TGIF2-C20orf24, ABI3BP, CD3E, FAM222B, KIAA0101, NUDT5, RHBDD3, TGIF2LX, ABL1, CD3EAP, FAM227A, KIAA0141, NUDT6, RHBDF1, TGIF2LY, ABL2, CD3G, FAM227B, KIAA0195, NUDT7, RHBDF2, TGM1, ABLIM1, CD4, FAM228A, KIAA0196, NUDT8, RHBDL1, TGM2, ABLIM2, CD40, FAM228B, KIAA0226, NUDT9, RHBDL2, TGM3, ABLIM3, CD40LG, FAM229A, KIAA0226L, NUF2, RHBDL3, TGM4, ABO, CD44, FAM229B, KIAA0232, NUFIP1, RHBG, TGM5, ABR, CD46, FAM230A, KIAA0247, NUFIP2, RHCE, TGM6, ABRA, CD47, FAM24A, KIAA0319, NUGGC, RHCG, TGM7, ABRACL, CD48, FAM24B, KIAA0319L, NUMA1, RHD, TGOLN2, ABT1, CD5, FAM25A, KIAA0355, NUMB, RHEB, TGS1, ABTB1, CD52, FAM25C, KIAA0368, NUMBL, RHEBL1, TH, ABTB2, CD53, FAM25G, KIAA0391, NUP107, RHNO1, THADA, ACAA1, CD55, FAM26D, KIAA0408, NUP133, RHO, THAP1, ACAA2, CD58, FAM26E, KIAA0430, NUP153, RHOA, THAP10, ACACA, CD59, FAM26F, KIAA0513, NUP155, RHOB, THAP11, ACACB, CD5L, FAM32A, KIAA0556, NUP160, RHOBTB1, THAP2, ACAD10, CD6, FAM35A, KIAA0586, NUP188, RHOBTB2, THAP3, ACAD11, CD63, FAM3A, KIAA0753, NUP205, RHOBTB3, THAP4, ACAD8, CD68, FAM3B, KIAA0754, NUP210, RHOC, THAP5, ACAD9, CD69, FAM3C, KIAA0825, NUP210L, RHOD, THAP6, ACADL, CD7, FAM3D, KIAA0895, NUP214, RHOF, THAP7, ACADM, CD70, FAM43A, KIAA0895L, NUP35, RHOG, THAP8, ACADS, CD72, FAM43B, KIAA0907, NUP37, RHOH, THAP9, ACADSB, CD74, FAM45A, KIAA0922, NUP43, RHOJ, THBD, ACADVL, CD79A, FAM46A, KIAA0930, NUP50, RHOQ, THBS1, ACAN, CD79B, FAM46B, KIAA0947, NUP54, RHOT1, THBS2, ACAP1, CD80, FAM46C, KIAA1009, NUP62, RHOT2, THBS3, ACAP2, CD81, FAM46D, KIAA1024, NUP62CL, RHOU, THBS4, ACAP3, CD82, FAM47A, KIAA1024L, NUP85, RHOV, THEG, ACAT1, CD83, FAM47B, KIAA1033, NUP88, RHOXF1, THEG5, ACAT2, CD84, FAM47C, KIAA1045, NUP93, RHOXF2, THEGL, ACBD3, CD86, FAM47E, KIAA1107, NUP98, RHOXF2B, THEM4, ACBD4, CD8A, FAM47E-STBD1, KIAA1109, NUPL1, RHPN1, THEM5, ACBD5, CD8B, FAM49A, KIAA1143, NUPL2, RHPN2, THEM6, ACBD6, CD9, FAM49B, KIAA1147, NUPR1, RIBC1, THEMIS, ACBD7, CD93, FAM50A, KIAA1161, NUPR1L, RIBC2, THEMIS2, ACCS, CD96, FAM50B, KIAA1191, NUS1, RIC3, THG1L, ACCSL, CD97, FAM53A, KIAA1199, NUSAP1, TABLE 1-continued List of examples of target genes (e.g., encoding a protein of interest)
List of target genes/proteins of interest RIC8A, THNSL1, ACD, CD99, FAM53B, KIAA1210, NUTF2, RIC8B, THNSL2, ACE, CD99L2, FAM53C, KIAA1211, NUTM1, RICTOR, THOC1, ACE2, CDA, FAM57A, KIAA1211L, NUTM2A, RIF1, THOC2, ACER1, CDADC1, FAM57B, KIAA1217, NUTM2B, RIIAD1, THOC3, ACER2, CDAN1, FAM58A, KIAA1239, NUTM2F, RILP, THOC5, ACER3, CDC123, FAM60A, KIAA1244, NUTM2G, RILPL1, THOC6, ACHE, CDC14A, FAM63A, KIAA1257, NVL, RILPL2, THOC7, ACIN1, CDC14B, FAM63B, KIAA1279, NWD1, RIMBP2, THOP1, ACKR1, CDC16, FAM64A, KIAA1324, NXF1, RIMBP3, THPO, ACKR2, CDC20, FAM65A, KIAA1324L, NXF2, RIMBP3B, THRA, ACKR3, CDC20B, FAM65B, KIAA1328, NXF2B, RIMBP3C, THRAP3, ACKR4, CDC23, FAM65C, KIAA1377, NXF3, RIMKLA, THRB, ACLY, CDC25A, FAM69A, KIAA1407, NXF5, RIMKLB, THRSP, ACMSD, CDC25B, FAM69B, KIAA1429, NXN, RIMS1, THSD1, ACN9, CDC25C, FAM69C, KIAA1430, NXNL1, RIMS2, THSD4, ACO1, CDC26, FAM71A, KIAA1432, NXNL2, RIMS3, THSD7A, ACO2, CDC27, FAM71B, KIAA1456, NXPE1, RIMS4, THSD7B, ACOT1, CDC34, FAM71C, KIAA1462, NXPE2, RIN1, THTPA, ACOT11, CDC37, FAM71D, KIAA1467, NXPE3, RIN2, THUMPD1, ACOT12, CDC37L1, FAM71E1, KIAA1468, NXPE4, RIN3, THUMPD2, ACOT13, CDC40, FAM71E2, KIAA1522, NXPH1, RING1, THUMPD3, ACOT2, CDC42, FAM71F1, KIAA1524, NXPH2, RINL, THY1, ACOT4, CDC42BPA, FAM71F2, KIAA1549, NXPH3, RINT1, THYN1, ACOT6, CDC42BPB, FAM72A, KIAA1549L, NXPH4, RIOK1, TIA1, ACOT7, CDC42BPG, FAM72B, KIAA1551, NXT1, RIOK2, TIAF1, ACOT8, CDC42EP1, FAM73D, KIAA1586, NXT2, RIOK3, TIAL1, ACOT9, CDC42EP2, FAM73A, KIAA1598, NYAP1, RIPK1, TIAM1, ACOX1, CDC42EP3, FAM73B, KIAA1614, NYAP2, RIPK2, TIAM2, ACOX2, CDC42EP4, FAM76A, KIAA1644, NYNRIN, RIPK3, TICAM1, ACOX3, CDC42EP5, FAM76B, KIAA1671, NYX, RIPK4, TICAM2, ACOXL, CDC42SE1, FAM78A, KIAA1683, OAF, RIPPLY1, TICRR, ACP1, CDC42SE2, FAM78B, KIAA1715, OARD1, RIPPLY2, TIE1, ACP2, CDC45, FAM81A, KIAA1731, OAS1, RIPPLY3, TIFA, ACP5, CDC5L, FAM81B, KIAA1737, OAS2, RIT1, TIFAB, ACP6, CDC6, FAM83A, KIAA1751, OAS3, RIT2, TIGD2, ACPL2, CDC7, FAM83B, KIAA1755, OASL, RLBP1, TIGD3, ACPP, CDC73, FAM83C, KIAA1804, OAT, RLF, TIGD4, ACPT, CDCA2, FAM83D, KIAA1841, OAZ1, RLIM, TIGD5, ACR, CDCA3, FAM83E, KIAA1919, OAZ2, RLN1, TIGD6, ACRBP, CDCA4, FAM83F, KIAA1958, OAZ3, RLN2, TIGD7, ACRC, CDCA5, FAM83G, KIAA1984, OBFC1, RLN3, TIGIT, ACRV1, CDCA7, FAM83H, KIAA2013, OBP2A, RLTPR, TIMD4, ACSBG1, CDCA7L, FAM84A, KIAA2018, OBP2B, RMDN1, TIMELESS, ACSBG2, CDCA8, FAM84B, KIAA2022, OBSCN, RMDN2, TIMM10, ACSF2, CDCP1, FAM86A, KIAA2026, OBSL1, RMDN3, TIMM10B, ACSF3, CDCP2, FAM86B1, KIDINS220, OC90, RMI1, TIMM13, ACSL1, CDH1, FAM86B2, KIF11, OCA2, RMI2, TIMM17A, ACSL3, CDH10, FAM86C1, KIF12, OCEL1, RMND1, TIMM17B, ACSL4, CDH11, FAM86KP, KIF13A, OCIAD1, RMND5A, TIMM21, ACSL5, CDH12, FAM89A, KIF13B, OCIAD2, RMND5B, TIMM22, ACSL6, CDH13, FAM89B, KIF14, OCLM, RNASE1, TIMM23, ACSM1, CDH15, FAM8A1, KIF15, OCLN, RNASE10, TIMM23B, ACSM2A, CDH16, FAM90A1, KIF16B, OCM, RNASE11, TIMM44, ACSM2B, CDH17, FAM91A1, KIF17, OCM2, RNASE12, TIMM50, ACSM3, CDH18, FAM92A1, KIF18A, OCRL, RNASE13, TIMM8A, ACSM4, CDH19, FAM92B, KIF18B, OCSTAMP, RNASE2, TIMM8B, ACSM5, CDH2, FAM96A, KIF19, ODAM, RNASE3, TIMM9, ACSS1, CDH20, FAM96B, KIF1A, ODC1, RNASE4, TIMMDC1, ACSS2, CDH22, FAM98A, KIF1B, ODF1, RNASE6, TIMP1, ACSS3, CDH23, FAM98B, KIF1C, ODF2, RNASE7, TIMP2, ACTA1, CDH24, FAM98C, KIF20A, ODF2L, RNASE8, TIMP3, ACTA2, CDH26, FAM9A, KIF20B, ODF3, RNASE9, TIMP4, ACTB, CDH3, FAM9B, KIF21A, ODF3B, RNASEH1, TINAG, ACTBL2, CDH4, FAM9C, KIF21B, ODF3L1, RNASEH2A, TINAGL1, ACTC1, CDH5, FAN1, KIF22, ODF3L2, RNASEH2B, TINF2, ACTG1, CDH6, FANCA, KIF23, ODF4, RNASEH2C, TIPARP, ACTG2, CDH7, FANCB, KIF24, OFCC1, RNASEK, TIPIN, ACTL10, CDH8, FANCC, KIF25, OFD1, RNASEL, TIPRL, ACTL6A, CDH9, FANCD2, KIF26A, OGDH, RNASET2, TIRAP, ACTL6B, CDHR1, FANCD2OS, KIF26B, OGDHL, RND1, TJAP1, ACTL7A, CDHR2, FANCE, KIF27, OGFOD1, RND2, TJP1, ACTL7B, CDHR3, FANCF, KIF28P, OGFOD2, RND3, TJP2, ACTL8, CDHR4, FANCG, KIF2A, OGFOD3, RNF10, TJP3, ACTL9, CDHR5, FANCI, KIF2B, OGFR, RNF103, TK1, ACTN1, CDIP1, FANCL, KIF2C, OGFRL1, RNF103-CHMP3, TK2, ACTN2, CDIPT, FANCM, KIF3A, OGG1, RNF11, TKT, ACTN3, CDK1, FANK1, KIF3B, OGN, RNF111, TKTL1, ACTN4, CDK10, FAP, KIF3C, OGT, RNF112, TKTL2, ACTR10, CDK11A, FAR1, KIF4A, OIP5, RNF113A, TLCD1, ACTR1A, CDK11B, FAR2, KIF4B, OIT3, RNF113B, TLCD2, ACTR1B, CDK12, FARP1, KIF5A, OLA1, RNF114, TLDC1, ACTR2, CDK13, FARP2, KIF5B, OLAH, RNF115, TLDC2, ACTR3, CDK14, FARS2, KIF5C, OLFM1, RNF121, TLE1, ACTR3B, CDK15, FARSA, KIF6, OLFM2, RNF122, TLE2, ACTR3C, CDK16, FARSB, KIF7, OLFM3, RNF123, TLE3, ACTR5, CDK17, FAS, KIF9, OLFM4, RNF125, TLE4, ACTR6, CDK18, FASLG, KIFAP3, OLFML1, RNF126, TLE6, ACTR8, CDK19, FASN, KIFC1, OLFML2A, RNF128, TLK1, ACTRT1, CDK2, FASTK, KIFC2, OLFML2B, RNF13, TLK2, ACTRT2, CDK20, FASTKD1, KIFC3, OLFML3, RNF130, TLL1, ACTRT3, CDK2AP1, FASTKD2, KIN, OLIG1, RNF133, TLL2, ACVR1, CDK2AP2, FASTKD3, KIR2DL1, OLIG2, RNF135, TLN1, ACVR1B, CDK3, FASTKD5, KIR2DL3, OLIG3, RNF138, TLN2, ACVR1C, CDK4, FAT1, KIR2DL4, OLR1, RNF139, TLR1, ACVR2A, CDK5, FAT2, KIR2DS4, OMA1, RNF14, TLR10, ACVR2B, CDK5R1, FAT3, KIR3DL1, OMD, RNF141, TLR2, ACVRL1, CDK5R2, FAT4, KIR3DL2, OMG, RNF144A, TLR3, ACY1, CDK5RAP1, FATE1, KIR3DL3, OMP, RNF144B, TLR4, ACY3, CDK5RAP2, FAU, KIRREL, ONECUT1, RNF145, TLR5, ACYP1, CDK5RAP3, FAXC, KIRREL2, ONECUT2, RNF146, TLR6, ACYP2, CDK6, FAXDC2, KIRREL3, ONECUT3, RNF148, TLR7, ADA, CDK7, FBF1, KISS1, OOEP, RNF149, TLR8, ADAD1, CDK8, FBL, KISS1R, OOSP2, RNF150, TLR9, ADAD2, CDK9, FBLIM1, KIT, OPA1, RNF151, TLX1, ADAL, CDKAL1, FBLN1, KITLG, OPA3, RNF152, TLX1NB, ADAM10, CDKL1, FBLN2, KL, OPALIN, RNF157, TLX2, ADAM11, CDKL2, FBLN5, KLB, OPCML, RNF165, TLX3, ADAM12, CDKL3, FBLN7, KLC1, OPHN1, RNF166, TM2D1, ADAM15, CDKL4, FBN1, KLC2, OPLAH, RNF167, TM2D2, ADAM17, CDKL5, FBN2, KLC3, OPN1LW, RNF168, TM2D3, ADAM18, CDKN1A, FBN3, KLC4, OPN1MW, RNF169, TM4SF1, ADAM19, CDKN1B, FBP1, KLF1, OPN1MW2, RNF17, TM4SF18, ADAM2, CDKN1C, FBP2, KLF10, OPN1SW, RNF170, TM4SF19, ADAM20, CDKN2A, FBRS, KLF11, OPN3, RNF175, TM4SF20, ADAM21, CDKN2AIP, FBRSL1, KLF12, OPN4, RNF180, TM4SF4, ADAM22, CDKN2AIPNL, FBXL12, KLF13, OPN5, RNF181, TM4SF5, ADAM23, CDKN2B, FBXL13, KLF14, OPRD1, RNF182, TM6SF1, ADAM28, CDKN2C, TABLE 1-continued List of examples of target genes (e.g., encoding a protein of interest)
List of target genes/proteins of interest FBXL14, KLF15, OPRK1, RNF183, TM6SF2, ADAM29, CDKN2D, FBXL15, KLF16, OPRL1,
RNF185, TM7SF2, ADAM30, CDKN3, FBXL16, KLF17, OPRM1, RNF186, TM7SF3, ADAM32,
CDNF, FBXL17, KLF2, OPTC, RNF187, TM9SF1, ADAM33, CDO1, FBXL18, KLF3, OPTN,
RNF19A, TM9SF2, ADAM7, CDON, FBXL19, KLF4, OR10A2, RNF19B, TM9SF3, ADAM8, CDPF1,
FBXL2, KLF5, OR10A3, RNF2, TM9SF4, ADAM9, CDR1, FBXL20, KLF6, OR10A4, RNF20,
TMA16, ADAMDEC1, CDR2, FBXL21, KLF7, OR10A5, RNF207, TMA7, ADAMTS1, CDR2L,
FBXL22, KLF8, OR10A6, RNF208, TMBIM1, ADAMTS10, CDRT1, FBXL3, KLF9, OR10A7,
RNF212, TMBIM4, ADAMTS12, CDRT15, FBXL4, KLHDC1, OR10AG1, RNF213, TMBIM6,
ADAMTS13, CDRT15L2, FBXL5, KLHDC10, OR10C1, RNF214, TMC1, ADAMTS14, CDRT4,
FBXL6, KLHDC2, OR10G2, RNF215, TMC2, ADAMTS15, CDS1, FBXL7, KLHDC3, OR10G3,
RNF216, TMC3, ADAMTS16, CDS2, FBXL8, KLHDC4, OR10G4, RNF217, TMC4, ADAMTS17,
CDSN, FBXO10, KLHDC7A, OR10G7, RNF219, TMC5, ADAMTS18, CDT1, FBXO11, KLHDC7B,
OR10G8, RNF220, TMC6, ADAMTS19, CDV3, FBXO15, KLHDC8A, OR10G9, RNF222, TMC7,
ADAMTS2, CDX1, FBXO16, KLHDC8B, OR10H1, RNF223, TMC8, ADAMTS20, CDX2, FBXO17,
KLHDC9, OR10H2, RNF224, TMCC1, ADAMTS3, CDX4, FBXO18, KLHL1, OR10H3, RNF24,
TMCC2, ADAMTS4, CDY1, FBXO2, KLHL10, OR10H4, RNF25, TMCC3, ADAMTS5, CDY1B,
FBXO21, KLHL11, OR10H5, RNF26, TMCO1, ADAMTS6, CDY2A, FBXO22, KLHL12, OR10J1,
RNF31, TMCO2, ADAMTS7, CDY2B, FBXO24, KLHL13, OR10J3, RNF32, TMCO3, ADAMTS8,
CDYL, FBXO25, KLHL14, OR10J5, RNF34, TMCO4, ADAMTS9, CDYL2, FBXO27, KLHL15,
OR10K1, RNF38, TMCO5A, ADAMTSLI, CEACAM1, FBXO28, KLHL17, OR10K2, RNF39,
TMCO6, ADAMTSL2, CEACAM16, FBXO3, KLHL18, OR10P1, RNF4, TMED1, ADAMTSL3,
CEACAM18, FBXO30, KLHL2, OR10Q1, RNF40, TMED10, ADAMTSL4, CEACAM19, FBXO31,
KLHL20, OR10R2, RNF41, TMED2, ADAMTSL5, CEACAM20, FBXO32, KLHL21, OR10S1, RNF43,
TMED3, ADAP1, CEACAM21, FBXO33, KLHL22, OR10T2, RNF44, TMED4, ADAP2, CEACAM3,
FBXO34, KLHL23, OR10V1, RNF5, TMED5, ADAR, CEACAM4, FBXO36, KLHL24, OR10W1,
RNF6, TMED6, ADARB1, CEACAM5, FBXO38, KLHL25, OR10X1, RNF7, TMED7, ADARB2,
CEACAM6, FBXO39, KLHL26, OR10Z1, RNF8, TMED7-TICAM2, ADAT1, CEACAM7, FBXO4,
KLHL28, OR11A1, RNFT1, TMED8, ADAT2, CEACAM8, FBXO40, KLHL29, OR11G2, RNFT2,
TMED9, ADAT3, CEBPA, FBXO41, KLHL3, OR11H1, RNGTT, TMEFF1, ADC, CEBPB, FBXO42,
KLHL30, OR11H12, RNH1, TMEFF2, ADCK1, CEBPD, FBXO43, KLHL31, OR11H2, RNLS,
TMEM100, ADCK2, CEBPE, FBXO44, KLHL32, OR11H4, RNMT, TMEM101, ADCK3, CEBPG,
FBXO45, KLHL33, OR11H6, RNMTL1, TMEM102, ADCK4, CEBPZ, FBXO46, KLHL34, OR11L1,
RNPC3, TMEM104, ADCK5, CECR1, FBXO47, KLHL35, OR12D2, RNPEP, TMEM105, ADCY1,
CECR2, FBXO48, KLHL36, OR12D3, RNPEPL1, TMEM106A, ADCY10, CECR5, FBXO5, KLHL38,
OR13A1, RNPS1, TMEM106B, ADCY2, CECR6, FBXO6, KLHL4, OR13C2, ROBO1, TMEM106C,
ADCY3, CEL, FBXO7, KLHL40, OR13C3, ROBO2, TMEM107, ADCY4, CELA1, FBXO8, KLHL41,
OR13C4, ROBO3, TMEM108, ADCY5, CELA2A, FBXO9, KLHL42, OR13C5, ROBO4, TMEM109,
ADCY6, CELA2B, FBXW10, KLHL5, OR13C8, ROCK1, TMEM11, ADCY7, CELA3A, FBXW11,
KLHL6, OR13C9, ROCK2, TMEM110, ADCY8, CELA3B, FBXW12, KLHL7, OR13D1, ROGDI,
TMEM110-MUSTN1, ADCY9, CELF1, FBXW2, KLHL8, OR13F1, ROM1, TMEM114, ADCYAP1,
CELF2, FBXW4, KLHL9, OR13G1, ROMO1, TMEM115, ADCYAP1R1, CELF3, FBXW5, KLK1,
OR13H1, ROPN1, TMEM116, ADD1, CELF4, FBXW7, KLK10, OR13J1, ROPN1B, TMEM117,
ADD2, CELF5, FBXW8, KLK11, OR14A16, ROPN1L, TMEM119, ADD3, CELF6, FBXW9, KLK12,
OR14C36, ROR1, TMEM120A, ADGB, CELSR1, FCAMR, KLK13, OR14J1, ROR2, TMEM120B,
ADH1A, CELSR2, FCAR, KLK14, OR1A1, RORA, TMEM121, ADH1B, CELSR3, FCER1A, KLK15,
OR1A2, RORB, TMEM123, ADH1C, CEMP1, FCER1G, KLK2, OR1B1, RORC, TMEM125, ADH4,
CEND1, FCER2, KLK3, OR1C1, ROS1, TMEM126A, ADH5, CENPA, FCF1, KLK4, OR1D2, RP1,
TMEM126B, ADH6, CENPB, FCGBP, KLK5, OR1D5, RP1L1, TMEM127, ADH7, CENPBD1,
FCGR1A, KLK6, OR1E1, RP2, TMEM128, ADHFE1, CENPC, FCGR1B, KLK7, OR1E2, RP9,
TMEM129, ADI1, CENPE, FCGR2A, KLK8, OR1F1, RPA1, TMEM130, ADIG, CENPF, FCGR2B,
KLK9, OR1G1, RPA2, TMEM131, ADIPOQ, CENPH, FCGR2C, KLKB1, OR1I1, RPA3, TMEM132A,
ADIPOR1, CENPI, FCGR3A, KLLN, OR1J1, RPA4, TMEM132B, ADIPOR2, CENPJ, FCGR3B,
KLRB1, OR1J4, RPAIN, TMEM132C, ADIRF, CENPK, FCGRT, KLRC1, OR1K1, RPAP1,
TMEM132D, ADK, CENPL, FCHO1, KLRC2, OR1L1, RPAP2, TMEM132E, ADM, CENPM, FCHO2,
KLRC3, OR1L3, RPAP3, TMEM133, ADM2, CENPN, FCHSD1, KLRC4, OR1L4, RPE, TMEM134,
ADM5, CENPO, FCHSD2, KLRC4-KLRK1, OR1L6, RPE65, TMEM135, ADNP, CENPP, FCN1,
KLRD1, OR1L8, RPF1, TMEM136, ADNP2, CENPQ, FCN2, KLRF1, OR1M1, RPF2, TMEM138,
ADO, CENPT, FCN3, KLRF2, OR1N1, RPGR, TMEM139, ADORA1, CENPU, FCRL1, KLRG1,
OR1N2, RPGRIP1, TMEM140, ADORA2A, CENPV, FCRL2, KLRG2, OR1Q1, RPGRIP1L,
TMEM141, ADORA2B, CENPW, FCRL3, KLRK1, OR1S1, RPH3A, TMEM143, ADORA3, CEP104,
FCRL4, KMO, OR1S2, RPH3AL, TMEM144, ADPGK, CEP112, FCRL5, KMT2A, OR2A12, RPIA,
TMEM145, ADPRH, CEP120, FCRL6, KMT2B, OR2A14, RPL10, TMEM147, ADPRHL1, CEP128,
FCRLA, KMT2C, OR2A2, RPL10A, TMEM14A, ADPRHL2, CEP135, FCRLB, KMT2D, OR2A25,
RPL10L, TMEM14B, ADPRM, CEP152, FDCSP, KMT2E, OR2A4, RPL11, TMEM14C, ADRA1A,
CEP164, FDFT1, KNCN, OR2A5, RPL12, TMEM14E, ADRA1B, CEP170, FDPS, KNDC1, OR2A7,
RPL13, TMEM150A, ADRA1D, CEP170B, FDX1, KNG1, OR2AE1, RPL13A, TMEM150B, ADRA2A,
CEP19, FDX1L, KNOP1, OR2AG1, RPL14, TMEM150C, ADRA2B, CEP192, FDXACB1, KNSTRN,
OR2AG2, RPL15, TMEM151A, ADRA2C, CEP250, FDXR, KNTC1, OR2AK2, RPL17, TMEM151B,
ADRB1, CEP290, FECH, KPNA1, OR2AP1, RPL17-C18orf32, TMEM154, ADRB2, CEP350, FEM1A,
KPNA2, OR2AT4, RPL18, TMEM155, ADRB3, CEP41, FEM1B, KPNA3, OR2B11, RPL18A,
TMEM156, ADRBK1, CEP44, FEM1C, KPNA4, OR2B2, RPL19, TMEM158, ADRBK2, CEP55, FEN1,
KPNA5, OR2B3, RPL21, TMEM159, ADRM1, CEP57, FER, KPNA6, OR2B6, RPL22, TMEM160,
ADSL, CEP57L1, FER1L5, KPNA7, OR2C1, RPL22L1, TMEM161A, ADSS, CEP63, FER1L6,
KPNB1, OR2C3, RPL23, TMEM161B, ADSSL1, CEP68, FERD3L, KPRP, OR2D2, RPL23A,
TMEM163, ADTRP, CEP70, FERMT1, KPTN, OR2D3, RPL24, TMEM164, AEBP1, CEP72, FERMT2,
KRAS, OR2F1, RPL26, TMEM165, AEBP2, CEP76, FERMT3, KRBA1, OR2F2, RPL26L1,
TMEM167A, AEN, CEP78, FES, KRBA2, OR2G2, RPL27, TMEM167B, AES, CEP85, FETUB, TABLE 1-continued List of examples of target genes (e.g., encoding a protein of interest)
List of target genes/proteins of interest KRBOX1, OR2G3, RPL27A, TMEM168, AFAP1, CEP85L, FEV, KRBOX4, OR2G6, RPL28, TMEM169, AFAP1L1, CEP89, FEZ1, KRCC1, OR2H1, RPL29, TMEM17, AFAP1L2, CEP95, FEZ2, KREMEN1, OR2J2, RPL3, TMEM170A, AFF1, CEP97, FEZF1, KREMEN2, OR2J3, RPL30, TMEM170B, AFF2, CEPT1, FEZF2, KRI1, OR2K2, RPL31, TMEM171, AFF3, CER1, FFAR1, KRIT1, OR2L13, RPL32, TMEM173, AFF4, CERCAM, FFAR2, KRR1, OR2L2, RPL34, TMEM174, AFG3L2, CERK, FFAR3, KRT1, OR2L3, RPL35, TMEM175, AFM, CERKL, FFAR4, KRT10, OR2L5, RPL35A, TMEM176A, AFMID, CERS1, FGA, KRT12, OR2L8, RPL36, TMEM176B, AFP, CERS2, FGB, KRT13, OR2M2, RPL36A, TMEM177, AFTPH, CERS3, FGD1, KRT14, OR2M3, RPL36A-HNRNPH2, TMEM178A, AGA, CERS4, FGD2, KRT15, OR2M4, RPL36AL, TMEM178B, AGAP1, CERS5, FGD3, KRT16, OR2M5, RPL37, TMEM179, AGAP10, CERS6, FGD4, KRT17, OR2M7, RPL37A, TMEM179B, AGAP11, CES1, FGD5, KRT18, OR2S2, RPL38, TMEM18, AGAP2, CES2, FGD6, KRT19, OR2T1, RPL39, TMEM180, AGAP3, CES3, FGF1, KRT2, OR2T10, RPL39L, TMEM181, AGAP4, CES4A, FGF10, KRT20, OR2T11, RPL3L, TMEM182, AGAP5, CES5A, FGF11, KRT222, OR2T12, RPL4, TMEM183A, AGAP6, CETN1, FGF12, KRT23, OR2T2, RPL41, TMEM183B, AGAP7, CETN2, FGF13, KRT24, OR2T27, RPL5, TMEM184A, AGAP8, CETN3, FGF14, KRT25, OR2T29, RPL6, TMEM184B, AGAP9, CETP, FGF16, KRT26, OR2T3, RPL7, TMEM184C, AGBL1, CFB, FGF17, KRT27, OR2T33, RPL7A, TMEM185A, AGBL2, CFC1, FGF18, KRT28, OR2T34, RPL7L1, TMEM185B, AGBL3, CFC1B, FGF19, KRT3, OR2T35, RPL8, TMEM186, AGBL4, CFD, FGF2, KRT31, OR2T4, RPL9, TMEM187, AGBL5, CFDP1, FGF20, KRT32, OR2T5, RPLP0, TMEM189, AGER, CFH, FGF21, KRT33A, OR2T6, RPLP1, TMEM189-UBE2V1, AGFG1, CFHR1, FGF22, KRT33B, OR2T8, RPLP2, TMEM19, AGFG2, CFHR2, FGF23, KRT34, OR2V1, RPN1, TMEM190, AGGF1, CFHR3, FGF3, KRT35, OR2V2, RPN2, TMEM191B, AGK, CFHR4, FGF4, KRT36, OR2W1, RPP14, TMEM191C, AGL, CFHR5, FGF5, KRT37, OR2W3, RPP21, TMEM192, AGMAT, CFI, FGF6, KRT38, OR2W5, RPP25, TMEM194A, AGMO, CFL1, FGF7, KRT39, OR2Y1, RPP25L, TMEM194B, AGO1, CFL2, FGF8, KRT4, OR2Z1, RPP30, TMEM196, AGO2, CFLAR, FGF9, KRT40, OR3A1, RPP38, TMEM198, AGO3, CFP, FGFBP1, KRT5, OR3A2, RPP40, TMEM199, AGO4, CFTR, FGFBP2, KRT6A, OR3A3, RPRD1A, TMEM2, AGPAT1, CGA, FGFBP3, KRT6B, OR4A15, RPRD1B, TMEM200A, AGPAT2, CGB, FGFR1, KRT6C, OR4A16, RPRD2, TMEM200B, AGPAT3, CGB1, FGFR1OP, KRT7, OR4A47, RPRM, TMEM201, AGPAT4, CGB2, FGFR1OP2, KRT71, OR4A5, RPRML, TMEM202, AGPAT5, CGB5, FGFR2, KRT72, OR4B1, RPS10, TMEM203, AGPAT6, CGB7, FGFR3, KRT73, OR4C11, RPS10-NUDT3, TMEM204, AGPAT9, CGB8, FGFR4, KRT74, OR4C12, RPS11, TMEM205, AGPS, CGGBP1, FGFRL1, KRT75, OR4C13, RPS12, TMEM206, AGR2, CGN, FGG, KRT76, OR4C15, RPS13, TMEM207, AGR3, CGNL1, FGGY, KRT77, OR4C16, RPS14, TMEM208, AGRN, CGREF1, FGL1, KRT78, OR4C3, RPS15, TMEM209, AGRP, CGRRF1, FGL2, KRT79, OR4C45, RPS15A, TMEM210, AGT, CH25H, FGR, KRT8, OR4C46, RPS16, TMEM211, AGTPBP1, CHAC1, FH, KRT80, OR4C6, RPS17, TMEM212, AGTR1, CHAC2, FHAD1, KRT81, OR4D1, RPS17L, TMEM213, AGTR2, CHAD, FHDC1, KRT82, OR4D10, RPS18, TMEM214, AGTRAP, CHADL, FHIT, KRT83, OR4D11, RPS19, TMEM215, AGXT, CHAF1A, FHL1, KRT84, OR4D2, RPS19BP1, TMEM216, AGXT2, CHAF1B, FHL2, KRT85, OR4D5, RPS2, TMEM217, AHCTF1, CHAMP1, FHL3, KRT86, OR4D6, RPS20, TMEM218, AHCY, CHAT, FHL5, KRT9, OR4D9, RPS21, TMEM219, AHCYL1, CHCHD1, FHOD1, KRTAP10-1, OR4E2, RPS23, TMEM220, AHCYL2, CHCHD10, FHOD3, KRTAP10-10, OR4F15, RPS24, TMEM221, AHDC1, CHCHD2, FIBCD1, KRTAP10-11, OR4F16, RPS25, TMEM222, AHI1, CHCHD3, FIBIN, KRTAP10-12, OR4F21, RPS26, TMEM223, AHNAK, CHCHD4, FIBP, KRTAP10-2, OR4F29, RPS27, TMEM225, AHNAK2, CHCHD5, FICD, KRTAP10-3, OR4F3, RPS27A, TMEM229A, AHR, CHCHD6, FIG. 4, KRTAP10-4, OR4F4, RPS27L, TMEM229B, AHRR, CHCHD7, FIGF, KRTAP10-5, OR4F5, RPS28, TMEM230, AHSA1, CHD1, FIGLA, KRTAP10-6, OR4F6, RPS29, TMEM231, AHSA2, CHD1L, FIGN, KRTAP10-7, OR4K1, RPS3, TMEM232, AHSG, CHD2, FIGNL1, KRTAP10-8, OR4K13, RPS3A, TMEM233, AHSP, CHD3, FIGNL2, KRTAP10-9, OR4K14, RPS4X, TMEM234, AICDA, CHD4, FILIP1, KRTAP1-1, OR4K15, RPS4Y1, TMEM235, AIDA, CHD5, FILIP1L, KRTAP11-1, OR4K17, RPS4Y2, TMEM236, AIF1, CHD6, FIPIL1, KRTAP12-1, OR4K2, RPS5, TMEM237, AIF1L, CHD7, FIS1, KRTAP12-2, OR4K5, RPS6, TMEM238, AIFM1, CHD8, FITM1, KRTAP12-3, OR4L1, RPS6KA1, TMEM239, AIFM2, CHD9, FITM2, KRTAP12-4, OR4M1, RPS6KA2, TMEM240, AIFM3, CHDC2, FIZ1, KRTAP1-3, OR4M2, RPS6KA3, TMEM241, AIG1, CHDH, FJX1, KRTAP13-1, OR4N2, RPS6KA4, TMEM242, AIM1, CHEK1, FKBP10, KRTAP13-2, OR4N4, RPS6KA5, TMEM243, AIM1L, CHEK2, FKBP11, KRTAP13-3, OR4N5, RPS6KA6, TMEM244, AIM2, CHERP, FKBP14, KRTAP13-4, OR4P4, RPS6KB1, TMEM245, AIMP1, CHFR, FKBP15, KRTAP1-4, OR4Q3, RPS6KB2, TMEM246, AIMP2, CHGA, FKBP1A, KRTAP1-5, OR4S1, RPS6KC1, TMEM247, AIP, CHGB, FKBP1B, KRTAP15-1, OR4S2, RPS6KL1, TMEM248, AIPL1, CHI3L1, FKBP2, KRTAP16-1, OR4X1, RPS7, TMEM249, AIRE, CHI3L2, FKBP3, KRTAP17-1, OR4X2, RPS8, TMEM25, AJAP1, CHIA, FKBP4, KRTAP19-1, OR51A2, RPS9, TMEM251, AJUBA, CHIC1, FKBP5, KRTAP19-2, OR51A4, RPSA, TMEM252, AK1, CHIC2, FKBP6, KRTAP19-3, OR51A7, RPTN, TMEM253, AK2, CHID1, FKBP7, KRTAP19-4, OR51B2, RPTOR, TMEM254, AK3, CHIT1, FKBP8, KRTAP19-5, OR51B4, RPUSD1, TMEM255A, AK4, CHKA, FKBP9, KRTAP19-6, OR51B5, RPUSD2, TMEM255B, AK5, CHKB, FKBPL, KRTAP19-7, OR51B6, RPUSD3, TMEM256, AK6, CHL1, FKRP, KRTAP19-8, OR51D1, RPUSD4, TMEM257, AK7, CHM, FKTN, KRTAP20-1, OR51E1, RQCD1, TMEM258, AK8, CHML, FLAD1, KRTAP20-2, OR51E2, RRAD, TMEM259, AK9, CHMP1A, FLCN, KRTAP20-3, OR51F1, RRAGA, TMEM26, AKAP1, CHMP1B, FLG, KRTAP2-1, OR51F2, RRAGB, TMEM260, AKAP10, CHMP2A, FLG2, KRTAP21-1, OR51G1, RRAGC, TMEM261, AKAP11, CHMP2B, FLI1, KRTAP21-2, OR51G2, RRAGD, TMEM27, AKAP12, CHMP3, FLII, KRTAP21-3, OR51I1, RRAS, TMEM30A, AKAP13, CHMP4A, FLJ22184, KRTAP2-2, OR51I2, RRAS2, TMEM30B, AKAP14, CHMP4B, FLJ25363, KRTAP22-1, OR51L1, RRBP1, TMEM31, AKAP17A, CHMP4C, FLJ44313, KRTAP22-2, OR51M1, RREB1, TMEM33, AKAP2, CHMP5, FLJ44635, KRTAP2-3, OR51Q1, RRH, TMEM35, AKAP3, CHMP6, FLJ45513, KRTAP23-1, OR51S1, RRM1, TMEM37, AKAP4, CHMP7, FLNA, KRTAP2-4, OR51T1, RRM2, TMEM38A, AKAP5, CHN1, FLNB, KRTAP24-1, OR51V1, RRM2B, TMEM38B, AKAP6, CHN2, FLNC, KRTAP25-1, OR52A1, RRN3, TMEM39A, AKAP7, CHODL, FLOT1, KRTAP26-1, OR52A5, RRNAD1, TMEM39B, AKAP8, CHORDC1, FLOT2, TABLE 1-continued List of examples of target genes (e.g., encoding a protein of interest)
List of target genes/proteins of interest KRTAP27-1, OR52B2, RRP1, TMEM40, AKAP8L, CHP1, FLRT1, KRTAP29-1, OR52B4, RRP12, TMEM41A, AKAP9, CHP2, FLRT2, KRTAP3-1, OR52B6, RRP15, TMEM41B, AKIP1, CHPF, FLRT3, KRTAP3-2, OR52D1, RRP1B, TMEM42, AKIRIN1, CHPF2, FLT1, KRTAP3-3, OR52E2, RRP36, TMEM43, AKIRIN2, CHPT1, FLT3, KRTAP4-1, OR52E4, RRP7A, TMEM44, AKNA, CHRAC1, FLT3LG, KRTAP4-11, OR52E6, RRP8, TMEM45A, AKNAD1, CHRD, FLT4, KRTAP4-12, OR52E8, RRP9, TMEM45B, AKR1A1, CHRDL1, FLVCR1, KRTAP4-2, OR52H1, RRS1, TMEM47, AKR1B1, CHRDL2, FLVCR2, KRTAP4-3, OR52I1, RS1, TMEM5, AKR1B10, CHRFAM7A, FLYWCH1, KRTAP4-4, OR52I2, RSAD1, TMEM50A, AKR1B15, CHRM1, FLYWCH2, KRTAP4-5, OR52J3, RSAD2, TMEM50B, AKR1C1, CHRM2, FMN1, KRTAP4-6, OR52K1, RSBN1, TMEM51, AKR1C2, CHRM3, FMN2, KRTAP4-7, OR52K2, RSBN1L, TMEM52, AKR1C3, CHRM4, FMNL1, KRTAP4-8, OR52L1, RSC1A1, TMEM52B, AKR1C4, CHRM5, FMNL2, KRTAP4-9, OR52M1, RSF1, TMEM53, AKR1D1, CHRNA1, FMNL3, KRTAP5-1, OR52N1, RSG1, TMEM54, AKR1E2, CHRNA10, FMO1, KRTAP5-10, OR52N4, RSL1D1, TMEM55A, AKR7A2, CHRNA2, FMO2, KRTAP5-11, OR52N5, RSL24D1, TMEM55B, AKR7A3, CHRNA3, FMO3, KRTAP5-2, OR52R1, RSPH1, TMEM56, AKT1, CHRNA4, FMO4, KRTAP5-3, OR52W1, RSPH10B, TMEM56-RWDD3, AKT1S1, CHRNA5, FMO5, KRTAP5-4, OR56A1, RSPH10B2, TMEM57, AKT2, CHRNA6, FMOD, KRTAP5-5, OR56A3, RSPH3, TMEM59, AKT3, CHRNA7, FMR1, KRTAP5- 6, OR56A4, RSPH4A, TMEM59L, AKTIP, CHRNA9, FMR1NB, KRTAP5-7, OR56A5, RSPH6A, TMEM60, ALAD, CHRNB1, FN1, KRTAP5-8, OR56B1, RSPH9, TMEM61, ALAS1, CHRNB2, FN3K, KRTAP5-9, OR56B4, RSPO1, TMEM62, ALAS2, CHRNB3, FN3KRP, KRTAP6-1, OR5A1, RSPO2, TMEM63A, ALB, CHRNB4, FNBP1, KRTAP6-2, OR5A2, RSPO3, TMEM63B, ALCAM, CHRND, FNBP1L, KRTAP6-3, OR5AC2, RSPO4, TMEM63C, ALDH16A1, CHRNE, FNBP4, KRTAP7-1, OR5AK2, RSPRY1, TMEM64, ALDH18A1, CHRNG, FNDC1, KRTAP8-1, OR5AN1, RSRC1, TMEM65, ALDH1A1, CHST1, FNDC3A, KRTAP9-1, OR5AP2, RSRC2, TMEM66, ALDH1A2, CHST10, FNDC3B, KRTAP9-2, OR5AR1, RSU1, TMEM67, ALDH1A3, CHST11, FNDC4, KRTAP9-3, OR5AS1, RTBDN, TMEM68, ALDH1B1, CHST12, FNDC5, KRTAP9-4, OR5AU1, RTCA, TMEM69, ALDH1L1, CHST13, FNDC7, KRTAP9-6, OR5B12, RTCB, TMEM70, ALDH1L2, CHST14, FNDC8, KRTAP9-7, OR5B17, RTDR1, TMEM71, ALDH2, CHST15, FNDC9, KRTAP9- 8, OR5B2, RTEL1, TMEM72, ALDH3A1, CHST2, FNIP1, KRTAP9-9, OR5B21, RTF1, TMEM74, ALDH3A2, CHST3, FNIP2, KRTCAP2, OR5B3, RTFDC1, TMEM74B, ALDH3B1, CHST4, FNTA, KRTCAP3, OR5C1, RTKN, TMEM79, ALDH3B2, CHST5, FNTB, KRTDAP, OR5D13, RTKN2, TMEM80, ALDH4A1, CHST6, FOCAD, KSR1, OR5D14, RTL1, TMEM81, ALDH5A1, CHST7, FOLH1, KSR2, OR5D16, RTN1, TMEM82, ALDH6A1, CHST8, FOLH1B, KTI12, OR5D18, RTN2, TMEM86A, ALDH7A1, CHST9, FOLR1, KTN1, OR5F1, RTN3, TMEM86B, ALDH8A1, CHSY1, FOLR2, KXD1, OR5H1, RTN4, TMEM87A, ALDH9A1, CHSY3, FOLR3, KY, OR5H14, RTN4IP1, TMEM87B, ALDOA, CHTF18, FOLR4, KYNU, OR5H15, RTN4R, TMEM88, ALDOB, CHTF8, FOPNL, L1CAM, OR5H2, RTN4RL1, TMEM88B, ALDOC, CHTOP, FOS, L1TD1, OR5H6, RTN4RL2, TMEM89, ALG1, CHUK, FOSB, L2HGDH, OR5I1, RTP1, TMEM8A, ALG10, CHURC1, FOSL1, L3HYPDH, OR5J2, RTP2, TMEM8B, ALG10B, CHURC1-FNTB, FOSL2, L3MBTL1, OR5K1, RTP3, TMEM8C, ALG11, CIAO1, FOXA1, L3MBTL2, OR5K2, RTP4, TMEM9, ALG12, CIAPIN1, FOXA2, L3MBTL3, OR5K3, RTTN, TMEM91, ALG13, CIB1, FOXA3, L3MBTL4, OR5K4, RUFY1, TMEM92, ALG14, CIB2, FOXB1, LACC1, OR5L1, RUFY2, TMEM95, ALG1L, CIB3, FOXB2, LACE1, OR5L2, RUFY3, TMEM97, ALG1L2, CIB4, FOXC1, LACRT, OR5M1, RUFY4, TMEM98, ALG2, CIC, FOXC2, LACTB, OR5M10, RUNDC1, TMEM99, ALG3, CIDEA, FOXD1, LACTB2, OR5M11, RUNDC3A, TMEM9B, ALG5, CIDEB, FOXD2, LACTBL1, OR5M3, RUNDC3B, TMF1, ALG6, CIDEC, FOXD3, LAD1, OR5M8, RUNX1, TMIE, ALG8, CIITA, FOXD4, LAG3, OR5M9, RUNX1T1, TMIGD1, ALG9, CILP, FOXD4L1, LAGE3, OR5P2, RUNX2, TMIGD2, ALK, CILP2, FOXD4L2, LAIR1, OR5P3, RUNX3, TMLHE, ALKBH1, CINP, FOXD4L3, LAIR2, OR5R1, RUSC1, TMOD1, ALKBH2, CIR1, FOXD4L4, LALBA, OR5T1, RUSC1-AS1, TMOD2, ALKBH3, CIRBP, FOXD4L5, LAMA1, OR5T2, RUSC2, TMOD3, ALKBH4, CIRH1A, FOXD4L6, LAMA2, OR5T3, RUVBL1, TMOD4, ALKBH5, CISD1, FOXE1, LAMA3, OR5V1, RUVBL2, TMPO, ALKBH6, CISD2, FOXE3, LAMA4, OR5W2, RWDD1, TMPPE, ALKBH7, CISD3, FOXF1, LAMA5, OR6A2, RWDD2A, TMPRSS11A, ALKBH8, CISH, FOXF2, LAMB1, OR6B1, RWDD2B, TMPRSS11B, ALLC, CIT, FOXG1, LAMB2, OR6B3, RWDD3, TMPRSS11D, ALMS1, CITED1, FOXH1, LAMB3, OR6C1, RWDD4, TMPRSS11E, ALOX12, CITED2, FOXI1, LAMB4, OR6C2, RXFP1, TMPRSS11F, ALOX12B, CITED4, FOXI2, LAMC1, OR6C3, RXFP2, TMPRSS12, ALOX15, CIZ1, FOXI3, LAMC2, OR6C4, RXFP3, TMPRSS13, ALOX15B, CKAP2, FOXJ1, LAMC3, OR6C6, RXFP4, TMPRSS15, ALOX5, CKAP2L, FOXJ2, LAMP1, OR6C65, RXRA, TMPRSS2, ALOX5AP, CKAP4, FOXJ3, LAMP2, OR6C68, RXRB, TMPRSS3, ALOXE3, CKAP5, FOXK1, LAMP3, OR6C70, RXRG, TMPRSS4, ALPI, CKB, FOXK2, LAMP5, OR6C74, RYBP, TMPRSS5, ALPK1, CKLF, FOXL1, LAMTOR1, OR6C75, RYK, TMPRSS6, CKLF-CMTM1, FOXL2, LAMTOR2, OR6C76, RYR1, TMPRSS7, ALPK3, CKM, FOXM1, LAMTOR3, OR6F1, RYR2, TMPRSS9, ALPL, CKMT1A, FOXN1, LAMTOR4, OR6K2, RYR3, TMSB10, ALPP, CKMT1B, FOXN2, LAMTOR5, OR6K3, S100A1, TMSB15A, ALPPL2, CKMT2, FOXN3, LANCLI, OR6K6, S100A10, TMSB15B, ALS2, CKS1B, FOXN4, LANCL2, OR6M1, S100A11, TMSB4X, ALS2CL, CKS2, FOXO1, LANCL3, OR6N1, S100A12, TMSB4Y, ALS2CR11, CLASP1, FOX03, LAP3, OR6N2, S100A13, TMTC1, ALS2CR12, CLASP2, FOXO4, LAPTM4A, OR6P1, S100A14, TMTC2, ALX1, CLASRP, FOXO6, LAPTM4B, OR6Q1, S100A16, TMTC3, ALX3, CLC, FOXP1, LAPTM5, OR6S1, S100A2, TMTC4, ALX4, CLCA1, FOXP2, LARGE, OR6T1, S100A3, TMUB1, ALYREF, CLCA2, FOXP3, LARP1, OR6V1, S100A4, TMUB2, AMACR, CLCA4, FOXP4, LARP1B, OR6X1, S100A5, TMX1, AMBN, CLCC1, FOXQ1, LARP4, OR6Y1, S100A6, TMX2, AMBP, CLCF1, FOXR1, LARP4B, OR7A10, S100A7, TMX3, AMBRA1, CLCN1, FOXR2, LARP6, OR7A17, S100A7A, TMX4, AMD1, CLCN2, FOXRED1, LARP7, OR7A5, S100A7L2, TNC, AMDHD1, CLCN3, FOXRED2, LARS, OR7C1, S100A8, TNF, AMDHD2, CLCN4, FOXS1, LARS2, OR7C2, S100A9, TNFAIP1, AMELX, CLCN5, FPGS, LAS1L, OR7D2, S100B, TNFAIP2, AMELY, CLCN6, FPGT, LASP1, OR7D4, S100G, TNFAIP3, AMER1, CLCN7, FPGT-TNNI3K, LAT, OR7E24, S100P, TNFAIP6, AMER2, CLCNKA, FPR1, LAT2, OR7G1, S100PBP, TNFAIP8, AMER3, CLCNKB, FPR2, LATS1, OR7G2, S100Z, TNFAIP8L1, AMFR, CLDN1, FPR3, LATS2, OR7G3, S1PR1, TNFAIP8L2, AMH, TABLE 1-continued List of examples of target genes (e.g., encoding a protein of interest)
List of target genes/proteins of interest CLDN10, FRA10AC1, LAX1, OR8A1, S1PR2, TNFAIP8L2-SCNM1, AMHR2, CLDN11, FRAS1, LAYN, OR8B12, S1PR3, TNFAIP8L3, AMICA1, CLDN12, FRAT1, LBH, OR8B2, S1PR4, TNFRSF10A, AMIGO1, CLDN14, FRAT2, LBP, OR8B3, S1PR5, TNFRSF10B, AMIGO2, CLDN15, FREM1, LBR, OR8B4, SAA1, TNFRSF10C, AMIGO3, CLDN16, FREM2, LBX1, OR8B8, SAA2, TNFRSF10D, AMMECR1, CLDN17, FREM3, LBX2, OR8D1, SAA2-SAA4, TNFRSF11A, AMMECR1L, CLDN18, FRG1, LCA5, OR8D2, SAA4, TNFRSF11B, AMN, CLDN19, FRG2, LCA5L, OR8D4, SAAL1, TNFRSF12A, AMN1, CLDN2, FRG2B, LCAT, OR8G1, SAC3D1, TNFRSF13B, AMOT, CLDN20, FRG2C, LCE1A, OR8G2, SACM1L, TNFRSF13C, AMOTL1, CLDN22, FRK, LCE1B, OR8G5, SACS, TNFRSF14, AMOTL2, CLDN23, FRMD1, LCE1C, OR8H1, SAE1, TNFRSF17, AMPD1, CLDN24, FRMD3, LCE1D, OR8H2, SAFB, TNFRSF18, AMPD2, CLDN25, FRMD4A, LCE1E, OR8H3, SAFB2, TNFRSF19, AMPD3, CLDN3, FRMD4B, LCE1F, OR8I2, SAG, TNFRSF1A, AMPH, CLDN4, FRMD5, LCE2A, OR8J1, SAGE1, TNFRSF1B, AMT, CLDN5, FRMD6, LCE2B, OR8J3, SALL1, TNFRSF21, AMTN, CLDN6, FRMD7, LCE2C, OR8K1, SALL2, TNFRSF25, AMY1A, CLDN7, FRMD8, LCE2D, OR8K3, SALL3, TNFRSF4, AMY1B, CLDN8, FRMPD1, LCE3A, OR8K5, SALL4, TNFRSF6B, AMY1C, CLDN9, FRMPD2, LCE3B, OR8S1, SAMD1, TNFRSF8, AMY2A, CLDND1, FRMPD3, LCE3C, OR8U1, SAMD10, TNFRSF9, AMY2B, CLDND2, FRMPD4, LCE3D, OR8U8, SAMD11, TNFSF10, AMZ1, CLEC10A, FRRS1, LCE3E, OR9A2, SAMD12, TNFSF11, AMZ2, CLEC11A, FRRS1L, LCE4A, OR9A4, SAMD13, TNFSF12, ANAPC1, CLEC12A, FRS2, LCE5A, OR9G1, SAMD14, TNFSF12-TNFSF13, ANAPC10, CLEC12B, FRS3, LCE6A, OR9G4, SAMD15, TNFSF13, ANAPC11, CLEC14A, FRY, LCK, OR9G9, SAMD3, TNFSF13B, ANAPC13, CLEC16A, FRYL, LCLAT1, OR9I1, SAMD4A, TNFSF14, ANAPC15, CLEC17A, FRZB, LCMT1, OR9K2, SAMD4B, TNFSF15, ANAPC16, CLEC18A, FSBP, LCMT2, OR9Q1, SAMD5, TNFSF18, ANAPC2, CLEC18B, FSCB, LCN1, OR9Q2, SAMD7, TNFSF4, ANAPC4, CLEC18C, FSCN1, LCN10, ORAI1, SAMD8, TNFSF8, ANAPC5, CLEC19A, FSCN2, LCN12, ORAI2, SAMD9, TNFSF9, ANAPC7, CLEC1A, FSCN3, LCN15, ORAI3, SAMD9L, TNIK, ANG, CLEC1B, FSD1, LCN2, ORAOV1, SAMHD1, TNIP1, ANGEL1, CLEC2A, FSD1L, LCN6, ORC1, SAMM50, TNIP2, ANGEL2, CLEC2B, FSD2, LCN8, ORC2, SAMSN1, TNIP3, ANGPT1, CLEC2D, FSHB, LCN9, ORC3, SAP130, TNK1, ANGPT2, CLEC2L, FSHR, LCNL1, ORC4, SAP18, TNK2, ANGPT4, CLEC3A, FSIP1, LCOR, ORC5, SAP25, TNKS, ANGPTL1, CLEC3B, FSIP2, LCORL, ORC6, SAP30, TNKS1BP1, ANGPTL2, CLEC4A, FST, LCP1, ORM1, SAP30BP, TNKS2, ANGPTL3, CLEC4C, FSTL1, LCP2, ORM2, SAP30L, TNMD, ANGPTL4, CLEC4D, FSTL3, LCT, ORMDL1, SAPCD1, TNN, ANGPTL5, CLEC4E, FSTL4, LCTL, ORMDL2, SAPCD2, TNNC1, ANGPTL6, CLEC4F, FSTL5, LDB1, ORMDL3, SAR1A, TNNC2, ANGPTL7, CLEC4G, FTCD, LDB2, OS9, SAR1B, TNNI1, ANHX, CLEC4M, FTH1, LDB3, OSBP, SARDH, TNNI2, ANK1, CLEC5A, FTH1P18, LDHA, OSBP2, SARM1, TNNI3, ANK2, CLEC6A, FTHL17, LDHAL6A, OSBPL10, SARNP, TNNI3K, ANK3, CLEC7A, FTL, LDHAL6B, OSBPL11, SARS, TNNT1, ANKAR, CLEC9A, FTMT, LDHB, OSBPL1A, SARS2, TNNT2, ANKDD1A, CLECL1, FTO, LDHC, OSBPL2, SART1, TNNT3, ANKDD1B, CLGN, FTSJ1, LDHD, OSBPL3, SART3, TNP1, ANKEF1, CLHC1, FTSJ2, LDLR, OSBPL5, SASH1, TNP2, ANKFN1, CLIC1, FTSJ3, LDLRAD1, OSBPL6, SASH3, TNPO1, ANKFY1, CLIC2, FUBP1, LDLRAD2, OSBPL7, SASS6, TNPO2, ANKH, CLIC3, FUBP3, LDLRAD3, OSBPL8, SAT1, TNPO3, ANKHD1, CLIC4, FUCA1, LDLRAD4, OSBPL9, SAT2, TNR, ANKHD1-EIF4EBP3, CLIC5, FUCA2, LDLRAP1, OSCAR, SATB1, TNRC18, ANKIB1, CLIC6, FUK, LDOC1, OSCP1, SATB2, TNRC6A, ANKK1, CLINT1, FUNDC1, LDOC1L, OSER1, SATL1, TNRC6B, ANKLE1, CLIP1, FUNDC2, LEAP2, OSGEP, SAV1, TNRC6C, ANKLE2, CLIP2, FUOM, LECT1, OSGEPL1, SAYSD1, TNS1, ANKMY1, CLIP3, FURIN, LECT2, OSGIN1, SBDS, TNS3, ANKMY2, CLIP4, FUS, LEF1, OSGIN2, SBF1, TNS4, ANKRA2, CLK1, FUT1, LEFTY1, OSM, SBF2, TNXB, ANKRD1, CLK2, FUT10, LEFTY2, OSMR, SBK1, TOB1, ANKRD10, CLK3, FUT11, LEKR1, OSR1, SBK2, TOB2, ANKRD11, CLK4, FUT2, LELP1, OSR2, SBK3, TOE1, ANKRD12, CLLU1, FUT3, LEMD1, OST4, SBNO1, TOLLIP, ANKRD13A, CLLU1OS, FUT4, LEMD2, OSTC, SBNO2, TOM1, ANKRD13B, CLMN, FUT5, LEMD3, OSTF1, SBSN, TOM1L1, ANKRD13C, CLMP, FUT6, LENEP, OSTM1, SBSPON, TOM1L2, ANKRD13D, CLN3, FUT7, LENG1, OSTN, SC5D, TOMM20, ANKRD16, CLN5, FUT8, LENG8, OTC, SCAF1, TOMM20L, ANKRD17, CLN6, FUT9, LENG9, OTOA, SCAF11, TOMM22, ANKRD18A, CLN8, FUZ, LEO1, OTOF, SCAF4, TOMM34, ANKRD18B, CLNK, FXN, LEP, OTOG, SCAF8, TOMM40, ANKRD2, CLNS1A, FXR1, LEPR, OTOGL, SCAI, TOMM40L, ANKRD20A1, CLOCK, FXR2, LEPRE1, OTOL1, SCAMP1, TOMM5, ANKRD20A2, CLP1, FXYD1, LEPREL1, OTOP1, SCAMP2, TOMM6, ANKRD20A3, CLPB, FXYD2, LEPREL2, OTOP2, SCAMP3, TOMM7, ANKRD20A4, CLPP, FXYD3, LEPREL4, OTOP3, SCAMP4, TOMM70A, ANKRD22, CLPS, FXYD4, LEPROT, OTOR, SCAMP5, TONSL, ANKRD23, CLPSL1, FXYD5, LEPROTL1, OTOS, SCAND1, TOP1, ANKRD24, CLPSL2, FXYD6, LETM1, OTP, SCAND3, TOP1MT, ANKRD26, CLPTM1, FXYD6-FXYD2, LETM2, OTUB1, SCAP, TOP2A, ANKRD27, CLPTM1L, FXYD7, LETMD1, OTUB2, SCAPER, TOP2B, ANKRD28, CLPX, FYB, LEUTX, OTUD1, SCARA3, TOP3A, ANKRD29, CLRN1, FYCO1, LFNG, OTUD3, SCARA5, TOP3B, ANKRD30A, CLRN2, FYN, LGALS1, OTUD4, SCARB1, TOPAZ1, ANKRD30B, CLRN3, FYTTD1, LGALS12, OTUD5, SCARB2, TOPBP1, ANKRD31, CLSPN, FZD1, LGALS13, OTUD6A, SCARF1, TOPORS, ANKRD32, CLSTN1, FZD10, LGALS14, OTUD6B, SCARF2, TOR1A, ANKRD33, CLSTN2, FZD2, LGALS16, OTUD7A, SCCPDH, TOR1AIP1, ANKRD33B, CLSTN3, FZD3, LGALS2, OTUD7B, SCD, TOR1AIP2, ANKRD34A, CLTA, FZD4, LGALS3, OTX1, SCD5, TOR1B, ANKRD34B, CLTB, FZD5, LGALS3BP, OTX2, SCEL, TOR2A, ANKRD34C, CLTC, FZD6, LGALS4, OVCA2, SCFD1, TOR3A, ANKRD35, CLTCL1, FZD7, LGALS7, OVCH1, SCFD2, TOR4A, ANKRD36, CLU, FZD8, LGALS7B, OVCH2, SCG2, TOX, ANKRD36B, CLUAP1, FZD9, LGALS8, OVGP1, SCG3, TOX2, ANKRD36C, CLUH, FZR1, LGALS9, OVOL1, SCG5, TOX3, ANKRD37, CLUL1, G0S2, LGALS9B, OVOL2, SCGB1A1, TOX4, ANKRD39, CLVS1, G2E3, LGALS9C, OVOL3, SCGB1C1, TP53, ANKRD40, CLVS2, G3BP1, LGALSL, OVOS, SCGB1D1, TP53AIP1, ANKRD42, CLYBL, G3BP2, LGI1, OVOS2, SCGB1D2, TP53BP1, ANKRD44, CMA1, G6PC, LGI2, OXA1L, SCGB1D4, TP53BP2, ANKRD45, CMAS, G6PC2, LGI3, OXCT1, SCGB2A1, TP53I11, ANKRD46, CMBL, G6PC3, LGI4, OXCT2, SCGB2A2, TP53I3, ANKRD49, CMC1, G6PD, LGMN, OXER1, SCGB2B2, TP53I3, ANKRD50, CMC2, GAA, LGR4, OXGR1, SCGB3A1, TP53INP1, ANKRD52, CMC4, GAB1, LGR5, OXLD1, SCGB3A2, TP53INP2, ANKRD53, TABLE 1-continued List of examples of target genes (e.g., encoding a protein of interest)
List of target genes/proteins of interest CMIP, GAB2, LGR6, OXNAD1, SCGN, TP53RK, ANKRD54, CMKLR1, GAB3, LGSN, OXR1,
SCHIP1, TP53TG3, ANKRD55, CMPK1, GAB4, LHB, OXSM, SCIMP, TP53TG3B, ANKRD6,
CMPK2, GABARAP, LHCGR, OXSR1, SCIN, TP53TG3C, ANKRD60, CMSS1, GABARAPL1, LHFP,
OXT, SCLT1, TP53TG3D, ANKRD61, CMTM1, GABARAPL2, LHFPL1, OXTR, SCLY, TP53TG5,
ANKRD62, CMTM2, GABBR1, LHFPL2, P2RX1, SCMH1, TP63, ANKRD63, CMTM3, GABBR2,
LHFPL3, P2RX2, SCML1, TP73, ANKRD65, CMTM4, GABPA, LHFPL4, P2RX3, SCML2, TPBG,
ANKRD66, CMTM5, GABPB1, LHFPL5, P2RX4, SCML4, TPBGL, ANKRD7, CMTM6, GABPB2,
LHPP, P2RX5, SCN10A, TPCN1, ANKRD9, CMTM7, GABRA1, LHX1, P2RX6, SCN11A, TPCN2,
ANKS1A, CMTM8, GABRA2, LHX2, P2RX7, SCN1A, TPD52, ANKS1B, CMTR1, GABRA3, LHX3,
P2RY1, SCN1B, TPD52L1, ANKS3, CMTR2, GABRA4, LHX4, P2RY10, SCN2A, TPD52L2,
ANKS4B, CMYA5, GABRA5, LHX5, P2RY11, SCN2B, TPD52L3, ANKS6, CNBD1, GABRA6,
LHX6, P2RY12, SCN3A, TPGS1, ANKUB1, CNBD2, GABRB1, LHX8, P2RY13, SCN3B, TPGS2,
ANKZF1, CNBP, GABRB2, LHX9, P2RY14, SCN4A, TPH1, ANLN, CNDP1, GABRB3, LIAS,
P2RY2, SCN4B, TPH2, ANO1, CNDP2, GABRD, LIF, P2RY4, SCN5A, TPI1, ANO10, CNEP1R1,
GABRE, LIFR, P2RY6, SCN7A, TPK1, ANO2, CNFN, GABRG1, LIG1, P2RY8, SCN8A, TPM1,
ANO3, CNGA1, GABRG2, LIG3, P4HA1, SCN9A, TPM2, ANO4, CNGA2, GABRG3, LIG4, P4HA2,
SCNM1, TPM3, ANO5, CNGA3, GABRP, LILRA1, P4HA3, SCNN1A, TPM4, ANO6, CNGA4,
GABRQ, LILRA2, P4HB, SCNN1B, TPMT, ANO7, CNGB1, GABRR1, LILRA3, P4HTM, SCNN1D,
TPO, ANO8, CNGB3, GABRR2, LILRA4, PA2G4, SCNN1G, TPP1, ANO9, CNIH1, GABRR3,
LILRA5, PAAF1, SCO1, TPP2, ANP32A, CNIH2, GAD1, LILRA6, PABPC1, SCO2, TPPP, ANP32B,
CNIH3, GAD2, LILRB1, PABPC1L, SCOC, TPPP2, ANP32C, CNIH4, GADD45A, LILRB2,
PABPC1L2A, SCP2, TPPP3, ANP32D, CNKSR1, GADD45B, LILRB3, PABPC1L2B, SCP2D1, TPR,
ANP32E, CNKSR2, GADD45G, LILRB4, PABPC3, SCPEP1, TPRA1, ANPEP, CNKSR3,
GADD45GIP1, LILRB5, PABPC4, SCRG1, TPRG1, ANTXR1, CNN1, GADL1, LIM2, PABPC4L,
SCRIB, TPRG1L, ANTXR2, CNN2, GAGE1, LIMA1, PABPC5, SCRN1, TPRKB, ANTXRL, CNN3,
GAGE10, LIMCH1, PABPN1, SCRN2, TPRN, ANXA1, CNNM1, GAGE12B, LIMD1, PABPN1L,
SCRN3, TPRX1, ANXA10, CNNM2, GAGE12C, LIMD2, PACRG, SCRT1, TPSAB1, ANXA11,
CNNM3, GAGE12D, LIME1, PACRGL, SCRT2, TPSB2, ANXA13, CNNM4, GAGE12E, LIMK1,
PACS1, SCT, TPSD1, ANXA2, CNOT1, GAGE12F, LIMK2, PACS2, SCTR, TPSG1, ANXA2R,
CNOT10, GAGE12G, LIMS1, PACSIN1, SCUBE1, TPST1, ANXA3, CNOT11, GAGE12H, LIMS2,
PACSIN2, SCUBE2, TPST2, ANXA4, CNOT2, GAGE12I, LIMS3, PACSIN3, SCUBE3, TPT1,
ANXA5, CNOT3, GAGE12J, LIN28A, PADI1, SCXA, TPTE, ANXA6, CNOT4, GAGE13, LIN28B,
PADI2, SCXB, TPTE2, ANXA7, CNOT6, GAGE2A, LIN37, PADI3, SCYL1, TPX2, ANXA8,
CNOT6L, GAGE2B, LIN52, PADI4, SCYL2, TRA2A, ANXA8L1, CNOT7, GAGE2C, LIN54, PADI6,
SCYL3, TRA2B, ANXA8L2, CNOT8, GAGE2D, LIN7A, PAEP, SDAD1, TRABD, ANXA9, CNP,
GAGE2E, LIN7B, PAF1, SDC1, TRABD2A, AOAH, CNPPD1, GAGE4, LIN7C, PAFAH1B1, SDC2,
TRABD2B, AOC1, CNPY1, GAGE5, LIN9, PAFAH1B2, SDC3, TRADD, AOC2, CNPY2, GAGE6,
LINC00452, PAFAH1B3, SDC4, TRAF1, AOC3, CNPY3, GAGE7, LINC00984, PAFAH2, SDCBP,
TRAF2, AOX1, CNPY4, GAGE8, LINGO1, PAG1, SDCBP2, TRAF3, AP1AR, CNR1, GAK, LINGO2,
PAGE1, SDCCAG3, TRAF3IP1, AP1B1, CNR2, GAL, LINGO3, PAGE2, SDCCAG8, TRAF3IP2,
APIG1, CNRIP1, GAL3ST1, LINGO4, PAGE2B, SDE2, TRAF3IP3, AP1G2, CNST, GAL3ST2, LINS,
PAGE4, SDF2, TRAF4, AP1M1, CNTD1, GAL3ST3, LIPA, PAGE5, SDF2L1, TRAF5, AP1M2,
CNTD2, GAL3ST4, LIPC, PAGR1, SDF4, TRAF6, AP1S1, CNTF, GALC, LIPE, PAH, SDHA, TRAF7,
AP1S2, CNTFR, GALE, LIPF, PAICS, SDHAF1, TRAFD1, APIS3, CNTLN, GALK1, LIPG, PAIP1,
SDHAF2, TRAIP, AP2A1, CNTN1, GALK2, LIPH, PAIP2, SDHB, TRAK1, AP2A2, CNTN2, GALM,
LIPI, PAIP2B, SDHC, TRAK2, AP2B1, CNTN3, GALNS, LIPJ, PAK1, SDHD, TRAM1, AP2M1,
CNTN4, GALNT1, LIPK, PAK1IP1, SDK1, TRAM1L1, AP2S1, CNTN5, GALNT10, LIPM, PAK2,
SDK2, TRAM2, AP3B1, CNTN6, GALNT11, LIPN, PAK3, SDPR, TRANK1, AP3B2, CNTNAP1,
GALNT12, LIPT1, PAK4, SDR16C5, TRAP1, AP3D1, CNTNAP2, GALNT13, LIPT2, PAK6,
SDR39U1, TRAPPC1, AP3M1, CNTNAP3, GALNT14, LITAF, PAK7, SDR42E1, TRAPPC10, AP3M2,
CNTNAP3B, GALNT15, LIX1, PALB2, SDR9C7, TRAPPC11, AP3S1, CNTNAP4, GALNT16, LIX1L,
PALD1, SDS, TRAPPC12, AP3S2, CNTNAP5, GALNT18, LLGL1, PALLD, SDSL, TRAPPC13,
AP4B1, CNTRL, GALNT2, LLGL2, PALM, SEBOX, TRAPPC2, AP4E1, CNTROB, GALNT3, LLPH,
PALM2, SEC11A, TRAPPC2L, AP4M1, COA1, GALNT4, LMAN1, PALM2-AKAP2, SEC11C,
TRAPPC3, AP4S1, COA3, GALNT5, LMAN1L, PALM3, SEC13, TRAPPC3L, AP5B1, COA4,
GALNT6, LMAN2, PALMD, SEC14L1, TRAPPC4, AP5M1, COA5, GALNT7, LMAN2L, PAM,
SEC14L2, TRAPPC5, AP5S1, COA6, GALNT8, LMBR1, PAM16, SEC14L3, TRAPPC6A, AP5Z1,
COASY, GALNT9, LMBR1L, PAMR1, SEC14L4, TRAPPC6B, APAF1, COBL, GALNTL5, LMBRD1,
PAN2, SEC14L5, TRAPPC8, APBA1, COBLL1, GALNTL6, LMBRD2, PAN3, SEC14L6, TRAPPC9,
APBA2, COCH, GALP, LMCD1, PANK1, SEC16A, TRAT1, APBA3, COG1, GALR1, LMF1, PANK2,
SEC16B, TRDMT1, APBB1, COG2, GALR2, LMF2, PANK3, SEC22A, TRDN, APBB1IP, COG3,
GALR3, LMLN, PANK4, SEC22B, TREH, APBB2, COG4, GALT, LMNA, PANX1, SEC22C, TREM1,
APBB3, COG5, GAMT, LMNB1, PANX2, SEC23A, TREM2, APC, COG6, GAN, LMNB2, PANX3,
SEC23B, TREML1, APC2, COG7, GANAB, LMO1, PAOX, SEC23IP, TREML2, APCDD1, COG8,
GANC, LMO2, PAPD4, SEC24A, TREML4, APCDD1L, COIL, GAP43, LMO3, PAPD5, SEC24B,
TRERF1, APCS, COL10A1, GAPDH, LMO4, PAPD7, SEC24C, TREX1, APEH, COL11A1, GAPDHS,
LMO7, PAPL, SEC24D, TREX2, APEX1, COL11A2, GAPT, LMOD1, PAPLN, SEC31A, TRH,
APEX2, COL12A1, GAPVD1, LMOD2, PAPOLA, SEC31B, TRHDE, APH1A, COL13A1, GAR1,
LMOD3, PAPOLB, SEC61A1, TRHR, APH1B, COL14A1, GAREM, LMTK2, PAPOLG, SEC61A2,
TRIAP1, API5, COL15A1, GAREML, LMTK3, PAPPA, SEC61B, TRIB1, APIP, COL16A1, GARNL3,
LMX1A, PAPPA2, SEC61G, TRIB2, APITD1, COL17A1, GARS, LMX1B, PAPSS1, SEC62, TRIB3,
APITD1-CORT, COL18A1, GART, LNP1, PAPSS2, SEC63, TRIL, APLF, COL19A1, GAS1, LNPEP,
PAQR3, SECISBP2, TRIM10, APLN, COL1A1, GAS2, LNX1, PAQR4, SECISBP2L, TRIM11,
APLNR, COL1A2, GAS2L1, LNX2, PAQR5, SECTM1, TRIM13, APLP1, COL20A1, GAS2L2,
LOH12CR1, PAQR6, SEH1L, TRIM14, APLP2, COL21A1, GAS2L3, LONP1, PAQR7, SEL1L,
TRIM15, APMAP, COL22A1, GAS6, LONP2, PAQR8, SEL1L2, TRIM16, APOA1, COL23A1, GAS7,
LONRF1, PAQR9, SEL1L3, TRIM16L, APOA1BP, COL24A1, GAS8, LONRF2, PARD3, SELE, TABLE 1-continued List of examples of target genes (e.g., encoding a protein of interest)
List of target genes/proteins of interest TRIM17, APOA2, COL25A1, GAST, LONRF3, PARD3B, SELENBP1, TRIM2, APOA4, COL26A1, GATA1, LOR, PARD6A, SELK, TRIM21, APOA5, COL27A1, GATA2, LOX, PARD6B, SELL, TRIM22, APOB, COL28A1, GATA3, LOXHD1, PARD6G, SELM, TRIM23, APOBEC1, COL2A1, GATA4, LOXL1, PARG, SELO, TRIM24, APOBEC2, COL3A1, GATA5, LOXL2, PARK2, SELP, TRIM25, APOBEC3A, COL4A1, GATA6, LOXL3, PARK7, SELPLG, TRIM26, APOBEC3B, COL4A2, GATAD1, LOXL4, PARL, SELRC1, TRIM27, APOBEC3C, COL4A3, GATAD2A, LPA, PARM1, SELT, TRIM28, APOBEC3D, COL4A3BP, GATAD2B, LPAR1, PARN, SELV, TRIM29, APOBEC3F, COL4A4, GATC, LPAR2, PARP1, SEMA3A, TRIM3, APOBEC3G, COL4A5, GATM, LPAR3, PARP10, SEMA3B, TRIM31, APOBEC3H, COL4A6, GATS, LPAR4, PARP11, SEMA3C, TRIM32, APOBEC4, COL5A1, GATSL1, LPAR5, PARP12, SEMA3D, TRIM33, APOBR, COL5A2, GATSL2, LPAR6, PARP14, SEMA3E, TRIM34, APOC1, COL5A3, GATSL3, LPCAT1, PARP15, SEMA3F, TRIM35, APOC2, COL6A1, GBA, LPCAT2, PARP16, SEMA3G, TRIM36, APOC3, COL6A2, GBA2, LPCAT3, PARP2, SEMA4A, TRIM37, APOC4, COL6A3, GBA3, LPCAT4, PARP3, SEMA4B, TRIM38, APOD, COL6A5, GBAS, LPGAT1, PARP4, SEMA4C, TRIM39, APOE, COL6A6, GBE1, LPHN1, PARP6, SEMA4D, TRIM39-RPP21, APOF, COL7A1, GBF1, LPHN2, PARP8, SEMA4F, TRIM4, APOH, COL8A1, GBGT1, LPHN3, PARP9, SEMA4G, TRIM40, APOL1, COL8A2, GBP1, LPIN1, PARPBP, SEMA5A, TRIM41, APOL2, COL9A1, GBP2, LPIN2, PARS2, SEMA5B, TRIM42, APOL3, COL9A2, GBP3, LPIN3, PARVA, SEMA6A, TRIM43, APOL4, COL9A3, GBP4, LPL, PARVB, SEMA6B, TRIM43B, APOL5, COLCA2, GBP5, LPO, PARVG, SEMA6C, TRIM44, APOL6, COLEC10, GBP6, LPP, PASD1, SEMA6D, TRIM45, APOLD1, COLEC11, GBP7, LPPR1, PASK, SEMA7A, TRIM46, APOM, COLEC12, GBX1, LPPR2, PATE1, SEMG1, TRIM47, APOO, COLGALT1, GBX2, LPPR3, PATE2, SEMG2, TRIM48, APOOL, COLGALT2, GC, LPPR4, PATE3, SENP1, TRIM49, APOPT1, COLQ, GCA, LPPR5, PATE4, SENP2, TRIM49B, APP, COMMD1, GCAT, LPXN, PATL1, SENP3, TRIM49C, APPBP2, COMMD10, GCC1, LRAT, PATL2, SENP5, TRIM49D1, APPL1, COMMD2, GCC2, LRBA, PATZ1, SENP6, TRIM49D2P, APPL2, COMMD3, GCDH, LRCH1, PAWR, SENP7, TRIM5, APRT, COMMD3-BMI1, GCFC2, LRCH2, PAX1, SENP8, TRIM50, APTX, COMMD4, GCG, LRCH3, PAX2, SEPHS1, TRIM51, AQP1, COMMD5, GCGR, LRCH4, PAX3, SEPHS2, TRIM52, AQP10, COMMD6, GCH1, LRCOL1, PAX4, SEPN1, TRIM54, AQP11, COMMD7, GCHFR, LRFN1, PAX5, SEPP1, TRIM55, AQP12A, COMMD8, GCK, LRFN2, PAX6, SEPSECS, TRIM56, AQP12B, COMMD9, GCKR, LRFN3, PAX7, SEPT1, TRIM58, AQP2, COMP, GCLC, LRFN4, PAX8, SEPT10, TRIM59, AQP3, COMT, GCLM, LRFN5, PAX9, SEPT11, TRIM6, AQP4, COMTD1, GCM1, LRG1, PAXBP1, SEPT12, TRIM60, AQP5, COPA, GCM2, LRGUK, PAXIP1, SEPT14, TRIM61, AQP6, COPB1, GCN1L1, LRIF1, PBDC1, SEPT15, TRIM62, AQP7, COPB2, GCNT1, LRIG1, PBK, SEPT2, TRIM63, AQP8, COPE, GCNT2, LRIG2, PBLD, SEPT3, TRIM64, AQP9, COPG1, GCNT3, LRIG3, PBOV1, SEPT4, TRIM64B, AQPEP, COPG2, GCNT4, LRIT1, PBRM1, SEPT5, TRIM64C, AQR, COPRS, GCNT7, LRIT3, PBX1, SEPT6, TRIM65, AR, COPS2, GCOM1, LRIT3, PBX2, SEPT7, TRIM66, ARAF, COPS3, GCSAM, LRMP, PBX3, SEPT8, TRIM67, ARAP1, COPS4, GCSAML, LRP1, PBX4, SEPT9, TRIM68, ARAP2, COPS5, GCSH, LRP10, PBXIP1, SEPW1, TRIM69, ARAP3, COPS6, GDA, LRP11, PC, SERAC1, TRIM6-TRIM34, ARC, COPS7A, GDAP1, LRP12, PCBD1, SERBP1, TRIM7, ARCN1, COPS7B, GDAP1L1, LRP1B, PCBD2, SERF1A, TRIM71, AREG, COPS8, GDAP2, LRP2, PCBP1, SERF1B, TRIM72, AREGB, COPZ1, GDE1, LRP2BP, PCBP2, SERF2, TRIM73, AREL1, COPZ2, GDF1, LRP3, PCBP3, SERGEF, TRIM74, ARF1, COQ10A, GDF10, LRP4, PCBP4, SERHL2, TRIM77, ARF3, COQ10B, GDF11, LRP5, PCCA, SERINC1, TRIM8, ARF4, COQ2, GDF15, LRP5L, PCCB, SERINC2, TRIM9, ARF5, COQ3, GDF2, LRP6, PCDH1, SERINC3, TRIML1, ARF6, COQ4, GDF3, LRP8, PCDH10, SERINC4, TRIML2, ARFGAP1, COQ5, GDF5, LRPAP1, PCDH11X, SERINC5, TRIO, ARFGAP2, COQ6, GDF6, LRPPRC, PCDH11Y, SERP1, TRIOBP, ARFGAP3, COQ7, GDF7, LRR1, PCDH12, SERP2, TRIP10, ARFGEF1, COQ9, GDF9, LRRC1, PCDH15, SERPINA1, TRIP11, ARFGEF2, CORIN, GDI1, LRRC10, PCDH17, SERPINA10, TRIP12, ARFIP1, CORO1A, GDI2, LRRC10B, PCDH18, SERPINA11, TRIP13, ARFIP2, CORO1B, GDNF, LRRC14, PCDH19, SERPINA12, TRIP4, ARFRP1, CORO1C, GDNF-AS1, LRRC14B, PCDH20, SERPINA3, TRIP6, ARG1, CORO2A, GDPD1, LRRC15, PCDH7, SERPINA4, TRIQK, ARG2, CORO2B, GDPD2, LRRC16A, PCDH8, SERPINA5, TRIT1, ARGFX, CORO6, GDPD3, LRRC16B, PCDH9, SERPINA6, TRMT1, ARGLU1, CORO7, GDPD4, LRRC17, PCDHA1, SERPINA7, TRMT10A, ARHGAP1, CORO7-PAM16, GDPD5, LRRC18, PCDHA10, SERPINA9, TRMT10B, ARHGAP10, CORT, GDPGP1, LRRC19, PCDHA11, SERPINB1, TRMT10C, ARHGAP11A, COTL1, GEM, LRRC2, PCDHA12, SERPINB10, TRMT11, ARHGAP11B, COX10, GEMIN2, LRRC20, PCDHA13, SERPINB11, TRMT112, ARHGAP12, COX11, GEMIN4, LRRC23, PCDHA2, SERPINB12, TRMT12, ARHGAP15, COX14, GEMIN5, LRRC24, PCDHA3, SERPINB13, TRMT13, ARHGAP17, COX15, GEMIN6, LRRC25, PCDHA4, SERPINB2, TRMT1L, ARHGAP18, COX16, GEMIN7, LRRC26, PCDHA5, SERPINB3, TRMT2A, ARHGAP19, COX17, GEMIN8, LRRC27, PCDHA6, SERPINB4, TRMT2B, ARHGAP20, COX18, GEN1, LRRC28, PCDHA7, SERPINB5, TRMT44, ARHGAP21, COX19, GET4, LRRC29, PCDHA8, SERPINB6, TRMT5, ARHGAP22, COX20, GFAP, LRRC3, PCDHA9, SERPINB7, TRMT6, ARHGAP23, COX4I1, GFER, LRRC30, PCDHAC1, SERPINB8, TRMT61A, ARHGAP24, COX4I2, GFI1, LRRC31, PCDHAC2, SERPINB9, TRMT61B, ARHGAP25, COX5A, GFI1B, LRRC32, PCDHB1, SERPINC1, TRMU, ARHGAP26, COX5B, GFM1, LRRC34, PCDHB10, SERPIND1, TRNAU1AP, ARHGAP27, COX6A1, GFM2, LRRC36, PCDHB11, SERPINE1, TRNP1, ARHGAP28, COX6A2, GFOD1, LRRC37A2, PCDHB12, SERPINE2, TRNT1, ARHGAP29, COX6B1, GFOD2, LRRC37A3, PCDHB13, SERPINE3, TRO, ARHGAP30, COX6B2, GFPT1, LRRC37B, PCDHB14, SERPINF1, TROAP, ARHGAP31, COX6C, GFPT2, LRRC38, PCDHB15, SERPINF2, TROVE2, ARHGAP32, COX7A1, GFRA1, LRRC39, PCDHB16, SERPING1, TRPA1, ARHGAP33, COX7A2, GFRA2, LRRC3B, PCDHB2, SERPINH1, TRPC1, ARHGAP35, COX7A2L, GFRA3, LRRC3C, PCDHB3, SERPINI1, TRPC3, ARHGAP36, COX7B, GFRA4, LRRC4, PCDHB4, SERPINI2, TRPC4, ARHGAP39, COX7B2, GFRAL, LRRC40, PCDHB5, SERTAD1, TRPC4AP, ARHGAP4, COX7C, GGA1, LRRC41, PCDHB6, SERTAD2, TRPC5, ARHGAP40, COX8A, GGA2, LRRC42, PCDHB7, SERTAD3, TRPC5OS, ARHGAP42, COX8C, GGA3, LRRC43, PCDHB8, SERTAD4, TRPC6, ARHGAP44, CP, GGACT, LRRC45, PCDHB9, SERTM1, TRPC7, ARHGAP5, CPA1, GGCT, LRRC46, PCDHGA1, SESN1,

TABLE 1-continued

List of examples of target genes (e.g., encoding a protein of interest)
List of target genes/proteins of interest TRPM1, ARHGAP6, CPA2, GGCX, LRRC47, PCDHGA10, SESN2, TRPM2, ARHGAP8, CPA3, GGH, LRRC48, PCDHGA11, SESN3, TRPM3, ARHGAP9, CPA4, GGN, LRRC49, PCDHGA12, SESTD1, TRPM4, ARHGDIA, CPA5, GGNBP2, LRRC4B, PCDHGA2, SET, TRPM5, ARHGDIB, CPA6, GGPS1, LRRC4C, PCDHGA3, SETBP1, TRPM6, ARHGDIG, CPAMD8, GGT1, LRRC52, PCDHGA4, SETD1A, TRPM7, ARHGEF1, CPB1, GGT2, LRRC55, PCDHGA5, SETD1B, TRPM8, ARHGEF10, CPB2, GGT5, LRRC56, PCDHGA6, SETD2, TRPS1, ARHGEF10L, CPD, GGT6, LRRC57, PCDHGA7, SETD3, TRPT1, ARHGEF11, CPE, GGT7, LRRC58, PCDHGA8, SETD4, TRPV1, ARHGEF12, CPEB1, GGTLC1, LRRC59, PCDHGA9, SETD5, TRPV2, ARHGEF15, CPEB2, GGTLC2, LRRC6, PCDHGB1, SETD6, TRPV3, ARHGEF16, CPEB3, GH1, LRRC61, PCDHGB2, SETD7, TRPV4, ARHGEF17, CPEB4, GH2, LRRC63, PCDHGB3, SETD8, TRPV5, ARHGEF18, CPED1, GHDC, LRRC66, PCDHGB4, SETD9, TRPV6, ARHGEF19, CPLX1, GHITM, LRRC69, PCDHGB5, SETDB1, TRRAP, ARHGEF2, CPLX2, GHR, LRRC7, PCDHGB6, SETDB2, TRUB1, ARHGEF25, CPLX3, GHRH, LRRC70, PCDHGB7, SETMAR, TRUB2, ARHGEF26, CPLX4, GHRHR, LRRC71, PCDHGC3, SETSIP, TSACC, ARHGEF28, CPM, GHRL, LRRC72, PCDHGC4, SETX, TSC1, ARHGEF3, CPN1, GHSR, LRRC73, PCDHGC5, SEZ6, TSC2, ARHGEF33, CPN2, GID4, LRRC8A, PCDP1, SEZ6L, TSC22D1, ARHGEF35, CPNE1, GID8, LRRC8B, PCED1A, SEZ6L2, TSC22D2, ARHGEF37, CPNE2, GIF, LRRC8C, PCED1B, SF1, TSC22D3, ARHGEF38, CPNE3, GIGYF1, LRRC8D, PCF11, SF3A1, TSC22D4, ARHGEF39, CPNE4, GIGYF2, LRRC8E, PCGF1, SF3A2, TSEN15, ARHGEF4, CPNE5, GIMAP1, LRRCC1, PCGF2, SF3A3, TSEN2, ARHGEF40, CPNE6, GIMAP1-GIMAP5, LRRD1, PCGF3, SF3B1, TSEN34, ARHGEF5, CPNE7, GIMAP2, LRRFIP1, PCGF5, SF3B14, TSEN54, ARHGEF6, CPNE8, GIMAP4, LRRFIP2, PCGF6, SF3B2, TSFM, ARHGEF7, CPNE9, GIMAP5, LRRIQ1, PCID2, SF3B3, TSG101, GIMAP6, LRRIQ3, PCIF1, SF3B4, TSGA10, ARID1A, CPOX, GIMAP7, LRRIQ4, PCK1, SF3B5, TSGA10IP, ARID1B, CPPED1, GIMAP8, LRRK1, PCK2, SFI1, TSGA13, ARID2, CPQ, GIMD1, LRRK2, PCLO, SFMBT1, TSHB, ARID3A, CPS1, GIN1, LRRN1, PCM1, SFMBT2, TSHR, ARID3B, CPSF1, GINM1, LRRN2, PCMT1, SFN, TSHZ1, ARID3C, CPSF2, GINS1, LRRN3, PCMTD1, SFPQ, TSHZ2, ARID4A, CPSF3, GINS2, LRRN4, PCMTD2, SFR1, TSHZ3, ARID4B, CPSF3L, GINS3, LRRN4CL, PCNA, SFRP1, TSKS, ARID5A, CPSF4, GINS4, LRRTM1, PCNP, SFRP2, TSKU, ARID5B, CPSF4L, GIP, LRRTM2, PCNT, SFRP4, TSLP, ARIH1, CPSF6, GIPC1, LRRTM3, PCNX, SFRP5, TSN, ARIH2, CPSF7, GIPC2, LRRTM4, PCNXL2, SFSWAP, TSNARE1, ARIH2OS, CPT1A, GIPC3, LRSAM1, PCNXL3, SFT2D1, TSNAX, ARL1, CPT1B, GIPR, LRTM1, PCNXL4, SFT2D2, TSNAXIP1, ARL10, CPT1C, GIT1, LRTM2, PCOLCE, SFT2D3, TSPAN1, ARL11, CPT2, GIT2, LRTOMT, PCOLCE2, SFTA2, TSPAN10, ARL13A, CPVL, GJA1, LRWD1, PCP2, SFTA3, TSPAN11, ARL13B, CPXCR1, GJA10, LSAMP, PCP4, SFTPA1, TSPAN12, ARL14, CPXM1, GJA3, LSG1, PCP4L1, SFTPA2, TSPAN13, ARL14EP, CPXM2, GJA4, LSM1, PCSK1, SFTPB, TSPAN14, ARL14EPL, CPZ, GJA5, LSM10, PCSK1N, SFTPC, TSPAN15, ARL15, CR1, GJA8, LSM11, PCSK2, SFTPD, TSPAN16, ARL16, CR1L, GJA9, LSM12, PCSK4, SFXN1, TSPAN17, ARL17A, CR2, GJB1, LSM14A, PCSK5, SFXN2, TSPAN18, ARL17B, CRABP1, GJB2, LSM14B, PCSK6, SFXN3, TSPAN19, ARL2, CRABP2, GJB3, LSM2, PCSK7, SFXN4, TSPAN2, ARL2BP, CRADD, GJB4, LSM3, PCSK9, SFXN5, TSPAN3, ARL3, CRAMP1L, GJB5, LSM4, PCTP, SGCA, TSPAN31, ARL4A, CRAT, GJB6, LSM5, PCYOX1, SGCB, TSPAN32, ARL4C, CRB1, GJB7, LSM6, PCYOX1L, SGCD, TSPAN33, ARL4D, CRB2, GJC1, LSM7, PCYT1A, SGCE, TSPAN4, ARL5A, CRB3, GJC2, LSMD1, PCYT1B, SGCG, TSPAN5, ARL5B, CRBN, GJC3, LSMEM1, PCYT2, SGCZ, TSPAN6, ARL5C, CRCP, GJD2, LSMEM2, PDAP1, SGIP1, TSPAN7, ARL6, CRCT1, GJD3, LSP1, PDC, SGK1, TSPAN8, ARL6IP1, CREB1, GJD4, LSR, PDCD1, SGK2, TSPAN9, ARL6IP4, CREB3, GK, LSS, PDCD10, SGK223, TSPEAR, ARL6IP5, CREB3L1, GK2, LST1, PDCD11, SGK3, TSPO, ARL6IP6, CREB3L2, GK5, LTA, PDCD1LG2, SGK494, TSPO2, ARL8A, CREB3L3, GKAP1, LTA4H, PDCD2, SGMS1, TSPY1, ARL8B, CREB3L4, GKN1, LTB, PDCD2L, SGMS2, TSPY10, ARL9, CREB5, GKN2, LTB4R, PDCD4, SGOL1, TSPY2, ARMC1, CREBBP, GLA, LTB4R2, PDCD5, SGOL2, TSPY3, ARMC10, CREBL2, GLB1, LTBP1, PDCD6, SGPL1, TSPY4, ARMC12, CREBRF, GLB1L, LTBP2, PDCD6IP, SGPP1, TSPY8, ARMC2, CREBZF, GLB1L2, LTBP3, PDCD7, SGPP2, TSPYL1, ARMC3, CREG1, GLB1L3, LTBP4, PDCL, SGSH, TSPYL2, ARMC4, CREG, GLCCI1, LTBR, PDCL2, SGSM1, TSPYL4, ARMC5, CRELD1, GLCE, LTC4S, PDCL3, SGSM2, TSPYL5, ARMC6, CRELD2, GLDC, LTF, PDDC1, SGSM3, TSPYL6, ARMC7, CREM, GLDN, LTK, PDE10A, SGTA, TSR1, ARMC8, CRH, GLE1, LTN1, PDE11A, SGTB, TSR2, ARMC9, CRHBP, GLG1, LTV1, PDE12, SH2B1, TSR3, ARMCX1, CRHR1, GLI1, LUC7L, PDE1A, SH2B2, TSSC1, ARMCX2, CRHR2, GLI2, LUC7L2, PDE1B, SH2B3, TSSC4, ARMCX3, CRIM1, GLI3, LUC7L3, PDE1C, SH2D1A, TSSK1B, ARMCX4, CRIP1, GLI4, LUM, PDE2A, SH2D1B, TSSK2, ARMCX5, CRIP2, GLIPR1, LURAP1, PDE3A, SH2D2A, TSSK3, ARMCX5-GPRASP2, CRIP3, GLIPR1L1, LURAP1L, PDE3B, SH2D3A, TSSK4, ARMCX6, CRIPAK, GLIPR1L2, LUZP1, PDE4A, SH2D3C, TSSK6, ARMS2, CRIPT, GLIPR2, LUZP2, PDE4B, SH2D4A, TST, ARNT, CRISP1, GLIS1, LUZP4, PDE4C, SH2D4B, TSTA3, ARNT2, CRISP2, GLIS2, LUZP6, PDE4D, SH2D5, TSTD1, ARNTL, CRISP3, GLIS3, LXN, PDE4DIP, SH2D6, TSTD2, ARNTL2, CRISPLD1, GLMN, LY6D, PDE5A, SH2D7, TSTD3, ARPC1A, CRISPLD2, GLO1, LY6E, PDE6A, SH3BGR, TTBK1, ARPC1B, CRK, GLOD4, LY6G5B, PDE6B, SH3BGRL, TTBK2, ARPC2, CRKL, GLOD5, LY6G5C, PDE6C, SH3BGRL2, TTC1, ARPC3, CRLF1, GLP1R, LY6G6C, PDE6D, SH3BGRL3, TTC12, ARPC4, CRLF2, GLP2R, LY6G6D, PDE6G, SH3BP1, TTC13, ARPC4-TTLL3, CRLF3, GLRA1, LY6G6F, PDE6H, SH3BP2, TTC14, ARPC5, CRLS1, GLRA2, LY6H, PDE7A, SH3BP4, TTC16, ARPC5L, CRMP1, GLRA3, LY6K, PDE7B, SH3BP5, TTC17, ARPP19, CRNKL1, GLRA4, LY75, PDE8A, SH3BP5L, TTC18, ARPP21, CRNN, GLRB, LY75-CD302, PDE8B, SH3D19, TTC19, ARR3, CROCC, GLRX, LY86, PDE9A, SH3D21, TTC21A, ARRB1, CROT, GLRX2, LY9, PDF, SH3GL1, TTC21B, ARRB2, CRP, GLRX3, LY96, PDGFA, SH3GL2, TTC22, ARRDC1, CRTAC1, GLRX5, LYAR, PDGFB, SH3GL3, TTC23, ARRDC2, CRTAM, GLS, LYG1, PDGFC, SH3GLB1, TTC23L, ARRDC3, CRTAP, GLS2, LYG2, PDGFD, SH3GLB2, TTC24, ARRDC4, CRTC1, GLT1D1, LYL1, PDGFRA, SH3KBP1, TTC25, ARRDC5, CRTC2, GLT6D1, LYN, PDGFRB, SH3PXD2A, TTC26, ARSA, CRTC3, GLT8D1, LYNX1, PDGFRL, SH3PXD2B, TTC27, ARSB, CRX, GLT8D2, LYPD1, PDHA1, SH3RF1, TTC28, ARSD, CRY1, GLTP, LYPD2, PDHA2, SH3RF2, TTC29, ARSE, CRY2, GLTPD1, LYPD3, PDHB, SH3RF3, TTC3, ARSF, CRYAA, GLTPD2, LYPD4, PDHX, TABLE 1-continued List of examples of target genes (e.g., encoding a protein of interest)
List of target genes/proteins of interest SH3TC1, TTC30A, ARSG, CRYAB, GLTSCR1, LYPD5, PDIA2, SH3TC2, TTC30B, ARSH, CRYBA1, GLTSCR1L, LYPD6, PDIA3, SH3YL1, TTC31, ARSI, CRYBA2, GLTSCR2, LYPD6B, PDIA4, SHANK1, TTC32, ARSJ, CRYBA4, GLUD1, LYPD8, PDIA5, SHANK2, TTC33, ARSK, CRYBB1, GLUD2, LYPLA1, PDIA6, SHANK3, TTC34, ARTI, CRYBB2, GLUL, LYPLA2, PDIK1L, SHARPIN, TTC36, ART3, CRYBB3, GLYAT, LYPLAL1, PDILT, SHB, TTC37, ART4, CRYBG3, GLYATL1, LYRM1, PDK1, SHBG, TTC38, ART5, CRYGA, GLYATL2, LYRM2, PDK2, SHC1, TTC39A, ARTN, CRYGB, GLYATL3, LYRM4, PDK3, SHC2, TTC39B, ARV1, CRYGC, GLYCTK, LYRM5, PDK4, SHC3, TTC39C, ARVCF, CRYGD, GLYR1, LYRM7, PDLIM1, SHC4, TTC4, ARX, CRYGN, GM2A, LYRM9, PDLIM2, SHCBP1, TTC40, AS3MT, CRYGS, GMCL1, LYSMD1, PDLIM3, SHCBP1L, TTC5, ASAH1, CRYL1, GMDS, LYSMD2, PDLIM4, SHD, TTC6, ASAH2, CRYM, GMEB1, LYSMD3, PDLIM5, SHE, TTC7A, ASAH2B, CRYZ, GMEB2, LYSMD4, PDLIM7, SHF, TTC7B, ASAP1, CRYZL1, GMFB, LYST, PDP1, SHFM1, TTC8, ASAP2, CS, GMFG, LYVE1, PDP2, SHH, TTC9, ASAP3, CSAD, GMIP, LYZ, PDPK1, SHISA2, TTC9B, ASB1, CSAG1, GML, LYZL1, PDPN, SHISA3, TTC9C, ASB10, CSAG2, GMNC, LYZL2, PDPR, SHISA4, TTF1, ASB11, CSAG3, GMNN, LYZL4, PDRG1, SHISA5, TTF2, ASB12, CSDC2, GMPPA, LYZL6, PDS5A, SHISA6, TTI1, ASB13, CSDE1, GMPPB, LZIC, PDS5B, SHISA7, TTI2, ASB14, CSE1L, GMPR, LZTFL1, PDSS1, SHISA8, TTK, ASB15, CSF1, GMPR2, LZTR1, PDSS2, SHISA9, TTL, ASB16, CSF1R, GMPS, LZTS1, PDX1, SHKBP1, TTLL1, ASB17, CSF2, GNA11, LZTS2, PDXDC1, SHMT1, TTLL10, ASB18, CSF2RA, GNA12, LZTS3, PDXK, SHMT2, TTLL11, ASB2, CSF2RB, GNA13, M1AP, PDXP, SHOC2, TTLL12, ASB3, CSF3, GNA14, M6PR, PDYN, SHOX, TTLL13, ASB4, CSF3R, GNA15, MAATS1, PDZD11, SHOX2, TTLL2, ASB5, CSGALNACT1, GNAI1, MAB21L1, PDZD2, SHPK, TTLL3, ASB6, CSGALNACT2, GNAI2, MAB21L2, PDZD3, SHPRH, TTLL4, ASB7, CSH1, GNAI3, MAB21L3, PDZD4, SHQ1, TTLL5, ASB8, CSH2, GNAL, MACC1, PDZD7, SHROOM1, TTLL6, ASB9, CSHL1, GNAO1, MACF1, PDZD8, SHROOM2, TTLL7, ASCC1, CSK, GNAQ, MACROD1, PDZD9, SHROOM3, TTLL8, ASCC2, CSMD1, GNAS, MACROD2, PDZK1, SHROOM4, TTLL9, ASCC3, CSMD2, GNAT1, MAD1L1, PDZK1IP1, SI, TTN, ASCL1, CSMD3, GNAT2, MAD2L1, PDZRN3, SIAE, TTPA, ASCL2, CSN1S1, GNAT3, MAD2L1BP, PDZRN4, SIAH1, TTPAL, ASCL3, CSN2, GNAZ, MAD2L2, PEA15, SIAH2, TTR, ASCL4, CSN3, GNB1, MADCAM1, PEAK1, SIAH3, TTYH1, ASCL5, CSNK1A1, GNB1L, MADD, PEAR1, SIDT1, TTYH2, ASF1A, CSNK1A1L, GNB2, MAEA, PEBP1, SIDT2, TTYH3, ASF1B, CSNK1D, GNB2L1, MAEL, PEBP4, SIGIRR, TUB, ASGR1, CSNK1E, GNB3, MAF, PECAM1, SIGLEC1, TUBA1A, ASGR2, CSNK1G1, GNB4, MAF1, PECR, SIGLEC10, TUBA1B, ASH1L, CSNK1G2, GNB5, MAFA, PEF1, SIGLEC11, TUBA1C, ASH2L, CSNK1G3, GNE, MAFB, PEG10, SIGLEC12, TUBA3C, ASIC1, CSNK2A1, GNG10, MAFF, PEG3, SIGLEC14, TUBA3D, ASIC2, CSNK2A2, GNG11, MAFG, PELI1, SIGLEC15, TUBA3E, ASIC3, CSNK2A3, GNG12, MAFK, PELI2, SIGLEC5, TUBA4A, ASIC4, CSNK2B, GNG13, MAG, PELI3, SIGLEC6, TUBA8, ASIC5, CSPG4, GNG2, MAGEA1, PELO, SIGLEC7, TUBAL3, ASIP, CSPG5, GNG3, MAGEA10, PELP1, SIGLEC8, TUBB, ASL, CSPP1, GNG4, MAGEA10-MAGEA5, PEMT, SIGLEC9, TUBB1, ASMT, CSRNP1, GNG5, MAGEA11, PENK, SIGLECL1, TUBB2A, ASMTL, CSRNP2, GNG7, MAGEA12, PEPD, SIGMAR1, TUBB2B, ASNA1, CSRNP3, GNG8, MAGEA3, PER1, SIK1, TUBB3, ASNS, CSRP1, GNGT1, MAGEA4, PER2, SIK2, TUBB4A, ASNSD1, CSRP2, GNGT2, MAGEA5, PER3, SIK3, TUBB4B, ASPA, CSRP2BP, GNL1, MAGEA6, PERM1, SIKE1, TUBB6, ASPDH, CSRP3, GNL2, MAGEA8, PERP, SIL1, TUBB8, ASPG, CST1, GNL3, MAGEB1, PES1, SIM1, TUBD1, ASPH, CST11, GNL3L, MAGEB10, PET100, SIM2, TUBE1, ASPHD1, CST2, GNLY, MAGEB16, PET112, SIMC1, TUBG1, ASPHD2, CST3, GNMT, MAGEB17, PET117, SIN3A, TUBG2, ASPM, CST4, GNPAT, MAGEB18, PEX1, SIN3B, TUBGCP2, ASPN, CST5, GNPDA1, MAGEB2, PEX10, SIPA1, TUBGCP3, ASPRV1, CST6, GNPDA2, MAGEB3, PEX11A, SIPA1L1, TUBGCP4, ASPSCR1, CST7, GNPNAT1, MAGEB4, PEX11B, SIPA1L2, TUBGCP5, ASRGL1, CST8, GNPTAB, MAGEB5, PEX11G, SIPAIL3, TUBGCP6, ASS1, CST9, GNPTG, MAGEB6, PEX12, SIRPA, TUFM, ASTE1, CST9L, GNRH1, MAGEC1, PEX13, SIRPB1, TUFT1, ASTL, CSTA, GNRH2, MAGEC2, PEX14, SIRPB2, TULP1, ASTN1, CSTB, GNRHR, MAGEC3, PEX16, SIRPD, TULP2, ASTN2, CSTF1, GNS, MAGED1, PEX19, SIRPG, TULP3, ASUN, CSTF2, GOLGA1, MAGED2, PEX2, SIRT1, TULP4, ASXL1, CSTF2T, GOLGA2, MAGEE1, PEX26, SIRT2, TUSC1, ASXL2, CSTF3, GOLGA3, MAGEE2, PEX3, SIRT3, TUSC2, ASXL3, CSTL1, GOLGA4, MAGEF1, PEX5, SIRT4, TUSC3, ASZ1, CT45A1, GOLGA5, MAGEH1, PEX5L, SIRT5, TUSC5, ATAD1, CT45A2, GOLGA6A, MAGEL2, PEX6, SIRT6, TUT1, ATAD2, CT45A3, GOLGA6B, MAGI1, PEX7, SIRT7, TVP23A, ATAD2B, CT45A4, GOLGA6C, MAGI2, PF4, SIT1, TVP23B, ATAD3A, CT45A5, GOLGA6D, MAGI3, PF4V1, SIVA1, TVP23C, ATAD3B, CT45A6, GOLGA6L1, MAGIX, PFAS, SIX1, TVP23C-CDRT4, ATAD3C, CT47A1, GOLGA6L10, MAGOH, PFDN1, SIX2, TWF1, ATAD5, CT47A10, GOLGA6L2, MAGOHB, PFDN2, SIX3, TWF2, ATAT1, CT47A11, GOLGA6L3, MAGT1, PFDN4, SIX4, TWIST1, ATCAY, CT47A12, GOLGA6L4, MAK, PFDN5, SIX5, TWIST2, ATE1, CT47A2, GOLGA6L6, MAK16, PFDN6, SIX6, TWISTNB, ATF1, CT47A3, GOLGA6L9, MAL, PFKFB1, SKA1, TWSG1, ATF2, CT47A4, GOLGA7, MAL2, PFKFB2, SKA2, TXK, ATF3, CT47A5, GOLGA7B, MALL, PFKFB3, SKA3, TXLNA, ATF4, CT47A6, GOLGA8A, MALSU1, PFKFB4, SKAP1, TXLNB, ATF5, CT47A7, GOLGA8B, MALT1, PFKL, SKAP2, TXLNG, ATF6, CT47A8, GOLGA8H, MAMDC2, PFKM, SKI, TXN, ATF6B, CT47A9, GOLGA8J, MAMDC4, PFKP, SKIDA1, TXN2, ATF7, CT47B1, GOLGA8K, MAML1, PFN1, SKIL, TXNDC11, ATF7IP, CT62, GOLGA8M, MAML2, PFN2, SKIV2L, TXNDC12, ATF7IP2, CTAG1A, GOLGA80, MAML3, PFN3, SKIV2L2, TXNDC15, ATG10, CTAG1B, GOLGA8R, MAMLD1, PFN4, SKOR1, TXNDC16, ATG12, CTAG2, GOLGB1, MAMSTR, PGA3, SKOR2, TXNDC17, ATG13, CTAGE1, GOLIM4, MAN1A1, PGA4, SKP1, TXNDC2, ATG14, CTAGE15, GOLM1, MAN1A2, PGA5, SKP2, TXNDC5, ATG16L1, CTAGE4, GOLPH3, MAN1B1, PGAM1, SLA, TXNDC8, ATG16L2, CTAGE5, GOLPH3L, MAN1C1, PGAM2, SLA2, TXNDC9, ATG2A, CTAGE6, GOLT1A, MAN2A1, PGAM4, SLAIN1, TXNIP, ATG2B, CTAGE8, GOLT1B, MAN2A2, PGAM5, SLAIN2, TXNL1, ATG3, CTAGE9, GON4L, MAN2B1, PGAP1, SLAMF1, TXNL4A, ATG4A, CTBP1, GOPC, MAN2B2, PGAP2, SLAMF6, TXNL4B, ATG4B, CTBP2, GORAB, MAN2C1, PGAP3, SLAMF7, TXNRD1, ATG4C, CTBS, GORASP1, MANBA, PGBD1, SLAMF8, TXNRD2, ATG4D, CTC1, GORASP2, MANBAL, PGBD2, SLAMF9, TXNRD3, ATG5, CTCF, GOSR1, MANEA, PGBD3, SLBP, TXNRD3NB, ATG7, CTCFL, TABLE 1-continued List of examples of target genes (e.g., encoding a protein of interest)
List of target genes/proteins of interest GOSR2, MANEAL, PGBD4, SLC10A1, TYK2, ATG9A, CTDNEP1, GOT1, MANF, PGBD5, SLC10A2, TYMP, ATG9B, CTDP1, GOT1L1, MANSC1, PGC, SLC10A3, TYMS, ATHL1, CTDSP1, GOT2, MANSC4, PGD, SLC10A4, TYR, ATIC, CTDSP2, GP1BA, MAOA, PGF, SLC10A5, TYRO3, ATL1, CTDSPL, GP1BB, MAOB, PGGT1B, SLC10A6, TYROBP, ATL2, CTDSPL2, GP2, MAP10, PGK1, SLC10A7, TYRP1, ATL3, CTF1, GP5, MAP1A, PGK2, SLC11A1, TYSND1, ATM, CTGF, GP6, MAP1B, PGLS, SLC11A2, TYW1, ATMIN, CTH, GP9, MAP1LC3A, PGLYRP1, SLC12A1, TYW1B, ATN1, CTHRC1, GPA33, MAP1LC3B, PGLYRP2, SLC12A2, TYW3, ATOH1, CTIF, GPAA1, MAP1LC3B2, PGLYRP3, SLC12A3, TYW5, ATOH7, CTLA4, GPALPP1, MAP1LC3C, PGLYRP4, SLC12A4, U2AF1, ATOH8, CTNNA1, GPAM, MAP1S, PGM1, SLC12A5, U2AF1L4, ATOX1, CTNNA2, GPANK1, MAP2, PGM2, SLC12A6, U2AF2, ATP10A, CTNNA3, GPAT2, MAP2K1, PGM2L1, SLC12A7, U2SURP, ATP10B, CTNNAL1, GPATCH1, MAP2K2, PGM3, SLC12A8, UACA, ATP10D, CTNNB1, GPATCH11, MAP2K3, PGM5, SLC12A9, UAP1, ATP11A, CTNNBIP1, GPATCH2, MAP2K4, PGP, SLC13A1, UAP1L1, ATP11B, CTNNBL1, GPATCH2L, MAP2K5, PGPEP1, SLC13A2, UBA1, ATP11C, CTNND1, GPATCH3, MAP2K6, PGPEP1L, SLC13A3, UBA2, ATP12A, CTNND2, GPATCH4, MAP2K7, PGR, SLC13A4, UBA3, ATP13A1, CTNS, GPATCH8, MAP3K1, PGRMC1, SLC13A5, UBA5, ATP13A2, CTPS1, GPBAR1, MAP3K10, PGRMC2, SLC14A1, UBA52, ATP13A3, CTPS2, GPBP1, MAP3K11, PGS1, SLC14A2, UBA6, ATP13A4, CTR9, GPBP1L1, MAP3K12, PHACTR1, SLC15A1, UBA7, ATP13A5, CTRB1, GPC1, MAP3K13, PHACTR2, SLC15A2, UBAC1, ATP1A1, CTRB2, GPC2, MAP3K14, PHACTR3, SLC15A3, UBAC2, ATP1A2, CTRC, GPC3, MAP3K15, PHACTR4, SLC15A4, UBALD1, ATP1A3, CTRL, GPC4, MAP3K19, PHAX, SLC15A5, UBALD2, ATP1A4, CTSA, GPC5, MAP3K2, PHB, SLC16A1, UBAP1, ATP1B1, CTSB, GPC6, MAP3K3, PHB2, SLC16A10, UBAP1L, ATP1B2, CTSC, GPCPD1, MAP3K4, PHC1, SLC16A11, UBAP2, ATP1B3, CTSD, GPD1, MAP3K5, PHC2, SLC16A12, UBAP2L, ATP1B4, CTSE, GPD1L, MAP3K6, PHC3, SLC16A13, UBASH3A, ATP2A1, CTSF, GPD2, MAP3K7, PHEX, SLC16A14, UBASH3B, ATP2A2, CTSG, GPER1, MAP3K7CL, PHF1, SLC16A2, UBB, ATP2A3, CTSH, GPHA2, MAP3K8, PHF10, SLC16A3, UBC, ATP2B1, CTSK, GPHB5, MAP3K9, PHF11, SLC16A4, UBD, ATP2B2, CTSL, GPHN, MAP4, PHF12, SLC16A5, UBE2A, ATP2B3, CTSO, GPI, MAP4K1, PHF13, SLC16A6, UBE2B, ATP2B4, CTSS, GPIHBP1, MAP4K2, PHF14, SLC16A7, UBE2C, ATP2C1, CTSV, GPKOW, MAP4K3, PHF19, SLC16A8, UBE2D1, ATP2C2, CTSW, GPLD1, MAP4K4, PHF2, SLC16A9, UBE2D2, ATP4A, CTSZ, GPM6A, MAP4K5, PHF20, SLC17A1, UBE2D3, ATP4B, CTTN, GPM6B, MAP6, PHF20L1, SLC17A2, UBE2D4, ATP5A1, CTTNBP2, GPN1, MAP6D1, PHF21A, SLC17A3, UBE2E1, ATP5B, CTTNBP2NL, GPN2, MAP7, PHF21B, SLC17A4, UBE2E2, ATP5C1, CTU1, GPN3, MAP7D1, PHF23, SLC17A5, UBE2E2-AS1, ATP5D, CTU2, GPNMB, MAP7D2, PHF3, SLC17A6, UBE2E3, ATP5E, CTXN1, GPR1, MAP7D3, PHF5A, SLC17A7, UBE2F, ATP5F1, CTXN2, GPR3, MAP9, PHF6, SLC17A8, UBE2G1, ATP5G1, CTXN3, GPR107, MAPK1, PHF7, SLC17A9, UBE2G2, ATP5G2, CUBN, GPR108, MAPK10, PHF8, SLC18A1, UBE2H, ATP5G3, CUEDC1, GPR110, MAPK11, PHGDH, SLC18A2, UBE2I, ATP5H, CUEDC2, GPR111, MAPK12, PHGR1, SLC18A3, UBE2J1, ATP5I, CUL1, GPR112, MAPK13, PHIP, SLC18B1, UBE2J2, ATP5J, CUL2, GPR113, MAPK14, PHKA1, SLC19A1, UBE2K, ATP5J2, CUL3, GPR114, MAPK15, PHKA2, SLC19A2, UBE2L3, ATP5J2-PTCD1, CUL4A, GPR115, MAPK1IP1L, PHKB, SLC19A3, UBE2L6, ATP5L, CUL4B, GPR116, MAPK3, PHKG1, SLCIA1, UBE2M, ATP5L2, CUL5, GPR119, MAPK4, PHKG2, SLC1A2, UBE2N, ATP5O, CUL7, GPR12, MAPK6, PHLDA1, SLC1A3, UBE2NL, ATP5S, CUL9, GPR123, MAPK7, PHLDA2, SLC1A4, UBE2O, ATP5SL, CUTA, GPR124, MAPK8, PHLDA3, SLC1A5, UBE2Q1, ATP6AP1, CUTC, GPR125, MAPK8IP1, PHLDB1, SLC1A6, UBE2Q2, ATP6AP1L, CUX1, GPR126, MAPK8IP2, PHLDB2, SLC1A7, UBE2QL1, ATP6AP2, CUX2, GPR128, MAPK8IP3, PHLDB3, SLC20A1, UBE2R2, ATP6V0A1, CUZD1, GPR132, MAPK9, PHLPP1, SLC20A2, UBE2S, ATP6V0A2, CWC15, GPR133, MAPKAP1, PHLPP2, SLC22A1, UBE2T, ATP6V0A4, CWC22, GPR135, MAPKAPK2, PHOSPHO1, SLC22A10, UBE2U, ATP6V0B, CWC25, GPR137, MAPKAPK3, PHOSPHO2, SLC22A11, UBE2V1, ATP6V0C, CWC27, GPR137B, MAPKAPK5, PHOSPHO2-KLHL23, SLC22A12, UBE2V2, ATP6V0D1, CWF19L1, GPR137C, MAPKBP1, PHOX2A, SLC22A13, UBE2W, ATP6V0D2, CWF19L2, GPR139, MAPRE1, PHOX2B, SLC22A14, UBE2Z, ATP6V0E1, CWH43, GPR142, MAPRE2, PHPT1, SLC22A15, UBE3A, ATP6V0E2, CX3CL1, GPR143, MAPRE3, PHRF1, SLC22A16, UBE3B, ATP6V1A, CX3CR1, GPR148, MAPT, PHTF1, SLC22A17, UBE3C, ATP6V1B1, CXADR, GPR149, 1-Mar, PHTF2, SLC22A18, UBE3D, ATP6V1B2, CXCL1, GPR15, 10-Mar, PHYH, SLC22A18AS, UBE4A, ATP6V1C1, CXCL10, GPR150, 11- Mar, PHYHD1, SLC22A2, UBE4B, ATP6V1C2, CXCL11, GPR151, 2-Mar, PHYHIP, SLC22A20, UBFD1, ATP6V1D, CXCL12, GPR152, 3-Mar, PHYHIPL, SLC22A23, UBIAD1, ATP6V1E1, CXCL13, GPR153, 4- Mar, PHYKPL, SLC22A24, UBL3, ATP6V1E2, CXCL14, GPR155, 5-Mar, PI15, SLC22A25, UBL4A, ATP6V1F, CXCL16, GPR156, 6-Mar, PI16, SLC22A3, UBL4B, ATP6V1G1, CXCL17, GPR157, 7-Mar, PI3, SLC22A31, UBL5, ATP6V1G2, CXCL2, GPR158, 8-Mar, PI4K2A, SLC22A4, UBL7, ATP6V1G3, CXCL3, GPR160, 9-Mar, PI4K2B, SLC22A5, UBLCP1, ATP6V1H, CXCL5, GPR161, MARCKS, PI4KA, SLC22A6, UBN1, ATP7A, CXCL6, GPR162, MARCKSL1, PI4KB, SLC22A7, UBN2, ATP7B, CXCL9, GPR17, MARCO, PIANP, SLC22A8, UBOX5, ATP8A1, CXCR1, GPR171, MARK1, PIAS1, SLC22A9, UBP1, ATP8A2, CXCR2, GPR173, MARK2, PIAS2, SLC23A1, UBQLN1, ATP8B1, CXCR3, GPR174, MARK3, PIAS3, SLC23A2, UBQLN2, ATP8B2, CXCR4, GPR176, MARK4, PIAS4, SLC23A3, UBQLN3, ATP8B3, CXCR5, GPR179, MARS, PIBF1, SLC24A1, UBQLN4, ATP8B4, CXCR6, GPR18, MARS2, PICALM, SLC24A2, UBQLNL, ATP9A, CXorf21, GPR180, MARVELD1, PICK1, SLC24A3, UBR1, ATP9B, CXorf22, GPR182, MARVELD2, PID1, SLC24A4, UBR2, ATPAF1, CXorf23, GPR183, MARVELD3, PIDD, SLC24A5, UBR3, ATPAF2, CXorf27, GPR19, MAS1, PIEZO1, SLC25A1, UBR4, ATPIF1, CXorf30, GPR20, MAS1L, PIEZO2, SLC25A10, UBR5, ATR, CXorf36, GPR21, MASP1, PIF1, SLC25A11, UBR7, ATRAID, CXorf38, GPR22, MASP2, PIFO, SLC25A12, UBTD1, ATRIP, CXorf40A, GPR25, MAST1, PIGA, SLC25A13, UBTD2, ATRN, CXorf40B, GPR26, MAST2, PIGB, SLC25A14, UBTF, ATRNL1, CXorf48, GPR27, MAST3, PIGC, SLC25A15, UBTFL1, ATRX, CXorf49, GPR3, MAST4, PIGF, SLC25A16, UBXN1, ATXN1, CXorf49B, GPR31, MASTL, PIGG, SLC25A17, UBXN10, ATXN10, CXorf51A, GPR32, MAT1A, PIGH, SLC25A18, UBXN11, ATXN1L, CXorf51B, GPR33, MAT2A, PIGK, SLC25A19, UBXN2A, TABLE 1-continued List of examples of target genes (e.g., encoding a protein of interest)
List of target genes/proteins of interest ATXN2, CXorf56, GPR34, MAT2B, PIGL, SLC25A2, UBXN2B, ATXN2L, CXorf57, GPR35, MATK, PIGM, SLC25A20, UBXN4, ATXN3, CXorf58, GPR37, MATN1, PIGN, SLC25A21, UBXN6, ATXN3L, CXorf61, GPR37L1, MATN2, PIGO, SLC25A22, UBXN7, ATXN7, CXorf64, GPR39, MATN3, PIGP, SLC25A23, UBXN8, ATXN7L1, CXorf65, GPR4, MATN4, PIGQ, SLC25A24, UCHL1, ATXN7L2, CXorf66, GPR45, MATR3, PIGR, SLC25A25, UCHL3, ATXN7L3, CXXC1, GPR50, MAU2, PIGS, SLC25A26, UCHL5, ATXN7L3B, CXXC11, GPR52, MAVS, PIGT, SLC25A27, UCK1, AUH, CXXC4, GPR55, MAX, PIGU, SLC25A28, UCK2, AUNIP, CXXC5, GPR56, MAZ, PIGV, SLC25A29, UCKL1, AUP1, CYB561, GPR6, MB, PIGW, SLC25A3, UCMA, AURKA, CYB561A3, GPR61, MB21D1, PIGX, SLC25A30, UCN, AURKAIP1, CYB561D1, GPR62, MB21D2, PIGY, SLC25A31, UCN2, AURKB, CYB561D2, GPR63, MBD1, PIGZ, SLC25A32, UCN3, AURKC, CYB5A, GPR64, MBD2, PIH1D1, SLC25A33, UCP1, AUTS2, CYB5B, GPR65, MBD3, PIH1D2, SLC25A34, UCP2, AVEN, CYB5D1, GPR68, MBD3L1, PIH1D3, SLC25A35, UCP3, AVIL, CYB5D2, GPR75, MBD4, PIK3AP1, SLC25A36, UEVLD, AVL9, CYB5R1, GPR75-ASB3, MBD5, PIK3C2A, SLC25A37, UFC1, AVP, CYB5R2, GPR78, MBD6, PIK3C2B, SLC25A38, UFD1L, AVPI1, CYB5R3, GPR82, MBIP, PIK3C2G, SLC25A39, UFL1, AVPR1A, CYB5R4, GPR83, MBL2, PIK3C3, SLC25A4, UFM1, AVPR1B, CYB5RL, GPR84, MBLAC1, PIK3CA, SLC25A40, UFSP1, AVPR2, CYBA, GPR85, MBLAC2, PIK3CB, SLC25A41, UFSP2, AWAT1, CYBB, GPR87, MBNL1, PIK3CD, SLC25A42, UGCG, AWAT2, CYBRD1, GPR88, MBNL2, PIK3CG, SLC25A43, UGDH, AXDND1, CYC1, GPR89A, MBNL3, PIK3IP1, SLC25A44, UGGT1, AXIN1, CYCS, GPR89B, MBOAT1, PIK3R1, SLC25A45, UGGT2, AXIN2, CYFIP1, GPR89C, MBOAT2, PIK3R2, SLC25A46, UGP2, AXL, CYFIP2, GPR97, MBOAT4, PIK3R3, SLC25A47, UGT1A1, AZGP1, CYGB, GPR98, MBOAT7, PIK3R4, SLC25A48, UGT1A10, AZI1, CYHR1, GPRASP1, MBP, PIK3R5, SLC25A5, UGT1A3, AZI2, CYLC1, GPRASP2, MBTD1, PIK3R6, SLC25A51, UGT1A4, AZIN1, CYLC2, GPRC5A, MBTPS1, PIKFYVE, SLC25A52, UGT1A5, AZU1, CYLD, GPRC5B, MBTPS2, PILRA, SLC25A53, UGT1A6, B2M, CYorf17, GPRC5C, MC1R, PILRB, SLC25A6, UGT1A7, B3GALNT1, CYP11A1, GPRC5D, MC2R, PIM1, SLC26A1, UGT1A8, B3GALNT2, CYP11B1, GPRC6A, MC3R, PIM2, SLC26A10, UGT1A9, B3GALT1, CYP11B2, GPRIN1, MC4R, PIM3, SLC26A11, UGT2A1, B3GALT2, CYP17A1, GPRIN2, MC5R, PIN1, SLC26A2, UGT2A2, B3GALT4, CYP19A1, GPRIN3, MCAM, PIN4, SLC26A3, UGT2A3, B3GALT5, CYP1A1, GPS1, MCAT, PINK1, SLC26A4, UGT2B10, B3GALT6, CYP1A2, GPS2, MCC, PINLYP, SLC26A5, UGT2B11, B3GALTL, CYP1B1, GPSM1, MCCC1, PINX1, SLC26A6, UGT2B15, B3GAT1, CYP20A1, GPSM2, MCCC2, PIP, SLC26A7, UGT2B17, B3GAT2, CYP21A2, GPSM3, MCCD1, PIP4K2A, SLC26A8, UGT2B28, B3GAT3, CYP24A1, GPT, MCEE, PIP4K2B, SLC26A9, UGT2B4, B3GNT1, CYP26A1, GPT2, MCF2, PIP4K2C, SLC27A1, UGT2B7, B3GNT2, CYP26B1, GPX1, MCF2L, PIP5K1A, SLC27A2, UGT3A1, B3GNT3, CYP26C1, GPX2, MCF2L2, PIP5K1B, SLC27A3, UGT3A2, B3GNT4, CYP27A1, GPX3, MCFD2, PIP5K1C, SLC27A4, UGT8, B3GNT5, CYP27B1, GPX4, MCHR1, PIP5KL1, SLC27A5, UHMK1, B3GNT6, CYP27C1, GPX5, MCHR2, PIPOX, SLC27A6, UHRF1, B3GNT7, CYP2A13, GPX6, MCIDAS, PIR, SLC28A1, UHRF1BP1, B3GNT8, CYP2A6, GPX7, MCL1, PIRT, SLC28A2, UHRF1BP1L, B3GNT9, CYP2A7, GPX8, MCM10, PISD, SLC28A3, UHRF2, B3GNTL1, CYP2B6, GRAMD1A, MCM2, PITHD1, SLC29A1, UIMC1, B4GALNT1, CYP2C18, GRAMD1B, MCM3, PITPNA, SLC29A2, ULBP1, B4GALNT2, CYP2C19, GRAMD1C, MCM3AP, PITPNB, SLC29A3, ULBP2, B4GALNT3, CYP2C8, GRAMD2, MCM4, PITPNC1, SLC29A4, ULBP3, B4GALNT4, CYP2C9, GRAMD3, MCM5, PITPNM1, SLC2A1, ULK1, B4GALT1, CYP2D6, GRAMD4, MCM6, PITPNM2, SLC2A10, ULK2, B4GALT2, CYP2E1, GRAP, MCM7, PITPNM3, SLC2A11, ULK3, B4GALT3, CYP2F1, GRAP2, MCM8, PITRM1, SLC2A12, ULK4, B4GALT4, CYP2J2, GRAPL, MCM9, PITX1, SLC2A13, UMOD, B4GALT5, CYP2R1, GRASP, MCMBP, PITX2, SLC2A14, UMODL1, B4GALT6, CYP2S1, GRB10, MCMDC2, PITX3, SLC2A2, UMPS, B4GALT7, CYP2U1, GRB14, MCOLN1, PIWIL1, SLC2A3, UNC119, B9D1, CYP2W1, GRB2, MCOLN2, PIWIL2, SLC2A4, UNC119B, B9D2, CYP39A1, GRB7, MCOLN3, PIWIL3, SLC2A4RG, UNC13A, BAALC, CYP3A4, GREB1, MCPH1, PIWIL4, SLC2A5, UNC13B, BAAT, CYP3A43, GREM1, MCRS1, PJA1, SLC2A6, UNC13C, BABAM1, CYP3A5, GREM2, MCTP1, PJA2, SLC2A7, UNC13D, BACE1, CYP3A7, GRHL1, MCTP2, PKD1, SLC2A8, UNC45A, BACE2, CYP3A7- CYP3AP1, GRHL2, MCTS1, PKD1L1, SLC2A9, UNC45B, BACH1, CYP46A1, GRHL3, MCU, PKD1L2, SLC30A1, UNC50, BACH2, CYP4A11, GRHPR, MCUR1, PKD1L3, SLC30A10, UNC5A, BAD, CYP4A22, GRIA1, MDC1, PKD2, SLC30A2, UNC5B, BAG1, CYP4B1, GRIA2, MDFI, PKD2L1, SLC30A3, UNC5C, BAG2, CYP4F11, GRIA3, MDFIC, PKD2L2, SLC30A4, UNC5CL, BAG3, CYP4F12, GRIA4, MDGA1, PKDCC, SLC30A5, UNC5D, BAG4, CYP4F2, GRID1, MDGA2, PKDREJ, SLC30A6, UNC79, BAG5, CYP4F22, GRID2, MDH1, PKHD1, SLC30A7, UNC80, BAG6, CYP4F3, GRID2IP, MDH1B, PKHD1L1, SLC30A8, UNC93A, BAGE, CYP4F8, GRIFIN, MDH2, PKIA, SLC30A9, UNC93B1, BAGE2, CYP4V2, GRIK1, MDK, PKIB, SLC31A1, UNCX, BAGE3, CYP4X1, GRIK2, MDM1, PKIG, SLC31A2, UNG, BAHCC1, CYP4Z1, GRIK3, MDM2, PKLR, SLC32A1, UNK, BAHD1, CYP51A1, GRIK4, MDM4, PKM, SLC33A1, UNKL, BAI1, CYP7A1, GRIK5, MDN1, PKMYT1, SLC34A1, UPB1, BAI2, CYP7B1, GRIN1, MDP1, PKN1, SLC34A2, UPF1, BAI3, CYP8B1, GRIN2A, ME1, PKN2, SLC34A3, UPF2, BAIAP2, CYR61, GRIN2B, ME2, PKN3, SLC35A1, UPF3A, BAIAP2L1, CYS1, ME3, PKNOX1, SLC35A2, UPF3B, BAIAP2L2, CYSLTR1, GRIN2D, MEA1, PKNOX2, SLC35A3, UPK1A, BAIAP3, CYSLTR2, GRIN3A, MEAF6, PKP1, SLC35A4, UPK1B, BAK1, CYSTM1, GRIN3B, MECOM, PKP2, SLC35A5, UPK2, BAMBI, CYTH1, GRINA, MECP2, PKP3, SLC35B1, UPK3A, BANF1, CYTH2, GRIP1, MECR, PKP4, SLC35B2, UPK3B, BANF2, CYTH3, GRIP2, MED1, PLA1A, SLC35B3, UPK3BL, BANK1, CYTH4, GRIPAP1, MED10, PLA2G10, SLC35B4, UPP1, BANP, CYTIP, GRK1, MED11, PLA2G12A, SLC35C1, UPP2, BAP1, CYTL1, GRK4, MED12, PLA2G12B, SLC35C2, UPRT, BARD1, CYYR1, GRK5, MED12L, PLA2G15, SLC35D1, UQCC1, BARHL1, D2HGDH, GRK6, MED13, PLA2G16, SLC35D2, UQCC2, BARHL2, DAAM1, GRK7, MED13L, PLA2G1B, SLC35D3, UQCR10, BARX1, DAAM2, GRM1, MED14, PLA2G2A, SLC35E1, UQCR11, BARX2, DAB1, GRM2, MED15, PLA2G2C, SLC35E2, UQCRB, BASP1, DAB2, GRM3, MED16, PLA2G2D, SLC35E2B, UQCRC1, BATF, DAB2IP, GRM4, MED17, PLA2G2E, SLC35E3, UQCRC2, BATF2, DACH1, GRM5, MED18, PLA2G2F, SLC35E4, UQCRFS1, BATF3, DACH2, GRM6, MED19, PLA2G3, SLC35F1, UQCRH, BAX, DACT1, GRM7, MED20, PLA2G4A, SLC35F2, UQCRHL, BAZ1A, DACT2, GRM8, MED21, TABLE 1-continued List of examples of target genes (e.g., encoding a protein of interest)
List of target genes/proteins of interest PLA2G4B, SLC35F3, UQCRQ, BAZ1B, DACT3, GRN, MED22, PLA2G4C, SLC35F4, URAD,
BAZ2A, DAD1, GRP, MED23, PLA2G4D, SLC35F5, URB1, BAZ2B, DAG1, GRPEL1, MED24,
PLA2G4E, SLC35F6, URB2, BBC3, DAGLA, GRPEL2, MED25, PLA2G4F, SLC35G1, URGCP,
BBIP1, DAGLB, GRPR, MED26, PLA2G5, SLC35G2, URGCP-MRPS24, BBOX1, DAK, GRSF1,
MED27, PLA2G6, SLC35G3, URI1, BBS1, DALRD3, GRTP1, MED28, PLA2G7, SLC35G4, URM1,
BBS10, DAND5, GRWD1, MED29, PLA2R1, SLC35G5, UROC1, BBS12, DAO, GRXCR1, MED30,
PLAA, SLC35G6, UROD, BBS2, DAOA, GRXCR2, MED31, PLAC1, SLC36A1, UROS, BBS4, DAP,
GSAP, MED4, PLAC4, SLC36A2, USB1, BBS5, DAP3, GSC, MED6, PLAC8, SLC36A3, USE1, BBS7,
DAPK1, GSC2, MED7, PLAC8L1, SLC36A4, USF1, BBS9, DAPK2, GSDMA, MED8, PLAC9,
SLC37A1, USF2, BBX, DAPK3, GSDMB, MED9, PLAG1, SLC37A2, USH1C, BCAM, DAPL1,
GSDMC, MEDAG, PLAGL1, SLC37A3, USH1G, BCAN, DAPP1, GSDMD, MEF2A, PLAGL2,
SLC37A4, USH2A, BCAP29, DARS, GSE1, MEF2B, PLAT, SLC38A1, USHBP1, BCAP31, DARS2,
GSG1, MEF2BNB, PLAU, SLC38A10, USMG5, BCAR1, DAW1, GSG1L, MEF2BNB-MEF2B,
PLAUR, SLC38A11, USO1, BCAR3, DAXX, GSG2, MEF2C, PLB1, SLC38A2, USP1, BCAS1, DAZ1,
GSK3A, MEF2D, PLBD1, SLC38A3, USP10, BCAS2, DAZ2, GSK3B, MEFV, PLBD2, SLC38A4,
USP11, BCAS3, DAZ3, GSKIP, MEGF10, PLCB1, SLC38A5, USP12, BCAS4, DAZ4, GSN, MEGF11,
PLCB2, SLC38A6, USP13, BCAT1, DAZAP1, GSPT1, MEGF6, PLCB3, SLC38A7, USP14, BCAT2,
DAZAP2, GSPT2, MEGF8, PLCB4, SLC38A8, USP15, BCCIP, DAZL, GSR, MEGF9, PLCD1,
SLC38A9, USP16, BCDIN3D, DBF4, GSS, MEI1, PLCD3, SLC39A1, USP17L24, BCHE, DBF4B,
GSTA1, MEI4, PLCD4, SLC39A10, USP17L25, BCKDHA, DBH, GSTA2, MEIG1, PLCE1,
SLC39A11, USP17L26, BCKDHB, DBI, GSTA3, MEIOB, PLCG1, SLC39A12, USP17L28, BCKDK,
DBN1, GSTA4, MEIS1, PLCG2, SLC39A13, USP17L29, BCL10, DBNDD1, GSTA5, MEIS2, PLCH1,
SLC39A14, USP18, BCL11A, DBNDD2, GSTCD, MEIS3, PLCH2, SLC39A2, USP19, BCL11B,
DBNL, GSTK1, MELK, PLCL1, SLC39A3, USP2, BCL2, DBP, GSTM1, MEMO1, PLCL2, SLC39A4,
USP20, BCL2A1, DBR1, GSTM2, MEN1, PLCXD1, SLC39A5, USP21, BCL2L1, DBT, GSTM3,
MEOX1, PLCXD2, SLC39A6, USP22, BCL2L10, DBX1, GSTM4, MEOX2, PLCXD3, SLC39A7,
USP24, BCL2L11, DBX2, GSTM5, MEP1A, PLCZ1, SLC39A8, USP25, BCL2L12, DCAF10, GSTO1,
MEP1B, PLD1, SLC39A9, USP26, BCL2L13, DCAF11, GSTO2, MEPCE, PLD2, SLC3A1, USP27X,
BCL2L14, DCAF12, GSTP1, MEPE, PLD3, SLC3A2, USP28, BCL2L15, DCAF12L1, GSTT1,
MERTK, PLD4, SLC40A1, USP29, BCL2L2, DCAF12L2, GSTT2, MESDC1, PLD5, SLC41A1, USP3,
BCL2L2-PABPN1, DCAF13, GSTT2B, MESDC2, PLD6, SLC41A2, USP30, BCL3, DCAF15, GSTZ1,
MESP1, PLEC, SLC41A3, USP31, BCL6, DCAF16, GSX1, MESP2, PLEK, SLC43A1, USP32, BCL6B,
DCAF17, GSX2, MEST, PLEK2, SLC43A2, USP33, BCL7A, DCAF4, GTDC1, MET, PLEKHA1,
SLC43A3, USP34, BCL7B, DCAF4L1, GTF2A1, METAP1, PLEKHA2, SLC44A1, USP35, BCL7C,
DCAF4L2, GTF2A1L, METAP1D, PLEKHA3, SLC44A2, USP36, BCL9, DCAF5, GTF2A2, METAP2,
PLEKHA4, SLC44A3, USP37, BCL9L, DCAF6, GTF2B, METRN, PLEKHA5, SLC44A4, USP38,
BCLAF1, DCAF7, GTF2E1, METRNL, PLEKHA6, SLC44A5, USP39, BCMO1, DCAF8, GTF2E2,
METTL1, PLEKHA7, SLC45A1, USP4, BCO2, DCAF8L1, GTF2F1, METTL10, PLEKHA8, SLC45A2,
USP40, BCOR, DCAKD, GTF2F2, METTL11B, PLEKHB1, SLC45A3, USP41, BCORL1, DCBLD1,
GTF2H1, METTL12, PLEKHB2, SLC45A4, USP42, BCR, DCBLD2, GTF2H2, METTL13, PLEKHD1,
SLC46A1, USP43, BCS1L, DCC, GTF2H2C, METTL14, PLEKHF1, SLC46A2, USP44, BDH1, DCD,
GTF2H3, METTL15, PLEKHF2, SLC46A3, USP45, BDH2, DCDC1, GTF2H4, METTL16, PLEKHG1,
SLC47A1, USP46, BDKRB1, DCDC2, GTF2H5, METTL17, PLEKHG2, SLC47A2, USP47, BDKRB2,
DCDC2B, GTF2I, METTL18, PLEKHG3, SLC48A1, USP48, BDNF, DCDC2C, GTF2IRD1, METTL20,
PLEKHG4, SLC4A1, USP49, BDP1, DCDC5, GTF2IRD2, METTL21A, PLEKHG4B, SLC4A10, USP5,
BEAN1, DCHS1, GTF2IRD2B, METTL21B, PLEKHG5, SLC4A11, USP50, BECN1, DCHS2, GTF3A,
METTL21C, PLEKHG6, SLC4A1AP, USP51, BECN1P1, DCK, GTF3C1, METTL22, PLEKHG7,
SLC4A2, USP53, BEGAIN, DCLK1, GTF3C2, METTL23, PLEKHH1, SLC4A3, USP54, BEND2,
DCLK2, GTF3C3, METTL24, PLEKHH2, SLC4A4, USP6, BEND3, DCLK3, GTF3C4, METTL25,
PLEKHH3, SLC4A5, USP6NL, BEND4, DCLRE1A, GTF3C5, METTL2A, PLEKHJ1, SLC4A7, USP7,
BEND5, DCLRE1B, GTF3C6, METTL2B, PLEKHM1, SLC4A8, USP8, BEND6, DCLRE1C, GTPBP1,
METTL3, PLEKHM2, SLC4A9, USP9X, BEND7, DCN, GTPBP10, METTL4, PLEKHM3, SLC50A1,
USP9Y, BEST1, DCP1A, GTPBP2, METTL5, PLEKHN1, SLC51A, USPL1, BEST2, DCP1B, GTPBP3,
METTL6, PLEKHO1, SLC51B, UST, BEST3, DCP2, GTPBP4, METTL7A, PLEKHO2, SLC52A1,
UTF1, BEST4, DCPS, GTPBP6, METTL7B, PLEKHS1, SLC52A2, UTP11L, BET1, DCST1, GTPBP8,
METTL8, PLET1, SLC52A3, UTP14A, BET1L, DCST2, GTSCR1, METTL9, PLG, SLC5A1, UTP14C,
BEX1, DCSTAMP, GTSE1, MEX3A, PLGLB1, SLC5A10, UTP15, BEX2, DCT, GTSF1, MEX3B,
PLGLB2, SLC5A11, UTP18, BEX4, DCTD, GTSF1L, MEX3C, PLGRKT, SLC5A12, UTP20, BEX5,
DCTN1, GUCA1A, MEX3D, PLIN1, SLC5A2, UTP23, BFAR, DCTN2, GUCA1B, MFAP1, PLIN2,
SLC5A3, UTP3, BFSP1, DCTN3, GUCA1C, MFAP2, PLIN3, SLC5A4, UTP6, BFSP2, DCTN4,
GUCA2A, MFAP3, PLIN4, SLC5A5, UTRN, BGLAP, DCTN5, GUCA2B, MFAP3L, PLIN5, SLC5A6,
UTS2, BGN, DCTN6, GUCD1, MFAP4, PLK1, SLC5A7, UTS2B, BHLHA15, DCTPP1, GUCY1A2,
MFAP5, PLK1S1, SLC5A8, UTY, BHLHA9, DCUN1D1, GUCY1A3, MFF, PLK2, SLC5A9, UVRAG,
BHLHB9, DCUN1D2, GUCY1B3, MFGE8, PLK3, SLC6A1, UVSSA, BHLHE22, DCUN1D3,
GUCY2C, MFHAS1, PLK4, SLC6A11, UXS1, BHLHE23, DCUN1D4, GUCY2D, MFI2, PLK5,
SLC6A12, UXT, BHLHE40, DCUN1D5, GUCY2F, MFN1, PLLP, SLC6A13, VAC14, BHLHE41,
DCX, GUF1, MFN2, PLN, SLC6A14, VAMP1, BHMT, DCXR, GUK1, MFNG, PLOD1, SLC6A15,
VAMP2, BHMT2, DDA1, GULP1, MFRP, PLOD2, SLC6A16, VAMP3, BICC1, DDAH1, GUSB,
MFSD1, PLOD3, SLC6A17, VAMP4, BICD1, DDAH2, GXYLT1, MFSD10, PLP1, SLC6A18, VAMP5,
BICD2, DDB1, GXYLT2, MFSD11, PLP2, SLC6A19, VAMP7, BID, DDB2, GYG1, MFSD12, PLRG1,
SLC6A2, VAMP8, BIK, DDC, GYG2, MFSD2A, PLS1, SLC6A20, VANGL1, BIN1, DDHD1,
GYLTL1B, MFSD2B, PLS3, SLC6A3, VANGL2, BIN2, DDHD2, GYPA, MFSD3, PLSCR1, SLC6A4,
VAPA, BIN3, DDI1, GYPB, MFSD4, PLSCR2, SLC6A5, VAPB, BIRC2, DDI2, GYPC, MFSD5,
PLSCR3, SLC6A6, VARS, BIRC3, DDIT3, GYPE, MFSD6, PLSCR4, SLC6A7, VARS2, BIRC5,
DDIT4, GYS1, MFSD6L, PLSCR5, SLC6A8, VASH1, BIRC6, DDIT4L, GYS2, MFSD7, PLTP,
SLC6A9, VASH2, BIRC7, DDN, GZF1, MFSD8, PLVAP, SLC7A1, VASN, BIRC8, DDO, GZMA,
MFSD9, PLXDC1, SLC7A10, VASP, BIVM, DDOST, GZMB, MGA, PLXDC2, SLC7A11, VAT1, TABLE 1-continued List of examples of target genes (e.g., encoding a protein of interest)
List of target genes/proteins of interest BIVM-ERCC5, DDR1, GZMH, MGAM, PLXNA1, SLC7A13, VAT1L, BLCAP, DDR2, GZMK, MGARP, PLXNA2, SLC7A14, VAV1, BLID, DDRGK1, GZMM, MGAT1, PLXNA3, SLC7A2, VAV2, BLK, DDT, H1F0, MGAT2, PLXNA4, SLC7A3, VAV3, BLM, DDTL, H1FNT, MGAT3, PLXNB1, SLC7A4, VAX1, BLMH, DDX1, H1FOO, MGAT4A, PLXNB2, SLC7A5, VAX2, BLNK, DDX10, H1FX, MGAT4B, PLXNB3, SLC7A6, VBP1, BLOC1S1, DDX11, H2AFB1, MGAT4C, PLXNC1, SLC7A6OS, VCAM1, BLOC1S2, DDX17, H2AFB2, MGAT5, PLXND1, SLC7A7, VCAN, BLOC1S3, DDX18, H2AFB3, MGAT5B, PM20D1, SLC7A8, VCL, BLOC1S4, DDX19A, H2AFJ, MGEA5, PM20D2, SLC7A9, VCP, BLOC1S5, DDX19B, H2AFV, MGLL, PMAIP1, SLC8A1, VCPIP1, BLOC1S6, DDX20, H2AFX, MGME1, PMCH, SLC8A2, VCPKMT, BLVRA, DDX21, H2AFY, MGMT, PMEL, SLC8A3, VCX, BLVRB, DDX23, H2AFY2, MGP, PMEPA1, SLC8B1, VCX2, BLZF1, DDX24, H2AFZ, MGRN1, PMF1, SLC9A1, VCX3A, BMF, DDX25, H2BFM, MGST1, PMF1-BGLAP, SLC9A2, VCX3B, BMI1, DDX26B, H2BFWT, MGST2, PMFBP1, SLC9A3, VCY, BMP1, DDX27, H3F3A, MGST3, PML, SLC9A3R1, VCY1B, BMP10, DDX28, H3F3B, MIA, PMM1, SLC9A3R2, VDAC1, BMP15, DDX31, H3F3C, MIA2, PMM2, SLC9A4, VDAC2, BMP2, DDX39A, H6PD, MIA3, PMP2, SLC9A5, VDAC3, BMP2K, DDX39B, HAAO, MIB1, PMP22, SLC9A6, VDR, BMP3, DDX3X, HABP2, MIB2, PMPCA, SLC9A7, VEGFA, BMP4, DDX3Y, HABP4, MICA, PMPCB, SLC9A8, VEGFB, BMP5, DDX4, HACE1, MICAL1, PMS1, SLC9A9, VEGFC, BMP6, DDX41, HACL1, MICAL2, PMS2, SLC9B1, VENTX, BMP7, DDX42, HADH, MICAL3, PMVK, SLC9B2, VEPH1, BMP8A, DDX43, HADHA, MICALCL, PNCK, SLC9C1, VEZF1, BMP8B, DDX46, HADHB, MICALL1, PNISR, SLC9C2, VEZT, BMPER, DDX47, HAGH, MICALL2, PNKD, SLCO1A2, VGF, BMPR1A, DDX49, HAGHL, MICB, PNKP, SLCO1B1, VGLL1, BMPR1B, DDX5, HAL, MICU1, PNLDC1, SLCO1B3, VGLL2, BMPR2, DDX50, HAMP, MICU2, PNLIP, SLCO1B7, VGLL3, BMS1, DDX51, HAND1, MICU3, PNLIPRP1, SLCO1C1, VGLL4, BMX, DDX52, HAND2, MID1, PNLIPRP2, SLCO2A1, VHL, BNC1, DDX53, HAO1, MID1IP1, PNLIPRP3, SLCO2B1, VHLL, BNC2, DDX54, HAO2, MID2, PNMA2, SLCO3A1, VIL1, BNIP1, DDX55, HAP1, MIDN, PNMA3, SLCO4A1, VILL, BNIP2, DDX56, HAPLN1, MIEF1, PNMA5, SLCO4C1, VIM, BNIP3, DDX58, HAPLN2, MIEF2, PNMA6A, SLCO5A1, VIMP, BNIP3L, DDX59, HAPLN3, MIEN1, PNMA6C, SLCO6A1, VIP, BNIPL, DDX6, HAPLN4, MIER1, PNMAL1, SLFN11, VIPAS39, BOC, DDX60, HARBI1, MIER2, PNMAL2, SLFN12, VIPR1, BOD1, DDX60L, HARS, MIER3, PNMT, SLFN12L, VIPR2, BOD1L1, DEAF1, HARS2, MIF, PNN, SLFN13, VIT, BOD1L2, 1-Dec, HAS1, MIF4GD, PNO1, SLFN14, VKORC1, BOK, DECR1, HAS2, MIIP, PNOC, SLFN5, VKORC1L1, BOLA1, DECR2, HAS3, MILR1, PNP, SLFNL1, VLDLR, BOLA2, DEDD, HAT1, MINA, PNPLA1, SLIRP, VMA21, BOLA2B, DEDD2, HAUS1, MINK1, PNPLA2, SLIT1, VMAC, BOLA3, DEF6, HAUS2, MINOS1, PNPLA3, SLIT2, VMO1, BOLL, DEF8, HAUS3, MINOS1-NBL1, PNPLA4, SLIT3, VMP1, BOP1, DEFA1, HAUS4, MINPP1, PNPLA5, SLITRK1, VN1R1, BORA, DEFA1B, HAUS5, MIOS, PNPLA6, SLITRK2, VN1R2, BPGM, DEFA3, HAUS6, MIOX, PNPLA7, SLITRK3, VN1R4, BPHL, DEFA4, HAUS7, MIP, PNPLA8, SLITRK4, VN1R5, BPI, DEFA5, HAUS8, MIPEP, PNPO, SLITRK5, VNN1, BPIFA1, DEFA6, HAVCR1, MIPOL1, PNPT1, SLITRK6, VNN2, BPIFA2, DEFB1, HAVCR2, MIR205HG, PNRC1, SLK, VOPP1, BPIFA3, DEFB103A, HAX1, MIS12, PNRC2, SLMAP, VPRBP, BPIFB1, DEFB103B, HBA1, MIS18A, POC1A, SLMO1, VPREB1, BPIFB2, DEFB104A, HBA2, MIS18BP1, POC1B, SLMO2, VPREB3, BPIFB3, DEFB104B, HBB, MISP, POC1B-GALNT4, SLN, VPS11, BPIFB4, DEFB105A, HBD, MITD1, POC5, SLPI, VPS13A, BPIFB6, DEFB105B, HBE1, MITF, PODN, SLTM, VPS13B, BPIFC, DEFB106A, HBEGF, MIXL1, PODNL1, SLU7, VPS13C, BPNT1, DEFB106B, HBG1, MKI67, PODXL, SLURP1, VPS13D, BPTF, DEFB107A, HBG2, MKKS, PODXL2, SLX1A, VPS16, BPY2, DEFB107B, HBM, MKL1, POF1B, SLX1B, VPS18, BPY2B, DEFB108B, HBP1, MKL2, POFUT1, SLX4, VPS25, BPY2C, DEFB110, HBQ1, MKLN1, POFUT2, SLX4IP, VPS26A, BRAF, DEFB112, HBS1L, MKNK1, POGK, SMAD1, VPS26B, BRAP, DEFB113, HBZ, MKNK2, POGLUT1, SMAD2, VPS28, BRAT1, DEFB114, HCAR1, MKRN1, POGZ, SMAD3, VPS29, BRCA1, DEFB115, HCAR2, MKRN2, POLA1, SMAD4, VPS33A, BRCA2, DEFB116, HCAR3, MKRN3, POLA2, SMAD5, VPS33B, BRCC3, DEFB118, HCCS, MKS1, POLB, SMAD6, VPS35, BRD1, DEFB119, HCFC1, MKX, POLD1, SMAD7, VPS36, BRD2, DEFB121, HCFC1R1, MLANA, POLD2, SMAD9, VPS37A, BRD3, DEFB123, HCFC2, MLC1, POLD3, SMAGP, VPS37B, BRD4, DEFB124, HCK, MLEC, POLD4, SMAP1, VPS37C, BRD7, DEFB125, HCLS1, MLF1, POLDIP2, SMAP2, VPS37D, BRD8, DEFB126, HCN1, MLF2, POLDIP3, SMARCA1, VPS39, BRD9, DEFB127, HCN2, MLH1, POLE, SMARCA2, VPS41, BRDT, DEFB128, HCN3, MLH3, POLE2, SMARCA4, VPS45, BRE, DEFB129, HCN4, MLIP, POLE3, SMARCA5, VPS4A, BRF1, DEFB130, HCRT, MLKL, POLE4, SMARCAD1, VPS4B, BRF2, DEFB131, HCRTR1, MLLT1, POLG, SMARCAL1, VPS51, BRI3, DEFB132, HCRTR2, MLLT10, POLG2, SMARCB1, VPS52, BRI3BP, DEFB133, HCST, MLLT11, POLH, SMARCC1, VPS53, BRICD5, DEFB134, HDAC1, MLLT3, POLI, SMARCC2, VPS54, BRINP1, DEFB135, HDAC10, MLLT4, POLK, SMARCD1, VPS72, BRINP2, DEFB136, HDAC11, MLLT6, POLL, SMARCD2, VPS8, BRINP3, DEFB4A, HDAC2, MLN, POLM, SMARCD3, VPS9D1, BRIP1, DEFB4B, HDAC3, MLNR, POLN, SMARCE1, VRK1, BRIX1, DEGS1, HDAC4, MLPH, POLQ, SMC1A, VRK2, BRK1, DEGS2, HDAC5, MLST8, POLR1A, SMC1B, VRK3, BRMS1, DEK, HDAC6, MLX, POLR1B, SMC2, VRTN, BRMS1L, DENND1A, HDAC7, MLXIP, POLR1C, SMC3, VSIG1, BROX, DENND1B, HDAC8, MLXIPL, POLR1D, SMC4, VSIG10, BRPF1, DENND1C, HDAC9, MLYCD, POLR1E, SMC5, VSIG10L, BRPF3, DENND2A, HDC, MMAA, POLR2A, SMC6, VSIG2, BRS3, DENND2C, HDDC2, MMAB, POLR2B, SMCHD1, VSIG4, BRSK1, DENND2D, HDDC3, MMACHC, POLR2C, SMCO2, VSIG8, BRSK2, DENND3, HDGF, MMADHC, POLR2D, SMCO3, VSNL1, BRWD1, DENND4A, HDGFL1, MMD, POLR2E, SMCO4, VSTM1, BRWD3, DENND4B, HDGFRP2, MMD2, POLR2F, SMCP, VSTM2A, BSCL2, DENND4C, HDGFRP3, MME, POLR2G, SMCR8, VSTM2B, BSDC1, DENND5A, HDHD1, MMEL1, POLR2H, SMCR9, VSTM2L, BSG, DENND5B, HDHD2, MMGT1, POLR2I, SMDT1, VSTM4, BSN, DENND6A, HDHD3, MMP1, POLR2J, SMEK1, VSTM5, BSND, DENND6B, HDLBP, MMP10, POLR2J2, SMEK2, VSX1, BSPH1, DENR, HDX, MMP11, POLR2J3, SMG1, VSX2, BSPRY, DEPDC1, HEATR1, MMP12, POLR2K, SMG5, VTA1, BST1, DEPDC1B, HEATR2, MMP13, POLR2L, SMG6, VTCN1, BST2, DEPDC4, HEATR3, MMP14, POLR2M, SMG7, VTI1A, BSX, DEPDC5, HEATR4, MMP15, POLR3A, SMG8, VTI1B, BTAF1, DEPDC7, HEATR5A, MMP16, POLR3B, SMG9, VTN, BTBD1, DEPTOR, TABLE 1-continued List of examples of target genes (e.g., encoding a protein of interest)
List of target genes/proteins of interest HEATR5B, MMP17, POLR3C, SMIM1, VWA1, BTBD10, DERA, HEATR6, MMP19, POLR3D,
SMIM10, VWA2, BTBD11, DERL1, HEBP1, MMP2, POLR3E, SMIM11, VWA3A, BTBD16, DERL2,
HEBP2, MMP20, POLR3F, SMIM12, VWA3B, BTBD17, DERL3, HECA, MMP21, POLR3G,
SMIM13, VWA5A, BTBD18, DES, HECTD1, MMP23B, POLR3GL, SMIM14, VWA5B1, BTBD19,
DESI1, HECTD2, MMP24, POLR3H, SMIM15, VWA5B2, BTBD2, DESI2, HECTD3, MMP25,
POLR3K, SMIM17, VWA7, BTBD3, DET1, HECTD4, MMP26, POLRMT, SMIM18, VWA8, BTBD6,
DEXI, HECW1, MMP27, POM121, SMIM19, VWA9, BTBD7, DFFA, HECW2, MMP28, POM121C,
SMIM2, VWC2, BTBD8, DFFB, HEG1, MMP3, POM121L12, SMIM20, VWC2L, BTBD9, DFNA5,
HELB, MMP7, POM121L2, SMIM21, VWCE, BTC, DFNB31, HELLS, MMP8, POMC, SMIM22,
VWDE, BTD, DFNB59, HELQ, MMP9, POMGNT1, SMIM3, VWF, BTF3, DGAT1, HELT, MMRN1,
POMGNT2, SMIM4, WAC, BTF3L4, DGAT2, HELZ, MMRN2, POMK, SMIM5, WAPAL, BTG1,
DGAT2L6, HELZ2, MMS19, POMP, SMIM6, WARS, BTG2, DGCR14, HEMGN, MMS22L, POMT1,
SMIM7, WARS2, BTG3, DGCR2, HEMK1, MN1, POMT2, SMIM8, WAS, BTG4, DGCR6, HENMT1,
MNAT1, POMZP3, SMIM9, WASF1, BTK, DGCR6L, HEPACAM, MND1, PON1, SMKR1, WASF2,
BTLA, DGCR8, HEPACAM2, MNDA, PON2, SMLR1, WASF3, BTN1A1, DGKA, HEPH, MNS1,
PON3, SMN1, WASH1, BTN2A1, DGKB, HEPHL1, MNT, POP1, SMN2, WASL, BTN2A2, DGKD,
HEPN1, MNX1, POP4, SMNDC1, WBP1, BTN3A1, DGKE, HERC1, MOAP1, POP5, SMO, WBP11,
BTN3A2, DGKG, HERC2, MOB1A, POP7, SMOC1, WBP1L, BTN3A3, DGKH, HERC3, MOB1B,
POPDC2, SMOC2, WBP2, BTNL10, DGKI, HERC4, MOB2, POPDC3, SMOX, WBP2NL, BTNL2,
DGKK, HERC5, MOB3A, POR, SMPD1, WBP4, BTNL3, DGKQ, HERC6, MOB3B, PORCN, SMPD2,
WBP5, BTNL8, DGKZ, HERPUD1, MOB3C, POSTN, SMPD3, WBSCR16, BTNL9, DGUOK,
HERPUD2, MOB4, POT1, SMPD4, WBSCR17, BTRC, DHCR24, HES1, MOBP, POTEA, SMPD5,
WBSCR22, BUB1, DHCR7, HES2, MOCOS, POTEB, SMPDL3A, WBSCR27, BUB1B, DHDDS,
HES3, MOCS1, POTEB2, SMPDL3B, WBSCR28, BUB3, DHDH, HES4, MOCS2, POTEC, SMPX,
WDFY1, BUD13, DHFR, HES5, MOCS3, POTED, SMR3A, WDFY2, BUD31, DHFRL1, HES6, MOG,
POTEE, SMR3B, WDFY3, BVES, DHH, HES7, MOGAT1, POTEF, SMS, WDFY4, BYSL, DHODH,
HESX1, MOGAT2, POTEG, SMTN, WDHD1, BZRAP1, DHPS, HEXA, MOGAT3, POTEH, SMTNL1,
WDPCP, BZW1, DHRS1, HEXB, MOGS, POTEI, SMTNL2, WDR1, BZW2, DHRS11, HEXDC, MOK,
POTEJ, SMU1, WDR11, C10orf10, DHRS12, HEXIM1, MON1A, POTEM, SMUG1, WDR12,
C10orf105, DHRS13, HEXIM2, MON1B, POU1F1, SMURF1, WDR13, C10orf107, DHRS2, HEY1,
MON2, POU2AF1, SMURF2, WDR16, C10orf11, DHRS3, HEY2, MORC1, POU2F1, SMYD1,
WDR17, C10orf111, DHRS4, HEYL, MORC2, POU2F2, SMYD2, WDR18, C10orf112, DHRS4L1,
HFE, MORC3, POU2F3, SMYD3, WDR19, C10orf113, DHRS4L2, HFE2, MORC4, POU3F1, SMYD4,
WDR20, C10orf118, DHRS7, HFM1, MORF4L1, POU3F2, SMYD5, WDR24, C10orf12, DHRS7B,
HGC6.3, MORF4L2, POU3F3, SNAI1, WDR25, C10orf120, DHRS7C, HGD, MORN1, POU3F4,
SNAI2, WDR26, C10orf126, DHRS9, HGF, MORN2, POU4F1, SNAI3, WDR27, C10orf128, DHRSX,
HGFAC, MORN3, POU4F2, SNAP23, WDR3, C10orf129, DHTKD1, HGS, MORN4, POU4F3,
SNAP25, WDR31, C10orf131, DHX15, HGSNAT, MORN5, POU5F1, SNAP29, WDR33, C10orf137,
DHX16, HHAT, MOS, POU5F1B, SNAP47, WDR34, C10orf2, DHX29, HHATL, MOSPD1, POU5F2,
SNAP91, WDR35, C10orf25, DHX30, HHEX, MOSPD2, POU6F1, SNAPC1, WDR36, C10orf32,
DHX32, HHIP, MOSPD3, POU6F2, SNAPC2, WDR37, C10orf35, DHX33, HHIPL1, MOV10, PP2D1,
SNAPC3, WDR38, C10orf53, DHX34, HHIPL2, MOV10L1, PPA1, SNAPC4, WDR4, C10orf54,
DHX35, HHLA1, MOXD1, PPA2, SNAPC5, WDR41, C10orf55, HHLA2, MPC1, PPAN,
SNAPIN, WDR43, C10orf62, DHX37, HHLA3, MPC1L, PPAN-P2RY11, SNCA, WDR44, C10orf67,
DHX38, HIAT1, MPC2, PPAP2A, SNCAIP, WDR45, C10orf68, DHX40, HIATL1, MPDU1, PPAP2B,
SNCB, WDR45B, C10orf71, DHX57, HIBADH, MPDZ, PPAP2C, SNCG, WDR46, C10orf76, DHX58,
HIBCH, MPEG1, PPAPDC1A, SND1, WDR47, C10orf82, DHX8, HIC1, MPG, PPAPDC1B, SNED1,
WDR48, C10orf88, DHX9, HIC2, MPHOSPH10, PPAPDC2, SNF8, WDR49, C10orf90, DIABLO,
HID1, MPHOSPH6, PPAPDC3, SNIP1, WDR5, C10orf91, DIAPH1, HIF1A, MPHOSPH8, PPARA,
SNN, WDR52, C10orf95, DIAPH2, HIF1AN, MPHOSPH9, PPARD, SNPH, WDR53, C10orf99,
DIAPH3, HIF3A, MPI, PPARG, SNRK, WDR54, C11orf1, DICER1, HIGD1A, MPL, PPARGC1A,
SNRNP200, WDR55, C11orf16, DIDO1, HIGD1B, MPLKIP, PPARGC1B, SNRNP25, WDR59,
C11orf21, DIEXF, HIGDIC, MPND, PPAT, SNRNP27, WDR5B, C11orf24, DIMT1, HIGD2A, MPO,
PPBP, SNRNP35, WDR6, C11orf30, DIO1, HILPDA, MPP1, PPCDC, SNRNP40, WDR60, C11orf31,
DIO2, HINFP, MPP2, PPCS, SNRNP48, WDR61, C11orf35, DIO3, HINT1, MPP3, PPDPF, SNRNP70,
WDR62, C11orf40, DIP2A, HINT2, MPP4, PPEF1, SNRPA, WDR63, C11orf42, DIP2B, HINT3, MPP5,
PPEF2, SNRPA1, WDR64, C11orf44, DIP2C, HIP1, MPP6, PPFIA1, SNRPB, WDR65, C11orf45,
DIRAS1, HIP1R, MPP7, PPFIA2, SNRPB2, WDR66, C11orf48, DIRAS2, HIPK1, MPPE1, PPFIA3,
SNRPC, WDR7, C11orf49, DIRAS3, HIPK2, MPPED1, PPFIA4, SNRPD1, WDR70, C11orf52, DIRC1,
HIPK3, MPPED2, PPFIBP1, SNRPD2, WDR72, C11orf53, DIRC2, HIPK4, MPRIP, PPFIBP2,
SNRPD3, WDR73, C11orf54, DIS3, HIRA, MPST, PPHLN1, SNRPE, WDR74, C11orf57, DIS3L,
HIRIP3, MPV17, PPIA, SNRPF, WDR75, C11orf58, DIS3L2, HIST1H1A, MPV17L, PPIAL4A,
SNRPG, WDR76, C11orf63, DISC1, HIST1H1B, MPV17L2, PPIAL4B, SNRPN, WDR77, C11orf65,
DISP1, HIST1H1C, MPZ, PPIAL4C, SNTA1, WDR78, C11orf68, DISP2, HIST1H1D, MPZL1,
PPIAL4D, SNTB1, WDR81, C11orf70, DIXDC1, HIST1H1E, MPZL2, PPIAL4E, SNTB2, WDR82,
C11orf71, DKC1, HIST1H1T, MPZL3, PPIAL4F, SNTG1, WDR83, C11orf73, DKK1, HIST1H2AA,
MR1, PPIAL4G, SNTG2, WDR83OS, C11orf74, DKK2, HIST1H2AB, MRAP, PPIB, SNTN, WDR86,
C11orf80, DKK3, HIST1H2AC, MRAP2, PPIC, SNUPN, WDR87, C11orf82, DKK4, HIST1H2AD,
MRAS, PPID, SNURF, WDR88, C11orf83, DKKL1, HIST1H2AE, MRC2, PPIE, SNW1, WDR89,
C11orf84, DLAT, HIST1H2AG, MRE11A, PPIF, SNX1, WDR90, C11orf85, DLC1, HIST1H2AH,
MREG, PPIG, SNX10, WDR91, C11orf86, DLD, HIST1H2AI, MRFAP1, PPIH, SNX11, WDR92,
C11orf87, DLEC1, HIST1H2AJ, MRFAP1L1, PPIL1, SNX12, WDR93, C11orf88, DLEU7,
HIST1H2AK, MRGBP, PPIL2, SNX13, WDR96, C11orf91, DLG1, HIST1H2AL, MRGPRD, PPIL3,
SNX14, WDSUB1, C11orf94, DLG2, HIST1H2AM, MRGPRE, PPIL4, SNX15, WDTC1, C11orf95,
DLG3, HIST1H2BA, MRGPRF, PPIL6, SNX16, WDYHV1, C11orf96, DLG4, HIST1H2BB, MRGPRG,
PPIP5K1, SNX17, WEE1, C12orf10, DLG5, HIST1H2BC, MRGPRX1, PPIP5K2, SNX18, WEE2,
C12orf23, DLGAP1, HIST1H2BD, MRGPRX2, PPL, SNX19, WFDC1, C12orf29, DLGAP2,

TABLE 1-continued

List of examples of target genes (e.g., encoding a protein of interest)
List of target genes/proteins of interest HIST1H2BE, MRGPRX3, PPM1A, SNX2, WFDC10A, C12orf39, DLGAP4, HIST1H2BF, MRGPRX4, PPM1B, SNX20, WFDC10B, C12orf4, DLGAP5, HIST1H2BG, MRI1, PPM1D, SNX21, WFDC11, C12orf40, DLK1, HIST1H2BH, MRM1, PPM1E, SNX22, WFDC12, C12orf42, DLK2, HIST1H2BI, MRO, PPM1F, SNX24, WFDC13, C12orf43, DLL1, HIST1H2BJ, MROH1, PPM1G, SNX25, WFDC2, C12orf44, DLL3, HIST1H2BK, MROH2A, PPM1H, SNX27, WFDC3, C12orf45, DLL4, HIST1H2BL, MROH2B, PPM1J, SNX29, WFDC5, C12orf49, DLST, HIST1H2BM, MROH5, PPM1K, SNX3, WFDC6, C12orf5, DLX1, HIST1H2BN, MROH6, PPM1L, SNX30, WFDC8, C12orf50, DLX2, HIST1H2BO, MROH7, PPM1M, SNX31, WFDC9, C12orf52, DLX3, HIST1H3A, MROH8, PPM1N, SNX32, WFIKKN1, C12orf54, DLX4, HIST1H3B, MROH9, PPME1, SNX33, WFIKKN2, C12orf55, DLX5, HIST1H3C, MRP63, PPOX, SNX4, WFS1, C12orf56, DLX6, HIST1H3D, MRPL1, PPP1CA, SNX5, WHAMM, C12orf57, DMAP1, HIST1H3E, MRPL10, PPP1CB, SNX6, WHSC1, C12orf60, DMBT1, HIST1H3F, MRPL11, PPP1CC, SNX7, WHSC1L1, C12orf61, DMBX1, HIST1H3G, MRPL12, PPP1R10, SNX8, WIBG, C12orf65, DMC1, HIST1H3H, MRPL13, PPP1R11, SNX9, WIF1, C12orf66, DMD, HIST1H3I, MRPL14, PPP1R12A, SOAT1, WIPF1, C12orf68, DMGDH, HIST1H3J, MRPL15, PPP1R12B, SOAT2, WIPF2, C12orf71, DMKN, HIST1H4A, MRPL16, PPP1R12C, SOBP, WIPF3, C12orf73, DMP1, HIST1H4B, MRPL17, PPP1R13B, SOCS1, WIPI1, C12orf74, DMPK, HIST1H4C, MRPL18, PPP1R13L, SOCS2, WIPI2, C12orf75, DMRT1, HIST1H4D, MRPL19, PPP1R14A, SOCS3, WISP1, C12orf76, DMRT2, HIST1H4E, MRPL2, PPP1R14B, SOCS4, WISP2, C12orf77, DMRT3, HIST1H4F, MRPL20, PPP1R14C, SOCS5, WISP3, C12orf79, DMRTA1, HIST1H4G, MRPL21, PPP1R14D, SOCS6, WIZ, C12orf80, DMRTA2, HIST1H4H, MRPL22, PPP1R15A, SOCS7, WLS, C13orf35, DMRTB1, HIST1H4I, MRPL23, PPP1R15B, SOD1, WNK1, C13orf45, DMRTC1, HIST1H4J, MRPL24, PPP1R16A, SOD2, WNK2, C14orf1, DMRTC1B, HIST1H4K, MRPL27, PPP1R16B, SOD3, WNK3, C14orf105, DMRTC2, HIST1H4L, MRPL28, PPP1R17, SOGA1, WNK4, C14orf119, DMTF1, HIST2H2AA3, MRPL3, PPP1R18, SOGA2, WNT1, C14orf132, DMTN, HIST2H2AA4, MRPL30, PPP1R1A, SOGA3, WNT10A, C14orf142, DMWD, HIST2H2AB, MRPL32, PPP1R1B, SOHLH1, WNT10B, C14orf159, DMXL1, HIST2H2AC, MRPL33, PPP1R1C, SOHLH2, WNT11, C14orf164, DMXL2, HIST2H2BE, MRPL34, PPP1R2, SON, WNT16, C14orf166, DNA2, HIST2H2BF, MRPL35, PPP1R21, SORBS1, WNT2, C14orf166B, DNAAF1, HIST2H3A, MRPL36, PPP1R26, SORBS2, WNT2B, C14orf169, DNAAF2, HIST2H3C, MRPL37, PPP1R27, SORBS3, WNT3, C14orf177, DNAAF3, HIST2H3D, MRPL38, PPP1R32, SORCS1, WNT3A, C14orf178, DNAH1, HIST2H4A, MRPL39, PPP1R35, SORCS2, WNT4, C14orf180, DNAH10, HIST2H4B, MRPL4, PPP1R36, SORCS3, WNT5A, C14orf182, DNAH11, HIST3H2A, MRPL40, PPP1R37, SORD, WNT5B, C14orf183, DNAH12, HIST3H2BB, MRPL41, PPP1R3A, SORL1, WNT6, C14orf2, DNAH14, HIST3H3, MRPL42, PPP1R3B, SORT1, WNT7A, C14orf28, DNAH17, HIST4H4, MRPL43, PPP1R3C, SOS1, WNT7B, C14orf37, DNAH2, HIVEP1, MRPL44, PPP1R3D, SOS2, WNT8A, C14orf39, DNAH3, HIVEP2, MRPL45, PPP1R3E, SOST, WNT8B, C14orf79, DNAH5, HIVEP3, MRPL46, PPP1R3F, SOSTDC1, WNT9A, C14orf80, DNAH6, HJURP, MRPL47, PPP1R3G, SOWAHA, WNT9B, C14orf93, DNAH7, HK1, MRPL48, PPP1R42, SOWAHB, WRAP53, C15orf26, DNAH8, HK2, MRPL49, PPP1R7, SOWAHC, WRAP73, C15orf27, DNAH9, HK3, MRPL50, PPP1R8, SOWAHD, WRB, C15orf32, DNAI1, HKDC1, MRPL51, PPP1R9A, SOX1, WRN, C15orf38, DNAI2, HKR1, MRPL52, PPP1R9B, SOX10, WRNIP1, C15orf38-AP3S2, DNAJA1, HLA-A, MRPL53, PPP2CA, SOX11, WSB1, C15orf39, DNAJA2, HLA-B, MRPL54, PPP2CB, SOX12, WSB2, C15orf40, DNAJA3, HLA-C, MRPL55, PPP2R1A, SOX13, WSCD1, C15orf41, DNAJA4, HLA-DMA, MRPL9, PPP2R1B, SOX14, WSCD2, C15orf43, DNAJB1, HLA-DMB, MRPS10, PPP2R2A, SOX15, WT1, C15orf48, DNAJB11, HLA-DOA, MRPS11, PPP2R2B, SOX17, WTAP, C15orf52, DNAJB12, HLA-DOB, MRPS12, PPP2R2C, SOX18, WTH3DI, C15orf53, DNAJB13, HLA-DPA1, MRPS14, PPP2R2D, SOX2, WTIP, C15orf54, DNAJB14, HLA-DPB1, MRPS15, PPP2R3A, SOX21, WWC1, C15orf56, DNAJB2, HLA- DQA1, MRPS16, PPP2R3B, SOX3, WWC2, C15orf57, DNAJB3, HLA-DQA2, MRPS17, PPP2R3C, SOX30, WWC3, C15orf59, DNAJB4, HLA-DQB1, MRPS18A, PPP2R4, SOX4, WWOX, C15orf60, DNAJB5, HLA-DQB2, MRPS18B, PPP2R5A, SOX5, WWP1, C15orf61, DNAJB6, HLA-DRA, MRPS18C, PPP2R5B, SOX6, WWP2, C15orf62, DNAJB7, HLA-DRB1, MRPS2, PPP2R5C, SOX7, WWTR1, C15orf65, DNAJB8, HLA- DRB5, MRPS21, PPP2R5D, SOX8, XAB2, C16orf11, DNAJB9, HLA-E, MRPS22, PPP2R5E, SOX9, XAF1, C16orf13, DNAJC1, HLA-F, MRPS23, PPP3CA, SP1, XAGE1D, C16orf3, DNAJC10, HLA-G, MRPS24, PPP3CB, SP100, XAGE2, C16orf45, DNAJC11, HLCS, MRPS25, PPP3CC, SP110, XAGE3, C16orf46, DNAJC12, HLF, MRPS26, PPP3R1, SP140, XAGE5, C16orf47, DNAJC13, HLTF, MRPS27, PPP3R2, SP140L, XBP1, C16orf52, DNAJC14, HLX, MRPS28, PPP4C, SP2, XCL1, C16orf54, DNAJC15, HM13, MRPS30, PPP4R1, SP3, XCL2, C16orf58, DNAJC16, HMBOX1, MRPS31, PPP4R2, SP4, XCR1, C16orf59, DNAJC17, HMBS, MRPS33, PPP4R4, SP5, XDH, C16orf62, DNAJC18, HMCES, MRPS34, PPP5C, SP6, XG, C16orf70, DNAJC19, HMCN1, MRPS35, PPP5D1, SP7, XIAP, C16orf71, DNAJC2, HMCN2, MRPS36, PPP6C, SP8, XIRP1, C16orf72, DNAJC21, HMG20A, MRPS5, PPP6R1, SP9, XIRP2, C16orf74, DNAJC22, HMG20B, MRPS6, PPP6R2, SPA17, XK, C16orf78, DNAJC24, HMGA1, MRPS7, PPP6R3, SPACA1, XKR3, C16orf80, DNAJC25, HMGA2, MRPS9, PPRC1, SPACA3, XKR4, C16orf82, DNAJC25-GNG10, HMGB1, MRRF, PPT1, SPACA4, XKR5, C16orf86, DNAJC27, HMGB2, MRS2, PPT2, SPACA5, XKR6, C16orf87, DNAJC28, HMGB3, MRTO4, PPTC7, SPACA5B, XKR7, C16orf89, DNAJC3, HMGB4, MRVI1, PPWD1, SPACA7, XKR8, C16orf90, DNAJC30, HMGCL, MS4A1, PPY, SPAG1, XKR9, C16orf91, DNAJC4, HMGCLL1, MS4A10, PQBP1, SPAG11A, XKRX, C16orf92, DNAJC5, HMGCR, MS4A12, PQLC1, SPAG11B, XKRY, C16orf93, DNAJC5B, HMGCS1, MS4A13, PQLC2, SPAG16, XKRY2, C16orf95, DNAJC5G, HMGCS2, MS4A14, PQLC3, SPAG17, XPA, C16orf96, DNAJC6, HMGN1, MS4A15, PRAC1, SPAG4, XPC, C16orf97, DNAJC7, HMGN2, MS4A2, PRAC2, SPAG5, XPNPEP1, C17orf100, DNAJC8, HMGN3, MS4A3, PRADC1, SPAG6, XPNPEP2, C17orf102, DNAJC9, HMGN4, MS4A4A, PRAF2, SPAG7, XPNPEP3, C17orf103, DNAL1, HMGN5, MS4A4E, PRAM1, SPAG8, XPO1, C17orf104, DNAL4, HMGXB3, MS4A5, PRAME, SPAG9, XPO4, C17orf105, DNALI1, HMGXB4, MS4A6A, PRAMEF1, SPAM1, XPO5, C17orf107, DNASE1, HMHA1, MS4A6E, PRAMEF10, SPANXA1, XPO6, C17orf112, DNASE1L1, HMHB1, MS4A7, PRAMEF11, SPANXA2, XPO7, C17orf47, DNASE1L2, HMMR, MS4A8, PRAMEF12, SPANXB1, XPOT, C17orf49, DNASE1L3, HMOX1, MSANTD1, PRAMEF13, SPANXB2, XPR1, C17orf50, DNASE2, HMOX2,

TABLE 1-continued

List of examples of target genes (e.g., encoding a protein of interest)
List of target genes/proteins of interest MSANTD2, PRAMEF14, SPANXC, XRCC1, C17orf51, DNASE2B, HMP19, MSANTD3, PRAMEF15, SPANXD, XRCC2, C17orf53, DND1, HMSD, MSANTD3-TMEFF1, PRAMEF16, SPANXN1, XRCC3, C17orf58, DNER, HMX1, MSANTD4, PRAMEF17, SPANXN2, XRCC4, C17orf59, DNHD1, HMX2, MSC, PRAMEF18, SPANXN3, XRCC5, C17orf62, DNLZ, HMX3, MSGN1, PRAMEF19, SPANXN4, XRCC6, C17orf64, DNM1, HN1, MSH2, PRAMEF2, SPANXN5, XRCC6BP1, C17orf66, DNM1L, HN1L, MSH3, PRAMEF20, SPARC, XRN1, C17orf67, DNM2, HNF1A, MSH4, PRAMEF21, SPARCL1, XRN2, C17orf70, DNM3, HNF1B, MSH5, PRAMEF22, SPAST, XRRA1, C17orf72, DNMBP, HNF4A, MSH6, PRAMEF23, SPATA1, XXYLT1, C17orf74, DNMT1, HNF4G, MSI1, PRAMEF25, SPATA12, XYLB, C17orf75, DNMT3A, HNMT, MSI2, PRAMEF3, SPATA13, XYLT1, C17orf77, DNMT3B, HNRNPA0, MSL1, PRAMEF4, SPATA16, XYLT2, C17orf78, DNMT3L, HNRNPA1, MSL2, PRAMEF5, SPATA17, YAE1D1, C17orf80, DNPEP, HNRNPA1L2, MSL3, PRAMEF6, SPATA18, YAF2, C17orf82, DNPH1, HNRNPA2B1, MSLN, PRAMEF7, SPATA19, YAP1, C17orf85, DNTT, HNRNPA3, MSMB, PRAMEF8, SPATA2, YARS, C17orf89, DNTTIP1, HNRNPAB, MSMO1, PRAMEF9, SPATA20, YARS2, C17orf96, DNTTIP2, HNRNPC, MSMP, PRAP1, SPATA21, YBEY, C17orf97, DOC2A, HNRNPCL1, MSN, PRB1, SPATA22, YBX1, C17orf98, DOC2B, HNRNPCP5, MSR1, PRB2, SPATA24, YBX2, C17orf99, DOCK1, HNRNPD, MSRA, PRB3, SPATA25, YBX3, C18orf21, DOCK10, HNRNPDL, MSRB1, PRB4, SPATA2L, YDJC, C18orf25, DOCK11, HNRNPF, MSRB2, PRC1, SPATA3, YEATS2, C18orf32, DOCK2, HNRNPH1, MSRB3, PRCC, SPATA31A1, YEATS4, C18orf42, DOCK3, HNRNPH2, MSS51, PRCD, SPATA31A2, YES1, C18orf54, DOCK4, HNRNPH3, MST1, PRCP, SPATA31A3, YIF1A, C18orf56, DOCK5, HNRNPK, MST1L, PRDM1, SPATA31A4, YIF1B, C18orf63, DOCK6, HNRNPL, MST1R, PRDM10, SPATA31A5, YIPF1, C18orf8, DOCK7, HNRNPLL, MST4, PRDM11, SPATA31A6, YIPF2, C19orf10, DOCK8, HNRNPM, MSTN, PRDM12, SPATA31A7, YIPF3, C19orf12, DOCK9, HNRNPR, MSTO1, PRDM13, SPATA31C1, YIPF4, C19orf18, DOHH, HNRNPU, MSX1, PRDM14, SPATA31C2, YIPF5, C19orf24, DOK1, HNRNPUL1, MSX2, PRDM15, SPATA31D1, YIPF6, C19orf25, DOK2, HNRNPUL2, MT1A, PRDM16, SPATA31D3, YIPF7, C19orf26, DOK3, HOGA1, MT1B, PRDM2, SPATA31D4, YJEFN3, C19orf33, DOK4, HOMER1, MT1E, PRDM4, SPATA31E1, YKT6, C19orf35, DOK5, HOMER2, MT1F, PRDM5, SPATA32, YLPM1, C19orf38, DOK6, HOMER3, MT1G, PRDM6, SPATA33, YME1L1, C19orf40, DOK7, HOMEZ, MT1H, PRDM7, SPATA4, YOD1, C19orf43, DOLK, HOOK1, MT1HL1, PRDM8, SPATA5, YPEL1, C19orf44, DOLPP1, HOOK2, MT1M, PRDM9, SPATA5L1, YPEL2, C19orf45, DONSON, HOOK3, MT1X, PRDX1, SPATA6, YPEL3, C19orf47, DOPEY1, HOPX, MT2A, PRDX2, SPATA6L, YPEL4, C19orf48, DOPEY2, HORMAD1, MT3, PRDX3, SPATA7, YPEL5, C19orf52, DOT1L, HORMAD2, MT4, PRDX4, SPATA8, YRDC, C19orf53, DPAGT1, HOXA1, MTA1, PRDX5, SPATA9, YTHDC1, C19orf54, DPCD, HOXA10, MTA2, PRDX6, SPATC1, YTHDC2, C19orf55, DPCR1, HOXA11, MTA3, PREB, SPATC1L, YTHDF1, C19orf57, DPEP1, HOXA13, MTAP, PRELID1, SPATS1, YTHDF2, C19orf59, DPEP2, HOXA2, MTBP, PRELID2, SPATS2, YTHDF3, C19orf60, DPEP3, HOXA3, MTCH1, PRELP, SPATS2L, YWHAB, C19orf66, DPF1, HOXA4, MTCH2, PREP, SPC24, YWHAE, C19orf67, DPF2, HOXA5, MTCP1, PREPL, SPC25, YWHAG, C19orf68, DPF3, HOXA6, MTDH, PREX1, SPCS1, YWHAH, C19orf69, DPH1, HOXA7, MTERF, PREX2, SPCS2, YWHAQ, C19orf70, DPH2, HOXA9, MTERFD1, PRF1, SPCS3, YWHAZ, C19orf71, DPH3, HOXB1, MTERFD2, PRG2, SPDEF, YY1, C19orf73, DPH3P1, HOXB13, MTERFD3, PRG3, SPDL1, YY1AP1, C19orf77, DPH5, HOXB2, MTF1, PRG4, SPDYA, YY2, C19orf80, DPH6, HOXB3, MTF2, PRH1, SPDYC, ZACN, C19orf81, DPH7, HOXB4, MTFMT, PRH2, SPDYE1, ZADH2, C19orf82, DPM1, HOXB5, MTFP1, PRICKLE1, SPDYE2, ZAK, C1D, DPM2, HOXB6, MTFR1, PRICKLE2, SPDYE2B, ZAN, C1GALT1, DPM3, HOXB7, MTFR1L, PRICKLE3, SPDYE3, ZAP70, C1GALT1C1, DPP10, HOXB8, MTFR2, PRICKLE4, SPDYE4, ZAR1, C1orf100, DPP3, HOXB9, MTG1, PRIM1, SPDYE5, ZAR1L, C1orf101, DPP4, HOXC10, MTG2, PRIM2, SPDYE6, ZBBX, C1orf105, DPP6, HOXC11, MTHFD1, PRIMA1, SPECC1, ZBED1, C1orf106, DPP7, HOXC12, MTHFD1L, PRIMPOL, SPECC1L, ZBED2, C1orf109, DPP8, HOXC13, MTHFD2, PRKAA1, SPEF1, ZBED3, C1orf110, DPP9, HOXC4, MTHFD2L, PRKAA2, SPEF2, ZBED4, C1orf111, DPPA2, HOXC5, MTHFR, PRKAB1, SPEG, ZBED5, C1orf112, DPPA3, HOXC6, MTHFS, PRKAB2, SPEMI, ZBED6, C1orf115, DPPA4, HOXC8, MTHFSD, PRKACA, SPEN, ZBED6CL, C1orf116, DPPA5, HOXC9, MTIF2, PRKACB, SPERT, ZBP1, C1orf122, DPRX, HOXD1, MTIF3, PRKACG, SPESP1, ZBTB1, C1orf123, DPT, HOXD10, MTL5, PRKAG1, SPG11, ZBTB10, C1orf127, DPY19L1, HOXD11, MTM1, PRKAG2, SPG20, ZBTB11, C1orf131, DPY19L2, HOXD12, MTMR1, PRKAG3, SPG21, ZBTB12, C1orf137, DPY19L3, HOXD13, MTMR10, PRKAR1A, SPG7, ZBTB14, C1orf141, DPY19L4, HOXD3, MTMR11, PRKAR1B, SPHAR, ZBTB16, C1orf146, DPY30, HOXD4, MTMR12, PRKAR2A, SPHK1, ZBTB17, C1orf158, DPYD, HOXD8, MTMR14, PRKAR2B, SPHK2, ZBTB18, C1orf159, DPYS, HOXD9, MTMR2, PRKCA, SPHKAP, ZBTB2, C1orf162, DPYSL2, HP, MTMR3, PRKCB, SPI1, ZBTB20, C1orf167, DPYSL3, HP1BP3, MTMR4, PRKCD, SPIB, ZBTB21, C1orf168, DPYSL4, HPCA, MTMR6, PRKCDBP, SPIC, ZBTB22, C1orf172, DPYSL5, HPCAL1, MTMR7, PRKCE, SPICE1, ZBTB24, C1orf173, DQX1, HPCAL4, MTMR8, PRKCG, SPIDR, ZBTB25, C1orf174, DR1, HPD, MTMR9, PRKCH, SPIN1, ZBTB26, C1orf177, DRAM1, HPDL, MTNR1A, PRKCI, SPIN2A, ZBTB3, C1orf185, DRAM2, HPGD, MTNR1B, PRKCQ, SPIN2B, ZBTB32, C1orf186, DRAP1, HPGDS, MTO1, PRKCSH, SPIN3, ZBTB33, C1orf189, DRAXIN, HPN, MTOR, PRKCZ, SPIN4, ZBTB34, C1orf192, DRC1, HPR, MTPAP, PRKD1, SPINK1, ZBTB37, C1orf194, DRD1, HPRT1, MTPN, PRKD2, SPINK13, ZBTB38, C1orf195, DRD2, HPS1, MTR, PRKD3, SPINK14, ZBTB39, C1orf198, DRD3, HPS3, MTRF1, PRKDC, SPINK2, ZBTB4, C1orf204, DRD4, HPS4, MTRF1L, PRKG1, SPINK4, ZBTB40, C1orf21, DRD5, HPS5, MTRNR2L10, PRKG2, SPINK5, ZBTB41, C1orf210, DRG1, HPS6, MTRNR2L2, PRKRA, SPINK6, ZBTB42, C1orf216, DRG2, HPSE, MTRNR2L3, PRKRIP1, SPINK7, ZBTB43, C1orf226, DRGX, HPSE2, MTRNR2L4, PRKRIR, SPINK8, ZBTB44, C1orf227, DROSHA, HPX, MTRNR2L5, PRKX, SPINK9, ZBTB45, C1orf228, DRP2, HR, MTRNR2L6, PRL, SPINT1, ZBTB46, C1orf229, DSC1, HRAS, MTRNR2L7, PRLH, SPINT2, ZBTB47, C1orf233, DSC2, HRASLS, MTRNR2L9, PRLHR, SPINT3, ZBTB48, C1orf234, DSC3, HRASLS2, MTRR, PRLR, SPINT4, ZBTB49, C1orf27, DSCAM, HRASLS5, MTSS1, PRM1, SPIRE1, ZBTB5, C1orf35, DSCAML1, HRC, MTSS1L, PRM2, SPIRE2, ZBTB6, C1orf43, DSCC1, HRCT1, MTTP, PRM3, SPN, ZBTB7A, C1orf50, DSCR3, HRG, MTURN, PRMT1, SPNS1,

TABLE 1-continued

List of examples of target genes (e.g., encoding a protein of interest)
List of target genes/proteins of interest ZBTB7B, C1orf51, DSCR4, HRH1, MTUS1, PRMT10, SPNS2, ZBTB7C, C1orf52, DSE, HRH2,
MTUS2, PRMT2, SPNS3, ZBTB8A, C1orf53, DSEL, HRH3, MTX1, PRMT3, SPO11, ZBTB8B,
C1orf54, DSG1, HRH4, MTX2, PRMT5, SPOCD1, ZBTB8OS, C1orf56, DSG2, HRK, MTX3, PRMT6,
SPOCK1, ZBTB9, C1orf61, DSG3, HRNR, MUC1, PRMT7, SPOCK2, ZC2HC1A, C1orf63, DSG4,
HRSP12, MUC12, PRMT8, SPOCK3, ZC2HC1B, C1orf64, DSN1, MUS1BP3, MUC13, PRND, SPON1,
ZC2HC1C, C1orf65, DSP, HS2ST1, MUC15, PRNP, SPON2, ZC3H10, C1orf68, DSPP, HS3ST1,
MUC16, PROB1, SPOP, ZC3H11A, C1orf74, DST, HS3ST2, MUC17, PROC, SPOPL, ZC3H12A,
C1orf85, DSTN, HS3ST3A1, MUC19, PROCA1, SPP1, ZC3H12B, C1orf86, DSTNP4, HS3ST3B1,
MUC2, PROCR, SPP2, ZC3H12C, C1orf87, DSTYK, HS3ST4, MUC20, PRODH, SPPL2A, ZC3H12D,
C1orf94, DTD1, HS3ST5, MUC21, PRODH2, SPPL2B, ZC3H13, C1orf95, DTD2, HS3ST6, MUC22,
PROK1, SPPL2C, ZC3H14, C1QA, DTHD1, HS6ST1, MUC3A, PROK2, SPPL3, ZC3H15, C1QB, DTL,
HS6ST2, MUC4, PROKR1, SPR, ZC3H18, C1QBP, DTNA, HS6ST3, MUC5AC, PROKR2, SPRED1,
ZC3H3, C1QC, DTNB, HSBP1, MUC5B, PROL1, SPRED2, ZC3H4, C1QL1, DTNBP1, HSBP1L1,
MUC6, PROM1, SPRED3, ZC3H6, C1QL2, DTWD1, HSCB, MUC7, PROM2, SPRN, ZC3H7A,
C1QL3, DTWD2, HSD11B1, MUC8, PROP1, SPRR1A, ZC3H7B, C1QL4, DTX1, HSD11B1L,
MUCL1, PROS1, SPRR1B, ZC3H8, C1QTNF1, DTX2, HSD11B2, MUL1, PROSC, SPRR2A,
ZC3HAV1, C1QTNF2, DTX3, HSD17B1, MUM1, PROSER1, SPRR2B, ZC3HAV1L, C1QTNF3,
DTX3L, HSD17B10, MUM1L1, PROSER2, SPRR2D, ZC3HC1, C1QTNF4, DTX4, HSD17B11,
MURC, PROX1, SPRR2E, ZC4H2, C1QTNF5, DTYMK, HSD17B12, MUS81, PROX2, SPRR2F,
ZCCHC10, C1QTNF6, DUOX1, HSD17B13, MUSK, PROZ, SPRR2G, ZCCHC11, C1QTNF7, DUOX2,
HSD17B14, MUSTN1, PRPF18, SPRR3, ZCCHC12, C1QTNF8, DUOXA1, HSD17B2, MUT, PRPF19,
SPRR4, ZCCHC13, C1QTNF9, DUOXA2, HSD17B3, MUTYH, PRPF3, SPRTN, ZCCHC14,
C1QTNF9B, DUPD1, HSD17B4, MVB12A, PRPF31, SPRY1, ZCCHC16, C1QTNF9B-AS1, DUS1L,
HSD17B6, MVB12B, PRPF38A, SPRY2, ZCCHC17, C1R, DUS2, HSD17B7, MVD, PRPF38B, SPRY3,
ZCCHC18, C1RL, DUS3L, HSD17B8, MVK, PRPF39, SPRY4, ZCCHC2, C1S, DUS4L, HSD3B1,
MVP, PRPF4, SPRYD3, ZCCHC24, C2, DUSP1, HSD3B2, MX1, PRPF40A, SPRYD4, ZCCHC3,
C20orf112, DUSP10, HSD3B7, MX2, PRPF40B, SPRYD7, ZCCHC4, C20orf141, DUSP11, HSDL1,
MXD1, PRPF4B, SPSB1, ZCCHC5, C20orf144, DUSP12, HSDL2, MXD3, PRPF6, SPSB2, ZCCHC6,
C20orf166, DUSP13, HSF1, MXD4, PRPF8, SPSB3, ZCCHC7, C20orf173, DUSP14, HSF2, MXI1,
PRPH, SPSB4, ZCCHC8, C20orf194, DUSP15, HSF2BP, MXRA5, PRPH2, SPTA1, ZCCHC9,
C20orf195, DUSP16, HSF4, MXRA7, PRPS1, SPTAN1, ZCRB1, C20orf196, DUSP18, HSF5, MXRA8,
PRPS1L1, SPTB, ZCWPW1, C20orf197, DUSP19, HSFX1, MYADM, PRPS2, SPTBN1, ZCWPW2,
C20orf201, DUSP2, HSFX2, MYADML2, PRPSAP1, SPTBN2, ZDBF2, C20orf202, DUSP21, HSFY1,
MYB, PRPSAP2, SPTBN4, ZDHHC1, C20orf203, DUSP22, HSFY2, MYBBP1A, PRR11, SPTBN5,
ZDHHC11, C20orf24, DUSP23, HSH2D, MYBL1, PRR12, SPTLC1, ZDHHC11B, C20orf26, DUSP26,
HSP90AA1, MYBL2, PRR13, SPTLC2, ZDHHC12, C20orf27, DUSP27, HSP90AB1, MYBPC1,
PRR14, SPTLC3, ZDHHC13, C20orf62, DUSP28, HSP90B1, MYBPC2, PRR14L, SPTSSA, ZDHHC14,
C20orf78, DUSP3, HSPA12A, MYBPC3, PRR15, SPTSSB, ZDHHC15, C20orf85, DUSP4, HSPA12B,
MYBPH, PRR15L, SPTY2D1, ZDHHC16, C20orf96, DUSP5, HSPA13, MYBPHL, PRR16, SPZ1,
ZDHHC17, C21orf140, DUSP6, HSPA14, MYC, PRR18, SQLE, ZDHHC18, C21orf2, DUSP7,
HSPA1A, MYCBP, PRR19, SQRDL, ZDHHC19, C21orf33, DUSP8, HSPA1B, MYCBP2, PRR20A,
SQSTM1, ZDHHC2, C21orf58, DUSP9, HSPA1L, MYCBPAP, PRR20B, SRA1, ZDHHC20, C21orf59,
DUT, HSPA2, MYCL, PRR20C, SRBD1, ZDHHC21, C21orf62, DUXA, HSPA4, MYCN, PRR20D,
SRC, ZDHHC22, C21orf91, DVL1, HSPA4L, MYCT1, PRR20E, SRCAP, ZDHHC23, C22orf15, DVL2,
HSPA5, MYD88, PRR21, SRCIN1, ZDHHC24, C22orf23, DVL3, HSPA6, MYEF2, PRR22, SRCRB4D,
ZDHHC3, C22orf24, DXO, HSPA8, MYEOV, PRR23A, SRD5A1, ZDHHC4, C22orf26, DYDC1,
HSPA9, MYEOV2, PRR23B, SRD5A2, ZDHHC5, C22orf29, DYDC2, HSPB1, MYF5, PRR23C,
SRD5A3, ZDHHC6, C22orf31, DYM, HSPB11, MYF6, PRR24, SREBF1, ZDHHC7, C22orf39,
DYNAP, HSPB2, MYH1, PRR25, SREBF2, ZDHHC8, C22orf42, DYNC1H1, HSPB3, MYH10, PRR3,
SREK1, ZDHHC9, C22orf43, DYNC1I1, HSPB6, MYH11, PRR30, SREK1IP1, ZEB1, C22orf46,
DYNC1I2, HSPB7, MYH13, PRR4, SRF, ZEB2, C2CD2, DYNC1LI1, HSPB8, MYH14, PRR5,
SRFBP1, ZER1, C2CD2L, DYNC1LI2, HSPB9, MYH15, PRR5-ARHGAP8, SRGAP1, ZFAND1,
C2CD3, DYNC2H1, HSPBAP1, MYH2, PRR5L, SRGAP2, ZFAND2A, C2CD4A, DYNC2LI1,
HSPBP1, MYH3, PRR7, SRGAP2B, ZFAND2B, C2CD4B, DYNLL1, HSPD1, MYH4, PRR9,
SRGAP2C, ZFAND3, C2CD4C, DYNLL2, HSPE1, MYH6, PRRC1, SRGAP3, ZFAND4, C2CD4D,
DYNLRB1, HSPE1-MOB4, MYH7, PRRC2A, SRGN, ZFAND5, C2CD5, DYNLRB2, HSPG2,
MYH7B, PRRC2B, SRI, ZFAND6, C2orf15, DYNLT1, HSPH1, MYH8, PRRC2C, SRL, ZFAT,
C2orf16, DYNLT3, HTATIP2, MYH9, PRRG1, SRM, ZFC3H1, C2orf27A, DYRK1A, HTATSF1,
MYL1, PRRG2, SRMS, ZFHX2, C2orf27B, DYRK1B, HTN1, MYL10, PRRG3, SRP14, ZFHX3,
C2orf40, DYRK2, HTN3, MYL12A, PRRG4, SRP19, ZFHX4, C2orf42, DYRK3, HTR1A, MYL12B,
PRRT1, SRP54, ZFP1, C2orf43, DYRK4, HTR1B, MYL2, PRRT2, SRP68, ZFP14, C2orf44, DYSF,
HTR1D, MYL3, PRRT3, SRP72, ZFP2, C2orf47, DYTN, HTR1E, MYL4, PRRT4, SRP9, ZFP28,
C2orf48, DYX1C1, HTR1F, MYL5, PRRX1, SRPK1, ZFP3, C2orf49, DZANK1, HTR2A, MYL6,
PRRX2, SRPK2, ZFP30, C2orf50, DZIP1, HTR2B, MYL6B, PRSS1, SRPK3, ZFP36, C2orf53, DZIP1L,
HTR2C, MYL7, PRSS12, SRPR, ZFP36L1, C2orf54, DZIP3, HTR3A, MYL9, PRSS16, SRPRB,
ZFP36L2, C2orf57, E2F1, HTR3B, MYLIP, PRSS2, SRPX, ZFP37, C2orf61, E2F2, HTR3C, MYLK,
PRSS21, SRPX2, ZFP41, C2orf62, E2F3, HTR3D, MYLK2, PRSS22, SRR, ZFP42, C2orf66, E2F4,
HTR3E, MYLK3, PRSS23, SRRD, ZFP57, C2orf68, E2F5, HTR4, MYLK4, PRSS27, SRRM1, ZFP62,
C2orf69, E2F6, HTR5A, MYLPF, PRSS3, SRRM2, ZFP64, C2orf70, E2F7, HTR6, MYNN, PRSS33,
SRRM3, ZFP69, C2orf71, E2F8, HTR7, MYO10, PRSS35, SRRM4, ZFP69B, C2orf72, E4F1, HTRA1,
MYO15A, PRSS36, SRRM5, ZFP82, C2orf73, EAF1, HTRA2, MYO16, PRSS37, SRRT, ZFP90,
C2orf74, EAF2, HTRA3, MYO18A, PRSS38, SRSF1, ZFP91, C2orf76, EAPP, HTRA4, MYO18B,
PRSS41, SRSF10, ZFP92, C2orf78, EARS2, HTT, MYO19, PRSS42, SRSF11, ZFPL1, C2orf80,
EBAG9, HUNK, MYO1A, PRSS44, SRSF12, ZFPM1, C2orf81, EBF1, HUS1, MYO1B, PRSS45,
SRSF2, ZFPM2, C2orf82, EBF2, HUS1B, MYO1C, PRSS46, SRSF3, ZFR, C2orf83, EBF3, HUWE1,
MYO1D, PRSS48, SRSF4, ZFR2, C2orf88, EBF4, HVCN1, MYO1E, PRSS50, SRSF5, ZFX, C2orf91,
EBI3, HYAL1, MYO1F, PRSS53, SRSF6, ZFY, C3, EBLN1, HYAL2, MYO1G, PRSS54, SRSF7,

TABLE 1-continued

List of examples of target genes (e.g., encoding a protein of interest)
List of target genes/proteins of interest ZFYVE1, C3AR1, EBLN2, HYAL3, MYO1H, PRSS55, SRSF8, ZFYVE16, C3orf14, EBNA1BP2, HYAL4, MYO3A, PRSS56, SRSF9, ZFYVE19, C3orf17, EBP, HYDIN, MYO3B, PRSS57, SRXN1, ZFYVE20, C3orf18, EBPL, HYI, MYO5A, PRSS58, SRY, ZFYVE21, C3orf20, ECD, HYKK, MYO5B, PRSS8, SS18, ZFYVE26, C3orf22, ECE1, HYLS1, MYO5C, PRTFDC1, SS18L1, ZFYVE27, C3orf27, ECE2, HYOU1, MYO6, PRTG, SS18L2, ZFYVE28, C3orf30, ECEL1, HYPK, MYO7A, PRTN3, SSB, ZFYVE9, C3orf33, ECH1, IAH1, MYO7B, PRUNE, SSBP1, ZG16, C3orf35, ECHDC1, IAPP, MYO9A, PRUNE2, SSBP2, ZG16B, C3orf36, ECHDC2, IARS, MYO9B, PRX, SSBP3, ZGLP1, C3orf38, ECHDC3, IARS2, MYOC, PRY, SSBP4, ZGPAT, C3orf43, ECHS1, IBA57, MYOCD, PRY2, SSC5D, ZHX1, C3orf52, ECI1, IBSP, MYOD1, PSAP, SSFA2, ZHX1-C8ORF76, C3orf55, ECI2, IBTK, MYOF, PSAPL1, SSH1, ZHX2, C3orf56, ECM1, ICA1, MYOG, PSAT1, SSH2, ZHX3, C3orf58, ECM2, ICA1L, MYOM1, PSCA, SSH3, ZIC1, C3orf62, ECSCR, ICAM1, MYOM2, PSD, SSMEM1, ZIC2, C3orf67, ECSIT, ICAM2, MYOM3, PSD2, SSNA1, ZIC3, C3orf70, ECT2, ICAM3, MYOT, PSD3, SSPN, ZIC4, C3orf72, ECT2L, ICAM4, MYOZ1, PSD4, SSPO, ZIC5, C3orf79, EDA, ICAM5, MYOZ2, PSEN1, SSR1, ZIK1, C3orf80, EDA2R, ICK, MYOZ3, PSEN2, SSR2, C3orf83, EDAR, ICMT, MYPN, PSENEN, SSR3, ZIM3, C3orf84, EDARADD, ICOS, MYPOP, PSG1, SSR4, ZKSCAN1, C4A, EDC3, ICOSLG, MYRF, PSG11, SSRP1, ZKSCAN2, C4B, EDC4, ICT1, MYRFL, PSG2, SSSCA1, ZKSCAN3, C4B_2, EDDM3A, ID1, MYRIP, PSG3, SST, ZKSCAN4, C4BPA, EDDM3B, ID2, MYSM1, PSG4, SSTR1, ZKSCAN5, C4BPB, EDEM1, ID3, MYT1, PSG5, SSTR2, ZKSCAN7, C4orf17, EDEM2, ID4, MYT1L, PSG6, SSTR3, ZKSCAN8, C4orf19, EDEM3, IDE, MYZAP, PSG7, SSTR4, ZMAT1, C4orf21, EDF1, IDH1, MZB1, PSG8, SSTR5, ZMAT2, C4orf22, EDIL3, IDH2, MZF1, PSG9, SSU72, ZMAT3, C4orf26, EDN1, IDH3A, MZT1, PSIP1, SSUH2, ZMAT4, C4orf27, EDN2, IDH3B, MZT2A, PSKH1, SSX1, ZMAT5, C4orf29, EDN3, IDH3G, MZT2B, PSKH2, SSX2, ZMIZ1, C4orf3, EDNRA, IDI1, N4BP1, PSMA1, SSX2B, ZMIZ2, C4orf32, EDNRB, IDI2, N4BP2, PSMA2, SSX2IP, ZMPSTE24, C4orf33, EEA1, IDNK, N4BP2L1, PSMA3, SSX3, ZMYM1, C4orf36, EED, IDO1, N4BP2L2, PSMA4, SSX4, ZMYM2, C4orf40, EEF1A1, IDO2, N4BP3, PSMA5, SSX4B, ZMYM3, C4orf45, EEF1A2, IDS, N6AMT1, PSMA6, SSX5, ZMYM4, C4orf46, EEF1B2, IDUA, N6AMT2, PSMA7, SSX7, ZMYM5, C4orf47, EEF1D, IER2, NAA10, PSMA8, ST13, ZMYM6, C4orf48, EEF1E1, IER3, NAA11, PSMB1, ST14, ZMYM6NB, C4orf50, EEF1G, IER3IP1, NAA15, PSMB10, ST18, ZMYND10, C4orf51, EEF2, IER5, NAA16, PSMB11, ST20, ZMYND11, C4orf6, EEF2K, IER5L, NAA20, PSMB2, ST20-MTHFS, ZMYND12, C5, EEFSEC, IFFO1, NAA25, PSMB3, ST3GAL1, ZMYND15, C5AR1, EEPD1, IFFO2, NAA30, PSMB4, ST3GAL2, ZMYND19, C5AR2, EFCAB1, IFI16, NAA35, PSMB5, ST3GAL3, ZMYND8, C5orf15, EFCAB11, IFI27, NAA38, PSMB6, ST3GAL4, ZNF10, C5orf20, EFCAB12, IFI27L1, NAA40, PSMB7, ST3GAL5, ZNF100, C5orf22, EFCAB13, IFI27L2, NAA50, PSMB8, ST3GAL6, ZNF101, C5orf24, EFCAB14, IFI30, NAA60, PSMB9, ST5, ZNF106, C5orf28, EFCAB2, IFI35, NAA6, PSMC1, ST6GAL1, ZNF107, C5orf30, EFCAB3, IFI44, NAALAD2, PSMC2, ST6GAL2, ZNF112, C5orf34, EFCAB4A, IFI44L, NAALADL1, PSMC3, ST6GALNAC1, ZNF114, C5orf38, EFCAB4B, IFI6, NAALADL2, PSMC3IP, ST6GALNAC2, ZNF117, C5orf42, EFCAB5, IFIH1, NAB1, PSMC4, ST6GALNAC3, ZNF12, C5orf45, EFCAB6, IFIT1, NAB2, PSMC5, ST6GALNAC4, ZNF121, C5orf46, EFCAB7, IFIT1B, NABP1, PSMC6, ST6GALNAC5, ZNF124, C5orf47, EFCAB8, IFIT2, NABP2, PSMD1, ST6GALNAC6, ZNF131, C5orf48, EFCAB9, IFIT3, NACA, PSMD10, ST7, ZNF132, C5orf49, EFCC1, IFIT5, NACA2, PSMD11, ST7L, ZNF133, C5orf50, EFEMP1, IFITM1, NACAD, PSMD12, ST8SIA1, ZNF134, C5orf51, EFEMP2, IFITM10, NACC1, PSMD13, ST8SIA2, ZNF135, C5orf52, EFHB, IFITM2, NACC2, PSMD14, ST8SIA3, ZNF136, C5orf55, EFHC1, IFITM3, NADK, PSMD2, ST8SIA4, ZNF138, C5orf58, EFHC2, IFITM5, NADK2, PSMD3, ST8SIA5, ZNF14, C5orf60, EFHD1, IFLTD1, NADSYN1, PSMD4, ST8SIA6, ZNF140, C5orf63, EFHD2, IFNA1, NAE1, PSMD5, STAB1, ZNF141, C5orf64, EFNA1, IFNA10, NAF1, PSMD6, STAB2, ZNF142, C6, EFNA2, IFNA13, NAGA, PSMD7, STAC, ZNF143, C6orf1, EFNA3, IFNA14, NAGK, PSMD8, STAC2, ZNF146, C6orf10, EFNA4, IFNA16, NAGLU, PSMD9, STAC3, ZNF148, C6orf106, EFNA5, IFNA17, NAGPA, PSME1, STAG1, ZNF154, C6orf118, EFNB1, IFNA2, NAGS, PSME2, STAG2, ZNF155, C6orf132, EFNB2, IFNA21, NAIF1, PSME3, STAG3, ZNF157, C6orf136, EFNB3, IFNA4, NAIP, PSME4, STAM, ZNF16, C6orf141, EFR3A, IFNA5, NALCN, PSMF1, STAM2, ZNF160, C6orf15, EFR3B, IFNA6, NAMPT, PSMG1, STAMBP, ZNF165, C6orf163, EFS, IFNA7, NANOG, PSMG2, STAMBPL1, ZNF169, C6orf165, EFTUD1, IFNA8, NANOGNB, PSMG3, STAP1, ZNF17, C6orf183, EFTUD2, IFNAR1, NANOS1, PSMG4, STAP2, ZNF174, C6orf195, EGF, IFNAR2, NANOS2, PSORS1C1, STAR, ZNF175, C6orf201, EGFL6, IFNB1, NANOS3, PSORS1C2, STARD10, ZNF177, C6orf203, EGFL7, IFNE, NANP, PSPC1, STARD13, ZNF18, C6orf211, EGFL8, IFNG, NANS, PSPH, STARD3, ZNF180, C6orf222, EGFLAM, IFNGR1, NAP1L1, PSPN, STARD3NL, ZNF181, C6orf223, EGFR, IFNGR2, NAP1L2, PSRC1, STARD4, ZNF182, C6orf226, EGLN1, IFNK, NAP1L3, PSTK, STARD5, ZNF184, C6orf25, EGLN2, IFNL1, NAP1L4, PSTPIP1, STARD6, ZNF185, C6orf47, EGLN3, IFNL2, NAP1L5, PSTPIP2, STARD7, ZNF189, C6orf48, EGR1, IFNL3, NAPA, PTAFR, STARD8, ZNF19, C6orf52, EGR2, IFNL4, NAPB, PTAR1, STARD9, ZNF195, C6orf57, EGR3, IFNLR1, NAPEPLD, PTBP1, STAT1, ZNF197, C6orf58, EGR4, IFNW1, NAPG, PTBP2, STAT2, ZNF2, C6orf62, EHBP1, IFRD1, NAPRT1, PTBP3, STAT3, ZNF20, C6orf7, EHBP1L1, IFRD2, NAPSA, PTCD1, STAT4, ZNF200, C6orf89, EHD1, IFT122, NARF, PTCD2, STAT5A, ZNF202, C6orf99, EHD2, IFT140, NARFL, PTCD3, STAT5B, ZNF205, C7, EHD3, IFT172, NARG2, PTCH1, STAT6, ZNF207, C7orf10, EHD4, IFT20, NARR, PTCH2, STATH, ZNF208, C7orf25, EHF, IFT27, NARS, PTCHD1, STAU1, ZNF211, C7orf26, EHHADH, IFT43, NARS2, PTCHD2, STAU2, ZNF212, C7orf31, EHMT1, IFT46, NASP, PTCHD3, STBD1, ZNF213, C7orf33, EHMT2, IFT52, NAT1, PTCHD4, STC1, ZNF214, C7orf34, EI24, IFT57, NAT10, PTCRA, STC2, ZNF215, C7orf43, EID1, IFT74, NAT14, PTDSS1, STEAP1, ZNF217, C7orf49, EID2, IFT80, NAT16, PTDSS2, STEAP1B, ZNF219, C7orf50, EID2B, IFT81, NAT2, PTEN, STEAP2, ZNF22, C7orf55, EID3, IFT88, NAT6, PTER, STEAP3, ZNF221, C7orf57- LUC7L2, EIF1, IGBP1, NAT8, PTF1A, STEAP4, ZNF222, C7orf57, EIF1AD, IGDCC3, NAT8B, PTGDR, STH, ZNF223, C7orf60, EIF1AX, IGDCC4, NAT8L, PTGDR2, STIL, ZNF224, C7orf61, EIF1AY, IGF1, NAT9, PTGDS, STIM1, ZNF225, C7orf62, EIF1B, IGF1R, NAV1, PTGER1, STIM2, ZNF226, C7orf63, EIF2A, IGF2, NAV2, PTGER2, STIP1, ZNF227, C7orf65, EIF2AK1, IGF2BP1, NAV3, PTGER3, STK10, ZNF229, C7orf66, EIF2AK2, IGF2BP2, NBAS, PTGER4, STK11, ZNF23, C7orf69, EIF2AK3, IGF2BP3, NBEA, PTGES, STK11IP, ZNF230, C7orf71, EIF2AK4, IGF2R,

TABLE 1-continued

List of examples of target genes (e.g., encoding a protein of interest)
List of target genes/proteins of interest NBEAL1, PTGES2, STK16, ZNF232, C7orf72, EIF2B1, IGFALS, NBEAL2, PTGES3, STK17A,
ZNF233, C7orf73, EIF2B2, IGFBP1, NBL1, PTGES3L, STK17B, ZNF234, C7orf76, EIF2B3, IGFBP2,
NBN, PTGES3L-AARSD1, STK19, ZNF235, C8A, EIF2B4, IGFBP3, NBPF14, PTGFR, STK24,
ZNF236, C8B, EIF2B5, IGFBP4, NBPF3, PTGFRN, STK25, ZNF239, C8G, EIF2D, IGFBP5, NBPF4,
PTGIR, STK3, ZNF24, C8orf22, EIF2S1, IGFBP6, NBPF6, PTGIS, STK31, ZNF248, C8orf31, EIF2S2,
IGFBP7, NBPF7, PTGR1, STK32A, ZNF25, C8orf33, EIF2S3, IGFBPL1, NBR1, PTGR2, STK32B,
ZNF250, C8orf34, EIF3A, IGFL1, NCALD, PTGS1, STK32C, ZNF251, C8orf37, EIF3B, IGFL2,
NCAM1, PTGS2, STK33, ZNF253, C8orf4, EIF3C, IGFL3, NCAM2, PTH, STK35, ZNF254, C8orf44,
EIF3CL, IGFL4, NCAN, PTH1R, STK36, ZNF256, C8orf44-SGK3, EIF3D, IGFLR1, NCAPD2, PTH2,
STK38, ZNF257, C8orf46, EIF3E, IGFN1, NCAPD3, PTH2R, STK38L, ZNF259, C8orf47, EIF3F,
IGHMBP2, NCAPG, PTHLH, STK39, ZNF26, C8orf48, EIF3G, IGIP, NCAPG2, PTK2, STK4, ZNF260,
C8orf58, EIF3H, IGJ, NCAPH, PTK2B, STK40, ZNF263, C8orf59, EIF3I, IGLL1, NCAPH2, PTK6,
STMN1, ZNF264, C8orf74, EIF3J, IGLL5, NCBP1, PTK7, STMN2, ZNF266, C8orf76, EIF3K,
IGLON5, NCBP2, PTMA, STMN3, ZNF267, C8orf82, EIF3L, IGSF1, NCCRP1, PTMS, STMN4,
ZNF268, C8orf86, EIF3M, IGSF10, NCDN, PTN, STMND1, ZNF273, C8orf87, EIF4A1, IGSF11,
NCEH1, PTOV1, STOM, ZNF274, C9, EIF4A2, IGSF21, NCF1, PTP4A1, STOML1, ZNF275,
C9orf106, EIF4A3, IGSF22, NCF2, PTP4A2, STOML2, ZNF276, C9orf114, EIF4B, IGSF23, NCF4,
PTP4A3, STOML3, ZNF277, C9orf116, EIF4E, IGSF3, NCK1, PTPDC1, STON1, ZNF28, C9orf117,
EIF4E1B, IGSF5, NCK2, PTPLA, STON1-GTF2A1L, ZNF280A, C9orf129, EIF4E2, IGSF6, NCKAP1,
PTPLAD1, STON2, ZNF280B, C9orf131, EIF4E3, IGSF8, NCKAP1L, PTPLAD2, STOX1, ZNF280C,
C9orf135, EIF4EBP1, IGSF9, NCKAP5, PTPLB, STOX2, ZNF280D, C9orf139, EIF4EBP2, IGSF9B,
NCKAP5L, PTPMT1, STPG1, ZNF281, C9orf142, EIF4EBP3, IHH, NCKIPSD, PTPN1, STPG2,
ZNF282, C9orf152, EIF4ENIF1, IK, NCL, PTPN11, STRA13, ZNF283, C9orf153, EIF4G1, IKBIP,
NCLN, PTPN12, STRA6, ZNF284, C9orf156, EIF4G2, IKBKAP, NCMAP, PTPN13, STRA8, ZNF285,
C9orf16, EIF4G3, IKBKB, NCOA1, PTPN14, STRADA, ZNF286A, C9orf163, EIF4H, IKBKE,
NCOA2, PTPN18, STRADB, ZNF286B, C9orf169, EIF5, IKBKG, NCOA3, PTPN2, STRAP, ZNF287,
C9orf170, EIF5A, IKZF1, NCOA4, PTPN20A, STRBP, ZNF292, C9orf171, EIF5A2, IKZF2, NCOA5,
PTPN20B, STRC, ZNF296, C9orf173, EIF5AL1, IKZF3, NCOA6, PTPN21, STRIP1, ZNF3, C9orf24,
EIF5B, IKZF4, NCOA7, PTPN22, STRIP2, ZNF30, C9orf3, EIF6, IKZF5, NCOR1, PTPN23, STRN,
ZNF300, C9orf37, ELAC1, INTERLEUKIN, IL10, NCOR2, PTPN3, STRN3, ZNF302, C9orf40,
ELAC2, IL10RA, NCR1, PTPN4, STRN4, ZNF304, C9orf41, ELANE, IL10RB, NCR2, PTPN5, STS,
ZNF311, C9orf43, ELAVL1, IL11, NCR3, PTPN6, STT3A, ZNF316, C9orf47, ELAVL2, IL11RA,
NCR3LG1, PTPN7, STT3B, ZNF317, C9orf50, ELAVL3, IL12A, NCS1, PTPN9, STUB1, ZNF318,
C9orf57, ELAVL4, IL12B, NCSTN, PTPRA, STX10, ZNF319, C9orf62, ELF1, IL12RB1, NDC1,
PTPRB, STX11, ZNF32, C9orf64, ELF2, IL12RB2, NDC80, PTPRC, STX12, ZNF320, C9orf66, ELF3,
IL13, NDE1, PTPRCAP, STX16, ZNF322, C9orf69, ELF4, IL13RA1, NDEL1, PTPRD, STX17,
ZNF324, C9orf72, ELF5, IL13RA2, NDFIP1, PTPRE, STX18, ZNF324B, C9orf78, ELFN1, IL15,
NDFIP2, PTPRF, STX19, ZNF326, C9orf84, ELFN2, IL15RA, NDN, PTPRG, STX1A, ZNF329,
C9orf85, ELK1, IL16, NDNF, PTPRH, STX1B, ZNF330, C9orf89, IL17A, NDNL2, PTPRJ,
STX2, ZNF331, C9orf9, ELK4, IL17B, NDOR1, PTPRK, STX3, ZNF333, C9orf91, ELL, IL17C, NDP,
PTPRM, STX4, ZNF334, C9orf92, ELL2, IL17D, NDRG1, PTPRN, STX5, ZNF335, C9orf96, ELL3,
IL17F, NDRG2, PTPRN2, STX6, ZNF337, CA1, ELMO1, IL17RA, NDRG3, PTPRO, STX7, ZNF33A,
CA10, ELMO2, IL17RB, NDRG4, PTPRQ, STX8, ZNF33B, CA11, ELMO3, IL17RC, NDST1, PTPRR,
STXBP1, ZNF34, CA12, ELMOD1, IL17RD, NDST2, PTPRS, STXBP2, ZNF341, CA13, ELMOD2,
IL17RE, NDST3, PTPRT, STXBP3, ZNF343, CA14, ELMOD3, IL17REL, NDST4, PTPRU, STXBP4,
ZNF345, CA2, ELMSAN1, IL18, NDUFA1, PTPRZ1, STXBP5, ZNF346, CA3, ELN, IL18BP,
NDUFA10, PTRF, STXBP5L, ZNF347, CA4, ELOF1, IL18R1, NDUFA11, PTRH1, STXBP6, ZNF35,
CASA, ELOVL1, IL18RAP, NDUFA12, PTRH2, STYK1, ZNF350, CA5B, ELOVL2, IL19, NDUFA13,
PTRHD1, STYX, ZNF354A, CA6, ELOVL3, IL1A, NDUFA2, PTS, STYXL1, ZNF354B, CA7,
ELOVL4, IL1B, NDUFA3, PTTG1, SUB1, ZNF354C, CA8, ELOVL5, IL1F10, NDUFA4, PTTG1IP,
SUCLA2, ZNF358, CA9, ELOVL6, IL1R1, NDUFA4L2, PTTG2, SUCLG1, ZNF362, CAAP1,
ELOVL7, IL1R2, NDUFA5, PTX3, SUCLG2, ZNF365, CAB39, ELP2, IL1RAP, NDUFA6, PTX4,
SUCNR1, ZNF366, CAB39L, ELP3, IL1RAPL1, NDUFA7, PUF60, SUCO, ZNF367, CABIN1, ELP4,
IL1RAPL2, NDUFA8, PUM1, SUDS3, ZNF37A, CABLES1, ELP5, IL1RL1, NDUFA9, PUM2, SUFU,
ZNF382, CABLES2, ELP6, IL1RL2, NDUFAB1, PURA, SUGP1, ZNF383, CABP1, ELSPBP1, IL1RN,
NDUFAF1, PURB, SUGP2, ZNF384, CABP2, ELTD1, IL2, NDUFAF2, PURG, SUGT1, ZNF385A,
CABP4, EMB, IL20, NDUFAF3, PUS1, SULF1, ZNF385B, CABP5, EMC1, IL20RA, NDUFAF4,
PUS10, SULF2, ZNF385C, CABP7, EMC10, IL20RB, NDUFAF5, PUS3, SULT1A1, ZNF385D,
CABS1, EMC2, IL21, NDUFAF6, PUS7, SULT1A2, ZNF391, CABYR, EMC3, IL21R, NDUFAF7,
PUS7L, SULT1A3, ZNF394, CACFD1, EMC4, IL22, NDUFB1, PUSL1, SULT1A4, ZNF395,
CACHD1, EMC6, IL22RA1, NDUFB10, PVALB, SULT1B1, ZNF396, CACNA1A, EMC7, IL22RA2,
NDUFB11, PVR, SULT1C2, ZNF397, CACNA1B, EMC8, IL23A, NDUFB2, PVRIG, SULT1C3,
ZNF398, CACNA1C, EMC9, IL23R, NDUFB3, PVRL1, SULT1C4, ZNF404, CACNA1D, EMCN, IL24,
NDUFB4, PVRL2, SULT1E1, ZNF407, CACNA1E, EMD, IL25, NDUFB5, PVRL3, SULT2A1,
ZNF408, CACNA1F, EME1, IL26, NDUFB6, PVRL4, SULT2B1, ZNF41, CACNA1G, EME2, IL27,
NDUFB7, PWP1, SULT4A1, ZNF410, CACNA1H, EMG1, IL27RA, NDUFB8, PWP2, SULT6B1,
ZNF414, CACNA1I, EMID1, IL2RA, NDUFB9, PWWP2A, SUMF1, ZNF415, CACNA1S, EMILIN1,
IL2RB, NDUFC1, PWWP2B, SUMF2, ZNF416, CACNA2D1, EMILIN2, IL2RG, NDUFC2, PXDC1,
SUMO1, ZNF417, CACNA2D2, EMILIN3, IL3, NDUFC2-KCTD14, PXDN, SUMO2, ZNF418,
CACNA2D3, EML1, IL31, NDUFS1, PXDNL, SUMO3, ZNF419, CACNA2D4, EML2, IL31RA,
NDUFS2, PXK, SUMO4, ZNF420, CACNB1, EML3, IL32, NDUFS3, PXMP2, SUN1, ZNF423,
CACNB2, EML4, IL33, NDUFS4, PXMP4, SUN2, ZNF425, CACNB3, EML5, IL34, NDUFS5, PXN,
SUN3, ZNF426, CACNB4, EML6, IL36A, NDUFS6, PXT1, SUN5, ZNF428, CACNG1, EMP1, IL36B,
NDUFS7, PYCARD, SUOX, ZNF429, CACNG2, EMP2, IL36G, NDUFS8, PYCR1, SUPT16H, ZNF43,
CACNG3, EMP3, IL36RN, NDUFV1, PYCR2, SUPT20H, ZNF430, CACNG4, EMR1, IL37, NDUFV2,
PYCRL, SUPT3H, ZNF431, CACNG5, EMR2, IL3RA, NDUFV3, PYDC1, SUPT4H1, ZNF432,
CACNG6, EMR3, IL4, NEB, PYDC2, SUPT5H, ZNF433, CACNG7, EMX1, IL4I1, NEBL, PYGB,

TABLE 1-continued

List of examples of target genes (e.g., encoding a protein of interest)
List of target genes/proteins of interest SUPT6H, ZNF436, CACNG8, EMX2, IL4R, NECAB1, PYGL, SUPT7L, ZNF438, CACTIN, EN1, IL5, NECAB2, PYGM, SUPV3L1, ZNF439, CACUL1, EN2, IL5RA, NECAB3, PYGO1, SURF1, ZNF44, CACYBP, ENAH, IL6, NECAP1, PYGO2, SURF2, ZNF440, CAD, ENAM, IL6R, NECAP2, PYHIN1, SURF4, ZNF441, CADM1, ENC1, IL6ST, NEDD1, PYROXD1, SURF6, ZNF442, CADM2, ENDOD1, IL7, NEDD4, PYROXD2, SUSD1, ZNF443, CADM3, ENDOG, IL7R, NEDD4L, PYURF, SUSD2, ZNF444, CADM4, ENDOU, IL8, NEDD8, PYY, SUSD3, ZNF445, CADPS, ENDOV, IL9, NEDD8-MDP1, PZP, SUSD4, ZNF446, CADPS2, ENG, IL9R, NEDD9, QARS, SUSD5, ZNF449, CAGE1, ENGASE, ILDR1, NEFH, QDPR, SUV39H1, ZNF45, CALB1, ENHO, ILDR2, NEFL, QKI, SUV39H2, ZNF451, CALB2, ENKD1, ILF2, NEFM, QPCT, SUV420H1, ZNF454, CALCA, ENKUR, ILF3, NEGR1, QPCTL, SUV420H2, ZNF460, CALCB, ENO1, ILK, NEIL1, QPRT, SUZ12, ZNF461, CALCOCO1, ENO2, ILKAP, NEIL2, QRFP, SV2A, ZNF462, CALCOCO2, ENO3, ILVBL, NEIL3, QRFPR, SV2B, ZNF467, CALCR, ENO4, IMMP1L, NEK1, QRICH1, SV2C, ZNF468, CALCRL, ENOPH1, IMMP2L, NEK10, QRICH2, SVEP1, ZNF469, CALD1, ENOSF1, IMMT, NEK11, QRSL1, SVIL, ZNF470, CALHM1, ENOX1, IMP3, NEK2, QSER1, SVIP, ZNF471, CALHM2, ENOX2, IMP4, NEK3, QSOX1, SVOP, ZNF473, CALHM3, ENPEP, IMPA1, NEK4, QSOX2, SVOPL, ZNF474, CALM1, ENPP1, IMPA2, NEK5, QTRT1, SWAP70, ZNF479, CALM2, ENPP2, IMPACT, NEK6, QTRTD1, SWI5, ZNF48, CALM3, ENPP3, IMPAD1, NEK7, R3HCC1, SWSAP1, ZNF480, CALML3, ENPP4, IMPDH1, NEK8, R3HCC1L, SWT1, ZNF483, CALML4, IMPDH2, NEK9, R3HDM1, SYAP1, ZNF484, CALML5, ENPP6, IMPG1, NELFA, R3HDM2, SYBU, ZNF485, CALML6, ENPP7, IMPG2, NELFB, R3HDM4, SYCE1, ZNF486, CALN1, ENSA, INA, NELFCD, R3HDML, SYCE1L, ZNF488, CALR, ENTHD1, INADL, NELFE, RAB10, SYCE2, ZNF490, CALR3, ENTHD2, INCA1, NELL1, RAB11A, SYCE3, ZNF491, CALU, ENTPD1, INCENP, NELL2, RAB11B, SYCN, ZNF492, CALY, ENTPD2, INF2, NEMF, RAB11FIP1, SYCP1, ZNF493, CAMK1, ENTPD3, ING1, NENF, RAB11FIP2, SYCP2, ZNF496, CAMK1D, ENTPD4, ING2, NEO1, RAB11FIP3, SYCP2L, ZNF497, CAMK1G, ENTPD5, ING3, NES, RAB11FIP4, SYCP3, ZNF500, CAMK2A, ENTPD6, ING4, NET1, RAB11FIP5, SYDE1, ZNF501, CAMK2B, ENTPD7, ING5, NETO1, RAB12, SYDE2, ZNF502, CAMK2D, ENTPD8, INHA, NETO2, RAB13, SYF2, ZNF503, CAMK2G, ENY2, INHBA, NEU1, RAB14, SYK, ZNF506, CAMK2N1, EOGT, INHBB, NEU2, RAB15, SYMPK, ZNF507, CAMK2N2, EOMES, INHBC, NEU3, RAB17, SYN1, ZNF510, CAMK4, EP300, INHBE, NEU4, RAB18, SYN2, ZNF511, CAMKK1, EP400, INIP, NEURL1, RAB19, SYN3, ZNF512, CAMKK2, EPAS1, INMT, NEURL1B, RAB1A, SYNC, ZNF512B, CAMKMT, EPB41, INO80, NEURL2, RAB1B, SYNCRIP, ZNF513, CAMKV, EPB41L1, INO80B, NEURL3, RAB20, SYNDIG1, ZNF514, CAMLG, EPB41L2, INO80C, NEURL4, RAB21, SYNDIG1L, ZNF516, CAMP, EPB41L3, INO80D, NEUROD1, RAB22A, SYNE1, ZNF517, CAMSAP1, EPB41L4A, INO80E, NEUROD2, RAB23, SYNE2, ZNF518A, CAMSAP2, EPB41L4B, INPP1, NEUROD4, RAB24, SYNE3, ZNF518B, CAMSAP3, EPB41L5, INPP4A, NEUROD6, RAB25, SYNE4, ZNF519, CAMTA1, EPB42, INPP4B, NEUROG1, RAB26, SYNGAP1, ZNF521, CAMTA2, EPC1, INPP5A, NEUROG2, RAB27A, SYNGR1, ZNF524, CAND1, EPC2, INPP5B, NEUROG3, RAB27B, SYNGR2, ZNF526, CAND2, EPCAM, INPP5D, NEXN, RAB28, SYNGR3, ZNF527, CANT1, EPDR1, INPP5E, NF1, RAB2A, SYNGR4, ZNF528, CANX, EPG5, INPP5F, NF2, RAB2B, SYNJ1, ZNF529, CAP1, EPGN, INPP5J, NFAM1, RAB30, SYNJ2, ZNF530, CAP2, EPHA1, INPP5K, NFASC, RAB31, SYNJ2BP, ZNF532, CAPG, EPHA10, INPPL1, NFAT5, RAB32, SYNJ2BP-COX16, ZNF534, CAPN1, EPHA2, INS, NFATC1, RAB33A, SYNM, ZNF536, CAPN10, EPHA3, INSC, NFATC2, RAB33B, SYNPO, ZNF540, CAPN11, EPHA4, INSIG1, NFATC2IP, RAB34, SYNPO2, ZNF541, CAPN12, EPHA5, INSIG2, NFATC3, RAB35, SYNPO2L, ZNF543, CAPN13, EPHA6, INS-IGF2, NFATC4, RAB36, SYNPR, ZNF544, CAPN14, EPHA7, INSL3, NFE2, RAB37, SYNRG, ZNF546, CAPN15, EPHA8, INSL4, NFE2L1, RAB38, SYP, ZNF547, CAPN2, EPHB1, INSL5, NFE2L2, RAB39A, SYPL1, ZNF548, CAPN3, EPHB2, INSL6, NFE2L3, RAB39B, SYPL2, ZNF549, CAPN5, EPHB3, INSM1, NFIA, RAB3A, SYS1, ZNF550, CAPN6, EPHB4, INSM2, NFIB, RAB3B, SYT1, ZNF551, CAPN7, EPHB6, INSR, NFIC, RAB3C, SYT10, ZNF552, CAPN8, EPHX1, INSRR, NFIL3, RAB3D, SYT11, ZNF554, CAPN9, EPHX2, INTS1, NFIX, RAB3GAP1, SYT12, ZNF555, CAPNS1, EPHX3, INTS10, NFKB1, RAB3GAP2, SYT13, ZNF556, CAPNS2, EPHX4, INTS12, NFKB2, RAB3IL1, SYT14, ZNF557, CAPRIN1, EPM2A, INTS2, NFKBIA, RAB3IP, SYT15, ZNF558, CAPRIN2, EPM2AIP1, INTS3, NFKBIB, RAB40A, SYT16, ZNF559, CAPS, EPN1, INTS4, NFKBID, RAB40AL, SYT17, ZNF559-ZNF177, CAPS2, EPN2, INTS5, NFKBIE, RAB40B, SYT2, ZNF560, CAPSL, EPN3, INTS6, NFKBIL1, RAB40C, SYT3, ZNF561, CAPZA1, EPO, INTS7, NFKBIZ, RAB41, SYT4, ZNF562, CAPZA2, EPOR, INTS8, NFRKB, RAB42, SYT5, ZNF563, CAPZA3, EPPIN, INTS9, NFS1, RAB43, SYT6, ZNF564, CAPZB, EPPIN-WFDC6, INTU, NFU1, RAB44, SYT7, ZNF565, CARD10, EPPK1, INVS, NFX1, RAB4A, SYT8, ZNF566, CARD11, EPRS, IP6K1, NFXL1, RAB4B, SYT9, ZNF567, CARD14, EPS15, IP6K2, NFYA, RAB5A, SYTL1, ZNF568, CARD16, EPS15L1, IP6K3, NFYB, RAB5B, SYTL2, ZNF569, CARD17, EPS8, IPCEF1, NFYC, RAB5C, SYTL3, ZNF57, CARD18, EPS8L1, IPMK, NGB, RAB6A, SYTL4, ZNF570, CARD6, EPS8L2, IPO11, NGDN, RAB6B, SYTL5, ZNF571, CARD8, EPS8L3, IPO13, NGEF, RAB6C, SYVN1, ZNF572, CARD9, EPSTI1, IPO4, NGF, RAB7A, SZT2, ZNF573, CARF, EPT1, IPO5, NGFR, RAB7L1, T, ZNF574, CARHSP1, EPX, IPO7, NGFRAP1, RAB8A, TAAR1, ZNF575, CARKD, EPYC, IPO8, NGLY1, RAB8B, TAAR2, ZNF576, CARM1, EQTN, IPO9, NGRN, RAB9A, TAAR5, ZNF577, CARNS1, ERAL1, IPP, NHEJ1, RAB9B, TAAR6, ZNF578, CARS, ERAP1, IPPK, NHLH1, RABAC1, TAAR8, ZNF579, CARS2, ERAP2, IQCA1, NHLH2, RABEP1, TAAR9, ZNF580, CARTPT, ERAS, IQCB1, NHLRC1, RABEP2, TAB1, ZNF581, CASC1, ERBB2, IQCC, NHLRC2, RABEPK, TAB2, ZNF582, CASC10, ERBB2IP, IQCD, NHLRC3, RABGAP1, TAB3, ZNF583, CASC3, ERBB3, IQCE, NHLRC4, RABGAP1L, TAC1, ZNF584, CASC4, ERBB4, IQCF1, NHP2, RABGEF1, TAC3, ZNF585A, CASC5, ERC1, IQCF2, NHP2L1, RABGGTA, TAC4, ZNF585B, CASD1, ERC2, IQCF3, NHS, RABGGTB, TACC1, ZNF586, CASK, ERCC1, IQCF5, NHSL1, RABIF, TACC2, ZNF587, CASKIN1, ERCC2, IQCF6, NHSL2, RABL2A, TACC3, ZNF587B, CASKIN2, ERCC3, IQCG, NICN1, RABL2B, TACO1, ZNF589, CASP1, ERCC4, IQCH, NID1, RABL3, TACR1, ZNF592, CASP10, ERCC5, IQCJ, NID2, RABL5, TACR2, ZNF593, CASP12, ERCC6, IQCJ-SCHIP1, NIF3L1, RABL6, TACR3, ZNF594, CASP14, ERCC6L, IQCK, NIFK, RAC1, TACSTD2, ZNF595, CASP16, ERCC6L2, IQGAP1, NIM1, RAC2, TADA1, ZNF596, CASP2, ERCC6-PGBD3, IQGAP2, NIN, RAC3, TADA2A, TABLE 1-continued List of examples of target genes (e.g., encoding a protein of interest)
List of target genes/proteins of interest ZNF597, CASP3, ERCC8, IQGAP3, NINJ1, RACGAP1, TADA2B, ZNF598, CASP4, EREG, IQSEC1, NINJ2, RAD1, TADA3, ZNF599, CASP5, ERF, IQSEC2, NINL, RAD17, TAF1, ZNF600, CASP6, ERG, IQSEC3, NIP7, RAD18, TAF10, ZNF605, CASP7, ERGIC1, IQUB, NIPA1, RAD21, TAF11, ZNF606, CASP8, ERGIC2, IRAK1, NIPA2, RAD21L1, TAF12, ZNF607, CASP8AP2, ERGIC3, IRAK1BP1, NIPAL1, RAD23A, TAF13, ZNF608, CASP9, ERH, IRAK2, NIPAL2, RAD23B, TAF15, ZNF609, CASQ1, ERI1, IRAK3, NIPAL3, RAD50, TAF1A, ZNF610, CASQ2, ERI2, IRAK4, NIPAL4, RAD51, TAF1B, ZNF611, CASR, ERI3, IREB2, NIPBL, RAD51AP1, TAF1C, ZNF613, CASS4, ERICH1, IRF1, NIPSNAP1, RAD51AP2, TAF1D, ZNF614, CAST, ERICH2, IRF2, NIPSNAP3A, RAD51B, TAF1L, ZNF615, CASZ1, ERLEC1, IRF2BP1, NIPSNAP3B, RAD51C, TAF2, ZNF616, CAT, ERLIN1, IRF2BP2, NISCH, RAD51D, TAF3, ZNF618, CATSPER1, ERLIN2, IRF2BPL, NIT1, RAD52, TAF4, ZNF619, CATSPER2, ERMAP, IRF3, NIT2, RAD54B, TAF4B, ZNF620, CATSPER3, ERMARD, IRF4, NKAIN1, RAD54L, TAF5, ZNF621, CATSPER4, ERMN, IRF5, NKAIN2, RAD54L2, TAF5L, ZNF622, CATSPERB, ERMP1, IRF6, NKAIN3, RAD9A, TAF6, ZNF623, CATSPERD, ERN1, IRF7, NKAIN4, RAD9B, TAF6L, ZNF624, CATSPERG, ERN2, IRF8, NKAP, RADIL, TAF7, ZNF625, CAV1, ERO1L, IRF9, NKAPL, RAE1, TAF7L, ZNF626, CAV2, ERO1LB, IRG1, NKD1, RAET1E, TAF8, ZNF627, CAV3, ERP27, IRGC, NKD2, RAET1G, TAF9, ZNF628, CBFA2T2, ERP29, IRGM, NKG7, RAET1L, TAF9B, ZNF629, CBFA2T3, ERP44, IRGQ, NKIRAS1, RAF1, TAGAP, ZNF630, CBFB, ERRFI1, IRS1, NKIRAS2, RAG1, TAGLN, ZNF638, CBL, ERVFRD-1, IRS2, NKPD1, RAG2, TAGLN2, ZNF639, CBLB, ERVMER34-1, IRS4, NKRF, RAI1, TAGLN3, ZNF641, CBLC, ERVV-1, IRX1, NKTR, RAI14, TAL1, ZNF644, CBLL1, ERVV-2, IRX2, NKX1-2, RAI2, TAL2, ZNF645, CBLN1, ESAM, IRX3, NKX2-1, RALA, TALDO1, ZNF646, CBLN2, ESCO1, IRX4, NKX2-2, RALB, TAMM41, ZNF648, CBLN3, ESCO2, IRX5, NKX2-3, RALBP1, TANC1, ZNF649, CBLN4, ESD, IRX6, NKX2-4, RALGAPA1, TANC2, ZNF652, CBR1, ESF1, ISCA1, NKX2-5, RALGAPA2, TANGO2, ZNF653, CBR3, ESM1, ISCA2, NKX2-6, RALGAPB, TANGO6, ZNF654, CBR4, ESPL1, ISCU, NKX2-8, RALGDS, TANK, ZNF655, CBS, ESPN, ISG15, NKX3- 1, RALGPS1, TAOK1, ZNF658, CBWD1, ESPNL, ISG20, NKX3-2, RALGPS2, TAOK2, ZNF660, CBWD2, ESR1, ISG20L2, NKX6-1, RALY, TAOK3, ZNF662, CBWD3, ESR2, ISL1, NKX6-2, RALYL, TAP1, ZNF664, CBWD5, ESRP1, ISL2, NKX6-3, RAMP1, TAP2, ZNF664-FAM101A, CBWD6, ESRP2, ISLR, NLE1, RAMP2, TAPBP, ZNF665, CBWD7, ESRRA, ISLR2, NLGN1, RAMP3, TAPBPL, ZNF667, CBX1, ESRRB, ISM1, NLGN2, RAN, TAPT1, ZNF668, CBX2, ESRRG, ISM2, NLGN3, RANBP1, TARBP1, ZNF669, CBX3, ESX1, ISOC1, NLGN4X, RANBP10, TARBP2, ZNF670, CBX4, ESYT1, ISOC2, NLGN4Y, RANBP17, TARDBP, ZNF671, CBX5, ESYT2, ISPD, NLK, RANBP2, TARM1, ZNF672, CBX6, ESYT3, IST1, NLN, RANBP3, TARP, ZNF674, CBX7, ETAA1, ISX, NLRC3, RANBP3L, TARS, ZNF675, CBX8, ETF1, ISY1, NLRC4, RANBP6, TARS2, ZNF676, CBY1, ETFA, ISY1-RAB43, NLRC5, RANBP9, TARSL2, ZNF677, CBY3, ETFB, ISYNA1, NLRP1, RANGAP1, TAS1R1, ZNF678, CC2D1A, ETFDH, ITCH, NLRP10, RANGRF, TAS1R2, ZNF679, CC2D1B, ETHE1, ITFG1, NLRP11, RAP1A, TAS1R3, ZNF680, CC2D2A, ETNK1, ITFG2, NLRP12, RAP1B, TAS2R1, ZNF681, CC2D2B, ETNK2, ITFG3, NLRP13, RAP1GAP, TAS2R10, ZNF682, CCAR1, ETNPPL, ITGA1, NLRP14, RAPIGAP2, TAS2R13, ZNF683, CCAR2, ETS1, ITGA10, RAP1GDS1, TAS2R14, ZNF684, CCBE1, ETS2, ITGA11, NLRP3, RAP2A, TAS2R16, ZNF687, CCBL1, ETV1, ITGA2, NLRP4, RAP2B, TAS2R19, ZNF688, CCBL2, ETV2, ITGA2B, NLRP5, RAP2C, TAS2R20, ZNF689, CCDC101, ETV3, ITGA3, NLRP6, RAPGEF1, TAS2R3, ZNF69, CCDC102A, ETV3L, ITGA4, NLRP7, RAPGEF2, TAS2R30, ZNF691, CCDC102B, ETV4, ITGA5, NLRP8, RAPGEF3, TAS2R31, ZNF692, CCDC103, ETV5, ITGA6, NLRP9, RAPGEF4, TAS2R38, ZNF695, CCDC104, ETV6, ITGA7, NLRX1, RAPGEF5, TAS2R39, ZNF696, CCDC105, ETV7, ITGA8, NMB, RAPGEF6, TAS2R4, ZNF697, CCDC106, EVA1A, ITGA9, NMBR, RAPGEFL1, TAS2R40, ZNF699, CCDC107, EVA1B, ITGAD, NMD3, RAPH1, TAS2R41, ZNF7, CCDC108, EVA1C, ITGAE, NME1, RAPSN, TAS2R42, ZNF70, CCDC109B, EVC, ITGAL, NME1-NME2, RARA, TAS2R43, ZNF700, CCDC11, EVC2, ITGAM, NME2, RARB, TAS2R46, ZNF701, CCDC110, EVI2A, ITGAV, NME3, RARG, TAS2R5, ZNF703, CCDC112, EVI2B, ITGAX, NME4, RARRES1, TAS2R50, ZNF704, CCDC113, EVI5, ITGB1, NME5, RARRES2, TAS2R60, ZNF705A, CCDC114, EVI5L, ITGB1BP1, NME6, RARRES3, TAS2R7, ZNF705B, CCDC115, EVL, ITGB1BP2, NME7, RARS, TAS2R8, ZNF705D, CCDC116, EVPL, ITGB2, NME8, RARS2, TAS2R9, ZNF705E, CCDC117, EVPLL, ITGB3, NME9, RASA1, TASP1, ZNF705G, CCDC12, EVX1, ITGB3BP, NMI, RASA2, TAT, ZNF706, CCDC120, EVX2, ITGB4, NMNAT1, RASA3, TATDN1, ZNF707, CCDC121, EWSR1, ITGB5, NMNAT2, RASA4, TATDN2, ZNF708, CCDC122, EXD1, ITGB6, NMNAT3, RASA4B, TATDN3, ZNF709, CCDC124, EXD2, ITGB7, NMRAL1, RASAL1, TAX1BP1, ZNF71, CCDC125, EXD3, ITGB8, NMRK1, RASAL2, TAX1BP3, ZNF710, CCDC126, EXO1, ITGBL1, NMRK2, RASAL3, TAZ, ZNF711, CCDC127, EXO5, ITIH1, NMS, RASD1, TBATA, ZNF713, CCDC129, EXOC1, ITIH2, NMT1, RASD2, TBC1D1, ZNF714, CCDC13, EXOC2, ITIH3, NMT2, RASEF, TBC1D10A, ZNF716, CCDC130, EXOC3, ITIH4, NMU, RASGEF1A, TBC1D10B, ZNF717, CCDC132, EXOC3L1, ITIH5, NMUR1, RASGEF1B, TBC1D10C, ZNF718, CCDC134, EXOC3L2, ITIH6, NMUR2, RASGEF1C, TBCID12, ZNF720, CCDC135, EXOC3L4, ITK, NNAT, RASGRF1, TBC1D13, ZNF721, CCDC136, EXOC4, ITLN1, NNMT, RASGRF2, TBC1D14, ZNF726, CCDC137, EXOC5, ITLN2, NNT, RASGRP1, TBC1D15, ZNF727, CCDC138, EXOC6, ITM2A, NOA1, RASGRP2, TBC1D16, ZNF728, CCDC14, EXOC6B, ITM2B, NOB1, RASGRP3, TBC1D17, ZNF729, CCDC140, EXOC7, ITM2C, NOBOX, RASGRP4, TBC1D19, ZNF730, CCDC141, EXOC8, ITPA, NOC2L, RASIP1, TBC1D2, ZNF732, CCDC142, EXOG, ITPK1, NOC3L, RASL10A, TBC1D20, ZNF735, CCDC144A, EXOSC1, ITPKA, NOC4L, RASL10B, TBC1D21, ZNF736, CCDC144NL, EXOSC10, ITPKB, NOD1, RASL11A, TBC1D22A, ZNF737, CCDC146, EXOSC2, ITPKC, NOD2, RASL11B, TBC1D22B, ZNF74, CCDC147, EXOSC3, ITPR1, NODAL, RASL12, TBC1D23, ZNF740, CCDC148, EXOSC4, ITPR2, NOG, RASSF1, TBC1D24, ZNF746, CCDC149, EXOSC5, ITPR3, NOL10, RASSF10, TBC1D25, ZNF747, CCDC15, EXOSC6, ITPRIP, NOL11, RASSF2, TBC1D26, ZNF749, CCDC150, EXOSC7, ITPRIPL1, NOL12, RASSF3, TBC1D27, ZNF750, CCDC151, EXOSC8, ITPRIPL2, NOL3, RASSF4, TBC1D28, ZNF75A, CCDC152, EXOSC9, ITSN1, NOL4, RASSF5, TBC1D29, ZNF75D, CCDC153, EXPH5, ITSN2, NOL6, RASSF6, TBC1D2B, ZNF76, CCDC154, EXT1, IVD, NOL7, RASSF7, TBC1D3, ZNF761, CCDC155, EXT2, IVL, NOL8, RASSF8, TBC1D30, ZNF763, CCDC157, EXTL1, IVNS1ABP, NOL9, RASSF9, TABLE 1-continued List of examples of target genes (e.g., encoding a protein of interest)
List of target genes/proteins of interest TBC1D31, ZNF764, CCDC158, EXTL2, IWS1, NOLC1, RAVER1, TBC1D32, ZNF765, CCDC159, EXTL3, IYD, NOM1, RAVER2, TBC1D3B, ZNF766, CCDC160, EYA1, IZUMO1, NOMO1, RAX, TBC1D3C, ZNF768, CCDC166, EYA2, IZUMO2, NOMO2, RAX2, TBC1D3F, ZNF77, CCDC167, EYA3, IZUMO3, NOMO3, RB1, TBC1D3G, ZNF770, CCDC168, EYA4, IZUMO4, NONO, RB1CC1, TBC1D3H, ZNF771, CCDC169, EYS, JADE1, NOP10, RBAK, TBC1D4, ZNF772, CCDC169-SOHLH2, EZH1, JADE2, NOP14, RBAK-RBAKDN, TBC1D5, ZNF773, CCDC17, EZH2, JADE3, NOP16, RBBP4, TBC1D7, ZNF774, CCDC170, EZR, JAG1, NOP2, RBBP5, TBC1D8, ZNF775, CCDC171, F10, JAG2, NOP56, RBBP6, TBC1D8B, ZNF776, CCDC172, F11, JAGN1, NOP58, RBBP7, TBC1D9, ZNF777, CCDC173, F11R, JAK1, NOP9, RBBP8, TBC1D9B, ZNF778, CCDC174, F12, JAK2, NOS1, RBBP8NL, TBCA, ZNF780A, CCDC175, F13A1, JAK3, NOS1AP, RBBP9, TBCB, ZNF780B, CCDC176, F13B, JAKMIP1, NOS2, RBCK1, TBCC, ZNF781, CCDC177, F2, JAKMIP2, NOS3, RBFA, TBCCD1, ZNF782, CCDC178, F2R, JAKMIP3, NOSIP, RBFOX1, TBCD, ZNF783, CCDC179, F2RL1, JAM2, NOSTRIN, RBFOX2, TBCE, ZNF784, CCDC18, F2RL2, JAM3, NOTCH1, RBFOX3, TBCEL, ZNF785, CCDC180, F2RL3, JARID2, NOTCH2, RBKS, TBCK, ZNF786, CCDC181, F3, JAZF1, NOTCH2NL, RBL1, TBK1, ZNF787, CCDC19, F5, JDP2, NOTCH3, RBL2, TBKBP1, ZNF789, CCDC22, F7, JHDM1D, NOTCH4, RBM10, TBL1X, ZNF79, CCDC23, F8, JKAMP, NOTO, RBM11, TBL1XR1, ZNF790, CCDC24, F8A1, JMJD1C, NOTUM, RBM12, TBL1Y, ZNF791, CCDC25, F8A2, JMJD4, NOV, RBM12B, TBL2, ZNF792, CCDC27, F8A3, JMJD6, NOVA1, RBM14, TBL3, ZNF793, CCDC28A, F9, JMJD7, NOVA2, RBM14-RBM4, TBP, ZNF799, CCDC28B, FA2H, JMJD7-PLA2G4B, NOX1, RBM15, TBPL1, ZNF8, CCDC3, FAAH, JMJD8, NOX3, RBM15B, TBPL2, ZNF80, CCDC30, FAAH2, JMY, NOX4, RBM17, TBR1, ZNF800, CCDC33, FABP1, JOSD1, NOX5, RBM18, TBRG1, ZNF804A, CCDC34, FABP12, JOSD2, NOXA1, RBM19, TBRG4, ZNF804B, CCDC36, FABP2, JPH1, NOXO1, RBM20, TBX1, ZNF805, CCDC37, FABP3, JPH2, NOXRED1, RBM22, TBX10, ZNF806, CCDC38, FABP4, JPH3, NPAP1, RBM23, TBX15, ZNF808, CCDC39, FABP5, JPH4, NPAS1, RBM24, TBX18, ZNF81, CCDC40, FABP6, JRK, NPAS2, RBM25, TBX19, ZNF812, CCDC41, FABP7, JRKL, NPAS3, RBM26, TBX2, ZNF813, CCDC42, FABP9, JSRP1, NPAS4, RBM27, TBX20, ZNF814, CCDC42B, FADD, JTB, NPAT, RBM28, TBX21, ZNF816, CCDC43, FADS1, JUN, NPB, RBM3, TBX22, ZNF816-ZNF321P, CCDC47, FADS2, JUNB, NPBWR1, RBM33, TBX3, ZNF821, CCDC50, FADS3, JUND, NPBWR2, RBM34, TBX4, ZNF823, CCDC51, FADS6, JUP, NPC1, RBM38, TBX5, ZNF827, CCDC53, FAF1, KAAG1, NPC1L1, RBM39, TBX6, ZNF829, CCDC54, FAF2, KAL1, NPC2, RBM4, TBXA2R, ZNF83, CCDC57, FAH, KALRN, NPDC1, RBM41, TBXAS1, ZNF830, CCDC58, FAHD1, KANK1, NPEPL1, RBM42, TC2N, ZNF831, CCDC59, FAHD2A, KANK2, NPEPPS, RBM43, TCAIM, ZNF835, CCDC6, FAHD2B, KANK3, NPFF, RBM46, TCAP, ZNF836, CCDC60, FAIM, KANK4, NPFFR1, RBM47, TCEA1, ZNF837, CCDC61, FAIM2, KANSL1, NPFFR2, RBM48, TCEA2, ZNF839, CCDC62, FAIM3, KANSL1L, NPHP1, RBM4B, TCEA3, ZNF84, CCDC63, FAM101A, KANSL2, NPHP3, RBM5, TCEAL1, ZNF841, CCDC64, FAM101B, KANSL3, NPHP4, RBM6, TCEAL2, ZNF843, CCDC64B, FAM102A, KARS, NPHS1, RBM7, TCEAL3, ZNF844, CCDC65, FAM102B, KAT2A, NPHS2, RBM8A, TCEAL4, ZNF845, CCDC66, FAM103A1, KAT2B, NPIPA1, RBMS1, TCEAL5, ZNF846, CCDC67, FAM104A, KAT5, NPIPA2, RBMS2, TCEAL6, ZNF85, CCDC68, FAM104B, KAT6A, NPIPA3, RBMS3, TCEAL7, ZNF850, CCDC69, FAM105A, KAT6B, NPIPA5, RBMX, TCEAL8, ZNF852, CCDC7, FAM105B, KAT7, NPIPA7, RBMX2, TCEANC, ZNF853, CCDC70, FAM107A, KAT8, NPIPA8, RBMXL1, TCEANC2, ZNF860, CCDC71, FAM107B, KATNA1, NPIPB11, RBMXL2, TCEB1, ZNF862, CCDC71L, FAM109A, KATNAL1, NPIPB15, RBMXL3, TCEB2, ZNF865, CCDC73, FAM109B, KATNAL2, NPIPB3, RBMY1A1, TCEB3, ZNF878, CCDC74A, FAM110A, KATNB1, NPIPB4, RBMY1B, TCEB3B, ZNF879, CCDC74B, FAM110B, KATNBL1, NPIPB5, RBMY1D, TCEB3C, ZNF880, CCDC77, FAM110C, KAZALD1, NPIPB6, RBMY1E, TCEB3CL, ZNF883, CCDC78, FAM110D, KAZN, NPIPB8, RBMY1F, TCEB3CL2, ZNF888, CCDC79, FAM111A, KBTBD11, NPIPB9, RBMY1J, TCERG1, ZNF891, CCDC8, FAM111B, KBTBD12, NPL, RBP1, TCERG1L, ZNF90, CCDC80, FAM114A1, KBTBD13, NPLOC4, RBP2, TCF12, ZNF91, CCDC81, FAM114A2, KBTBD2, NPM1, RBP3, TCF15, ZNF92, CCDC82, FAM115A, KBTBD3, NPM2, RBP4, TCF19, ZNF93, CCDC83, FAM115C, KBTBD4, NPM3, RBP5, TCF20, ZNF98, CCDC84, FAM117A, KBTBD6, NPNT, RBP7, TCF21, ZNF99, CCDC85A, FAM117B, KBTBD7, NPPA, RBPJ, TCF23, ZNFX1, CCDC85B, FAM118A, KBTBD8, NPPB, RBPJL, TCF24, ZNHIT1, CCDC85C, FAM118B, KCMF1, NPPC, RBPMS, TCF25, ZNHIT2, CCDC86, FAM120A, RCAN1, NPR1, RBPMS2, TCF3, ZNHIT3, CCDC87, FAM120AOS, KCNA10, NPR2, RBX1, TCF4, ZNHIT6, CCDC88A, FAM120B, KCNA2, NPR3, RC3H1, TCF7, ZNRD1, CCDC88B, FAM120C, KCNA3, NPRL2, RC3H2, TCF7L1, ZNRF1, CCDC88C, FAM122A, KCNA4, NPRL3, RCAN1, TCF7L2, ZNRF2, CCDC89, FAM122B, KCNA5, NPS, RCAN2, TCFL5, ZNRF3, CCDC9, FAM122C, KCNA6, NPSR1, RCAN3, TCHH, ZNRF4, CCDC90B, FAM124A, KCNA7, NPTN, RCBTB1, TCHHL1, ZP1, CCDC91, FAM124B, KCNAB1, NPTX1, RCBTB2, TCHP, ZP2, CCDC92, FAM126A, KCNAB2, NPTX2, RCC1, TCIRG1, ZP3, CCDC93, FAM126B, KCNAB3, NPTXR, RCC2, TCL1A, ZP4, CCDC94, FAM127A, KCNB1, NPVF, RCCD1, TCL1B, ZPBP, CCDC96, FAM127B, KCNB2, NPW, RCE1, TCN1, ZPBP2, CCDC97, FAM127C, KCNC1, NPY, RCHY1, TCN2, ZPLD1, CCER1, FAM129A, KCNC2, NPY1R, RCL1, TCOF1, ZRANB1, CCHCR1, FAM129B, KCNC3, NPY2R, RCN1, TCP1, ZRANB2, CCIN, FAM129C, KCNC4, NPY4R, RCN2, TCP10, ZRANB3, CCK, FAM131A, KCND1, NPY5R, RCN3, TCP10L, ZRSR2, CCKAR, FAM131B, KCND2, NQO1, RCOR1, TCP10L2, ZSCAN1, CCKBR, FAM131C, KCND3, NQO2, RCOR2, TCP11, ZSCAN10, CCL1, FAM132A, KCNE1, NR0B1, RCOR3, TCP11L1, ZSCAN12, CCL11, FAM132B, KCNE1L, NR0B2, RCSD1, TCP11L2, ZSCAN16, CCL13, FAM133A, KCNE2, NR1D1, RCVRN, TCP11X1, ZSCAN18, CCL14, FAM133B, KCNE3, NR1D2, RD3, TCP11X2, ZSCAN2, CCL15, FAM134A, KCNE4, NR1H2, RD3L, TCTA, ZSCAN20, CCL16, FAM134B, KCNF1, NR1H3, RDH10, TCTE1, ZSCAN21, CCL17, FAM134C, KCNG1, NR1H4, RDH11, TCTE3, ZSCAN22, CCL18, FAM135A, KCNG2, NR1I2, RDH12, TCTEX1D1, ZSCAN23, CCL19, FAM135B, KCNG3, NR1I3, RDH13, TCTEX1D2, ZSCAN25, CCL2, FAM136A, KCNG4, NR2C1, RDH14, TCTEX1D4, ZSCAN26, CCL20, FAM13A, KCNH1, NR2C2, RDH16, TCTN1, ZSCAN29, CCL21, FAM13B, KCNH2, NR2C2AP, RDH5, TCTN2, ZSCAN30, CCL22, FAM13C, KCNH3, NR2E1, RDH8, TCTN3, ZSCAN31, CCL23, FAM149A, KCNH4, NR2E3, RDM1, TDG,

TABLE 1-continued

List of examples of target genes (e.g., encoding a protein of interest)
List of target genes/proteins of interest ZSCAN32, CCL24, FAM149B1, KCNH5, NR2F1, RDX, TDGF1, ZSCAN4, CCL25, FAM150A, KCNH6, NR2F2, REC8, TDO2, ZSCAN5A, CCL26, FAM150B, KCNH7, NR2F6, RECK, TDP1, ZSCAN5B, CCL27, FAM151A, KCNH8, NR3C1, RECQL, TDP2, ZSCAN9, CCL28, FAM151B, KCNIP1, NR3C2, RECQL4, TDRD1, ZSWIM1, CCL3, FAM153A, KCNIP2, NR4A1, RECQL5, TDRD10, ZSWIM2, CCL3L1, FAM153B, KCNIP3, NR4A2, REEP1, TDRD12, ZSWIM3, CCL3L3, FAM154A, KCNIP4, NR4A3, REEP2, TDRD3, ZSWIM4, CCL4, FAM154B, KCNJ1, NR5A1, REEP3, TDRD5, ZSWIM5, CCL4L1, FAM155A, KCNJ10, NR5A2, REEP4, TDRD6, ZSWIM6, CCL4L2, FAM155B, KCNJ11, NR6A1, REEP5, TDRD7, ZSWIM7, CCL5, FAM156A, KCNJ12, NRAP, REEP6, TDRD9, ZSWIM8, CCL7, FAM156B, KCNJ13, NRARP, REG1A, TDRKH, ZUFSP, CCL8, FAM157A, KCNJ14, NRAS, REG1B, TDRP, ZW10, CCM2, FAM157B, KCNJ15, NRBF2, REG3A, TEAD1, ZWILCH, CCM2L, FAM159A, KCNJ16, NRBP1, REG3G, TEAD2, ZWINT, CCNA1, FAM159B, KCNJ18, NRBP2, REG4, TEAD3, ZXDA, CCNA2, FAM160A1, KCNJ2, NRCAM, REL, TEAD4, ZXDB, CCNB1, FAM160A2, KCNJ3, NRD1, RELA, TEC, ZXDC, CCNB1IP1, FAM160B1, KCNJ4, NRDE2, RELB, TECPR1, ZYG11A, CCNB2, FAM160B2, KCNJ5, NREP, RELL1, TECPR2, ZYG11B, CCNB3, FAM161A, KCNJ6, NRF1, RELL2, TECR, ZYX, CCNC, FAM161B, KCNJ8, NRG1, RELN, TECRL, ZZEF1, CCND1, FAM162A, KCNJ9, NRG2, RELT, TECTA, ZZZ3, CCND2, FAM162B, KCNK1, NRG, RHODOPSIN, RdCVF, RdCVFL, GIRK, DUX4, and DBET (or DBET lncRNA).

TABLE 2

List of naturally occurring Cas12f proteins.

| Cas protein | SEQ ID NO | Amino acid sequence |
|---|---|---|
| Un2Cas12f1 | 2 | Provided herein (SEQ ID NO: 2) |
| AsCas12f | 3 | Provided herein (SEQ ID NO: 3) |
| Mi1Cas12f2 | 13 | MNMSKTTISVKLKIIDLSSEKKEFLDNYFNEYAKATTFCQLRIRRLLRNT HWLGKKEKSSKKWIFESGICDLCGENKELVNEDRNSGEPAKICKRCYNGR YGNQMIRKLFVSTKKREVQENMDIRRVAKLNNTHYHRIPEEAFDMIKAAD TAEKRRKKNVEYDKKRQMEFIEMFNDEKKRAARPKKPNERETRYVHISKL ESPSKGYTLNGIKRKIDGMGKKIERAEKGLSRKKIFGYQGNRIKLDSNWV RFDLAESEITIPSLFKEMKLRITGPTNVHSKSGQIYFAEWFERINKQPNN YCYLIRKTSSNGKYEYYLQYTYEAEVEANKEYAGCLGVDIGCSKLAAAVY YDSKNKKAQKPIEIFTNPIKKIKMRREKLIKLLSRVKVRHRRRKLMQLSK TEPIIDYTCHKTARKIVEMANTAKAFISMENLETGIKQKQQARETKKQKF YRNMPLFRKLSKLIEYKALLKGIKIVYVKPDYTSQTCSSCGADKEKTERP SQAIFRCLNPTCRYYQRDINADFNAAVNIAKKALNNTEVVTTLL |
| Mi2Cas12f2 | 14 | MPSETYITKTLSLKLIPSDEEKQALENYFITFQRAVNFAIDRIVDIRSSF RYLNKNEQFPAVCDCCGKKEKIMYVNISNKTFKFKPSRNQKDRYTKDIYT IKPNAHICKTCYSGVAGNMFIRKQMYPNDKEGWKVSRSYNIKVNAPGLTG TEYAMAIRKAISILRSFEKRRRNAERRIIEYEKSKKEYLELIDDVEKGKT NKIVVLEKEGHQRVKRYKHKNWPEKWQGISLNKAKSKVKDIEKRIKKLKE WKHPTLNRPYVELHKNNVRIVGYETVELKLGNKMYTIHFASISNLRKPFR KQKKKSIEYLKHLLTLALKRNLETYPSIIKRGKNFFLQYPVRVTVKVPKL TKNFKAFGIDRGVNRLAVGCIISKDGKLTNKNIFFFHGKEAWAKENRYKK IRDRLYAMAKKLRGDKTKKIRLYHEIRKKFRHKVKYFRRNYLHNISKQIV EIAKENTPTVIVLEDLRYLRERTYRGKGRSKKAKKTNYKLNTFTYRMLID MIKYKAEEAGVPVMIIDPRNTSRKCSKCGYVDENNRKQASFKCLKCGYSL NADLNAAVNIAKAFYECPTFRWEEKLHAYVCSEPDK |
| AuCas12f2 | 15 | MKSFKLKLLPTDEQNVLLNEVFCKWASLCTRMASKGHDKERLAPPDSSGN YFNKTQLNQVNTDVTDHMGALEESASQKERAVEKVKRRLKLISDMLSEPN LRDVSQQKPTTFRPLEWVKEGLLKTKYHTVHYWQKECDKLTKQKERMEKT IEKIKKGKITFKPTKMSLHQNCFSLSFGKGTFSMRPFSDTKRGINLDMLT APIQPAIGKNDGKSSLRSKEFIARNIENYIIFSIHSQLFGLSRSEELLLN AKKEELVAKRDAMLKKKSDSLSKKIKELEKIVGRKITDSERSEIMSQGGK LSSEKFSEDNSYLKTLKVLAKDIIGREELFRLKKYPIVIRKPLNERKKLK NLKPDEWEYYLQLSYDELEKKEFTPKTIMGIDRGLKHILAIAIYDPVQNK FVKNMLIPNPILGWKWKLRKIKRSIQHMERRIRAQQNAHVPENQLKKRLK SIENKIDYYYHNVSRQILNLAHDFKSAIVVEDLQNMKQHGRKKSKGLRGL NYALSNFDYGKIMGLVKYKAESENVPLLTVLPAGTSQNCAYCLLYGKEQG NYVRNNVNSKIGKCKLHGEIDADINAARTIAICYHKNINEPKPYGERKTF KRK |
| PtCas12f1 | 16 | MKYTKVMRYQIIKPLNAEWDELGMVLRDIQKETRAALNKTIQLCWEYQGF SADYKQIHGQYPKPKDVLGYTSMHGYAYDRLKNEFSKIASSNLSQTIKRA VDKWNSDLKEILRGDRSIPNFRKDCPIDIVKQSTKIQKCNDGYVLSLGLI NREYKNELGRKNGVFDVLIKANDKTQQTILERIINGDYTYTASQIINHKN KWFINLTYQFETKETALDPNNVMGVDLGIVYPVYIAFNNSLHRYHIKGGE IERFRRQVEKRKRELLNQGKYCGDGRKGHGYATRTKSIESISDKIARFRD |

TABLE 2-continued

List of naturally occurring Cas12f proteins.

| Cas protein | SEQ ID NO | Amino acid sequence |
|---|---|---|
| | | TCNHKYSRFIVDMALKHNCGIIQMEDLTGISKESTFLKNWTYYDLQQKIE YKAREAGIQVIKIEPQYTSQRCSKCGYIDKENRQEQATFKCIECGFKTNA DYNAARNIAIPNIDKIIRKTLKMQ |
| RuCas12f1 | 17 | MTLLVKVVKIHLISEQFDKAGNRIDYEEVNKILWELQKQTREAKNKTVQL LWEWNNFSSDYVKASGIYPKAKDIFGYSSVHGQANKELRTKLALNSSNLS TTTMDVCKNFNTYKKEVWKGKRSVPSYKSDQPLDLHKDSIKLIYENNEFY VRLALLKKAEFAKYGFKDGFRFKMQVKDNSTKTILERCFDEVYKINASKL LYDQKKKKWKLNLSYSFDNKNISELDKEKILGVDVGVNCPLVASVFGDRD RFIIKGGEIEKFRKSVEARRRSMLEQTKYCGDGRIGHGRKKRTEPALNIG DKIARFRDTTNHKYSRALIEYAVKKGCGTIQMEKLTGITSKSDRFLKDWT YYDLQTKIENKAKEVGINVVYIAPKYTSQRCSKCGYIHKDNRPNQAKFRC LECDFESNADYNASQNIGIKNIDKIIEKDLQKQESEVQVNENK |
| SpCas12f1 | 18 | MGESVKAIKLKILDMFLDPECTKQDDNWRKDLSTMSRFCAEAGNMCLRDL YNYFSMPKEDRISSKDLYNAMYHKTKLLHPELPGKVANQIVNHAKDVWKR NAKLIYRNQISMPTYKITTAPIRLQNNIYKLIKNKNKYIIDVQLYSKEYS KDSGKGTHRYFLVAVRDSSTRMIFDRIMSKDHIDSSKSYTQGQLQIKKDH QGKWYCIIPYTFPTHETVLDPDKVMGVDLGVAKAVYWAFNSSYKRGCIDG GEIEHFRKMIRARRVSIQNQIKHSGDARKGHGRKRALKPIETLSEKEKNF RDTINHRYANRIVEAAIKQGCGTIQIENLEGIADTTGSKFLKNWPYYDLQ TKIVNKAKEHGITVVAINPQYTSQRCSMCGYIEKTNRSSQAVFECKQCGY GSRTICINCRHVQVSGDVCEECGGIVKKENVNADYNAAKNISTPYIDQII MEKCLELGIPYRSITCKECGHIQASGNTCEVCGSTNILKPKKIRKAK |
| CnCas12f1 | 19 | MITVRKIKLTIMGDKDTRNSQYKWIRDEQYNQYRALNMGMTYLAVNDILY MNESGLEIRTIKDLKDCEKDIDKNKKEIEKLTARLEKEQNKKNSSSEKLD EIKYKISLVENKIEDYKLKIVELNKILEETQKERMDIQKEFKEKYVDDLY QVLDKIPFKHLDNKSLVTQRIKADIKSDKSNGLLKGERSIRNYKRNFPLM TRGRDLKFKYDDNDDIEIKWMEGIKFKVILGNRIKNSLELRHTLHKVIEG KYKICDSSLQFDKNNNLILNLTLDIPIDIVNKKVSGRVVGVDLGLKIPAY CALNDVEYIKKSIGRIDDFLKVRTQMQSRRRRLQIAIQSAKGGKGRVNKL QALERFAEKEKNFAKTYNHFLSSNIVKFAVSNQAEQINMELLSLKETQNK SILRNWSYYQLQTMIEYKAQREGIKVKYIDPYHTSQTCSKCGNYEEGQRE SQADFICKKCGYKVNADYNAARNIAMSNKYITKKEESKYYKIKESMV |

TABLE 3A

List of engineered nuclease variants, such as dCasMINI and chimeric engineered nuclease variants. The number of asterisks represent the relative degree of gene modulation activity of the engineered nuclease variants.

| Engineered nuclease variant | Size (amino acids) | Activation of IFN gamma | Activation of CD2 | Chimera design |
|---|---|---|---|---|
| dCasMINI | 529 | ** | ** | SEQ ID NO: 10 |
| cA1 | 495 | — | — | Substitute K31-L105 of dCasMINI with K32-L72 of Un2Cas12f1 |
| cA2 | 495 | *** | * | Substitute K31-L77 of dCasMINI with K32-L44 of Un2Cas12f1 |
| cA3 | 496 | — | — | Substitute M1-L77 of dCasMINI with M1-L44 of Un2Cas12f1 |
| cA4 | 495 | * | — | Substitute P17-L77 of dCasMINI with P18-L44 of Un2Cas12f1 |
| cA5 | 451 | — | — | Substitute M1-W95 of dCasMINI with M1-W17 of AsCas12f1 |
| cA6 | 485 | — | — | Substitute M1-D91 of dCasMINI with M1-D47 of CnCas12f1 |
| cA7 | 462 | — | — | Substitute M1-W95 of dCasMINI with M1-W28 of SpCas12f1 |
| cA8 | 453 | — | — | Substitute M1-W95 of dCasMINI with M1-W19 of PtCas12f1 |
| cA9 | 460 | — | — | Substitute M1-E97 of dCasMINI with M1-E28 of RuCas12f1 |

TABLE 3B

Amino acid sequences of chimeric engineered nuclease variants from TABLE 3A.

| Engineered nuclease variant | SEQ ID NO | Amino acid sequence |
|---|---|---|
| cA1 | 20 | MAKNTITKTLKLRIVRPYNSAEVEKIVADEKERRKQAGGTGELDGGFYKKL EKKHSEMFSFDRLNLLLNQLQKQAAEIYNQSLIELYYEIFIKGKGIANASS VEHYLSRVCYRRAAELFKNAAIASGLRSKIKSNFRLKELKNMKSGLPTTKS DNFPIPLVKQKGGQYTGFEISNHNSDFIIKIPFGRWQVKKEIDKYRPWEKF DFEQVQKSPKPISLLLSTQRRKRNKGWSKDEGTEAEIKKVMNGDYQTSYIE VKRGSKICEKSAWMLNLSIDVPKIDKGVDPSIIGGIAVGVRSPLVCAINNA FSRYSISDNDLFHFNKKMFARRRILLKKNRHKRAGHGAKNKLKPITILTEK SERFRKKLIERWACEIADFFIKNKVGTVQMENLESMKRKEDSYFNIRLRGF WPYAEMQNKIEFKLKQYGIEIRKVAPNNTSKTCSKCGHLNNYFNFEYRKKN KFPHFKCEKCNFKENAAYNAALNISNPKLKSTKERP |
| cA3 | 21 | MEVQKTVMKTLSLRILRPLYSQEIEKEIKEEKERRKQAGGTGELDDKFYQK LRGQFPDAVFWQEISEIFRQLQKQAAEIYNQSLIELYYEIFIKGKGIANAS SVEHYLSRVCYRRAAELFKNAAIASGLRSKIKSNFRLKELKNMKSGLPTTK SDNFPIPLVKQKGGQYTGFEISNHNSDFIIKIPFGRWQVKKEIDKYRPWEK FDFEQVQKSPKPISLLLSTQRRKRNKGWSKDEGTEAEIKKVMNGDYQTSYI EVKRGSKICEKSAWMLNLSIDVPKIDKGVDPSIIGGIAVGVRSPLVCAINN AFSRYSISDNDLFHFNKKMFARRRILLKKNRHKRAGHGAKNKLKPITILTE KSERFRKKLIERWACEIADFFIKNKVGTVQMENLESMKRKEDSYFNIRLRG FWPYAEMQNKIEFKLKQYGIEIRKVAPNNTSKTCSKCGHLNNYFNFEYRKK NKFPHFKCEKCNFKENAAYNAALNISNPKLKSTKERP |
| cA4 | 22 | MAKNTITKTLKLRIVRPLYSQEIEKEIKEEKERRKQAGGTGELDDKFYQKL RGQFPDAVFWQEISEIFRQLQKQAAEIYNQSLIELYYEIFIKGKGIANASS VEHYLSRVCYRRAAELFKNAAIASGLRSKIKSNFRLKELKNMKSGLPTTKS DNFPIPLVKQKGGQYTGFEISNHNSDFIIKIPFGRWQVKKEIDKYRPWEKF DFEQVQKSPKPISLLLSTQRRKRNKGWSKDEGTEAEIKKVMNGDYQTSYIE VKRGSKICEKSAWMLNLSIDVPKIDKGVDPSIIGGIAVGVRSPLVCAINNA FSRYSISDNDLFHFNKKMFARRRILLKKNRHKRAGHGAKNKLKPITILTEK SERFRKKLIERWACEIADFFIKNKVGTVQMENLESMKRKEDSYFNIRLRGF WPYAEMQNKIEFKLKQYGIEIRKVAPNNTSKTCSKCGHLNNYFNFEYRKKN KFPHFKCEKCNFKENAAYNAALNISNPKLKSTKERP |
| cA5 | 23 | MIKVYRYEIVKPLDLDWQEISEIFRQLQKQAAEIYNQSLIELYYEIFIKGK GIANASSVEHYLSRVCYRRAAELFKNAAIASGLRSKIKSNFRLKELKNMKS GLPTTKSDNFPIPLVKQKGGQYTGFEISNHNSDFIIKIPFGRWQVKKEIDK YRPWEKFDFEQVQKSPKPISLLLSTQRRKRNKGWSKDEGTEAEIKKVMNGD YQTSYIEVKRGSKICEKSAWMLNLSIDVPKIDKGVDPSIIGGIAVGVRSPL VCAINNAFSRYSISDNDLFHFNKKMFARRRILLKKNRHKRAGHGAKNKLKP ITILTEKSERFRKKLIERWACEIADFFIKNKVGTVQMENLESMKRKEDSYF NIRLRGFWPYAEMQNKIEFKLKQYGIEIRKVAPNNTSKTCSKCGHLNNYFN FEYRKKNKFPHFKCEKCNFKENAAYNAALNISNPKLKSTKERP |
| cA6 | 24 | MITVRKIKLTIMGDKDTRNSQYKWIRDEQYNQYRALNMGMTYLAVNDAVFW QEISEIFRQLQKQAAEIYNQSLIELYYEIFIKGKGIANASSVEHYLSRVCY RRAAELFKNAAIASGLRSKIKSNFRLKELKNMKSGLPTTKSDNFPIPLVKQ KGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEK SAWMLNLSIDVPKIDKGVDPSIIGGIAVGVRSPLVCAINNAFSRYSISDND LFHFNKKMFARRRILLKKNRHKRAGHGAKNKLKPITILTEKSERFRKKLIE RWACEIADFFIKNKVGTVQMENLESMKRKEDSYFNIRLRGFWPYAEMQNKI EFKLKQYGIEIRKVAPNNTSKTCSKCGHLNNYFNFEYRKKNKFPHFKCEKC NFKENAAYNAALNISNPKLKSTKERP |
| cA7 | 25 | MGESVKAIKLKILDMFLDPECTKQDDNWQEISEIFRQLQKQAAEIYNQSLI ELYYEIFIKGKGIANASSVEHYLSRVCYRRAAELFKNAAIASGLRSKIKSN FRLKELKNMKSGLPTTKSDNFPIPLVKQKGGQYTGFEISNHNSDFIIKIPF GRWQVKKEIDKYRPWEKFDFEQVQKSPKPISLLLSTQRRKRNKGWSKDEGT EAEIKKVMNGDYQTSYIEVKRGSKICEKSAWMLNLSIDVPKIDKGVDPSII GGIAVGVRSPLVCAINNAFSRYSISDNDLFHFNKKMFARRRILLKKNRHKR AGHGAKNKLKPITILTEKSERFRKKLIERWACEIADFFIKNKVGTVQMENL ESMKRKEDSYFNIRLRGFWPYAEMQNKIEFKLKQYGIEIRKVAPNNTSKTC SKCGHLNNYFNFEYRKKNKFPHFKCEKCNFKENAAYNAALNISNPKLKSTK ERP |
| cA8 | 26 | MKYTKVMRYQIIKPLNAEWQEISEIFRQLQKQAAEIYNQSLIELYYEIFIK GKGIANASSVEHYLSRVCYRRAAELFKNAAIASGLRSKIKSNFRLKELKNM KSGLPTTKSDNFPIPLVKQKGGQYTGFEISNHNSDFIIKIPFGRWQVKKEI DKYRPWEKFDFEQVQKSPKPISLLLSTQRRKRNKGWSKDEGTEAEIKKVMN GDYQTSYIEVKRGSKICEKSAWMLNLSIDVPKIDKGVDPSIIGGIAVGVRS |

TABLE 3B-continued

Amino acid sequences of chimeric engineered nuclease variants from TABLE 3A.

| Engineered nuclease variant | SEQ ID NO | Amino acid sequence |
|---|---|---|
| | | PLVCAINNAFSRYSISDNDLFHFNKKMFARRRILLKKNRHKRAGHGAKNKL KPITILTEKSERFRKKLIERWACEIADFFIKNKVGTVQMENLESMKRKEDS YFNIRLRGFWPYAEMQNKIEFKLKQYGIEIRKVAPNNTSKTCSKCGHLNNY FNFEYRKKNKFPHFKCEKCNFKENAAYNAALNISNPKLKSTKERP |
| cA9 | 27 | MTLLVKVVKIHLISEQFDKAGNRIDYEEISEIFRQLQKQAAEIYNQSLIEL YYEIFIKGKGIANASSVEHYLSRVCYRRAAELFKNAAIASGLRSKIKSNFR LKELKNMKSGLPTTKSDNFPIPLVKQKGGQYTGFEISNHNSDFIIKIPFGR WQVKKEIDKYRPWEKFDFEQVQKSPKPISLLLSTQRRKRNKGWSKDEGTEA EIKKVMNGDYQTSYIEVKRGSKICEKSAWMLNLSIDVPKIDKGVDPSIIGG IAVGVRSPLVCAINNAFSRYSISDNDLFHFNKKMFARRRILLKKNRHKRAG HGAKNKLKPITILTEKSERFRKKLIERWACEIADFFIKNKVGTVQMENLES MKRKEDSYFNIRLRGFWPYAEMQNKIEFKLKQYGIEIRKVAPNNTSKTCSK CGHLNNYFNFEYRKKNKFPHFKCEKCNFKENAAYNAALNISNPKLKSTKER P |

TABLE 4A

List of engineered nuclease variants. The number of asterisks represent the relative degree of gene modulation activity of the engineered nuclease variants.

| Engineered nuclease variant | Size (amino acids) | Activation of IFN gamma | Activation of CD2 | Repression of eGFP (repressor type A) | Repression of eGFP (repressor type B) |
|---|---|---|---|---|---|
| dCasMINI | 529 | ** | ** | ** | ** |
| cA2 | 495 | *** | * | **** | ** |
| mA8 | 529 | **** | ** | ** | — |
| mA10 | 529 | — | ** | * | — |
| mA11 | 529 | * | * | ** | — |
| mA12 | 529 | * | * | * | * |
| mA14 | 529 | * | * | * | * |
| mB9 | 529 | — | — | * | — |
| mC7 | 529 | ** | * | ** | (no data) |
| mC16 | 529 | — | * | * | * |
| mC18 | 529 | *** | ** | (no data) | *** |
| mC21 | 529 | — | * | *** | * |
| mD2 | 529 | **** | **** | **** | (no data) |
| mD4 | 529 | **** | ** | *** | *** |
| mD5 | 529 | — | * | *** | — |
| mD6 | 529 | — | * | ** | — |
| mD7 | 529 | — | ** | *** | (no data) |
| mD15 | 529 | — | * | * | ** |

TABLE 4B

Amino acid sequences of chimeric engineered nuclease variants from TABLE 4A.

| Engineered nuclease variant | SEQ ID NO | Amino acid sequence |
|---|---|---|
| mA1 | 28 | MAKNTITKTLKLRIVRPYYSQEIEKIVAEEKNRREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mA2 | 29 | MAKNTITKTLKLRIVRPYYSAEVEKIVAEEKNNREKIALDKNKDKVKEACSK HLKVAAYCTTQVERNACLFCKARKLDDKFYKKLRGQFPDAVFWQEISEIFRQ LQKQAREIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK |

TABLE 4B-continued

Amino acid sequences of chimeric engineered nuclease variants from TABLE 4A.

| Engineered nuclease variant | SEQ ID NO | Amino acid sequence |
|---|---|---|
| | | RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mA3 | 30 | MAKNTITKTLKLRIVRPYYSAEIEKIVADEKNRREKIALEKNKDKVKEACSK HLKVAAYCTTQVERNACLFCKARKLDDKFYQKLRKQFPDAVFWQEISEIFRQ LQKQAREIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mA4 | 31 | MAKNTITKTLKLRIVRPYNSQEVEKIVAEEKNRREKIALDKNKDKVKEACSK HLKVAAYCTTQVERNACLFCKARKLDDKFYQKLRKQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mA5 | 32 | MAKNTITKTLKLRIVRPYNSQEVEKIVAEEKNNREKIALDKNKDKVKEACSK HLKVAAYCTTQVERNACLFCKARKLDDKFYKKLRKQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mA6 | 33 | MAKNTITKTLKLRIVRPYNSQEVEKIVAEEKNNREKIALDKNKDKVKEACSK HLKVAAYCTTQVERNACLFCKARKLDDKFYKKLRGQFPDAVFWQEISEIFRQ LQKQAREIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mA7 | 34 | MAKNTITKTLKLRIVRPYYSAEVEKIVAEEKNNREKIALDKNKDKVKEACSK HLKVAAYCTTQVERNACLFCKARKLDDKFYKKLRKQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mA8 | 35 | MAKNTITKTLKLRIVRPYNSAEIEKIVADEKNRREKIALDKNKDKVKEACSK HLKVAAYCTTQVERNACLFCKARKLDDKFYKKLRKQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK |

TABLE 4B-continued

Amino acid sequences of chimeric engineered nuclease variants from TABLE 4A.

| Engineered nuclease variant | SEQ ID NO | Amino acid sequence |
|---|---|---|
| | | IDKGVDPSIIGGIAVGVRSPLVCAINNAFSRYSISDNDLFHFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mA9 | 36 | MAKNTITKTLKLRIVRPYNSAEIEKIVADEKNRREKIALDKNKDKVKEACSK<br>HLKVAAYCTTQVERNACLFCKARKLDDKFYKKLRGQFPDAVFWQEISEIFRQ<br>LQKQAREIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mA10 | 37 | MAKNTITKTLKLRIVRPYNSQEIEKIVAEEKNRREKIALDKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mA11 | 38 | MAKNTITKTLKLRIVRPYNSAEIEKIVAEEKNRREKIALDKNKDKVKEACSK<br>HLKVAAYCTTQVERNACLFCKARKLDDKFYKKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mA12 | 39 | MAKNTITKTLKLRIVRPYNSAEVEKIVAEEKNRREKIALDKNKDKVKEACSK<br>HLKVAAYCTTQVERNACLFCKARKLDDKFYKKLRKQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mA13 | 40 | MAKNTITKTLKLRIVRPYNSAEVEKIVADEKNRREKIALDKNKDKVKEACSK<br>HLKVAAYCTTQVERNACLFCKARKLDDKFYKKLRKQFPDAVFWQEISEIFRQ<br>LQKQAREIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mA14 | 41 | MAKNTITKTLKLRIVRPYYSAEIEKIVADEKNRREKIALDKNKDKVKEACSK<br>HLKVAAYCTTQVERNACLFCKARKLDDKFYQKLRKQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI |

TABLE 4B-continued

Amino acid sequences of chimeric engineered nuclease variants from TABLE 4A.

| Engineered nuclease variant | SEQ ID NO | Amino acid sequence |
|---|---|---|
| | | LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mA15 | 42 | MAKNTITKTLKLRIVRPYYSAEIEKIVAEEKNRREKIALEKNKDKVKEACSK HLKVAAYCTTQVERNACLFCKARKLDDKFYQKLRKQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mA16 | 43 | MAKNTITKTLKLRIVRPYYSAEIEKIVAEEKNNREKIALDKNKDKVKEACSK HLKVAAYCTTQVERNACLFCKARKLDDKFYQKLRGQFPDAVFWQEISEIFRQ LQKQAREIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVA PNNTSKTCSKCGHLNNYFNFEYRKKNKFPHFKCEKCNFKENAAYNAALNIS NPKLKSTKERP |
| mB1 | 44 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAARLFKNA AIASGLRSKIKSNFRLKELKNMKSGLPTTKSDNFPIPLVKQKGGQYTGFKIS NHNSDFIIKIPFGRWQVKKEIDKYRPWEKFDFRQVQKSPKPISLLLSTQRRK RNKGWSKDEGTEAEIRKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPIEQLTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mB2 | 45 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAALFKNA AIASGLRSKIKSNFRLKELKNMKSGLPTTKSDNFPIPLVKQKGGQYTGFKIS NHNSDFIIKIPFGRWQVKKEIDKYRPWEKFDFRQVQKSPKPISLLLSTQRRK RNKGWSKDEGTEAEIRKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPIEQLTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mB3 | 46 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAGLFKNA AIASGLRSKIKSNFRLKELKNMKSGLPTTKSDNFPIPLVKQKGGQYTGFKIS NHNSDFIIKIPFGRWQVKKEIDKYRPWEKFDFRQVQKSPKPISLLLSTQRRK RNKGWSKDEGTEAEIRKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPIEQLTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mB4 | 47 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAARLFKNA AIASGLRSKIKSNFRLKELKNMKSGLPTTKSDNFPIPLVKQKGGQYTGFRIS NHNSDFIIKIPFGRWQVKKEIDKYRPWEKFDFRQVQKSPKPISLLLSTQRRK RNKGWSKDEGTEAEIRKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPIEQLTEKSERFRKKLIERWACEIADFFIKNKV |

TABLE 4B-continued

Amino acid sequences of chimeric engineered nuclease variants from TABLE 4A.

| Engineered nuclease variant | SEQ ID NO | Amino acid sequence |
|---|---|---|
| | | GTVQMENLESMKREDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mB5 | 48 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAALFKNA<br>AIASGLRSKIKSNFRLKELKNMKSGLPTTKSDNFPIPLVKQKGGQYTGFRIS<br>NHNSDFIIKIPFGRWQVKKEIDKYRPWEKFDFRQVQKSPKPISLLLSTQRRK<br>RNKGWSKDEGTEAEIRKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPIEQLTEKSERFRKKLIERWACEIADFFIKNKV<br>GTVQMENLESMKREDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mB6 | 49 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAGLFKNA<br>AIASGLRSKIKSNFRLKELKNMKSGLPTTKSDNFPIPLVKQKGGQYTGFRIS<br>NHNSDFIIKIPFGRWQVKKEIDKYRPWEKFDFRQVQKSPKPISLLLSTQRRK<br>RNKGWSKDEGTEAEIRKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPIEQLTEKSERFRKKLIERWACEIADFFIKNKV<br>GTVQMENLESMKREDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mB7 | 50 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAARLFKNA<br>AIASGLRSKIKSNFRLKELKNMKSGLPTTKSDNFPIPLVKQKGGQYTGFSIS<br>NHNSDFIIKIPFGRWQVKKEIDKYRPWEKFDFRQVQKSPKPISLLLSTQRRK<br>RNKGWSKDEGTEAEIRKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPIEQLTEKSERFRKKLIERWACEIADFFIKNKV<br>GTVQMENLESMKREDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mB8 | 51 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAALFKNA<br>AIASGLRSKIKSNFRLKELKNMKSGLPTTKSDNFPIPLVKQKGGQYTGFSIS<br>NHNSDFIIKIPFGRWQVKKEIDKYRPWEKFDFRQVQKSPKPISLLLSTQRRK<br>RNKGWSKDEGTEAEIRKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPIEQLTEKSERFRKKLIERWACEIADFFIKNKV<br>GTVQMENLESMKREDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mB9 | 52 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAGLFKNA<br>AIASGLRSKIKSNFRLKELKNMKSGLPTTKSDNFPIPLVKQKGGQYTGFSIS<br>NHNSDFIIKIPFGRWQVKKEIDKYRPWEKFDFRQVQKSPKPISLLLSTQRRK<br>RNKGWSKDEGTEAEIRKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPIEQLTEKSERFRKKLIERWACEIADFFIKNKV<br>GTVQMENLESMKREDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC1 | 53 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK |

TABLE 4B-continued

Amino acid sequences of chimeric engineered nuclease variants from TABLE 4A.

| Engineered nuclease variant | SEQ ID NO | Amino acid sequence |
|---|---|---|
| | | IDKGVDPSIIGGIAVGVRSPLVCAINNAFSRYSISDNDLENFNKKMFARRRI<br>LLKKNRHKRGGHGAKNKLKPIEQLTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC2 | 54 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSIEGGDLFHFNKKMFARRRI<br>LLKKNRHKRAGHGAKNKLKPIEQLTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC3 | 55 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSIEGGDLENFNKKMFARRRI<br>LLKKNRHKRGGHGRDKKLKPIEQLTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC4 | 56 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSIEGGDLENFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC5 | 57 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGRDKKLKPIEQLTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC6 | 58 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLENFNKKMFARRRI<br>LLKKNRHKRAGHGRDKKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC7 | 59 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLEHENKKMFARRRI |

TABLE 4B-continued

Amino acid sequences of chimeric engineered nuclease variants from TABLE 4A.

| Engineered nuclease variant | SEQ ID NO | Amino acid sequence |
|---|---|---|
| | | LLKKNRHKRKGHGAKNKLKPIETLTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC8 | 60 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSIDGGDLEHFNKKMFARRRI<br>LLKKNRHKRKGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC9 | 61 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSIDGGDLFHFNKKMFARRRI<br>LLKKNRHKRAGHGAKNKLKPIETLTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC10 | 62 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSIDGGDLEHFNKKMFARRRI<br>LLKKNRHKRKGHGAKNKLKPIETLTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC11 | 63 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNSFSRYSIDSNDLFKFNKKMFARRRI<br>LLKKNRHKRKGHGAKNKLKPITELTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC12 | 64 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNSFSRYSIDSNDLFHFNKKMFARRRI<br>LLKKNRHKRAGHGAAHKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC13 | 65 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNSFSRYSIDSNDLFKFNKKMFARRRI<br>LLKKNRHKRAGHGAAHKLKPITELTEKSERFRKKLIERWACEIADFFIKNKV |

TABLE 4B-continued

Amino acid sequences of chimeric engineered nuclease variants from TABLE 4A.

| Engineered nuclease variant | SEQ ID NO | Amino acid sequence |
|---|---|---|
| | | GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mC14 | 66 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSIDSNDLFKFNKKMFARRRI LLKKNRHKRAGHGAAHKLKPITILTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mC15 | 67 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNSFSRYSISDNDLFKFNKKMFARRRI LLKKNRHKRAGHGAKNKLKPITELTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mC16 | 68 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNSFSRYSISDNDLFKFNKKMFARRRI LLKKNRHKRKGHGAKNKLKPITELTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mC17 | 69 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSIDSNDLFKFNKKMFARRRI LLKKNRHKRKGHGAKNKLKPITELTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mC18 | 70 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFKFNKKMFARRRI LLKKNRHKRKGHGAAHKLKPITELTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNISNP KLKSTKERP |
| mC19 | 71 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK |

TABLE 4B-continued

Amino acid sequences of chimeric engineered nuclease variants from TABLE 4A.

| Engineered nuclease variant | SEQ ID NO | Amino acid sequence |
|---|---|---|
| | | IDKGVDPSIIGGIAVGVRSPLVCAINNAFSRYSIKGGDLERFNKKMFARRRI<br>LLKKNRHKRKGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC20 | 72 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSIKGGDLERFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC21 | 73 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSIKGGDLEKFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC22 | 74 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSIKGGDLFHFNKKMFARRRI<br>LLKKNRHKRAGHGRKKKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC23 | 75 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLEKFNKKMFARRRI<br>LLKKNRHKRAGHGRKKKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mC24 | 76 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSIKGGDLEKFNKKMFARRRI<br>LLKKNRHKRAGHGRKKKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAALNISNP<br>KLKSTKERP |
| mD1 | 77 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI |

TABLE 4B-continued

Amino acid sequences of chimeric engineered nuclease variants from TABLE 4A.

| Engineered nuclease variant | SEQ ID NO | Amino acid sequence |
|---|---|---|
| | | LLKKNRHKRAGHGAKNKLKPITILTEKSERFRKKLIERWAKEIADFFIKNKV GTVQMEDLSTMKRKEDSYFNIRLRGFWPYYEMQNKIEFKLKQYGIEIRKVAP NNTSQLCSKCGHLNNYFNFEYRKKNKFPKFKCEKCNFKENAAYNAARNISTP DIKSTKERP |
| mD2 | 78 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMEDLESMKRKEDSYFNIRLRGFWPYAEMQNKIEFKLKQYGIEIRKVAP NNTSQLCSKCGHLNNYFNFEYRKKNKFPHFKCEKCNFKENAAYNAALNISNP DIKSTKERP |
| mD3 | 79 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWAKEIADFFIKNKV GTVQMEDLSTMKRKEDSYFNIRLRGFWPYYEMQNKIEFKLKQYGIEIRKVAP NNTSKTCSKCGHLNNYFNFEYRKKNKFPHFKCEKCNFKENAAYNAALNISNP KLKSTKERP |
| mD4 | 80 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVAP NNTSQLCSKCGHLNNYFNFEYRKKNKFPKFKCEKCNFKENAAYNAALNISNP DIKSTKERP |
| mD5 | 81 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVAP NNTSQLCSKCGHLNNYFNFEYRKKNKFPHFKCEKCNFKENAAYNAALNISTP DIKSTKERP |
| mD6 | 82 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMEDLSTMKRKEDSYFNIRLRGFWPYYEMQNKIEFKLKQYGIEIRKVAP NNTSKTCSKCGHLNNYFNFEYRKKNKFPHFKCEKCNFKENAAYNAALNISNP KLKSTKERP |
| mD7 | 83 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV |

TABLE 4B-continued

Amino acid sequences of chimeric engineered nuclease variants from TABLE 4A.

| Engineered nuclease variant | SEQ ID NO | Amino acid sequence |
|---|---|---|
| | | GTVQMEDLESMKRKEDSYFNIRLRGFWPYAEMQNKIEFKLKQYGIEIRKVAP<br>NNTSQLCSKCGHLNNYFNFEYRKKNKFPFKCEKCNFKENAAYNAALNISTP<br>DIKSTKERP |
| mD8 | 84 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPFKCEKCNFKENAAYNAARNISTP<br>DIKSTKERP |
| mD9 | 85 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWSRYIADFFIKNKV<br>GTVQMEDLESMKRKEDSYFNIRLRGFWPYYEMQNKIEFKLKQYGIKIRKVAP<br>NNTSQRCSKCGHLNNYFNFEYRKKNKFPHFKCEKCNFKANAAYNAARNISNP<br>NIKSTKERP |
| mD10 | 86 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACYIADFFIKNKV<br>GTVQMEDLESMKRKEDSYFNIRLRGFWPYAEMQNKIEFKLKQYGIEIRKVAP<br>NNTSQRCSKCGHLNNYFNFEYRKKNKFPHFKCEKCNFKENAAYNAARNISNP<br>NIKSTKERP |
| mD11 | 87 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACYIADFFIKNKV<br>GTVQMENLESMKRKEDSYFNIRLRGFWPYAEMQNKIEFKLKQYGIEIRKVAP<br>NNTSQRCSKCGHLNNYFNFEYRKKNKFPHFKCEKCNFKRNAAYNAARNISNP<br>KLKSTKERP |
| mD12 | 88 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACYIADFFIKNKV<br>GTVQMEDLESMKRKEDSYFNIRLRGFWPYAEMQNKIEFKLKQYGIEIRKVAP<br>NNTSKTCSKCGHLNNYFNFEYRKKNKFPHFKCEKCNFKENAAYNAARNISNP<br>NIKSTKERP |
| mD13 | 89 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWARYIADFFIKNKV<br>GTVQMEDLESMKRKEDSYFNIRLRGFWPYYEMQNKIEFKLKQYGIKIRKVAP |

TABLE 4B-continued

Amino acid sequences of chimeric engineered nuclease variants from TABLE 4A.

| Engineered nuclease variant | SEQ ID NO | Amino acid sequence |
|---|---|---|
| | | NNTSKTCSKCGHLNNYFNFEYRKKNKFPHFKCEKCNFKENAAYNAALNISNP<br>KLKSTKERP |
| mD14 | 90 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSQRCSKCGHLNNYFNFEYRKKNKFPHFKCEKCNFKRNAAYNAARNISNP<br>NIKSTKERP |
| mD15 | 91 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACEIADFFIKNKV<br>GTVQMEDLESMKRKEDSYFNIRLRGFWPYAEMQNKIEFKLKQYGIEIRKVAP<br>NNTSQRCSKCGHLNNYFNFEYRKKNKFPHFKCEKCNFKENAAYNAARNISNP<br>NIKSTKERP |
| mD16 | 92 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSKTCSKCGHLNNYFNFEYRKKNKFPHFKCEKCNFKRNAAYNAARNISNP<br>NIKSTKERP |
| mD17 | 93 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWANRIADFFIKNKV<br>GTVQMENLESMKRKEDSYFNIRLRGFWPYAEMQNKIEFKLKQYGIKIRKVAP<br>NNTSQRCSKCGHLNNYFNFEYRKKNKFPHFKCEKCNFKRNAAYNAAKNISNP<br>KLKSTKERP |
| mD18 | 94 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIEIRKVAP<br>NNTSQRCSKCGHLNNYFNFEYRKKNKFPHFKCEKCNFKRNAAYNAAKNISNP<br>KLKSTKERP |
| mD19 | 95 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWACEIADFFIKNKV<br>GTVQMENLESMKRKEDSYFNIRLRGFWPYAEMQNKIEFKLKQYGIKIRKVAP<br>NNTSQRCSKCGHLNNYFNFEYRKKNKFPHFKCEKCNFKRNAAYNAAKNISNP |

TABLE 4B-continued

Amino acid sequences of chimeric engineered nuclease variants from TABLE 4A.

| Engineered nuclease variant | SEQ ID NO | Amino acid sequence |
|---|---|---|
| | | KLKSTKERP |
| mD20 | 96 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWANRIADFFIKNKV<br>GTVQMENLESMKRKEDSYFNIRLRGFWPYAEMQNKIEFKLKQYGIKIRKVAP<br>NNTSQRCSKCGHLNNYFNFEYRKKNKFPHFKCEKCNFKENAAYNAALNISNP<br>KLKSTKERP |
| mD21 | 97 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWANRIADFFIKNKV<br>GTVQMENLESMKRKEDSYFNIRLRGFWPYAEMQNKIEFKLKQYGIEIRKVAP<br>NNTSQRCSKCGHLNNYFNFEYRKKNKFPHFKCEKCNFKRNAAYNAALNISNP<br>KLKSTKERP |
| mD22 | 98 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPSIIGGIAVGVRSPLVCAINNAFSRYSISDNDLFHFNKKMFARRRI<br>LLKKNRHKRAGHGAKNKLKPITILTEKSERFRKKLIERWSRFIADFFIKNKV<br>GTVQMEDLESMKRKEDSYFNIRLRGFWPYYEMQNKIEFKLKQYGIEIRKVAP<br>NNTSQRCSKCGHLNNYFNFEYRKKNKFPHFKCEKCNFKENAAYNAARNISNP<br>NIKSTKERP |
| cB2 | 99 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIDVQLYSKEYSKDSGKGTHRYFLLSTQRRKRNKGWSKDEGTEAEI<br>KKVMNGDYQTSYIEVKRGSKICEKSAWMLNLSIDVPKIDKGVDPSIIGGIAV<br>GVRSPLVCAINNAFSRYSISDNDLFHFNKKMFARRRILLKKNRHKRAGHGAK<br>NKLKPITILTEKSERFRKKLIERWACEIADFFIKNKVGTVQMENLESMKRKE<br>DSYFNIRLRGFWPYAEMQNKIEFKLKQYGIEIRKVAPNNTSKTCSKCGHLNN<br>YFNFEYRKKNKFPHFKCEKCNFKENAAYNAALNISNPKLKSTKERP |
| cB3 | 100 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIASLSLLSNPAKQEMNVKRKISLLLSTQRRKRNKGWSKDEGTEAEI<br>KKVMNGDYQTSYIEVKRGSKICEKSAWMLNLSIDVPKIDKGVDPSIIGGIAV<br>GVRSPLVCAINNAFSRYSISDNDLFHFNKKMFARRRILLKKNRHKRAGHGAK<br>NKLKPITILTEKSERFRKKLIERWACEIADFFIKNKVGTVQMENLESMKRKE<br>DSYFNIRLRGFWPYAEMQNKIEFKLKQYGIEIRKVAPNNTSKTCSKCGHLNN<br>YFNFEYRKKNKFPHFKCEKCNFKENAAYNAALNISNPKLKSTKERP |
| cD1 | 101 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPI<br>YERKPNRSIVGGLAVGIRSPLVCAINNSFSRYSVDSNDVFKFSKQVFAFRRR<br>LLSKNSLKRKGHGAAHKLEPITEMTEKNDKFRKKIIERWAKEVTNFFVKNQV<br>GIVQIEDLSTMKDREDHFFNQYLRGFWPYYQMQTLIENKLKEYGIEVKRVQA<br>KYTSQLCSNPNCRYWNNYFNFEYRKVNKFPKFKCEKCNLEISAAYNAARNLS<br>TPDIEKFVAKATKGINLPEK |

TABLE 4B-continued

Amino acid sequences of chimeric engineered nuclease variants from TABLE 4A.

| Engineered nuclease variant | SEQ ID NO | Amino acid sequence |
|---|---|---|
| cD2 | 102 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPT<br>HETVLDPDKVMGVALGVAKAVYWAFNSSYKRGCIDGGEIEHFRKMIRARRVS<br>IQNQIKHSGDARKGHGRKRALKPIETLSEKEKNFRDTINHRYANRIVEAAIK<br>QGCGTIQIENLEGIADTTGSKFLKNWPYYDLQTKIVNKAKEHGITVVAINPQ<br>YTSQRCSMCGYIEKTNRSSQAVFECKQCGYGSRTICINCRHVQVSGDVCEEC<br>GGIVKKENVNAAYNAAKNISTPYIDQIIMEKCLELGIPYRSITCKECGHIQA<br>SGNTCEVCGSTNILKPKK |
| cD3 | 103 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPQ<br>TRVLDLNKIMGIALGVAVAVYMAFQHTPARYKLEGGEIENFRRQVESRRISM<br>LRQGKYAGGARGGHGRDKRIKPIEQLRDKIANFRDTTNHRYSRYIVDMAIKE<br>GCGTIQMEDLTNIRDIGSRFLQNWTYYDLQQKIIYKAEEAGIKVIKIDPQYT<br>SQRCSECGNIDSGNRIGQAIFKCRACGYEANAAYNAARNIAIPNIDKIIAES<br>IK |
| cD4 | 104 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPI<br>DIVNKKVSGRVVGVALGLKIPAYCALNDVEYIKKSIGRIDDFLKVRTQMQSR<br>RRRLQIAIQSAKGGKGRVNKLQALERFAEKEKNFAKTYNHFLSSNIVKFAVS<br>NQAEQINMELLSLKETQNKSILRNWSYYQLQTMIEYKAQREGIKVKYIDPYH<br>TSQTCSKCGNYEEGQRESQADFICKKCGYKVNAAYNAARNIAMSNKYITKKE<br>ESKYYKIKESMV |
| cD5 | 105 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVET<br>KETALDPNNVMGVALGIVYPVYIAFNNSLHRYHIKGGEIERFRRQVEKRKRE<br>LLNQGKYCGDGRKGHGYATRTKSIESISDKIARFRDTCNHKYSRFIVDMALK<br>HNCGIIQMEDLTGISKESTFLKNWTYYDLQQKIEYKAREAGIQVIKIEPQYT<br>SQRCSKCGYIDKENRQEQATFKCIECGFKTNAAYNAARNIAIPNIDKIIRKT<br>LKMQ |
| cD6 | 106 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVNRSIVGGLAVGIRSPLVCAINNSFSRYSVDSNDVPKFSKQVFAFRRR<br>LLSKNSLKRKGHGAAHKLEPITEMTEKNDKFRKKIIERWAKEVTNFFVKNQV<br>GIVQIEDLSTMKDREDHFFNQYLRGFWPYYQMQTLIENKLKEYGIEVKRVQA<br>KYTSQLCSNPNCRYWNNYFNFEYRKVNKFPKFKCEKCNLEISAAYNAARNLS<br>TPDIEKFVAKATKGINLPEK |
| cD7 | 107 | MAKNTITKTLKLRIVRPYNSAEVEKIVADEKNNREKIALEKNKDKVKEACSK<br>HLKVAAYCTTQVERNACLFCKARKLDDKFYQKLRGQFPDAVFWQEISEIFRQ<br>LQKQAAEIYNQSLIELYYEIFIKGKGIANASSVEHYLSRVCYRRAAELFKNA<br>AIASGLRSKIKSNFRLKELKNMKSGLPTTKSDNFPIPLVKQKGGQYTGFEIS<br>NHNSDFIIKIPFGRWQVKKEIDKYRPWEKFDFEQVQKSPKPISLLLSTQRRK<br>RNKGWSKDEGTEAEIKKVMNGDYQTSYIEVKRGSKICEKSAWMLNLSIDVPK<br>IDKGVDPDKVMGVALGVAKAVYWAFNSSYKRGCIDGGEIEHFRKMIRARRVS<br>IQNQIKHSGDARKGHGRKRALKPIETLSEKEKNFRDTINHRYANRIVEAAIK<br>QGCGTIQIENLEGIADTTGSKFLKNWPYYDLQTKIVNKAKEHGITVVAINPQ<br>YTSQRCSMCGYIEKTNRSSQAVFECKQCGYGSRTICINCRHVQVSGDVCEEC<br>GGIVKKENVNAAYNAAKNISTPYIDQIIMEKCLELGIPYRSITCKECGHIQA<br>SGNTCEVCGSTNILKPKK |

TABLE 4B-continued

Amino acid sequences of chimeric engineered nuclease variants from TABLE 4A.

| Engineered nuclease variant | SEQ ID NO | Amino acid sequence |
|---|---|---|
| CD8 | 108 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDLNKIMGIALGVAVAVYMAFQHTPARYKLEGGEIENFRRQVESRRIS MLRQGKYAGGARGGHGRDKRIKPIEQLRDKIANFRDTTNHRYSRYIVDMAIK EGCGTIQMEDLTNIRDIGSRFLQNWTYYDLQQKIIYKAEEAGIKVIKIDPQY TSQRCSECGNIDSGNRIGQAIFKCRACGYEANAAYNAARNIAIPNIDKIIAE SIK |
| cD9 | 109 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPNNVMGVALGIVYPVYIAFNNSLHRYHIKGGEIERFRRQVEKRKRE LLNQGKYCGDGRKGHGYATRTKSIESISDKIARFRDTCNHKYSRFIVDMALK HNCGIIQMEDLTGISKESTFLKNWTYYDLQQKIEYKAREAGIQVIKIEPQYT SQRCSKCGYIDKENRQEQATFKCIECGFKTNAAYNAARNIAIPNIDKIIRKT LKMQ |
| cD10 | 110 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDKEKILGVAVGVNCPLVASVFGDRDRFIIKGGEIEKFRKSVEARRS MLEQTKYCGDGRIGHGRKKRTEPALNIGDKIARFRDTTNHKYSRALIEYAVK KGCGTIQMEKLTGITSKSDRFLKDWTYYDLQTKIENKAKEVGINVVYIAPKY TSQRCSKCGYIHKDNRPNQAKFRCLECDFESNAAYNASQNIGIKNIDKIIEK DLQKQESEVQVNENK |
| t1 | 111 | MAKNTITKTLKLRIVRPYNSAEVEKIVADEKNNREKIALEKNKDKVKEACSK HLKVAAYCTTQVERNACLFCKARKLDDKFYQKLRGQFPDAVFWQEISEIFRQ LQKQAAEIYNQSLIELYYEIFIKGKGIANASSVEHYLSRVCYRRAAELFKNA AIASGLRSKIKSNFRLKELKNMKSGLPTTKSDNFPIPLVKQKGGQYTGFEIS NHNSDFIIKIPFGRWQVKKEIDKYRPWEKFDFEQVQKSPKPISLLLSTQRRK RNKGWSKDEGTEAEIKKVMNGDYQTSYIEVKRGSKICEKSAWMLNLSIDVPK IDKGVDPSIIGGIAVGVRSPLVCAINNAFSRYSISDNDLFHFNKKMFARRRI LLKKNRHKRAGHGAKNKLKPITILTEKSERFRKKLIERWACEIADFFIKNKV GTVQMENLESMKRKEDSYFNIRLRGFWPYAEMQNKIEFKLKQYGIEIRKVAP NNTSKTCSKCGHLNNYFNFEYRKKNKFPHFKCEKCNFKENAAYNAALNI |

TABLE 5A

Engineered nuclease variants and their set of modification(s) relative to SEQ ID NO: 1 or SEQ ID NO: 10.

| Engineered nuclease variant | Set of non-limiting modifications relative to the amino acid sequence of UnlCas12f1 (SEQ ID NO: 1) or dCasMINI (SEQ ID NO: 10), for enhanced activity as compared to dCasMINI (SEQ ID NO: 10) |
|---|---|
| cA2 | deletions: amino acids 39-72; mutations: N32E, N33R, E35K, K36Q, I37A, A38G, K73G, A74T, R75G, K76E |
| t1 | deletions: amino acids 518-529 |
| mA8 | mutations: V23I, N33R, E40D, Q83K, and G87K |
| mA10 | mutations: A21Q, V23I, D29E, N33R, and E40D |
| mC16 | mutations: A340S, H353K, A374K, and I387E |
| mD2 | mutations: N423D, K473Q, T474L, K521D, and L522I |
| mD4 | mutations: K473Q, T474L, H497K, K521D, and L522I |
| mD7 | mutations: N423D, K473Q, T474L, H497K, N519T, K521D, and L522I |
| mD15 | mutations: N423D, K473Q, T474R, L515R, K521N, and L522I |
| additional variant 1 | mutations: E151A |

TABLE 5A-continued

Engineered nuclease variants and their set of modification(s) relative to SEQ ID NO: 1 or SEQ ID NO: 10.

| Engineered nuclease variant | Set of non-limiting modifications relative to the amino acid sequence of Un1Cas12f1 (SEQ ID NO: 1) or dCasMINI (SEQ ID NO: 10), for enhanced activity as compared to dCasMINI (SEQ ID NO: 10) |
|---|---|
| additional variant 2 | mutations: N423D |
| additional variant 3 | mutations: K473Q, and T474L |
| additional variant 4 | mutations: K521D, and L522I |
| additional variant 5 | mutations: K473Q, T474L, K521D, and L522I |

TABLE 5B

Engineered nuclease variants generated by grafting different combinations of modifications onto "cA2" starting sequence, along with their efficacy in enhancing target gene activity as compared to dCasMINI (SEQ ID NO: 10).

| Engineered nuclease variant | Combination of modifications, from TABLE 5A | Enhanced activity as compared to dCasMINI (SEQ ID NO: 10)? | Size (amino acids) |
|---|---|---|---|
| cA2 | — | yes | 495 |
| cA2.1 | cA2, E151A, mC16, mD2 | yes | 495 |
| cA2.2 | cA2, E151A, mC16, mD4 | yes | 495 |
| cA2.3 | cA2, E151A, mC16, mD7 | yes | 495 |
| cA2.4 | cA2, E151A, mC16, mD15 | yes | 495 |
| cA2.5 | cA2, E151A, mC16 | yes | 495 |
| cA2.6 | cA2, E151A, mC16, mD2, t1 | yes | 483 |
| cA2.7 | cA2, E151A, mC16, mD4, t1 | yes | 483 |
| cA2.8 | cA2, E151A, mC16, mD7, t1 | yes | 483 |
| cA2.9 | cA2, E151A, mC16, mD15, t1 | yes | 483 |
| cA2.10 | cA2, E151A, mC16, t1 | yes | 483 |
| cA2.11 | cA2, E151A, mD2 | yes | 495 |
| cA2.12 | cA2, E151A, mD4 | yes | 495 |
| cA2.13 | cA2, E151A, mD7 | yes | 495 |
| cA2.14 | cA2, E151A, mD15 | yes | 495 |
| cA2.15 | cA2, E151A | yes | 495 |
| cA2.16 | cA2, E151A, mD2, t1 | yes | 483 |
| cA2.17 | cA2, E151A, mD4, t1 | yes | 483 |
| cA2.18 | cA2, E151A, mD7, t1 | yes | 483 |
| cA2.19 | cA2, E151A, mD15, t1 | yes | 483 |
| cA2.20 | cA2, E151A, t1 | yes | 483 |
| cA2.21 | cA2, mC16, mD2 | yes | 495 |
| cA2.22 | cA2, mC16, mD4 | yes | 495 |
| cA2.23 | cA2, mC16, mD7 | yes | 495 |
| cA2.24 | cA2, mC16, mD15 | yes | 495 |
| cA2.25 | cA2, mC16 | yes | 495 |
| cA2.26 | cA2, mC16, mD2, t1 | yes | 483 |
| cA2.27 | cA2, mC16, mD4, t1 | yes | 483 |
| cA2.28 | cA2, mC16, mD7, t1 | yes | 483 |
| cA2.29 | cA2, mC16, mD15, t1 | yes | 483 |
| cA2.30 | cA2, mC16, t1 | yes | 483 |
| cA2.31 | cA2, mD2 | yes | 495 |
| cA2.32 | cA2, mD4 | yes | 495 |
| cA2.33 | cA2, mD7 | yes | 495 |
| cA2.34 | cA2, mD15 | yes | 495 |
| cA2.36 | cA2, mD2, t1 | yes | 483 |
| cA2.37 | cA2, mD4, t1 | yes | 483 |
| cA2.38 | cA2, mD7, t1 | yes | 483 |
| cA2.39 | cA2, mD15, t1 | yes | 483 |
| cA2.40 | cA2, t1 | yes | 483 |
| cA2.41 | cA2, mA10, E151A, mC16, mD2 | yes | 495 |
| cA2.42 | cA2, mA10, E151A, mC16, mD4 | yes | 495 |
| cA2.43 | cA2, mA10, E151A, mC16, mD7 | yes | 495 |
| cA2.44 | cA2, mA10, E151A, mC16, mD15 | yes | 495 |
| cA2.45 | cA2, mA10, E151A, mC16 | yes | 495 |
| cA2.46 | cA2, mA10, E151A, mC16, mD2, t1 | yes | 483 |
| cA2.47 | cA2, mA10, E151A, mC16, mD4, t1 | yes | 483 |
| cA2.48 | cA2, mA10, E151A, mC16, mD7, t1 | yes | 483 |
| cA2.49 | cA2, mA10, E151A, mC16, mD15, t1 | yes | 483 |
| cA2.50 | cA2, mA10, E151A, mC16, t1 | yes | 483 |
| cA2.51 | cA2, mA10, E151A, mD2 | yes | 495 |

TABLE 5B-continued

Engineered nuclease variants generated by grafting different combinations of modifications onto "cA2" starting sequence, along with their efficacy in enhancing target gene activity as compared to dCasMINI (SEQ ID NO: 10).

| Engineered nuclease variant | Combination of modifications, from TABLE 5A | Enhanced activity as compared to dCasMINI (SEQ ID NO: 10)? | Size (amino acids) |
|---|---|---|---|
| cA2.52 | cA2, mA10, E151A, mD4 | yes | 495 |
| cA2.53 | cA2, mA10, E151A, mD7 | yes | 495 |
| cA2.54 | cA2, mA10, E151A, mD15 | yes | 495 |
| cA2.55 | cA2, mA10, E151A | no | 495 |
| cA2.56 | cA2, mA10, E151A, mD2, t1 | yes | 483 |
| cA2.57 | cA2, mA10, E151A, mD4, t1 | yes | 483 |
| cA2.58 | cA2, mA10, E151A, mD7, t1 | yes | 483 |
| cA2.59 | cA2, mA10, E151A, mD15, t1 | yes | 483 |
| cA2.60 | cA2, mA10, E151A, t1 | yes | 483 |
| cA2.61 | cA2, mA10, mC16, mD2 | yes | 495 |
| cA2.62 | cA2, mA10, mC16, mD4 | yes | 495 |
| cA2.63 | cA2, mA10, mC16, mD7 | yes | 495 |
| cA2.64 | cA2, mA10, mC16, mD15 | yes | 495 |
| cA2.65 | cA2, mA10, mC16 | yes | 495 |
| cA2.66 | cA2, mA10, mC16, mD2, t1 | yes | 483 |
| cA2.67 | cA2, mA10, mC16, mD4, t1 | yes | 483 |
| cA2.68 | cA2, mA10, mC16, mD7, t1 | yes | 483 |
| cA2.69 | cA2, mA10, mC16, mD15, t1 | yes | 483 |
| cA2.70 | cA2, mA10, mC16, t1 | yes | 483 |
| cA2.71 | cA2, mA10, mD2 | yes | 495 |
| cA2.72 | cA2, mA10, mD4 | yes | 495 |
| cA2.73 | cA2, mA10, mD7 | yes | 495 |
| cA2.74 | cA2, mA10, mD15 | yes | 495 |
| cA2.75 | cA2, mA10 | yes | 495 |
| cA2.76 | cA2, mA10, mD2, t1 | yes | 483 |
| cA2.77 | cA2, mA10, mD4, t1 | yes | 483 |
| cA2.78 | cA2, mA10, mD7, t1 | yes | 483 |
| cA2.79 | cA2, mA10, mD15, t1 | yes | 483 |
| cA2.80 | cA2, mA10, t1 | yes | 483 |
| cA2.81 | E151A, mC16, mD2 | yes | 529 |
| cA2.82 | E151A, mD2 | yes | 529 |
| cA2.83 | cA2, mA8, E151A, mD2 | yes | 495 |
| cA2.84 | cA2, mA8, E151A, mD4 | no | 495 |
| cA2.85 | cA2, mA8, mD2 | yes | 495 |
| cA2.86 | cA2, mA8, mD4 | yes | 495 |
| cA2.87 | cA2, N423D | yes | 495 |
| cA2.88 | cA2, K473Q, T474L | yes | 495 |
| cA2.89 | cA2, K521D, L522I | yes | 495 |
| cA2.90 | cA2, K473Q, T474L, K521D, L522I | yes | 495 |

TABLE 5C

The amino acid sequence of each of the engineered nuclease variants listed in TABLE 5B

| Engineered nuclease variant | SEQ ID NO | Amino acid sequence |
|---|---|---|
| cA2.1 | 112 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRRILLKKNRHKRKGHGAKNKLKPITELTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPHFKCE KCNFKENAAYNAALNISNPDIKSTKERP |
| cA2.2 | 113 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRRILLKKNRHKRKGHGAKNKLKPITELTEKSERFRKK LIERWACEIADFFIKNKVGTVQMENLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNISNPDIKSTKERP |

TABLE 5C-continued

The amino acid sequence of each of the engineered nuclease variants listed in TABLE 5B

| Engineered nuclease variant | SEQ ID NO | Amino acid sequence |
|---|---|---|
| cA2.3 | 114 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNISTPDIKSTKERP |
| cA2.4 | 115 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQRCSKCGHLNNYFNFEYRKKNKFPHFKC<br>EKCNFKENAAYNAARNISNPNIKSTKERP |
| cA2.5 | 116 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMENLESMKRKEDSYFNIRLRGFWPYAEMQ<br>NKIEFKLKQYGIEIRKVAPNNTSKTCSKCGHLNNYFNFEYRKKNKFPHFKCE<br>KCNFKENAAYNAALNISNPKLKSTKERP |
| cA2.6 | 117 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPHFKCE<br>KCNFKENAAYNAALNI |
| cA2.7 | 118 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMENLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNI |
| cA2.8 | 119 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNI |
| cA2.9 | 120 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK |

TABLE 5C-continued

The amino acid sequence of each of the engineered nuclease variants listed in TABLE 5B

| Engineered nuclease variant | SEQ ID NO | Amino acid sequence |
|---|---|---|
| | | LIERWACEIADFFIKNKVGTVQMEDLESMKRKEDSYFNIRLRGFWPYAEMQ NKIEFKLKQYGIEIRKVAPNNTSQRCSKCGHLNNYFNFEYRKKNKFPHFKC EKCNFKENAAYNAARNI |
| cA2.10 | 121 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRRILLKKNRHKRKGHGAKNKLKPITELTEKSERFRKK LIERWACEIADFFIKNKVGTVQMENLESMKRKEDSYFNIRLRGFWPYAEMQ NKIEFKLKQYGIEIRKVAPNNTSKTCSKCGHLNNYFNFEYRKKNKFPHFKCE KCNFKENAAYNAALNI |
| cA2.11 | 122 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPHFKCE KCNFKENAAYNAALNISNPDIKSTKERP |
| cA2.12 | 123 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMENLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNISNPDIKSTKERP |
| cA2.13 | 124 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNISTPDIKSTKERP |
| cA2.14 | 125 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMEDLESMKRKEDSYFNIRLRGFWPYAEMQ NKIEFKLKQYGIEIRKVAPNNTSQRCSKCGHLNNYFNFEYRKKNKFPHFKC EKCNFKENAAYNAARNISNPNIKSTKERP |
| cA2.15 | 126 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMENLESMKRKEDSYFNIRLRGFWPYAEMQ NKIEFKLKQYGIEIRKVAPNNTSKTCSKCGHLNNYFNFEYRKKNKFPHFKCE KCNFKENAAYNAALNISNPKLKSTKERP |
| cA2.16 | 127 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ |

TABLE 5C-continued

The amino acid sequence of each of the engineered nuclease variants listed in TABLE 5B

| Engineered nuclease variant | SEQ ID NO | Amino acid sequence |
|---|---|---|
| | | VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPHFKCE<br>KCNFKENAAYNAALNI |
| cA2.17 | 128 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMENLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNI |
| cA2.18 | 129 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNI |
| cA2.19 | 130 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMEDLESMKRKEDSYFNIRLRGFWPYAEMQ<br>NKIEFKLKQYGIEIRKVAPNNTSQRCSKCGHLNNYFNFEYRKKNKFPHFKC<br>EKCNFKENAAYNAARNI |
| cA2.20 | 131 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMEDLESMKRKEDSYFNIRLRGFWPYAEMQ<br>NKIEFKLKQYGIEIRKVAPNNTSKTCSKCGHLNNYFNFEYRKKNKFPHFKCE<br>KCNFKENAAYNAALNI |
| cA2.21 | 132 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPHFKCE<br>KCNFKENAAYNAALNISNPDIKSTKERP |
| cA2.22 | 133 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMENLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNISNPDIKSTKERP |

TABLE 5C-continued

The amino acid sequence of each of the engineered nuclease variants listed in TABLE 5B

| Engineered nuclease variant | SEQ ID NO | Amino acid sequence |
|---|---|---|
| cA2.23 | 134 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNISTPDIKSTKERP |
| cA2.24 | 135 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQRCSKCGHLNNYFNFEYRKKNKFPHFKC<br>EKCNFKENAAYNAARNISNPNIKSTKERP |
| cA2.25 | 136 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRILLKKNRHKRKGHGAKNKLKPITELTEKSERFRKK<br>LIERWACEIADFFIKNKVGTVQMENLESMKRKEDSYFNIRLRGFWPYAEMQ<br>NKIEFKLKQYGIEIRKVAPNNTSKTCSKCGHLNNYFNFEYRKKNKFPHFKCE<br>KCNFKENAAYNAALNISNPKLKSTKERP |
| cA2.26 | 137 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPHFKCE<br>KCNFKENAAYNAALNI |
| cA2.27 | 138 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRILLKKNRHKRKGHGAKNKLKPITELTEKSERFRKK<br>LIERWACEIADFFIKNKVGTVQMENLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNI |
| cA2.28 | 139 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNI |
| cA2.29 | 140 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRILLKKNRHKRKGHGAKNKLKPITELTEKSERFRKK<br>LIERWACEIADFFIKNKVGTVQMEDLESMKRKEDSYFNIRLRGFWPYAEMQ |

TABLE 5C-continued

The amino acid sequence of each of the engineered nuclease variants listed in TABLE 5B

| Engineered nuclease variant | SEQ ID NO | Amino acid sequence |
|---|---|---|
| | | NKIEFKLKQYGIEIRKVAPNNTSQRCSKCGHLNNYFNFEYRKKNKFPHFKC EKCNFKENAAYNAARNI |
| cA2.30 | 141 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRRILLKKNRHKRKGHGAKNLKPITELTEKSERFRKK LIERWACEIADFFIKNKVGTVQMENLESMKRKEDSYFNIRLRGFWPYAEMQ NKIEFKLKQYGIEIRKVAPNNTSKTCSKCGHLNNYFNFEYRKKNKFPHFKCE KCNFKENAAYNAALNI |
| cA2.31 | 142 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNLKPITILTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPHFKCE KCNFKENAAYNAALNISNPDIKSTKERP |
| cA2.32 | 143 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNLKPITILTEKSERFRKK LIERWACEIADFFIKNKVGTVQMENLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNISNPDIKSTKERP |
| cA2.33 | 144 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNLKPITILTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNISTPDIKSTKERP |
| cA2.34 | 145 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNLKPITILTEKSERFRKK LIERWACEIADFFIKNKVGTVQMEDLESMKRKEDSYFNIRLRGFWPYAEMQ NKIEFKLKQYGIEIRKVAPNNTSQRCSKCGHLNNYFNFEYRKKNKFPHFKC EKCNFKENAAYNAARNISNPNIKSTKERP |
| cA2.35 | 146 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNLKPITILTEKSERFRKK LIERWACEIADFFIKNKVGTVQMENLESMKRKEDSYFNIRLRGFWPYAEMQ NKIEFKLKQYGIEIRKVAPNNTSKTCSKCGHLNNYFNFEYRKKNKFPHFKCE KCNFKENAAYNAALNISNPKLKSTKERP |
| cA2.36 | 147 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG |

TABLE 5C-continued

The amino acid sequence of each of the engineered nuclease variants listed in TABLE 5B

| Engineered nuclease variant | SEQ ID NO | Amino acid sequence |
|---|---|---|
| | | SKICEKSAWMLNLSIDVPKIDKGVDPSIIGGIAVGVRSPLVCAINNAFSRYSIS DNDLFHFNKKMFARRRILLKKNRHKRAGHGAKNLKPITILTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPHFKCE KCNFKENAAYNAALNI |
| cA2.37 | 148 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNLKPITILTEKSERFRKK LIERWACEIADFFIKNKVGTVQMENLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNI |
| cA2.38 | 149 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNLKPITILTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNI |
| cA2.39 | 150 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNLKPITILTEKSERFRKK LIERWACEIADFFIKNKVGTVQMEDLESMKRKEDSYFNIRLRGFWPYAEMQ NKIEFKLKQYGIEIRKVAPNNTSQRCSKCGHLNNYFNFEYRKKNKFPHFKC EKCNFKENAAYNAARNI |
| cA2.40 | 151 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNLKPITILTEKSERFRKK LIERWACEIADFFIKNKVGTVQMENLESMKRKEDSYFNIRLRGFWPYAEMQ NKIEFKLKQYGIEIRKVAPNNTSKTCSKCGHLNNYFNFEYRKKNKFPHFKCE KCNFKENAAYNAALNI |
| cA2.41 | 152 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRRILLKKNRHKRKGHGAKNLKPITELTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPHFKCE KCNFKENAAYNAALNISNPDIKSTKERP |
| cA2.42 | 153 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRRILLKKNRHKRKGHGAKNLKPITELTEKSERFRKK LIERWACEIADFFIKNKVGTVQMENLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNISNPDIKSTKERP |
| cA2.43 | 154 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE |

TABLE 5C-continued

The amino acid sequence of each of the engineered nuclease variants listed in TABLE 5B

| Engineered nuclease variant | SEQ ID NO | Amino acid sequence |
|---|---|---|
| | | HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRRILLKKNRHKRKGHGAKNLKPITELTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNISTPDIKSTKERP |
| cA2.44 | 155 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRILLKKNRHKRKGHGAKNLKPITELTEKSERFRKK LIERWACEIADFFIKNKVGTVQMEDLESMKRKEDSYFNIRLRGFWPYAEMQ NKIEFKLKQYGIEIRKVAPNNTSQRCSKCGHLNNYFNFEYRKKNKFPHFKC EKCNFKENAAYNAARNISNPNIKSTKERP |
| cA2.45 | 156 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRILLKKNRHKRKGHGAKNLKPITELTEKSERFRKK LIERWACEIADFFIKNKVGTVQMENLESMKRKEDSYFNIRLRGFWPYAEMQ NKIEFKLKQYGIEIRKVAPNNTSKTCSKCGHLNNYFNFEYRKKNKFPHFKCE KCNFKENAAYNAALNISNPKLKSTKERP |
| cA2.46 | 157 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRILLKKNRHKRKGHGAKNLKPITELTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPHFKCE KCNFKENAAYNAALNI |
| cA2.47 | 158 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRILLKKNRHKRKGHGAKNLKPITELTEKSERFRKK LIERWACEIADFFIKNKVGTVQMENLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNI |
| cA2.48 | 159 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRILLKKNRHKRKGHGAKNLKPITELTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNI |
| cA2.49 | 160 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRILLKKNRHKRKGHGAKNLKPITELTEKSERFRKK LIERWACEIADFFIKNKVGTVQMEDLESMKRKEDSYFNIRLRGFWPYAEMQ NKIEFKLKQYGIEIRKVAPNNTSQRCSKCGHLNNYFNFEYRKKNKFPHFKC EKCNFKENAAYNAARNI |

TABLE 5C-continued

The amino acid sequence of each of the engineered nuclease variants listed in TABLE 5B

| Engineered nuclease variant | SEQ ID NO | Amino acid sequence |
|---|---|---|
| cA2.50 | 161 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMENLESMKRKEDSYFNIRLRGFWPYAEMQ<br>NKIEFKLKQYGIEIRKVAPNNTSKTCSKCGHLNNYFNFEYRKKNKFPHFKCE<br>KCNFKENAAYNAALNI |
| cA2.51 | 162 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPHFKCE<br>KCNFKENAAYNAALNISNPDIKSTKERP |
| cA2.52 | 163 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMENLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNISNPDIKSTKERP |
| cA2.53 | 164 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNISTPDIKSTKERP |
| cA2.54 | 165 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMEDLESMKRKEDSYFNIRLRGFWPYAEMQ<br>NKIEFKLKQYGIEIRKVAPNNTSQRCSKCGHLNNYFNFEYRKKNKFPHFKC<br>EKCNFKENAAYNAARNISNPNIKSTKERP |
| cA2.55 | 166 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMENLESMKRKEDSYFNIRLRGFWPYAEMQ<br>NKIEFKLKQYGIEIRKVAPNNTSKTCSKCGHLNNYFNFEYRKKNKFPHFKCE<br>KCNFKENAAYNAALNISNPKLKSTKERP |
| cA2.56 | 167 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK |

TABLE 5C-continued

The amino acid sequence of each of the engineered nuclease variants listed in TABLE 5B

| Engineered nuclease variant | SEQ ID NO | Amino acid sequence |
|---|---|---|
| | | LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPHFKCE<br>KCNFKENAAYNAALNI |
| cA2.57 | 168 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMENLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNI |
| cA2.58 | 169 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNI |
| cA2.59 | 170 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMEDLESMKRKEDSYFNIRLRGFWPYAEMQ<br>NKIEFKLKQYGIEIRKVAPNNTSQRCSKCGHLNNYFNFEYRKKNKFPHFKC<br>EKCNFKENAAYNAARNI |
| cA2.60 | 171 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMENLESMKRKEDSYFNIRLRGFWPYAEMQ<br>NKIEFKLKQYGIEIRKVAPNNTSKTCSKCGHLNNYFNFEYRKKNKFPHFKCE<br>KCNFKENAAYNAALNI |
| cA2.61 | 172 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPHFKCE<br>KCNFKENAAYNAALNISNPDIKSTKERP |
| cA2.62 | 173 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMENLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNISNPDIKSTKERP |
| cA2.63 | 174 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ |

TABLE 5C-continued

The amino acid sequence of each of the engineered nuclease variants listed in TABLE 5B

| Engineered nuclease variant | SEQ ID NO | Amino acid sequence |
|---|---|---|
| | | VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNISTPDIKSTKERP |
| cA2.64 | 175 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQRCSKCGHLNNYFNFEYRKKNKFPHFKC<br>EKCNFKENAAYNAARNISNPNIKSTKERP |
| cA2.65 | 176 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMENLESMKRKEDSYFNIRLRGFWPYAEMQ<br>NKIEFKLKQYGIEIRKVAPNSKTCSKCGHLNNYFNFEYRKKNKFPHFKCE<br>KCNFKENAAYNAALNISNPKLKSTKERP |
| cA2.66 | 177 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPHFKCE<br>KCNFKENAAYNAALNI |
| cA2.67 | 178 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMENLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNI |
| cA2.68 | 179 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNI |
| cA2.69 | 180 | MAKNTITKTLKLRIVRPYNSQEIEKIVAEEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNSFSRYSIS<br>DNDLFKFNKKMFARRRILLKKNRHKRKGHGAKNKLKPITELTEKSERFRKK<br>LIERWACEIADFFIKNKVGTVQMEDLESMKRKEDSYFNIRLRGFWPYAEMQ<br>NKIEFKLKQYGIEIRKVAPNNTSQRCSKCGHLNNYFNFEYRKKNKFPHFKC<br>EKCNFKENAAYNAARNI |

TABLE 5C-continued

The amino acid sequence of each of the engineered nuclease variants listed in TABLE 5B

| Engineered nuclease variant | SEQ ID NO | Amino acid sequence |
|---|---|---|
| cA2.70 | 181 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNSFSRYSIS DNDLFKFNKKMFARRRILLKKNRHKRKGHGAKNKLKPITELTEKSERFRKK LIERWACEIADFFIKNKVGTVQMENLESMKRKEDSYFNIRLRGFWPYAEMQ NKIEFKLKQYGIEIRKVAPNNTSKTCSKCGHLNNYFNFEYRKKNKFPHFKCE KCNFKENAAYNAALNI |
| cA2.71 | 182 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPHFKCE KCNFKENAAYNAALNISNPDIKSTKERP |
| cA2.72 | 183 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMENLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNISNPDIKSTKERP |
| cA2.73 | 184 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNISTPDIKSTKERP |
| cA2.74 | 185 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMEDLESMKRKEDSYFNIRLRGFWPYAEMQ NKIEFKLKQYGIEIRKVAPNNTSQRCSKCGHLNNYFNFEYRKKNKFPHFKC EKCNFKENAAYNAARNISNPNIKSTKERP |
| cA2.75 | 186 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMENLESMKRKEDSYFNIRLRGFWPYAEMQ NKIEFKLKQYGIEIRKVAPNNTSKTCSKCGHLNNYFNFEYRKKNKFPHFKCE KCNFKENAAYNAALNISNPKLKSTKERP |
| cA2.76 | 187 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMEDLESMKRKEDSYFNIRLRGFWPYAEMQ |

TABLE 5C-continued

The amino acid sequence of each of the engineered nuclease variants listed in TABLE 5B

| Engineered nuclease variant | SEQ ID NO | Amino acid sequence |
|---|---|---|
| | | NKIEFKLKQYGIEIRKVAPNNTSQLCSKCGHLNNYFNFEYRKKNKFPHFKCE KCNFKENAAYNAALNI |
| cA2.77 | 188 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMENLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNI |
| cA2.78 | 189 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMEDLESMKRKEDSYFNIRLRGFWPYAEMQ NKIEFKLKQYGIEIRKVAPNNTSQLCSKCGHLNNYFNFEYRKKNKFPKFKCE KCNFKENAAYNAALNI |
| cA2.79 | 190 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMEDLESMKRKEDSYFNIRLRGFWPYAEMQ NKIEFKLKQYGIEIRKVAPNNTSQRCSKCGHLNNYFNFEYRKKNKFPHFKC EKCNFKENAAYNAARNI |
| cA2.80 | 191 | MAKNTITKTLKLRIVRPYNSQEIEKIVAEEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMENLESMKRKEDSYFNIRLRGFWPYAEMQ NKIEFKLKQYGIEIRKVAPNNTSKTCSKCGHLNNYFNFEYRKKNKFPHFKCE KCNFKENAAYNAALNI |
| cA2.81 | 192 | MAKNTITKTLKLRIVRPYNSAEVEKIVADEKNNREKIALEKNKDKVKEACS KHLKVAAYCTTQVERNACLFCKARKLDDKFYQKLRGQFPDAVFWQEISEI FRQLQKQAAEIYNQSLIELYYEIFIKGKGIANASSVEHYLSRVCYRRAAALF KNAAIASGLRSKIKSNFRLKELKNMKSGLPTTKSDNFPIPLVKQKGGQYTGF EISNHNSDFIIKIPFGRWQVKKEIDKYRPWEKFDFEQVQKSPKPISLLLSTQR RKRNKGWSKDEGTEAEIKKVMNGDYQTSYIEVKRGSKICEKSAWMLNLSI DVPKIDKGVDPSIIGGIAVGVRSPLVCAINNSFSRYSISDNDLFKFNKKMFAR RRILLKKNRHKRKGHGAKNKLKPITELTEKSERFRKKLIERWACEIADFFIK NKVGTVQMEDLESMKRKEDSYFNIRLRGFWPYAEMQNKIEFKLKQYGIEIR KVAPNNTSQLCSKCGHLNNYFNFEYRKKNKFPHFKCEKCNFKENAAYNAA LNISNPDIKSTKERP |
| cA2.82 | 193 | MAKNTITKTLKLRIVRPYNSAEVEKIVADEKNNREKIALEKNKDKVKEACS KHLKVAAYCTTQVERNACLFCKARKLDDKFYQKLRGQFPDAVFWQEISEI FRQLQKQAAEIYNQSLIELYYEIFIKGKGIANASSVEHYLSRVCYRRAAALF KNAAIASGLRSKIKSNFRLKELKNMKSGLPTTKSDNFPIPLVKQKGGQYTGF EISNHNSDFIIKIPFGRWQVKKEIDKYRPWEKFDFEQVQKSPKPISLLLSTQR RKRNKGWSKDEGTEAEIKKVMNGDYQTSYIEVKRGSKICEKSAWMLNLSI DVPKIDKGVDPSIIGGIAVGVRSPLVCAINNAFSRYSISDNDLFHFNKKMFAR RRILLKKNRHKRAGHGAKNKLKPITILTEKSERFRKKLIERWACEIADFFIKN KVGTVQMEDLESMKRKEDSYFNIRLRGFWPYAEMQNKIEFKLKQYGIEIRK VAPNNTSQLCSKCGHLNNYFNFEYRKKNKFPHFKCEKCNFKENAAYNAAL NISNPDIKSTKERP |
| cA2.83 | 194 | MAKNTITKTLKLRIVRPYNSAEIEKIVADEKERRKQAGGTGELDDKFYKKL RKQFPDAVFWQEISEIFRQLQKQAAEIYNQSLIELYYEIFIKGKGIANASSVE HYLSRVCYRRAAALFKNAAIASGLRSKIKSNFRLKELKNMKSGLPTTKSDN |

TABLE 5C-continued

The amino acid sequence of each of the engineered nuclease variants listed in TABLE 5B

| Engineered nuclease variant | SEQ ID NO | Amino acid sequence |
|---|---|---|
| | | FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPHFKCE<br>KCNFKENAAYNAALNISNPDIKSTKERP |
| cA2.84 | 195 | MAKNTITKTLKLRIVRPYNSAEIEKIVADEKERRKQAGGTGELDDKFYKKL<br>RKQFPDAVFWQEISEIFRQLQKQAAEIYNQSLIELYYEIFIKGKGIANASSVE<br>HYLSRVCYRRAAALFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMENLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNISNPDIKSTKERP |
| cA2.85 | 196 | MAKNTITKTLKLRIVRPYNSAEIEKIVADEKERRKQAGGTGELDDKFYKKL<br>RKQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMEDLESMKRKEDSYFNIRLRGFWPYAEMQ<br>NKIEFKLKQYGIEIRKVAPNNTSQLCSKCGHLNNYFNFEYRKKNKFPHFKCE<br>KCNFKENAAYNAALNISNPDIKSTKERP |
| cA2.86 | 197 | MAKNTITKTLKLRIVRPYNSAEIEKIVADEKERRKQAGGTGELDDKFYKKL<br>RKQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMENLESMKRKEDSYFNIRLRGFWPYAEMQ<br>NKIEFKLKQYGIEIRKVAPNNTSQLCSKCGHLNNYFNFEYRKKNKFPKFKCE<br>KCNFKENAAYNAALNISNPDIKSTKERP |
| cA2.87 | 198 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMEDLESMKRKEDSYFNIRLRGFWPYAEMQ<br>NKIEFKLKQYGIEIRKVAPNNTSKTCSKCGHLNNYFNFEYRKKNKFPHFKCE<br>KCNFKENAAYNAALNISNPKLKSTKERP |
| cA2.88 | 199 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMENLESMKRKEDSYFNIRLRGFWPYAEMQ<br>NKIEFKLKQYGIEIRKVAPNNTSQLCSKCGHLNNYFNFEYRKKNKFPHFKCE<br>KCNFKENAAYNAALNISNPKLKSTKERP |
| cA2.89 | 200 | MAKNTITKTLKLRIVRPYNSAEVEKIVADEKERRKQAGGTGELDDKFYQKL<br>RGQFPDAVFWQEISEIFRQLQKQAAEIYNQSLIELYYEIFIKGKGIANASSVE<br>HYLSRVCYRRAAELFKNAAIASGLRSKIKSNFRLKELKNMKSGLPTTKSDN<br>FPIPLVKQKGGQYTGFEISNHNSDFIIKIPFGRWQVKKEIDKYRPWEKFDFEQ<br>VQKSPKPISLLLSTQRRKRNKGWSKDEGTEAEIKKVMNGDYQTSYIEVKRG<br>SKICEKSAWMLNLSIDVPKIDKGVDPSIIGGIAVGVRSPLVCAINNAFSRYSIS<br>DNDLFHFNKKMFARRRILLKKNRHKRAGHGAKNKLKPITILTEKSERFRKK<br>LIERWACEIADFFIKNKVGTVQMENLESMKRKEDSYFNIRLRGFWPYAEMQ<br>NKIEFKLKQYGIEIRKVAPNNTSKTCSKCGHLNNYFNFEYRKKNKFPHFKCE<br>KCNFKENAAYNAALNISNPDIKSTKERP |

TABLE 5C-continued

The amino acid sequence of each of the engineered nuclease variants listed in TABLE 5B

| Engineered nuclease variant | SEQ ID NO | Amino acid sequence |
|---|---|---|
| cA2.90 | 201 | MAKNTITKTLKLRIVRPYNSAEVEKIVADEKERRKQAGGTGELDDKFYQKL RGQFPDAVFWQEISEIFRQLQKQAAEIYNQSLIELYYEIFIKGKGIANASSVE HYLSRVCYRRAAELFKNAAIASGLRSKIKSNFRLKELKNMKSGLPTTKSDN FPIPLVKQKGGQYTGFEISNHNSDFIIKIPFGRWQVKKEIDKYRPWEKFDFEQ VQKSPKPISLLLSTQRRKRNKGWSKDEGTEAEIKKVMNGDYQTSYIEVKRG SKICEKSAWMLNLSIDVPKIDKGVDPSIIGGIAVGVRSPLVCAINNAFSRYSIS DNDLFHFNKKMFARRRILLKKNRHKRAGHGAKNKLKPITILTEKSERFRKK LIERWACEIADFFIKNKVGTVQMENLESMKRKEDSYFNIRLRGFWPYAEMQ NKIEFKLKQYGIEIRKVAPNNTSQLCSKCGHLNNYFNFEYRKKNKFPHFKCE KCNFKENAAYNAALNISNPDIKSTKERP |

TABLE 6A

List of gRNA scaffold variants from first round. The number of asterisks represent the relative degree of gene modulation activity of the gRNA scaffold variants.

| Guide NA scaffold (first round) | Length w/o spacer (bp) | Suppression of GFP (5 d.p.t.) | Comparable or improved activity to SQ w/reduced size |
|---|---|---|---|
| SQ (positive control) | 159 | *** | |
| 2 | 139 | — | |
| 3 | 138 | * | |
| 4 | 137 | *** | yes |
| 5 | 136 | *** | yes |
| 6 | 151 | *** | yes |
| 7 | 148 | *** | yes |
| 8 | 157 | *** | yes |
| 9 | 153 | *** | yes |
| 10 | 153 | *** | yes |
| 11 | 151 | *** | yes |
| 12 | 153 | *** | yes |
| 13 | 149 | *** | yes |
| 14 | 132 | * | |
| 15 | 132 | * | |
| 16 | 131 | * | |
| 17 | 134 | * | |
| 18 | 134 | * | |
| 19 | 136 | ** | |
| 20 | 135 | *** | yes |
| 21 | 133 | * | |
| 22 | 131 | * | |
| 23 | 129 | * | |
| 24 | 126 | ** | |
| 25 | 124 | *** | yes |
| 26 | 122 | — | |
| 27 | 120 | * | |
| 28 | 118 | ** | |
| 29 | 116 | ** | yes |
| 30 | 114 | — | |
| 31 | 161 | — | |
| 32 | 164 | — | |
| 33 | 164 | ** | |
| 34 | 169 | ** | |
| 35 | 140 | * | |
| 36 | 149 | ** | |
| 37 | 142 | * | |
| 38 | 140 | — | |
| 39 | 122 | ** | |
| 40 | 120 | * | |
| 41 | 100 | ** | |
| 42 | 98 | — | |
| 43 | 110 | ** | |
| 44 | 108 | * | |
| 45 | 104 | *** | yes |
| 46 | 109 | ** | |

TABLE 6B

List of gRNA scaffold variants and the respective polynucleotide sequences from TABLE 6A.

| Guide NA scaffold | Position relative to spacer | SEQ ID NO | Guide nucleic acid (NA) scaffold sequence (without spacer) |
|---|---|---|---|
| SQ | 5' of spacer | 500 | GGCTTCACTGATAAAGTGGAGAACCGCTTCACCAAAAGCTGTC CCTTAGGGGATTAGAACTTGAGTGAAGGTGGGCTGCTTGCATC AGCCTAATGTCGAGAAGTGCTTTCTTCGGAAAGTAACCCTCGA AACAAATTCATTTGAATGAAGGAATGCAAC |
| 2 | 5' of spacer | 501 | GAACCGCTTCACCAAAAGCTGTCCCTTAGGGGATTAGAACTTG AGTGAAGGTGGGCTGCTTGCATCAGCCTAATGTCGAGAAGTGC TTTCTTCGGAAAGTAACCCTCGAAACAAATTCATTTGAATGAA GGAATGCAAC |
| 3 | 5' of spacer | 502 | AACCGCTTCACCAAAAGCTGTCCCTTAGGGGATTAGAACTTGA GTGAAGGTGGGCTGCTTGCATCAGCCTAATGTCGAGAAGTGCT TTCTTCGGAAAGTAACCCTCGAAACAAATTCATTTGAATGAAG GAATGCAAC |

TABLE 6B-continued

List of gRNA scaffold variants and the respective polynucleotide sequences from TABLE 6A.

| Guide NA scaffold | Position relative to spacer | SEQ ID NO | Guide nucleic acid (NA) scaffold sequence (without spacer) |
|---|---|---|---|
| 4 | 5' of spacer | 503 | ACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 5 | 5' of spacer | 504 | CCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 6 | 5' of spacer | 505 | GGCTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAGCAATAAGGAATGCAAC |
| 7 | 5' of spacer | 506 | GGCTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAGAAAGGAATGCAAC |
| 8 | 5' of spacer | 507 | GGCTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATCTTCGGATTAAGGAATGCAAC |
| 9 | 5' of spacer | 508 | GGCTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTGCAAAAGGAATGCAAC |
| 10 | 5' of spacer | 509 | GGCTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCGTTAAGGAATGCAAC |
| 11 | 5' of spacer | 510 | GGCTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATGCAAAGGAATGCAAC |
| 12 | 5' of spacer | 511 | GGCTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAAGCAATTAAGGAATGCAAC |
| 13 | 5' of spacer | 512 | GGCTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAAGAAAGGAATGCAAC |
| 14 | 5' of spacer | 513 | GGCTTCACTGATAAAGTGGAGAACCGCTTCACTTAGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 15 | 5' of spacer | 514 | GGCTTCACTGATAAAGTGGAGAACCGCTTCACTTCGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 16 | 5' of spacer | 515 | GGCTTCACTGATAAAGTGGAGAACCGCTTCACTTCGGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 17 | 5' of spacer | 516 | GGCTTCACTGATAAAGTGGAGAACCGCTTCACCTTAGGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |

TABLE 6B-continued

List of gRNA scaffold variants and the respective polynucleotide sequences from TABLE 6A.

| Guide NA scaffold | Position relative to spacer | SEQ ID NO | Guide nucleic acid (NA) scaffold sequence (without spacer) |
|---|---|---|---|
| 18 | 5' of spacer | 517 | GGCTTCACTGATAAAGTGGAGAACCGCTTCACCTTCGGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 19 | 5' of spacer | 518 | GGCTTCACTGATAAAGTGGAGAACCGCTTCACGCTTCGGCAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 20 | 5' of spacer | 519 | ACCGCTTCACCAAAAGCTGTCCTTAGGGATTAGAACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 21 | 5' of spacer | 520 | ACCGCTTCACCAAAAGCTGTCTTAGGATTAGAACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 22 | 5' of spacer | 521 | ACCGCTTCACCAAAAGCTGTTTAGATTAGAACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 23 | 5' of spacer | 522 | ACCGCTTCACCAAAAGCTGTTAGTTAGAACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 24 | 5' of spacer | 523 | ACCGCTTCACCAAAAGCTTTAGAGAACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 25 | 5' of spacer | 524 | ACCGCTTCACCAAAAGCTTCGGCACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 26 | 5' of spacer | 525 | ACCGCTTCACCAAAAGTTCGCACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 27 | 5' of spacer | 526 | ACCGCTTCACCAAAATTCGTCTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 28 | 5' of spacer | 527 | ACCGCTTCACCAAGTTCGCTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 29 | 5' of spacer | 528 | ACCGCTTCACCAATTCGTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 30 | 5' of spacer | 529 | ACCGCTTCACCATTCGTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
| 31 | 5' of spacer | 530 | GGCTTCACTGATAAAGTGGAGAACCGCTTCACCAAAAGCTGTCCTTAGGGATTAGAACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
|  | 3' of spacer | 531 | TT |
| 32 | 5' of spacer | 532 | GGCTTCACTGATAAAGTGGAGAACCGCTTCACCAAAAGCTGTCCTTAGGGGATTAGAACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
|  | 3' of spacer | 533 | TTTTA |

TABLE 6B-continued

List of gRNA scaffold variants and the respective
polynucleotide sequences from TABLE 6A.

| Guide NA scaffold | Position relative to spacer | SEQ ID NO | Guide nucleic acid (NA) scaffold sequence (without spacer) |
|---|---|---|---|
| 33 | 5' of spacer | 534 | GGCTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
|  | 3' of spacer | 535 | TTTTG |
| 34 | 5' of spacer | 536 | GGCTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
|  | 3' of spacer | 537 | TTTTATTTTT |
| 35 | 5' of spacer | 538 | GGCTTCACTGATAAAGTGGAGAACCGCTTCACCGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
|  | 3' of spacer | 539 | TTTTATTTTT |
| 36 | 5' of spacer | 540 | GGCTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAAGAAAGGAATGCAAC |
| 37 | 5' of spacer | 541 | GGCTTCACTGATAAAGTGGAGAACCGCTTCACTTAGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
|  | 3' of spacer | 542 | TTTTATTTTT |
| 38 | 5' of spacer | 543 | GGCTTCACTGATAAAGTGGAGAACCGCTTCACCGAGTGAAGGTGGGCTGCTTGCATCAGCCTAATGTCGAGAAGTGCTTTCTTCGGAAAGTAACCCTCGAAACAAATTCATTTGAATGAAGGAATGCAAC |
|  | 3' of spacer | 544 | TTTTATTTTT |
| 39 | 5' of spacer | 545 | GGCTTCACTGATAAAGTGGAGAACCGCTTCACTTAGAGTGAAGGTGGGCTGCTTGCATCAGCCTAATGTCGAGAAGTGCTTTCTTCGGAAAGTAACCCTCGAAACAAAGAAAGGAATGCAAC |
| 40 | 5' of spacer | 546 | GGCTTCACTGATAAAGTGGAGAACCGCTTCACCGAGTGAAGGTGGGCTGCTTGCATCAGCCTAATGTCGAGAAGTGCTTTCTTCGGAAAGTAACCCTCGAAACAAAGAAAGGAATGCAAC |
| 41 | 5' of spacer | 547 | ACCGCTTCACTTAGAGTGAAGGTGGGCTGCTTGCATCAGCCTAATGTCGAGAAGTGCTTTCTTCGGAAAGTAACCCTCGAAACAAAGAAAGGAATGCAAC |
| 42 | 5' of spacer | 548 | ACCGCTTCACCGAGTGAAGGTGGGCTGCTTGCATCAGCCTAATGTCGAGAAGTGCTTTCTTCGGAAAGTAACCCTCGAAACAAAGAAAGGAATGCAAC |
| 43 | 5' of spacer | 549 | ACCGCTTCACTTAGAGTGAAGGTGGGCTGCTTGCATCAGCCTAATGTCGAGAAGTGCTTTCTTCGGAAAGTAACCCTCGAAACAAAGAAAGGAATGCAAC |
|  | 3' of spacer | 550 | TTTTATTTTT |
| 44 | 5' of spacer | 551 | ACCGCTTCACCGAGTGAAGGTGGGCTGCTTGCATCAGCCTAATGTCGAGAAGTGCTTTCTTCGGAAAGTAACCCTCGAAACAAAGAAAGGAATGCAAC |
|  | 3' of spacer | 552 | TTTTATTTTT |
| 45 | 5' of spacer | 553 | ACCGCTTCACGCTTCGGCAGTGAAGGTGGGCTGCTTGCATCAGCCTAATGTCGAGAAGTGCTTTCTTCGGAAAGTAACCCTCGAAACAAAGAAAGGAATGCAAC |

TABLE 6B-continued

List of gRNA scaffold variants and the respective polynucleotide sequences from TABLE 6A.

| Guide NA scaffold | Position relative to spacer | SEQ ID NO | Guide nucleic acid (NA) scaffold sequence (without spacer) |
|---|---|---|---|
| 46 | 5' of spacer | 554 | ACCGCTTCACGCTTCGGCAGTGAAGGTGGGCTGCTTGCATCAGCCTAATGTCGAGAAGTGCTTTCTTCGGAAAGTAACCCTCGAAACAAAGAAAGGAATGCAAC |
|  | 3' of spacer | 602 | TTTTA |

TABLE 7A

List of gRNA scaffold variants from second round. The number of asterisks represent the relative degree of gene modulation activity of the gRNA scaffold variants.

| Guide NA scaffold (second round) | Length w/o spacer (bp) | Suppression of GFP (5 d.p.t.) | Comparable or improved activity to SQ w/reduced size |
|---|---|---|---|
| SQ (positive control) | 159 | *** |  |
| 45.1 | 103 | *** |  |
| 2-5 | 103 | ** | yes |
| 2-6 | 103 | *** | yes |
| 2-7 | 103 | *** |  |
| 2-8 | 104 | ** |  |
| 2-9 | 105 | * |  |
| 2-10 | 102 | ** |  |
| 2-11 | 101 | — |  |
| 2-12 | 102 | * |  |
| 2-13 | 111 | — |  |
| 2-14 | 112 | * |  |
| 2-15 | 102 | ** |  |
| 2-16 | 101 | ** | yes |
| 2-17 | 100 | *** | yes |
| 2-18 | 99 | *** |  |
| 2-19 | 98 | ** |  |
| 2-20 | 97 | ** |  |
| 2-21 | 96 | — |  |
| 2-22 | 95 | — |  |
| 2-23 | 94 | — |  |
| 2-24 | 93 | — |  |
| 2-25 | 97 | ** |  |
| 2-26 | 99 | ** | yes |
| 2-27 | 98 | *** |  |
| 2-28 | 102 | * | yes |
| 2-29 | 100 | *** |  |
| 2-30 | 99 | — |  |
| 2-31 | 96 | ** |  |
| 2-32 | 95 | — |  |
| 2-33 | 103 | ** |  |
| 2-34 | 103 | — |  |
| 2-35 | 103 | — |  |
| 2-36 | 97 | — |  |
| 2-37 | 97 | * |  |

TABLE 7B

List of gRNA scaffold variants and the respective polynucleotide sequences from TABLE 7A.

| Guide NA scaffold | Position relative to spacer | SEQ ID NO | Guide nucleic acid (NA) scaffold sequence (without spacer) |
|---|---|---|---|
| 45.1 | 5' of spacer | 555 | CCGCTTCACGCTTCGGCAGTGAAGGTGGGCTGCTTGCATCAGCTAATGTCGAGAAGTGCTTTCTTCGGAAAGTAACCCTCGAAACAAAGAAAGGAATGCAAC |
| 2-5 | 5' of spacer | 556 | CCGCTTCACGCTTAGGCAGTGAAGGTGGGCTGCTTGCATCAGCTAATGTCGAGAAGTGCTTTCTTCGGAAAGTAACCCTCGAAACAAAGAAAGGAATGCAAC |
| 2-6 | 5' of spacer | 557 | CCGCTTCACTCTTAGGAAGTGAAGGTGGGCTGCTTGCATCAGCTAATGTCGAGAAGTGCTTTCTTCGGAAAGTAACCCTCGAAACAAAGAAAGGAATGCAAC |
| 2-7 | 5' of spacer | 558 | CCGCTTCACGTTTAGACAGTGAAGGTGGGCTGCTTGCATCAGCTAATGTCGAGAAGTGCTTTCTTCGGAAAGTAACCCTCGAAACAAAGAAAGGAATGCAAC |
| 2-8 | 5' of spacer | 559 | GCCGCTTCACGCTTCGGCAGTGAAGGTGGGCTGCTTGCATCAGCCTAATGTCGAGAAGTGCTTTCTTCGGAAAGTAACCCTCGAAACAAAGAAAGGAATGCAAC |
| 2-9 | 5' of spacer | 560 | GGCCGCTTCACGCTTCGGCAGTGAAGGTGGGCTGCTTGCATCAGCCTAATGTCGAGAAGTGCTTTCTTCGGAAAGTAACCCTCGAAACAAAGAAAGGAATGCAAC |

TABLE 7B-continued

List of gRNA scaffold variants and the respective polynucleotide sequences from TABLE 7A.

| Guide NA scaffold | Position relative to spacer | SEQ ID NO | Guide nucleic acid (NA) scaffold sequence (without spacer) |
|---|---|---|---|
| 2-10 | 5' of spacer | 561 | CGCTTCACGCTTCGGCAGTGAAGGTGGGCTGCTTGCATCAGCCTAATGTCGAGAAGTGCTTTCTTCGGAAAGTAACCCTCGAAACAAAGAAAGGAATGCAAC |
| 2-11 | 5' of spacer | 562 | GCTTCACGCTTCGGCAGTGAAGGTGGGCTGCTTGCATCAGCCTAATGTCGAGAAGTGCTTTCTTCGGAAAGTAACCCTCGAAACAAAGAAAGGAATGCAAC |
| 2-12 | 5' of spacer | 563 | GGCTTCACGCTTCGGCAGTGAAGGTGGGCTGCTTGCATCAGCCTAATGTCGAGAAGTGCTTTCTTCGGAAAGTAACCCTCGAAACAAAGAAAGGAATGCAAC |
| 2-13 | 5' of spacer | 564 | GCTTCACGCTTCGGCAGTGAAGGTGGGCTGCTTGCATCAGCCTAATGTCGAGAAGTGCTTTCTTCGGAAAGTAACCCTCGAAACAAAGAAAGGAATGCAAC |
|  | 3' of spacer |  | TTTTATTTTT |
| 2-14 | 5' of spacer | 565 | GGCTTCACGCTTCGGCAGTGAAGGTGGGCTGCTTGCATCAGCCTAATGTCGAGAAGTGCTTTCTTCGGAAAGTAACCCTCGAAACAAAGAAAGGAATGCAAC |
|  | 3' of spacer |  | TTTTATTTTT |
| 2-15 | 5' of spacer | 566 | CCGCTTCACGCTTCGGCAGTGAAGGTGGGCTGCTTGCATCAGCCTAATGTCGAGAAGTGCTTTCTTCGGAAAGTAACCCTCGAAACAAAGAAGGAATGCAAC |
| 2-16 | 5' of spacer | 567 | CCGCTTCACGCTTCGGCAGTGAAGGTGGGCTGCTTGCATCAGCCTAATGTCGAGAAGTGCTTTCTTCGGAAAGTAACCCTCGAAACAAAGAGGAATGCAAC |
| 2-17 | 5' of spacer | 568 | CCGCTTCACGCTTCGGCAGTGAAGGTGGGCTGCTTGCATCAGCCTAATGTCGAGAAGTGCTTTCTTCGGAAAGTAACCCTCGAAACAAAGGGAATGCAAC |
| 2-18 | 5' of spacer | 569 | CCGCTTCACGCTTCGGCAGTGAAGGTGGGCTGCTTGCATCAGCCTAATGTCGAGAAGTGCTTTCTTCGGAAAGTAACCCTCGAAACAAAGGAATGCAAC |
| 2-19 | 5' of spacer | 570 | CCGCTTCACGCTTCGGCAGTGAAGGTGGGCTGCTTGCATCAGCCTAATGTCGAGAAGTGCTTTCTTCGGAAAGTAACCCTCGAAACAAGGAATGCAAC |
| 2-20 | 5' of spacer | 571 | CCGCTTCACGCTTCGGCAGTGAAGGTGGGCTGCTTGCATCAGCCTAATGTCGAGAAGTGCTTTCTTCGGAAAGTAACCCTCGAAACAGGAATGCAAC |
| 2-21 | 5' of spacer | 572 | CCGCTTCACGCTTCGGCAGTGAAGGTGGGCTGCTTGCATCAGCCTAATGTCGAGAAGTGCTTTCTTCGGAAAGTAACCCTCGAAACGGAATGCAAC |
| 2-22 | 5' of spacer | 573 | CCGCTTCACGCTTCGGCAGTGAAGGTGGGCTGCTTGCATCAGCCTAATGTCGAGAAGTGCTTTCTTCGGAAAGTAACCCTCGAAAGGAATGCAAC |
| 2-23 | 5' of spacer | 574 | CCGCTTCACGCTTCGGCAGTGAAGGTGGGCTGCTTGCATCAGCCTAATGTCGAGAAGTGCTTTCTTCGGAAAGTAACCCTCGAAGGAATGCAAC |
| 2-24 | 5' of spacer | 575 | CCGCTTCACGCTTCGGCAGTGAAGGTGGGCTGCTTGCATCAGCCTAATGTCGAGAAGTGCTTTCTTCGGAAAGTAACCCTCGAGGAATGCAAC |
| 2-25 | 5' of spacer | 576 | CCGCTTCACGCTTCGGCAGTGAAGGTGGGCTGCTTGCATCAGCCTAATGTCGAGAAGTGCTTTCTTCGGAAAGTAACCCTCGAAACAAGAATGCAAC |
| 2-26 | 5' of spacer | 577 | CCGCTTCACGCTTCGGCAGTGAAGGTGGGCTGCTTGCATCAGCCTAATGTCGAGAAGTGCTTTCTTCGGAAAGTAACCCTCGAAACAAAGGAATGCAAC |

TABLE 7B-continued

List of gRNA scaffold variants and the respective polynucleotide sequences from TABLE 7A.

| Guide NA scaffold | Position relative to spacer | SEQ ID NO | Guide nucleic acid (NA) scaffold sequence (without spacer) |
|---|---|---|---|
| 2-27 | 5' of spacer | 578 | CCGCTTCACGCTTCGGCAGTGAAGGTGGGCTGCTTGCATCAGCCTAATGTCGAGAAGTGCTTTCTTCGGAAAGTAACCCTCGAAACAAAGAATGCAAC |
| 2-28 | 5' of spacer | 579 | CCGCTTCACGCTTCGGCAGTGAAGGTGGGCTGCTTGCATCAGCCTAATGTCGAGAAGTGCTTTCTTCGGAAAGTAACCCTCGAAACAAAGAAAGAATGCAAC |
| 2-29 | 5' of spacer | 580 | CCGCTTCACGCTTCGGCAGTGAAGGTGGGCTGCTTGCATCAGCCTAATGTCGAGAAGTGCTTTCTTCGGAAAGTAACCCTCGAAACAAAGAGAATGCAAC |
| 2-30 | 5' of spacer | 581 | CCGCTTCACGCTTCGGCAGTGAAGGTGGGCTGCTTGCATCAGCCTAATGTCGAGAAGTGCTTTCTTCGGAAAGTAACCCTCGAAACAAAGAAATGCAAC |
| 2-31 | 5' of spacer | 582 | CCGCTTCACGCTTCGGCAGTGAAGGTGGGCTGCTTGCATCAGCCTAATGTCGAGAAGTGCTTTCTTCGGAAAGTAACCCTCGAAACAGAATGCAAC |
| 2-32 | 5' of spacer | 583 | CCGCTTCACGCTTCGGCAGTGAAGGTGGGCTGCTTGCATCAGCCTAATGTCGAGAAGTGCTTTCTTCGGAAAGTAACCCTCGAAACAAATGCAAC |
| 2-33 | 5' of spacer | 584 | CCGCTTCACGCTTCGGCAGTGAAGGTGGGCTGATTGCATCAGCCTAATGTCGAGAAGTGCTTTCTTCGGAAAGTAACCCTCGAAACAAAGAAAGGAATGCAAC |
| 2-34 | 5' of spacer | 585 | CCGCTTCACGCTTCGGCAGTGAAGGTAGGCTGCTTGCATCAGCCTAATGTCGAGAAGTGCTTTCTTCGGAAAGTAACCCTCGAAACAAAGAAAGGAATGCAAC |
| 2-35 | 5' of spacer | 586 | CCGCTTCACGCTTCGGCAGTGAAGGTGGGCTGCTTGCATCAGCCCAATGTCGAGAAGTGCTTTCTTCGGAAAGTAACCCTCGAAACAAAGAAAGGAATGCAAC |
| 2-36 | 5' of spacer | 587 | GGCTTCACGCTTCGGCAGTGAAGGTAGGCTGCTTGCATCAGCCTAATGTCGAGAAGTGCTTTCTTCGGAAAGTAACCCTCGAAACAAGGAATGCAAC |
| 2-37 | 5' of spacer | 588 | GGCTTCACGCTTCGGCAGTGAAGGTGGGCTGCTTGCATCAGCCCAATGTCGAGAAGTGCTTTCTTCGGAAAGTAACCCTCGAAACAAGGAATGCAAC |

TABLE 8A

List of additional gRNA scaffold variants. The number of asterisks represent the relative degree of gene modulation activity of the gRNA scaffold variants.

| Guide NA scaffold | Length w/o spacer (bp) | Activation of CD2 (2 d.p.t.) | Comparable or improved activity to SQ w/reduced size | SEQ ID NO |
|---|---|---|---|---|
| SQ (positive control) | 159 | ** | | 500 |
| 45.1 | 103 | **** | yes | 555 |
| 2-6 | 103 | **** | yes | 557 |
| 2-17 | 100 | *** | yes | 568 |
| 2-18 | 99 | *** | yes | 569 |
| 2-25 | 97 | ** | yes | 576 |
| 2-26 | 99 | ** | yes | 577 |
| 2-27 | 98 | *** | yes | 578 |
| 2-29 | 100 | ** | yes | 580 |
| 2-33 | 103 | — | | 584 |
| 2-31 | 96 | * | | 582 |
| 3-1 | 103 | * | | 589 |
| 3-2 | 100 | * | | 590 |
| 3-3 | 99 | — | | 591 |
| 3-4 | 98 | — | | 592 |
| 3-5 | 97 | ** | yes | 593 |
| 3-6 | 99 | * | | 594 |
| 3-7 | 98 | — | | 595 |
| 3-8 | 96 | — | | 596 |
| 6 | 151 | — | | 505 |
| 20 | 135 | ** | yes | 519 |
| 29 | 116 | *** | yes | 528 |

TABLE 8B

List of additional gRNA scaffold variants from TABLE 8A.

| Guide NA scaffold | SEQ ID NO | Guide nucleic acid (NA) scaffold sequence (without spacer) |
|---|---|---|
| 3-1 | 589 | CCGCTTCACTCTTAGGAAGTGAAGGTGGGCTGATTGCATCAGCCTAATGTCGAGAAGTGCTTTCTTCGGAAAGTAACCCTCGAAACAAAGAAAGGAATGCAAC |
| 3-2 | 590 | CCGCTTCACGCTTCGGCAGTGAAGGTGGGCTGATTGCATCAGCCTAATGTCGAGAAGTGCTTTCTTCGGAAAGTAACCCTCGAAACAAAGGGAATGCAAC |
| 3-3 | 591 | CCGCTTCACGCTTCGGCAGTGAAGGTGGGCTGATTGCATCAGCCTAATGTCGAGAAGTGCTTTCTTCGGAAAGTAACCCTCGAAACAAAGGAATGCAAC |
| 3-4 | 592 | CCGCTTCACGCTTCGGCAGTGAAGGTGGGCTGATTGCATCAGCCTAATGTCGAGAAGTGCTTTCTTCGGAAAGTAACCCTCGAAACAAGGAATGCAAC |
| 3-5 | 593 | CCGCTTCACGCTTCGGCAGTGAAGGTGGGCTGATTGCATCAGCCTAATGTCGAGAAGTGCTTTCTTCGGAAAGTAACCCTCGAAACAAGAATGCAAC |
| 3-6 | 594 | CCGCTTCACGCTTCGGCAGTGAAGGTGGGCTGATTGCATCAGCCTAATGTCGAGAAGTGCTTTCTTCGGAAAGTAACCCTCGAAACAAAGGAATGCAAC |
| 3-7 | 595 | CCGCTTCACGCTTCGGCAGTGAAGGTGGGCTGATTGCATCAGCCTAATGTCGAGAAGTGCTTTCTTCGGAAAGTAACCCTCGAAACAAAGAATGCAAC |
| 3-8 | 596 | CCGCTTCACGCTTCGGCAGTGAAGGTGGGCTGATTGCATCAGCCTAATGTCGAGAAGTGCTTTCTTCGGAAAGTAACCCTCGAAACAGAATGCAAC |

TABLE 9

List of fragments derived from gRNA scaffold variants.

| Guide NA scaffold fragment | SEQ ID NO | Guide nucleic acid (NA) scaffold fragment sequence |
|---|---|---|
| Fragment of 45.1, 2-27, 2-17, and/or 2-18 | 597 | CCGCTTCACGCTTCGGCAGTGAAGGTGGGC |
| Fragment of 2-6 | 598 | CCGCTTCACTCTTAGGAAGTGAAGGTGGGC |
| Fragment of 2-27 | 599 | GAAAGTAACCCTCGAAACAAAGAATGCAAC |
| Fragment of 2-17 | 600 | AAGTAACCCTCGAAACAAAGGGAATGCAAC |
| Fragment of 2-18 | 601 | AAAGTAACCCTCGAAACAAAGGAATGCAAC |

EMBODIMENTS

The following non-limiting embodiments provide illustrative examples of the invention, but do not limit the scope of the invention.

Embodiment 1. An engineered polypeptide comprising an engineered nuclease, wherein the engineered nuclease comprises an amino acid sequence that is at least 80% identical to the polypeptide sequence of SEQ ID NO: 1,
  wherein the amino acid sequence comprises at least one deletion from the amino acid resides 2-100, as compared to the polypeptide sequence of SEQ ID NO: 1, optionally wherein:
  (1) the at least one deletion is from one or more members selected from the group consisting of the amino acid residues 30-40, the amino acid residues 40-50, the amino acid residues 50-60, the amino acid residues 60-70, and the amino acid residues 70-80, as compared to the polypeptide sequence of SEQ ID NO: 1; and/or
  (2) the at least one deletion is from one or more members selected from the group consisting of the amino acid residues 30-35, the amino acid residues 35-40, the amino acid residues 40-45, the amino acid residues 45-50, the amino acid residues 50-55, the amino acid residues 55-60, the amino acid residues 60-65, the amino acid residues 65-70, the amino acid residues 70-75, and the amino acid residues 75-80, as compared to the polypeptide sequence of SEQ ID NO: 1; and/or
  (3) the at least one deletion comprises a plurality of amino acid residues from the amino acid residues 30-80, as compared to the polypeptide sequence of SEQ ID NO: 1; and/or
  (4) the at least one deletion is from the amino acid residues 2-80, as compared to the polypeptide sequence of SEQ ID NO: 1,
    optionally wherein:
    (a) the at least one deletion is from the amino acid residues 2-60, as compared to the polypeptide sequence of SEQ ID NO: 1; and/or
    (b) the at least one deletion is from the amino acid residues 2-40, as compared to the polypeptide sequence of SEQ ID NO: 1; and/or
    (c) the at least one deletion is from the amino acid residues 2-30, as compared to the polypeptide sequence of SEQ ID NO: 1; and/or
  (5) the at least one deletion is from the amino acid residues 30-100, as compared to the polypeptide sequence of SEQ ID NO: 1,
    optionally wherein the at least one deletion is from the amino acid residues 30-80, as compared to the polypeptide sequence of SEQ ID NO: 1, further optionally wherein the at least one deletion comprises deletion of the amino acid residues 55-56, the amino acid residues 54-57, the amino acid residues 54-58, the amino acid residues 53-59, the amino acid residues 52-60, the amino acid residues 51-61, the amino acid residues 50-62, the amino acid residues 49-63, the amino acid residues 48-64, the amino acid residues 47-65, the amino acid residues 46-66, the amino acid residues 45-67, the amino acid residues 44-68, the amino acid residues 43-69, the amino acid residues 42-70, or the amino acid residues 41-71, as compared to the polypeptide sequence of SEQ ID NO: 1; and/or (6) the at least one deletion is from one or more members selected from the group consisting of the amino acid resides 2-10, the amino acid resides 11-20, the amino acid resides 21-30, the amino acid resides 31-40, the amino acid resides 41-50, the amino acid resides 51-60, the amino acid resides 61-70, and the amino acid resides 71-80, as compared to the polypeptide sequence of SEQ ID NO: 1, optionally wherein the at least one deletion is from two or more members selected from the group consisting of amino acid resides 2-10, amino acid resides 11-20, amino acid resides 21-30, amino acid resides 31-40, amino acid resides 41-50, amino acid resides 51-60, amino acid resides 61-70, and amino acid resides 71-80, as compared to the polypeptide sequence of SEQ ID NO: 1; and/or (7) the engineered nuclease comprises an amino acid substitution at D326 or D510, as compared to the amino acid sequence of SEQ ID NO: 1, thereby to reduce nuclease activity of the engineered nuclease; and/or (8) the engineered nuclease comprises one or more amino acid substitutions selected from the group consisting of D143R, T147R, K330R, and E528R, as compared to the amino acid sequence of SEQ ID NO: 1.

Embodiment 2. An engineered polypeptide comprising an engineered nuclease, wherein the engineered nuclease comprises an amino acid sequence that is at least 80% identical to the polypeptide sequence of SEQ ID NO: 1, wherein the amino acid sequence comprises at least one deletion from the amino acid resides 430-529, as compared to the polypeptide sequence of SEQ ID NO: 1, optionally wherein:
  (1) the at least one deletion is from the amino acid residues 450-529, as compared to the polypeptide sequence of SEQ ID NO: 1,
    optionally wherein:
    (a) the at least one deletion is from the amino acid residues 470-529, as compared to the polypeptide sequence of SEQ ID NO: 1; and/or
    (b) the at least one deletion is from the amino acid residues 490-529, as compared to the polypeptide sequence of SEQ ID NO: 1; and/or
    (c) the at least one deletion is from the amino acid residues 500-529, as compared to the polypeptide sequence of SEQ ID NO: 1; and/or
  (2) the at least one deletion is from one or more members selected from the group consisting of amino acid resides 450-459, amino acid resides 460-469, amino acid resides 470-479, amino acid resides 480-489, amino acid resides 490-499, amino acid resides 500-509, amino acid resides 510-519, and amino acid resides 520-529, as compared to the polypeptide sequence of SEQ ID NO: 1,
    optionally wherein the at least one deletion is from two or more members selected from the group consisting of amino acid resides 450-459, amino acid resides 460-469, amino acid resides 470-479, amino acid resides 480-489, amino acid resides 490-499, amino acid resides 500-509, amino acid resides 510-519, and amino acid resides 520-529, as compared to the polypeptide sequence of SEQ ID NO: 1; and/or
  (3) the at least one deletion is from the amino acid residues 500-529, as compared to the polypeptide sequence of SEQ ID NO: 1; and/or
  (4) the amino acid sequence is at least 85% identical, at least 90% identical, at least 95% identical, at least 96% identical, at least 97% identical, at least 98% identical, or at least 99% identical to the polypeptide sequence of SEQ ID NO: 1; and/or
  (5) the at least one deletion comprises a plurality of amino acid deletions,
    optionally wherein:
    (a) the plurality of amino acid deletions comprises at least 3 amino acid deletions, at least 4 amino acid deletions, at least 5 amino acid deletions, at least 10 amino acid deletions, at least 15 amino acid deletions, at least 20 amino acid deletions, at least 25 amino acid deletions, at least 30 amino acid deletions, at least 35 amino acid deletions, or at least 40 amino acid deletions; and/or
    (b) the plurality of amino acid deletions comprises deletion of a plurality of non-consecutive amino acids; and/or
  (6) the at least one deletion comprises deletion of a plurality of consecutive amino acid residues,
    optionally wherein the plurality of consecutive amino acid residues comprises at least 3 consecutive amino acid residues, at least 4 consecutive amino acid residues, at least 5 consecutive amino acid residues, at least 10 consecutive amino acid residues, at least 15 consecutive amino acid residues, at least 20 consecutive amino acid residues, at least 25 consecutive amino acid residues, or at least 30 consecutive amino acid residues; and/or
  (7) the engineered polypeptide further comprises one or more additional deletions from the amino acid residues 101-429, as compared to the polypeptide sequence of SEQ ID NO: 1,
    optionally wherein the one or more additional deletions comprises a plurality of additional deletions; and/or
  (8) the amino acid sequence has a length of at most 528 amino acids, at most 527 amino acids, at most 526 amino acids, at most 525 amino acids, at most 524 amino acids, at most 519 amino acids, at most 514 amino acids, at most 509 amino acids, at most 514 amino acids, at most 509 amino acids, at most 504 amino acids, or at most 489 amino acids; and/or
  (9) the engineered nuclease has a length of at most about 600 amino acids, at most about 550 amino acids, at most about 540 amino acids, or at most about 530 amino acids; and/or
  (10) the engineered nuclease exhibits reduced nuclease activity as compared to a protein encoded by SEQ ID NO: 1, optionally wherein the engineered nuclease comprises a substitution at D326 and/or D510, further optionally wherein the D326 and/or the D510 is substituted with alanine; and/or
(11) the engineered polypeptide further comprises a gene modulator coupled to the engineered nuclease, optionally wherein:
  (a) the gene modulator is fused to the engineered nuclease; and/or
  (b) the gene modulator is a transcriptional activator; and/or
  (c) the gene modulator is a transcriptional repressor; and/or
  (d) the gene modulator is a histone modifier, further optionally wherein the histone modifier is a histone methylation modifier; and/or
  (e) the gene modulator is a gene methylation modifier; and/or
  (f) the engineered polypeptide is capable of regulating expression and/or activity level of a target gene in a cell, wherein the expression and/or activity level that is regulated by the engineered polypeptide is comparable to a control polypeptide, wherein the control polypeptide comprises (i) a deactivated nuclease comprising the polypeptide sequence of SEQ ID NO: 10 and (ii) the gene modulator; and/or
(12) the engineered nuclease comprises an amino acid sequence that is at least about 80% identical to the polypeptide sequence of SEQ ID NO: 11; and/or
(13) the engineered nuclease comprises an amino acid sequence that is at least about 90% identical to the polypeptide sequence of SEQ ID NO: 11; and/or
(14) the engineered nuclease comprises one or more amino acid substitutions selected from the group consisting of D143R, T147R, K330R, and E528R, as compared to the amino acid sequence of SEQ ID NO: 1.

Embodiment 3. An engineered polypeptide comprising an engineered nuclease, wherein the engineered nuclease comprises an amino acid sequence that is greater than 92% identical to the polypeptide sequence of SEQ ID NO: 12, optionally wherein:
  (1) the amino acid sequence of the engineered nuclease is at least about 93% identical to the polypeptide sequence of SEQ ID NO: 12; and/or
  (2) the amino acid sequence of the engineered nuclease is at least about 95%, at least about 98%, or at least about 99% identical to the polypeptide sequence of SEQ ID NO: 12; and/or
  (3) the amino acid sequence of the engineered nuclease is substantially identical to the polypeptide sequence of SEQ ID NO: 12; and/or
  (4) the amino acid sequence has a length of less than or equal to about 600 amino acids, less than or equal to about 550 amino acids, or less than or equal to about 500 amino acids; and/or
  (5) the engineered nuclease comprises an amino acid substitution at D326 or D510, as compared to the amino acid sequence of SEQ ID NO: 1, thereby to reduce nuclease activity of the engineered nuclease; and/or
  (6) said engineered nuclease comprises one or more amino acid substitutions selected from the group consisting of D143R, T147R, K330R, and E528R, as compared to the amino acid sequence of SEQ ID NO: 1.

Embodiment 4. An engineered polypeptide comprising an engineered nuclease variant, wherein the engineered nuclease variant comprises an amino acid sequence that is at least 70% identical to the polypeptide sequence of SEQ ID NO: 12,
  wherein the amino acid sequence comprises a modification as compared to the polypeptide sequence of SEQ ID NO: 1, wherein the modification comprises one or more members selected from the group consisting of A21Q, V23I, N32E, D29E, N33R, E35K, K36Q, I37A, A38G, E40D, K73G, A74T, R75G, K76E, Q83K, G87K, E151A, A340S, H353K, A374K, I387E, N423D, K473Q, T474L, T474R, H497K, L515R, N519T, K521D, K521N, L522I, and at least one deletion from the amino acid residues 400-529 of SEQ ID NO: 1,
  optionally wherein:
  (1) the amino acid sequence is at least 80%, at least 85%, at least 90%, or at least 95% identical to the polypeptide sequence of SEQ ID NO: 12; and/or
  (2) the amino acid sequence is at least 80% or at least 85% identical to the polypeptide sequence of SEQ ID NO: 1; and/or
  (3) the amino acid sequence is at most 95% or at most 90% identical to the polypeptide sequence of SEQ ID NO: 1; and/or
  (4) the modification comprises at least two members, at least three members, at least four members, or at least five members selected from the group consisting of A21Q, V23I, N32E, D29E, N33R, E35K, K36Q, I37A, A38G, E40D, K73G, A74T, R75G, K76E, Q83K, G87K, E151A, A340S, H353K, A374K, I387E, N423D, K473Q, T474L, T474R, H497K, L515R, N519T, K521D, K521N, L522I, and at least one deletion from the amino acid residues 400-529 of SEQ ID NO: 1; and/or
  (5) the modification comprises the at least one deletion from the amino acid residues 400-529 of SEQ ID NO: 1 and one or more members selected from the group consisting of A21Q, V23I, D29E, N33R, E40D, Q83K, G87K, E151A, A340S, H353K, A374K, I387E, N423D, K473Q, T474L, T474R, H497K, L515R, N519T, K521D, K521N, and L522I; and/or
  (6) the modification comprises the at least one deletion from the amino acid residues 400-529 of SEQ ID NO: 1 and one or more members selected from the group consisting of N32E, N33R, E35K, K36Q, I37A, A38G, K73G, A74T, R75G, K76E; and/or
  (7) the modification comprises two or more members selected from the group consisting of N32E, N33R, E35K, K36Q, I37A, A38G, K73G, A74T, R75G, K76E; and/or
  (8) the at least one deletion is from the amino acid residues 450-529 or the amino acid residues 500-529 of SEQ ID NO: 1; and/or
  (9) the modification comprises a set of modifications selected from TABLE 5A; and/or
  (10) the modification comprises a combination of modifications selected from TABLE 5B; and/or
  (11) the combination of modifications is not cA2.55 or cA2.84 from TABLE 5B; and/or
  (12) the amino acid sequence has a length of less than or equal to about 600 amino acids, less than or equal to about 550 amino acids, or less than or equal to about 500 amino acids; and/or

(13) the engineered nuclease variant comprises an amino acid substitution at D326 or D510, as compared to the amino acid sequence of SEQ ID NO: 1, thereby to reduce nuclease activity of the engineered nuclease variant; and/or

(14) the engineered nuclease variant comprises one or more amino acid substitutions selected from the group consisting of D143R, T147R, K330R, and E528R, as compared to the amino acid sequence of SEQ ID NO: 1.

Embodiment 5. An engineered polypeptide comprising an engineered nuclease variant, wherein the engineered nuclease variant is a chimeric polypeptide comprising:

a first polypeptide sequence comprising at least 3 contiguous amino acid residues in common with a first Cas protein; and a second polypeptide sequence comprising at least 3 contiguous amino acid residues in common with a second Cas protein, wherein the second Cas protein is different from the first Cas protein, wherein the first Cas protein comprises an amino acid sequence that is at least 80% identical to the polypeptide sequence of SEQ ID NO: 1, optionally wherein:
(1) first Cas protein comprises an amino acid sequence that is at least 85%, at least 90%, at last 95%, at least 99%, or 100% identical to the polypeptide sequence of SEQ ID NO: 1; and/or
(2) the second Cas protein comprises an amino acid sequence that is at least 80%, at least 85%, at least 90%, at least 95%, at least 99%, or 100% identical to the polypeptide sequence of a Cas protein selected from TABLE 2; and/or
(3) the Cas protein is selected from TABLE 2 is Un2Cas12f1; and/or
(4) the first polypeptide comprises at least or up to about 5 contiguous amino acid residues, at least or up to about 10 contiguous amino acid residues, at least or up to about 20 contiguous amino acid residues, at least or up to about 30 contiguous amino acid residues, at least or up to about 40 contiguous amino acid residues, or at least or up to about 50 contiguous amino acid residues in common with the first Cas protein; and/or
(5) the second polypeptide comprises at least or up to about 5 contiguous amino acid residues, at least or up to about 8 contiguous amino acid residues, at least or up to about 10 contiguous amino acid residues, or at least or up to about 20 contiguous amino acid residues in common with the second Cas protein; and/or
(6) the length of the first polypeptide sequence is greater than a length of the second polypeptide sequence; and/or
(7) the second polypeptide is derived from the N-terminal 50%, from the N-terminal 40%, or from the N-terminal 20% of the second Cas protein; and/or
(8) the second polypeptide does not comprise at least the first 5 amino acids, at least the first 10 amino acids, at least the first 20 amino acids, or at least the first 30 amino acids from the N-terminus of the second Cas protein; and/or
(9) the engineered polypeptide further comprises a third polypeptide sequence comprising at least 3 contiguous amino acid residues in common with the first Cas protein, wherein the first polypeptide sequence and the third polypeptide sequence are not contiguous in the chimeric polypeptide; and/or
(10) the chimeric polypeptide has a length of less than or equal to about 600 amino acids, less than or equal to about 550 amino acids, or less than or equal to about 500 amino acids; and/or
(11) a naturally occurring form of the first Cas protein or the second Cas protein has a length of less than or equal to about 600 amino acids, less than or equal to about 550 amino acids, or less than or equal to about 500 amino acids; and/or
(12) the engineered nuclease variant comprises an amino acid substitution at D326 or D510, as compared to the amino acid sequence of SEQ ID NO: 1, thereby to reduce nuclease activity of the engineered nuclease variant; and/or
(13) the engineered nuclease variant comprises one or more amino acid substitutions selected from the group consisting of D143R, T147R, K330R, and E528R, as compared to the amino acid sequence of SEQ ID NO: 1.

Embodiment 6. An engineered polypeptide comprising an engineered nuclease variant, wherein the engineered nuclease is a chimeric polypeptide comprising:

a first polypeptide sequence (CP1) comprising at least 3 contiguous amino acid residues in common with a portion of a first Cas protein;

a second polypeptide sequence (CP2) comprising at least 3 contiguous amino acid residues in common with a portion of a second Cas protein that is different from the first Cas protein; and a third polypeptide sequence (CPx) comprising at least 3 contiguous amino acid residues in common with:
(i) an additional portion of the first Cas protein, wherein the portion and the additional portion of the first Cas protein are not directly adjacent to each other in the first Cas protein;
(ii) an additional portion of the second Cas protein, wherein the portion and the additional portion of the second Cas protein are not directly adjacent to each other in the second Cas protein; or
(iii) a portion of a third Cas protein that is different from the first Cas protein and the second Cas protein, wherein the chimeric polypeptide has a length of less than or equal to about 1,000 amino acids, optionally wherein:
(1) the chimeric polypeptide has a structure, from N-terminus to C-terminus, as shown in formula CP1-CP2-CPx     (I); and/or (2) the first Cas protein, the second Cas protein, or the third Cas protein is not Cas12a; and/or
(3) the first Cas protein or the third Cas protein comprises an amino acid sequence that is at least 85%, at least 90%, at last 95%, at least 99%, or 100% identical to the polypeptide sequence of SEQ ID NO: 1; and/or
(4) the second Cas protein comprises an amino acid sequence that is at least 80%, at least 85%, at least 90%, at least 95%, at least 99%, or 100% identical to the polypeptide sequence of a Cas protein from TABLE 2; and/or
(5) the Cas protein selected from TABLE 2 is Un2Cas12f1; and/or
(6) the third Cas protein comprises an amino acid sequence that is at least 80%, at least 85%, at least 90%, at least 95%, at least 99%, or 100% identical to the polypeptide sequence of a different Cas protein from TABLE 2; and/or (7) the CP1 polypeptide comprises at least or up to about 5 contiguous amino acid residues, at least or up to about 10 contiguous amino acid residues, at least or up to about 20 contiguous amino acid residues, at least or up to about 30 contiguous amino acid residues, at least or up to about 40 contiguous amino acid residues, or at least or up to about 50 contiguous amino acid residues in common with the portion of the first Cas protein; and/or (8) the CP2 polypeptide comprises at least or up to about 5 contiguous amino acid residues, at least or up to about 8 contiguous amino acid residues, at least or up to about 10 contiguous amino acid residues, or at least or up to about 20 contiguous amino acid residues in common with the portion of the second Cas protein; and/or (9) the CPx polypeptide comprises at least or up to about 5 contiguous amino acid residues, at least or up to about 10 contiguous amino acid residues, at least or up to about 20 contiguous amino acid residues, at least or up to about 30 contiguous amino acid residues, at least or up to about 40 contiguous amino acid residues, or at least or up to about 50 contiguous amino acid residues in common with (i), (ii), and/or (iii); and/or

(10) the chimeric polypeptide has a length of less than or equal to about 600 amino acids, less than or equal to about 550 amino acids, or less than or equal to about 500 amino acids; and/or

(11) a naturally occurring form of the first Cas protein, the second Cas protein, or the third Cas protein has a length of less than or equal to about 600 amino acids, less than or equal to about 550 amino acids, or less than or equal to about 500 amino acids; and/or

(12) the engineered nuclease variant comprises an amino acid substitution at D326 or D510, as compared to the amino acid sequence of SEQ ID NO: 1, thereby to reduce nuclease activity of the engineered nuclease variant; and/or

(13) the engineered nuclease variant comprises one or more amino acid substitutions selected from the group consisting of D143R, T147R, K330R, and E528R, as compared to the amino acid sequence of SEQ ID NO: 1.

Embodiment 7. An engineered polypeptide comprising an engineered nuclease variant, wherein the engineered nuclease variant is a chimeric polypeptide comprising:

a first polypeptide comprising at least 3 contiguous amino acid residues in common with a first Cas protein; and a second polypeptide comprising at least 3 contiguous amino acid residues in common with a second Cas protein, wherein the second Cas protein is different from the first Cas protein, wherein a length of the second polypeptide sequence is less than about 20% than that of the first polypeptide sequence, optionally wherein:

(1) the length of the second polypeptide sequence is less than about 10% than that of the first polypeptide sequence; and/or (2) the length of the second polypeptide sequence is greater than about 1% than that of the first polypeptide sequence; and/or (3) the first Cas protein, the second Cas protein, or the third Cas protein is not Cas12a; and/or (4) the first polypeptide sequence comprises a first sub-domain and a second sub-domain that (i) each comprises at least 3 contiguous amino acid residues in common with the first Cas protein, (ii) are different from each other, and (ii) are not contiguous in the chimeric polypeptide; and/or (5) the first Cas protein comprises an amino acid sequence that is at least 85%, at least 90%, at last 95%, at least 99%, or 100% identical to the polypeptide sequence of SEQ ID NO: 1; and/or (6) the second Cas protein comprises an amino acid sequence that is at least 80%, at least 85%, at least 90%, at least 95%, at least 99%, or 100% identical to the polypeptide sequence of a Cas protein selected from TABLE 2; and/or (7) the Cas protein selected from TABLE 2 is Un2Cas12f1; and/or (8) the first polypeptide comprises at least or up to about 5 contiguous amino acid residues, at least or up to about 10 contiguous amino acid residues, at least or up to about 20 contiguous amino acid residues, at least or up to about 30 contiguous amino acid residues, at least or up to about 40 contiguous amino acid residues, or at least or up to about 50 contiguous amino acid residues in common with the first Cas protein; and/or (9) the second polypeptide comprises at least or up to about 5 contiguous amino acid residues, at least or up to about 8 contiguous amino acid residues, at least or up to about 10 contiguous amino acid residues, or at least or up to about 20 contiguous amino acid residues in common with the second Cas protein; and/or

(10) the chimeric polypeptide has a length of less than or equal to about 600 amino acids, less than or equal to about 550 amino acids, or less than or equal to about 500 amino acids; and/or

(11) a naturally occurring form of the first Cas protein or the second Cas protein has a length of less than or equal to about 600 amino acids, less than or equal to about 550 amino acids, or less than or equal to about 500 amino acids; and/or

(12) the engineered nuclease variant comprises an amino acid substitution at D326 or D510, as compared to the amino acid sequence of SEQ ID NO: 1, thereby to reduce nuclease activity of the engineered nuclease variant; and/or

(13) the engineered nuclease variant comprises one or more amino acid substitutions selected from the group consisting of D143R, T147R, K330R, and E528R, as compared to the amino acid sequence of SEQ ID NO: 1.

Embodiment 8. An engineered polypeptide comprising an engineered nuclease variant, wherein the engineered nuclease variant:

(i) comprises an amino acid sequence that is at least 80% identical to the polypeptide sequence of a member selected from TABLE 3B, TABLE 4B, or TABLE 5C (ii) is not any one of SEQ ID NOs: 1-3, 10, and 13-19; and (iii) has a length of less than or equal to about 800 amino acids, optionally wherein:

(1) the amino acid sequence is at least 85%, at least 90%, or at least 95% identical to the polypeptide sequence of the member selected from TABLE 3B, TABLE 4B, or TABLE 5C; and/or
(2) the member is mA8, mC18, mC21, mD2, mD4, mD5, or mD7 from TABLE 4B; and/or
(3) the member is cA2.6, cA2.39, cA2.69, cA2.29, cA2.10, cA2.4, cA2.21, cA2.13, cA2.3, cA2.16, cA2.23, cA2.8, cA2.31, cA2.30, cA2.11, cA2.5, cA2.41, cA2.49, cA2.26, cA2.14, cA2.20, cA2.1, cA2.24, cA2.58, cA2.61, cA2.38, cA2.88, cA2.2, cA2.51, cA2.34, cA2.25, cA2.85, cA2.54, cA2.15, cA2.75, cA2.32, cA2.90, cA2.89, or cA2.46 from TABLE 5C; and/or
(4) the member is not cA2.55 or cA2.84 from TABLE 5C; and/or
(5) the amino acid sequence has a length of less than or equal to about 600 amino acids, less than or equal to about 550 amino acids, or less than or equal to about 500 amino acids; and/or
(6) the engineered nuclease variant comprises an amino acid substitution at D326 or D510, as compared to the amino acid sequence of SEQ ID NO: 1, thereby to reduce nuclease activity of the engineered nuclease variant; and/or
(7) the engineered nuclease variant comprises one or more amino acid substitutions selected from the group consisting of D143R, T147R, K330R, and E528R, as compared to the amino acid sequence of SEQ ID NO: 1.

Embodiment 9. An engineered polypeptide comprising an engineered nuclease variant operatively coupled to a gene modulator, wherein the engineered nuclease variant:
(i) comprises an amino acid sequence that is at least 70% identical to the polypeptide sequence of a member selected from SEQ ID NOs: 1-3 and 13-19; and
(ii) when operatively coupled to the gene modulator, induces an enhanced modulation of a target gene in a cell, as compared to that by a control engineered polypeptide comprising SEQ ID NO: 10 operatively coupled to the gene modulator,
optionally wherein:
(1) the amino acid sequence is at least 70% identical to the polypeptide sequence of SEQ ID NO: 1; and/or
(2) the enhanced modulation of the target gene is characterized by a greater change in expression level of the target gene that is at least 50%, at least 80%, or at least 100% greater than that by the control engineered polypeptide; and/or
(3) the enhanced modulation of the target gene is characterized by a greater increase in expression level of the target gene, as compared to that by the control engineered polypeptide; and/or
(4) the enhanced modulation of the target gene is characterized by a greater decrease in expression level of the target gene, as compared to that by the control engineered polypeptide; and/or
(5) the enhanced modulation of the target gene is characterized by a prolonged change in expression level of the target gene that is longer than that by the control engineered polypeptide; and/or
(6) the prolonged change is at least 20%, at least 50%, at least 80%, or at least 100% longer than that by the control engineered polypeptide; and/or
(7) the amino acid sequence has a length of less than or equal to about 600 amino acids, less than or equal to about 550 amino acids, or less than or equal to about 500 amino acids; and/or
(8) the amino acid sequence has a length of less than 529 amino acids; and/or
(9) the engineered nuclease variant exhibits reduced nuclease activity as compared to a nuclease encoded by SEQ ID NO: 1; and/or
(10) the amino acid sequence is at least 75%, at least 80%, or at least 85% identical to the polypeptide sequence of SEQ ID NO: 1; and/or
(11) the amino acid sequence is at most 95% identical to the polypeptide sequence of SEQ ID NO: 1; and/or
(12) the amino acid sequence is at least 70%, at least 80%, at least 85%, at least 90%, or at least 95% identical to the polypeptide sequence of SEQ ID NO: 12; and/or
(13) the cell a mammalian cell; and/or
(14) the target gene is a genomic sequence; and/or
(15) the gene modulator is a gene activator; and/or
(16) the gene modulator is a gene repressor; and/or
(17) the gene modulator is fused to the engineered nuclease variant in the engineered polypeptide; and/or
(18) the gene modulator is not fused to the engineered nuclease variant; and/or
(19) the engineered nuclease variant comprises an amino acid substitution at D326 or D510, as compared to the amino acid sequence of SEQ ID NO: 1, thereby to reduce nuclease activity of the engineered nuclease variant; and/or
(20) the engineered nuclease variant comprises one or more amino acid substitutions selected from the group consisting of D143R, T147R, K330R, and E528R, as compared to the amino acid sequence of SEQ ID NO: 1.

Embodiment 10. A system comprising the engineered polypeptide of any one of the Embodiments provided herein, optionally wherein:
(1) the system further comprises a guide nucleic acid capable of forming a complex with the engineered polypeptide, wherein the complex exhibits specific binding to a target gene in a cell; and/or
(2) the guide nucleic acid molecule of any one of the Embodiments provided herein, optionally wherein the guide nucleic acid exhibits at least 80% sequence identity to the polynucleotide sequence of a member selected from TABLE 6B, TABLE 7B, and TABLE 8B; and/or
(3) a scaffold sequence of the guide nucleic acid molecule is not identical to a member selected from SEQ ID NOs: 500, 549, 550, 551, and/or 552.

Embodiment 11. One or more polynucleotides encoding the system of any one of the Embodiments provided herein.

Embodiment 12. A cell comprising the system of any one of the Embodiments provided herein.

Embodiment 13. A method of controlling a target gene in a cell, the method comprising contacting the cell with the engineered polypeptide or the system of any one of the Embodiments provided herein,
optionally wherein:
(1) the controlling comprises insertion, deletion, and/or mutation of one or more bases in the target gene in the cell; and/or
(2) the controlling comprises regulating expression and/or activity level of the target gene in the cell; and/or
(3) the regulating comprises activating the expression and/or activity level of the target gene;

and/or
(4) the regulating comprises reducing the expression and/or activity level of the target gene; and/or
(5) the engineered nuclease (or the engineered nuclease variant) that is operatively coupled to a gene modulator induces an enhanced modulation of a target gene in a cell, as compared to that by a control engineered polypeptide comprising SEQ ID NO: 10 operatively coupled to the gene modulator.

Embodiment 14. A method of modulating a target gene in a cell, the method comprising:
contacting the cell with an engineered polypeptide comprising an engineered nuclease variant operatively coupled to a gene modulator, wherein the engineered nuclease variant comprises an amino acid sequence that is at least 70% identical to the polypeptide sequence of a member selected from SEQ ID NOs: 1-3 and 13-19,
wherein the contacting effects enhanced modulation of the target gene in the cell, as compared to that by a control engineered polypeptide comprising SEQ ID NO: 10 operatively coupled to the gene modulator,
optionally wherein:
(1) the amino acid sequence is at least 70% identical to the polypeptide sequence of SEQ ID NO: 1; and/or
(2) the enhanced modulation of the target gene is characterized by a greater change in expression level of the target gene that is at least 50%, at least 80%, or at least 100% greater than that by the control engineered polypeptide; and/or
(3) the enhanced modulation of the target gene is characterized by a greater increase in expression level of the target gene, as compared to that by the control engineered polypeptide; and/or
(4) the enhanced modulation of the target gene is characterized by a greater decrease in expression level of the target gene, as compared to that by the control engineered polypeptide; and/or
(5) the enhanced modulation of the target gene is characterized by a prolonged change in expression level of the target gene that is longer than that by the control engineered polypeptide; and/or
(6) the prolonged change is at least 20%, at least 50%, at least 80%, or at least 100% longer than that by the control engineered polypeptide; and/or
(7) the amino acid sequence of the engineered nuclease comprises at least one deletion from the amino acid resides 2-100, as compared to the polypeptide sequence of SEQ ID NO: 1; and/or
(8) the engineered nuclease comprises an amino acid sequence that is greater than 92% identical to the polypeptide sequence of SEQ ID NO: 12; and/or
(9) the engineered nuclease variant comprises an amino acid sequence that is at least 70% identical to the polypeptide sequence of SEQ ID NO: 12, wherein the amino acid sequence comprises a modification as compared to the polypeptide sequence of SEQ ID NO: 1, wherein the modification comprises one or more members selected from the group consisting of A21Q, V23I, N32E, D29E, N33R, E35K, K36Q, I37A, A38G, E40D, K73G, A74T, R75G, K76E, Q83K, G87K, E151A, A340S, H353K, A374K, I387E, N423D, K473Q, T474L, T474R, H497K, L515R, N519T, K521D, K521N, L522I, and at least one deletion from the amino acid residues 400-529 of SEQ ID NO: 1; and/or
(10) the engineered nuclease variant is a chimeric polypeptide comprising:
a first polypeptide sequence comprising at least 3 contiguous amino acid residues in common with a first Cas protein; and
a second polypeptide sequence comprising at least 3 contiguous amino acid residues in common with a second Cas protein, wherein the second Cas protein is different from the first Cas protein,
wherein the first Cas protein comprises an amino acid sequence that is at least 80% identical to the polypeptide sequence of SEQ ID NO: 1; and/or
(11) the engineered nuclease is a chimeric polypeptide comprising:
a first polypeptide sequence (CP1) comprising at least 3 contiguous amino acid residues in common with a portion of a first Cas protein;
a second polypeptide sequence (CP2) comprising at least 3 contiguous amino acid residues in common with a portion of a second Cas protein that is different from the first Cas protein; and
a third polypeptide sequence (CPx) comprising at least 3 contiguous amino acid residues in common with:
(i) an additional portion of the first Cas protein, wherein the portion and the additional portion of the first Cas protein are not directly adjacent to each other in the first Cas protein;
(ii) an additional portion of the second Cas protein, wherein the portion and the additional portion of the second Cas protein are not directly adjacent to each other in the second Cas protein; or
(iii) a portion of a third Cas protein that is different from the first Cas protein and the second Cas protein,
wherein the chimeric polypeptide has a length of less than or equal to about 1,000 amino acids; and/or
(12) the engineered nuclease variant is a chimeric polypeptide comprising:
a first polypeptide comprising at least 3 contiguous amino acid residues in common with a first Cas protein; and
a second polypeptide comprising at least 3 contiguous amino acid residues in common with a second Cas protein, wherein the second Cas protein is different from the first Cas protein,
wherein a length of the second polypeptide sequence is less than about 20% than that of the first polypeptide sequence; and/or
(13) the engineered nuclease variant:
(i) comprises an amino acid sequence that is at least 80% identical to the polypeptide sequence of a member selected from TABLE 3B, TABLE 4B, or TABLE 5C;
(ii) is not any one of SEQ ID NOs: 1-3, 10, and 13-19; and
(iii) has a length of less than or equal to about 800 amino acids; and/or
(14) the engineered nuclease variant:
(i) comprises an amino acid sequence that is at least 70% identical to the polypeptide sequence of SEQ ID NO: 1; and
(ii) when operatively coupled to the gene modulator, induces an enhanced modulation of a target gene in a cell, as compared to that by a control engineered polypeptide comprising SEQ ID NO: 10 operatively coupled to the gene modulator; and/or
(15) the amino acid sequence has a length of less than or equal to about 600 amino acids, less than or equal to about 550 amino acids, or less than or equal to about 500 amino acids; and/or
(16) the amino acid sequence has a length of less than 529 amino acids; and/or
(17) the engineered nuclease variant exhibits reduced nuclease activity as compared to a nuclease encoded by SEQ ID NO: 1; and/or
(18) the amino acid sequence is at least 75%, at least 80%, or at least 85% identical to the polypeptide sequence of SEQ ID NO: 1; and/or
(19) the amino acid sequence is at most 95% identical to the polypeptide sequence of SEQ ID NO: 1; and/or
(20) the amino acid sequence is at least 70%, at least 80%, at least 85%, at least 90%, or at least 95% identical to the polypeptide sequence of SEQ ID NO: 12; and/or
(21) the cell a mammalian cell; and/or
(22) the target gene is a genomic sequence; and/or
(23) the gene modulator is a gene activator; and/or
(24) the gene modulator is a gene repressor; and/or
(25) the gene modulator is fused to the engineered nuclease variant in the engineered polypeptide; and/or
(26) the gene modulator is not fused to the engineered nuclease variant; and/or
(27) wherein the contacting comprises transfecting the cell with a complex comprising the engineered polypeptide and a guide nucleic acid molecule exhibiting specific affinity to a target polynucleotide sequence operatively coupled to the target gene; and/or
(28) the contacting comprises transfecting the cell with a vector encoding the engineered polypeptide and a guide nucleic acid molecule exhibiting specific affinity to a target polynucleotide sequence operatively coupled to the target gene; and/or
(29) the vector is a plasmid or a viral vector.

Embodiment 15. A composition comprising a guide nucleic acid molecule configured to form a complex with a Cas protein, wherein the guide nucleic acid molecule comprises:
a spacer sequence exhibiting specific binding to a target polynucleotide sequence; and
a scaffold sequence for forming the complex with the Cas protein, wherein the scaffold sequence is characterized by:
(i) having a consecutive polynucleotide sequence having at least 96% sequence identity to the polynucleotide sequence of SEQ ID NO: 555; and/or having a consecutive polynucleotide sequence having at least 84% sequence identity to the polynucleotide sequence of SEQ ID NO: 597; and/or
(ii) having a consecutive polynucleotide sequence having at least 97% sequence identity to the polynucleotide sequence of SEQ ID NO: 557; and/or having a consecutive polynucleotide sequence having at least 88% sequence identity to the polynucleotide sequence of SEQ ID NO: 598; and/or
(iii) having a consecutive polynucleotide sequence having at least 90% sequence identity to the polynucleotide sequence of SEQ ID NO: 578; and/or having a consecutive polynucleotide sequence having at least 84% sequence identity to the polynucleotide sequence of SEQ ID NO: 597; and/or having a consecutive polynucleotide sequence having at least 81% sequence identity to the polynucleotide sequence of SEQ ID NO: 599; and/or
(iv) having a consecutive polynucleotide sequence having at least 93% sequence identity to the polynucleotide sequence of SEQ ID NO: 568; and/or having a consecutive polynucleotide sequence having at least 84% sequence identity to the polynucleotide sequence of SEQ ID NO: 597; and/or having a consecutive polynucleotide sequence having at least 67% sequence identity to the polynucleotide sequence of SEQ ID NO: 600; and/or
(v) having a consecutive polynucleotide sequence having at least 95% sequence identity to the polynucleotide sequence of SEQ ID NO: 569; and/or having a consecutive polynucleotide sequence having at least 84% sequence identity to the polynucleotide sequence of SEQ ID NO: 597; and/or having a consecutive polynucleotide sequence having at least 71% sequence identity to the polynucleotide sequence of SEQ ID NO: 601,
optionally wherein:
(1) the scaffold sequence (i-a) has the consecutive polynucleotide sequence having at least 96%, at least 97%, at least 98%, at least 99%, or 100% sequence identity to the polynucleotide sequence of SEQ ID NO: 555; or (i-b) has the consecutive polynucleotide sequence having at least 84%, at least 85%, at least 86%, at least 87%, at least 88%, at least 89%, at least 89%, at least 90%, at least 95%, at least 98%, at least 99%, or 100% sequence identity to the polynucleotide sequence of SEQ ID NO: 597; and/or
(2) the scaffold sequence (ii-a) has the consecutive polynucleotide sequence having at least 97%, at least 98%, at least 99%, or 100% sequence identity to the polynucleotide sequence of SEQ ID NO: 557; or (ii-b) has the consecutive polynucleotide sequence having at least 88%, at least 89%, at least 90%, at least 95%, at least 98%, at least 99%, or 100% sequence identity to the polynucleotide sequence of SEQ ID NO: 598; and/or
(3) the scaffold sequence (iii-a) has the consecutive polynucleotide sequence having at least 90%, at least 91%, at least 92%, at least 93%, at least 94%, at least 95%, at least 96%, at least 97%, at least 98%, at least 99%, or 100% sequence identity to the polynucleotide sequence of SEQ ID NO: 578; (iii-b) has the consecutive polynucleotide sequence having at least 84%, at least 85%, at least 86%, at least 87%, at least 88%, at least 89%, at least 89%, at least 90%, at least 95%, at least 98%, at least 99%, or 100% sequence identity to the polynucleotide sequence of SEQ ID NO: 597; or (iii-c) has the consecutive polynucleotide sequence having at least 81%, at least 82%, at least 83%, at least 84%, at least 85%, at least 86%, at least 87%, at least 88%, at least 89%, at least 89%, at least 90%, at least 95%, at least 98%, at least 99%, or 100% sequence identity to the polynucleotide sequence of SEQ ID NO: 599; and/or
(4) the scaffold sequence (iv-a) has the consecutive polynucleotide sequence having at least 93%, at least 94%, at least 95%, at least 96%, at least 97%, at least 98%, at least 99%, or 100% sequence identity to the polynucleotide sequence of SEQ ID NO: 568; (iv-b) has the consecutive polynucleotide sequence having at least 84%, at least 85%, at least 86%, at least 87%, at least 88%, at least 89%, at least 89%, at least 90%, at least 95%, at least 98%, at least 99%, or 100% sequence identity to the polynucleotide sequence of SEQ ID NO: 597; or (iv-c) has the consecutive polynucleotide sequence having at least 67%, at least 68%, at least 69%, at least 70%, at least 75%, at least 80%, at least 85%, at least 90%, at least 95%, at least 98%, at least 99%, or 100% sequence identity to the polynucleotide sequence of SEQ ID NO: 600; and/or (5) the scaffold sequence (v-a) has the consecutive polynucleotide sequence having at least 95%, at least 96%, at least 97%, at least 98%, at least 99%, or 100% sequence identity to the polynucleotide sequence of SEQ ID NO: 569; (v-b) has the consecutive polynucleotide sequence having at least 84%, at least 85%, at least 86%, at least 87%, at least 88%, at least 89%, at least 89%, at least 90%, at least 95%, at least 98%, at least 99%, or 100% sequence identity to the polynucleotide sequence of SEQ ID NO: 597; or (v-c) has the consecutive polynucleotide sequence having at least 71%, at least 72%, at least 73%, at least 74%, at least 75%, at least 80%, at least 85%, at least 90%, at least 95%, at least 98%, at least 99%, or 100% sequence identity to the polynucleotide sequence of SEQ ID NO: 601; and/or (6) the guide nucleic acid molecule has a length of at most about 150, at most about 140, at most about 130, or at most about 125 nucleotides; and/or (7) the scaffold sequence has a length of at most about 130, at most about 120, at most about 110, or at most about 105 nucleotides; and/or (8) the scaffold sequence has a length of at least about 95, at least about 99, or at least about 100 nucleotides; and/or (9) binding of the complex to the target polynucleotide sequence in a cell effects modulated expression level of a target gene in the cell, wherein (A1) the modulated expression level of the target gene by the complex is comparable to or superior than (A2) that by a control complex comprising the Cas protein and a control guide nucleic acid molecule comprising the polynucleotide sequence of SEQ ID NO: 500.

Embodiment 16. A composition comprising a guide nucleic acid molecule configured to form a complex with a Cas protein, wherein the guide nucleic acid molecule comprises:

a spacer sequence exhibiting specific binding to a target polynucleotide sequence operatively coupled to a target gene; and a scaffold sequence for forming the complex with the Cas protein, wherein the scaffold sequence exhibits at least 80% sequence identity to the polynucleotide sequence of a member selected from TABLE 6B, TABLE 7B, and TABLE 8B, wherein the scaffold sequence is not identical to SEQ ID NO: 500, optionally wherein binding of the complex to the target polynucleotide sequence in a cell effects modulated expression level of the target gene in the cell, wherein (A1) the modulated expression level of the target gene by the complex is comparable to or superior than (A2) that by a control complex comprising the Cas protein and a control guide nucleic acid molecule comprising the polynucleotide sequence of SEQ ID NO: 500, further optionally wherein:

(1) the scaffold sequence exhibits at least 80%, at least 85%, at least 90%, at least 95%, or at least 99% sequence identity to the polynucleotide sequence of a member selected from the group consisting of SEQ ID NOs: 503-152, 519, 524, 528, and 553; and/or (2) the scaffold sequence exhibits at least 80%, at least 85%, at least 90%, at least 95%, or at least 99% sequence identity to the polynucleotide sequence of a member selected from the group consisting of SEQ ID NOs: 555, 557, 558, 568, 569, 578, and 580; and/or (3) the scaffold sequence exhibits at least 80%, at least 85%, at least 90%, at least 95%, or at least 99% sequence identity to the polynucleotide sequence of a member selected from the group consisting of SEQ ID NOs: 555, 557, 568, 569, 576, 577, 578, 580, 593, 519, and 528; and/or (4) the scaffold sequence has a length of at most about 158 nucleotides.

Embodiment 17. A composition comprising a guide nucleic acid molecule configured to form a complex with a Cas protein, wherein the guide nucleic acid molecule comprises:

a spacer sequence exhibiting specific binding to a target polynucleotide sequence operatively coupled to a target gene; and a scaffold sequence for forming the complex with the Cas protein, wherein the scaffold sequence has a length of at most about 158 nucleotides, wherein binding of the complex to the target polynucleotide sequence in a cell effects modulated expression level of the target gene in the cell, wherein (A1) the modulated expression level of the target gene by the complex is comparable to or superior than (A2) that by a control complex comprising the Cas protein and a control guide nucleic acid molecule comprising the polynucleotide sequence of SEQ ID NO: 500, optionally wherein:

(1) the scaffold sequence exhibits at least 80% complementarity to the polynucleotide sequence of a member selected from TABLE 6B, TABLE 7B, and TABLE 8B, wherein the scaffold sequence is not identical to SEQ ID NO: 500; and/or (2) the scaffold sequence exhibits at least 80%, at least 85%, at least 90%, at least 95%, or at least 99% sequence identity to the polynucleotide sequence of a member selected from the group consisting of SEQ ID NOs: 503-152, 519, 524, 528, and 553; and/or (3) the scaffold sequence exhibits at least 80%, at least 85%, at least 90%, at least 95%, or at least 99% sequence identity to the polynucleotide sequence of a member selected from the group consisting of SEQ ID NOs: 555, 557, 558, 568, 569, 578, and 580; and/or (4) the scaffold sequence exhibits at least 80%, at least 85%, at least 90%, at least 95%, or at least 99% sequence identity to the polynucleotide sequence of a member selected from the group consisting of SEQ ID NOs: 555, 557, 568, 569, 576, 577, 578, 580, 593, 519, and 528.

Embodiment 18. A composition comprising a vector encoding a Cas protein and a guide nucleic acid molecule configured to form a complex with the Cas protein, wherein the vector comprises:

a first polynucleotide sequence encoding the Cas protein; and a second polynucleotide sequence encoding a scaffold sequence of the guide nucleic acid molecule, for forming the complex with the Cas protein, wherein a sum of a length of the first polynucleotide sequence and a length of the second polynucleotide sequence combined is at most about 1700 nucleotides, optionally wherein:
- (1) the sum is at most about 1650, at most about 1620, or at most about 1600 nucleotides; and/or
- (2) the length of the first polynucleotide sequence is at most about 1550, at most about 1520, or at most about 1500 nucleotides; and/or
- (3) the length of the second polynucleotide sequence is at most about 135, at most about 130, at most about 125, at most about 120, at most about 115, at most about 110, or at most about 105 nucleotides; and/or
- (4) the composition further comprises a third polynucleotide sequence encoding a spacer sequence of the guide nucleic acid molecule, exhibiting specific binding to the target polynucleotide sequence; and/or
- (5) the complex is configured to bind to a target sequence operatively coupled to target gene, to effect modulated expression level of the target gene; and/or
- (6) the scaffold sequence exhibits at least 80% sequence identity to the polynucleotide sequence of a member selected from TABLE 6B, TABLE 7B, and TABLE 8B, wherein the scaffold sequence is not identical to SEQ ID NO: 500.

Embodiment 19. The composition of any one of the Embodiments provided herein, wherein:
- (1) the scaffold sequence has a length of at most about 150, at most about 140, at most about 130, at most about 102, at most about 110, or at most about 105 nucleotides; and/or
- (2) the Cas protein has a length of at most about 535 or at most about 530 amino acid residues; and/or
- (3) (A1) is comparable to (A2); and/or
- (4) (A1) is not different from (A2), by no more than 20%, no more than 15%, no more than 10%, no more than 5%, no more than 2%, or no more than 1% of (A2); and/or
- (5) (A1) is superior than (A2); and/or
- (6) (A1) is superior than (A2), by at least 5%, at least 10%, at least 15%, at least 20%, at least 50%, at least 100%, at least 150%, at least 200%, or at least 300% as compared to (A2); and/or
- (7) the modulated expression level of the target gene is characterized by decreased expression level of the target gen; and/or
- (8) the modulated expression level of the target gene is characterized by increased expression level of the target gene; and/or
- (9) the modulated expression level of the target gene is characterized by a duration of the modulated expression level of the target gene; and/or
- (10) the modulated expression level of the target gene by the complex is in absence of cleavage or indel of the target polynucleotide sequence; and/or
- (11) the Cas protein is operatively coupled to a gene modulator; and/or
- (12) the Cas protein is fused to the gene modulator; and/or
- (13) the gene modulator is a gene activator; and/or
- (14) the gene modulator is a gene repressor; and/or
- (15) the guide nucleic acid molecule further comprises an aptamer configured to recruit the gene modulator, to form the complex; and/or
- (16) the composition further comprises the engineered polypeptide of any one of the Embodiments provided herein.

Embodiment 20. A system comprising the composition of any one of the Embodiments provided herein, optionally wherein:
- (1) the system comprises the Cas protein; and/or
- (2) the Cas protein comprises the engineered polypeptide of any one of the Embodiments provided herein, further optionally wherein the engineered nuclease variant:
  - (i) comprises an amino acid sequence that is at least 80% identical to the polypeptide sequence of a member selected from TABLE 3B, TABLE 4B, or TABLE 5C;
  - (ii) is not any one of SEQ ID NOs: 1-3, 10, and 13-19; and
  - (iii) has a length of less than or equal to about 800 amino acids.

Embodiment 21. One or more polynucleotides encoding the system of any one of the Embodiments provided herein.

Embodiment 22. A cell comprising the system of any one of the Embodiments provided herein.

Embodiment 23. A method of controlling a target gene in a cell, the method comprising contacting the cell with the composition or the system of any one of the Embodiments provided herein, optionally wherein:
- (1) the controlling comprises insertion, deletion, and/or mutation of one or more bases in the target gene in the cell; and/or
- (2) the controlling comprises regulating expression and/or activity level of the target gene in the cell; and/or
- (3) the regulating comprises activating the expression and/or activity level of the target gene; and/or
- (4) the regulating comprises reducing the expression and/or activity level of the target gene.

Embodiment 24. A method of modulating a target gene in a cell, the method comprising:
contacting the cell with a complex comprising a guide nucleic acid molecule and a Cas protein, wherein the complex exhibits specific binding to a target polynucleotide sequence operatively coupled to the target gene, wherein binding of the complex to the target polynucleotide sequence effects modulated expression level of the target gene in the cell, wherein (A1) the modulated expression level of the target gene by the complex is comparable to or superior than (A2) that by a control complex comprising the Cas protein and a control guide nucleic acid molecule comprising the polynucleotide sequence of SEQ ID NO: 500,
optionally wherein:
- (1) (A1) is comparable to (A2); and/or
- (2) (A1) is not different from (A2), by no more than 20%, no more than 15%, no more than 10%, no more than 5%, no more than 2%, or no more than 1% of (A2); and/or
- (3) (A1) is superior than (A2); and/or
- (4) (A1) is superior than (A2), by at least 5%, at least 10%, at least 15%, at least 20%, at least 50%, at least 100%, at least 150%, at least 200%, or at least 300% as compared to (A2); and/or
- (5) the modulated expression level of the target gene is characterized by decreased expression level of the target gene; and/or
- (6) the modulated expression level of the target gene is characterized by increased expression level of the target gene; and/or (7) the modulated expression level of the target gene is characterized by a duration of the modulated expression level of the target gene; and/or
(8) the guide nucleic acid molecule comprises:
a spacer sequence exhibiting specific binding to the target polynucleotide sequence; and
a scaffold sequence for forming the complex with the Cas protein, wherein the scaffold sequence is characterized by:
  (i) having a consecutive polynucleotide sequence having at least 96% sequence identity to the polynucleotide sequence of SEQ ID NO: 555; and/or having a consecutive polynucleotide sequence having at least 84% sequence identity to the polynucleotide sequence of SEQ ID NO: 597; and/or
  (ii) having a consecutive polynucleotide sequence having at least 97% sequence identity to the polynucleotide sequence of SEQ ID NO: 557; and/or having a consecutive polynucleotide sequence having at least 88% sequence identity to the polynucleotide sequence of SEQ ID NO: 598; and/or
  (iii) having a consecutive polynucleotide sequence having at least 90% sequence identity to the polynucleotide sequence of SEQ ID NO: 578; and/or having a consecutive polynucleotide sequence having at least 84% sequence identity to the polynucleotide sequence of SEQ ID NO: 597; and/or having a consecutive polynucleotide sequence having at least 81% sequence identity to the polynucleotide sequence of SEQ ID NO: 599; and/or
  (iv) having a consecutive polynucleotide sequence having at least 93% sequence identity to the polynucleotide sequence of SEQ ID NO: 568; and/or having a consecutive polynucleotide sequence having at least 84% sequence identity to the polynucleotide sequence of SEQ ID NO: 597; and/or having a consecutive polynucleotide sequence having at least 67% sequence identity to the polynucleotide sequence of SEQ ID NO: 600; and/or
  (v) having a consecutive polynucleotide sequence having at least 95% sequence identity to the polynucleotide sequence of SEQ ID NO: 569; and/or having a consecutive polynucleotide sequence having at least 84% sequence identity to the polynucleotide sequence of SEQ ID NO: 597; and/or having a consecutive polynucleotide sequence having at least 71% sequence identity to the polynucleotide sequence of SEQ ID NO: 601; and/or
(9) the guide nucleic acid molecule comprises:
  a spacer sequence exhibiting specific binding to the target polynucleotide sequence; and
  a scaffold sequence for forming the complex with the Cas protein, wherein the scaffold sequence exhibits at least 80% sequence identity to the polynucleotide sequence of a member selected from TABLE 6B, TABLE 7B, and TABLE 8B, wherein the scaffold sequence is not identical to SEQ ID NO: 500; and/or
(10) the guide nucleic acid molecule comprises:
  a spacer sequence exhibiting specific binding to the target polynucleotide sequence; and
  a scaffold sequence for forming the complex with the Cas protein, wherein the scaffold sequence has a length of at most about 158 nucleotides; and/or
(11) the contacting comprises utilizing a vector encoding the Cas protein and the guide nucleic acid molecule, wherein the vector comprises:
  a first polynucleotide sequence encoding the Cas protein; and
  a second polynucleotide sequence encoding a scaffold sequence of the guide nucleic acid molecule for forming the complex with the Cas protein,
  wherein a sum of a length of the first polynucleotide sequence and a length of the second polynucleotide sequence combined is at most about 1700 nucleotides; and/or
(12) the scaffold sequence of the guide nucleic acid molecule has a length of at most about 150, at most about 140, at most about 130, at most about 102, at most about 110, or at most about 105 nucleotides; and/or
(13) the Cas protein has a length of at most about 535 or at most about 530 amino acid residues; and/or
(14) the modulated expression level of the target gene by the complex is in absence of cleavage or indel of the target polynucleotide sequence; and/or
(15) the Cas protein is operatively coupled to a gene modulator; and/or
(16) the Cas protein is fused to the gene modulator; and/or
(17) the gene modulator is a gene activator; and/or
(18) the gene modulator is a gene repressor; and/or
(19) the guide nucleic acid molecule further comprises an aptamer configured to recruit the gene modulator, to form the complex; and/or
(20) the Cas protein comprises the engineered nuclease variant of the engineered polypeptide of any one of the Embodiments provided herein.

It shall be understood that different aspects of the invention can be appreciated individually, collectively, or in combination with each other. Various aspects of the invention described herein may be applied to any of the particular applications disclosed herein. The compositions of matter disclosed herein in the composition section of the present disclosure may be utilized in the method section including methods of use and production disclosed herein, or vice versa.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An engineered polypeptide comprising an engineered nuclease, wherein said engineered nuclease comprises the amino acid sequence of any one of SEQ ID NOs: 132, 134, 135, 140, and 146.

2. The engineered polypeptide of claim 1, wherein the engineered nuclease consists of the amino acid sequence of any one of SEQ ID NOs: 132, 134, 135, 140, and 146.

3. The engineered polypeptide of claim 1, wherein the engineered nuclease comprises the amino acid sequence of SEQ ID NO:132.

4. The engineered polypeptide of claim 1, wherein the engineered nuclease comprises the amino acid sequence of SEQ ID NO: 134.

5. The engineered polypeptide of claim 1, wherein the engineered nuclease comprises the amino acid sequence of SEQ ID NO:135.

6. The engineered polypeptide of claim 1, wherein the engineered nuclease comprises the amino acid sequence of SEQ ID NO:140.

7. The engineered polypeptide of claim 1, wherein the engineered nuclease comprises the amino acid sequence of SEQ ID NO:146.

8. The engineered polypeptide of claim 1, wherein the engineered nuclease consists of the amino acid sequence of SEQ ID NO:132.

9. The engineered polypeptide of claim 1, wherein the engineered nuclease consists of the amino acid sequence of SEQ ID NO:134.

10. The engineered polypeptide of claim 1, wherein the engineered nuclease consists of the amino acid sequence of SEQ ID NO:135.

11. The engineered polypeptide of claim 1, wherein the engineered nuclease consists of the amino acid sequence of SEQ ID NO:140.

12. The engineered polypeptide of claim 1, wherein the engineered nuclease consists of the amino acid sequence of SEQ ID NO:146.

13. The engineered polypeptide of claim 1, wherein the engineered nuclease has a length of at most 495 amino acids.

* * * * *

SEQUENCE LISTING

```
Sequence total quantity: 604
SEQ ID NO: 1              moltype = AA  length = 529
FEATURE                   Location/Qualifiers
source                    1..529
                          mol_type = protein
                          organism = synthetic construct
SEQUENCE: 1
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKIGEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 2              moltype = AA  length = 500
FEATURE                   Location/Qualifiers
source                    1..500
                          mol_type = protein
                          organism = synthetic construct
SEQUENCE: 2
MEVQKTVMKT LSLRILRPLY SQEIEKEIKE EKERRKQAGG TGELDGGFYK KLEKKHSEMF    60
SFDRLNLLLN QLQREIAKVY NHAISELYIA TIAQGNKSNK HYISSIVYNR AYGYFYNAYI   120
ALGICSKVEA NFRSNELLTQ QSALPTAKSD NFPIVLHKQK GAEGEDGGFR ISTEGSDLIF   180
EIPIPFYEYN GENRKEPYKW VKKGGQKPVL KLILSTFRRQ RNKGWAKDEG TDAEIRKVTE   240
GKYQVSQIEI NRGKKLGEHQ KWFANFSIEQ PIYERKPNRS IVGGLDVGIR SPLVCAINNS   300
FSRYSVDSND VFKFSKQVFA FRRRLLSKNS LKRKGHGAAH KLEPITEMTE KNDKFRKKII   360
ERWAKEVTNF FVKNQVGIVQ IEDLSTMKDR EDHFFNQYLR GFWPYYQMQT LIENKLKEYG   420
IEVKRVQAKY TSQLCSNPNC RYWNNYFNFE YRKVNKFPKF KCEKCNLEIS ADYNAARNLS   480
TPDIEKFVAK ATKGINLPEK                                              500

SEQ ID NO: 3              moltype = AA  length = 422
FEATURE                   Location/Qualifiers
source                    1..422
                          mol_type = protein
                          organism = synthetic construct
SEQUENCE: 3
MIKVYRYEIV KPLDLDWKEF GTILRQLQQE TRFALNKATQ LAWEWMGFSS DYKDNHGEYP    60
KSKDILGYTN VHGYAYHTIK TKAYRLNSGN LSQTIKRATD RFKAYQKEIL RGDMSIPSYK   120
RDIPLDDLIKE NISVNRMNHG DYIASLSLLS NPAKQEMNVK RKISVIIIVR GAGKTIMDRI   180
LSGEYQVSAS QIIHDDRKNK WYLNISYDFE PQTRVLDLNK IMGIDLGVAV AVYMAFQHTP   240
ARYKLEGGEI ENFRRQVESR RISMLRQGKY AGGARGGHRK DKRIKPIEQL RDKIANFRDT   300
TNHRYSRYIV DMAIKEGCGT IQMEDLTNIR DIGSRFLQNW TYYDLQQKII YKAEEAGIKV   360
IKIDPQYTSQ RCSECGNIDS GNRIGQAIFK CRACGYEANA DYNAARNIAI PNIDKIIAES   420
IK                                                                 422

SEQ ID NO: 4              moltype = AA  length = 509
FEATURE                   Location/Qualifiers
source                    1..509
                          mol_type = protein
                          organism = synthetic construct
SEQUENCE: 4
MEVEKIVADE KNNREKIALE KNKDKVKEAC SKHLKVAAYC TTQVERNACL FCKARKLDDK    60
FYQKLRGQFP DAVFWQEISE IFRQLQKQAA EIYNQSLIEL YYEIFIKGKG IANASSVEHY   120
LSRVCYRRAA ELFKNAAIAS GLRSKIKSNF RLKELKNMKS GLPTTKSDNF PIPLVKQKGG   180
QYTGFEISNH NSDFIIKIPF GRWQVKKEID KYRPWEKFDF EQVQKSPKPI SLLLSTQRRK   240
RNKGWSKDEG TEAEIKKVMN GDYQTSYIEV KRGSKICEKS AWMLNLSIDV PKIDKGVDPS   300
IIGGIAVGVR SPLVCAINNA FSRYSISDND LFHFNKKMFA RRRILLKKNR HKRAGHGAKN   360
KLKPITILTE KSERFRKKLI ERWACEIADF FIKNKVGTVQ MENLESMKRK EDSYFNIRLR   420
GFWPYAEMQN KIEFKLKQYG IEIRKVAPNN TSKTCSKCGH LNNYFNFEYR KKNKFPHFKC   480
EKCNFKENAA YNAALNISNP KLKSTKERP                                    509

SEQ ID NO: 5              moltype = AA  length = 499
FEATURE                   Location/Qualifiers
source                    1..499
                          mol_type = protein
                          organism = synthetic construct
SEQUENCE: 5
MNNREKIALE KNKDKVKEAC SKHLKVAAYC TTQVERNACL FCKARKLDDK FYQKLRGQFP    60
DAVFWQEISE IFRQLQKQAA EIYNQSLIEL YYEIFIKGKG IANASSVEHY LSRVCYRRAA   120
ELFKNAAIAS GLRSKIKSNF RLKELKNMKS GLPTTKSDNF PIPLVKQKGG QYTGFEISNH   180
NSDFIIKIPF GRWQVKKEID KYRPWEKFDF EQVQKSPKPI SLLLSTQRRK RNKGWSKDEG   240
TEAEIKKVMN GDYQTSYIEV KRGSKICEKS AWMLNLSIDV PKIDKGVDPS IIGGIAVGVR   300
SPLVCAINNA FSRYSISDND LFHFNKKMFA RRRILLKKNR HKRAGHGAKN KLKPITILTE   360
KSERFRKKLI ERWACEIADF FIKNKVGTVQ MENLESMKRK EDSYFNIRLR GFWPYAEMQN   420
KIEFKLKQYG IEIRKVAPNN TSKTCSKCGH LNNYFNFEYR KKNKFPHFKC EKCNFKENAA   480
```

```
YNAALNISNP KLKSTKERP                                                           499

SEQ ID NO: 6            moltype = AA  length = 509
FEATURE                 Location/Qualifiers
source                  1..509
                        mol_type = protein
                        organism = synthetic construct
SEQUENCE: 6
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENA                                    509

SEQ ID NO: 7            moltype = AA  length = 499
FEATURE                 Location/Qualifiers
source                  1..499
                        mol_type = protein
                        organism = synthetic construct
SEQUENCE: 7
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFK                                               499

SEQ ID NO: 8            moltype = AA  length = 509
FEATURE                 Location/Qualifiers
source                  1..509
                        mol_type = protein
                        organism = synthetic construct
SEQUENCE: 8
MAKNTITKTL KLRIVRPYNS AEVEKIVADE KNNREKIALE KNKDKVNACL FCKARKLDDK    60
FYQKLRGQFP DAVFWQEISE IFRQLQKQAA EIYNQSLIEL YYEIFIKGKG IANASSVEHY   120
LSRVCYRRAA ELFKNAAIAS GLRSKIKSNF RLKELKNMKS GLPTTKSDNF PIPLVKQKGG   180
QYTGFEISNH NSDFIIKIPF GRWQVKKEID KYRPWEKFDF EQVQKSPKPI SLLLSTQRRK   240
RNKGWSKDEG TEAEIKKVMN GDYQTSYIEV KRGSKICEKS AWMLNLSIDV PKIDKGVDPS   300
IIGGIAVGVR SPLVCAINNA FSRYSISDND LFHFNKKMFA RRRILLKKNR HKRAGHGAKN   360
KLKPITILTE KSERFRKKLI ERWACEIADF FIKNKVGTVQ MENLESMKRK EDSYFNIRLR   420
GFWPYAEMQN KIEFKLKQYG IEIRKVAPNN TSKTCSKCGH LNNYFNFEYR KKNKFPHFKC   480
EKCNFKENAA YNAALNISNP KLKSTKERP                                    509

SEQ ID NO: 9            moltype = AA  length = 498
FEATURE                 Location/Qualifiers
source                  1..498
                        mol_type = protein
                        organism = synthetic construct
SEQUENCE: 9
MAKNTITKTL KLRIVRPYNS AEVEKIVADE KNNREKIALE CKARKLDDKF YQKLRGQFPD    60
AVFWQEISEI FRQLQKQAAE IYNQSLIELY YEIFIKGKGI ANASSVEHYL SRVCYRRAAE   120
LFKNAAIASG LRSKIKSNFR LKELKNMKSG LPTTKSDNFP IPLVKQKGGQ YTGFEISNHN   180
SDFIIKIPFG RWQVKKEIDK YRPWEKFDFE QVQKSPKPIS LLLSTQRRKR NKGWSKDEGT   240
EAEIKKVMNG DYQTSYIEVK RGSKICEKSA WMLNLSIDVP KIDKGVDPSI IGGIAVGVRS   300
PLVCAINNAF SRYSISDNDL FHFNKKMFAR RRILLKKNRH KRAGHGAKNK LKPITILTEK   360
SERFRKKLIE RWACEIADFF IKNKVGTVQM ENLESMKRKE DSYFNIRLRG FWPYAEMQNK   420
IEFKLKQYGI EIRKVAPNNT SKTCSKCGHL NNYFNFEYRK KNKFPHFKCE KCNFKENAAY   480
NAALNISNPK LKSTKERP                                                498

SEQ ID NO: 10           moltype = AA  length = 529
FEATURE                 Location/Qualifiers
source                  1..529
                        mol_type = protein
                        organism = synthetic construct
SEQUENCE: 10
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
```

```
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKERP              529

SEQ ID NO: 11           moltype = AA  length = 11
FEATURE                 Location/Qualifiers
source                  1..11
                        mol_type = protein
                        organism = synthetic construct
SEQUENCE: 11
ERRKQAGGTG E                                                        11

SEQ ID NO: 12           moltype = AA  length = 495
FEATURE                 Location/Qualifiers
source                  1..495
                        mol_type = protein
                        organism = synthetic construct
SEQUENCE: 12
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAELFK  120
NAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNAFSRY SISDNDLFHF NKKMFARRRI LLKKNRHKRA GHGAKNLKLP ITILTEKSER  360
FRKKLIERWA CEIADFFIKN KVGTVQMENL ESMKRKEDSY FNIRLRGFWP YAEMQNKIEF  420
KLKQYGIEIR KVAPNNTSKT CSKCGHLNNY FNFEYRKKNK FPHFKCEKCN FKENAAYNAA  480
LNISNPKLKS TKERP                                                   495

SEQ ID NO: 13           moltype = AA  length = 544
FEATURE                 Location/Qualifiers
source                  1..544
                        mol_type = protein
                        organism = unidentified
SEQUENCE: 13
MNMSKTTISV KLKIIDLSSE KKEFLDNYFN EYAKATTFCQ LRIRRLLRNT HWLGKKEKSS   60
KKWIFESGIC DLCGENKELV NEDRNSGEPA KICKRCYNGR YGNQMIRKLF VSTKKREVQE  120
NMDIRRVAKL NNTHYHRIPE EAFDMIKAAD TAEKRRKKNV EYDKKRQMEF IEMFNDEKKR  180
AARPKKPNER ETRYVHISKL ESPSKGYTLN GIKRKIDGMG KKIERAEKGL SRKKIFGYQG  240
NRIKLDSNWV RFDLAESEIT IPSLFKEMKL RITGPTNVHS KSGQIYFAEW FERINKQPNN  300
YCYLIRKTSS NGKYEYYLQY TYEAEVEANK EYAGCLGVDI GCSKLAAAVY DSKNKKAQK   360
PIEIFTNPIK KIKMRREKLI KLLSRVKVRH RRRKLMQLSK TEPIIDYTCH KTARKIVEMA  420
NTAKAFISME NLETGIKQKQ QARETKKQKF YRNMFLFRKL SKLIEYKALL KGIKIVYVKP  480
DYTSQTCSSC GADKEKTERP SQAIFRCLNP TCRYYQRDIN ADFNAAVNIA KKALNNTEVV  540
TTLL                                                               544

SEQ ID NO: 14           moltype = AA  length = 586
FEATURE                 Location/Qualifiers
source                  1..586
                        mol_type = protein
                        organism = unidentified
SEQUENCE: 14
MPSETYITKT LSLKLIPSDE EKQALENYFI TFQRAVNFAI DRIVDIRSSF RYLNKNEQFP   60
AVCDCCGKKE KIMYVNISNK TFKFKPSRNQ KDRYTKDIYT IKPNAHICKT CYSGVAGNMF  120
IRKQMYPNDK EGWKVSRSYN IKVNAPGLTG TEYAMAIRKA ISILRSFEKR RRNAERRIIE  180
YEKSKKEYLE LIDDVEKGKT NKIVVLEKEG HQRVKRYKHK NWPEKWQGIS LNKAKSKVKD  240
IEKRIKKLKE WKHPTLNRPY VELHKNNVRI VGYETVELKL KQKMYTIHFA SISNLRKPFR  300
KQKKKSIEYL KHLLTLALKR NLETYPSIIK RGKNFFLQYP VRVTVKVPKL TKNFKAFGID  360
RGVNRLAVGC IISKDGKLTN KNIFFFHGKE AWAKENRYKK IRDRLYAMAK KLRGDKTKKI  420
RLYHEIRKKF RHKVKYFRRN YLHNISKQIV EIAKENTPTV IVLEDLRYLR ERTYRGKGRS  480
KKAKKTNYKL NTFTYRMLID MIKYKAEEAG VPVMIIDPRN TSRKCSKCGY VDENNRKQAS  540
FKCLKCGYSL NADLNAAVNI AKAFYECPTF RWEEKLHAYV CSEPDK                 586

SEQ ID NO: 15           moltype = AA  length = 603
FEATURE                 Location/Qualifiers
source                  1..603
                        mol_type = protein
                        organism = unidentified
SEQUENCE: 15
MKSFKLKLLP TDEQNVLLNE VFCKWASLCT RMASKGHDKE RLAPPDSSGN YFNKTQLNQV   60
NTDVTDHMGA LEESASQKER AVEKVKRRLK LISDMLSEPN LRDVSQQKPT TFRPLEWVKE  120
GLLKTKYHTV HYWQKECDKL TKQKERMEKT IEKIKKGKIT FKPTKMSLHQ NCFSLSFGKG  180
TFSMRPFSDT KRGINLDMLT APIQPAIGKN DGKSSLRSKE FIARNIENYI IFSIHSQLFG  240
LSRSEELLLN AKKEELVAKR DAMLKKKSDS LSKKIKELEK IVGRKITDSE RSEIMSQGGK  300
LSSEKFSEDN SYLKTLKVLA KDIIGREELF RLKKYPIVIR KPLNERKKLK NLKPDEWEYY  360
LQLSYDELEK KEFTPKTIMG IDRGLKHILA IAIYDPVQNK FVKNMLIPNP ILGWKWKLRK  420
IKRSIQHMER RIRAQQNAHV PENQLKKRLK SIENKIDYYY HNVSRQILNL AHDFKSAIVV  480
EDLQNMKQHG RKKSKGLRGL NYALSNFDYG KIMGLVKYKA ESENVPLLTV LPAGTSQNCA  540
YCLLYGKEQG NYVRNNVNSK IGKCKLHGEI DADINAARTI AICYHKNINE PKPYGERKTF  600
KRK                                                                603
```

```
SEQ ID NO: 16              moltype = AA  length = 424
FEATURE                    Location/Qualifiers
source                     1..424
                           mol_type = protein
                           organism = Geobacillus thermoglucosidasius
SEQUENCE: 16
MKYTKVMRYQ IIKPLNAEWD ELGMVLRDIQ KETRAALNKT IQLCWEYQGF SADYKQIHGQ    60
YPKPKDVLGY TSMHGYAYDR LKNEFSKIAS SNLSQTIKRA VDKWNSDLKE ILRGDRSIPN   120
FRKDCPIDIV KQSTKIQKCN DGYVLSLGLI NREYKNELGR KNGVFDVLIK ANDKTQQTIL   180
ERIINGDYTY TASQIINHKN KWFINLTYQF ETKETALDPN NVMGVDLGIV YPVYIAFNNS   240
LHRYHIKGGE IERFRRQVEK RKRELLNQGK YCGDGRKGHG YATRTKSIES ISDKIARFRD   300
TCNHKYSRFI VDMALKHNCG IIQMEDLTGI SKESTFLKNW TYYDLQQKIE YKAREAGIQV   360
IKIEPQYTSQ RCSKCGYIDK ENRQEQATFK CIECGFKTNA DYNAARNIAI PNIDKIIRKT   420
LKMQ                                                                424

SEQ ID NO: 17              moltype = AA  length = 443
FEATURE                    Location/Qualifiers
source                     1..443
                           mol_type = protein
                           organism = Ruminococcus sp.
SEQUENCE: 17
MTLLVKVVKI HLISEQFDKA GNRIDYEEVN KILWELQKQT REAKNKTVQL LWEWNNFSSD    60
YVKASGIYPK AKDIFGYSSV HGQANKELRT KLALNSSNLS TTTMDVCKNF NTYKKEVWKG   120
KRSVPSYKSD QPLDLHKDSI KLIYENNEFY VRLALLKKAE FAKYGFKDGF RFKMQVKDNS   180
TKTILERCFD EVYKINASKL LYDQKKKKWK LNLSYSFDNK NISELDKEKI LGVDVGVNCP   240
LVASVFGDRD RFIIKGGEIE KFRKSVEARR RSMLEQTKYC GDGRIGHGRK KRTEPALNIG   300
DKIARFRDTT NHKYSRALIE YAVKKGCGTI QMEKLTGITS KSDRFLKDWT YYDLQTKIEN   360
KAKEVGINVV YIAPKYTSQR CSKCGYIHKD NRPNQAKFRC LECDFESNAD YNASQNIGIK   420
NIDKIIEKDL QKQESEVQVN ENK                                           443

SEQ ID NO: 18              moltype = AA  length = 497
FEATURE                    Location/Qualifiers
source                     1..497
                           mol_type = protein
                           organism = Syntrophomonas palmitatica
SEQUENCE: 18
MGESVKAIKL KILDMFLDPE CTKQDDNWRK DLSTMSRFCA EAGNMCLRDL YNYFSMPKED    60
RISSKDLYNA MYHKTKLLHP ELPGKVANQI VNHAKDVWKR NAKLIYRNQI SMPTYKITTA   120
PIRLQNNIYK LIKNKNKYII DVQLYSKEYS KDSGKGTHRY FLVAVRDSST RMIFDRIMSK   180
DHIDSSKSYT QGQLQIKKDH QGKWYCIIPY TFPTHETVLD PDKVMGVDLG VAKAVYWAFN   240
SSYKRGCIDG GEIEHFRKMI RARRVSIQNQ IKHSGDARKG HGRKRALKPI ETLSEKEKNF   300
RDTINHRYAN RIVEAAIKQG CGTIQIENLE GIADTTGSKF LKNWPYYDLQ TKIVNKAKEH   360
GITVVAINPQ YTSQRCSMCG YIEKTNRSSQ AVFECKQCGY GSRTICINCR HVQVSGDVCE   420
ECGGIVKKEN VNADYNAAKN ISTPYIDQII MEKCLELGIP YRSITCKECG HIQASGNTCE   480
VCGSTNILKP KKIRKAK                                                  497

SEQ ID NO: 19              moltype = AA  length = 497
FEATURE                    Location/Qualifiers
source                     1..497
                           mol_type = protein
                           organism = Clostridium novyi
SEQUENCE: 19
MITVRKIKLT IMGDKDTRNS QYKWIRDEQY NQYRALNMGM TYLAVNDILY MNESGLEIRT    60
IKDLKDCEKD IDKNKKEIEK LTARLEKEQN KKNSSSEKLD EIKYKISLVE NKIEDYKLKI   120
VELNKILEET QKERMDIQKE FKEKYVDDLY QVLDKIPFKH LDNKSLVTQR IKADIKSDKS   180
NGLLKGERSI RNYKRNFPLM TRGRDLKFKY DDNDDIEIKW MEGIKFKVIL GNRIKNSLEL   240
RHTLHKVIEG KYKICDSSLQ FDKNNNLILN LTLDIPIDIV NKKVSGRVVG VDLGLKIPAY   300
CALNDVEYIK KSIGRIDDFL KVRTQMQSRR RRLQIAIQSA KGGKGRVNKL QALERFEAKE   360
KNFAKTYNHF LSSNIVKFAV SNQAEQINME LLSLKETQNK SILRNWSYYQ LQTMIEYKAQ   420
REGIKVKYID PYHTSQTCSK CGNYEEGQRE SQADFICKKC GYKVNADYNA ARNIAMSNKY   480
ITKKEESKYY KIKESMV                                                  497

SEQ ID NO: 20              moltype = AA  length = 495
FEATURE                    Location/Qualifiers
source                     1..495
                           mol_type = protein
                           organism = synthetic construct
SEQUENCE: 20
MAKNTITKTL KLRIVRPYNS AEVEKIVADE KERRKQAGGT GELDGGFYKK LEKKHSEMFS    60
FDRLNLLLNQ LQKQAAEIYN QSLIELYYEI FIKGKGIANA SSVEHYLSRV CYRRAAELFK   120
NAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVVSRPLV   300
CAINNAFSRY SISDNDLFHF NKKMFARRRI LLKKNRHKRA GHGAKNKLKP ITILTEKSER   360
FRKKLIERWA CEIADFFIKN KVGTVQMENL ESMKRKEDSY FNIRLRGFWP YAEMQNKIEF   420
KLKQYGIEIR KVAPNNTSKT CSKCGHLNNY FNFEYRKKNK FPHFKCEKCN FKENAAYNAA   480
LNISNPKLKS TKERP                                                    495

SEQ ID NO: 21              moltype = AA  length = 496
```

```
FEATURE                 Location/Qualifiers
source                  1..496
                        mol_type = protein
                        organism = synthetic construct
SEQUENCE: 21
MEVQKTVMKT LSLRILRPLY SQEIEKEIKE EKERRKQAGG TGELDDKFYQ KLRGQFPDAV   60
FWQEISEIFR QLQKQAAEIY NQSLIELYYE IFIKGKGIAN ASSVEHYLSR VCYRRAAELF  120
KNAAIASGLR SKIKSNFRLK ELKNMKSGLP TTKSDNFPIP LVKQKGGQYT GFEISNHNSD  180
FIIKIPFGRW QVKKEIDKYR PWEKFDFEQV QKSPKPISLL LSTQRRKRNK GWSKDEGTEA  240
EIKKVMNGDY QTSYIEVKRG SKICEKSAWM LNLSIDVPKI DKGVDPSIIG GIAVGVRSPL  300
VCAINNAFSR YSISDNDLFH FNKKMFARRR ILLKKNRHKR AGHGAKNLKL KPITILTEKSE 360
RFRKKLIERW ACEIADFFIK NKVGTVQMEN LESMKRKEDS YFNIRLRGFW PYAEMQNKIE  420
FKLKQYGIEI RKVAPNNTSK TCSKCGHLNN YFNFEYRKKN KFPHFKCEKC NFKENAAYNA  480
ALNISNPKLK STKERP                                                 496

SEQ ID NO: 22           moltype = AA  length = 495
FEATURE                 Location/Qualifiers
source                  1..495
                        mol_type = protein
                        organism = synthetic construct
SEQUENCE: 22
MAKNTITKTL KLRIVRPLYS QEIEKEIKEE KERRKQAGGT GELDDKFYQK LRGQFPDAVF   60
WQEISEIFRQ LQKQAAEIYN QSLIELYYEI FIKGKGIANA SSVEHYLSRV CYRRAAELFK  120
NAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNAFSRY SISDNDLFHF NKKMFARRRI LLKKNRHKRA GHGAKNLKLK PITILTEKSER 360
FRKKLIERWA CEIADFFIKN KVGTVQMENL ESMKRKEDSY FNIRLRGFWP YAEMQNKIEF  420
KLKQYGIEIR KVAPNNTSKT CSKCGHLNNY FNFEYRKKNK FPHFKCEKCN FKENAAYNAA  480
LNISNPKLKS TKERP                                                  495

SEQ ID NO: 23           moltype = AA  length = 451
FEATURE                 Location/Qualifiers
source                  1..451
                        mol_type = protein
                        organism = synthetic construct
SEQUENCE: 23
MIKVYRYEIV KPLDLDWQEI SEIFRQLQKQ AAEIYNQSLI ELYYEIFIKG KGIANASSVE   60
HYLSRVCYRR AAELFKNAAI ASGLRSKIKS NFRLKELKNM KSGLPTTKSD NFPIPLVKQK  120
GGQYTGFEIS NHNSDFIIKI PFGRWQVKKE IDKYRPWEKF DFEQVQKSPK PISLLLSTQR  180
RKRNKGWSKD EGTEAEIKKV MNGDYQTSYI EVKRGSKICE KSAWMLNLSI DVPKIDKGVD  240
PSIIGGIAVG VRSPLVCAIN NAFSRYSISD NDLFHFNKKM FARRRILLKK NRHKRAGHGA  300
KNLKPITIL TEKSERFRKK LIERWACEIA DFFIKNKVGT VQMENLESMK RKEDSYFNIR  360
LRGFWPYAEM QNKIEFKLKQ YGIEIRKVAP NNTSKTCSKC GHLNNYFNFE YRKKNKFPHF  420
KCEKCNFKEN AAYNAALNIS NPKLKSTKER P                                451

SEQ ID NO: 24           moltype = AA  length = 485
FEATURE                 Location/Qualifiers
source                  1..485
                        mol_type = protein
                        organism = synthetic construct
SEQUENCE: 24
MITVRKIKLT IMGDKDTRNS QYKWIRDEQY NQYRALNMGM TYLAVNDAVF WQEISEIFRQ   60
LQKQAAEIYN QSLIELYYEI FIKGKGIANA SSVEHYLSRV CYRRAAELFK NAAIASGLRS  120
KIKSNFRLKE LKNMKSGLPT TKSDNFPIPL VKQKGGQYTG FEISNHNSDF IIKIPFGRWQ  180
VKKEIDKYRP WEKFDFEQVQ KSPKPISLLL STQRRKRNKG WSKDEGTEAE IKKVMNGDYQ  240
TSYIEVKRGS KICEKSAWML NLSIDVPKID KGVDPSIIGG IAVGVRSPLV CAINNAFSRY  300
SISDNDLFHF NKKMFARRRI LLKKNRHKRA GHGAKNLKLP ITILTEKSER FRKKLIERWA  360
CEIADFFIKN KVGTVQMENL ESMKRKEDSY FNIRLRGFWP YAEMQNKIEF KLKQYGIEIR  420
KVAPNNTSKT CSKCGHLNNY FNFEYRKKNK FPHFKCEKCN FKENAAYNAA LNISNPKLKS  480
TKERP                                                             485

SEQ ID NO: 25           moltype = AA  length = 462
FEATURE                 Location/Qualifiers
source                  1..462
                        mol_type = protein
                        organism = synthetic construct
SEQUENCE: 25
MGESVKAIKL KILDMFLDPE CTKQDDNWQE ISEIFRQLQK QAAEIYNQSL IELYYEIFIK   60
GKGIANASSV EHYLSRVCYR RAAELFKNAA IASGLRSKIK SNFRLKELKN MKSGLPTTKS  120
DNFPIPLVKQ KGGQYTGFEI SNHNSDFIIK IPFGRWQVKK EIDKYRPWEK FDFEQVQKSP  180
KPISLLLSTQ RRKRNKGWSK DEGTEAEIKK VMNGDYQTSY IEVKRGSKIC EKSAWMLNLS  240
IDVPKIDKGV DPSIIGGIAV GVRSPLVCAI NNAFSRYSIS DNDLFHFNKK MFARRRILLK  300
KNRHKRAGHG AKNLKPITIL TEKSERFRKK LIERWACEIA DFFIKNKVGT VQMENLESM  360
KRKEDSYFNI RLRGFWPYAE MQNKIEFKLK QYGIEIRKVA PNNTSKTCSK CGHLNNYFNF  420
EYRKKNKFPH FKCEKCNFKE NAAYNAALNI SNPKLKSTKE RP                    462

SEQ ID NO: 26           moltype = AA  length = 453
FEATURE                 Location/Qualifiers
```

```
source                          1..453
                                mol_type = protein
                                organism = synthetic construct
SEQUENCE: 26
MKYTKVMRYQ IIKPLNAEWQ EISEIFRQLQ KQAAEIYNQS LIELYYEIFI KGKGIANASS    60
VEHYLSRVCY RRAAELFKNA AIASGLRSKI KSNFRLKELK NMKSGLPTTK SDNFPIPLVK   120
QKGGQYTGFE ISNHNSDFII KIPFGRWQVK KEIDKYRPWE KFDFEQVQKS PKPISLLLST   180
QRRKRNKGWS KDEGTEAEIK KVMNGDYQTS YIEVKRGSKI CEKSAWMLNL SIDVPKIDKG   240
VDPSIIGGIA VGVRSPLVCA INNAFSRYSI SDNDLFHFNK KMFARRRILL KKNRHKRAGH   300
GAKNKLKPIT ILTEKSERFR KKLIERWACE IADFFIKNKV GTVQMENLES MKRKEDSYFN   360
IRLRGFWPYA EMQNKIEFKL KQYGIEIRKV APNNTSKTCS KCGHLNNYFN FEYRKKNKFP   420
HFKCEKCNFK ENAAYNAALN ISNPKLKSTK ERP                                453

SEQ ID NO: 27                   moltype = AA  length = 460
FEATURE                         Location/Qualifiers
source                          1..460
                                mol_type = protein
                                organism = synthetic construct
SEQUENCE: 27
MTLLVKVVKI HLISEQFDKA GNRIDYEEIS EIFRQLQKQA AEIYNQSLIE LYYEIFIKGK    60
GIANASSVEH YLSRVCYRRA AELFKNAAIA SGLRSKIKSN FRLKELKNMK SGLPTTKSDN   120
FPIPLVKQKG GQYTGFEISN HNSDFIIKIP FGRWQVKKEI DKYRPWEKFD FEQVQKSPKP   180
ISLLLSTQRR KRNKGWSKDE GTEAEIKKVM NGDYQTSYIE VKRGSKICEK SAWMLNLSID   240
VPKIDKGVDP SIIGGIAVGV RSPLVCAINN AFSRYSISDN DLFHFNKKMF ARRRILLKKN   300
RHKRAGHGAK NKLKPITILT EKSERFRKKL IERWACEIAD FFIKNKVGTV QMENLESMKR   360
KEDSYFNIRL RGFWPYAEMQ NKIEFKLKQY GIEIRKVAPN NTSKTCSKCG HLNNYFNFEY   420
RKKNKFPHFK CEKCNFKENA AYNAALNISN PKLKSTKERP                         460

SEQ ID NO: 28                   moltype = AA  length = 529
FEATURE                         Location/Qualifiers
source                          1..529
                                mol_type = protein
                                organism = synthetic construct
SEQUENCE: 28
MAKNTITKTL KLRIVRPYYS QEIEKIVAEE KNRREKIALE KNKDKVKEAC SKHLKVAAYC    60
TTQVERNACL FCKARKLDDK FYQKLRGQFP DAVFWQEISE IFRQLQKAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP               529

SEQ ID NO: 29                   moltype = AA  length = 529
FEATURE                         Location/Qualifiers
source                          1..529
                                mol_type = protein
                                organism = synthetic construct
SEQUENCE: 29
MAKNTITKTL KLRIVRPYYS AEVEKIVAEE KNNREKIALD KNKDKVKEAC SKHLKVAAYC    60
TTQVERNACL FCKARKLDDK FYKKLRGQFP DAVFWQEISE IFRQLQKAR EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP               529

SEQ ID NO: 30                   moltype = AA  length = 529
FEATURE                         Location/Qualifiers
source                          1..529
                                mol_type = protein
                                organism = synthetic construct
SEQUENCE: 30
MAKNTITKTL KLRIVRPYYS AEIEKIVADE KNRREKIALE KNKDKVKEAC SKHLKVAAYC    60
TTQVERNACL FCKARKLDDK FYQKLRKQFP DAVFWQEISE IFRQLQKAR EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP               529

SEQ ID NO: 31                   moltype = AA  length = 529
FEATURE                         Location/Qualifiers
source                          1..529
```

```
                        mol_type = protein
                        organism = synthetic construct
SEQUENCE: 31
MAKNTITKTL KLRIVRPYNS QEVEKIVAEE KNRREKIALD KNKDKVKEAC SKHLKVAAYC     60
TTQVERNACL FCKARKLDDK FYQKLRKQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP               529

SEQ ID NO: 32           moltype = AA   length = 529
FEATURE                 Location/Qualifiers
source                  1..529
                        mol_type = protein
                        organism = synthetic construct
SEQUENCE: 32
MAKNTITKTL KLRIVRPYNS QEVEKIVAEE KNNREKIALD KNKDKVKEAC SKHLKVAAYC     60
TTQVERNACL FCKARKLDDK FYKKLRKQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP               529

SEQ ID NO: 33           moltype = AA   length = 529
FEATURE                 Location/Qualifiers
source                  1..529
                        mol_type = protein
                        organism = synthetic construct
SEQUENCE: 33
MAKNTITKTL KLRIVRPYNS QEVEKIVAEE KNNREKIALD KNKDKVKEAC SKHLKVAAYC     60
TTQVERNACL FCKARKLDDK FYKKLRGQFP DAVFWQEISE IFRQLQKQAR EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP               529

SEQ ID NO: 34           moltype = AA   length = 529
FEATURE                 Location/Qualifiers
source                  1..529
                        mol_type = protein
                        organism = synthetic construct
SEQUENCE: 34
MAKNTITKTL KLRIVRPYYS AEVEKIVAEE KNNREKIALD KNKDKVKEAC SKHLKVAAYC     60
TTQVERNACL FCKARKLDDK FYKKLRKQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP               529

SEQ ID NO: 35           moltype = AA   length = 529
FEATURE                 Location/Qualifiers
source                  1..529
                        mol_type = protein
                        organism = synthetic construct
SEQUENCE: 35
MAKNTITKTL KLRIVRPYNS AEIEKIVADE KNRREKIALD KNKDKVKEAC SKHLKVAAYC     60
TTQVERNACL FCKARKLDDK FYKKLRKQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP               529

SEQ ID NO: 36           moltype = AA   length = 529
FEATURE                 Location/Qualifiers
```

| source | 1..529 |
| --- | --- |
| | mol_type = protein |
| | organism = synthetic construct |

SEQUENCE: 36
```
MAKNTITKTL KLRIVRPYNS AEIEKIVADE KNRREKIALD KNKDKVKEAC SKHLKVAAYC    60
TTQVERNACL FCKARKLDDK FYKKLRGQFP DAVFWQEISE IFRQLQKQAR EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP              529
```

SEQ ID NO: 37    moltype = AA    length = 529
FEATURE          Location/Qualifiers
source           1..529
                 mol_type = protein
                 organism = synthetic construct SEQUENCE: 37
```
MAKNTITKTL KLRIVRPYNS QEIEKIVAEE KNRREKIALD KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP              529
```

SEQ ID NO: 38    moltype = AA    length = 529
FEATURE          Location/Qualifiers
source           1..529
                 mol_type = protein
                 organism = synthetic construct SEQUENCE: 38
```
MAKNTITKTL KLRIVRPYNS AEIEKIVAEE KNRREKIALD KNKDKVKEAC SKHLKVAAYC    60
TTQVERNACL FCKARKLDDK FYKKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP              529
```

SEQ ID NO: 39    moltype = AA    length = 529
FEATURE          Location/Qualifiers
source           1..529
                 mol_type = protein
                 organism = synthetic construct SEQUENCE: 39
```
MAKNTITKTL KLRIVRPYNS AEVEKIVAEE KNRREKIALD KNKDKVKEAC SKHLKVAAYC    60
TTQVERNACL FCKARKLDDK FYKKLRKQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP              529
```

SEQ ID NO: 40    moltype = AA    length = 529
FEATURE          Location/Qualifiers
source           1..529
                 mol_type = protein
                 organism = synthetic construct SEQUENCE: 40
```
MAKNTITKTL KLRIVRPYNS AEVEKIVADE KNRREKIALD KNKDKVKEAC SKHLKVAAYC    60
TTQVERNACL FCKARKLDDK FYKKLRKQFP DAVFWQEISE IFRQLQKQAR EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP              529
```

SEQ ID NO: 41    moltype = AA    length = 529

```
FEATURE                 Location/Qualifiers
source                  1..529
                        mol_type = protein
                        organism = synthetic construct
SEQUENCE: 41
MAKNTITKTL KLRIVRPYYS AEIEKIVADE KNRREKIALD KNKDKVKEAC SKHLKVAAYC    60
TTQVERNACL FCKARKLDDK FYQKLRKQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP               529

SEQ ID NO: 42           moltype = AA  length = 529
FEATURE                 Location/Qualifiers
source                  1..529
                        mol_type = protein
                        organism = synthetic construct
SEQUENCE: 42
MAKNTITKTL KLRIVRPYYS AEIEKIVAEE KNRREKIALE KNKDKVKEAC SKHLKVAAYC    60
TTQVERNACL FCKARKLDDK FYQKLRKQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP               529

SEQ ID NO: 43           moltype = AA  length = 529
FEATURE                 Location/Qualifiers
source                  1..529
                        mol_type = protein
                        organism = synthetic construct
SEQUENCE: 43
MAKNTITKTL KLRIVRPYYS AEIEKIVAEE KNREKIALD KNKDKVKEAC SKHLKVAAYC    60
TTQVERNACL FCKARKLDDK FYQKLRGQFP DAVFWQEISE IFRQLQKQAR EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP               529

SEQ ID NO: 44           moltype = AA  length = 529
FEATURE                 Location/Qualifiers
source                  1..529
                        mol_type = protein
                        organism = synthetic construct
SEQUENCE: 44
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA RLFKNAAIAS GLRSKIKSNF RLKELKNMKS   180
GLPTTKSDNF PIPLVKQKGG QYTGFKISNH NSDFIIKIPF GRWQVKKEID KYRPWEKFDF   240
RQVQKSPKPI SLLLSTQRRK RNKGWSKDEG TEAEIRKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPIEQLTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP               529

SEQ ID NO: 45           moltype = AA  length = 529
FEATURE                 Location/Qualifiers
source                  1..529
                        mol_type = protein
                        organism = synthetic construct
SEQUENCE: 45
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ALFKNAAIAS GLRSKIKSNF RLKELKNMKS   180
GLPTTKSDNF PIPLVKQKGG QYTGFKISNH NSDFIIKIPF GRWQVKKEID KYRPWEKFDF   240
RQVQKSPKPI SLLLSTQRRK RNKGWSKDEG TEAEIRKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPIEQLTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP               529
```

```
SEQ ID NO: 46            moltype = AA  length = 529
FEATURE                  Location/Qualifiers
source                   1..529
                         mol_type = protein
                         organism = synthetic construct
SEQUENCE: 46
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKAAA EIYNQSLIEL  120
YYEIFIKGKG IANASSVEHY LSRVCYRRAA GLFKNAAIAS GLRSKIKSNF RLKELKNMKS  180
GLPTTKSDNF PIPLVKQKGG QYTGFKISNH NSDFIIKIPF GRWQVKKEID KYRPWEKFDF  240
RQVQKSPKPI SLLLSTQRRK RNKGWSKDEG TEAEIRKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPIEQLTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKERP             529

SEQ ID NO: 47            moltype = AA  length = 529
FEATURE                  Location/Qualifiers
source                   1..529
                         mol_type = protein
                         organism = synthetic construct
SEQUENCE: 47
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKAAA EIYNQSLIEL  120
YYEIFIKGKG IANASSVEHY LSRVCYRRAA RLFKNAAIAS GLRSKIKSNF RLKELKNMKS  180
GLPTTKSDNF PIPLVKQKGG QYTGFRISNH NSDFIIKIPF GRWQVKKEID KYRPWEKFDF  240
RQVQKSPKPI SLLLSTQRRK RNKGWSKDEG TEAEIRKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPIEQLTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKERP             529

SEQ ID NO: 48            moltype = AA  length = 529
FEATURE                  Location/Qualifiers
source                   1..529
                         mol_type = protein
                         organism = synthetic construct
SEQUENCE: 48
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKAAA EIYNQSLIEL  120
YYEIFIKGKG IANASSVEHY LSRVCYRRAA ALFKNAAIAS GLRSKIKSNF RLKELKNMKS  180
GLPTTKSDNF PIPLVKQKGG QYTGFRISNH NSDFIIKIPF GRWQVKKEID KYRPWEKFDF  240
RQVQKSPKPI SLLLSTQRRK RNKGWSKDEG TEAEIRKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPIEQLTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKERP             529

SEQ ID NO: 49            moltype = AA  length = 529
FEATURE                  Location/Qualifiers
source                   1..529
                         mol_type = protein
                         organism = synthetic construct
SEQUENCE: 49
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKAAA EIYNQSLIEL  120
YYEIFIKGKG IANASSVEHY LSRVCYRRAA GLFKNAAIAS GLRSKIKSNF RLKELKNMKS  180
GLPTTKSDNF PIPLVKQKGG QYTGFRISNH NSDFIIKIPF GRWQVKKEID KYRPWEKFDF  240
RQVQKSPKPI SLLLSTQRRK RNKGWSKDEG TEAEIRKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPIEQLTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKERP             529

SEQ ID NO: 50            moltype = AA  length = 529
FEATURE                  Location/Qualifiers
source                   1..529
                         mol_type = protein
                         organism = synthetic construct
SEQUENCE: 50
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKAAA EIYNQSLIEL  120
YYEIFIKGKG IANASSVEHY LSRVCYRRAA RLFKNAAIAS GLRSKIKSNF RLKELKNMKS  180
GLPTTKSDNF PIPLVKQKGG QYTGFSISNH NSDFIIKIPF GRWQVKKEID KYRPWEKFDF  240
RQVQKSPKPI SLLLSTQRRK RNKGWSKDEG TEAEIRKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPIEQLTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKERP             529
```

```
SEQ ID NO: 51               moltype = AA  length = 529
FEATURE                     Location/Qualifiers
source                      1..529
                            mol_type = protein
                            organism = synthetic construct
SEQUENCE: 51
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ALFKNAAIAS GLRSKIKSNF RLKELKNMKS   180
GLPTTKSDNF PIPLVKQKGG QYTGFSISNH NSDFIIKIPF GRWQVKKEID KYRPWEKFDF   240
RQVQKSPKPI SLLLSTQRRK RNKGWSKDEG TEAEIRKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPIEQLTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP              529

SEQ ID NO: 52               moltype = AA  length = 529
FEATURE                     Location/Qualifiers
source                      1..529
                            mol_type = protein
                            organism = synthetic construct
SEQUENCE: 52
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA GLFKNAAIAS GLRSKIKSNF RLKELKNMKS   180
GLPTTKSDNF PIPLVKQKGG QYTGFSISNH NSDFIIKIPF GRWQVKKEID KYRPWEKFDF   240
RQVQKSPKPI SLLLSTQRRK RNKGWSKDEG TEAEIRKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPIEQLTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP              529

SEQ ID NO: 53               moltype = AA  length = 529
FEATURE                     Location/Qualifiers
source                      1..529
                            mol_type = protein
                            organism = synthetic construct
SEQUENCE: 53
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LENFNKKMFA   360
RRRILLKKNR HKRGGHGAKN KLKPIEQLTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP              529

SEQ ID NO: 54               moltype = AA  length = 529
FEATURE                     Location/Qualifiers
source                      1..529
                            mol_type = protein
                            organism = synthetic construct
SEQUENCE: 54
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSIEGGD LFHFNKKMFA   360
RRRILLKKNR HKRAGHGAKN KLKPIEQLTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP              529

SEQ ID NO: 55               moltype = AA  length = 529
FEATURE                     Location/Qualifiers
source                      1..529
                            mol_type = protein
                            organism = synthetic construct
SEQUENCE: 55
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSIEGGD LENFNKKMFA   360
RRRILLKKNR HKRGGHGRDK KLKPIEQLTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
```

```
LNNYFNFEYR KKNKFPHFKC EKCNFKENAA YNAALNISNP KLKSTKERP           529

SEQ ID NO: 56            moltype = AA  length = 529
FEATURE                  Location/Qualifiers
source                   1..529
                         mol_type = protein
                         organism = synthetic construct
SEQUENCE: 56
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL 120
YYEIFIKGKG IANASSVEHY LSRVCYRRAA ELFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIAVGVR SPLVCAINNA FSRYSIEGGD LENFNKKMFA 360
RRRILLKKNR HKRAGHGAKN KLKPITILTE KSERFRKKLI ERWACEIADF FIKNKVGTVQ 420
MENLESMKRK EDSYFNIRLR GFWPYAEMQN KIEFKLKQYG IEIRKVAPNN TSKTCSKCGH 480
LNNYFNFEYR KKNKFPHFKC EKCNFKENAA YNAALNISNP KLKSTKERP           529

SEQ ID NO: 57            moltype = AA  length = 529
FEATURE                  Location/Qualifiers
source                   1..529
                         mol_type = protein
                         organism = synthetic construct
SEQUENCE: 57
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL 120
YYEIFIKGKG IANASSVEHY LSRVCYRRAA ELFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIAVGVR SPLVCAINNA FSRYSISDND LPHFNKKMFA 360
RRRILLKKNR HKRAGHGRDK KLKPIEQLTE KSERFRKKLI ERWACEIADF FIKNKVGTVQ 420
MENLESMKRK EDSYFNIRLR GFWPYAEMQN KIEFKLKQYG IEIRKVAPNN TSKTCSKCGH 480
LNNYFNFEYR KKNKFPHFKC EKCNFKENAA YNAALNISNP KLKSTKERP           529

SEQ ID NO: 58            moltype = AA  length = 529
FEATURE                  Location/Qualifiers
source                   1..529
                         mol_type = protein
                         organism = synthetic construct
SEQUENCE: 58
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL 120
YYEIFIKGKG IANASSVEHY LSRVCYRRAA ELFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIAVGVR SPLVCAINNA FSRYSISDND LENFNKKMFA 360
RRRILLKKNR HKRAGHGRDK KLKPITILTE KSERFRKKLI ERWACEIADF FIKNKVGTVQ 420
MENLESMKRK EDSYFNIRLR GFWPYAEMQN KIEFKLKQYG IEIRKVAPNN TSKTCSKCGH 480
LNNYFNFEYR KKNKFPHFKC EKCNFKENAA YNAALNISNP KLKSTKERP           529

SEQ ID NO: 59            moltype = AA  length = 529
FEATURE                  Location/Qualifiers
source                   1..529
                         mol_type = protein
                         organism = synthetic construct
SEQUENCE: 59
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL 120
YYEIFIKGKG IANASSVEHY LSRVCYRRAA ELFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIAVGVR SPLVCAINNA FSRYSISDND LEHFNKKMFA 360
RRRILLKKNR HKRKGHGAKN KLKPIETLTE KSERFRKKLI ERWACEIADF FIKNKVGTVQ 420
MENLESMKRK EDSYFNIRLR GFWPYAEMQN KIEFKLKQYG IEIRKVAPNN TSKTCSKCGH 480
LNNYFNFEYR KKNKFPHFKC EKCNFKENAA YNAALNISNP KLKSTKERP           529

SEQ ID NO: 60            moltype = AA  length = 529
FEATURE                  Location/Qualifiers
source                   1..529
                         mol_type = protein
                         organism = synthetic construct
SEQUENCE: 60
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL 120
YYEIFIKGKG IANASSVEHY LSRVCYRRAA ELFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIAVGVR SPLVCAINNA FSRYSIDGGD LEHFNKKMFA 360
RRRILLKKNR HKRKGHGAKN KLKPITILTE KSERFRKKLI ERWACEIADF FIKNKVGTVQ 420
```

```
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP               529

SEQ ID NO: 61           moltype = AA  length = 529
FEATURE                 Location/Qualifiers
source                  1..529
                        mol_type = protein
                        organism = synthetic construct
SEQUENCE: 61
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSIDGGD LFHFNKKMFA    360
RRRILLKKNR HKRAGHGAKN KLKPIETLTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP               529

SEQ ID NO: 62           moltype = AA  length = 529
FEATURE                 Location/Qualifiers
source                  1..529
                        mol_type = protein
                        organism = synthetic construct
SEQUENCE: 62
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSIDGGD LEHFNKKMFA    360
RRRILLKKNR HKRKGHGAKN KLKPIETLTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP               529

SEQ ID NO: 63           moltype = AA  length = 529
FEATURE                 Location/Qualifiers
source                  1..529
                        mol_type = protein
                        organism = synthetic construct
SEQUENCE: 63
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSIDSND LFHFNKKMFA    360
RRRILLKKNR HKRKGHGAKN KLKPITELTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP               529

SEQ ID NO: 64           moltype = AA  length = 529
FEATURE                 Location/Qualifiers
source                  1..529
                        mol_type = protein
                        organism = synthetic construct
SEQUENCE: 64
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSIDSND LPHFNKKMFA    360
RRRILLKKNR HKRAGHGAAH KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP               529

SEQ ID NO: 65           moltype = AA  length = 529
FEATURE                 Location/Qualifiers
source                  1..529
                        mol_type = protein
                        organism = synthetic construct
SEQUENCE: 65
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNS FSRYSIDSND LFKFNKKMFA    360
```

```
RRRILLKKNR HKRAGHGAAH KLKPITELTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 66           moltype = AA   length = 529
FEATURE                 Location/Qualifiers
source                  1..529
                        mol_type = protein
                        organism = synthetic construct
SEQUENCE: 66
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSIDSND LFKFNKKMFA    360
RRRILLKKNR HKRAGHGAAH KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 67           moltype = AA   length = 529
FEATURE                 Location/Qualifiers
source                  1..529
                        mol_type = protein
                        organism = synthetic construct
SEQUENCE: 67
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNS FSRYSIDSND LFKFNKKMFA    360
RRRILLKKNR HKRAGHGAKN KLKPITELTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 68           moltype = AA   length = 529
FEATURE                 Location/Qualifiers
source                  1..529
                        mol_type = protein
                        organism = synthetic construct
SEQUENCE: 68
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNS FSRYSIDSND LFKFNKKMFA    360
RRRILLKKNR HKRKGHGAKN KLKPITELTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 69           moltype = AA   length = 529
FEATURE                 Location/Qualifiers
source                  1..529
                        mol_type = protein
                        organism = synthetic construct
SEQUENCE: 69
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSIDSND LFKFNKKMFA    360
RRRILLKKNR HKRKGHGAKN KLKPITELTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 70           moltype = AA   length = 529
FEATURE                 Location/Qualifiers
source                  1..529
                        mol_type = protein
                        organism = synthetic construct
SEQUENCE: 70
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
```

```
AWMLNLSIDV PKIDKGVDPS IIGGIAVGVR SPLVCAINNA FSRYSISDND LFKFNKKMFA    360
RRRILLKKNR HKRKGHGAAH KLKPITELTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 71              moltype = AA   length = 529
FEATURE                    Location/Qualifiers
source                     1..529
                           mol_type = protein
                           organism = synthetic construct
SEQUENCE: 71
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSIKGGD LERFNKKMFA    360
RRRILLKKNR HKRKGHGAKN KLKPITELTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 72              moltype = AA   length = 529
FEATURE                    Location/Qualifiers
source                     1..529
                           mol_type = protein
                           organism = synthetic construct
SEQUENCE: 72
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSIKGGD LERFNKKMFA    360
RRRILLKKNR HKRAGHGAKN KLKPITELTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 73              moltype = AA   length = 529
FEATURE                    Location/Qualifiers
source                     1..529
                           mol_type = protein
                           organism = synthetic construct
SEQUENCE: 73
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSIKGGD LEKFNKKMFA    360
RRRILLKKNR HKRAGHGAKN KLKPITELTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 74              moltype = AA   length = 529
FEATURE                    Location/Qualifiers
source                     1..529
                           mol_type = protein
                           organism = synthetic construct
SEQUENCE: 74
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSIKGGD LPHFNKKMFA    360
RRRILLKKNR HKRAGHGRKK KLKPITELTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 75              moltype = AA   length = 529
FEATURE                    Location/Qualifiers
source                     1..529
                           mol_type = protein
                           organism = synthetic construct
SEQUENCE: 75
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
```

```
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LEKFNKKMFA    360
RRRILLKKNR HKRAGHGRKK KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 76           moltype = AA   length = 529
FEATURE                 Location/Qualifiers
source                  1..529
                        mol_type = protein
                        organism = synthetic construct
SEQUENCE: 76
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSIKGGD LEKFNKKMFA    360
RRRILLKKNR HKRAGHGRKK KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 77           moltype = AA   length = 529
FEATURE                 Location/Qualifiers
source                  1..529
                        mol_type = protein
                        organism = synthetic construct
SEQUENCE: 77
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWAKEIADF FIKNKVGTVQ    420
MEDLSTMKRK EDSYFNIRLR GFWPYYEMQN KIEFKLKQYG IEIRKVAPNN TSQLCSKCGH    480
LNNYFNFEYR KKNKFPKFKC EKCNFKENAA YNAARNISTP DIKSTKERP                529

SEQ ID NO: 78           moltype = AA   length = 529
FEATURE                 Location/Qualifiers
source                  1..529
                        mol_type = protein
                        organism = synthetic construct
SEQUENCE: 78
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWACEIADF FIKNKVGTVQ    420
MEDLESMKRK EDSYFNIRLR GFWPYAEMQN KIEFKLKQYG IEIRKVAPNN TSQLCSKCGH    480
LNNYFNFEYR KKNKFPHFKC EKCNFKENAA YNAALNISNP DIKSTKERP                529

SEQ ID NO: 79           moltype = AA   length = 529
FEATURE                 Location/Qualifiers
source                  1..529
                        mol_type = protein
                        organism = synthetic construct
SEQUENCE: 79
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWAKEIADF FIKNKVGTVQ    420
MEDLSTMKRK EDSYFNIRLR GFWPYYEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 80           moltype = AA   length = 529
FEATURE                 Location/Qualifiers
source                  1..529
                        mol_type = protein
                        organism = synthetic construct
SEQUENCE: 80
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
```

```
GLPTTKSDNF PIPLVKQKGG QYTGFEISNH NSDFIIKIPF GRWQVKKEID KYRPWEKFDF     240
EQVQKSPKPI SLLLSTQRRK RNKGWSKDEG TEAEIKKVMN GDYQTSYIEV KRGSKICEKS     300
AWMLNLSIDV PKIDKGVDPS IIGGIAVGVR SPLVCAINNA FSRYSISDND LFHFNKKMFA     360
RRRILLKKNR HKRAGHGAKN KLKPITILTE KSERFRKKLI ERWACEIADF FIKNKVGTVQ     420
MENLESMKRK EDSYFNIRLR GFWPYAEMQN KIEFKLKQYG IEIRKVAPNN TSQLCSKCGH     480
LNNYFNFEYR KKNKFPKFKC EKCNFKENAA YNAALNISNP DIKSTKERP                529

SEQ ID NO: 81             moltype = AA  length = 529
FEATURE                   Location/Qualifiers
source                    1..529
                          mol_type = protein
                          organism = synthetic construct
SEQUENCE: 81
MAKNTITKTL KLRIVRPYNS AEVEKIVADE KNNREKIALE KNKDKVKEAC SKHLKVAAYC      60
TTQVERNACL FCKARKLDDK FYQKLRGQFP DAVFWQEISE IFRQLQKQAA EIYNQSLIEL     120
YYEIFIKGKG IANASSVEHY LSRVCYRRAA ELFKNAAIAS GLRSKIKSNF RLKELKNMKS     180
GLPTTKSDNF PIPLVKQKGG QYTGFEISNH NSDFIIKIPF GRWQVKKEID KYRPWEKFDF     240
EQVQKSPKPI SLLLSTQRRK RNKGWSKDEG TEAEIKKVMN GDYQTSYIEV KRGSKICEKS     300
AWMLNLSIDV PKIDKGVDPS IIGGIAVGVR SPLVCAINNA FSRYSISDND LFHFNKKMFA     360
RRRILLKKNR HKRAGHGAKN KLKPITILTE KSERFRKKLI ERWACEIADF FIKNKVGTVQ     420
MENLESMKRK EDSYFNIRLR GFWPYAEMQN KIEFKLKQYG IEIRKVAPNN TSQLCSKCGH     480
LNNYFNFEYR KKNKFPHFKC EKCNFKENAA YNAALNISTP DIKSTKERP                529

SEQ ID NO: 82             moltype = AA  length = 529
FEATURE                   Location/Qualifiers
source                    1..529
                          mol_type = protein
                          organism = synthetic construct
SEQUENCE: 82
MAKNTITKTL KLRIVRPYNS AEVEKIVADE KNNREKIALE KNKDKVKEAC SKHLKVAAYC      60
TTQVERNACL FCKARKLDDK FYQKLRGQFP DAVFWQEISE IFRQLQKQAA EIYNQSLIEL     120
YYEIFIKGKG IANASSVEHY LSRVCYRRAA ELFKNAAIAS GLRSKIKSNF RLKELKNMKS     180
GLPTTKSDNF PIPLVKQKGG QYTGFEISNH NSDFIIKIPF GRWQVKKEID KYRPWEKFDF     240
EQVQKSPKPI SLLLSTQRRK RNKGWSKDEG TEAEIKKVMN GDYQTSYIEV KRGSKICEKS     300
AWMLNLSIDV PKIDKGVDPS IIGGIAVGVR SPLVCAINNA FSRYSISDND LFHFNKKMFA     360
RRRILLKKNR HKRAGHGAKN KLKPITILTE KSERFRKKLI ERWACEIADF FIKNKVGTVQ     420
MEDLSTMKRK EDSYFNIRLR GFWPYYEMQN KIEFKLKQYG IEIRKVAPNN TSKTCSKCGH     480
LNNYFNFEYR KKNKFPKFKC EKCNFKENAA YNAALNISNP KLKSTKERP                529

SEQ ID NO: 83             moltype = AA  length = 529
FEATURE                   Location/Qualifiers
source                    1..529
                          mol_type = protein
                          organism = synthetic construct
SEQUENCE: 83
MAKNTITKTL KLRIVRPYNS AEVEKIVADE KNNREKIALE KNKDKVKEAC SKHLKVAAYC      60
TTQVERNACL FCKARKLDDK FYQKLRGQFP DAVFWQEISE IFRQLQKQAA EIYNQSLIEL     120
YYEIFIKGKG IANASSVEHY LSRVCYRRAA ELFKNAAIAS GLRSKIKSNF RLKELKNMKS     180
GLPTTKSDNF PIPLVKQKGG QYTGFEISNH NSDFIIKIPF GRWQVKKEID KYRPWEKFDF     240
EQVQKSPKPI SLLLSTQRRK RNKGWSKDEG TEAEIKKVMN GDYQTSYIEV KRGSKICEKS     300
AWMLNLSIDV PKIDKGVDPS IIGGIAVGVR SPLVCAINNA FSRYSISDND LFHFNKKMFA     360
RRRILLKKNR HKRAGHGAKN KLKPITILTE KSERFRKKLI ERWACEIADF FIKNKVGTVQ     420
MEDLESMKRK EDSYFNIRLR GFWPYAEMQN KIEFKLKQYG IEIRKVAPNN TSQLCSKCGH     480
LNNYFNFEYR KKNKFPKFKC EKCNFKENAA YNAALNISTP DIKSTKERP                529

SEQ ID NO: 84             moltype = AA  length = 529
FEATURE                   Location/Qualifiers
source                    1..529
                          mol_type = protein
                          organism = synthetic construct
SEQUENCE: 84
MAKNTITKTL KLRIVRPYNS AEVEKIVADE KNNREKIALE KNKDKVKEAC SKHLKVAAYC      60
TTQVERNACL FCKARKLDDK FYQKLRGQFP DAVFWQEISE IFRQLQKQAA EIYNQSLIEL     120
YYEIFIKGKG IANASSVEHY LSRVCYRRAA ELFKNAAIAS GLRSKIKSNF RLKELKNMKS     180
GLPTTKSDNF PIPLVKQKGG QYTGFEISNH NSDFIIKIPF GRWQVKKEID KYRPWEKFDF     240
EQVQKSPKPI SLLLSTQRRK RNKGWSKDEG TEAEIKKVMN GDYQTSYIEV KRGSKICEKS     300
AWMLNLSIDV PKIDKGVDPS IIGGIAVGVR SPLVCAINNA FSRYSISDND LFHFNKKMFA     360
RRRILLKKNR HKRAGHGAKN KLKPITILTE KSERFRKKLI ERWACEIADF FIKNKVGTVQ     420
MENLESMKRK EDSYFNIRLR GFWPYAEMQN KIEFKLKQYG IEIRKVAPNN TSKTCSKCGH     480
LNNYFNFEYR KKNKFPKFKC EKCNFKENAA YNAARNISTP DIKSTKERP                529

SEQ ID NO: 85             moltype = AA  length = 529
FEATURE                   Location/Qualifiers
source                    1..529
                          mol_type = protein
                          organism = synthetic construct
SEQUENCE: 85
MAKNTITKTL KLRIVRPYNS AEVEKIVADE KNNREKIALE KNKDKVKEAC SKHLKVAAYC      60
TTQVERNACL FCKARKLDDK FYQKLRGQFP DAVFWQEISE IFRQLQKQAA EIYNQSLIEL     120
```

```
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWSRYIADF FIKNKVGTVQ    420
MEDLESMKRK EDSYFNIRLR GFWPYYEMQN KIEFKLKQYG IKIRKVAPNN TSQRCSKCGH    480
LNNYFNFEYR KKNKFPHFKC EKCNFKANAA YNAARNISNP NIKSTKERP               529

SEQ ID NO: 86            moltype = AA   length = 529
FEATURE                  Location/Qualifiers
source                   1..529
                         mol_type = protein
                         organism = synthetic construct
SEQUENCE: 86
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWACYIADF FIKNKVGTVQ    420
MEDLESMKRK EDSYFNIRLR GFWPYAEMQN KIEFKLKQYG IEIRKVAPNN TSQRCSKCGH    480
LNNYFNFEYR KKNKFPHFKC EKCNFKENAA YNAARNISNP NIKSTKERP               529

SEQ ID NO: 87            moltype = AA   length = 529
FEATURE                  Location/Qualifiers
source                   1..529
                         mol_type = protein
                         organism = synthetic construct
SEQUENCE: 87
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWACYIADF FIKNKVGTVQ    420
MENLESMKRK EDSYFNIRLR GFWPYAEMQN KIEFKLKQYG IEIRKVAPNN TSQRCSKCGH    480
LNNYFNFEYR KKNKFPHFKC EKCNFKRNAA YNAARNISNP KLKSTKERP               529

SEQ ID NO: 88            moltype = AA   length = 529
FEATURE                  Location/Qualifiers
source                   1..529
                         mol_type = protein
                         organism = synthetic construct
SEQUENCE: 88
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWACYIADF FIKNKVGTVQ    420
MEDLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAARNISNP NIKSTKERP               529

SEQ ID NO: 89            moltype = AA   length = 529
FEATURE                  Location/Qualifiers
source                   1..529
                         mol_type = protein
                         organism = synthetic construct
SEQUENCE: 89
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVR SPLVCAINNA FSRYSISDND LFHFNKKMFA    360
RRRILLKKNR HKRAGHGAKN KLKPITILTE KSERFRKKLI ERWARYIADF FIKNKVGTVQ    420
MEDLESMKRK EDSYFNIRLR GFWPYYEMQN KIEFKLKQYG IKIRKVAPNN TSKTCSKCGH    480
LNNYFNFEYR KKNKFPHFKC EKCNFKENAA YNAALNISNP KLKSTKERP               529

SEQ ID NO: 90            moltype = AA   length = 529
FEATURE                  Location/Qualifiers
source                   1..529
                         mol_type = protein
                         organism = synthetic construct
SEQUENCE: 90
MAKNTITKTL KLRIVRPYNS AEVEKIVADE KNNREKIALE KNKDKVKEAC SKHLKVAAYC     60
```

```
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLQYG  IEIRKVAPNN TSQRCSKCGH  480
LNNYFNFEYR KKNKFPHFKC EKCNFKRNAA YNAARNISNP NIKSTKERP             529

SEQ ID NO: 91           moltype = AA   length = 529
FEATURE                 Location/Qualifiers
source                  1..529
                        mol_type = protein
                        organism = synthetic construct
SEQUENCE: 91
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPITILTE KSERFRKKLI ERWACEIADF FIKNKVGTVQ  420
MEDLESMKRK EDSYFNIRLR GFWPYAEMQN KIEFKLQYG  IEIRKVAPNN TSQRCSKCGH  480
LNNYFNFEYR KKNKFPHFKC EKCNFKENAA YNAARNISNP NIKSTKERP             529

SEQ ID NO: 92           moltype = AA   length = 529
FEATURE                 Location/Qualifiers
source                  1..529
                        mol_type = protein
                        organism = synthetic construct
SEQUENCE: 92
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLQYG  IEIRKVAPNN TSKTCSKCGH  480
LNNYFNFEYR KKNKFPHFKC EKCNFKRNAA YNAARNISNP NIKSTKERP             529

SEQ ID NO: 93           moltype = AA   length = 529
FEATURE                 Location/Qualifiers
source                  1..529
                        mol_type = protein
                        organism = synthetic construct
SEQUENCE: 93
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPITILTE KSERFRKKLI ERWANRIADF FIKNKVGTVQ  420
MENLESMKRK EDSYFNIRLR GFWPYAEMQN KIEFKLQYG  IKIRKVAPNN TSQRCSKCGH  480
LNNYFNFEYR KKNKFPHFKC EKCNFKRNAA YNAAKNISNP KLKSTKERP             529

SEQ ID NO: 94           moltype = AA   length = 529
FEATURE                 Location/Qualifiers
source                  1..529
                        mol_type = protein
                        organism = synthetic construct
SEQUENCE: 94
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLQYG  IEIRKVAPNN TSQRCSKCGH  480
LNNYFNFEYR KKNKFPHFKC EKCNFKRNAA YNAAKNISNP KLKSTKERP             529

SEQ ID NO: 95           moltype = AA   length = 529
FEATURE                 Location/Qualifiers
source                  1..529
                        mol_type = protein
                        organism = synthetic construct
SEQUENCE: 95
```

```
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IKIRKVAPNN TSQRCSKCGH  480
LNNYFNFEYR KKNKFPHFKC EKCNFKRNAA YNAAKNISNP KLKSTKERP             529

SEQ ID NO: 96           moltype = AA   length = 529
FEATURE                 Location/Qualifiers
source                  1..529
                        mol_type = protein
                        organism = synthetic construct
SEQUENCE: 96
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPITILTE KSERFRKKLI ERWANRIADF FIKNKVGTVQ  420
MENLESMKRK EDSYFNIRLR GFWPYAEMQN KIEFKLKQYG IKIRKVAPNN TSQRCSKCGH  480
LNNYFNFEYR KKNKFPHFKC EKCNFKENAA YNAALNISNP KLKSTKERP             529

SEQ ID NO: 97           moltype = AA   length = 529
FEATURE                 Location/Qualifiers
source                  1..529
                        mol_type = protein
                        organism = synthetic construct
SEQUENCE: 97
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPITILTE KSERFRKKLI ERWANRIADF FIKNKVGTVQ  420
MENLESMKRK EDSYFNIRLR GFWPYAEMQN KIEFKLKQYG IEIRKVAPNN TSQRCSKCGH  480
LNNYFNFEYR KKNKFPHFKC EKCNFKRNAA YNAALNISNP KLKSTKERP             529

SEQ ID NO: 98           moltype = AA   length = 529
FEATURE                 Location/Qualifiers
source                  1..529
                        mol_type = protein
                        organism = synthetic construct
SEQUENCE: 98
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPITILTE KSERFRKKLI ERWSRFIADF FIKNKVGTVQ  420
MEDLESMKRK EDSYFNIRLR GFWPYYEMQN KIEFKLKQYG IEIRKVAPNN TSQRCSKCGH  480
LNNYFNFEYR KKNKFPHFKC EKCNFKENAA YNAARNISNP NIKSTKERP             529

SEQ ID NO: 99           moltype = AA   length = 514
FEATURE                 Location/Qualifiers
source                  1..514
                        mol_type = protein
                        organism = synthetic construct
SEQUENCE: 99
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQGG QYTGFEISNH NSDFIIDVQL YSKEYSKDSG KGTHRYFLLS  240
TQRRKRNKGW SKDEGTEAEI KKVMNGDYQT SYIEVKRGSK ICEKSAWMLN LSIDVPKIDK  300
GVDPSIIGGI AVGVRSPLVC AINNAFSRYS ISDNDLFHFN KKMFARRRIL LKKNRHKRAG  360
HGAKNKLKPI TILTEKSERF RKKLIERWAC EIADFFIKNK VGTVQMENLE SMKRKEDSYF  420
NIRLRGFWPY AEMQNKIEFK LKQYGIEIRK VAPNNTSKTC SKCGHLNNYF NFEYRKKNKF  480
PHFKCEKCNF KENAAYNAAL NISNPKLKST KERP                             514

SEQ ID NO: 100          moltype = AA   length = 514
FEATURE                 Location/Qualifiers
source                  1..514
                        mol_type = protein
                        organism = synthetic construct
```

```
SEQUENCE: 100
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIASLSL LSNPAKQEMN VKRKISLLLS   240
TQRRKRNKGW SKDEGTEAEI KKVMNGDYQT SYIEVKRGSK ICEKSAWMLN LSIDVPKIDK   300
GVDPSIIGGI AVGVRSPLVC AINNAFSRYS ISDNDLFHFN KKMFARRRIL LKKNRHKRAG   360
HGAKNKLKPI TILTEKSERF RKKLIERWAC EIADFFIKNK VGTVQMENLE SMKRKEDSYF   420
NIRLRGFWPY AEMQNKIEFK LKQYGIEIRK VAPNNTSKTC SKCGHLNNYF NFEYRKKNKF   480
PHFKCEKCNF KENAAYNAAL NISNPKLKST KERP                              514

SEQ ID NO: 101           moltype = AA   length = 540
FEATURE                  Location/Qualifiers
source                   1..540
                         mol_type = protein
                         organism = synthetic construct
SEQUENCE: 101
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PIYERKPNRS IVGGLAVGIR SPLVCAINNS FSRYSVDSND VFKFSKQVFA   360
FRRRLLSKNS LKRKGHGAAH KLEPITEMTE KNDKFRKKII ERWAKEVTNF FVKNQVGIVQ   420
IEDLSTMKDR EDHFFNQYLR GFWPYYQMQT LIENKLKEYG IEVKRVQAKY TSQLCSNPNC   480
RYWNNYFNFE YRKVNKFPKF KCEKCNLEIS AAYNAARNLS TPDIEKFVAK ATKGINLPEK   540

SEQ ID NO: 102           moltype = AA   length = 590
FEATURE                  Location/Qualifiers
source                   1..590
                         mol_type = protein
                         organism = synthetic construct
SEQUENCE: 102
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PTHETVLDPD KVMGVALGVA KAVYWAFNSS YKRGCIDGGE IEHFRKMIRA   360
RRVSIQNQIK HSGDARKGHG RKRALKPIET LSEKEKNFRD TINHRYANRI VEAAIKQGCG   420
TIQIENLEGI ADTTGSKFLK NWPYYDLQTK IVNKAKEHGI TVVAINPQYT SQRCSMCGYI   480
EKTNRSSQAV FECKQCGYGS RTICINCRHV QVSGDVCEEC GGIVKKENVN AAYNAAKNIS   540
TPYIDQIIME KCLELGIPYR SITCKECGHI QASGNTCEVC GSTNILKPKK             590

SEQ ID NO: 103           moltype = AA   length = 522
FEATURE                  Location/Qualifiers
source                   1..522
                         mol_type = protein
                         organism = synthetic construct
SEQUENCE: 103
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PQTRVLDNLK IMGIALGVAV AVYMAFQHTP ARYKLEGGEI ENFRRQVESR   360
RISMLRQGKY AGGARGGHGR DKRIKPIEQL RDKIANFRDT TNHRYSRYIV DMAIKEGCGT   420
IQMEDLTNIR DIGSRFLQNW TYYDLQQKII YKAEEAGIKV IKIDPQYTSQ RCSECGNIDS   480
GNRIGQAIFK CRACGYEANA AYNAARNIAI PNIDKIIAES IK                     522

SEQ ID NO: 104           moltype = AA   length = 532
FEATURE                  Location/Qualifiers
source                   1..532
                         mol_type = protein
                         organism = synthetic construct
SEQUENCE: 104
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PIDIVNKKVS GRVVGVALGL KIPAYCALND VEYIKKSIGR IDDFLKVRTQ   360
MQSRRRRLQI AIQSAKGGKG RVNKLQALER FAEKEKNFAK TYNHFLSSNI VKFAVSNQAE   420
QINMELLSLK ETQNKSILRN WSYYQLQTMI EYKAQREGIK VKYIDPYHTS QTCSKCGNYE   480
EGQRESQADF ICKKCGYKVN AAYNAARNIA MSNKYITKKE ESKYYKIKES MV           532

SEQ ID NO: 105           moltype = AA   length = 524
FEATURE                  Location/Qualifiers
source                   1..524
```

```
                       mol_type = protein
                       organism = synthetic construct
SEQUENCE: 105
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV ETKETALDPN NVMGVALGIV YPVYIAFNNS LHRYHIKGGE IERFRRQVEK   360
RKRELLNQGK YCGDGRKGHG YATRTKSIES ISDKIARFRD TCNHKYSRFI VDMALKHNCG   420
IIQMEDLTGI SKESTFLKNW TYYDLQQKIE YKAREAGIQV IKIEPQYTSQ RCSKCGYIDK   480
ENRQEQATFK CIECGFKTNA AYNAARNIAI PNIDKIIRKT LKMQ                    524

SEQ ID NO: 106         moltype = AA  length = 540
FEATURE                Location/Qualifiers
source                 1..540
                       mol_type = protein
                       organism = synthetic construct
SEQUENCE: 106
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVNRS IVGGLAVGIR SPLVCAINNS FSRYSVDSND VFKFSKQVFA   360
FRRRLLSKNS LKRKGHGAAH KLEPITEMTE KNDKFRKKII ERWAKEVTNF PVKNQVGIVQ   420
IEDLSTMKDR EDHFFNQYLR GFWPYYQMQT LIENKLKEYG IEVKRVQAKY TSQLCSNPNC   480
RYWNNYFNFE YRKVNKFPKF KCEKCNLEIS AAYNAARNLS TPDIEKFVAK ATKGINLPEK   540

SEQ ID NO: 107         moltype = AA  length = 590
FEATURE                Location/Qualifiers
source                 1..590
                       mol_type = protein
                       organism = synthetic construct
SEQUENCE: 107
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPD KVMGVALGVA KAVYWAFNSS YKRGCIDGGE IEHFRKMIRA   360
RRVSIQNQIK HSGDARKGHG RKRALKPIET LSEKEKNFRD TINHRYANRI VEAAIKQGCG   420
TIQIENLEGI ADTTGSKFLK NWPYYDLQTK IVNKAKEHGI TVVAINPQYT SQRCSMCGYI   480
EKTNRSSQAV FECKQCGYGS RTICINCRHV QVSGDVCEEC GGIVKKENVN AAYNAAKNIS   540
TPYIDQIIME KCLELGIPYR SITCKECGHI QASGNTCEVC GSTNILKPKK              590

SEQ ID NO: 108         moltype = AA  length = 523
FEATURE                Location/Qualifiers
source                 1..523
                       mol_type = protein
                       organism = synthetic construct
SEQUENCE: 108
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDLN KIMGIALGVA VAVYMAFQHT PARYKLEGGE IENFRRQVES   360
RRISMLRQGK YAGGARGGHG RDKRIKPIEQ LRDKIANFRD TTNHRYSRYI VDMAIKEGCG   420
TIQMEDLTNI RDIGSRFLQN WTYYDLQQKI IYKAEEAGIK VIKIDPQYTS QRCSECGNID   480
SGNRIGQAIF KCRACGYEAN AAYNAARNIA IPNIDKIIAE SIK                     523

SEQ ID NO: 109         moltype = AA  length = 524
FEATURE                Location/Qualifiers
source                 1..524
                       mol_type = protein
                       organism = synthetic construct
SEQUENCE: 109
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPN NVMGVALGIV YPVYIAFNNS LHRYHIKGGE IERFRRQVEK   360
RKRELLNQGK YCGDGRKGHG YATRTKSIES ISDKIARFRD TCNHKYSRFI VDMALKHNCG   420
IIQMEDLTGI SKESTFLKNW TYYDLQQKIE YKAREAGIQV IKIEPQYTSQ RCSKCGYIDK   480
ENRQEQATFK CIECGFKTNA AYNAARNIAI PNIDKIIRKT LKMQ                    524

SEQ ID NO: 110         moltype = AA  length = 535
```

```
FEATURE              Location/Qualifiers
source               1..535
                     mol_type = protein
                     organism = synthetic construct
SEQUENCE: 110
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDKE KILGVAVGVN CPLVASVFGD RDRFIIKGGE IEKFRKSVEA   360
RRRSMLEQTK YCGDGRIGHG RKKRTEPALN IGDKIARFRD TTNHKYSRAL IEYAVKKGCG   420
TIQMEKLTGI TSKSDRFLKD WTYYDLQTKI ENKAKEVGIN VVYIAPKYTS QRCSKCGYIH   480
KDNRPNQAKF RCLECDFESN AAYNASQNIG IKNIDKIIEK DLQKQESEVQ VNENK        535

SEQ ID NO: 111         moltype = AA   length = 517
FEATURE              Location/Qualifiers
source               1..517
                     mol_type = protein
                     organism = synthetic construct
SEQUENCE: 111
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNI                           517

SEQ ID NO: 112         moltype = AA   length = 495
FEATURE              Location/Qualifiers
source               1..495
                     mol_type = protein
                     organism = synthetic construct
SEQUENCE: 112
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKNRHKRK GHGAKNKLKP ITELTEKSER    360
FRKKLIERWA CEIADFFIKN KVGTVQMEDL ESMKRKEDSY FNIRLRGFWP YAEMQNKIEF   420
KLKQYGIEIR KVAPNNTSQL CSKCGHLNNY FNFEYRKKNK FPHFKCEKCN FKENAAYNAA   480
LNISNPDIKS TKERP                                                   495

SEQ ID NO: 113         moltype = AA   length = 495
FEATURE              Location/Qualifiers
source               1..495
                     mol_type = protein
                     organism = synthetic construct
SEQUENCE: 113
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKNRHKRK GHGAKNKLKP ITELTEKSER    360
FRKKLIERWA CEIADFFIKN KVGTVQMENL ESMKRKEDSY FNIRLRGFWP YAEMQNKIEF   420
KLKQYGIEIR KVAPNNTSQL CSKCGHLNNY FNFEYRKKNK FPKFKCEKCN FKENAAYNAA   480
LNISNPDIKS TKERP                                                   495

SEQ ID NO: 114         moltype = AA   length = 495
FEATURE              Location/Qualifiers
source               1..495
                     mol_type = protein
                     organism = synthetic construct
SEQUENCE: 114
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKNRHKRK GHGAKNKLKP ITELTEKSER    360
FRKKLIERWA CEIADFFIKN KVGTVQMEDL ESMKRKEDSY FNIRLRGFWP YAEMQNKIEF   420
KLKQYGIEIR KVAPNNTSQL CSKCGHLNNY FNFEYRKKNK FPKFKCEKCN FKENAAYNAA   480
LNISTPDIKS TKERP                                                   495
```

```
SEQ ID NO: 115           moltype = AA  length = 495
FEATURE                  Location/Qualifiers
source                   1..495
                         mol_type = protein
                         organism = synthetic construct
SEQUENCE: 115
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKKNRHKRK GHGAKNKLKP ITELTEKSER   360
FRKKLIERWA CEIADFFIKN KVGTVQMEDL ESMKRKEDSY FNIRLRGFWP YAEMQNKIEF   420
KLKQYGIEIR KVAPNNTSQR CSKCGHLNNY FNFEYRKKNP FPHFKCEKCN FKENAAYNAA   480
RNISNPNIKS TKERP                                                   495

SEQ ID NO: 116           moltype = AA  length = 495
FEATURE                  Location/Qualifiers
source                   1..495
                         mol_type = protein
                         organism = synthetic construct
SEQUENCE: 116
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKKNRHKRK GHGAKNKLKP ITELTEKSER   360
FRKKLIERWA CEIADFFIKN KVGTVQMENL ESMKRKEDSY FNIRLRGFWP YAEMQNKIEF   420
KLKQYGIEIR KVAPNNTSKT CSKCGHLNNY FNFEYRKKNP FPHFKCEKCN FKENAAYNAA   480
LNISNPKLKS TKERP                                                   495

SEQ ID NO: 117           moltype = AA  length = 483
FEATURE                  Location/Qualifiers
source                   1..483
                         mol_type = protein
                         organism = synthetic construct
SEQUENCE: 117
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKKNRHKRK GHGAKNKLKP ITELTEKSER   360
FRKKLIERWA CEIADFFIKN KVGTVQMEDL ESMKRKEDSY FNIRLRGFWP YAEMQNKIEF   420
KLKQYGIEIR KVAPNNTSQL CSKCGHLNNY FNFEYRKKNK FPHFKCEKCN FKENAAYNAA   480
LNI                                                                483

SEQ ID NO: 118           moltype = AA  length = 483
FEATURE                  Location/Qualifiers
source                   1..483
                         mol_type = protein
                         organism = synthetic construct
SEQUENCE: 118
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKKNRHKRK GHGAKNKLKP ITELTEKSER   360
FRKKLIERWA CEIADFFIKN KVGTVQMENL ESMKRKEDSY FNIRLRGFWP YAEMQNKIEF   420
KLKQYGIEIR KVAPNNTSQL CSKCGHLNNY FNFEYRKKNK FPKFKCEKCN FKENAAYNAA   480
LNI                                                                483

SEQ ID NO: 119           moltype = AA  length = 483
FEATURE                  Location/Qualifiers
source                   1..483
                         mol_type = protein
                         organism = synthetic construct
SEQUENCE: 119
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKKNRHKRK GHGAKNKLKP ITELTEKSER   360
FRKKLIERWA CEIADFFIKN KVGTVQMEDL ESMKRKEDSY FNIRLRGFWP YAEMQNKIEF   420
KLKQYGIEIR KVAPNNTSQL CSKCGHLNNY FNFEYRKKNK FPKFKCEKCN FKENAAYNAA   480
LNI                                                                483
```

```
SEQ ID NO: 120          moltype = AA  length = 483
FEATURE                 Location/Qualifiers
source                  1..483
                        mol_type = protein
                        organism = synthetic construct
SEQUENCE: 120
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNSFSRY SISDNDLFKF NKKMFARRRI LLKKNRHKRK GHGAKNKLKP ITELTEKSER  360
FRKKLIERWA CEIADFFIKN KVGTVQMEDL ESMKRKEDSY FNIRLRGFWP YAEMQNKIEF  420
KLKQYGIEIR KVAPNNTSQR CSKCGHLNNY FNFEYRKKNK FPHFKCEKCN FKENAAYNAA  480
RNI                                                                483

SEQ ID NO: 121          moltype = AA  length = 483
FEATURE                 Location/Qualifiers
source                  1..483
                        mol_type = protein
                        organism = synthetic construct
SEQUENCE: 121
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNSFSRY SISDNDLFKF NKKMFARRRI LLKKNRHKRK GHGAKNKLKP ITELTEKSER  360
FRKKLIERWA CEIADFFIKN KVGTVQMENL ESMKRKEDSY FNIRLRGFWP YAEMQNKIEF  420
KLKQYGIEIR KVAPNNTSKT CSKCGHLNNY FNFEYRKKNK FPHFKCEKCN FKENAAYNAA  480
LNI                                                                483

SEQ ID NO: 122          moltype = AA  length = 495
FEATURE                 Location/Qualifiers
source                  1..495
                        mol_type = protein
                        organism = synthetic construct
SEQUENCE: 122
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNAFSRY SISDNDLFHF NKKMFARRRI LLKKNRHKRA GHGAKNKLKP ITILTEKSER  360
FRKKLIERWA CEIADFFIKN KVGTVQMEDL ESMKRKEDSY FNIRLRGFWP YAEMQNKIEF  420
KLKQYGIEIR KVAPNNTSQL CSKCGHLNNY FNFEYRKKNK FPHFKCEKCN FKENAAYNAA  480
LNISNPDIKS TKERP                                                   495

SEQ ID NO: 123          moltype = AA  length = 495
FEATURE                 Location/Qualifiers
source                  1..495
                        mol_type = protein
                        organism = synthetic construct
SEQUENCE: 123
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNAFSRY SISDNDLFHF NKKMFARRRI LLKKNRHKRA GHGAKNKLKP ITILTEKSER  360
FRKKLIERWA CEIADFFIKN KVGTVQMENL ESMKRKEDSY FNIRLRGFWP YAEMQNKIEF  420
KLKQYGIEIR KVAPNNTSQL CSKCGHLNNY FNFEYRKKNK FPKFKCEKCN FKENAAYNAA  480
LNISNPDIKS TKERP                                                   495

SEQ ID NO: 124          moltype = AA  length = 495
FEATURE                 Location/Qualifiers
source                  1..495
                        mol_type = protein
                        organism = synthetic construct
SEQUENCE: 124
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNAFSRY SISDNDLFHF NKKMFARRRI LLKKNRHKRA GHGAKNKLKP ITILTEKSER  360
FRKKLIERWA CEIADFFIKN KVGTVQMEDL ESMKRKEDSY FNIRLRGFWP YAEMQNKIEF  420
KLKQYGIEIR KVAPNNTSQL CSKCGHLNNY FNFEYRKKNK FPKFKCEKCN FKENAAYNAA  480
```

```
LNISTPDIKS TKERP                                                        495

SEQ ID NO: 125            moltype = AA  length = 495
FEATURE                   Location/Qualifiers
source                    1..495
                          mol_type = protein
                          organism = synthetic construct
SEQUENCE: 125
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNAFSRY SISDNDLFHF NKKMFARRRI LLKKNRHKRA GHGAKNKLKP ITILTEKSER  360
FRKKLIERWA CEIADFFIKN KVGTVQMEDL ESMKRKEDSY FNIRLRGFWP YAEMQNKIEF  420
KLKQYGIEIR KVAPNNTSQR CSKCGHLNNY FNFEYRKKNK FPHFKCEKCN FKENAAYNAA  480
RNISNPNIKS TKERP                                                    495

SEQ ID NO: 126            moltype = AA  length = 495
FEATURE                   Location/Qualifiers
source                    1..495
                          mol_type = protein
                          organism = synthetic construct
SEQUENCE: 126
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNAFSRY SISDNDLFHF NKKMFARRRI LLKKNRHKRA GHGAKNKLKP ITILTEKSER  360
FRKKLIERWA CEIADFFIKN KVGTVQMENL ESMKRKEDSY FNIRLRGFWP YAEMQNKIEF  420
KLKQYGIEIR KVAPNNTSKT CSKCGHLNNY FNFEYRKKNK FPHFKCEKCN FKENAAYNAA  480
LNISNPKLKS TKERP                                                    495

SEQ ID NO: 127            moltype = AA  length = 483
FEATURE                   Location/Qualifiers
source                    1..483
                          mol_type = protein
                          organism = synthetic construct
SEQUENCE: 127
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNAFSRY SISDNDLFHF NKKMFARRRI LLKKNRHKRA GHGAKNKLKP ITILTEKSER  360
FRKKLIERWA CEIADFFIKN KVGTVQMEDL ESMKRKEDSY FNIRLRGFWP YAEMQNKIEF  420
KLKQYGIEIR KVAPNNTSQL CSKCGHLNNY FNFEYRKKNK FPHFKCEKCN FKENAAYNAA  480
LNI                                                                 483

SEQ ID NO: 128            moltype = AA  length = 483
FEATURE                   Location/Qualifiers
source                    1..483
                          mol_type = protein
                          organism = synthetic construct
SEQUENCE: 128
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNAFSRY SISDNDLFHF NKKMFARRRI LLKKNRHKRA GHGAKNKLKP ITILTEKSER  360
FRKKLIERWA CEIADFFIKN KVGTVQMENL ESMKRKEDSY FNIRLRGFWP YAEMQNKIEF  420
KLKQYGIEIR KVAPNNTSQL CSKCGHLNNY FNFEYRKKNK FPKFKCEKCN FKENAAYNAA  480
LNI                                                                 483

SEQ ID NO: 129            moltype = AA  length = 483
FEATURE                   Location/Qualifiers
source                    1..483
                          mol_type = protein
                          organism = synthetic construct
SEQUENCE: 129
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNAFSRY SISDNDLFHF NKKMFARRRI LLKKNRHKRA GHGAKNKLKP ITILTEKSER  360
FRKKLIERWA CEIADFFIKN KVGTVQMEDL ESMKRKEDSY FNIRLRGFWP YAEMQNKIEF  420
```

```
KLKQYGIEIR KVAPNNTSQL CSKCGHLNNY FNFEYRKKNK FPKFKCEKCN PKENAAYNAA   480
LNI                                                                483

SEQ ID NO: 130          moltype = AA  length = 483
FEATURE                 Location/Qualifiers
source                  1..483
                        mol_type = protein
                        organism = synthetic construct
SEQUENCE: 130
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMEDL ESMRKREDSY FNIRLRGFWP YAEMQNKIEF   420
KLKQYGIEIR KVAPNNTSQR CSKCGHLNNY FNFEYRKKNK FPHFKCEKCN PKENAAYNAA   480
RNI                                                                483

SEQ ID NO: 131          moltype = AA  length = 483
FEATURE                 Location/Qualifiers
source                  1..483
                        mol_type = protein
                        organism = synthetic construct
SEQUENCE: 131
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMENL ESMRKREDSY FNIRLRGFWP YAEMQNKIEF   420
KLKQYGIEIR KVAPNNTSKT CSKCGHLNNY FNFEYRKKNK FPHFKCEKCN PKENAAYNAA   480
LNI                                                                483

SEQ ID NO: 132          moltype = AA  length = 495
FEATURE                 Location/Qualifiers
source                  1..495
                        mol_type = protein
                        organism = synthetic construct
SEQUENCE: 132
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAELFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKKNRHKRK GHGAKNKLKP ITELTEKSER   360
FRKKLIERWA CEIADFFIKN KVGTVQMEDL ESMRKREDSY FNIRLRGFWP YAEMQNKIEF   420
KLKQYGIEIR KVAPNNTSQL CSKCGHLNNY FNFEYRKKNK FPHFKCEKCN PKENAAYNAA   480
LNISNPDIKS TKERP                                                   495

SEQ ID NO: 133          moltype = AA  length = 495
FEATURE                 Location/Qualifiers
source                  1..495
                        mol_type = protein
                        organism = synthetic construct
SEQUENCE: 133
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAALFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKKNRHKRK GHGAKNKLKP ITELTEKSER   360
FRKKLIERWA CEIADFFIKN KVGTVQMENL ESMRKREDSY FNIRLRGFWP YAEMQNKIEF   420
KLKQYGIEIR KVAPNNTSQL CSKCGHLNNY FNFEYRKKNK FPKFKCEKCN PKENAAYNAA   480
LNISNPDIKS TKERP                                                   495

SEQ ID NO: 134          moltype = AA  length = 495
FEATURE                 Location/Qualifiers
source                  1..495
                        mol_type = protein
                        organism = synthetic construct
SEQUENCE: 134
MAKNTITKTL KLRIVRPYNS AEVEKIVADE KERRKQAGGT GELDDKFYQK LRGQFPDAVF   60
WQEISEIFRQ LQKQAAEIYN QSLIELYYEI FIKGKGIANA SSVEHYLSRV CYRRAAELFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKKNRHKRK GHGAKNKLKP ITELTEKSER   360
```

```
FRKKLIERWA CEIADFFIKN KVGTVQMEDL ESMKRKEDSY FNIRLRGFWP YAEMQNKIEF    420
KLKQYGIEIR KVAPNNTSQL CSKCGHLNNY FNFEYRKKNK FPKFKCEKCN FKENAAYNAA    480
LNISTPDIKS TKERP                                                    495

SEQ ID NO: 135          moltype = AA   length = 495
FEATURE                 Location/Qualifiers
source                  1..495
                        mol_type = protein
                        organism = synthetic construct
SEQUENCE: 135
MAKNTITKTL KLRIVRPYNS AEVEKIVADE KERRQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKKNRHKRK GHGAKNKLKP ITELTEKSER   360
FRKKLIERWA CEIADFFIKN KVGTVQMEDL ESMKRKEDSY FNIRLRGFWP YAEMQNKIEF   420
KLKQYGIEIR KVAPNNTSQR CSKCGHLNNY FNFEYRKKNK FPHFKCEKCN FKENAAYNAA   480
RNISNPNIKS TKERP                                                    495

SEQ ID NO: 136          moltype = AA   length = 495
FEATURE                 Location/Qualifiers
source                  1..495
                        mol_type = protein
                        organism = synthetic construct
SEQUENCE: 136
MAKNTITKTL KLRIVRPYNS AEVEKIVADE KERRQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKKNRHKRK GHGAKNKLKP ITELTEKSER   360
FRKKLIERWA CEIADFFIKN KVGTVQMENL ESMKRKEDSY FNIRLRGFWP YAEMQNKIEF   420
KLKQYGIEIR KVAPNNTSKT CSKCGHLNNY FNFEYRKKNK FPHFKCEKCN FKENAAYNAA   480
LNISNPKLKS TKERP                                                    495

SEQ ID NO: 137          moltype = AA   length = 483
FEATURE                 Location/Qualifiers
source                  1..483
                        mol_type = protein
                        organism = synthetic construct
SEQUENCE: 137
MAKNTITKTL KLRIVRPYNS AEVEKIVADE KERRQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKKNRHKRK GHGAKNKLKP ITELTEKSER   360
FRKKLIERWA CEIADFFIKN KVGTVQMEDL ESMKRKEDSY FNIRLRGFWP YAEMQNKIEF   420
KLKQYGIEIR KVAPNNTSQL CSKCGHLNNY FNFEYRKKNK FPHFKCEKCN FKENAAYNAA   480
LNI                                                                 483

SEQ ID NO: 138          moltype = AA   length = 483
FEATURE                 Location/Qualifiers
source                  1..483
                        mol_type = protein
                        organism = synthetic construct
SEQUENCE: 138
MAKNTITKTL KLRIVRPYNS AEVEKIVADE KERRQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNSFSRY SISDNDLFKF NKKMFARRRI LLKKNRHKRK GHGAKNKLKP ITELTEKSER   360
FRKKLIERWA CEIADFFIKN KVGTVQMENL ESMKRKEDSY FNIRLRGFWP YAEMQNKIEF   420
KLKQYGIEIR KVAPNNTSQL CSKCGHLNNY FNFEYRKKNK FPKFKCEKCN FKENAAYNAA   480
LNI                                                                 483

SEQ ID NO: 139          moltype = AA   length = 483
FEATURE                 Location/Qualifiers
source                  1..483
                        mol_type = protein
                        organism = synthetic construct
SEQUENCE: 139
MAKNTITKTL KLRIVRPYNS AEVEKIVADE KERRQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
```

```
CAINNSFSRY SISDNDLFKF NKKMFARRRI LLKKNRHKRK GHGAKNKLKP ITELTEKSER     360
FRKKLIERWA CEIADFFIKN KVGTVQMEDL ESMKRKEDSY FNIRLRGFWP YAEMQNKIEF     420
KLKQYGIEIR KVAPNNTSQL CSKCGHLNNY FNFEYRKKNK FPKFKCEKCN FKENAAYNAA    480
LNI                                                                  483

SEQ ID NO: 140           moltype = AA  length = 483
FEATURE                  Location/Qualifiers
source                   1..483
                         mol_type = protein
                         organism = synthetic construct
SEQUENCE: 140
MAKNTITKTL KLRIVRPYNS AEVEKIVADE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNSFSRY SISDNDLFKF NKKMFARRRI LLKKNRHKRK GHGAKNKLKP ITELTEKSER    360
FRKKLIERWA CEIADFFIKN KVGTVQMEDL ESMKRKEDSY FNIRLRGFWP YAEMQNKIEF    420
KLKQYGIEIR KVAPNNTSQR CSKCGHLNNY FNFEYRKKNK FPHFKCEKCN FKENAAYNAA    480
RNI                                                                  483

SEQ ID NO: 141           moltype = AA  length = 483
FEATURE                  Location/Qualifiers
source                   1..483
                         mol_type = protein
                         organism = synthetic construct
SEQUENCE: 141
MAKNTITKTL KLRIVRPYNS AEVEKIVADE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNSFSRY SISDNDLFKF NKKMFARRRI LLKKNRHKRK GHGAKNKLKP ITELTEKSER    360
FRKKLIERWA CEIADFFIKN KVGTVQMENL ESMKRKEDSY FNIRLRGFWP YAEMQNKIEF    420
KLKQYGIEIR KVAPNNTSKT CSKCGHLNNY FNFEYRKKNK FPHFKCEKCN FKENAAYNAA    480
LNI                                                                  483

SEQ ID NO: 142           moltype = AA  length = 495
FEATURE                  Location/Qualifiers
source                   1..495
                         mol_type = protein
                         organism = synthetic construct
SEQUENCE: 142
MAKNTITKTL KLRIVRPYNS AEVEKIVADE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNAFSRY SISDNDLFHF NKKMFARRRI LLKKNRHKRA GHGAKNKLKP ITILTEKSER    360
FRKKLIERWA CEIADFFIKN KVGTVQMEDL ESMKRKEDSY FNIRLRGFWP YAEMQNKIEF    420
KLKQYGIEIR KVAPNNTSQL CSKCGHLNNY FNFEYRKKNK FPHFKCEKCN FKENAAYNAA    480
LNISNPDIKS TKERP                                                     495

SEQ ID NO: 143           moltype = AA  length = 495
FEATURE                  Location/Qualifiers
source                   1..495
                         mol_type = protein
                         organism = synthetic construct
SEQUENCE: 143
MAKNTITKTL KLRIVRPYNS AEVEKIVADE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNAFSRY SISDNDLFHF NKKMFARRRI LLKKNRHKRA GHGAKNKLKP ITILTEKSER    360
FRKKLIERWA CEIADFFIKN KVGTVQMENL ESMKRKEDSY FNIRLRGFWP YAEMQNKIEF    420
KLKQYGIEIR KVAPNNTSQL CSKCGHLNNY FNFEYRKKNK FPKFKCEKCN FKENAAYNAA    480
LNISNPDIKS TKERP                                                     495

SEQ ID NO: 144           moltype = AA  length = 495
FEATURE                  Location/Qualifiers
source                   1..495
                         mol_type = protein
                         organism = synthetic construct
SEQUENCE: 144
MAKNTITKTL KLRIVRPYNS AEVEKIVADE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE    240
```

```
IKKVMNGDYQ TSYIEVKRGS KICEKSAWML NLSIDVPKID KGVDPSIIGG IAVGVRSPLV    300
CAINNAFSRY SISDNDLFHF NKKMFARRRI LLKKNRHKRA GHGAKNKLKP ITILTEKSER    360
FRKKLIERWA CEIADFFIKN KVGTVQMEDL ESMRKREDSY FNIRLRGFWP YAEMQNKIEF    420
KLKQYGIEIR KVAPNNTSQL CSKCGHLNNY FNFEYRKKNK PPKFKCEKCN FKENAAYNAA    480
LNISTPDIKS TKERP                                                    495

SEQ ID NO: 145          moltype = AA  length = 495
FEATURE                 Location/Qualifiers
source                  1..495
                        mol_type = protein
                        organism = synthetic construct
SEQUENCE: 145
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV    300
CAINNAFSRY SISDNDLFHF NKKMFARRRI LLKKNRHKRA GHGAKNKLKP ITILTEKSER    360
FRKKLIERWA CEIADFFIKN KVGTVQMEDL ESMRKREDSY FNIRLRGFWP YAEMQNKIEF    420
KLKQYGIEIR KVAPNNTSQR CSKCGHLNNY FNFEYRKKNK PPHFKCEKCN FKENAAYNAA    480
RNISNPNIKS TKERP                                                    495

SEQ ID NO: 146          moltype = AA  length = 495
FEATURE                 Location/Qualifiers
source                  1..495
                        mol_type = protein
                        organism = synthetic construct
SEQUENCE: 146
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV    300
CAINNAFSRY SISDNDLFHF NKKMFARRRI LLKKNRHKRA GHGAKNKLKP ITILTEKSER    360
FRKKLIERWA CEIADFFIKN KVGTVQMENL ESMRKREDSY FNIRLRGFWP YAEMQNKIEF    420
KLKQYGIEIR KVAPNNTSKT CSKCGHLNNY FNFEYRKKNK PPHFKCEKCN FKENAAYNAA    480
LNISNPKLKS TKERP                                                    495

SEQ ID NO: 147          moltype = AA  length = 483
FEATURE                 Location/Qualifiers
source                  1..483
                        mol_type = protein
                        organism = synthetic construct
SEQUENCE: 147
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV    300
CAINNAFSRY SISDNDLFHF NKKMFARRRI LLKKNRHKRA GHGAKNKLKP ITILTEKSER    360
FRKKLIERWA CEIADFFIKN KVGTVQMEDL ESMRKREDSY FNIRLRGFWP YAEMQNKIEF    420
KLKQYGIEIR KVAPNNTSQL CSKCGHLNNY FNFEYRKKNK PPHFKCEKCN FKENAAYNAA    480
LNI                                                                 483

SEQ ID NO: 148          moltype = AA  length = 483
FEATURE                 Location/Qualifiers
source                  1..483
                        mol_type = protein
                        organism = synthetic construct
SEQUENCE: 148
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV    300
CAINNAFSRY SISDNDLFHF NKKMFARRRI LLKKNRHKRA GHGAKNKLKP ITILTEKSER    360
FRKKLIERWA CEIADFFIKN KVGTVQMENL ESMRKREDSY FNIRLRGFWP YAEMQNKIEF    420
KLKQYGIEIR KVAPNNTSQL CSKCGHLNNY FNFEYRKKNK PPKFKCEKCN FKENAAYNAA    480
LNI                                                                 483

SEQ ID NO: 149          moltype = AA  length = 483
FEATURE                 Location/Qualifiers
source                  1..483
                        mol_type = protein
                        organism = synthetic construct
SEQUENCE: 149
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
```

```
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNAFSRY SISDNDLFHF NKKMFARRRI LLKKNRHKRA GHGAKNKLKP ITILTEKSER    360
FRKKLIERWA CEIADFFIKN KVGTVQMEDL ESMKRKEDSY FNIRLRGFWP YAEMQNKIEF    420
KLKQYGIEIR KVAPNNTSQL CSKCGHLNNY FNFEYRKKNK PPKFKCEKCN FKENAAYNAA    480
LNI                                                                 483

SEQ ID NO: 150          moltype = AA  length = 483
FEATURE                 Location/Qualifiers
source                  1..483
                        mol_type = protein
                        organism = synthetic construct
SEQUENCE: 150
MAKNTITKTL KLRIVRPYNS AEVEKIVADE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAIASGLRS KIKSNPRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNAFSRY SISDNDLFHF NKKMFARRRI LLKKNRHKRA GHGAKNKLKP ITILTEKSER    360
FRKKLIERWA CEIADFFIKN KVGTVQMEDL ESMKRKEDSY FNIRLRGFWP YAEMQNKIEF    420
KLKQYGIEIR KVAPNNTSQR CSKCGHLNNY FNFEYRKKNK PPHFKCEKCN FKENAAYNAA    480
RNI                                                                 483

SEQ ID NO: 151          moltype = AA  length = 483
FEATURE                 Location/Qualifiers
source                  1..483
                        mol_type = protein
                        organism = synthetic construct
SEQUENCE: 151
MAKNTITKTL KLRIVRPYNS AEVEKIVADE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAIASGLRS KIKSNPRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNAFSRY SISDNDLFHF NKKMFARRRI LLKKNRHKRA GHGAKNKLKP ITILTEKSER    360
FRKKLIERWA CEIADFFIKN KVGTVQMENL ESMKRKEDSY FNIRLRGFWP YAEMQNKIEF    420
KLKQYGIEIR KVAPNNTSKT CSKCGHLNNY FNFEYRKKNK PPHFKCEKCN FKENAAYNAA    480
LNI                                                                 483

SEQ ID NO: 152          moltype = AA  length = 495
FEATURE                 Location/Qualifiers
source                  1..495
                        mol_type = protein
                        organism = synthetic construct
SEQUENCE: 152
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAIASGLRS KIKSNPRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNSFSRY SISDNDLFKF NKKMFARRRI LLKKNRHKRA GHGAKNKLKP ITELTEKSER    360
FRKKLIERWA CEIADFFIKN KVGTVQMEDL ESMKRKEDSY FNIRLRGFWP YAEMQNKIEF    420
KLKQYGIEIR KVAPNNTSQL CSKCGHLNNY FNFEYRKKNK PPHFKCEKCN FKENAAYNAA    480
LNISNPDIKS TKERP                                                    495

SEQ ID NO: 153          moltype = AA  length = 495
FEATURE                 Location/Qualifiers
source                  1..495
                        mol_type = protein
                        organism = synthetic construct
SEQUENCE: 153
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAIASGLRS KIKSNPRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNSFSRY SISDNDLFKF NKKMFARRRI LLKKNRHKRK GHGAKNKLKP ITELTEKSER    360
FRKKLIERWA CEIADFFIKN KVGTVQMENL ESMKRKEDSY FNIRLRGFWP YAEMQNKIEF    420
KLKQYGIEIR KVAPNNTSQL CSKCGHLNNY FNFEYRKKNK PPKFKCEKCN FKENAAYNAA    480
LNISNPDIKS TKERP                                                    495

SEQ ID NO: 154          moltype = AA  length = 495
FEATURE                 Location/Qualifiers
source                  1..495
                        mol_type = protein
                        organism = synthetic construct
SEQUENCE: 154
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
```

```
NAAIASGLRS KIKSNFRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNSFSRY SISDNDLFKF NKKMFARRRI LLKKNRHKRK GHGAKNKLKP ITELTEKSER    360
FRKKLIERWA CEIADFFIKN KVGTVQMEDL ESMKRKEDSY FNIRLRGFWP YAEMQNKIEF    420
KLKQYGIEIR KVAPNNTSQL CSKCGHLNNY FNFEYRKKNK FPKFKCEKCN FKENAAYNAA    480
LNISTPDIKS TKERP                                                     495

SEQ ID NO: 155           moltype = AA  length = 495
FEATURE                  Location/Qualifiers
source                   1..495
                         mol_type = protein
                         organism = synthetic construct
SEQUENCE: 155
MAKNTITKTL KLRIVRPYNS QEIEKIVAEE KERRKQAGGT GELDDKFYQK LRGQFPDAVF    60
WQEISEIFRQ LQKQAAEIYN QSLIELYYEI FIKGKGIANA SSVEHYLSRV CYRRAAALFK    120
NAAIASGLRS KIKSNFRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNSFSRY SISDNDLFKF NKKMFARRRI LLKKNRHKRK GHGAKNKLKP ITELTEKSER    360
FRKKLIERWA CEIADFFIKN KVGTVQMEDL ESMKRKEDSY FNIRLRGFWP YAEMQNKIEF    420
KLKQYGIEIR KVAPNNTSQR CSKCGHLNNY FNFEYRKKNK FPHFKCEKCN FKENAAYNAA    480
RNISNPNIKS TKERP                                                     495

SEQ ID NO: 156           moltype = AA  length = 495
FEATURE                  Location/Qualifiers
source                   1..495
                         mol_type = protein
                         organism = synthetic construct
SEQUENCE: 156
MAKNTITKTL KLRIVRPYNS QEIEKIVAEE KERRKQAGGT GELDDKFYQK LRGQFPDAVF    60
WQEISEIFRQ LQKQAAEIYN QSLIELYYEI FIKGKGIANA SSVEHYLSRV CYRRAAALFK    120
NAAIASGLRS KIKSNFRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNSFSRY SISDNDLFKF NKKMFARRRI LLKKNRHKRK GHGAKNKLKP ITELTEKSER    360
FRKKLIERWA CEIADFFIKN KVGTVQMENL ESMKRKEDSY FNIRLRGFWP YAEMQNKIEF    420
KLKQYGIEIR KVAPNNTSKT CSKCGHLNNY FNFEYRKKNK FPHFKCEKCN FKENAAYNAA    480
LNISNPKLKS TKERP                                                     495

SEQ ID NO: 157           moltype = AA  length = 483
FEATURE                  Location/Qualifiers
source                   1..483
                         mol_type = protein
                         organism = synthetic construct
SEQUENCE: 157
MAKNTITKTL KLRIVRPYNS QEIEKIVAEE KERRKQAGGT GELDDKFYQK LRGQFPDAVF    60
WQEISEIFRQ LQKQAAEIYN QSLIELYYEI FIKGKGIANA SSVEHYLSRV CYRRAAALFK    120
NAAIASGLRS KIKSNFRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNSFSRY SISDNDLFKF NKKMFARRRI LLKKNRHKRK GHGAKNKLKP ITELTEKSER    360
FRKKLIERWA CEIADFFIKN KVGTVQMEDL ESMKRKEDSY FNIRLRGFWP YAEMQNKIEF    420
KLKQYGIEIR KVAPNNTSQL CSKCGHLNNY FNFEYRKKNK FPHFKCEKCN FKENAAYNAA    480
LNI                                                                   483

SEQ ID NO: 158           moltype = AA  length = 483
FEATURE                  Location/Qualifiers
source                   1..483
                         mol_type = protein
                         organism = synthetic construct
SEQUENCE: 158
MAKNTITKTL KLRIVRPYNS QEIEKIVAEE KERRKQAGGT GELDDKFYQK LRGQFPDAVF    60
WQEISEIFRQ LQKQAAEIYN QSLIELYYEI FIKGKGIANA SSVEHYLSRV CYRRAAALFK    120
NAAIASGLRS KIKSNFRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNSFSRY SISDNDLFKF NKKMFARRRI LLKKNRHKRK GHGAKNKLKP ITELTEKSER    360
FRKKLIERWA CEIADFFIKN KVGTVQMENL ESMKRKEDSY FNIRLRGFWP YAEMQNKIEF    420
KLKQYGIEIR KVAPNNTSQL CSKCGHLNNY FNFEYRKKNK FPKFKCEKCN FKENAAYNAA    480
LNI                                                                   483

SEQ ID NO: 159           moltype = AA  length = 483
FEATURE                  Location/Qualifiers
source                   1..483
                         mol_type = protein
                         organism = synthetic construct
SEQUENCE: 159
MAKNTITKTL KLRIVRPYNS QEIEKIVAEE KERRKQAGGT GELDDKFYQK LRGQFPDAVF    60
```

```
WQEISEIFRQ LQKQAAEIYN QSLIELYYEI FIKGKGIANA SSVEHYLSRV CYRRAAALFK    120
NAAIASGLRS KIKSNFRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNSFSRY SISDNDLFKF NKKMFARRRI LLKKNRHKRK GHGAKNKLKP ITELTEKSER    360
FRKKLIERWA CEIADFFIKN KVGTVQMEDL ESMKRKEDSY FNIRLRGFWP YAEMQNKIEF    420
KLKQYGIEIR KVAPNNTSQL CSKCGHLNNY FNFEYRKKNK FPKFKCEKCN FKENAAYNAA    480
LNI                                                                 483

SEQ ID NO: 160          moltype = AA  length = 483
FEATURE                 Location/Qualifiers
source                  1..483
                        mol_type = protein
                        organism = synthetic construct
SEQUENCE: 160
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAALFK    120
NAAIASGLRS KIKSNFRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNSFSRY SISDNDLFKF NKKMFARRRI LLKKNRHKRK GHGAKNKLKP ITELTEKSER    360
FRKKLIERWA CEIADFFIKN KVGTVQMEDL ESMKRKEDSY FNIRLRGFWP YAEMQNKIEF    420
KLKQYGIEIR KVAPNNTSQR CSKCGHLNNY FNFEYRKKNK FPHFKCEKCN FKENAAYNAA    480
RNI                                                                 483

SEQ ID NO: 161          moltype = AA  length = 483
FEATURE                 Location/Qualifiers
source                  1..483
                        mol_type = protein
                        organism = synthetic construct
SEQUENCE: 161
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAALFK    120
NAAIASGLRS KIKSNFRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNSFSRY SISDNDLFKF NKKMFARRRI LLKKNRHKRK GHGAKNKLKP ITELTEKSER    360
FRKKLIERWA CEIADFFIKN KVGTVQMENL ESMKRKEDSY FNIRLRGFWP YAEMQNKIEF    420
KLKQYGIEIR KVAPNNTSKT CSKCGHLNNY FNFEYRKKNK FPHFKCEKCN FKENAAYNAA    480
LNI                                                                 483

SEQ ID NO: 162          moltype = AA  length = 495
FEATURE                 Location/Qualifiers
source                  1..495
                        mol_type = protein
                        organism = synthetic construct
SEQUENCE: 162
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAALFK    120
NAAIASGLRS KIKSNFRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNAFSRY SISDNDLFHF NKKMFARRRI LLKKNRHKRA GHGAKNKLKP ITILTEKSER    360
FRKKLIERWA CEIADFFIKN KVGTVQMEDL ESMKRKEDSY FNIRLRGFWP YAEMQNKIEF    420
KLKQYGIEIR KVAPNNTSQL CSKCGHLNNY FNFEYRKKNK FPHFKCEKCN FKENAAYNAA    480
LNISNPDIKS TKERP                                                    495

SEQ ID NO: 163          moltype = AA  length = 495
FEATURE                 Location/Qualifiers
source                  1..495
                        mol_type = protein
                        organism = synthetic construct
SEQUENCE: 163
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAALFK    120
NAAIASGLRS KIKSNFRLKE LKNMKSGLPT TKSDNFPIPL VKQKGGQYTG FEISNHNSDF    180
IIKIPFGRWQ VKKEIDKYRP WEKFDFEQVQ KSPKPISLLL STQRRKRNKG WSKDEGTEAE    240
IKKVMNGDYQ TSYIEVKRGS KICEKSAWML NLSIDVPKID KGVDPSIIGG IAVGVRSPLV    300
CAINNAFSRY SISDNDLFHF NKKMFARRRI LLKKNRHKRA GHGAKNKLKP ITILTEKSER    360
FRKKLIERWA CEIADFFIKN KVGTVQMENL ESMKRKEDSY FNIRLRGFWP YAEMQNKIEF    420
KLKQYGIEIR KVAPNNTSQL CSKCGHLNNY FNFEYRKKNK FPKFKCEKCN FKENAAYNAA    480
LNISNPDIKS TKERP                                                    495

SEQ ID NO: 164          moltype = AA  length = 495
FEATURE                 Location/Qualifiers
source                  1..495
                        mol_type = protein
                        organism = synthetic construct
SEQUENCE: 164
```

```
MAKNTITKTL KLRIVRPYNS QEIEKIVAEE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMEDL ESMKRKEDSY FNIRLRGFWP YAEMQNKIEF   420
KLKQYGIEIR KVAPNNTSQL CSKCGHLNNY FNFEYRKKNK FPKFKCEKCN FKENAAYNAA   480
LNISTPDIKS TKERP                                                    495

SEQ ID NO: 165          moltype = AA  length = 495
FEATURE                 Location/Qualifiers
source                  1..495
                        mol_type = protein
                        organism = synthetic construct
SEQUENCE: 165
MAKNTITKTL KLRIVRPYNS QEIEKIVAEE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMEDL ESMKRKEDSY FNIRLRGFWP YAEMQNKIEF   420
KLKQYGIEIR KVAPNNTSQR CSKCGHLNNY FNFEYRKKNK FPHFKCEKCN FKENAAYNAA   480
RNISNPNIKS TKERP                                                    495

SEQ ID NO: 166          moltype = AA  length = 495
FEATURE                 Location/Qualifiers
source                  1..495
                        mol_type = protein
                        organism = synthetic construct
SEQUENCE: 166
MAKNTITKTL KLRIVRPYNS QEIEKIVAEE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMENL ESMKRKEDSY FNIRLRGFWP YAEMQNKIEF   420
KLKQYGIEIR KVAPNNTSKT CSKCGHLNNY FNFEYRKKNK FPHFKCEKCN FKENAAYNAA   480
LNISNPKLKS TKERP                                                    495

SEQ ID NO: 167          moltype = AA  length = 483
FEATURE                 Location/Qualifiers
source                  1..483
                        mol_type = protein
                        organism = synthetic construct
SEQUENCE: 167
MAKNTITKTL KLRIVRPYNS QEIEKIVAEE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMEDL ESMKRKEDSY FNIRLRGFWP YAEMQNKIEF   420
KLKQYGIEIR KVAPNNTSQL CSKCGHLNNY FNFEYRKKNK FPHFKCEKCN FKENAAYNAA   480
LNI                                                                 483

SEQ ID NO: 168          moltype = AA  length = 483
FEATURE                 Location/Qualifiers
source                  1..483
                        mol_type = protein
                        organism = synthetic construct
SEQUENCE: 168
MAKNTITKTL KLRIVRPYNS QEIEKIVAEE KERRKQAGGT GELDDKFYQK LRGQFPDAVF    60
WQEISEIFRQ LQKQAAEIYN QSLIELYYEI FIKGKGIANA SSVEHYLSRV CYRRAAALFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMENL ESMKRKEDSY FNIRLRGFWP YAEMQNKIEF   420
KLKQYGIEIR KVAPNNTSQL CSKCGHLNNY FNFEYRKKNK FPKFKCEKCN FKENAAYNAA   480
LNI                                                                 483

SEQ ID NO: 169          moltype = AA  length = 483
FEATURE                 Location/Qualifiers
source                  1..483
                        mol_type = protein
                        organism = synthetic construct
```

```
SEQUENCE: 169
MAKNTITKTL KLRIVRPYNS QEIEKIVAEE KERRKQAGGT GELDDKFYQK LRGQFPDAVF      60
WQEISEIFRQ LQKQAAEIYN QSLIELYYEI FIKGKGIANA SSVEHYLSRV CYRRAAALFK     120
NAAIASGLRS KIKSNFRLKE LKNMKSGLPT TKSDNFPIPL VKQKGGQYTG FEISNHNSDF     180
IIKIPFGRWQ VKKEIDKYRP WEKFDFEQVQ KSPKPISLLL STQRRKRNKG WSKDEGTEAE     240
IKKVMNGDYQ TSYIEVKRGS KICEKSAWML NLSIDVPKID KGVDPSIIGG IAVGVRSPLV     300
CAINNAFSRY SISDNDLFHF NKKMFARRRI LLKKNRHKRA GHGAKNKLKP ITILTEKSER     360
FRKKLIERWA CEIADFFIKN KVGTVQMEDL ESMRKREDSY FNIRLRGFWP YAEMQNKIEF     420
KLKQYGIEIR KVAPNNTSQL CSKCGHLNNY FNFEYRKKNK FPKFKCEKCN FKENAAYNAA     480
LNI                                                                  483

SEQ ID NO: 170          moltype = AA  length = 483
FEATURE                 Location/Qualifiers
source                  1..483
                        mol_type = protein
                        organism = synthetic construct
SEQUENCE: 170
MAKNTITKTL KLRIVRPYNS QEIEKIVAEE KERRKQAGGT GELDDKFYQK LRGQFPDAVF      60
WQEISEIFRQ LQKQAAEIYN QSLIELYYEI FIKGKGIANA SSVEHYLSRV CYRRAAALFK     120
NAAIASGLRS KIKSNFRLKE LKNMKSGLPT TKSDNFPIPL VKQKGGQYTG FEISNHNSDF     180
IIKIPFGRWQ VKKEIDKYRP WEKFDFEQVQ KSPKPISLLL STQRRKRNKG WSKDEGTEAE     240
IKKVMNGDYQ TSYIEVKRGS KICEKSAWML NLSIDVPKID KGVDPSIIGG IAVGVRSPLV     300
CAINNAFSRY SISDNDLFHF NKKMFARRRI LLKKNRHKRA GHGAKNKLKP ITILTEKSER     360
FRKKLIERWA CEIADFFIKN KVGTVQMEDL ESMRKREDSY FNIRLRGFWP YAEMQNKIEF     420
KLKQYGIEIR KVAPNNTSQR CSKCGHLNNY FNFEYRKKNK FPHFKCEKCN FKENAAYNAA     480
RNI                                                                  483

SEQ ID NO: 171          moltype = AA  length = 483
FEATURE                 Location/Qualifiers
source                  1..483
                        mol_type = protein
                        organism = synthetic construct
SEQUENCE: 171
MAKNTITKTL KLRIVRPYNS QEIEKIVAEE KERRKQAGGT GELDDKFYQK LRGQFPDAVF      60
WQEISEIFRQ LQKQAAEIYN QSLIELYYEI FIKGKGIANA SSVEHYLSRV CYRRAAELFK     120
NAAIASGLRS KIKSNFRLKE LKNMKSGLPT TKSDNFPIPL VKQKGGQYTG FEISNHNSDF     180
IIKIPFGRWQ VKKEIDKYRP WEKFDFEQVQ KSPKPISLLL STQRRKRNKG WSKDEGTEAE     240
IKKVMNGDYQ TSYIEVKRGS KICEKSAWML NLSIDVPKID KGVDPSIIGG IAVGVRSPLV     300
CAINNAFSRY SISDNDLFHF NKKMFARRRI LLKKNRHKRA GHGAKNKLKP ITILTEKSER     360
FRKKLIERWA CEIADFFIKN KVGTVQMENL ESMRKREDSY FNIRLRGFWP YAEMQNKIEF     420
KLKQYGIEIR KVAPNNTSKT CSKCGHLNNY FNFEYRKKNK FPHFKCEKCN FKENAAYNAA     480
LNI                                                                  483

SEQ ID NO: 172          moltype = AA  length = 495
FEATURE                 Location/Qualifiers
source                  1..495
                        mol_type = protein
                        organism = synthetic construct
SEQUENCE: 172
MAKNTITKTL KLRIVRPYNS QEIEKIVAEE KERRKQAGGT GELDDKFYQK LRGQFPDAVF      60
WQEISEIFRQ LQKQAAEIYN QSLIELYYEI FIKGKGIANA SSVEHYLSRV CYRRAAALFK     120
NAAIASGLRS KIKSNFRLKE LKNMKSGLPT TKSDNFPIPL VKQKGGQYTG FEISNHNSDF     180
IIKIPFGRWQ VKKEIDKYRP WEKFDFEQVQ KSPKPISLLL STQRRKRNKG WSKDEGTEAE     240
IKKVMNGDYQ TSYIEVKRGS KICEKSAWML NLSIDVPKID KGVDPSIIGG IAVGVRSPLV     300
CAINNSFSRY SISDNDLFKF NKKMFARRRI LLKKNRHKRA GHGAKNKLKP ITELTEKSER     360
FRKKLIERWA CEIADFFIKN KVGTVQMEDL ESMRKREDSY FNIRLRGFWP YAEMQNKIEF     420
KLKQYGIEIR KVAPNNTSQL CSKCGHLNNY FNFEYRKKNK FPHFKCEKCN FKENAAYNAA     480
LNISNPDIKS TKERP                                                     495

SEQ ID NO: 173          moltype = AA  length = 495
FEATURE                 Location/Qualifiers
source                  1..495
                        mol_type = protein
                        organism = synthetic construct
SEQUENCE: 173
MAKNTITKTL KLRIVRPYNS QEIEKIVAEE KERRKQAGGT GELDDKFYQK LRGQFPDAVF      60
WQEISEIFRQ LQKQAAEIYN QSLIELYYEI FIKGKGIANA SSVEHYLSRV CYRRAAELFK     120
NAAIASGLRS KIKSNFRLKE LKNMKSGLPT TKSDNFPIPL VKQKGGQYTG FEISNHNSDF     180
IIKIPFGRWQ VKKEIDKYRP WEKFDFEQVQ KSPKPISLLL STQRRKRNKG WSKDEGTEAE     240
IKKVMNGDYQ TSYIEVKRGS KICEKSAWML NLSIDVPKID KGVDPSIIGG IAVGVRSPLV     300
CAINNSFSRY SISDNDLFKF NKKMFARRRI LLKKNRHKRK GHGAKNKLKP ITELTEKSER     360
FRKKLIERWA CEIADFFIKN KVGTVQMENL ESMRKREDSY FNIRLRGFWP YAEMQNKIEF     420
KLKQYGIEIR KVAPNNTSQL CSKCGHLNNY FNFEYRKKNK FPKFKCEKCN FKENAAYNAA     480
LNISNPDIKS TKERP                                                     495

SEQ ID NO: 174          moltype = AA  length = 495
FEATURE                 Location/Qualifiers
source                  1..495
                        mol_type = protein
```

```
                         organism = synthetic construct
SEQUENCE: 174
MAKNTITKTL KLRIVRPYNS QEIEKIVAEE KERRKQAGGT GELDDKFYQK LRGQFPDAVF   60
WQEISEIFRQ LQKQAAEIYN QSLIELYYEI FIKGKGIANA SSVEHYLSRV CYRRAAELFK  120
NAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNSFSRY SISDNDLFKF NKKMFARRRI LLKKNRHKRK GHGAKNKLKP ITELTEKSER  360
FRKKLIERWA CEIADPFFIKN KVGTVQMEDL ESMKRKEDSY FNIRLRGFWP YAEMQNKIEF  420
KLKQYGIEIR KVAPNNTSQL CSKCGHLNNY FNFEYRKKNK FPKFKCEKCN FKENAAYNAA  480
LNISTPDIKS TKERP                                                   495

SEQ ID NO: 175          moltype = AA  length = 495
FEATURE                 Location/Qualifiers
source                  1..495
                        mol_type = protein
                        organism = synthetic construct
SEQUENCE: 175
MAKNTITKTL KLRIVRPYNS QEIEKIVAEE KERRKQAGGT GELDDKFYQK LRGQFPDAVF   60
WQEISEIFRQ LQKQAAEIYN QSLIELYYEI FIKGKGIANA SSVEHYLSRV CYRRAAELFK  120
NAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNSFSRY SISDNDLFKF NKKMFARRRI LLKKNRHKRK GHGAKNKLKP ITELTEKSER  360
FRKKLIERWA CEIADPFFIKN KVGTVQMEDL ESMKRKEDSY FNIRLRGFWP YAEMQNKIEF  420
KLKQYGIEIR KVAPNNTSQR CSKCGHLNNY FNFEYRKKNK FPHFKCEKCN FKENAAYNAA  480
RNISNPNIKS TKERP                                                   495

SEQ ID NO: 176          moltype = AA  length = 495
FEATURE                 Location/Qualifiers
source                  1..495
                        mol_type = protein
                        organism = synthetic construct
SEQUENCE: 176
MAKNTITKTL KLRIVRPYNS QEIEKIVAEE KERRKQAGGT GELDDKFYQK LRGQFPDAVF   60
WQEISEIFRQ LQKQAAEIYN QSLIELYYEI FIKGKGIANA SSVEHYLSRV CYRRAAELFK  120
NAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNSFSRY SISDNDLFKF NKKMFARRRI LLKKNRHKRK GHGAKNKLKP ITELTEKSER  360
FRKKLIERWA CEIADPFFIKN KVGTVQMENL ESMKRKEDSY FNIRLRGFWP YAEMQNKIEF  420
KLKQYGIEIR KVAPNNTSKT CSKCGHLNNY FNFEYRKKNK FPHFKCEKCN FKENAAYNAA  480
LNISNPKLKS TKERP                                                   495

SEQ ID NO: 177          moltype = AA  length = 483
FEATURE                 Location/Qualifiers
source                  1..483
                        mol_type = protein
                        organism = synthetic construct
SEQUENCE: 177
MAKNTITKTL KLRIVRPYNS QEIEKIVAEE KERRKQAGGT GELDDKFYQK LRGQFPDAVF   60
WQEISEIFRQ LQKQAAEIYN QSLIELYYEI FIKGKGIANA SSVEHYLSRV CYRRAAELFK  120
NAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNSFSRY SISDNDLFKF NKKMFARRRI LLKKNRHKRK GHGAKNKLKP ITELTEKSER  360
FRKKLIERWA CEIADPFFIKN KVGTVQMEDL ESMKRKEDSY FNIRLRGFWP YAEMQNKIEF  420
KLKQYGIEIR KVAPNNTSQL CSKCGHLNNY FNFEYRKKNK FPHFKCEKCN FKENAAYNAA  480
LNI                                                                483

SEQ ID NO: 178          moltype = AA  length = 483
FEATURE                 Location/Qualifiers
source                  1..483
                        mol_type = protein
                        organism = synthetic construct
SEQUENCE: 178
MAKNTITKTL KLRIVRPYNS QEIEKIVAEE KERRKQAGGT GELDDKFYQK LRGQFPDAVF   60
WQEISEIFRQ LQKQAAEIYN QSLIELYYEI FIKGKGIANA SSVEHYLSRV CYRRAAELFK  120
NAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNSFSRY SISDNDLFKF NKKMFARRRI LLKKNRHKRK GHGAKNKLKP ITELTEKSER  360
FRKKLIERWA CEIADPFFIKN KVGTVQMENL ESMKRKEDSY FNIRLRGFWP YAEMQNKIEF  420
KLKQYGIEIR KVAPNNTSQL CSKCGHLNNY FNFEYRKKNK FPKFKCEKCN FKENAAYNAA  480
LNI                                                                483

SEQ ID NO: 179          moltype = AA  length = 483
FEATURE                 Location/Qualifiers
source                  1..483
```

```
                        mol_type = protein
                        organism = synthetic construct
SEQUENCE: 179
MAKNTITKTL KLRIVRPYNS QEIEKIVAEE KERRKQAGGT GELDDKFYQK LRGQFPDAVF   60
WQEISEIFRQ LQKQAAEIYN QSLIELYYEI FIKGKGIANA SSVEHYLSRV CYRRAAELFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNSFSRY SISDNDLFKF NKKMFARRRI LLKKNRHKRK GHGAKNKLKP ITELTEKSER  360
FRKKLIERWA CEIADFFIKN KVGTVQMEDL ESMKRKEDSY FNIRLRGFWP YAEMQNKIEF  420
KLKQYGIEIR KVAPNNTSQL CSKCGHLNNY FNFEYRKKNK FPKFKCEKCN FKENAAYNAA  480
LNI                                                                483

SEQ ID NO: 180          moltype = AA   length = 483
FEATURE                 Location/Qualifiers
source                  1..483
                        mol_type = protein
                        organism = synthetic construct
SEQUENCE: 180
MAKNTITKTL KLRIVRPYNS QEIEKIVAEE KERRKQAGGT GELDDKFYQK LRGQFPDAVF   60
WQEISEIFRQ LQKQAAEIYN QSLIELYYEI FIKGKGIANA SSVEHYLSRV CYRRAAELFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNSFSRY SISDNDLFKF NKKMFARRRI LLKKNRHKRK GHGAKNKLKP ITELTEKSER  360
FRKKLIERWA CEIADFFIKN KVGTVQMEDL ESMKRKEDSY FNIRLRGFWP YAEMQNKIEF  420
KLKQYGIEIR KVAPNNTSQR CSKCGHLNNY FNFEYRKKNK FPHFKCEKCN FKENAAYNAA  480
RNI                                                                483

SEQ ID NO: 181          moltype = AA   length = 483
FEATURE                 Location/Qualifiers
source                  1..483
                        mol_type = protein
                        organism = synthetic construct
SEQUENCE: 181
MAKNTITKTL KLRIVRPYNS QEIEKIVAEE KERRKQAGGT GELDDKFYQK LRGQFPDAVF   60
WQEISEIFRQ LQKQAAEIYN QSLIELYYEI FIKGKGIANA SSVEHYLSRV CYRRAAELFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNSFSRY SISDNDLFKF NKKMFARRRI LLKKNRHKRK GHGAKNKLKP ITELTEKSER  360
FRKKLIERWA CEIADFFIKN KVGTVQMENL ESMKRKEDSY FNIRLRGFWP YAEMQNKIEF  420
KLKQYGIEIR KVAPNNTSKT CSKCGHLNNY FNFEYRKKNK FPHFKCEKCN FKENAAYNAA  480
LNI                                                                483

SEQ ID NO: 182          moltype = AA   length = 495
FEATURE                 Location/Qualifiers
source                  1..495
                        mol_type = protein
                        organism = synthetic construct
SEQUENCE: 182
MAKNTITKTL KLRIVRPYNS QEIEKIVAEE KERRKQAGGT GELDDKFYQK LRGQFPDAVF   60
WQEISEIFRQ LQKQAAEIYN QSLIELYYEI FIKGKGIANA SSVEHYLSRV CYRRAAELFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNAFSRY SISDNDLFHF NKKMFARRRI LLKKNRHKRA GHGAKNKLKP ITILTEKSER  360
FRKKLIERWA CEIADFFIKN KVGTVQMEDL ESMKRKEDSY FNIRLRGFWP YAEMQNKIEF  420
KLKQYGIEIR KVAPNNTSQL CSKCGHLNNY FNFEYRKKNK FPHFKCEKCN FKENAAYNAA  480
LNISNPDIKS TKERP                                                   495

SEQ ID NO: 183          moltype = AA   length = 495
FEATURE                 Location/Qualifiers
source                  1..495
                        mol_type = protein
                        organism = synthetic construct
SEQUENCE: 183
MAKNTITKTL KLRIVRPYNS QEIEKIVAEE KERRKQAGGT GELDDKFYQK LRGQFPDAVF   60
WQEISEIFRQ LQKQAAEIYN QSLIELYYEI FIKGKGIANA SSVEHYLSRV CYRRAAELFK  120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE  240
IKKVMNGDYQ TSYIEVKRGS KICEKSAWML NLSIDVPKID KGVDPSIIGG IAVGVRSPLV  300
CAINNAFSRY SISDNDLFHF NKKMFARRRI LLKKNRHKRA GHGAKNKLKP ITILTEKSER  360
FRKKLIERWA CEIADFFIKN KVGTVQMENL ESMKRKEDSY FNIRLRGFWP YAEMQNKIEF  420
KLKQYGIEIR KVAPNNTSQL CSKCGHLNNY FNFEYRKKNK FPKFKCEKCN FKENAAYNAA  480
LNISNPDIKS TKERP                                                   495

SEQ ID NO: 184          moltype = AA   length = 495
FEATURE                 Location/Qualifiers
```

```
source                   1..495
                         mol_type = protein
                         organism = synthetic construct
SEQUENCE: 184
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMEDL ESMKRKEDSY FNIRLRGFWP YAEMQNKIEF   420
KLKQYGIEIR KVAPNNTSQL CSKCGHLNNY FNFEYRKKNK PPKFKCEKCN FKENAAYNAA   480
LNISTPDIKS TKERP                                                    495

SEQ ID NO: 185           moltype = AA  length = 495
FEATURE                  Location/Qualifiers
source                   1..495
                         mol_type = protein
                         organism = synthetic construct
SEQUENCE: 185
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMEDL ESMKRKEDSY FNIRLRGFWP YAEMQNKIEF   420
KLKQYGIEIR KVAPNNTSQR CSKCGHLNNY FNFEYRKKNK PPHFKCEKCN FKENAAYNAA   480
RNISNPNIKS TKERP                                                    495

SEQ ID NO: 186           moltype = AA  length = 495
FEATURE                  Location/Qualifiers
source                   1..495
                         mol_type = protein
                         organism = synthetic construct
SEQUENCE: 186
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMENL ESMKRKEDSY FNIRLRGFWP YAEMQNKIEF   420
KLKQYGIEIR KVAPNNTSKT CSKCGHLNNY FNFEYRKKNK PPHFKCEKCN FKENAAYNAA   480
LNISNPKLKS TKERP                                                    495

SEQ ID NO: 187           moltype = AA  length = 483
FEATURE                  Location/Qualifiers
source                   1..483
                         mol_type = protein
                         organism = synthetic construct
SEQUENCE: 187
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMEDL ESMKRKEDSY FNIRLRGFWP YAEMQNKIEF   420
KLKQYGIEIR KVAPNNTSQL CSKCGHLNNY FNFEYRKKNK PPHFKCEKCN FKENAAYNAA   480
LNI                                                                 483

SEQ ID NO: 188           moltype = AA  length = 483
FEATURE                  Location/Qualifiers
source                   1..483
                         mol_type = protein
                         organism = synthetic construct
SEQUENCE: 188
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMENL ESMKRKEDSY FNIRLRGFWP YAEMQNKIEF   420
KLKQYGIEIR KVAPNNTSQL CSKCGHLNNY FNFEYRKKNK PPKFKCEKCN FKENAAYNAA   480
LNI                                                                 483

SEQ ID NO: 189           moltype = AA  length = 483
```

```
FEATURE                 Location/Qualifiers
source                  1..483
                        mol_type = protein
                        organism = synthetic construct
SEQUENCE: 189
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMEDL ESMKRKEDSY FNIRLRGFWP YAEMQNKIEF   420
KLKQYGIEIR KVAPNNTSQL CSKCGHLNNY FNFEYRKKNK FPKFKCEKCN FKENAAYNAA   480
LNI                                                                 483

SEQ ID NO: 190          moltype = AA  length = 483
FEATURE                 Location/Qualifiers
source                  1..483
                        mol_type = protein
                        organism = synthetic construct
SEQUENCE: 190
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMEDL ESMKRKEDSY FNIRLRGFWP YAEMQNKIEF   420
KLKQYGIEIR KVAPNNTSQR CSKCGHLNNY FNFEYRKKNK FPHFKCEKCN FKENAAYNAA   480
RNI                                                                 483

SEQ ID NO: 191          moltype = AA  length = 483
FEATURE                 Location/Qualifiers
source                  1..483
                        mol_type = protein
                        organism = synthetic construct
SEQUENCE: 191
MAKNTITKTL KLRIVRPYNS QEIEKIVAEE KERRKQAGGT GELDDKFYQK LRGQFPDAVF     60
WQEISEIFRQ LQKQAAEIYN QSLIELYYEI FIKGKGIANA SSVEHYLSRV CYRRAAELFK    120
NAAAIASGLRS KIKSNFRLKE LKNMKSGLPT TKSDNFPIPL VKQKGGQYTG FEISNHNSDF   180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMENL ESMKRKEDSY FNIRLRGFWP YAEMQNKIEF   420
KLKQYGIEIR KVAPNNTSKT CSKCGHLNNY FNFEYRKKNK FPHFKCEKCN FKENAAYNAA   480
LNI                                                                 483

SEQ ID NO: 192          moltype = AA  length = 529
FEATURE                 Location/Qualifiers
source                  1..529
                        mol_type = protein
                        organism = synthetic construct
SEQUENCE: 192
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ALFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LPFHFNKKMFA  360
RRRILLKKNR HKRKGHGAKN KLKPITELTE KSERFRKKLI ERWACEIADF FIKNKVGTVQ   420
MEDLESMKRK EDSYFNIRLR GFWPYAEMQN KIEFKLKQYG IEIRKVAPNN TSQLCSKCGH   480
LNNYFNFEYR KKNKFPHFKC EKCNFKENAA YNAALNISNP DIKSTKERP               529

SEQ ID NO: 193          moltype = AA  length = 529
FEATURE                 Location/Qualifiers
source                  1..529
                        mol_type = protein
                        organism = synthetic construct
SEQUENCE: 193
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ALFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MEDLESMKRK EDSYFNIRLR GFWPYAEMQN KIEFKLKQYG IEIRKVAPNN TSQLCSKCGH   480
LNNYFNFEYR KKNKFPHFKC EKCNFKENAA YNAALNISNP DIKSTKERP               529
```

```
SEQ ID NO: 194          moltype = AA  length = 495
FEATURE                 Location/Qualifiers
source                  1..495
                        mol_type = protein
                        organism = synthetic construct
SEQUENCE: 194
MAKNTITKTL KLRIVRPYNS AEIEKIVADE KERRKQAGGT GELDDKFYKK LRKQFPDAVF    60
WQEISEIFRQ LQKQAAEIYN QSLIELYYEI FIKGKGIANA SSVEHYLSRV CYRRAAALFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMEDL ESMKRKEDSY FNIRLRGFWP YAEMQNKIEF   420
KLKQYGIEIR KVAPNNTSQL CSKCGHLNNY FNFEYRKKNK PPHFKCEKCN FKENAAYNAA   480
LNISNPDIKS TKERP                                                    495

SEQ ID NO: 195          moltype = AA  length = 495
FEATURE                 Location/Qualifiers
source                  1..495
                        mol_type = protein
                        organism = synthetic construct
SEQUENCE: 195
MAKNTITKTL KLRIVRPYNS AEIEKIVADE KERRKQAGGT GELDDKFYKK LRKQFPDAVF    60
WQEISEIFRQ LQKQAAEIYN QSLIELYYEI FIKGKGIANA SSVEHYLSRV CYRRAAALFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMENL ESMKRKEDSY FNIRLRGFWP YAEMQNKIEF   420
KLKQYGIEIR KVAPNNTSQL CSKCGHLNNY FNFEYRKKNK PPKFKCEKCN FKENAAYNAA   480
LNISNPDIKS TKERP                                                    495

SEQ ID NO: 196          moltype = AA  length = 495
FEATURE                 Location/Qualifiers
source                  1..495
                        mol_type = protein
                        organism = synthetic construct
SEQUENCE: 196
MAKNTITKTL KLRIVRPYNS AEIEKIVADE KERRKQAGGT GELDDKFYKK LRKQFPDAVF    60
WQEISEIFRQ LQKQAAEIYN QSLIELYYEI FIKGKGIANA SSVEHYLSRV CYRRAAELFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMEDL ESMKRKEDSY FNIRLRGFWP YAEMQNKIEF   420
KLKQYGIEIR KVAPNNTSQL CSKCGHLNNY FNFEYRKKNK PPHFKCEKCN FKENAAYNAA   480
LNISNPDIKS TKERP                                                    495

SEQ ID NO: 197          moltype = AA  length = 495
FEATURE                 Location/Qualifiers
source                  1..495
                        mol_type = protein
                        organism = synthetic construct
SEQUENCE: 197
MAKNTITKTL KLRIVRPYNS AEIEKIVADE KERRKQAGGT GELDDKFYKK LRKQFPDAVF    60
WQEISEIFRQ LQKQAAEIYN QSLIELYYEI FIKGKGIANA SSVEHYLSRV CYRRAAALFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMENL ESMKRKEDSY FNIRLRGFWP YAEMQNKIEF   420
KLKQYGIEIR KVAPNNTSQL CSKCGHLNNY FNFEYRKKNK PPKFKCEKCN FKENAAYNAA   480
LNISNPDIKS TKERP                                                    495

SEQ ID NO: 198          moltype = AA  length = 495
FEATURE                 Location/Qualifiers
source                  1..495
                        mol_type = protein
                        organism = synthetic construct
SEQUENCE: 198
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAELFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMEDL ESMKRKEDSY FNIRLRGFWP YAEMQNKIEF   420
KLKQYGIEIR KVAPNNTSKT CSKCGHLNNY FNFEYRKKNK PPHFKCEKCN FKENAAYNAA   480
LNISNPKLKS TKERP                                                    495
```

```
SEQ ID NO: 199          moltype = AA  length = 495
FEATURE                 Location/Qualifiers
source                  1..495
                        mol_type = protein
                        organism = synthetic construct
SEQUENCE: 199
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAELFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMENL ESMKRKEDSY FNIRLRGFWP YAEMQNKIEF   420
KLKQYGIEIR KVAPNNTSQL CSKCGHLNNY FNFEYRKKNK FPHFKCEKCN FKENAAYNAA   480
LNISNPKLKS TKERP                                                    495

SEQ ID NO: 200          moltype = AA  length = 495
FEATURE                 Location/Qualifiers
source                  1..495
                        mol_type = protein
                        organism = synthetic construct
SEQUENCE: 200
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAELFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMENL ESMKRKEDSY FNIRLRGFWP YAEMQNKIEF   420
KLKQYGIEIR KVAPNNTSKT CSKCGHLNNY FNFEYRKKNK FPHFKCEKCN FKENAAYNAA   480
LNISNPDIKS TKERP                                                    495

SEQ ID NO: 201          moltype = AA  length = 495
FEATURE                 Location/Qualifiers
source                  1..495
                        mol_type = protein
                        organism = synthetic construct
SEQUENCE: 201
MAKNTITKTL KLRIVRPYNS AEVEKIVADE KERRKQAGGT GELDDKFYQK LRGQFPDAVF    60
WQEISEIFRQ LQKQAAEIYN QSLIELYYEI FIKGKGIANA SSVEHYLSRV CYRRAAELFK   120
NAAAIASGLRS KIKSNFRLKE LKNMKSGLPT TKSDNFPIPL VKQKGGQYTG FEISNHNSDF  180
IIKIPFGRWQ VKKEIDKYRP WEKFDFEQVQ KSPKPISLLL STQRRKRNKG WSKDEGTEAE   240
IKKVMNGDYQ TSYIEVKRGS KICEKSAWML NLSIDVPKID KGVDPSIIGG IAVGVRSPLV   300
CAINNAFSRY SISDNDLFHF NKKMFARRRI LLKKNRHKRA GHGAKNKLKP ITILTEKSER   360
FRKKLIERWA CEIADFFIKN KVGTVQMENL ESMKRKEDSY FNIRLRGFWP YAEMQNKIEF   420
KLKQYGIEIR KVAPNNTSQL CSKCGHLNNY FNFEYRKKNK FPHFKCEKCN FKENAAYNAA   480
LNISNPDIKS TKERP                                                    495

SEQ ID NO: 202          moltype = AA  length = 20
FEATURE                 Location/Qualifiers
source                  1..20
                        mol_type = protein
                        organism = synthetic construct
SEQUENCE: 202
AKNTITKTLK LRIVRPYNSA                                                20

SEQ ID NO: 203          moltype = AA  length = 30
FEATURE                 Location/Qualifiers
source                  1..30
                        mol_type = protein
                        organism = synthetic construct
SEQUENCE: 203
AKNTITKTLK LRIVRPYNSA EVEKIVADEK                                     30

SEQ ID NO: 204          moltype = AA  length = 20
FEATURE                 Location/Qualifiers
source                  1..20
                        mol_type = protein
                        organism = synthetic construct
SEQUENCE: 204
DYNAALNISN PKLKSTKEEP                                                20

SEQ ID NO: 205          moltype = AA  length = 30
FEATURE                 Location/Qualifiers
source                  1..30
                        mol_type = protein
                        organism = synthetic construct
SEQUENCE: 205
```

CEKCNFKENA DYNAALNISN PKLKSTKEEP                                          30

SEQ ID NO: 207          moltype = AA  length = 20
FEATURE                 Location/Qualifiers
source                  1..20
                        mol_type = protein
                        organism = synthetic construct
SEQUENCE: 206
KEACSKHLKV AAYCTTQVER                                                    20

SEQ ID NO: 207          moltype = AA  length = 31
FEATURE                 Location/Qualifiers
source                  1..31
                        mol_type = protein
                        organism = synthetic construct
SEQUENCE: 207
KNKDKVKEAC SKHLKVAAYC TTQVERNACL F                                       31

SEQ ID NO: 208          moltype =     length =
SEQUENCE: 208
000

SEQ ID NO: 209          moltype =     length =
SEQUENCE: 209
000

SEQ ID NO: 210          moltype =     length =
SEQUENCE: 210
000

SEQ ID NO: 211          moltype =     length =
SEQUENCE: 211
000

SEQ ID NO: 212          moltype =     length =
SEQUENCE: 212
000

SEQ ID NO: 213          moltype =     length =
SEQUENCE: 213
000

SEQ ID NO: 214          moltype =     length =
SEQUENCE: 214
000

SEQ ID NO: 215          moltype =     length =
SEQUENCE: 215
000

SEQ ID NO: 216          moltype =     length =
SEQUENCE: 216
000

SEQ ID NO: 217          moltype =     length =
SEQUENCE: 217
000

SEQ ID NO: 218          moltype =     length =
SEQUENCE: 218
000

SEQ ID NO: 219          moltype =     length =
SEQUENCE: 219
000

SEQ ID NO: 220          moltype =     length =
SEQUENCE: 220
000

SEQ ID NO: 221          moltype =     length =
SEQUENCE: 221
000

SEQ ID NO: 222          moltype =     length =
SEQUENCE: 222
000

SEQ ID NO: 223          moltype =     length =

-continued

| | | |
|---|---|---|
| SEQUENCE: 223 000 | | |
| SEQ ID NO: 224 SEQUENCE: 224 000 | moltype = | length = |
| SEQ ID NO: 225 SEQUENCE: 225 000 | moltype = | length = |
| SEQ ID NO: 226 SEQUENCE: 226 000 | moltype = | length = |
| SEQ ID NO: 227 SEQUENCE: 227 000 | moltype = | length = |
| SEQ ID NO: 228 SEQUENCE: 228 000 | moltype = | length = |
| SEQ ID NO: 229 SEQUENCE: 229 000 | moltype = | length = |
| SEQ ID NO: 230 SEQUENCE: 230 000 | moltype = | length = |
| SEQ ID NO: 231 SEQUENCE: 231 000 | moltype = | length = |
| SEQ ID NO: 232 SEQUENCE: 232 000 | moltype = | length = |
| SEQ ID NO: 233 SEQUENCE: 233 000 | moltype = | length = |
| SEQ ID NO: 234 SEQUENCE: 234 000 | moltype = | length = |
| SEQ ID NO: 235 SEQUENCE: 235 000 | moltype = | length = |
| SEQ ID NO: 236 SEQUENCE: 236 000 | moltype = | length = |
| SEQ ID NO: 237 SEQUENCE: 237 000 | moltype = | length = |
| SEQ ID NO: 238 SEQUENCE: 238 000 | moltype = | length = |
| SEQ ID NO: 239 SEQUENCE: 239 000 | moltype = | length = |
| SEQ ID NO: 240 SEQUENCE: 240 000 | moltype = | length = |
| SEQ ID NO: 241 SEQUENCE: 241 000 | moltype = | length = |
| SEQ ID NO: 242 SEQUENCE: 242 000 | moltype = | length = |

| | | |
|---|---|---|
| SEQ ID NO: 243<br>SEQUENCE: 243<br>000 | moltype = | length = |
| SEQ ID NO: 244<br>SEQUENCE: 244<br>000 | moltype = | length = |
| SEQ ID NO: 245<br>SEQUENCE: 245<br>000 | moltype = | length = |
| SEQ ID NO: 246<br>SEQUENCE: 246<br>000 | moltype = | length = |
| SEQ ID NO: 247<br>SEQUENCE: 247<br>000 | moltype = | length = |
| SEQ ID NO: 248<br>SEQUENCE: 248<br>000 | moltype = | length = |
| SEQ ID NO: 249<br>SEQUENCE: 249<br>000 | moltype = | length = |
| SEQ ID NO: 250<br>SEQUENCE: 250<br>000 | moltype = | length = |
| SEQ ID NO: 251<br>SEQUENCE: 251<br>000 | moltype = | length = |
| SEQ ID NO: 252<br>SEQUENCE: 252<br>000 | moltype = | length = |
| SEQ ID NO: 253<br>SEQUENCE: 253<br>000 | moltype = | length = |
| SEQ ID NO: 254<br>SEQUENCE: 254<br>000 | moltype = | length = |
| SEQ ID NO: 255<br>SEQUENCE: 255<br>000 | moltype = | length = |
| SEQ ID NO: 256<br>SEQUENCE: 256<br>000 | moltype = | length = |
| SEQ ID NO: 257<br>SEQUENCE: 257<br>000 | moltype = | length = |
| SEQ ID NO: 258<br>SEQUENCE: 258<br>000 | moltype = | length = |
| SEQ ID NO: 259<br>SEQUENCE: 259<br>000 | moltype = | length = |
| SEQ ID NO: 260<br>SEQUENCE: 260<br>000 | moltype = | length = |
| SEQ ID NO: 261<br>SEQUENCE: 261<br>000 | moltype = | length = |
| SEQ ID NO: 262<br>SEQUENCE: 262<br>000 | moltype = | length = |

| | | |
|---|---|---|
| SEQ ID NO: 263 SEQUENCE: 263 000 | moltype = | length = |
| SEQ ID NO: 264 SEQUENCE: 264 000 | moltype = | length = |
| SEQ ID NO: 265 SEQUENCE: 265 000 | moltype = | length = |
| SEQ ID NO: 266 SEQUENCE: 266 000 | moltype = | length = |
| SEQ ID NO: 267 SEQUENCE: 267 000 | moltype = | length = |
| SEQ ID NO: 268 SEQUENCE: 268 000 | moltype = | length = |
| SEQ ID NO: 269 SEQUENCE: 269 000 | moltype = | length = |
| SEQ ID NO: 270 SEQUENCE: 270 000 | moltype = | length = |
| SEQ ID NO: 271 SEQUENCE: 271 000 | moltype = | length = |
| SEQ ID NO: 272 SEQUENCE: 272 000 | moltype = | length = |
| SEQ ID NO: 273 SEQUENCE: 273 000 | moltype = | length = |
| SEQ ID NO: 274 SEQUENCE: 274 000 | moltype = | length = |
| SEQ ID NO: 275 SEQUENCE: 275 000 | moltype = | length = |
| SEQ ID NO: 276 SEQUENCE: 276 000 | moltype = | length = |
| SEQ ID NO: 277 SEQUENCE: 277 000 | moltype = | length = |
| SEQ ID NO: 278 SEQUENCE: 278 000 | moltype = | length = |
| SEQ ID NO: 279 SEQUENCE: 279 000 | moltype = | length = |
| SEQ ID NO: 280 SEQUENCE: 280 000 | moltype = | length = |
| SEQ ID NO: 281 SEQUENCE: 281 000 | moltype = | length = |
| SEQ ID NO: 282 SEQUENCE: 282 | moltype = | length = |

000

SEQ ID NO: 283        moltype =      length =
SEQUENCE: 283
000

SEQ ID NO: 284        moltype =      length =
SEQUENCE: 284
000

SEQ ID NO: 285        moltype =      length =
SEQUENCE: 285
000

SEQ ID NO: 286        moltype =      length =
SEQUENCE: 286
000

SEQ ID NO: 287        moltype =      length =
SEQUENCE: 287
000

SEQ ID NO: 288        moltype =      length =
SEQUENCE: 288
000

SEQ ID NO: 289        moltype =      length =
SEQUENCE: 289
000

SEQ ID NO: 290        moltype =      length =
SEQUENCE: 290
000

SEQ ID NO: 291        moltype =      length =
SEQUENCE: 291
000

SEQ ID NO: 292        moltype =      length =
SEQUENCE: 292
000

SEQ ID NO: 293        moltype =      length =
SEQUENCE: 293
000

SEQ ID NO: 294        moltype =      length =
SEQUENCE: 294
000

SEQ ID NO: 295        moltype =      length =
SEQUENCE: 295
000

SEQ ID NO: 296        moltype =      length =
SEQUENCE: 296
000

SEQ ID NO: 297        moltype =      length =
SEQUENCE: 297
000

SEQ ID NO: 298        moltype =      length =
SEQUENCE: 298
000

SEQ ID NO: 299        moltype =      length =
SEQUENCE: 299
000

SEQ ID NO: 300        moltype =      length =
SEQUENCE: 300
000

SEQ ID NO: 301        moltype =      length =
SEQUENCE: 301
000

SEQ ID NO: 302        moltype =      length =

| | | |
|---|---|---|
| SEQUENCE: 302 000 | | |
| SEQ ID NO: 303 SEQUENCE: 303 000 | moltype = | length = |
| SEQ ID NO: 304 SEQUENCE: 304 000 | moltype = | length = |
| SEQ ID NO: 305 SEQUENCE: 305 000 | moltype = | length = |
| SEQ ID NO: 306 SEQUENCE: 306 000 | moltype = | length = |
| SEQ ID NO: 307 SEQUENCE: 307 000 | moltype = | length = |
| SEQ ID NO: 308 SEQUENCE: 308 000 | moltype = | length = |
| SEQ ID NO: 309 SEQUENCE: 309 000 | moltype = | length = |
| SEQ ID NO: 310 SEQUENCE: 310 000 | moltype = | length = |
| SEQ ID NO: 311 SEQUENCE: 311 000 | moltype = | length = |
| SEQ ID NO: 312 SEQUENCE: 312 000 | moltype = | length = |
| SEQ ID NO: 313 SEQUENCE: 313 000 | moltype = | length = |
| SEQ ID NO: 314 SEQUENCE: 314 000 | moltype = | length = |
| SEQ ID NO: 315 SEQUENCE: 315 000 | moltype = | length = |
| SEQ ID NO: 316 SEQUENCE: 316 000 | moltype = | length = |
| SEQ ID NO: 317 SEQUENCE: 317 000 | moltype = | length = |
| SEQ ID NO: 318 SEQUENCE: 318 000 | moltype = | length = |
| SEQ ID NO: 319 SEQUENCE: 319 000 | moltype = | length = |
| SEQ ID NO: 320 SEQUENCE: 320 000 | moltype = | length = |
| SEQ ID NO: 321 SEQUENCE: 321 000 | moltype = | length = |

| | | |
|---|---|---|
| SEQ ID NO: 322<br>SEQUENCE: 322<br>000 | moltype = | length = |
| SEQ ID NO: 323<br>SEQUENCE: 323<br>000 | moltype = | length = |
| SEQ ID NO: 324<br>SEQUENCE: 324<br>000 | moltype = | length = |
| SEQ ID NO: 325<br>SEQUENCE: 325<br>000 | moltype = | length = |
| SEQ ID NO: 326<br>SEQUENCE: 326<br>000 | moltype = | length = |
| SEQ ID NO: 327<br>SEQUENCE: 327<br>000 | moltype = | length = |
| SEQ ID NO: 328<br>SEQUENCE: 328<br>000 | moltype = | length = |
| SEQ ID NO: 329<br>SEQUENCE: 329<br>000 | moltype = | length = |
| SEQ ID NO: 330<br>SEQUENCE: 330<br>000 | moltype = | length = |
| SEQ ID NO: 331<br>SEQUENCE: 331<br>000 | moltype = | length = |
| SEQ ID NO: 332<br>SEQUENCE: 332<br>000 | moltype = | length = |
| SEQ ID NO: 333<br>SEQUENCE: 333<br>000 | moltype = | length = |
| SEQ ID NO: 334<br>SEQUENCE: 334<br>000 | moltype = | length = |
| SEQ ID NO: 335<br>SEQUENCE: 335<br>000 | moltype = | length = |
| SEQ ID NO: 336<br>SEQUENCE: 336<br>000 | moltype = | length = |
| SEQ ID NO: 337<br>SEQUENCE: 337<br>000 | moltype = | length = |
| SEQ ID NO: 338<br>SEQUENCE: 338<br>000 | moltype = | length = |
| SEQ ID NO: 339<br>SEQUENCE: 339<br>000 | moltype = | length = |
| SEQ ID NO: 340<br>SEQUENCE: 340<br>000 | moltype = | length = |
| SEQ ID NO: 341<br>SEQUENCE: 341<br>000 | moltype = | length = |

| | | |
|---|---|---|
| SEQ ID NO: 342<br>SEQUENCE: 342<br>000 | moltype = | length = |
| SEQ ID NO: 343<br>SEQUENCE: 343<br>000 | moltype = | length = |
| SEQ ID NO: 344<br>SEQUENCE: 344<br>000 | moltype = | length = |
| SEQ ID NO: 345<br>SEQUENCE: 345<br>000 | moltype = | length = |
| SEQ ID NO: 346<br>SEQUENCE: 346<br>000 | moltype = | length = |
| SEQ ID NO: 347<br>SEQUENCE: 347<br>000 | moltype = | length = |
| SEQ ID NO: 348<br>SEQUENCE: 348<br>000 | moltype = | length = |
| SEQ ID NO: 349<br>SEQUENCE: 349<br>000 | moltype = | length = |
| SEQ ID NO: 350<br>SEQUENCE: 350<br>000 | moltype = | length = |
| SEQ ID NO: 351<br>SEQUENCE: 351<br>000 | moltype = | length = |
| SEQ ID NO: 352<br>SEQUENCE: 352<br>000 | moltype = | length = |
| SEQ ID NO: 353<br>SEQUENCE: 353<br>000 | moltype = | length = |
| SEQ ID NO: 354<br>SEQUENCE: 354<br>000 | moltype = | length = |
| SEQ ID NO: 355<br>SEQUENCE: 355<br>000 | moltype = | length = |
| SEQ ID NO: 356<br>SEQUENCE: 356<br>000 | moltype = | length = |
| SEQ ID NO: 357<br>SEQUENCE: 357<br>000 | moltype = | length = |
| SEQ ID NO: 358<br>SEQUENCE: 358<br>000 | moltype = | length = |
| SEQ ID NO: 359<br>SEQUENCE: 359<br>000 | moltype = | length = |
| SEQ ID NO: 360<br>SEQUENCE: 360<br>000 | moltype = | length = |
| SEQ ID NO: 361<br>SEQUENCE: 361 | moltype = | length = |

000

SEQ ID NO: 362        moltype =    length =
SEQUENCE: 362
000

SEQ ID NO: 363        moltype =    length =
SEQUENCE: 363
000

SEQ ID NO: 364        moltype =    length =
SEQUENCE: 364
000

SEQ ID NO: 365        moltype =    length =
SEQUENCE: 365
000

SEQ ID NO: 366        moltype =    length =
SEQUENCE: 366
000

SEQ ID NO: 367        moltype =    length =
SEQUENCE: 367
000

SEQ ID NO: 368        moltype =    length =
SEQUENCE: 368
000

SEQ ID NO: 369        moltype =    length =
SEQUENCE: 369
000

SEQ ID NO: 370        moltype =    length =
SEQUENCE: 370
000

SEQ ID NO: 371        moltype =    length =
SEQUENCE: 371
000

SEQ ID NO: 372        moltype =    length =
SEQUENCE: 372
000

SEQ ID NO: 373        moltype =    length =
SEQUENCE: 373
000

SEQ ID NO: 374        moltype =    length =
SEQUENCE: 374
000

SEQ ID NO: 375        moltype =    length =
SEQUENCE: 375
000

SEQ ID NO: 376        moltype =    length =
SEQUENCE: 376
000

SEQ ID NO: 377        moltype =    length =
SEQUENCE: 377
000

SEQ ID NO: 378        moltype =    length =
SEQUENCE: 378
000

SEQ ID NO: 379        moltype =    length =
SEQUENCE: 379
000

SEQ ID NO: 380        moltype =    length =
SEQUENCE: 380
000

SEQ ID NO: 381        moltype =    length =

-continued

```
SEQUENCE: 381
000

SEQ ID NO: 382           moltype =    length =
SEQUENCE: 382
000

SEQ ID NO: 383           moltype =    length =
SEQUENCE: 383
000

SEQ ID NO: 384           moltype =    length =
SEQUENCE: 384
000

SEQ ID NO: 385           moltype =    length =
SEQUENCE: 385
000

SEQ ID NO: 386           moltype =    length =
SEQUENCE: 386
000

SEQ ID NO: 387           moltype =    length =
SEQUENCE: 387
000

SEQ ID NO: 388           moltype =    length =
SEQUENCE: 388
000

SEQ ID NO: 389           moltype =    length =
SEQUENCE: 389
000

SEQ ID NO: 390           moltype =    length =
SEQUENCE: 390
000

SEQ ID NO: 391           moltype =    length =
SEQUENCE: 391
000

SEQ ID NO: 392           moltype =    length =
SEQUENCE: 392
000

SEQ ID NO: 393           moltype =    length =
SEQUENCE: 393
000

SEQ ID NO: 394           moltype =    length =
SEQUENCE: 394
000

SEQ ID NO: 395           moltype =    length =
SEQUENCE: 395
000

SEQ ID NO: 396           moltype =    length =
SEQUENCE: 396
000

SEQ ID NO: 397           moltype =    length =
SEQUENCE: 397
000

SEQ ID NO: 398           moltype =    length =
SEQUENCE: 398
000

SEQ ID NO: 399           moltype =    length =
SEQUENCE: 399
000

SEQ ID NO: 400           moltype =    length =
SEQUENCE: 400
000
```

| | | |
|---|---|---|
| SEQ ID NO: 401 SEQUENCE: 401 | moltype = | length = 000 |
| SEQ ID NO: 402 SEQUENCE: 402 | moltype = | length = 000 |
| SEQ ID NO: 403 SEQUENCE: 403 | moltype = | length = 000 |
| SEQ ID NO: 404 SEQUENCE: 404 | moltype = | length = 000 |
| SEQ ID NO: 405 SEQUENCE: 405 | moltype = | length = 000 |
| SEQ ID NO: 406 SEQUENCE: 406 | moltype = | length = 000 |
| SEQ ID NO: 407 SEQUENCE: 407 | moltype = | length = 000 |
| SEQ ID NO: 408 SEQUENCE: 408 | moltype = | length = 000 |
| SEQ ID NO: 409 SEQUENCE: 409 | moltype = | length = 000 |
| SEQ ID NO: 410 SEQUENCE: 410 | moltype = | length = 000 |
| SEQ ID NO: 411 SEQUENCE: 411 | moltype = | length = 000 |
| SEQ ID NO: 412 SEQUENCE: 412 | moltype = | length = 000 |
| SEQ ID NO: 413 SEQUENCE: 413 | moltype = | length = 000 |
| SEQ ID NO: 414 SEQUENCE: 414 | moltype = | length = 000 |
| SEQ ID NO: 415 SEQUENCE: 415 | moltype = | length = 000 |
| SEQ ID NO: 416 SEQUENCE: 416 | moltype = | length = 000 |
| SEQ ID NO: 417 SEQUENCE: 417 | moltype = | length = 000 |
| SEQ ID NO: 418 SEQUENCE: 418 | moltype = | length = 000 |
| SEQ ID NO: 419 SEQUENCE: 419 | moltype = | length = 000 |
| SEQ ID NO: 420 SEQUENCE: 420 | moltype = | length = 000 |

| | | |
|---|---|---|
| SEQ ID NO: 421 SEQUENCE: 421 | moltype = 000 | length = |
| SEQ ID NO: 422 SEQUENCE: 422 | moltype = 000 | length = |
| SEQ ID NO: 423 SEQUENCE: 423 | moltype = 000 | length = |
| SEQ ID NO: 424 SEQUENCE: 424 | moltype = 000 | length = |
| SEQ ID NO: 425 SEQUENCE: 425 | moltype = 000 | length = |
| SEQ ID NO: 426 SEQUENCE: 426 | moltype = 000 | length = |
| SEQ ID NO: 427 SEQUENCE: 427 | moltype = 000 | length = |
| SEQ ID NO: 428 SEQUENCE: 428 | moltype = 000 | length = |
| SEQ ID NO: 429 SEQUENCE: 429 | moltype = 000 | length = |
| SEQ ID NO: 430 SEQUENCE: 430 | moltype = 000 | length = |
| SEQ ID NO: 431 SEQUENCE: 431 | moltype = 000 | length = |
| SEQ ID NO: 432 SEQUENCE: 432 | moltype = 000 | length = |
| SEQ ID NO: 433 SEQUENCE: 433 | moltype = 000 | length = |
| SEQ ID NO: 434 SEQUENCE: 434 | moltype = 000 | length = |
| SEQ ID NO: 435 SEQUENCE: 435 | moltype = 000 | length = |
| SEQ ID NO: 436 SEQUENCE: 436 | moltype = 000 | length = |
| SEQ ID NO: 437 SEQUENCE: 437 | moltype = 000 | length = |
| SEQ ID NO: 438 SEQUENCE: 438 | moltype = 000 | length = |
| SEQ ID NO: 439 SEQUENCE: 439 | moltype = 000 | length = |
| SEQ ID NO: 440 SEQUENCE: 440 | moltype = | length = |

000

SEQ ID NO: 441        moltype =     length =
SEQUENCE: 441
000

SEQ ID NO: 442        moltype =     length =
SEQUENCE: 442
000

SEQ ID NO: 443        moltype =     length =
SEQUENCE: 443
000

SEQ ID NO: 444        moltype =     length =
SEQUENCE: 444
000

SEQ ID NO: 445        moltype =     length =
SEQUENCE: 445
000

SEQ ID NO: 446        moltype =     length =
SEQUENCE: 446
000

SEQ ID NO: 447        moltype =     length =
SEQUENCE: 447
000

SEQ ID NO: 448        moltype =     length =
SEQUENCE: 448
000

SEQ ID NO: 449        moltype =     length =
SEQUENCE: 449
000

SEQ ID NO: 450        moltype =     length =
SEQUENCE: 450
000

SEQ ID NO: 451        moltype =     length =
SEQUENCE: 451
000

SEQ ID NO: 452        moltype =     length =
SEQUENCE: 452
000

SEQ ID NO: 453        moltype =     length =
SEQUENCE: 453
000

SEQ ID NO: 454        moltype =     length =
SEQUENCE: 454
000

SEQ ID NO: 455        moltype =     length =
SEQUENCE: 455
000

SEQ ID NO: 456        moltype =     length =
SEQUENCE: 456
000

SEQ ID NO: 457        moltype =     length =
SEQUENCE: 457
000

SEQ ID NO: 458        moltype =     length =
SEQUENCE: 458
000

SEQ ID NO: 459        moltype =     length =
SEQUENCE: 459
000

SEQ ID NO: 460        moltype =     length =

```
SEQUENCE: 460
000

SEQ ID NO: 461          moltype =    length =
SEQUENCE: 461
000

SEQ ID NO: 462          moltype =    length =
SEQUENCE: 462
000

SEQ ID NO: 463          moltype =    length =
SEQUENCE: 463
000

SEQ ID NO: 464          moltype =    length =
SEQUENCE: 464
000

SEQ ID NO: 465          moltype =    length =
SEQUENCE: 465
000

SEQ ID NO: 466          moltype =    length =
SEQUENCE: 466
000

SEQ ID NO: 467          moltype =    length =
SEQUENCE: 467
000

SEQ ID NO: 468          moltype =    length =
SEQUENCE: 468
000

SEQ ID NO: 469          moltype =    length =
SEQUENCE: 469
000

SEQ ID NO: 470          moltype =    length =
SEQUENCE: 470
000

SEQ ID NO: 471          moltype =    length =
SEQUENCE: 471
000

SEQ ID NO: 472          moltype =    length =
SEQUENCE: 472
000

SEQ ID NO: 473          moltype =    length =
SEQUENCE: 473
000

SEQ ID NO: 474          moltype =    length =
SEQUENCE: 474
000

SEQ ID NO: 475          moltype =    length =
SEQUENCE: 475
000

SEQ ID NO: 476          moltype =    length =
SEQUENCE: 476
000

SEQ ID NO: 477          moltype =    length =
SEQUENCE: 477
000

SEQ ID NO: 478          moltype =    length =
SEQUENCE: 478
000

SEQ ID NO: 479          moltype =    length =
SEQUENCE: 479
000
```

-continued

| | | |
|---|---|---|
| SEQ ID NO: 480
SEQUENCE: 480 | moltype = | length = 000 |
| SEQ ID NO: 481
SEQUENCE: 481 | moltype = | length = 000 |
| SEQ ID NO: 482
SEQUENCE: 482 | moltype = | length = 000 |
| SEQ ID NO: 483
SEQUENCE: 483 | moltype = | length = 000 |
| SEQ ID NO: 484
SEQUENCE: 484 | moltype = | length = 000 |
| SEQ ID NO: 485
SEQUENCE: 485 | moltype = | length = 000 |
| SEQ ID NO: 486
SEQUENCE: 486 | moltype = | length = 000 |
| SEQ ID NO: 487
SEQUENCE: 487 | moltype = | length = 000 |
| SEQ ID NO: 488
SEQUENCE: 488 | moltype = | length = 000 |
| SEQ ID NO: 489
SEQUENCE: 489 | moltype = | length = 000 |
| SEQ ID NO: 490
SEQUENCE: 490 | moltype = | length = 000 |
| SEQ ID NO: 491
SEQUENCE: 491 | moltype = | length = 000 |
| SEQ ID NO: 492
SEQUENCE: 492 | moltype = | length = 000 |
| SEQ ID NO: 493
SEQUENCE: 493 | moltype = | length = 000 |
| SEQ ID NO: 494
SEQUENCE: 494 | moltype = | length = 000 |
| SEQ ID NO: 495
SEQUENCE: 495 | moltype = | length = 000 |
| SEQ ID NO: 496
SEQUENCE: 496 | moltype = | length = 000 |
| SEQ ID NO: 497
SEQUENCE: 497 | moltype = | length = 000 |
| SEQ ID NO: 498
SEQUENCE: 498 | moltype = | length = 000 |
| SEQ ID NO: 499
SEQUENCE: 499 | moltype = | length = 000 |

```
SEQ ID NO: 500           moltype = DNA   length = 159
FEATURE                  Location/Qualifiers
source                   1..159
                         mol_type = other DNA
                         organism = synthetic construct
SEQUENCE: 500
ggcttcactg ataaagtgga gaaccgcttc accaaaagct gtcccttagg ggattagaac    60
ttgagtgaag gtgggctgct tgcatcagcc taatgtcgag aagtgctttc ttcggaaagt   120
aaccctcgaa acaaattcat ttgaatgaag gaatgcaac                          159

SEQ ID NO: 501           moltype = DNA   length = 139
FEATURE                  Location/Qualifiers
source                   1..139
                         mol_type = other DNA
                         organism = synthetic construct
SEQUENCE: 501
gaaccgcttc accaaaagct gtcccttagg ggattagaac ttgagtgaag gtgggctgct    60
tgcatcagcc taatgtcgag aagtgctttc ttcggaaagt aaccctcgaa acaaattcat   120
ttgaatgaag gaatgcaac                                                139

SEQ ID NO: 502           moltype = DNA   length = 138
FEATURE                  Location/Qualifiers
source                   1..138
                         mol_type = other DNA
                         organism = synthetic construct
SEQUENCE: 502
aaccgcttca ccaaaagctg tcccttaggg gattagaact tgagtgaagg tgggctgctt    60
gcatcagcct aatgtcgaga agtgctttct tcggaaagta accctcgaaa caaattcatt   120
tgaatgaagg aatgcaac                                                 138

SEQ ID NO: 503           moltype = DNA   length = 137
FEATURE                  Location/Qualifiers
source                   1..137
                         mol_type = other DNA
                         organism = synthetic construct
SEQUENCE: 503
accgcttcac caaaagctgt cccttagggg attagaactt gagtgaaggt gggctgcttg    60
catcagccta atgtcgagaa gtgctttctt cggaaagtaa ccctcgaaac aaattcattt   120
gaatgaagga atgcaac                                                  137

SEQ ID NO: 504           moltype = DNA   length = 136
FEATURE                  Location/Qualifiers
source                   1..136
                         mol_type = other DNA
                         organism = synthetic construct
SEQUENCE: 504
ccgcttcacc aaaagctgtc ccttagggga ttagaacttg agtgaaggtg ggctgcttgc    60
atcagcctaa tgtcgagaag tgctttcttc ggaaagtaac cctcgaaaca aattcatttg   120
aatgaaggaa tgcaac                                                   136

SEQ ID NO: 505           moltype = DNA   length = 151
FEATURE                  Location/Qualifiers
source                   1..151
                         mol_type = other DNA
                         organism = synthetic construct
SEQUENCE: 505
ggcttcactg ataaagtgga gaaccgcttc accaaaagct gtcccttagg ggattagaac    60
ttgagtgaag gtgggctgct tgcatcagcc taatgtcgag aagtgctttc ttcggaaagt   120
aaccctcgaa acaagcaata aggaatgcaa c                                  151

SEQ ID NO: 506           moltype = DNA   length = 148
FEATURE                  Location/Qualifiers
source                   1..148
                         mol_type = other DNA
                         organism = synthetic construct
SEQUENCE: 506
ggcttcactg ataaagtgga gaaccgcttc accaaaagct gtcccttagg ggattagaac    60
ttgagtgaag gtgggctgct tgcatcagcc taatgtcgag aagtgctttc ttcggaaagt   120
aaccctcgaa acaagaaagg aatgcaac                                      148

SEQ ID NO: 507           moltype = DNA   length = 157
FEATURE                  Location/Qualifiers
source                   1..157
                         mol_type = other DNA
                         organism = synthetic construct
SEQUENCE: 507
ggcttcactg ataaagtgga gaaccgcttc accaaaagct gtcccttagg ggattagaac    60
ttgagtgaag gtgggctgct tgcatcagcc taatgtcgag aagtgctttc ttcggaaagt   120
```

```
aaccctcgaa acaaatcttc ggattaagga atgcaac                                      157

SEQ ID NO: 508           moltype = DNA   length = 153
FEATURE                  Location/Qualifiers
source                   1..153
                         mol_type = other DNA
                         organism = synthetic construct
SEQUENCE: 508
ggcttcactg ataaagtgga gaaccgcttc accaaaagct gtcccttagg ggattagaac             60
ttgagtgaag gtgggctgct tgcatcagcc taatgtcgag aagtgctttc ttcggaaagt            120
aaccctcgaa acaaattgca aaaggaatgc aac                                         153

SEQ ID NO: 509           moltype = DNA   length = 153
FEATURE                  Location/Qualifiers
source                   1..153
                         mol_type = other DNA
                         organism = synthetic construct
SEQUENCE: 509
ggcttcactg ataaagtgga gaaccgcttc accaaaagct gtcccttagg ggattagaac             60
ttgagtgaag gtgggctgct tgcatcagcc taatgtcgag aagtgctttc ttcggaaagt            120
aaccctcgaa acaaattcgt taaggaatgc aac                                         153

SEQ ID NO: 510           moltype = DNA   length = 151
FEATURE                  Location/Qualifiers
source                   1..151
                         mol_type = other DNA
                         organism = synthetic construct
SEQUENCE: 510
ggcttcactg ataaagtgga gaaccgcttc accaaaagct gtcccttagg ggattagaac             60
ttgagtgaag gtgggctgct tgcatcagcc taatgtcgag aagtgctttc ttcggaaagt            120
aaccctcgaa acaaatgcaa aggaatgcaa c                                           151

SEQ ID NO: 511           moltype = DNA   length = 153
FEATURE                  Location/Qualifiers
source                   1..153
                         mol_type = other DNA
                         organism = synthetic construct
SEQUENCE: 511
ggcttcactg ataaagtgga gaaccgcttc accaaaagct gtcccttagg ggattagaac             60
ttgagtgaag gtgggctgct tgcatcagcc taatgtcgag aagtgctttc ttcggaaagt            120
aaccctcgaa acaaagcaat taaggaatgc aac                                         153

SEQ ID NO: 512           moltype = DNA   length = 149
FEATURE                  Location/Qualifiers
source                   1..149
                         mol_type = other DNA
                         organism = synthetic construct
SEQUENCE: 512
ggcttcactg ataaagtgga gaaccgcttc accaaaagct gtcccttagg ggattagaac             60
ttgagtgaag gtgggctgct tgcatcagcc taatgtcgag aagtgctttc ttcggaaagt            120
aaccctcgaa acaaagaaag gaatgcaac                                              149

SEQ ID NO: 513           moltype = DNA   length = 132
FEATURE                  Location/Qualifiers
source                   1..132
                         mol_type = other DNA
                         organism = synthetic construct
SEQUENCE: 513
ggcttcactg ataaagtgga gaaccgcttc acttagagtg aaggtgggct gcttgcatca            60
gcctaatgtc gagaagtgct ttcttcggaa agtaaccctc gaaacaaatt catttgaatg           120
aaggaatgca ac                                                               132

SEQ ID NO: 514           moltype = DNA   length = 132
FEATURE                  Location/Qualifiers
source                   1..132
                         mol_type = other DNA
                         organism = synthetic construct
SEQUENCE: 514
ggcttcactg ataaagtgga gaaccgcttc acttcgagtg aaggtgggct gcttgcatca            60
gcctaatgtc gagaagtgct ttcttcggaa agtaaccctc gaaacaaatt catttgaatg           120
aaggaatgca ac                                                               132

SEQ ID NO: 515           moltype = DNA   length = 131
FEATURE                  Location/Qualifiers
source                   1..131
                         mol_type = other DNA
                         organism = synthetic construct
SEQUENCE: 515
ggcttcactg ataaagtgga gaaccgcttc acttcggtga aggtgggctg cttgcatcag            60
```

```
cctaatgtcg agaagtgctt tcttcggaaa gtaaccctcg aaacaaattc atttgaatga    120
aggaatgcaa c                                                        131

SEQ ID NO: 516          moltype = DNA   length = 134
FEATURE                 Location/Qualifiers
source                  1..134
                        mol_type = other DNA
                        organism = synthetic construct
SEQUENCE: 516
ggcttcactg ataaagtgga gaaccgcttc accttaggag tgaaggtggg ctgcttgcat    60
cagcctaatg tcgagaagtg cttctcttcgg aaagtaaccc tcgaaacaaa ttcatttgaa   120
tgaaggaatg caac                                                     134

SEQ ID NO: 517          moltype = DNA   length = 134
FEATURE                 Location/Qualifiers
source                  1..134
                        mol_type = other DNA
                        organism = synthetic construct
SEQUENCE: 517
ggcttcactg ataaagtgga gaaccgcttc accttcggag tgaaggtggg ctgcttgcat    60
cagcctaatg tcgagaagtg cttctcttcgg aaagtaaccc tcgaaacaaa ttcatttgaa   120
tgaaggaatg caac                                                     134

SEQ ID NO: 518          moltype = DNA   length = 136
FEATURE                 Location/Qualifiers
source                  1..136
                        mol_type = other DNA
                        organism = synthetic construct
SEQUENCE: 518
ggcttcactg ataaagtgga gaaccgcttc acgcttcggc agtgaaggtg ggctgcttgc    60
atcagcctaa tgtcgagaag tgctttcttc ggaaagtaac cctcgaaaca aattcatttg   120
aatgaaggaa tgcaac                                                   136

SEQ ID NO: 519          moltype = DNA   length = 135
FEATURE                 Location/Qualifiers
source                  1..135
                        mol_type = other DNA
                        organism = synthetic construct
SEQUENCE: 519
accgcttcac caaaagctgt ccttagggat tagaacttga gtgaaggtgg gctgcttgca    60
tcagcctaat gtcgagaagt gctttcttcg gaaagtaacc ctcgaaacaa attcatttga   120
atgaaggaat gcaac                                                    135

SEQ ID NO: 520          moltype = DNA   length = 133
FEATURE                 Location/Qualifiers
source                  1..133
                        mol_type = other DNA
                        organism = synthetic construct
SEQUENCE: 520
accgcttcac caaaagctgt cttaggatta gaacttgagt gaaggtgggc tgcttgcatc    60
agcctaatgt cgagaagtgc tttcttcgga agtaaccct cgaaacaaat tcatttgaat   120
gaaggaatgc aac                                                      133

SEQ ID NO: 521          moltype = DNA   length = 131
FEATURE                 Location/Qualifiers
source                  1..131
                        mol_type = other DNA
                        organism = synthetic construct
SEQUENCE: 521
accgcttcac caaaagctgt ttagattaga acttgagtga aggtgggctg cttgcatcag    60
cctaatgtcg agaagtgctt tcttcggaaa gtaaccctcg aaacaaattc atttgaatga   120
aggaatgcaa c                                                        131

SEQ ID NO: 522          moltype = DNA   length = 129
FEATURE                 Location/Qualifiers
source                  1..129
                        mol_type = other DNA
                        organism = synthetic construct
SEQUENCE: 522
accgcttcac caaaagctgt tagttagaac ttgagtgaag gtgggctgct tgcatcagcc    60
taatgtcgag aagtgctttc ttcggaaagt aaccctcgaa acaaattcat tgaatgaag   120
gaatgcaac                                                           129

SEQ ID NO: 523          moltype = DNA   length = 126
FEATURE                 Location/Qualifiers
source                  1..126
                        mol_type = other DNA
                        organism = synthetic construct
SEQUENCE: 523
```

```
accgcttcac caaaagcttt agagaacttg agtgaaggtg ggctgcttgc atcagcctaa   60
tgtcgagaag tgctttcttc ggaaagtaac cctcgaaaca aattcatttg aatgaaggaa  120
tgcaac                                                             126
```

SEQ ID NO: 524          moltype = DNA   length = 124
FEATURE                 Location/Qualifiers
source                  1..124
                        mol_type = other DNA
                        organism = synthetic construct
SEQUENCE: 524
```
accgcttcac caaaagcttc ggcacttgag tgaaggtggg ctgcttgcat cagcctaatg   60
tcgagaagtg cttcttcgg aaagtaaccc tcgaaacaaa ttcatttgaa tgaaggaatg  120
caac                                                               124
```

SEQ ID NO: 525          moltype = DNA   length = 122
FEATURE                 Location/Qualifiers
source                  1..122
                        mol_type = other DNA
                        organism = synthetic construct
SEQUENCE: 525
```
accgcttcac caaaagttcg cacttgagtg aaggtgggct gcttgcatca gcctaatgtc   60
gagaagtgct tcttcggaa agtaaccctc gaaacaaatt catttgaatg aaggaatgca  120
ac                                                                 122
```

SEQ ID NO: 526          moltype = DNA   length = 120
FEATURE                 Location/Qualifiers
source                  1..120
                        mol_type = other DNA
                        organism = synthetic construct
SEQUENCE: 526
```
accgcttcac caaaattcgt cttgagtgaa ggtgggctgc ttgcatcagc ctaatgtcga   60
gaagtgcttt cttcggaaag taaccctcga aacaaattca tttgaatgaa ggaatgcaac  120
```

SEQ ID NO: 527          moltype = DNA   length = 118
FEATURE                 Location/Qualifiers
source                  1..118
                        mol_type = other DNA
                        organism = synthetic construct
SEQUENCE: 527
```
accgcttcac caagttcgct tgagtgaagg tgggctgctt gcatcagcct aatgtcgaga   60
agtgctttct tcggaaagta accctcgaaa caaattcatt tgaatgaagg aatgcaac    118
```

SEQ ID NO: 528          moltype = DNA   length = 116
FEATURE                 Location/Qualifiers
source                  1..116
                        mol_type = other DNA
                        organism = synthetic construct
SEQUENCE: 528
```
accgcttcac caattcgttg agtgaaggtg ggctgcttgc atcagcctaa tgtcgagaag   60
tgctttcttc ggaaagtaac cctcgaaaca aattcatttg aatgaaggaa tgcaac      116
```

SEQ ID NO: 529          moltype = DNA   length = 114
FEATURE                 Location/Qualifiers
source                  1..114
                        mol_type = other DNA
                        organism = synthetic construct
SEQUENCE: 529
```
accgcttcac cattcgtgag tgaaggtggg ctgcttgcat cagcctaatg tcgagaagtg   60
ctttcttcgg aaagtaaccc tcgaaacaaa ttcatttgaa tgaaggaatg caac        114
```

SEQ ID NO: 530          moltype = DNA   length = 159
FEATURE                 Location/Qualifiers
source                  1..159
                        mol_type = other DNA
                        organism = synthetic construct
SEQUENCE: 530
```
ggcttcactg ataaagtgga gaaccgcttc accaaaagct gtcccttagg ggattagaac   60
ttgagtgaag gtgggctgct tgcatcagcc taatgtcgag aagtgctttc ttcggaaagt  120
aaccctcgaa acaaattcat ttgaatgaag gaatgcaac                         159
```

SEQ ID NO: 531          moltype =   length =
SEQUENCE: 531
000

SEQ ID NO: 532          moltype = DNA   length = 159
FEATURE                 Location/Qualifiers
source                  1..159
                        mol_type = other DNA
                        organism = synthetic construct

```
SEQUENCE: 532
ggcttcactg ataaagtgga gaaccgcttc accaaaagct gtcccttagg ggattagaac    60
ttgagtgaag gtgggctgct tgcatcagcc taatgtcgag aagtgctttc ttcggaaagt   120
aaccctcgaa acaaattcat ttgaatgaag gaatgcaac                          159

SEQ ID NO: 533          moltype =    length =
SEQUENCE: 533
000

SEQ ID NO: 534          moltype = DNA   length = 159
FEATURE                 Location/Qualifiers
source                  1..159
                        mol_type = other DNA
                        organism = synthetic construct
SEQUENCE: 534
ggcttcactg ataaagtgga gaaccgcttc accaaaagct gtcccttagg ggattagaac    60
ttgagtgaag gtgggctgct tgcatcagcc taatgtcgag aagtgctttc ttcggaaagt   120
aaccctcgaa acaaattcat ttgaatgaag gaatgcaac                          159

SEQ ID NO: 535          moltype =    length =
SEQUENCE: 535
000

SEQ ID NO: 536          moltype = DNA   length = 159
FEATURE                 Location/Qualifiers
source                  1..159
                        mol_type = other DNA
                        organism = synthetic construct
SEQUENCE: 536
ggcttcactg ataaagtgga gaaccgcttc accaaaagct gtcccttagg ggattagaac    60
ttgagtgaag gtgggctgct tgcatcagcc taatgtcgag aagtgctttc ttcggaaagt   120
aaccctcgaa acaaattcat ttgaatgaag gaatgcaac                          159

SEQ ID NO: 537          moltype = DNA   length = 10
FEATURE                 Location/Qualifiers
source                  1..10
                        mol_type = other DNA
                        organism = synthetic construct
SEQUENCE: 537
ttttatttt                                                            10

SEQ ID NO: 538          moltype = DNA   length = 130
FEATURE                 Location/Qualifiers
source                  1..130
                        mol_type = other DNA
                        organism = synthetic construct
SEQUENCE: 538
ggcttcactg ataaagtgga gaaccgcttc accgagtgaa ggtgggctgc ttgcatcagc    60
ctaatgtcga gaagtgcttt cttcggaaag taaccctcga acaaattca tttgaatgaa   120
ggaatgcaac                                                          130

SEQ ID NO: 539          moltype = DNA   length = 10
FEATURE                 Location/Qualifiers
source                  1..10
                        mol_type = other DNA
                        organism = synthetic construct
SEQUENCE: 539
ttttatttt                                                            10

SEQ ID NO: 540          moltype = DNA   length = 149
FEATURE                 Location/Qualifiers
source                  1..149
                        mol_type = other DNA
                        organism = synthetic construct
SEQUENCE: 540
ggcttcactg ataaagtgga gaaccgcttc accaaaagct gtcccttagg ggattagaac    60
ttgagtgaag gtgggctgct tgcatcagcc taatgtcgag aagtgctttc ttcggaaagt   120
aaccctcgaa acaaagaaag gaatgcaac                                     149

SEQ ID NO: 541          moltype = DNA   length = 132
FEATURE                 Location/Qualifiers
source                  1..132
                        mol_type = other DNA
                        organism = synthetic construct
SEQUENCE: 541
ggcttcactg ataaagtgga gaaccgcttc acttagagtg aaggtgggct gcttgcatca    60
gcctaatgtc gagaagtgct tcttcggaa agtaaccctc gaaacaaatt catttgaatg   120
aaggaatgca ac                                                       132
```

```
SEQ ID NO: 542          moltype = DNA   length = 10
FEATURE                 Location/Qualifiers
source                  1..10
                        mol_type = other DNA
                        organism = synthetic construct
SEQUENCE: 542
ttttattttt                                                                  10

SEQ ID NO: 543          moltype = DNA   length = 130
FEATURE                 Location/Qualifiers
source                  1..130
                        mol_type = other DNA
                        organism = synthetic construct
SEQUENCE: 543
ggcttcactg ataaagtgga gaaccgcttc accgagtgaa ggtgggctgc ttgcatcagc            60
ctaatgtcga gaagtgcttt cttcggaaag taaccctcga aacaaattca tttgaatgaa          120
ggaatgcaac                                                                 130

SEQ ID NO: 544          moltype = DNA   length = 10
FEATURE                 Location/Qualifiers
source                  1..10
                        mol_type = other DNA
                        organism = synthetic construct
SEQUENCE: 544
ttttattttt                                                                  10

SEQ ID NO: 545          moltype = DNA   length = 122
FEATURE                 Location/Qualifiers
source                  1..122
                        mol_type = other DNA
                        organism = synthetic construct
SEQUENCE: 545
ggcttcactg ataaagtgga gaaccgcttc acttagagtg aaggtgggct gcttgcatca            60
gcctaatgtc gagaagtgct ttcttcggaa agtaaccctc gaaacaaaga aaggaatgca          120
ac                                                                         122

SEQ ID NO: 546          moltype = DNA   length = 120
FEATURE                 Location/Qualifiers
source                  1..120
                        mol_type = other DNA
                        organism = synthetic construct
SEQUENCE: 546
ggcttcactg ataaagtgga gaaccgcttc accgagtgaa ggtgggctgc ttgcatcagc            60
ctaatgtcga gaagtgcttt cttcggaaag taaccctcga aacaaagaaa ggaatgcaac          120

SEQ ID NO: 547          moltype = DNA   length = 100
FEATURE                 Location/Qualifiers
source                  1..100
                        mol_type = other DNA
                        organism = synthetic construct
SEQUENCE: 547
accgcttcac ttagagtgaa ggtgggctgc ttgcatcagc ctaatgtcga gaagtgcttt            60
cttcggaaag taaccctcga aacaaagaaa ggaatgcaac                                100

SEQ ID NO: 548          moltype = DNA   length = 98
FEATURE                 Location/Qualifiers
source                  1..98
                        mol_type = other DNA
                        organism = synthetic construct
SEQUENCE: 548
accgcttcac cgagtgaagg tgggctgctt gcatcagcct aatgtcgaga agtgctttct            60
tcggaaagta accctcgaaa caaagaaagg aatgcaac                                   98

SEQ ID NO: 549          moltype = DNA   length = 100
FEATURE                 Location/Qualifiers
source                  1..100
                        mol_type = other DNA
                        organism = synthetic construct
SEQUENCE: 549
accgcttcac ttagagtgaa ggtgggctgc ttgcatcagc ctaatgtcga gaagtgcttt            60
cttcggaaag taaccctcga aacaaagaaa ggaatgcaac                                100

SEQ ID NO: 550          moltype = DNA   length = 10
FEATURE                 Location/Qualifiers
source                  1..10
                        mol_type = other DNA
                        organism = synthetic construct
SEQUENCE: 550
ttttattttt                                                                  10
```

```
SEQ ID NO: 551          moltype = DNA   length = 98
FEATURE                 Location/Qualifiers
source                  1..98
                        mol_type = other DNA
                        organism = synthetic construct
SEQUENCE: 551
accgcttcac cgagtgaagg tgggctgctt gcatcagcct aatgtcgaga agtgctttct    60
tcggaaagta accctcgaaa caaagaaagg aatgcaac                           98

SEQ ID NO: 552          moltype = DNA   length = 10
FEATURE                 Location/Qualifiers
source                  1..10
                        mol_type = other DNA
                        organism = synthetic construct
SEQUENCE: 552
ttttattttt                                                          10

SEQ ID NO: 553          moltype = DNA   length = 104
FEATURE                 Location/Qualifiers
source                  1..104
                        mol_type = other DNA
                        organism = synthetic construct
SEQUENCE: 553
accgcttcac gcttcggcag tgaaggtggg ctgcttgcat cagcctaatg tcgagaagtg    60
ctttcttcgg aaagtaaccc tcgaaacaaa gaaggaatg caac                     104

SEQ ID NO: 554          moltype = DNA   length = 104
FEATURE                 Location/Qualifiers
source                  1..104
                        mol_type = other DNA
                        organism = synthetic construct
SEQUENCE: 554
accgcttcac gcttcggcag tgaaggtggg ctgcttgcat cagcctaatg tcgagaagtg    60
ctttcttcgg aaagtaaccc tcgaaacaaa gaaggaatg caac                     104

SEQ ID NO: 555          moltype = DNA   length = 103
FEATURE                 Location/Qualifiers
source                  1..103
                        mol_type = other DNA
                        organism = synthetic construct
SEQUENCE: 555
ccgcttcacg cttcggcagt gaaggtgggc tgcttgcatc agcctaatgt cgagaagtgc    60
tttcttcgga aagtaaccct cgaaacaaag aaggaatgc aac                      103

SEQ ID NO: 556          moltype = DNA   length = 103
FEATURE                 Location/Qualifiers
source                  1..103
                        mol_type = other DNA
                        organism = synthetic construct
SEQUENCE: 556
ccgcttcacg cttaggcagt gaaggtgggc tgcttgcatc agcctaatgt cgagaagtgc    60
tttcttcgga aagtaaccct cgaaacaaag aaggaatgc aac                      103

SEQ ID NO: 557          moltype = DNA   length = 103
FEATURE                 Location/Qualifiers
source                  1..103
                        mol_type = other DNA
                        organism = synthetic construct
SEQUENCE: 557
ccgcttcact cttaggaagt gaaggtgggc tgcttgcatc agcctaatgt cgagaagtgc    60
tttcttcgga aagtaaccct cgaaacaaag aaggaatgc aac                      103

SEQ ID NO: 558          moltype = DNA   length = 103
FEATURE                 Location/Qualifiers
source                  1..103
                        mol_type = other DNA
                        organism = synthetic construct
SEQUENCE: 558
ccgcttcacg tttagacagt gaaggtgggc tgcttgcatc agcctaatgt cgagaagtgc    60
tttcttcgga aagtaaccct cgaaacaaag aaggaatgc aac                      103

SEQ ID NO: 559          moltype = DNA   length = 104
FEATURE                 Location/Qualifiers
source                  1..104
                        mol_type = other DNA
                        organism = synthetic construct
SEQUENCE: 559
gccgcttcac gcttcggcag tgaaggtggg ctgcttgcat cagcctaatg tcgagaagtg    60
```

```
                                ctttcttcgg aaagtaaccc tcgaaacaaa gaaaggaatg caac              104

SEQ ID NO: 560                  moltype = DNA  length = 105
FEATURE                         Location/Qualifiers
source                          1..105
                                mol_type = other DNA
                                organism = synthetic construct
SEQUENCE: 560
ggccgcttca cgcttcggca gtgaaggtgg gctgcttgca tcagcctaat gtcgagaagt              60
gctttcttcg gaaagtaacc ctcgaaacaa agaaaggaat gcaac                              105

SEQ ID NO: 561                  moltype = DNA  length = 102
FEATURE                         Location/Qualifiers
source                          1..102
                                mol_type = other DNA
                                organism = synthetic construct
SEQUENCE: 561
cgcttcacgc ttcggcagtg aaggtgggct gcttgcatca gcctaatgtc gagaagtgct              60
ttcttcggaa agtaaccctc gaaacaaaga aggaatgcaa ac                                 102

SEQ ID NO: 562                  moltype = DNA  length = 101
FEATURE                         Location/Qualifiers
source                          1..101
                                mol_type = other DNA
                                organism = synthetic construct
SEQUENCE: 562
gcttcacgct tcggcagtga aggtgggctg cttgcatcag cctaatgtcg agaagtgctt              60
tcttcggaaa gtaaccctcg aaacaaagaa ggaatgcaa c                                   101

SEQ ID NO: 563                  moltype = DNA  length = 102
FEATURE                         Location/Qualifiers
source                          1..102
                                mol_type = other DNA
                                organism = synthetic construct
SEQUENCE: 563
ggcttcacgc ttcggcagtg aaggtgggct gcttgcatca gcctaatgtc gagaagtgct              60
ttcttcggaa agtaaccctc gaaacaaaga aggaatgca ac                                  102

SEQ ID NO: 564                  moltype = DNA  length = 101
FEATURE                         Location/Qualifiers
source                          1..101
                                mol_type = other DNA
                                organism = synthetic construct
SEQUENCE: 564
gcttcacgct tcggcagtga aggtgggctg cttgcatcag cctaatgtcg agaagtgctt              60
tcttcggaaa gtaaccctcg aaacaaagaa ggaatgcaa c                                   101

SEQ ID NO: 565                  moltype = DNA  length = 102
FEATURE                         Location/Qualifiers
source                          1..102
                                mol_type = other DNA
                                organism = synthetic construct
SEQUENCE: 565
ggcttcacgc ttcggcagtg aaggtgggct gcttgcatca gcctaatgtc gagaagtgct              60
ttcttcggaa agtaaccctc gaaacaaaga aggaatgca ac                                  102

SEQ ID NO: 566                  moltype = DNA  length = 102
FEATURE                         Location/Qualifiers
source                          1..102
                                mol_type = other DNA
                                organism = synthetic construct
SEQUENCE: 566
ccgcttcacg cttcggcagt gaaggtgggc tgcttgcatc agcctaatgt cgagaagtgc              60
tttcttcgga aagtaaccct cgaaacaaag aaggaatgca ac                                 102

SEQ ID NO: 567                  moltype = DNA  length = 101
FEATURE                         Location/Qualifiers
source                          1..101
                                mol_type = other DNA
                                organism = synthetic construct
SEQUENCE: 567
ccgcttcacg cttcggcagt gaaggtgggc tgcttgcatc agcctaatgt cgagaagtgc              60
tttcttcgga aagtaaccct cgaaacaaag aaggaatgca c                                  101

SEQ ID NO: 568                  moltype = DNA  length = 100
FEATURE                         Location/Qualifiers
source                          1..100
                                mol_type = other DNA
                                organism = synthetic construct
```

```
SEQUENCE: 568
ccgcttcacg cttcggcagt gaaggtgggc tgcttgcatc agcctaatgt cgagaagtgc   60
tttcttcgga aagtaaccct cgaaacaaag ggaatgcaac                        100

SEQ ID NO: 569          moltype = DNA   length = 99
FEATURE                 Location/Qualifiers
source                  1..99
                        mol_type = other DNA
                        organism = synthetic construct
SEQUENCE: 569
ccgcttcacg cttcggcagt gaaggtgggc tgcttgcatc agcctaatgt cgagaagtgc   60
tttcttcgga aagtaaccct cgaaacaaag gaatgcaac                         99

SEQ ID NO: 570          moltype = DNA   length = 98
FEATURE                 Location/Qualifiers
source                  1..98
                        mol_type = other DNA
                        organism = synthetic construct
SEQUENCE: 570
ccgcttcacg cttcggcagt gaaggtgggc tgcttgcatc agcctaatgt cgagaagtgc   60
tttcttcgga aagtaaccct cgaaacaagg aatgcaac                          98

SEQ ID NO: 571          moltype = DNA   length = 97
FEATURE                 Location/Qualifiers
source                  1..97
                        mol_type = other DNA
                        organism = synthetic construct
SEQUENCE: 571
ccgcttcacg cttcggcagt gaaggtgggc tgcttgcatc agcctaatgt cgagaagtgc   60
tttcttcgga aagtaaccct cgaaacagga atgcaac                           97

SEQ ID NO: 572          moltype = DNA   length = 96
FEATURE                 Location/Qualifiers
source                  1..96
                        mol_type = other DNA
                        organism = synthetic construct
SEQUENCE: 572
ccgcttcacg cttcggcagt gaaggtgggc tgcttgcatc agcctaatgt cgagaagtgc   60
tttcttcgga aagtaaccct cgaaacggaa tgcaac                            96

SEQ ID NO: 573          moltype = DNA   length = 95
FEATURE                 Location/Qualifiers
source                  1..95
                        mol_type = other DNA
                        organism = synthetic construct
SEQUENCE: 573
ccgcttcacg cttcggcagt gaaggtgggc tgcttgcatc agcctaatgt cgagaagtgc   60
tttcttcgga aagtaaccct cgaaaggaat gcaac                             95

SEQ ID NO: 574          moltype = DNA   length = 94
FEATURE                 Location/Qualifiers
source                  1..94
                        mol_type = other DNA
                        organism = synthetic construct
SEQUENCE: 574
ccgcttcacg cttcggcagt gaaggtgggc tgcttgcatc agcctaatgt cgagaagtgc   60
tttcttcgga aagtaaccct cgaaggaatg caac                              94

SEQ ID NO: 575          moltype = DNA   length = 93
FEATURE                 Location/Qualifiers
source                  1..93
                        mol_type = other DNA
                        organism = synthetic construct
SEQUENCE: 575
ccgcttcacg cttcggcagt gaaggtgggc tgcttgcatc agcctaatgt cgagaagtgc   60
tttcttcgga aagtaaccct cgaggaatgc aac                               93

SEQ ID NO: 576          moltype = DNA   length = 97
FEATURE                 Location/Qualifiers
source                  1..97
                        mol_type = other DNA
                        organism = synthetic construct
SEQUENCE: 576
ccgcttcacg cttcggcagt gaaggtgggc tgcttgcatc agcctaatgt cgagaagtgc   60
tttcttcgga aagtaaccct cgaaacaaga atgcaac                           97

SEQ ID NO: 577          moltype = DNA   length = 99
FEATURE                 Location/Qualifiers
source                  1..99
```

```
                        mol_type = other DNA
                        organism = synthetic construct
SEQUENCE: 577
ccgcttcacg cttcggcagt gaaggtgggc tgcttgcatc agcctaatgt cgagaagtgc    60
tttcttcgga aagtaaccct cgaaacaaag gaatgcaac                           99

SEQ ID NO: 578          moltype = DNA   length = 98
FEATURE                 Location/Qualifiers
source                  1..98
                        mol_type = other DNA
                        organism = synthetic construct
SEQUENCE: 578
ccgcttcacg cttcggcagt gaaggtgggc tgcttgcatc agcctaatgt cgagaagtgc    60
tttcttcgga aagtaaccct cgaaacaaag aatgcaac                            98

SEQ ID NO: 579          moltype = DNA   length = 102
FEATURE                 Location/Qualifiers
source                  1..102
                        mol_type = other DNA
                        organism = synthetic construct
SEQUENCE: 579
ccgcttcacg cttcggcagt gaaggtgggc tgcttgcatc agcctaatgt cgagaagtgc    60
tttcttcgga aagtaaccct cgaaacaaag aaagaatgca ac                      102

SEQ ID NO: 580          moltype = DNA   length = 100
FEATURE                 Location/Qualifiers
source                  1..100
                        mol_type = other DNA
                        organism = synthetic construct
SEQUENCE: 580
ccgcttcacg cttcggcagt gaaggtgggc tgcttgcatc agcctaatgt cgagaagtgc    60
tttcttcgga aagtaaccct cgaaacaaag agaatgcaac                         100

SEQ ID NO: 581          moltype = DNA   length = 99
FEATURE                 Location/Qualifiers
source                  1..99
                        mol_type = other DNA
                        organism = synthetic construct
SEQUENCE: 581
ccgcttcacg cttcggcagt gaaggtgggc tgcttgcatc agcctaatgt cgagaagtgc    60
tttcttcgga aagtaaccct cgaaacaaag aaatgcaac                           99

SEQ ID NO: 582          moltype = DNA   length = 96
FEATURE                 Location/Qualifiers
source                  1..96
                        mol_type = other DNA
                        organism = synthetic construct
SEQUENCE: 582
ccgcttcacg cttcggcagt gaaggtgggc tgcttgcatc agcctaatgt cgagaagtgc    60
tttcttcgga aagtaaccct cgaaacagaa tgcaac                              96

SEQ ID NO: 583          moltype = DNA   length = 95
FEATURE                 Location/Qualifiers
source                  1..95
                        mol_type = other DNA
                        organism = synthetic construct
SEQUENCE: 583
ccgcttcacg cttcggcagt gaaggtgggc tgcttgcatc agcctaatgt cgagaagtgc    60
tttcttcgga aagtaaccct cgaaacaaat gcaac                               95

SEQ ID NO: 584          moltype = DNA   length = 103
FEATURE                 Location/Qualifiers
source                  1..103
                        mol_type = other DNA
                        organism = synthetic construct
SEQUENCE: 584
ccgcttcacg cttcggcagt gaaggtgggc tgattgcatc agcctaatgt cgagaagtgc    60
tttcttcgga aagtaaccct cgaaacaaag aaaggaatgc aac                     103

SEQ ID NO: 585          moltype = DNA   length = 103
FEATURE                 Location/Qualifiers
source                  1..103
                        mol_type = other DNA
                        organism = synthetic construct
SEQUENCE: 585
ccgcttcacg cttcggcagt gaaggtaggc tgcttgcatc agcctaatgt cgagaagtgc    60
tttcttcgga aagtaaccct cgaaacaaag aaaggaatgc aac                     103

SEQ ID NO: 586          moltype = DNA   length = 103
```

```
FEATURE          Location/Qualifiers
source           1..103
                 mol_type = other DNA
                 organism = synthetic construct
SEQUENCE: 586
ccgcttcacg cttcggcagt gaaggtgggc tgcttgcatc agcccaatgt cgagaagtgc    60
tttcttcgga agtaaccct cgaaacaaag aaaggaatgc aac                      103

SEQ ID NO: 587   moltype = DNA  length = 97
FEATURE          Location/Qualifiers
source           1..97
                 mol_type = other DNA
                 organism = synthetic construct
SEQUENCE: 587
ggcttcacgc ttcggcagtg aaggtaggct gcttgcatca gcctaatgtc gagaagtgct    60
ttcttcggaa agtaaccctc gaaacaagga atgcaac                             97

SEQ ID NO: 588   moltype = DNA  length = 97
FEATURE          Location/Qualifiers
source           1..97
                 mol_type = other DNA
                 organism = synthetic construct
SEQUENCE: 588
ggcttcacgc ttcggcagtg aaggtgggct gcttgcatca gcccaatgtc gagaagtgct    60
ttcttcggaa agtaaccctc gaaacaagga atgcaac                             97

SEQ ID NO: 589   moltype = DNA  length = 103
FEATURE          Location/Qualifiers
source           1..103
                 mol_type = other DNA
                 organism = synthetic construct
SEQUENCE: 589
ccgcttcact cttaggaagt gaaggtgggc tgattgcatc agcctaatgt cgagaagtgc    60
tttcttcgga agtaaccct cgaaacaaag aaaggaatgc aac                      103

SEQ ID NO: 590   moltype = DNA  length = 100
FEATURE          Location/Qualifiers
source           1..100
                 mol_type = other DNA
                 organism = synthetic construct
SEQUENCE: 590
ccgcttcacg cttcggcagt gaaggtgggc tgattgcatc agcctaatgt cgagaagtgc    60
tttcttcgga agtaaccct cgaaacaaag ggaatgcaac                          100

SEQ ID NO: 591   moltype = DNA  length = 99
FEATURE          Location/Qualifiers
source           1..99
                 mol_type = other DNA
                 organism = synthetic construct
SEQUENCE: 591
ccgcttcacg cttcggcagt gaaggtgggc tgattgcatc agcctaatgt cgagaagtgc    60
tttcttcgga agtaaccct cgaaacaaag gaatgcaac                            99

SEQ ID NO: 592   moltype = DNA  length = 98
FEATURE          Location/Qualifiers
source           1..98
                 mol_type = other DNA
                 organism = synthetic construct
SEQUENCE: 592
ccgcttcacg cttcggcagt gaaggtgggc tgattgcatc agcctaatgt cgagaagtgc    60
tttcttcgga agtaaccct cgaaacaagg aatgcaac                             98

SEQ ID NO: 593   moltype = DNA  length = 97
FEATURE          Location/Qualifiers
source           1..97
                 mol_type = other DNA
                 organism = synthetic construct
SEQUENCE: 593
ccgcttcacg cttcggcagt gaaggtgggc tgattgcatc agcctaatgt cgagaagtgc    60
tttcttcgga agtaaccct cgaaacaaga atgcaac                              97

SEQ ID NO: 594   moltype = DNA  length = 99
FEATURE          Location/Qualifiers
source           1..99
                 mol_type = other DNA
                 organism = synthetic construct
SEQUENCE: 594
ccgcttcacg cttcggcagt gaaggtgggc tgattgcatc agcctaatgt cgagaagtgc    60
tttcttcgga agtaaccct cgaaacaaag gaatgcaac                            99
```

```
SEQ ID NO: 595          moltype = DNA   length = 98
FEATURE                 Location/Qualifiers
source                  1..98
                        mol_type = other DNA
                        organism = synthetic construct
SEQUENCE: 595
ccgcttcacg cttcggcagt gaaggtgggc tgattgcatc agcctaatgt cgagaagtgc    60
tttcttcgga aagtaaccct cgaaacaaag aatgcaac                            98

SEQ ID NO: 596          moltype = DNA   length = 96
FEATURE                 Location/Qualifiers
source                  1..96
                        mol_type = other DNA
                        organism = synthetic construct
SEQUENCE: 596
ccgcttcacg cttcggcagt gaaggtgggc tgattgcatc agcctaatgt cgagaagtgc    60
tttcttcgga aagtaaccct cgaaacagaa tgcaac                              96

SEQ ID NO: 597          moltype = DNA   length = 30
FEATURE                 Location/Qualifiers
source                  1..30
                        mol_type = other DNA
                        organism = synthetic construct
SEQUENCE: 597
ccgcttcacg cttcggcagt gaaggtgggc                                     30

SEQ ID NO: 598          moltype = DNA   length = 30
FEATURE                 Location/Qualifiers
source                  1..30
                        mol_type = other DNA
                        organism = synthetic construct
SEQUENCE: 598
ccgcttcact cttaggaagt gaaggtgggc                                     30

SEQ ID NO: 599          moltype = DNA   length = 30
FEATURE                 Location/Qualifiers
source                  1..30
                        mol_type = other DNA
                        organism = synthetic construct
SEQUENCE: 599
gaaagtaacc ctcgaaacaa agaatgcaac                                     30

SEQ ID NO: 600          moltype = DNA   length = 30
FEATURE                 Location/Qualifiers
source                  1..30
                        mol_type = other DNA
                        organism = synthetic construct
SEQUENCE: 600
aagtaaccct cgaaacaaag ggaatgcaac                                     30

SEQ ID NO: 601          moltype = DNA   length = 30
FEATURE                 Location/Qualifiers
source                  1..30
                        mol_type = other DNA
                        organism = synthetic construct
SEQUENCE: 601
aaagtaaccc tcgaaacaaa ggaatgcaac                                     30

SEQ ID NO: 602          moltype =       length =
SEQUENCE: 602
000

SEQ ID NO: 603          moltype = DNA   length = 10
FEATURE                 Location/Qualifiers
source                  1..10
                        mol_type = other DNA
                        organism = synthetic construct
SEQUENCE: 603
ttttattttt                                                           10

SEQ ID NO: 604          moltype = DNA   length = 10
FEATURE                 Location/Qualifiers
source                  1..10
                        mol_type = other DNA
                        organism = synthetic construct
SEQUENCE: 604
ttttattttt                                                           10
```